US008288523B2

(12) United States Patent
Sampath et al.

(10) Patent No.: US 8,288,523 B2
(45) Date of Patent: *Oct. 16, 2012

(54) COMPOSITIONS FOR USE IN IDENTIFICATION OF BACTERIA

(75) Inventors: Rangarajan Sampath, San Diego, CA (US); Thomas A. Hall, Oceanside, CA (US); David J. Ecker, Encinitas, CA (US); Lawrence Blyn, Mission Viejo, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 1382 days.

This patent is subject to a terminal disclaimer.

(21) Appl. No.: 11/683,254

(22) Filed: Mar. 7, 2007

(65) Prior Publication Data

US 2012/0122097 A1 May 17, 2012

Related U.S. Application Data

(63) Continuation of application No. 11/409,535, filed on Apr. 21, 2006, now abandoned, which is a continuation-in-part of application No. 11/060,135, filed on Feb. 17, 2005, now abandoned, said application No. 11/409,535 is a continuation-in-part of application No. 10/728,486, filed on Dec. 5, 2003, now Pat. No. 7,718,354.

(60) Provisional application No. 60/545,425, filed on Feb. 18, 2004, provisional application No. 60/559,754, filed on Apr. 5, 2004, provisional application No. 60/632,862, filed on Dec. 3, 2004, provisional application No. 60/639,068, filed on Dec. 22, 2004, provisional application No. 60/648,188, filed on Jan. 28, 2005, provisional application No. 60/501,926, filed on Sep. 11, 2003, provisional application No. 60/674,118, filed on Apr. 21, 2005, provisional application No. 60/705,631, filed on Aug. 3, 2005, provisional application No. 60/732,539, filed on Nov. 1, 2005, provisional application No. 60/773,124, filed on Feb. 13, 2006.

(51) Int. Cl.
*C07H 21/04* (2006.01)
*C12Q 1/68* (2006.01)

(52) U.S. Cl. .................... 536/24.33; 435/6.12; 435/91.2

(58) Field of Classification Search ........................ None
See application file for complete search history.

(56) References Cited

U.S. PATENT DOCUMENTS

| | | | |
|---|---|---|---|
| 5,436,129 | A | 7/1995 | Stapleton |
| 5,451,500 | A | 9/1995 | Stapleton |

(Continued)

FOREIGN PATENT DOCUMENTS

| | | | |
|---|---|---|---|
| DE | 19802905 | A1 | 7/1999 |

(Continued)

OTHER PUBLICATIONS

GenBank accession No. AJ271273 [online] Apr. 15, 2005 [retrieved on Oct. 20, 2011] retrieved from http://www.ncbi.nlm.nih.gov/nuccore/aj271273.*

(Continued)

*Primary Examiner* — Samuel Woolwine
(74) *Attorney, Agent, or Firm* — Casimir Jones S.C.; Christopher C. Sappenfield

(57) ABSTRACT

The present invention provides compositions, kits and methods for rapid identification and quantification of bacteria by molecular mass and base composition analysis.

19 Claims, 7 Drawing Sheets

Base Composition Signatures from primer pair 14 (16S rRNA)

U.S. PATENT DOCUMENTS

| | | | | |
|---|---|---|---|---|
| 5,484,908 | A | 1/1996 | Froehler et al. | |
| 5,523,217 | A | 6/1996 | Lupski et al. | |
| 5,547,835 | A | 8/1996 | Koster | |
| 5,567,587 | A | 10/1996 | Kohne | |
| 5,605,798 | A | 2/1997 | Koster | |
| 5,622,824 | A | 4/1997 | Koster | |
| 5,683,869 | A | 11/1997 | Ramsay Shaw et al. | |
| 5,691,141 | A | 11/1997 | Koster | |
| 5,702,895 | A | 12/1997 | Matsunaga et al. | |
| 5,707,802 | A | 1/1998 | Sandhu et al. | |
| 5,727,202 | A | 3/1998 | Kucala | |
| 5,745,751 | A | 4/1998 | Nelson et al. | |
| 5,759,771 | A | 6/1998 | Tilanus | |
| 5,763,169 | A | 6/1998 | Sandhu et al. | |
| 5,777,324 | A | 7/1998 | Hillenkamp | |
| 5,832,489 | A | 11/1998 | Kucala | |
| 5,849,492 | A | 12/1998 | Rogan | |
| 5,849,901 | A | 12/1998 | Mabilat et al. | |
| 5,851,765 | A | 12/1998 | Koster | |
| 5,871,697 | A | 2/1999 | Rothberg et al. | |
| 5,872,003 | A | 2/1999 | Koster | |
| 5,885,775 | A * | 3/1999 | Haff et al. | 435/6.18 |
| 5,900,481 | A | 5/1999 | Lough et al. | |
| 5,928,906 | A | 7/1999 | Koster et al. | |
| 5,965,363 | A | 10/1999 | Monforte et al. | |
| 5,972,693 | A | 10/1999 | Rothberg et al. | |
| 5,976,798 | A | 11/1999 | Parker et al. | |
| 5,981,176 | A | 11/1999 | Wallace | |
| 5,981,190 | A | 11/1999 | Israel | |
| 6,001,564 | A | 12/1999 | Bergeron et al. | |
| 6,018,713 | A | 1/2000 | Coli et al. | |
| 6,024,925 | A | 2/2000 | Little et al. | |
| 6,043,031 | A | 3/2000 | Koster et al. | |
| 6,051,378 | A | 4/2000 | Monforte et al. | |
| 6,055,487 | A | 4/2000 | Margery et al. | |
| 6,060,246 | A | 5/2000 | Summerton et al. | |
| 6,061,686 | A | 5/2000 | Gauvin et al. | |
| 6,074,823 | A | 6/2000 | Koster | |
| 6,074,831 | A | 6/2000 | Yakhini et al. | |
| 6,090,558 | A | 7/2000 | Butler et al. | |
| 6,111,251 | A | 8/2000 | Hillenkamp | |
| 6,133,436 | A | 10/2000 | Koster et al. | |
| 6,140,053 | A | 10/2000 | Koster | |
| 6,146,854 | A | 11/2000 | Koster et al. | |
| 6,180,339 | B1 | 1/2001 | Sandhu et al. | |
| 6,180,372 | B1 | 1/2001 | Franzen | |
| 6,194,144 | B1 | 2/2001 | Koster | |
| 6,197,498 | B1 | 3/2001 | Koster | |
| 6,218,118 | B1 * | 4/2001 | Sampson et al. | 506/4 |
| 6,221,598 | B1 | 4/2001 | Schumm et al. | |
| 6,221,601 | B1 | 4/2001 | Koster et al. | |
| 6,221,605 | B1 | 4/2001 | Koster | |
| 6,225,450 | B1 | 5/2001 | Koster | |
| 6,235,478 | B1 | 5/2001 | Koster | |
| 6,238,871 | B1 | 5/2001 | Koster | |
| 6,258,538 | B1 | 7/2001 | Koster et al. | |
| 6,268,131 | B1 | 7/2001 | Kang et al. | |
| 6,268,144 | B1 | 7/2001 | Koster | |
| 6,277,573 | B1 | 8/2001 | Koster | |
| 6,300,076 | B1 | 10/2001 | Koster | |
| 6,303,297 | B1 | 10/2001 | Lincoln et al. | |
| 6,322,970 | B1 | 11/2001 | Little et al. | |
| 6,389,428 | B1 | 5/2002 | Rigault et al. | |
| 6,393,367 | B1 | 5/2002 | Tang et al. | |
| 6,419,932 | B1 | 7/2002 | Dale | |
| 6,423,966 | B2 | 7/2002 | Hillenkamp et al. | |
| 6,428,955 | B1 | 8/2002 | Koster et al. | |
| 6,436,635 | B1 | 8/2002 | Fu et al. | |
| 6,453,244 | B1 | 9/2002 | Oefner | |
| 6,468,743 | B1 | 10/2002 | Romick et al. | |
| 6,468,748 | B1 | 10/2002 | Monforte et al. | |
| 6,475,143 | B2 | 11/2002 | Iliff | |
| 6,500,621 | B2 | 12/2002 | Koster | |
| 6,553,317 | B1 | 4/2003 | Ament et al. | |
| 6,558,902 | B1 | 5/2003 | Hillenkamp | |
| 6,563,025 | B1 | 5/2003 | Song et al. | |
| 6,566,055 | B1 | 5/2003 | Monforte et al. | |
| 6,589,485 | B2 | 7/2003 | Koster | |
| 6,602,662 | B1 | 8/2003 | Koster et al. | |
| 6,605,433 | B1 | 8/2003 | Fliss et al. | |
| 6,613,520 | B2 | 9/2003 | Ashby | |
| 6,680,476 | B1 | 1/2004 | Hidalgo et al. | |
| 6,706,530 | B2 | 3/2004 | Hillenkamp | |
| 7,074,599 | B2 | 7/2006 | Uhl et al. | |
| 7,108,974 | B2 | 9/2006 | Ecker et al. | |
| 7,198,893 | B1 | 4/2007 | Köster et al. | |
| 7,217,510 | B2 | 5/2007 | Ecker et al. | |
| 7,226,739 | B2 | 6/2007 | Ecker et al. | |
| 7,255,992 | B2 | 8/2007 | Ecker et al. | |
| 7,285,422 | B1 | 10/2007 | Little et al. | |
| 7,419,787 | B2 | 9/2008 | Köster | |
| 7,501,251 | B2 | 3/2009 | Köster et al. | |
| 7,741,036 | B2 | 6/2010 | Ecker et al. | |
| 7,956,175 | B2 | 6/2011 | Sampath et al. | |
| 8,013,142 | B2 | 9/2011 | Sampath et al. | |
| 2001/0046670 | A1 | 11/2001 | Brookes | |
| 2002/0042112 | A1 | 4/2002 | Koster et al. | |
| 2002/0055101 | A1 | 5/2002 | Bergeron et al. | |
| 2002/0138210 | A1 | 9/2002 | Wilkes et al. | |
| 2002/0168630 | A1 | 11/2002 | Fleming et al. | |
| 2003/0027135 | A1 | 2/2003 | Ecker et al. | |
| 2003/0050470 | A1 | 3/2003 | An et al. | |
| 2003/0113745 | A1 | 6/2003 | Monforte et al. | |
| 2003/0129589 | A1 | 7/2003 | Koster et al. | |
| 2003/0175695 | A1 | 9/2003 | Ecker et al. | |
| 2003/0175696 | A1 | 9/2003 | Ecker et al. | |
| 2003/0175697 | A1 | 9/2003 | Ecker et al. | |
| 2003/0190605 | A1 | 10/2003 | Ecker et al. | |
| 2003/0228597 | A1 | 12/2003 | Cowsert et al. | |
| 2004/0023207 | A1 * | 2/2004 | Polansky | 435/5 |
| 2004/0081993 | A1 | 4/2004 | Cantor et al. | |
| 2004/0110169 | A1 | 6/2004 | Ecker et al. | |
| 2004/0202997 | A1 | 10/2004 | Ecker et al. | |
| 2005/0266397 | A1 * | 12/2005 | Ecker et al. | 435/5 |
| 2007/0218489 | A1 | 9/2007 | Sampath et al. | |
| 2007/0238116 | A1 | 10/2007 | Sampath et al. | |
| 2007/0248969 | A1 | 10/2007 | Sampath et al. | |
| 2009/0042203 | A1 | 2/2009 | Koster | |
| 2009/0092977 | A1 | 4/2009 | Koster | |

FOREIGN PATENT DOCUMENTS

| | | | |
|---|---|---|---|
| DE | 19824280 | A1 | 12/1999 |
| DE | 19852167 | A1 | 5/2000 |
| EP | 620862 | B1 | 4/1998 |
| EP | 1138782 | A2 | 10/2001 |
| EP | 1333101 | A1 | 8/2003 |
| EP | 1541696 | A1 | 6/2005 |
| EP | 2076612 | A2 | 7/2009 |
| GB | 2325002 | A | 11/1998 |
| GB | 2339905 | A | 2/2000 |
| WO | WO9015157 | A1 | 12/1990 |
| WO | WO9208117 | A1 | 5/1992 |
| WO | WO9209703 | A1 | 6/1992 |
| WO | WO9303186 | A1 | 2/1993 |
| WO | WO9305182 | A1 | 3/1993 |
| WO | WO9308297 | A1 | 4/1993 |
| WO | WO9416101 | A2 | 7/1994 |
| WO | WO9421822 | A1 | 9/1994 |
| WO | WO9504161 | A1 | 2/1995 |
| WO | WO9513396 | A2 | 5/1995 |
| WO | WO9629431 | A2 | 9/1996 |
| WO | WO9632504 | A2 | 10/1996 |
| WO | WO9635450 | A1 | 11/1996 |
| WO | WO9637630 | A1 | 11/1996 |
| WO | WO9733000 | A1 | 9/1997 |
| WO | WO9737041 | A2 | 10/1997 |
| WO | WO9803694 | A1 | 1/1998 |
| WO | WO9812355 | A1 | 3/1998 |
| WO | WO9814616 | A1 | 4/1998 |
| WO | WO9815652 | A1 | 4/1998 |
| WO | WO9820020 | A2 | 5/1998 |
| WO | WO9820157 | A2 | 5/1998 |
| WO | WO9820166 | A2 | 5/1998 |
| WO | WO9826095 | A1 | 6/1998 |
| WO | WO9831830 | A1 | 7/1998 |
| WO | WO9840520 | A1 | 9/1998 |
| WO | WO9854751 | A1 | 12/1998 |

| | | | |
|---|---|---|---|
| WO | WO9905319 | A2 | 2/1999 |
| WO | WO9912040 | A2 | 3/1999 |
| WO | WO9929898 | A2 | 6/1999 |
| WO | WO9957318 | A2 | 11/1999 |
| WO | WO0107648 | A1 | 2/2001 |
| WO | WO0123604 | A2 | 4/2001 |
| WO | WO0132930 | A1 | 5/2001 |
| WO | WO0151661 | A2 | 7/2001 |
| WO | WO0157263 | A1 | 8/2001 |
| WO | WO0157518 | A2 | 8/2001 |
| WO | WO0173199 | A1 | 10/2001 |
| WO | WO0210186 | A1 | 2/2002 |
| WO | WO0210444 | A1 | 2/2002 |
| WO | WO0218641 | A2 | 3/2002 |
| WO | WO0221108 | A2 | 3/2002 |
| WO | WO0222873 | A1 | 3/2002 |
| WO | WO0250307 | A1 | 6/2002 |
| WO | WO02057491 | A2 | 7/2002 |
| WO | WO02070664 | A2 | 9/2002 |
| WO | WO02077278 | A1 | 10/2002 |
| WO | WO02099034 | A2 | 12/2002 |
| WO | WO03002750 | A2 | 1/2003 |
| WO | WO03008636 | A2 | 1/2003 |
| WO | WO03016546 | A1 | 2/2003 |
| WO | WO03060163 | A2 | 7/2003 |
| WO | WO03088979 | A2 | 10/2003 |
| WO | WO03093506 | A2 | 11/2003 |
| WO | WO03097869 | A2 | 11/2003 |
| WO | WO03102191 | A1 | 12/2003 |
| WO | WO2004013357 | A2 | 2/2004 |
| WO | WO2006116127 | A2 | 11/2006 |
| WO | WO2007086904 | A2 | 8/2007 |
| WO | WO2008118809 | A1 | 10/2008 |
| WO | WO2008127839 | A2 | 10/2008 |
| WO | WO2010039917 | A2 | 4/2010 |

OTHER PUBLICATIONS

GenBank accession No. AJ271274 [online] Apr. 15, 2005 [retrieved on Oct. 20, 2011] retrieved from http://www.ncbi.nlm.nih.gov/nuccore/aj271274.*

GenBank accession No. AJ271275 [online] Apr. 15, 2005 [retrieved on Oct. 20, 2011] retrieved from http://www.ncbi.nlm.nih.gov/nuccore/aj271275.*

GenBank accession No. AJ271276 [online] Apr. 15, 2005 [retrieved on Oct. 20, 2011] retrieved from http://www.ncbi.nlm.nih.gov/nuccore/aj271276.*

GenBank accession No. AJ271277 [online] Apr. 15, 2005 [retrieved on Oct. 20, 2011] retrieved from http://www.ncbi.nlm.nih.gov/nuccore/aj271277.*

GenBank accession No. AJ271278 [online] Apr. 15, 2005 [retrieved on Oct. 20, 2011] retrieved from http://www.ncbi.nlm.nih.gov/nuccore/aj271278.*

GenBank accession No. AJ271279 [online] Apr. 15, 2005 [retrieved on Oct. 20, 2011] retrieved from http://www.ncbi.nlm.nih.gov/nuccore/aj271279.*

GenBank accession No. AJ271280 [online] Apr. 15, 2005 [retrieved on Oct. 20, 2011] retrieved from http://www.ncbi.nlm.nih.gov/nuccore/aj271280.*

GenBank accession No. AJ271281 [online] Apr. 15, 2005 [retrieved on Oct. 20, 2011] retrieved from http://www.ncbi.nlm.nih.gov/nuccore/aj271281.*

GenBank accession No. AJ271283 [online] Apr. 15, 2005 [retrieved on Oct. 20, 2011] retrieved from http://www.ncbi.nlm.nih.gov/nuccore/aj271283.*

GenBank accession No. AJ271284 [online] Apr. 15, 2005 [retrieved on Oct. 20, 2011] retrieved from http://www.ncbi.nlm.nih.gov/nuccore/aj271284.*

GenBank accession No. AJ271285 [online] Apr. 15, 2005 [retrieved on Oct. 20, 2011] retrieved from http://www.ncbi.nlm.nih.gov/nuccore/aj271285.*

GenBank accession No. AJ271286 [online] Apr. 15, 2005 [retrieved on Oct. 20, 2011] retrieved from http://www.ncbi.nlm.nih.gov/nuccore/aj271286.*

GenBank accession No. AJ271287 [online] Apr. 15, 2005 [retrieved on Oct. 20, 2011] retrieved from http://www.ncbi.nlm.nih.gov/nuccore/aj271287.*

GenBank accession No. AJ271288 [online] Apr. 15, 2005 [retrieved on Oct. 20, 2011] retrieved from http://www.ncbi.nlm.nih.gov/nuccore/aj271288.*

GenBank accession No. AJ271289 [online] Apr. 15, 2005 [retrieved on Oct. 20, 2011] retrieved from http://www.ncbi.nlm.nih.gov/nuccore/aj271289.*

GenBank accession No. AJ252295 [online] Apr. 15, 2005 [retrieved on Oct. 21, 2011] retrieved from http://www.ncbi.nlm.nih.gov/nuccore/aj252295.*

GenBank accession No. AJ252296 [online] Apr. 15, 2005 [retrieved on Oct. 21, 2011] retrieved from http://www.ncbi.nlm.nih.gov/nuccore/aj252296.*

GenBank accession No. AJ252297 [online] Apr. 15, 2005 [retrieved on Oct. 21, 2011] retrieved from http://www.ncbi.nlm.nih.gov/nuccore/aj252297.*

GenBank accession No. AJ252298 [online] Apr. 15, 2005 [retrieved on Oct. 21, 2011] retrieved from http://www.ncbi.nlm.nih.gov/nuccore/aj252298.*

GenBank accession No. AJ252299 [online] Apr. 15, 2005 [retrieved on Oct. 21, 2011] retrieved from http://www.ncbi.nlm.nih.gov/nuccore/aj252299.*

GenBank accession No. AJ252300 [online] Apr. 15, 2005 [retrieved on Oct. 21, 2011] retrieved from http://www.ncbi.nlm.nih.gov/nuccore/aj252300.*

GenBank accession No. AJ252301 [online] Apr. 15, 2005 [retrieved on Oct. 21, 2011] retrieved from http://www.ncbi.nlm.nih.gov/nuccore/aj252301.*

GenBank accession No. AJ252302 [online] Apr. 15, 2005 [retrieved on Oct. 21, 2011] retrieved from http://www.ncbi.nlm.nih.gov/nuccore/aj252302.*

GenBank accession No. AJ252303 [online] Apr. 15, 2005 [retrieved on Oct. 21, 2011] retrieved from http://www.ncbi.nlm.nih.gov/nuccore/aj252303.*

GenBank accession No. AJ252304 [online] Apr. 15, 2005 [retrieved on Oct. 21, 2011] retrieved from http://www.ncbi.nlm.nih.gov/nuccore/aj252304.*

GenBank accession No. AJ252304 [online] Apr. 15, 2005 [retrieved on Oct. 21, 2011] retrieved from http://www.ncbi.nlm.nih.gov/nuccore/aj252305.*

GenBank accession No. AJ252306 [online] Apr. 15, 2005 [retrieved on Oct. 21, 2011] retrieved from http://www.ncbi.nlm.nih.gov/nuccore/aj252306.*

GenBank accession No. AJ252307 [online] Apr. 15, 2005 [retrieved on Oct. 21, 2011] retrieved from http://www.ncbi.nlm.nih.gov/nuccore/aj252307.*

GenBank accession No. AJ252308 [online] Apr. 15, 2005 [retrieved on Oct. 21, 2011] retrieved from http://www.ncbi.nlm.nih.gov/nuccore/aj252295308.*

GenBank accession No. AJ252309 [online] Apr. 15, 2005 [retrieved on Oct. 21, 2011] retrieved from http://www.ncbi.nlm.nih.gov/nuccore/aj252295309.*

GenBank accession No. AJ252310 [online] Apr. 15, 2005 [retrieved on Oct. 21, 2011] retrieved from http://www.ncbi.nlm.nih.gov/nuccore/aj252310.*

Allaouchiche, B. et al., "Clinical Impact of Rapid Oxacillin Susceptibility Testing Using a PCR Assay in *Staphylococcus aureus* Bactaeremia," *J. Infect.* (1999) 39(3):198-204.

Anthony, R. M. et al., "Use of the Polymerase Chain Reaction for Rapid Detection of High-Level Mupirocin Resistance in *Staphylococci*," *Eur. J. Clin. Microbiol. Infect. Dis.* (1999) 18(1):30-34.

Arbique, J. et al., "Comparison of the Velogene Rapid MRSA Identification Assay, Denka MRSA-Screen Assay, and BBL Crystal MRSA ID System for rapid identification of methicillin-resistant *Staphylococcus aureus*," *Diagn. Microbiol. Infect. Dis.* (2001) 40(1-2):5-10.

Archer, G. L. et al., "Detection of Methicillin Resistance in *Staphylococci* by Using a DNA Probe," *Antimicrob. Agents Chemother.* (1990) 34(9):1720-1724.

Baba, T. et al., "Genome and virulence determinants of high virulence community-acquired MRSA," *Lancet* (2002) 359:1819-1827.

Baron, E. J., "Genetic Aspects of Methicillin Resistance in *Staphylococcus aureus* and Methods Used for its Detection in Clinical Laboratories in the United States," *J. Chemother.* (1995) 7(Suppl. 3):87-92.
Barski, P. et al., "Rapid assay for detection of methicillin-resistant *Staphylococcus aureus* using multiplex PCR," *Mol. Cell Probes* (1996) 10:471-475.
Blaiotta, G. et al., "PCR detection of staphylococcal enterotoxin genes in *Staphylococcus* spp. strains isolated from meat and dairy products. Evidence for new variants of seG and seI in *S. aureus* AB-8802," *J. Appl. Microbiol.* (2004) 97:719-730.
Boubaker, K. et al., "Panton-Valentine Leukocidin and Staphyloccoccal Skin Infections in Schoolchildren," *Emerg. Infect. Dis.* (2004) 10(1):121-124.
Bowers, K. M. et al., "Screening for methicillin resistance in *Staphylococcus aureus* and coagulase-negative *staphylococci*: an evaluation of three selective media and Mastalex-MRSA latex agglutination," *Br. J. Biomed. Sci.*(2003) 60(2):71-74.
Brakstad, O. G. et al., "Multiplex polymerase chain reaction for detection of genes for *Staphylococcus aureus* thermonuclease and methicillin resistance and correlation with oxacillin resistance," *APMIS* (1993) 101:681-688.
Brakstad, O. G. et al., "Direct identification of *Staphylococcus aureus* in blood cultures by detection of the gene encoding the thermostable nuclease or the gene product," *APMIS* (1995) 103:209-218.
Brayshaw, D. P., "Methicillin-resistant *Staphylococcus aureus*: evaluation of detection techniques on laboratory-passaged organisms," *Br. J. Biomed. Sci.* (1999) 56:170-176.
Brunaud, V. et al., "T-DNA integration into the *Arabidopsis* genome depends on sequence of pre-insertion sites," *EMBO Rep.* (2002) 3(12):1152-1157.
Carroll, K. C. et al., "Rapid Detection of the Staphylococcal *mec*A Gene from BACTEC Blood Culture Bottles by the Polymerase Chain Reaction," *Am. J. Clin. Pathol.* (1996) 106:600-5.
Cavassini, M. et al., "Evaluation of MRSA-Screen, a Simple Anti-PBP 2a Slide Latex Agglutination Kit, for Rapid Detection of Methicillin Resistance in *Staphylococcus aureus," J. Clin. Microbiol.* (1999) 37(5):1591-1594.
Chaves, F. et al., "Molecular Characterization of Resistance to Mupirocin in Methicillin-Susceptible and -Resistant Isolates of *Staphylococcus aureus* from Nasal Samples," *J. Clin. Microbiol.* (2004) 42(2):822-824.
Cloney, L. et al., "Rapid detection of *mecA* in methicillin resistant *Staphylococcus aureus* using cycling probe technology," *Mol. Cell Probes* (1999) 13:191-197.
Couto, I. et al., "Development of Methicillin Resistance in Clinical Isolates of *Staphylococcus sciuri* by Transcriptional Activation of the *mecA* Homologue Native to the Species," *J. Bacteriol.* (2003) 185(2):645-653.
Cui, L. et al., "Contribution of a Thickened Cell Wall and Its Glutamine Nonamidated Component to the Vancomycin Resistance Expressed by *Staphylococcus aureus* Mu50," *Antimicrob. Agents Chemother.* (2000) 44(9):2276-2285.
De Sousa, M. A. et al., "Bridges from hospitals to the laboratory: genetic portraits of methicillin-resistant *Staphylococcus aureus* clones," *FEMS Immunol. Med. Microbiol.* (2004) 40:101-111.
Del Vecchio, V. G. et al., "Molecular Genotyping of Methicillin-Resistant *Staphylococcus aureus* via Fluorophore-Enhanced Repetitive-Sequence PCR," *J. Clin. Microbiol.* (1995) 33(8):2141-2144.
Deurenberg, R. H. et al., "Rapid detection of Panton-Valentine leukocidin from clinical isolates of *Staphylococcus aureus* strains by real-time PCR," *FEMS Microbiol. Lett.* (2004) 240(2):225-228.
Diep, B. A. et al., "Complete genome sequence of USA300, an epidemic clone of community-acquired meticillin-resistant *Staphylococcus aureus," Lancet* (2006) 367:731-739.
Elsayed, S. et al., "Development and Validation of a Molecular Beacon Probe-Based Real-Time Polymerase Chain Reaction Assay for Rapid Detection of Methicillin Resistance in *Staphylococcus aureus," Arch. Pathol. Lab. Med.* (2003) 127:845-849.
Enright, M. C. et al., "Multilocus Sequence Typing for Characterization of Methicillin-Resistant and Methicillin-Susceptible Clones of *Staphylococcus aureus," J. Clin. Microbiol.* (2000) 38(3):1008-1015.
Enright, M. C. et al., "The evolutionary history of methicillin-resistant *Staphylococcus aureus* (MRSA)," *PNAS* (2002) 99(11):7687-7692.
Enright, M. C. et al., "The evolution of a resistant pathogen-the case of MRSA," *Curr. Opin. Pharmacol.* (2003) 3:474-479.
Fang, H. et al., "Rapid Screening and Identification of Methicillin-Resistant *Staphylococcus aureus* from Clinical Samples by Selective-Broth and Real-Time PCR Assay," *J. Clin. Microbiol.* (2003) 41(7):2894-2899.
Farrell, D. J., "The Reliability of Microscan™ Conventional and Rapid Panels to Identify *Staphylococcus aureus* and Detect Methicillin Resistance: an Evaluation Using the Tube Coagulase Test and *mec*A PCR," *Pathology* (1997) 29:406-410.
Fong, W. K., et al., "Rapid Solid-Phase Immunoassay for Detection of Methicillin-Resistant *Staphylococcus aureus* Using Cycling Probe Technology," *J. Clin. Microbiol.* (2000) 38(7):2525-2529.
Francois, P. et al., "Rapid Detection of Methicillin-Resistant *Staphylococcus aureus* Directly from Sterile or Nonsterile Clinical Samples by a New Molecular Assay," *J. Clin. Microbiol.* (2003) 41(1):254-260.
Fujimura, S. et al., "Characterization of the *mupA* Gene in Strains of Methicillin-Resistant *Staphylococcus aureus* with a Low Level of Resistance to Mupirocin," *Antimicrob. Agents Chemother.* (2001) 45(2):641-642.
Fujimura, S. et al., "Isoleucyl-tRNA Synthetase Mutations in *Staphylococcus aureus* Clinical Isolates and in Vitro Selection of Low-Level Mupirocin-Resistant Strains," *Antimicrob. Agents Chemother.* (2003) 47(10):3373-3374.
Gill, S. R. et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain," *J. Bacteriol.* (2005) 187(7):2426-2438.
Gravet, A. et al., "Characterization of a novel structural member, LukE-LukD, of the bi-component staphylococcal leucotoxins family," *FEBS Lett.* (1998) 436(2):202-208.
Grundmann, H. et al., "Emergence and resurgence of meticillin-resistant *Staphylococcus aureus* as a public-health threat," *Lancet* (2006) 368:874-885.
Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible," *Microbial Drug Resistance* (2006) 12(3):177-185.
Hamel, S. et al., "Consensus PCR and Microarray for Diagnosis of the Genus *Staphylococcus*, Species, and Methicillin Resistance," *BioTechniques* (2001) 31(6):1364-1366.
Hanssen, A.-M. et al., "SCC*mec*in staphylococci: genes on the move," *FEMS Immuol. Med. Microbiol.* (2006) 46:8-20.
Hiramatsu, K. et al., "The emergence and evolution of methicillin-resistant *Staphylococcus aureus," Trends Microbiol.* (2001) 9(10):486-493.
Holden, M. T. G. et al., "Complete genomes of two clinical *Staphylococcus aureus* strain: Evidence for the rapid evolution of virulence and drug resistance," *PNAS* (2004) 101(26):9786-9791.
Huletsky, A. et al., New real-time PCR assay for rapid detection of methicillin-resistant *Staphylococcus aureus* directly from specimens containing a mixture of *Staphylococci*. J Clin Microbiol. (2004) 42(5):1875-84.
Hurdle, J. G. et al., "Analysis of Mupirocin Resistance and Fitness in *Staphylococcus aureus* by Molecular Genetic and Structural Modeling Techniques," *Antimicrob. Agents Chemother.* (2004) 48(11):4366-4376.
Ieven, M. et al., "Rapid Detection of Methicillin Resistance in Coagulase-Negative *Staphylococci* by Commercially Available Fluorescence Test," *J. Clin. Microbiol.* (1995) 33(8):2183-2185.
Inglis, T. J. et al., "Rapid Genotypic Confirmation of Methicillin Resistance," *Pathology* (1996) 28(3):259-261.
Ito, T. et al., "Structural Comparison of Three Types of Staphylococcal Cassette Chromosome *mec* Integrated in the Chromosome in Methicillin-Resistant *Staphylococcus aureus," Antimicrob. Agents Chemother.* (2001) 45(5):1323-1336.

Ito, T. et al., "Insights on antibiotic resistance of *Staphylococcus aureus* from its whole genome: genomic island SCC," *Drug Resist. Updat.* (2003) 6(1):41-52.
Jaulhac, B. et al., "Synthetic DNA probes for detection of genes for enterotoxins A, B, C, D, E and for TSST-1 in staphylococcal strains," *J. Appl. Bacteriol.* (1992) 72(5):386-392.
Jeong, J. et al., "Early Screening of Oxacillin-Resistant *Staphylococcus aureus* and *Staphylococcus epidermidis* from Blood Culture," *J. Korean Med. Sci.* (2002) 17:168-172.
Jonas, D. et al., "Rapid PCR-Based Identification of Methicillin-Resistant *Staphylococcus aureus* from Screening Swabs," *J. Clin. Microbiol.* (2002) 40(5):1821-1823.
Katayama, Y. et al., "Genetic Organization of the Chromosome Region Surrounding *mecA* in Clinical Staphylococcal Strains: Role of IS*431*-Mediated *mecI* Deletion in Expression of Resistance in *mecA*-Carrying, Low-Level Methicillin-Resistant *Staphylococcus haemolyticus*," *Antimicrob. Agents Chemother.* (2001) 45(7):1955-1963.
Kearns, A. M. et al., "Rapid detection of methicillin-resistant staphylococci by multiplex PCR," *J. Hosp. Infect.* (1999) 43:33-37.
Khan, S. A. et al., "Simultaneous detection of erythromycin-resistant methylase genes *ermA* and *ermC* from *Staphylococcus* spp. by multiplex-PCR," *Mol. Cell Probes* (1999) 13:381-387.
Kresken, M. et al., "Prevalence of mupirocin resistance in clinical isolates of *Staphylococcus aureus* and *Staphylococcus epidermidis*: results of the Antimicrobial Resistance Surveillance Study of the Paul-Ehrlich-Society for Chemotherapy, 2001," *Int. J. Antimicrob. Agents* (2004) 23:577-581.
Krishnan, P.U. et al., "Detection of methicillin and mupirocin resistance in *Staphylococcus aureus* isolates using conventional and molecular methods: a descriptive study from a burns unit with high prevalence of MRSA," *J. Clin. Pathol.* (2002) 55:745-748.
Labandeira-Rey, M. et al., "*Staphylococcus aureus* Panton Valentine Leukocidin Causes Necrotizing Pneumonia," *Sciencexpress* Jan. 18, 2007.
Levi, K. et al., "Evaluation of an Isothermal Signal Amplification Method for Rapid Detection of Methicillin-Resistant *Staphylococcus aureus* from Patient-Screening Swabs," *J. Clin. Microbiol.* (2003) 41(7):3187-3191.
Limoncu, M. H. et al., "Emergence of phenotypic resistance to ciprofloxacin and levofloxacin in methicillin-resistant and methicillin-sensitive *Staphylococcus aureus* strains," *Int. J. Antimicrob. Agents* (2003) 21:420-424.
Lina, G. et al., "Involvement of Panton-Valentine Leukocidin-Producing *Staphylococcus aureus* in Primary Skin Infections and Pneumonia," *Clin. Infect. Dis.* (1999) 29(5):1128-1132.
Lina, G. et al., "Bacterial Competition for Human Nasal Cavity Colonization: Role of Staphylococcal *agr* Alleles," *Appl. Environ. Microbiol.* (2003) 69(1):18-23.
Livermore, D. M., "The threat from the pink corner," *Ann. Med.* (2003) 35(4):226-234.
Louie, L. et al., "Evaluation of Three Rapid Methods for Detection of Methicillin Resistance in *Staphylococcus aureus*," *J. Clin. Microbiol.* (2000) 38(6):2170-2173.
Løvseth, A. et al., "Modified Multiplex PCR Method for Detection of Pyrogenic Exotoxin Genes in Staphylococcal Isolates," *J. Clin. Microbiol.* (2004) 42(8):3869-3872.
Ma, X. X. et al., "Novel Type of Staphylococcal Cassette Chromosome *mec* Identified in Community-Acquired Methicillin-Resistant *Staphylococcus aureus* Strains," *Antimicrob. Agents Chemother.* (2002) 46(4):1147-1152.
Manian, F. A., "Asymptomatic Nasal Carriage of Mupirocin-Resistant, Methicillin-Resistant *Staphylococcus aureus* (MRSA) in a Pet Dog Associated with MRSA Infection in Household Contacts," *Clin. Infect. Dis.* (2003) 36:e26-e28.
Martineau, F. et al., "Species-Specific and Ubiquitous-DNA-Based Assays for Rapid Identification of *Staphylococcus aureus*," *J. Clin, Microbiol.* (1998) 36(3):618-623.
Martineau, F. et al., "Development of a PCR Assay for Identification of Staphylococci at Genus and Species Levels," *J. Clin. Microbiol.* (2001) 39(7):2541-2547.
Martin-Lopez, J. V. et al., "Simultaneous PCR detection of *ica* cluster and methicillin and mupirocin resistance genes in catheter-isolated *Staphylococcus*," *Int. Microbiol.* (2004) 7:63-66.
Matsuoka, M. et al., "Characteristic expression of three genes, *msr*(A), *mph*(C) and *erm*(Y), that confer resistance to macrolide antibiotics on *Staphylococcus aureus*," *FEMS Microbiol. Lett.* (2003) 220:287-293.
Merlino, J. et al., "New Chromogenic Identification and Detection of *Staphylococcus aureus* and Methicillin-Resistant *S. aureus*," *J. Clin. Microbiol.* (2000) 38(6):2378-2380.
Merlino, J. et al., "Rapid Detection of Non-Multidrug-Resistant and Multidrug-Resistant Methicillin-Resistant *Staphylococcus aureus* Using Cycling Probe Technology for the *mecA* Gene," *Eur. J. Clin. Microbiol. Infect. Dis.* (2003) 22:322-323.
Miragaia, M. et al., "Genetic Diversity among Methicillin-Resistant *Staphylococcus epidermidis* (MRSE)," *Microbial Drug Resistance* (2005) 11(2):83-93.
Morinaga, N. et al., "Purification, Cloning and Characterization of Variant LukE-LukD with Strong Leukocidal Activity of Staphylococcal Bi-Component Leukotoxin Family," *Microbiol. Immunol.* (2003) 47(1):81-90.
Murakami, K. et al., "Identification of Methicillin-Resistant Strains of Staphylococci by Polymerase Chain Reaction," *J. Clin. Microbiol.* (1991) 29(10):2240-2244.
Nakagawa, S. et al., "Gene sequences and specific detection for Panton-Valentine leukocidin," *Biochem. Biophys. Res. Commun.* (2005) 328:995-1002.
Narita, S. et al., "Phage conversion of Panton-Valentine leukocidin in *Staphylococcus aureus*: molecular analysis of a PVL-converting phage, ϕSLT," *Gene* (2001) 268(1-2):195-206.
Nunes, E. L. et al., "Detection of *ileS*-2 Gene Encoding Mupirocin Resistance in Methicillin-Resistant *Staphylococcus aureus* by Multiplex PCR," *Diagn. Microbiol. Infect. Dis.* (1999) 34(2):77-81.
Okuma, K. et al., "Dissemination of New Methicillin-Resistant *Staphylococcus aureus* Clones in the Community," *J. Clin. Microbiol.* (2002) 40(11):4289-4294.
Oliveira, D. C. et al., "Genetic Organization of the Downstream Region of the *mecA* Element in Methicillin-Resistant *Staphylococcus aureus* Isolates Carrying Different Polymorphisms of This Region," *Antimicrob. Agents Chemother.* (2000) 44(7):1906-1910.
Oliveira, D. C. et al., "Multiplex PCR Strategy for Rapid Identification of Structural Types and Variants of the *mec* Element in Methicillin-Resistant *Staphylococcus aureus*," *Antimicrob. Agents Chemother.* (2002) 46(7):2155-2161.
Ounissi, H. et al., "Gene Homogeneity for Aminoglycoside-Modifying Enzymes in Gram-Positive Cocci," *Antimicrob. Agents Chemother.* (1990) 34(11):2164-2168.
Pawa, A. et al., "Co-transfer of plasmids in association with conjugative transfer of mupirocin or mupirocin and penicillin resistance in methicillin-resistant *Staphylococcus aureus*," *J. Med. Microbiol.* (2000) 49:1103-1107.
Perez-Roth, E. et al., "Multiplex PCR for Simultaneous Identification of *Staphylococcus aureus* and Detection of Methicillin and Mupirocin Resistance," *J. Clin. Microbiol.* (2001) 39(11):4037-4041.
Piper, J. et al., "Commercially Available Technique for Rapid Laboratory Detection of Methicillin Resistance Among *Staphylococcus aureus*," *Diagn. Microbiol. Infect. Dis.* (1988) 11(3):177-180.
Qadri, S. M. et al., "Rapid Detection of Methicillin-Resistant *Staphylococcus aureus* by Crystal MRSA ID System," *J. Clin. Microbiol.* (1994) 32(7):1830-1832.
Reischl, U. et al., "Rapid Identification of Methicillin-Resistant *Staphylococcus aureus* and Simultaneous Species Confirmation Using Real-Time Fluorescence PCR," *J. Clin. Microbiol.* (2000) 38(6):2429-2433.
Robinson, D. A. et al., "Multilocus sequence typing and the evolution of methicillin-resistant *Staphylococcus aureus*," *Clin. Microbiol. Infect.* (2004) 10:92-97.
Sabat, A. et al., "Comparison of PCR-Based Methods for Typing *Staphylococcus aureus* Isolates," *J. Clin. Microbiol.* (2006) 44(10):3804-3807.
Sakai, H. et al., "Simultaneous Detection of *Staphylococcus aureus* and Coagulase-Negative Staphylococci in Positive Blood Cultures by Real-Time PCR with Two Fluorescence Resonance Energy Transfer Probe Sets," *J. Clin. Microbiol.* (2004) 42(12):5739-5744.
Schmitz, F. J. et al., "Specific information concerning taxonomy, pathogenicity and methicillin resistance of staphylococci obtained by a multiplex PCR," *J. Med. Microbiol.* (1997) 46:773-778.
Schmitz, F. J. et al., "Development of a multiplex-PCR for direct detection of the genes for enterotoxin B and C, and toxic shock syndrome toxin-1 in *Staphylococcus aureus* isolates," *J. Med. Microbiol.* (1998) 47(4):335-340.
Schmitz, F. J. et al., "Development of Resistance to Ciprofloxacin, Rifampin, and Mupirocin in Methicillin-Susceptible and -Resistant *Staphylococcus aureus* Isolates," *Antimicrob. Agents Chemother.* (2000) 44(11):3229-3231.
Shimaoka, M. et al., "Development of Enzyme-Labeled Oligonucleotide Probe for Detection of *mecA* gene in Methicillin-Resistant *Staphylococcus aureus," J. Clin. Microbiol.* (1994) 32(8):1866-1869.
Shimaoka, M. et al., "Detection of the gene for toxic shock syndrome toxin 1 in *Staphylococcus aureus* by enzyme-labelled oligonucleotide probes," *J. Med. Microbiol.* (1996) 44:215-218.
Shrestha, N. K. et al., "Rapid Identification of *Staphylococcus aureus* and the *mecA* Gene from BacT/ALERT Blood Culture Bottles by Using the LightCycler System," *J. Clin. Microbiol.* (2002) 40(7):2659-2661.
Skov, R. L. et al., "Evaluation of a new 3-h hybridization method for detecting the *mecA* gene in *Staphylococcus aureus* and comparison with existing genotypic and phenotypic susceptibility testing methods," *J. Antimicrob. Chemother.* (1999) 43:467-475.
Strommenger, B. et al., "Multiplex PCR Assay for Simultaneous Detection of Nine Clinically Relevant Antibiotic Resistance Genes in *Staphylococcus aureus," J. Clin. Microbiol.* (2003) 41(9):4089-4094.
Stuhlmeier, R. et al., "Fast, simultaneous, and sensitive detection of staphylococci," *J. Clin. Pathol.* (2003) 56:782-785.
Sundsfjord, A. et al., "Genetic methods for detection of antimicrobial resistance," *APMIS* (2004) 112:815-837.
Swenson, J. M. et al., "Performance of Eight Methods, Including Two New Rapid Methods, for Detection of Oxacillin Resistance in a Challenge Set of *Staphylococcus aureus* Organisms," *J. Clin. Microbiol.* (2001) 39(10):3785-3788.
Tan, T. Y., "Use of molecular techniques for the detection of antibiotic resistance in bacteria," *Expert. Rev. Mol. Diagn.* (2003) 3(1):93-103.
Tanabe, F. et al., "The Properties and mec A Gene of the Methicillin-Resistant *Staphylococcus aureus* Isolated in Fukushima Medical College Hospital," *Fukushima J. Med. Sci.* (1993) 39(1):35-42.
Tenover, F. C. et al., "Characterization of a Strain of Community-Associated Methicillin-Resistant *Staphylococcus aureus* Widely Disseminated in the United States," *J. Clin.Microbiol.* (2006) 44(1):108-118.
Tokue, Y. et al., "Comparison of a Polymerase Chain Reaction Assay and a Conventional Microbiologic Method for Detection of Methicillin-Resistant *Staphylococcus aureus," Antimicrob. Agents Chemother.* (1992) 36(1):6-9.
Towner, K. J. et al., "Development and evaluation of a PCR-based immunoassay for the rapid detection of methicillin-resistant *Staphylococcus aureus," J. Med. Microbiol.* (1998) 47:607-613.
Udo, E. E. et al., "Rapid detection of methicillin resistance in staphylococci using a slide latex agglutination kit," *Int. J. Antimicrob. Agents.* (2000) 15(1):19-24.
Udo, E. E. et al., "Genetic analysis of methicillin-resistant *Staphylococcus aureus* expressing high-and low-level mupirocin resistance," *J. Med. Microbiol.* (2001) 50:909-515.
Udo, E. E. et al., "A chromosomal location of the *mupA* gene in *Staphylococcus aureus* expressing high-level mupirocin resistance," *J. Antimicrob. Chemother.* (2003) 51:1283-1286.
Ünal, S. et al., "Detection of Methicillin-Resistant Staphylococci by Using the Polymerase Chain Reaction," *J. Clin. Microbiol.* (1992) 30(7):1685-1691.
Upton, A. et al., "Mupirocin and *Staphylococcus aureus*: a recent paradigm of emerging antibiotic resistance," *J. Antimicrob. Chemother.* (2003) 51:613-617.
Van Leeuwen, W. B. et al., "Rapid Detection of Methicillin-Resistance in *Staphylococcus aureus* Isolates by the MRSA-Screen Latex Agglutination Test," *J. Clin. Microbiol.* (1999) 37(9):3029-3030.
Van Leeuwen, W. B. et al., "Multilocus Sequence Typing of *Staphylococcus aureus* with DNA Array Technology," *J. Clin. Microbiol.* (2003) 41(7):3323-3326.
Vannuffel, P. et al., "Specific Detection of Methicillin-Resistant *Staphylococcus* Species by Multiplex PCR," *J. Clin. Microbiol.* (1995) 33(11):2864-2867.
Vannuffel, P. et al., "Rapid and Specific Molecular Identification of Methicillin-Resistant *Staphylococcus aureus* in Endotracheal Aspirates from Mechanically Ventilated Patients," *J. Clin. Microbiol.* (1998) 36(8):2366-2368.
Von Eiff, C. et al., "Pathogenesis of infections due to coagulase-negative staphylococci," *Lancet Infect. Dis.* (2002) 2:677-685.
Walker, E. S. et al., "A Decline in Mupirocin Resistance in Methicillin-Resistant *Staphylococcus aureus* Accompanied Administrative Control of Prescriptions," *J. Clin. Microbiol.* (2004) 42(6):2792-2795.
Wallet, F. et al., "Choice of a routine method for detecting methicillin-resistance in staphylococci," *J. Antimicrob. Chemother.* (1996) 37:901-909.
Wertheim, H. F. et al., "Effect of Mupirocin Treatment on Nasal, Pharyngeal, and Perineal Carriage of *Staphylococcus aureus* in Healthy Adults," *Antimicrob. Agents Chemother.* (2005) 49(4):1465-1467.
Wichelhaus, T. A. et al., "Rapid Detection of Epidemic Strains of Methicillin-Resistant *Staphylococcus aureus," J. Clin. Microbiol.* (1999) 37(3):690-693.
Zhang, Y.-Q. et al., "Genome-based analysis of virulence genes in a non-biofilm-forming *Staphylococcus epidermidis* strain (ATCC 12228)," *Mol. Microbiol.* (2003) 49(6):1577-1593.
Zhang, K. et al., "New Quadriplex PCR Assay for Detection of Methicillin and Mupirocin Resistance and Simultaneous Discrimination of *Staphylococcus aureus* from Coagulase-Negative Staphylococci," *J. Clin. Microbiol.* (2004) 42(11):4947-4955.
Chen C.H., et al., Laser Desorption Mass Spectrometry for FastDNA Sequencing [online], Nov. 1994, Retrieved from the Internet:<URL:http://www.ornl.gove/sci/techresources/Human_Genome/publicat/94SANTA/sequencing/seqtoc.shtml>.
Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.
Ecker Supporting Information [online], May 23, 2005 [retrieved on Jul. 31, 2011]. Retrieved from the Internet< URL: http://www.pnas.org/content/102/22/8012/suppl/DC1>.
EMBL "Arabidopsis Thaliana T-DNA Flanking Sequence, Left Border, Clone 346C06," Accession No. AJ552897, Mar. 29, 2003.
EMBL "Human, muscle, Mitochondrial Mutant, 22 nt, segment 2 of 2," Accession No. S90302, Sep. 1, 2004.
EMBL "Sequence 10 from Patent US 6563025," Accession No. AR321656, Aug. 18, 2003.
Ex Parte Re-Examination Certificate for U.S. Application No. 90/010,209 mailed Jul. 7, 2009.
Ex Parte Re-Examination Certificate for U.S. Application No. 90/010,210, mailed Dec. 28, 2010.
Ex Parte Re-Examination Certificate for U.S. Application No. 90/010,447 mailed Feb. 15, 2011.
Final Office Action mailed Oct. 14, 2009 for U.S. Appl. No. 10/943,344, filed Sep. 17, 2004.
GENBANK "*Staphylococcus Aureus* LukS-PV, LukF-PV Genes for Panton-Valentine Leukocidin S, Panton-Valentine Leukocidin F, Complete cds," Accession No. AB186917, Feb. 8, 2005.
GENBANK "*Staphylococcus Aureus* Strain MSSA476, Complete Genome," Accession No. BX571857.1, Jun. 24, 2004.
GENBANK "*Streptococcus Agalactiae* 2603V/R, Complete Genome," Accession No. AE009948.1, Aug. 28, 2002.
GENBANK, "*Clostridium Tetani* E88, Complete Genome," Accession No. AE015927.1, Feb. 4, 2003.
GENBANK, "*Enterococcus Malodoratus* Strain ATCC43197 Elongation Factor Tu (tufA) Gene, Partial Cds," Accession No. AF274728, Dec. 11, 2000.

GENBANK, "*Staphylococcus Aureus* Genes for LukS-PV, LukF-PV and Integrase, Complete Cds," Accession No. AB006796, Dec. 17, 1997.
GENBANK, "*Staphylococcus Epidermidis* ATCC 12228, Complete Genome," Accession No. AE015929.1, Jan. 2, 2003.
GENBANK, "*Streptococcus Anginosus* Elongation Factor Tu (tuf) Gene, Partial cds," Accession No. AF276257.1, Jul. 1, 2001.
GENBANK, "*Streptococcus Pyogenes* Strain MGAS8232, Complete Genome," Accession No. AE009949.1, Apr. 3, 2002.
International Search Report and the Written Opinion for Application No. PCT/US2009/059169, mailed on May 11, 2010, 22 pages.
International Search Report and Written Opinion for Application No. PCT/US2006/015160, mailed on Oct. 10, 2006, 13 pages.
International Search Report for Application No. PCT/US2009/045635, mailed on Oct. 7, 2009, 9 pages.
Limbach P.A., et al., "Enzymatic Sequencing of *Oligonucleotides* with Electrospray Mass Spectrometry," 42nd ASMS Conference on Mass Spectrometry, 1994.
Lubman D.M., Application for Continuation Grant by David Mitchell Lubman dated Jun. 4, 1996 and Jun. 14, 1996.
Lubman D.M., Application for Continuation Grant by David Mitchell Lubman dated Jun. 10, 1994 and Jun. 24, 1994.
Lubman D.M., Application for Grant by David Mitchell Lubman dated Sep. 1, 1994 and Sep. 27, 1994.
Lubman D.M., Application for Grant by David Mitchell Lubman dated Oct. 25, 1992 and Oct. 29, 1992.
Non-Final Office Action mailed Oct. 7, 2011 for U.S. Appl. No. 11/683,302, filed Mar. 7, 2007.
Non-Final Office Action mailed Oct. 31, 2011 for U.S. Appl. No. 11/683,286, filed Mar. 7, 2007.
Office Action mailed May 4, 2010 for U.S. Application No. 90/010,447 filed Apr. 9, 2009.
Office Action mailed May 4, 2010 for U.S. Application No. 90/010,448 filed Apr. 9, 2009.
Office Action mailed Feb. 7, 2008 for European Application No. 06751025.5 filed Apr. 21, 2006.
Office Action mailed Dec. 9, 2009 for U.S. Application No. 90/010,210 filed Jun. 27, 2008.
Office Action mailed Dec. 9, 2009 for U.S. Application No. 90/010,447 filed Apr. 9, 2009.
Office Action mailed Dec. 9, 2009 for U.S. Application No. 90/010,448 filed Apr. 9, 2009.
Office Action mailed Jun. 10, 2009 for U.S. Application No. 90/010,210 filed Jun. 27, 2008.
Office Action mailed Jun. 10, 2010 for U.S. Application No. 90/010,447 filed Apr. 9, 2009.
Office Action mailed Jun. 10, 2010 for U.S. Application No. 90/010,448 filed Apr. 9, 2009.
Office Action mailed Aug. 11, 2010 for U.S. Application No. 90/010,447 filed Apr. 9, 2009.
Office Action mailed Aug. 11, 2010 for U.S. Application No. 90/010,448 filed Apr. 9, 2009.
Office Action mailed Jun. 11, 2010 for U.S. Application No. 90/010,210 filed Jun. 27, 2008.
Office Action mailed Apr.12, 2010 for Australian Application No. 2006239993 filed Apr. 21, 2006.
Office Action mailed Apr. 16, 2009 for U.S. Application No. 90/010,210 filed Jun. 27, 2008.
Office Action mailed Aug. 17, 2011 for European Application No. 06751025.5 filed Apr. 21, 2006.
Office Action mailed Sep. 20, 2010 for U.S. Application No. 90/010447 filed Apr. 9, 2009.
Office Action mailed Sep. 20, 2010 for U.S. Application No. 90/010,448 filed Apr. 9, 2009.
Office Action mailed Apr. 21, 2009 for U.S. Application No. 90/010,209 filed Jun. 27, 2008.
Office Action mailed Jul. 22, 2008 for U.S. Application No. 90/010,209 filed Jun. 27, 2008.
Office Action mailed Jul. 22, 2008 for U.S. Application No. 90/010,210 filed Jun. 27, 2008.
Office Action mailed Apr. 23, 2010 for U.S. Application No. 90/010,210 filed Jun. 27, 2008.
Office Action mailed Apr. 24, 2009 for U.S. Application No. 90/010,447 filed Apr. 9, 2009.
Office Action mailed Apr. 24, 2009 for U.S. Application No. 90/010,448 filed Apr. 9, 2009.
Office Action mailed Aug. 24, 2010 for U.S. Application No. 90/010,210 filed Jun. 27, 2008.
Office Action mailed Nov. 24, 2009 for Canadian Application No. 2607468 filed Apr. 21, 2006.
Office Action mailed Nov. 24, 2009 for U.S. Application No. 90/010,210 filed Jun. 27, 2008.
Office Action mailed Sep. 24, 2009 for U.S. Application No. 90/010,210 filed Jun. 27, 2008.
Office Action mailed Jun. 25, 2009 for U.S. Application No. 90/010,210 filed Jun. 27, 2008.
Office Action mailed Dec. 28, 2009 for European Application No. 06751025.5 filed Apr. 21, 2006.
Office Action mailed Jul. 28, 2010 for U.S. Application No. 90/010,210 filed Jun. 27, 2008.
Office Action mailed Oct. 29, 2009 for U.S. Application No. 90/010,447 filed Apr. 9, 2009.
Office Action mailed Oct. 29, 2009 for U.S. Application No. 90/010,448 filed Apr. 9, 2009.
Office Action mailed Jun. 30, 2010 for U.S. Application No. 90/010,210 filed Jun. 27, 2008.
Office Action mailed Jun. 30, 2010 for U.S. Application No. 90/010,447 filed Apr. 9, 2009.
Office Action mailed Jun. 30, 2010 for U.S. Application No. 90/010,448 filed Apr. 9, 2009.
Partial International Search Report for Application No. PCT/US2009/059169, mailed on Jan. 12, 2010, 7 pages.
Supplementary European Search Report for Application No. EP05753037, mailed on Aug. 21, 2009, 2 pages.
Tang K., et al., Double-Stranded DNA Analysis by Matrix Assisted Laser Desorption/Ionization, 42nd ASMS Conference on Mass Spectrometry, 1994.
Tang K., et al., Matrix-Assisted Laser Desorption/Ionization Mass Spectrometry of Oligonucleotides, Dissertation submitted to the Faculty of Vanderbilt University, 1994.
Aaserud D.J., et al., "Accurate Base Composition of Double-Strand DNA by Mass Spectrometry," American Society for Mass Spectrometry, 1996, vol. 7 (12), pp. 1266-1269.
Abdi F.A., et al., "Validation of DNA Sequences Using Mass Spectrometry Coupled with Nucleoside Mass Tagging," Genome Research, 2002, vol. 12 (7), pp. 1135-1141.
Alves-Silva J., et al., "The Ancestry of Brazilian mtDNA Linages," The American Journal of Human Genetics, 2000, vol. 67 (2), pp. 444-461.
Anderson S., et al., "Sequence and Organization of the Human Mitochondrial Genome," Nature, 1981, vol. 290 (5806), pp. 457-465.
Andreasson H., et al., "Mitochondrial Sequence Analysis for Forensic Identification Using Pyrosequencing Technology," BioTechniques, 2002, vol. 32 (1), pp. 124-133.
Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.
Baker G.C., et al., "Review and Re-Analysis of Domain-Specific 16S Primers," Journal of Microbiological Methods, 2003, vol. 55 (3), pp. 541-555.
Barbour A.G., et al., "Identification of an Uncultivatable *Borrelia* Species in the Hard Tick Amblyomma Americanum: Possible Agent of a Lyme Disease-Like Illness," The Journal of Infectious Diseases, 1996, vol. 173 (2), pp. 403-409.
Barns S.M., et al., "Detection of Diverse New *Francisella*-like Bacteria in Environmental Samples," Applied and Environmental Microbiology, 2005, vol. 71 (9), pp. 5494-5500.
Barr I.G., et al., "An Influenza A(H3) Reassortant was Epidemic in Australia and New Zealand in 2003," Journal of Medical Virology, 2005, vol. 76 (3), pp. 391-397.
Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.
Benson L.M., et al, "Advantages of *Thermococcus Kodakaraenis* (KOD) DNA Polymerase for PCR-Mass Spectrometry Based Analyses," American Society for Mass Spectrometry, 2003, vol. 14 (6), pp. 601-604.
Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Boivin-Jahns V., et al., "Bacterial Diversity in a Deep-Subsurface Clay Environment," Applied and Environmental Microbiology, 1996, vol. 62 (9), pp. 3405-3412.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Buck G.A., et al., "Design Strategies and Performance of Custom DNA Sequencing Primers," BioTechniques, 1999, vol. 27 (3), pp. 528-536.
Carracedo A., et al., "DNA Commission of the International Society for Forensic Genetics: Guidelines Formitochondrial DNA Typing," Forensic Science International, 2000, vol. 110 (2), pp. 79-85.
Case J.T., et al., "Maternal Inheritance of Mitochondrial DNA Polymorphisms in Cultured Human Fibroblasts," Somatic Cell Genetics, 1981, vol. 7 (1), pp. 103-108.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chen N., et al., "The Genomic Sequence of *Ectromelia* Virus, the Causative Agent of Mousepox," Virology, 2003, vol. 317 (1), pp. 165-186.
Crespillo M., et al., "Mitochondrial DNA Sequences for 118 Individuals from Northeastern Spain," International Journal of Legal Medicine, 2000, vol. 114 (1-2), pp. 130-132.
De La Puente-Redondo V.A., et al., "Comparison of Different PCR Approaches for Typing of *Francisella Tularensis* Strains," Journal of Clinical Microbiology, 2000, vol. 38 (3), pp. 1016-1022.
Del Blanco Garcia N., et al., "Genotyping of *Francisella Tularensis* Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Elnifro E.M., et al., "PCR and Restriction Endonuclease Analysis for Rapid Identification of *Adenovirus Subgenera*," Journal of Clinical Microbiology, 2000, vol. 38 (6), pp. 2055-2061.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Farlow J., et al., "*Francisella Tularensis* Strain Typing Using Multiple-Locus, Variable-Number Tandem Repeat Analysis," Journal of Critical Microbiology, 2001, vol. 39 (9), pp. 3186-3192.
Fraser C.M., et al., "The Mimimal Gene Complement of *Mycoplasma Genitalium*," Science, 1995, vol. 270 (5235), pp. 397-403.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Gendel S.M., "Computational Analysis of the Specificity of 16S rRNA-Derived Signature Sequencesfor Identifying Food-Related Microbes," Food Microbiology, 1996, vol. 13, pp. 1-15.
Giles R.E., et al., "Maternal Inheritance of Human Mitochondrial DNA," Proceedings of the National Academy of Sciences, 1980, vol. 77 (11), pp. 6715-6719.
Ginther C., et al., "Identifying Individuals by Sequencing Mitochondrial DNA from Teeth," Nature Genetics, 1992, vol. 2 (2), pp. 135-138.
Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.
Greenberg B.D., et al., "Intraspecific Nucleotide Sequence Variability Surrounding the Origin of Replicationin Human Mitochondrial DNA," Gene, 1983, vol. 21, pp. 33-49.
Griffin T.J., et al., "Single-Nucleotide Polymorphism Analysis by Maldi-TOF Mass Spectrometry," Trends in Biotechnology, 2000, vol. 18 (2), pp. 77-84.
Grzybowski T., et al., "Extremely High Levels of Human Mitochondrial DNA Heteroplasmy in Single Hair Roots," Electrophoresis, 2000, vol. 21 (3), pp. 548-553.
Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.
Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.
Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.
Hannis J.C., et al., "Genotyping Complex Short Tandem Repeats Using Electrospray lonzation Fourier Transform Ion Cyclotron Resonance Multi-Stage Mass Spectrometry," Proceedings of SPIE, 2000, vol. 3926, pp. 36-47.
Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Haugland R.A., et al., "Identification of Putative Sequence Specific PCR Primers for Detection of the Toxygenic Fungal Species *Stachybotrys Chartarum*," Molecular and Cellular Probes, 1998, vol. 12 (6), pp. 387-396.
Hofstadler S.A., et al., "TIGER: The Universal Biosensor," International Journal of Mass Spectrometry, 2005, vol. 242, pp. 23-41.
Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.
Holm L., et al., "Removing Near-Neighbour Redundancy from Large Protein Sequence Collections," Bioinformatics, 1998, vol. 14 (5), pp. 423-429.

Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Ingman M., et al., "Mitochondrial Genome Variation and the Origin of Modern Humans," Nature, 2000, vol. 408 (6813), pp. 708-713.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "*Borelia Lonestari* Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33- 37.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson a., et al., "Evaluation of PCR-based Methods for Discrimination of Francisella species and Subspecies and Development of a Specific PCR that Distinguishes the Two Major Subspecies of *Francisella Tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus Aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of *B. Subtilis* and *B. Atrophaeus*, Closely Related Species of *Bacilli*," Journal of Microbiological Methods, 2000, vol. 40 (3), pp. 241-254.
Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
KE D., et al., "Development of a PCR Assay for Rapid Detection of *Enterococci*," Journal of Clinical Microbiology, 1999, vol. 37 (11), pp. 3497-3503.
Keller A., et al., "Empirical Statistical Model to Estimate the Accuracy of Peptide Identifications Made by MS/MS and Database Search," Analytical Chemistry, 2002, vol. 74 (20), pp. 5383-5392.
Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.
Kowalak J.A., et al., "A Novel Method for the Determination of Post-Transcriptional Modification in RNA by Mass Spectrometry," Nucleic Acids Research, 1993, vol. 21 (19), pp. 4577-4585.
Kupke T., et al., "Molecular Characterization of Lantibiotic-Synthesizing Enzyme EpiD Reveals a Function for Bacterial Dfp Proteins in Coenzyme a Biosynthesis," Journal of Biological Chemistry, 2000, vol. 275 (41), pp. 31838-31846.
Lacroix J.M., et al, "PCR-Based Technique for the Detection of Bacteria in Semen and Urine," Journal of Microbiological Methods, 1996, vol. 26, pp. 61-71.
Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.
Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.
Leif H., et al., "Isolation and Characterization of the Proton-Translocating NADH: Ubiqu None Oxidoreductase from *Escherichia Coli*," European Journal of Biochemistry, 1995, vol. 230 (2), pp. 538-548.
Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.
Li J., et al., "Single Nucleotide Polymorphism Determination Using Primer Extension and Time-of-Flight Mass Spectrometry," Electrophoresis, 1999, vol. 20 (6), pp. 1258-1265.
Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.
Liu C., et al., "Improving the Microdialysis Procedure for Electrospray Ionization Mass Spectrometry of Biological Samples," Journal of Mass Spectrometry, 1997, vol. 32 (4), pp. 425-431.
Matray T.J., et al., "Synthesis and Properties of RNA Analogs-Oligoribonucleotide N3—>p5 Phosphoramidates," Nucleic Acids Research, 1999, vol. 27 (20), pp. 3976-3985.
McLafferty F.W., et al., "Comparison of Algorithms and Databases for Matching Unknown Mass Spectra," Journal of the American Society for Mass Spectrometry, 1998, vol. 9 (1), pp. 92-95.
McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.
Miller K.W., et al., "A Compendium of Human Mitochondria! DNA Control Region: Development of an International Standard Forensic Database," Croatian Medical Journal, 2001, vol. 42 (3), pp. 315-327.
Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.
Muddiman D.C., et al., "Characterization of PCR Products from *Bacilli* Using Electrospray Ionization FTICR Mass Spectrometry," Analytical Chemistry, 1996, vol. 68 (21), pp. 3705-3712.
Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.
Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.
Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.
Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.
Nakao H., et al., "Development of a Direct PCR Assay for Detection of the Diphtheria Toxin Gene," Journal of Clinical Microbiology, 1997, vol. 35 (7), pp. 1651-1655.
Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.
Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.
Nilsson M., et al., "Evaluation of Mitochondrial DNA Coding Region Assays for Increased Discrimination in Forensic Analysis," Forensic Science International: Genetics, 2008, vol. 2 (1), pp. 1-8.
Nishikawa T., et al., "Reconstitution of Active Recombinant Ship Toxin (STC)1 from Recombinant Stxl -A and Sbtl -B Subunits Independently Produced by *E. Coli* Clones," FEMS Microbiol Letters, 1999, vol. 178 (1), pp. 13-18.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/lonization Mass Spectrometry of Nucleic Acids with Wavelengths in the Ultraviolet and Infrared," Rapid Communications in Mass Spectrometry, 1992, vol. 6 (12), pp. 771-776.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Olsen B., et al., "Transhemispheric Exchange of Lyme Disease Spyrochetes by Seabirds," Journal of Clinical Microbiology, 1995, vol. 33 (12), pp. 3270-3274.
Parson W., et al., "Population Data for 101 Austrian Caucasian Mitochondrial DNA dLoop Sequences: Application of mtDNA Sequence Analysis to a Forensic Case," International Journal of Legal Medicine, 1998, vol. 111 (3), pp. 124-132.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pieles U., et al., "Matrix-Assisted Laser Desorption Ionization Time-of-Flight Spectrometry: APowerful Tool for the Mass and Sequence Analysis of Natural and Modified Oligonucleotides," Nucleic Acids Research, 1993, vol. 21 (14), pp. 3191-3196.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Schena M., et al., "Genome Analysis with Gene Expression Microarrays," Bioessays, 1996, vol. 18 (5), pp. 427-431.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.
Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., "Matrix-Assisted Laser Desorption/lonization of Restriction Enzyme-Digested DNA," Rapid Communications in Mass Spectrometry, 1994, vol. 8 (2), pp. 183-186.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Torroni A., et al., "Classification of European mtDNAs from an Analysis of Three European Populations," Genetics, 1996, vol. 144 (4), pp. 1835-1850.

Tristan A., et al., "Virulence Determinants in Community and Hospital Meticillin-Resistant *Staphylococcus Aureus*," The Journal of Hospital Infection, 2007, vol. 65 (2), pp. 105-109.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Van Baar B.L., "Characterisation of Bacteria by Matrix-Assisted Laser Desorption/lonisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Ert M.N., et al., "Mass Spectrometry Provides Accurate Characterization of Two Genetic Marker Types in *Bacillus Anthracis*," Bio Techniques, 2004, vol. 37 (4), pp. 642-651.
Vanderhallen H., et al., "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.
Wolk D.M., et al., "Pathogen Profiling: Rapid Molecular Characterization of *Staphylococcus Aureus* by PCR/electrospray Ionization-Mass Spectrometry and Correlation with Phenotype," Journal of Clinical Microbiology, 2009, vol. 47 (10), pp. 3129-3137.
Xu L., et al., "Electrophore Mass Tag Dideoxy DNA Sequencing," Analytical Chemistry, 1997, vol. 69 (17), pp. 3595-3602.
Yao Z.P., et al., "Mass Spectrometry Based Proteolytic Mapping for Rapid Virus Identification," Analytical Chemistry, 2002, vol. 74 (11), pp. 2529-2534.
Zeng Z.B., "Precision Mapping of Quantitative Trait Loci," Genetics, 1994, vol. 136 (4), pp. 1457-1468.
Co-pending U.S. Appl. No. 11/683,241, filed on Nov. 9, 2003.
Co-pending U.S. Appl. No. 11/683,286, filed on Mar. 7, 2007.
Co-pending U.S. Appl. No. 11/683,311, filed on Mar. 7, 2007.
Co-pending U.S. Appl. No. 11/683,351, filed on Mar. 7, 2007.
Co-pending U.S. Appl. No. 11/683,370, filed on Mar. 7, 2007.
Co-pending US patent application No. 90/010,209, filed on Jun. 27, 2008.
Co-pending US patent application No. 90/010,210, filed on Jun. 27, 2008.
Final Office Action mailed Apr. 9, 2012 for U.S. Appl. No. 11/683,302, filed Mar. 7, 2007.
Final Office Action mailed Apr. 25, 2012 for U.S. Appl. No. 11/683,241, filed Mar. 7, 2007.
Office Action mailed Apr. 3, 2012 for Japanese Application No. 2008507932 filed Apr. 21, 2006.
Crisostomo M.I., et al., "The Evolution of Methicillin Resistance in *Staphylococcus Aureus*: Similarity of Genetic Backgrounds in Historically Early Methicillin-Susceptible and -Resistant Isolates and Contemporary Epidemic Clones," Proceedings of the National Academy of Sciences, 2001, vol. 98 (17), pp. 9865-9870.
Fahle G.A., et al., "Comparison of Six Commercial DNA Extraction Kits for Recovery of Cytomegalovirus DNA from Spiked Human Specimens," Journal of Clinical Microbiology, 2000, vol. 38 (10), pp. 3860-3863.
Final Office Action mailed Jun. 4, 2012 for U.S. Appl. No. 11/683,286, filed Mar. 7, 2007.
Final Office Action mailed Jul. 5, 2012 for U.S. Appl. No. 11/683,370, filed Mar. 7, 2007.
Final Office Action mailed Oct. 21, 2011 for U.S. Appl. No. 11/582,873, filed Oct. 17, 2006.
GENBANK, DNA, Complete Genome, Accession No. BA000018.3 (GI 47118324) [online], Oct. 22, 2004 [retrieved on Oct. 19, 2011]. Retrieved from the Internet< URL: http://www.ncbi.nlm.nih.gov/nuccore/47118324''sat=34&satkey=4057422>.
Heusser R., et al., "Mosaic *Staphylococcal* Cassette Chromosome Mec Containing Two Recombinase Loci and a New Mec Complex, B2," Antimicrobial Agents and Chemotherapy, 2007, vol. 51 (1), pp. 390-393.
International Search Report and Written Opinion for Application No. PCT/US2008/057717, mailed on Jan. 13, 2009, 18 pages.
Kuroda M., et al., "Whole Genome Sequencing of Meticillin-Resistant *Staphylococcus Aureus*," The Lancet, 2001, vol. 357 (9264), pp. 1225-1240.
Levison P.R., et al., "Recent Developments of Magnetic Beads for Use in Nucleic Acid Purification," Journal of Chromatography A, 1998, vol. 816 (1), pp. 107-111.
Martineau F., et al., "Correlation Between the Resistance Genotype Determined by Multiplex PCR Assays and the Antibiotic Susceptibility Patterns of *Staphylococcus Aureus*and *Staphylococcus*," Antimicrobial Agents and Chemotherapy, 2000, vol. 44 (2), pp. 231-238.
Mehrotra M., et al., "Multiplex PCR for Detection of Genes for *Staphylococcus Aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.
Non-Final Office Action mailed Oct. 21, 2011 for U.S. Appl. No. 11/683,370, filed Mar. 7, 2007.
Non-Final Office Action mailed Apr. 27, 2012 for U.S. Appl. No. 11/683,360, filed Mar. 7, 2007.
Non-Final Office Action mailed Oct. 31, 2011 for U.S. Appl. No. 11/683,311, filed Mar. 7, 2007.
Notice of Allowance mailed May 10, 2012 for U.S. Appl. No. 11/683,311, filed Mar. 7, 2007.
Notice of Allowance mailed May 18, 2012 for U.S. Appl. No. 11/683,311, filed Mar. 7, 2007.
Office Action Appendix mailed Jun. 4, 2012 for U.S. Appl. No. 11/683,286, filed Mar. 7, 2007.
Office Action mailed Aug. 13, 2010 for European Application No. 08780484.5 filed Mar. 20, 2008.
Office Action mailed Aug. 19, 2009 for European Application No. 08780484.5 filed Mar. 20, 2008.
Shore A., et al., "Seven Novel Variants of the *Staphylococcal Chromosomal* Cassette Mec in Methicillin-Resistant *Staphylococcus Aureus* Isolates from Ireland," Antimicrobial Agents and Chemotherapy, 2005, vol. 49 (5), pp. 2070-2083.
Stratagene Catalog, Gene Characterization Kits, 1988, pp. 39.
Volokhov D., et al., "Microarray Analysis of *Erythromycin* Resistance Determinants," Journal of Applied Microbiology, 2003, vol. 95 (4), pp. 787-798.

* cited by examiner

Base Composition Signatures from primer pair 14 (16S rRNA)

Primer 356: rplB

SEQUENCE LISTING

<160> NUMBER OF SEQ ID NOS: 1464

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
aaactagata acagtagaca tcac 24

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
aaccttaatt ggaaagaaac ccaagaagt 29

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
aacgcacaat cagaagc 17

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
aactaccgtc cgcagttcta cttcc 25

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
aactaccgtc ctcagttcta cttcc 25

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
aagacgacct gcacgggc 18

<210> SEQ ID NO 7
<211> LENGTH: 18
<212> TYPE: DNA

<213> ORGANISM: Artificial Sequence
<220> FEATURE:
<223> OTHER INFORMATION: Primer

<400> SEQUENCE: 7
aagcggtgga gcatgtgg 18

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
aaggaaggcg tgatcaccgt tgaaga 26

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
aaggtactcc ggggataaca ggc 23

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
aagtcggaat cgctagtaat cg 22

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
aatctgctat ttggtcagg 19

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
acaacgaagt acaatacaag ac 22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
acaatacaag acaaaagaag g 21

-continued

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
accacgccgt aaacgatga 19

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
accatgacag aaggcatttt gaca 24

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
acccagtgct gctgaaccgt gc 22

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
accgagcaag gagaccagc 19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
acctgcccag tgctggaag 19

<210> SEQ ID NO 19
<211> LENGTH: 17
<212> TYPE: DNA
<213> ORGANISM: Artificial Sequence
<220> FEATURE:
<223> OTHER INFORMATION: Primer

<400> SEQUENCE: 19
acgcgaagaa ccttacc 17

<210> SEQ ID NO 20
<211> LENGTH: 20
<212> TYPE: DNA
<213> ORGANISM: Artificial Sequence
<220> FEATURE:
<223> OTHER INFORMATION: Primer -continued

<400> SEQUENCE: 20
actcgttttt aatcagcccg 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agaacaccga tggcgaaggc 20

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
agaatcaagt tcccaggggt tac 23

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
agagtttgat catggctcag 20

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
agcaggtggt gaaatcggcc acatgatt 28

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
agcgtaaagg tgaacctt 18

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
agcttttgca tattatatcg agccac 26

<210> SEQ ID NO 27
<211> LENGTH: 28
<212> TYPE: DNA

<213> ORGANISM: Artificial Sequence
<220> FEATURE:
<223> OTHER INFORMATION: Primer

<400> SEQUENCE: 27
aggacagagt gagtactttg accgaggt 28

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
agtctcaaga gtgaacacgt aa 22

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
agttataaac acggctttcc tatggcttat cc 32

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
atactcctga ctgaccgata g 21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
atatcgacgg cggtgtttgg 20

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
atcaatttgg tggccaagaa cctgg 25

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
atgattacaa ttcaagaagg tcgtcacgc 29

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
atggacaagg ttggcaagga agg 23

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
atggccatgg cagaagctca 20

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
atgtcgattg caatccgtac ttgtg 25

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
atgttgggtt aagtcccgc 19

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
atgttgggtt aagtcccgca acgag 25

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
caaaacttat taggtaagcg tgttgact 28

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
caaaggtaag caaggacgtt tccgtca 27

<210> SEQ ID NO 41
<211> LENGTH: 27
<212> TYPE: DNA
<213> ORGANISM: Artificial Sequence
<220> FEATURE:
<223> OTHER INFORMATION: Primer

<400> SEQUENCE: 41
caaaggtaag caaggtcgtt tccgtca 27

<210> SEQ ID NO 42
<211> LENGTH: 17
<212> TYPE: DNA
<213> ORGANISM: Artificial Sequence
<220> FEATURE:
<223> OTHER INFORMATION: Primer

<400> SEQUENCE: 42
caacgagcgc aaccctt 17

<210> SEQ ID NO 43
<211> LENGTH: 17
<212> TYPE: DNA
<213> ORGANISM: Artificial Sequence
<220> FEATURE:
<223> OTHER INFORMATION: Primer

<400> SEQUENCE: 43
caacggatgc tggcaag 17

<210> SEQ ID NO 44
<211> LENGTH: 31
<212> TYPE: DNA
<213> ORGANISM: Artificial Sequence
<220> FEATURE:
<223> OTHER INFORMATION: Primer

<400> SEQUENCE: 44
caagaagaaa aagagcttct aaaaagaata c 31

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
caagcaaacg cacaatcaga agc 23

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
caagtcatca tggccctta 19

<210> SEQ ID NO 47
<211> LENGTH: 26
<212> TYPE: DNA

<213> ORGANISM: Artificial Sequence
<220> FEATURE:
<223> OTHER INFORMATION: Primer

<400> SEQUENCE: 47
caataccgca acagcggtgg cttggg 26

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
cactggaact gagacacgg 19

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
cagaatcaag ttcccagggg 20

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
cagagaccgt tttatcctat cagc 24

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
cagcgtttcg gcgaaatgga 20

<210> SEQ ID NO 52
<211> LENGTH: 29
<212> TYPE: DNA
<213> ORGANISM: Artificial Sequence
<220> FEATURE:
<223> OTHER INFORMATION: Primer

<400> SEQUENCE: 52
caggagtcgt tcaactcgat ctacatgat 29

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
caggtttagt accagaacat gcag 24

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
catccacacg gtggtggtga agg 23

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
ccacacgccg ttcttcaaca act 23

<210> SEQ ID NO 56
<211> LENGTH: 28
<212> TYPE: DNA
<213> ORGANISM: Artificial Sequence
<220> FEATURE:
<223> OTHER INFORMATION: Primer

<400> SEQUENCE: 56
ccacagttct acttccgtac tactgacg 28

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
ccagcagccg cggtaatac 19

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
ccgtaacttc gggagaagg 19

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
ccgtggtatt ggagttattg 20

<210> SEQ ID NO 60
<211> LENGTH: 29
<212> TYPE: DNA
<213> ORGANISM: Artificial Sequence
<220> FEATURE:
<223> OTHER INFORMATION: Primer

<400> SEQUENCE: 60
cctatattaa tcgtttacag aaactggct 29

<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
cctgataagg gtgaggtcg 19

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
ccttacttcg aactatgaat cttttggaag 30

<210> SEQ ID NO 63
<211> LENGTH: 14
<212> TYPE: DNA
<213> ORGANISM: Artificial Sequence
<220> FEATURE:
<223> OTHER INFORMATION: Primer

<400> SEQUENCE: 63
cgaagaacct tacc 14

<210> SEQ ID NO 64
<211> LENGTH: 27
<212> TYPE: DNA
<213> ORGANISM: Artificial Sequence
<220> FEATURE:
<223> OTHER INFORMATION: Primer

<400> SEQUENCE: 64
cgaagtacaa tacaagacaa aagaagg 27

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
cgacgcgctg cgcttcac 18

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
cgagagggaa acaacccaga cc 22

<210> SEQ ID NO 67
<211> LENGTH: 30
<212> TYPE: DNA

<213> ORGANISM: Artificial Sequence
<220> FEATURE:
<223> OTHER INFORMATION: Primer

<400> SEQUENCE: 67
cgagtatagc taaaaaaata gtttatgaca 30

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
cgcaaaaaaa tccagctatt agc 23

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
cgccgacttc gacggtgacc 20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
cggaattact gggcgtaaag 20

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
cggattggag tctgcaactc g 21

<210> SEQ ID NO 72
<211> LENGTH: 22
<212> TYPE: DNA
<213> ORGANISM: Artificial Sequence
<220> FEATURE:
<223> OTHER INFORMATION: Primer

<400> SEQUENCE: 72
cggcgtactt caacgacagc ca 22

<210> SEQ ID NO 73
<211> LENGTH: 24
<212> TYPE: DNA
<213> ORGANISM: Artificial Sequence
<220> FEATURE:
<223> OTHER INFORMATION: Primer

<400> SEQUENCE: 73
cgtaactata acggtcctaa ggta 24

<210> SEQ ID NO 74
<211> LENGTH: 26
<212> TYPE: DNA
<213> ORGANISM: Artificial Sequence
<220> FEATURE:
<223> OTHER INFORMATION: Primer

<400> SEQUENCE: 74
cgtcagggta aattccgtga agttaa 26

<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
cgtcgggtga ttaaccgtaa caaccg 26

<210> SEQ ID NO 76
<211> LENGTH: 26
<212> TYPE: DNA
<213> ORGANISM: Artificial Sequence
<220> FEATURE:
<223> OTHER INFORMATION: Primer

<400> SEQUENCE: 76
cgtcgtgtaa ttaaccgtaa caaccg 26

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
cgtggcggcg tggttatcga 20

<210> SEQ ID NO 78
<211> LENGTH: 25
<212> TYPE: DNA
<213> ORGANISM: Artificial Sequence
<220> FEATURE:
<223> OTHER INFORMATION: Primer

<400> SEQUENCE: 78
cgtgttgact attcggggcg ttcag 25

<210> SEQ ID NO 79
<211> LENGTH: 18
<212> TYPE: DNA
<213> ORGANISM: Artificial Sequence
<220> FEATURE:
<223> OTHER INFORMATION: Primer

<400> SEQUENCE: 79
ctagtacgag aggaccgg 18

<210> SEQ ID NO 80
<211> LENGTH: 18
<212> TYPE: DNA
<213> ORGANISM: Artificial Sequence
<220> FEATURE:
<223> OTHER INFORMATION: Primer

<400> SEQUENCE: 80
ctgacacctg cccggtgc 18

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
ctggcaggta tgcgtggtct gatg 24

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
ctggctaaaa ctttggcaac ggt 23

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
ctgtccctag tacgagagga ccgg 24

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
ctgttcttag tacgagagga cc 22

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
cttctgcaac aagctgtgga acgc 24

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
cttgctggta tgcgtggtct gatg 24

<210> SEQ ID NO 87
<211> LENGTH: 29
<212> TYPE: DNA

<213> ORGANISM: Artificial Sequence
<220> FEATURE:
<223> OTHER INFORMATION: Primer

<400> SEQUENCE: 87
cttggaggta agtctcattt tggtgggca 29

<210> SEQ ID NO 88
<211> LENGTH: 19
<212> TYPE: DNA
<213> ORGANISM: Artificial Sequence
<220> FEATURE:
<223> OTHER INFORMATION: Primer

<400> SEQUENCE: 88
cttgtacaca ccgcccgtc 19

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
cttgtacttg tggctcacac ggctgtttgg 30

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
cttttgcata ttatatcgag c 21

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
gaatagcaat taatccaaat 20

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
gaaagagttc ggattggg 18

<210> SEQ ID NO 93
<211> LENGTH: 21
<212> TYPE: DNA
<213> ORGANISM: Artificial Sequence
<220> FEATURE:
<223> OTHER INFORMATION: Primer

<400> SEQUENCE: 93
gaaggatata cggttgatgt c 21

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
gaatagcaat taatccaaat 20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
gacacggtcc agactcctac 20

<210> SEQ ID NO 96
<211> LENGTH: 18
<212> TYPE: DNA
<213> ORGANISM: Artificial Sequence
<220> FEATURE:
<223> OTHER INFORMATION: Primer

<400> SEQUENCE: 96
gacagttcgg tccctatc 18

<210> SEQ ID NO 97
<211> LENGTH: 18
<212> TYPE: DNA
<213> ORGANISM: Artificial Sequence
<220> FEATURE:
<223> OTHER INFORMATION: Primer

<400> SEQUENCE: 97
gaccacctcg gcaaccgt 18

<210> SEQ ID NO 98
<211> LENGTH: 30
<212> TYPE: DNA
<213> ORGANISM: Artificial Sequence
<220> FEATURE:
<223> OTHER INFORMATION: Primer

<400> SEQUENCE: 98
gacctacagt aagaggttct gtaatgaacc 30

<210> SEQ ID NO 99
<211> LENGTH: 16
<212> TYPE: DNA
<213> ORGANISM: Artificial Sequence
<220> FEATURE:
<223> OTHER INFORMATION: Primer

<400> SEQUENCE: 99
gacgcctgcc cggtgc 16

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
gacttaccaa cccgatgcaa 20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
gagagcaagc ggacctcata 20

<210> SEQ ID NO 102
<211> LENGTH: 27
<212> TYPE: DNA
<213> ORGANISM: Artificial Sequence
<220> FEATURE:
<223> OTHER INFORMATION: Primer

<400> SEQUENCE: 102
gagagtttga tcctggctca gaacgaa 27

<210> SEQ ID NO 103
<211> LENGTH: 19
<212> TYPE: DNA
<213> ORGANISM: Artificial Sequence
<220> FEATURE:
<223> OTHER INFORMATION: Primer

<400> SEQUENCE: 103
gaggaaagtc catgctcac 19

<210> SEQ ID NO 104
<211> LENGTH: 19
<212> TYPE: DNA
<213> ORGANISM: Artificial Sequence
<220> FEATURE:
<223> OTHER INFORMATION: Primer

<400> SEQUENCE: 104
gaggaaagtc catgctcgc 19

<210> SEQ ID NO 105
<211> LENGTH: 17
<212> TYPE: DNA
<213> ORGANISM: Artificial Sequence
<220> FEATURE:
<223> OTHER INFORMATION: Primer

<400> SEQUENCE: 105
gaggaaagtc cgggctc 17

<210> SEQ ID NO 106
<211> LENGTH: 22
<212> TYPE: DNA
<213> ORGANISM: Artificial Sequence
<220> FEATURE:
<223> OTHER INFORMATION: Primer

<400> SEQUENCE: 106
gataccctgg tagtccacac cg 22

<210> SEQ ID NO 107
<211> LENGTH: 20
<212> TYPE: DNA

<213> ORGANISM: Artificial Sequence
<220> FEATURE:
<223> OTHER INFORMATION: Primer

<400> SEQUENCE: 107
gatctggagg aataccggtg 20

<210> SEQ ID NO 108
<211> LENGTH: 29
<212> TYPE: DNA
<213> ORGANISM: Artificial Sequence
<220> FEATURE:
<223> OTHER INFORMATION: Primer

<400> SEQUENCE: 108
gatgactttt tagctaatgg tcaggcagc 29

<210> SEQ ID NO 109
<211> LENGTH: 30
<212> TYPE: DNA
<213> ORGANISM: Artificial Sequence
<220> FEATURE:
<223> OTHER INFORMATION: Primer

<400> SEQUENCE: 109
gattattgtt atcctgttat gccatttgag 30

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
gcacaacctg cggctgcg 18

<210> SEQ ID NO 111
<211> LENGTH: 27
<212> TYPE: DNA
<213> ORGANISM: Artificial Sequence
<220> FEATURE:
<223> OTHER INFORMATION: Primer

<400> SEQUENCE: 111
gcactatgca cacgtagatt gtcctgg 27

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
gccttgtaca cacctcccgt c 21

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
gcgaagaacc ttaccaggtc 20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
gctacacacg tgctacaatg 20

<210> SEQ ID NO 115
<211> LENGTH: 30
<212> TYPE: DNA
<213> ORGANISM: Artificial Sequence
<220> FEATURE:
<223> OTHER INFORMATION: Primer

<400> SEQUENCE: 115
gctggtgaaa ataacccaga tgtcgtcttc 30

<210> SEQ ID NO 116
<211> LENGTH: 25
<212> TYPE: DNA
<213> ORGANISM: Artificial Sequence
<220> FEATURE:
<223> OTHER INFORMATION: Primer

<400> SEQUENCE: 116
gcttcaggaa tcaatgatgg agcag 25

<210> SEQ ID NO 117
<211> LENGTH: 19
<212> TYPE: DNA
<213> ORGANISM: Artificial Sequence
<220> FEATURE:
<223> OTHER INFORMATION: Primer

<400> SEQUENCE: 117
ggacggagaa ggctatgtt 19

<210> SEQ ID NO 118
<211> LENGTH: 22
<212> TYPE: DNA
<213> ORGANISM: Artificial Sequence
<220> FEATURE:
<223> OTHER INFORMATION: Primer

<400> SEQUENCE: 118
ggattagaga ccctggtagt cc 22

<210> SEQ ID NO 119
<211> LENGTH: 26
<212> TYPE: DNA
<213> ORGANISM: Artificial Sequence
<220> FEATURE:
<223> OTHER INFORMATION: Primer

<400> SEQUENCE: 119
ggattagata ccctggtagt ccacgc 26

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
ggctcagcca tttagttacc gctat 25

<210> SEQ ID NO 121
<211> LENGTH: 21
<212> TYPE: DNA
<213> ORGANISM: Artificial Sequence
<220> FEATURE:
<223> OTHER INFORMATION: Primer

<400> SEQUENCE: 121
gggaactgaa acatctaagt a 21

<210> SEQ ID NO 122
<211> LENGTH: 22
<212> TYPE: DNA
<213> ORGANISM: Artificial Sequence
<220> FEATURE:
<223> OTHER INFORMATION: Primer

<400> SEQUENCE: 122
gggagcaaac aggattagat ac 22

<210> SEQ ID NO 123
<211> LENGTH: 29
<212> TYPE: DNA
<213> ORGANISM: Artificial Sequence
<220> FEATURE:
<223> OTHER INFORMATION: Primer

<400> SEQUENCE: 123
gggcaacagc agcggattgc gattgcgcg 29

<210> SEQ ID NO 124
<211> LENGTH: 23
<212> TYPE: DNA
<213> ORGANISM: Artificial Sequence
<220> FEATURE:
<223> OTHER INFORMATION: Primer

<400> SEQUENCE: 124
gggcagcgtt tcggcgaaat gga 23

<210> SEQ ID NO 125
<211> LENGTH: 26
<212> TYPE: DNA
<213> ORGANISM: Artificial Sequence
<220> FEATURE:
<223> OTHER INFORMATION: Primer

<400> SEQUENCE: 125
ggggagtgaa agagatcctg aaaccg 26

<210> SEQ ID NO 126
<211> LENGTH: 30
<212> TYPE: DNA
<213> ORGANISM: Artificial Sequence
<220> FEATURE:
<223> OTHER INFORMATION: Primer

<400> SEQUENCE: 126
ggggattcag ccatcaaagc agctattgac 30

<210> SEQ ID NO 127
<211> LENGTH: 27
<212> TYPE: DNA

<213> ORGANISM: Artificial Sequence
<220> FEATURE:
<223> OTHER INFORMATION: Primer

<400> SEQUENCE: 127
ggggattgat atcaccgata agaagaa 27

<210> SEQ ID NO 128
<211> LENGTH: 24
<212> TYPE: DNA
<213> ORGANISM: Artificial Sequence
<220> FEATURE:
<223> OTHER INFORMATION: Primer

<400> SEQUENCE: 128
ggtgaaagaa gttgcctcta aagc 24

<210> SEQ ID NO 129
<211> LENGTH: 15
<212> TYPE: DNA
<213> ORGANISM: Artificial Sequence
<220> FEATURE:
<223> OTHER INFORMATION: Primer

<400> SEQUENCE: 129
ggtggatgcc ttggc 15

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
ggtgttaaat agcctggcag 20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
ggtttagtac cagaacatgc 20

<210> SEQ ID NO 132
<211> LENGTH: 23
<212> TYPE: DNA
<213> ORGANISM: Artificial Sequence
<220> FEATURE:
<223> OTHER INFORMATION: Primer

<400> SEQUENCE: 132
gtcaaagtgg cacgtttact ggc 23

<210> SEQ ID NO 133
<211> LENGTH: 22
<212> TYPE: DNA
<213> ORGANISM: Artificial Sequence
<220> FEATURE:
<223> OTHER INFORMATION: Primer

<400> SEQUENCE: 133
gtcgtgaaaa cgagctggaa ga 22

<210> SEQ ID NO 134
<211> LENGTH: 30
<212> TYPE: DNA
<213> ORGANISM: Artificial Sequence
<220> FEATURE:
<223> OTHER INFORMATION: Primer

<400> SEQUENCE: 134
gtgagatgtt gggttaagtc ccgtaacgag 30

<210> SEQ ID NO 135
<211> LENGTH: 23
<212> TYPE: DNA
<213> ORGANISM: Artificial Sequence
<220> FEATURE:
<223> OTHER INFORMATION: Primer

<400> SEQUENCE: 135
gtgcatgcgg atacagagca gag 23

<210> SEQ ID NO 136
<211> LENGTH: 26
<212> TYPE: DNA
<213> ORGANISM: Artificial Sequence
<220> FEATURE:
<223> OTHER INFORMATION: Primer

<400> SEQUENCE: 136
gtggcatgcc taatacatgc aagtcg 26

<210> SEQ ID NO 137
<211> LENGTH: 18
<212> TYPE: DNA
<213> ORGANISM: Artificial Sequence
<220> FEATURE:
<223> OTHER INFORMATION: Primer

<400> SEQUENCE: 137
gtgtagcggt gaaatgcg 18

<210> SEQ ID NO 138
<211> LENGTH: 21
<212> TYPE: DNA
<213> ORGANISM: Artificial Sequence
<220> FEATURE:
<223> OTHER INFORMATION: Primer

<400> SEQUENCE: 138
gttatcctgt tatgccattt g 21

<210> SEQ ID NO 139
<211> LENGTH: 28
<212> TYPE: DNA
<213> ORGANISM: Artificial Sequence
<220> FEATURE:
<223> OTHER INFORMATION: Primer

<400> SEQUENCE: 139
gttatttagc actcgttttt aatcagcc 28

<210> SEQ ID NO 140
<211> LENGTH: 22
<212> TYPE: DNA
<213> ORGANISM: Artificial Sequence
<220> FEATURE:
<223> OTHER INFORMATION: Primer

<400> SEQUENCE: 140
gttgtgaggt taagcgacta ag 22

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
gttgtgaggt taagcgacta ag 22

<210> SEQ ID NO 142
<211> LENGTH: 24
<212> TYPE: DNA
<213> ORGANISM: Artificial Sequence
<220> FEATURE:
<223> OTHER INFORMATION: Primer

<400> SEQUENCE: 142
tctagtaata ataggaccct cagc 24

<210> SEQ ID NO 143
<211> LENGTH: 15
<212> TYPE: DNA
<213> ORGANISM: Artificial Sequence
<220> FEATURE:
<223> OTHER INFORMATION: Primer

<400> SEQUENCE: 143
tatggctcta ctcaa 15

<210> SEQ ID NO 144
<211> LENGTH: 29
<212> TYPE: DNA
<213> ORGANISM: Artificial Sequence
<220> FEATURE:
<223> OTHER INFORMATION: Primer

<400> SEQUENCE: 144
taaaacaaac tacggtaaca ttgatcgca 29

<210> SEQ ID NO 145
<211> LENGTH: 33
<212> TYPE: DNA
<213> ORGANISM: Artificial Sequence
<220> FEATURE:
<223> OTHER INFORMATION: Primer

<400> SEQUENCE: 145
taaaactttt gccgtaatga tgggtgaaga tat 33

<210> SEQ ID NO 146
<211> LENGTH: 31
<212> TYPE: DNA
<213> ORGANISM: Artificial Sequence
<220> FEATURE:
<223> OTHER INFORMATION: Primer

<400> SEQUENCE: 146
taaacacggc tttcctatgg cttatccaaa t 31

<210> SEQ ID NO 147
<211> LENGTH: 28
<212> TYPE: DNA

<213> ORGANISM: Artificial Sequence
<220> FEATURE:
<223> OTHER INFORMATION: Primer

<400> SEQUENCE: 147
taaaccccat cgggagcaag accgaata 28

<210> SEQ ID NO 148
<211> LENGTH: 30
<212> TYPE: DNA
<213> ORGANISM: Artificial Sequence
<220> FEATURE:
<223> OTHER INFORMATION: Primer

<400> SEQUENCE: 148
taaagcccgt gaaatgactc gtcgtaaagg 30

<210> SEQ ID NO 149
<211> LENGTH: 28
<212> TYPE: DNA
<213> ORGANISM: Artificial Sequence
<220> FEATURE:
<223> OTHER INFORMATION: Primer

<400> SEQUENCE: 149
taaagttggt tttattggtt ggcgcgga 28

<210> SEQ ID NO 150
<211> LENGTH: 25
<212> TYPE: DNA
<213> ORGANISM: Artificial Sequence
<220> FEATURE:
<223> OTHER INFORMATION: Primer

<400> SEQUENCE: 150
taaatctgcc cgtgtcgttg gtgac 25

<210> SEQ ID NO 151
<211> LENGTH: 29
<212> TYPE: DNA
<213> ORGANISM: Artificial Sequence
<220> FEATURE:
<223> OTHER INFORMATION: Primer

<400> SEQUENCE: 151
taacaactcg ccttatgaaa cgggatata 29

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
taacacatgc aagtcgaacg 20

<210> SEQ ID NO 153
<211> LENGTH: 29
<212> TYPE: DNA
<213> ORGANISM: Artificial Sequence
<220> FEATURE:
<223> OTHER INFORMATION: Primer

<400> SEQUENCE: 153
taaccattca agaactagat cttcaggca 29

<210> SEQ ID NO 154
<211> LENGTH: 30
<212> TYPE: DNA
<213> ORGANISM: Artificial Sequence
<220> FEATURE:
<223> OTHER INFORMATION: Primer

<400> SEQUENCE: 154
taaccttaat tggaaagaaa cccaagaagt 30

<210> SEQ ID NO 155
<211> LENGTH: 25
<212> TYPE: DNA
<213> ORGANISM: Artificial Sequence
<220> FEATURE:
<223> OTHER INFORMATION: Primer

<400> SEQUENCE: 155
taacggttat catggcccag atggg 25

<210> SEQ ID NO 156
<211> LENGTH: 27
<212> TYPE: DNA
<213> ORGANISM: Artificial Sequence
<220> FEATURE:
<223> OTHER INFORMATION: Primer

<400> SEQUENCE: 156
taactctgat gtttttgatg ggaaggt 27

<210> SEQ ID NO 157
<211> LENGTH: 27
<212> TYPE: DNA
<213> ORGANISM: Artificial Sequence
<220> FEATURE:
<223> OTHER INFORMATION: Primer

<400> SEQUENCE: 157
taactgcatg gaacccttct ttactag 27

<210> SEQ ID NO 158
<211> LENGTH: 27
<212> TYPE: DNA
<213> ORGANISM: Artificial Sequence
<220> FEATURE:
<223> OTHER INFORMATION: Primer

<400> SEQUENCE: 158
taagaagccg gaaaccatca actaccg 27

<210> SEQ ID NO 159
<211> LENGTH: 22
<212> TYPE: DNA
<213> ORGANISM: Artificial Sequence
<220> FEATURE:
<223> OTHER INFORMATION: Primer

<400> SEQUENCE: 159
taagagcgca ccggtaagtt gg 22

<210> SEQ ID NO 160
<211> LENGTH: 28
<212> TYPE: DNA
<213> ORGANISM: Artificial Sequence
<220> FEATURE:
<223> OTHER INFORMATION: Primer

<400> SEQUENCE: 160
taagcatgct gtggcttatc gtgaaatg 28

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161
taagctgcca gcggaatgct ttc 23

<210> SEQ ID NO 162
<211> LENGTH: 29
<212> TYPE: DNA
<213> ORGANISM: Artificial Sequence
<220> FEATURE:
<223> OTHER INFORMATION: Primer

<400> SEQUENCE: 162
taaggatagt gcaacagaga tataccgcc 29

<210> SEQ ID NO 163
<211> LENGTH: 30
<212> TYPE: DNA
<213> ORGANISM: Artificial Sequence
<220> FEATURE:
<223> OTHER INFORMATION: Primer

<400> SEQUENCE: 163
taaggtatga caccggataa atcatataaa 30

<210> SEQ ID NO 164
<211> LENGTH: 33
<212> TYPE: DNA
<213> ORGANISM: Artificial Sequence
<220> FEATURE:
<223> OTHER INFORMATION: Primer

<400> SEQUENCE: 164
taaggtttat tgtctttgtg gagatgggga ttt 33

<210> SEQ ID NO 165
<211> LENGTH: 31
<212> TYPE: DNA
<213> ORGANISM: Artificial Sequence
<220> FEATURE:
<223> OTHER INFORMATION: Primer

<400> SEQUENCE: 165
taatcaagca ttggaagatg aaatgcatac c 31

<210> SEQ ID NO 166
<211> LENGTH: 29
<212> TYPE: DNA
<213> ORGANISM: Artificial Sequence
<220> FEATURE:
<223> OTHER INFORMATION: Primer

<400> SEQUENCE: 166
taatcggtaa atatcacccg catggtgac 29

<210> SEQ ID NO 167
<211> LENGTH: 29
<212> TYPE: DNA

<213> ORGANISM: Artificial Sequence
<220> FEATURE:
<223> OTHER INFORMATION: Primer

<400> SEQUENCE: 167
taatcggtaa gtatcaccct catggtgat 29

<210> SEQ ID NO 168
<211> LENGTH: 24
<212> TYPE: DNA
<213> ORGANISM: Artificial Sequence
<220> FEATURE:
<223> OTHER INFORMATION: Primer

<400> SEQUENCE: 168
taatcgtgga atacgggttt gcta 24

<210> SEQ ID NO 169
<211> LENGTH: 30
<212> TYPE: DNA
<213> ORGANISM: Artificial Sequence
<220> FEATURE:
<223> OTHER INFORMATION: Primer

<400> SEQUENCE: 169
taatgaaccc taatgaccat ccacacggtg 30

<210> SEQ ID NO 170
<211> LENGTH: 27
<212> TYPE: DNA
<213> ORGANISM: Artificial Sequence
<220> FEATURE:
<223> OTHER INFORMATION: Primer

<400> SEQUENCE: 170
taatgatgaa ttaggtgcgg gttcttt 27

<210> SEQ ID NO 171
<211> LENGTH: 29
<212> TYPE: DNA
<213> ORGANISM: Artificial Sequence
<220> FEATURE:
<223> OTHER INFORMATION: Primer

<400> SEQUENCE: 171
taatgggtaa atatcaccct catggtgac 29

<210> SEQ ID NO 172
<211> LENGTH: 31
<212> TYPE: DNA
<213> ORGANISM: Artificial Sequence
<220> FEATURE:
<223> OTHER INFORMATION: Primer

<400> SEQUENCE: 172
taattgggct ctttctcgct taaacacctt a 31

<210> SEQ ID NO 173
<211> LENGTH: 25
<212> TYPE: DNA
<213> ORGANISM: Artificial Sequence
<220> FEATURE:
<223> OTHER INFORMATION: Primer

<400> SEQUENCE: 173
tacaaagcaa gacactggct cacta 25

<210> SEQ ID NO 174
<211> LENGTH: 30
<212> TYPE: DNA
<213> ORGANISM: Artificial Sequence
<220> FEATURE:
<223> OTHER INFORMATION: Primer

<400> SEQUENCE: 174
tacaaaggtc aaccaatgac attcagacta 30

<210> SEQ ID NO 175
<211> LENGTH: 34
<212> TYPE: DNA
<213> ORGANISM: Artificial Sequence
<220> FEATURE:
<223> OTHER INFORMATION: Primer

<400> SEQUENCE: 175
tacaacatat tattaaagag acgggtttga atcc 34

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
tacaagcact cccagctgca 20

<210> SEQ ID NO 177
<211> LENGTH: 29
<212> TYPE: DNA
<213> ORGANISM: Artificial Sequence
<220> FEATURE:
<223> OTHER INFORMATION: Primer

<400> SEQUENCE: 177
tacaatgctt gtttatgctg gtaaagcag 29

<210> SEQ ID NO 178
<211> LENGTH: 25
<212> TYPE: DNA
<213> ORGANISM: Artificial Sequence
<220> FEATURE:
<223> OTHER INFORMATION: Primer

<400> SEQUENCE: 178
tacacaacaa tggcggtaaa gatgg 25

<210> SEQ ID NO 179
<211> LENGTH: 15
<212> TYPE: DNA
<213> ORGANISM: Artificial Sequence
<220> FEATURE:
<223> OTHER INFORMATION: Primer

<400> SEQUENCE: 179
tacagagttt gcgac 15

<210> SEQ ID NO 180
<211> LENGTH: 21
<212> TYPE: DNA
<213> ORGANISM: Artificial Sequence
<220> FEATURE:
<223> OTHER INFORMATION: Primer

<400> SEQUENCE: 180
tacaggccgt gttgaacgtg g 21

<210> SEQ ID NO 181
<211> LENGTH: 21
<212> TYPE: DNA
<213> ORGANISM: Artificial Sequence
<220> FEATURE:
<223> OTHER INFORMATION: Primer

<400> SEQUENCE: 181
tacatgctag ccgcgtctta c 21

<210> SEQ ID NO 182
<211> LENGTH: 27
<212> TYPE: DNA
<213> ORGANISM: Artificial Sequence
<220> FEATURE:
<223> OTHER INFORMATION: Primer

<400> SEQUENCE: 182
taccactatt aatgtcgctg gtgcttc 27

<210> SEQ ID NO 183
<211> LENGTH: 25
<212> TYPE: DNA
<213> ORGANISM: Artificial Sequence
<220> FEATURE:
<223> OTHER INFORMATION: Primer

<400> SEQUENCE: 183
taccatgaca gaaggcattt tgaca 25

<210> SEQ ID NO 184
<211> LENGTH: 19
<212> TYPE: DNA
<213> ORGANISM: Artificial Sequence
<220> FEATURE:
<223> OTHER INFORMATION: Primer

<400> SEQUENCE: 184
taccccaaac cgacacagg 19

<210> SEQ ID NO 185
<211> LENGTH: 23
<212> TYPE: DNA
<213> ORGANISM: Artificial Sequence
<220> FEATURE:
<223> OTHER INFORMATION: Primer

<400> SEQUENCE: 185
taccccaggg aaagtgccac aga 23

<210> SEQ ID NO 186
<211> LENGTH: 25
<212> TYPE: DNA
<213> ORGANISM: Artificial Sequence
<220> FEATURE:
<223> OTHER INFORMATION: Primer

<400> SEQUENCE: 186
taccggcgca aaaagtcgag attgg 25

<210> SEQ ID NO 187
<211> LENGTH: 21
<212> TYPE: DNA

<213> ORGANISM: Artificial Sequence
<220> FEATURE:
<223> OTHER INFORMATION: Primer

<400> SEQUENCE: 187
tacctatatg cgccagaccg c 21

<210> SEQ ID NO 188
<211> LENGTH: 26
<212> TYPE: DNA
<213> ORGANISM: Artificial Sequence
<220> FEATURE:
<223> OTHER INFORMATION: Primer

<400> SEQUENCE: 188
tacgatttca cttccgcagc cagatt 26

<210> SEQ ID NO 189
<211> LENGTH: 27
<212> TYPE: DNA
<213> ORGANISM: Artificial Sequence
<220> FEATURE:
<223> OTHER INFORMATION: Primer

<400> SEQUENCE: 189
tacgcgtctt gaagcgtttc gttatga 27

<210> SEQ ID NO 190
<211> LENGTH: 26
<212> TYPE: DNA
<213> ORGANISM: Artificial Sequence
<220> FEATURE:
<223> OTHER INFORMATION: Primer

<400> SEQUENCE: 190
tacgctgacg gaatcaacca aagcgg 26

<210> SEQ ID NO 191
<211> LENGTH: 21
<212> TYPE: DNA
<213> ORGANISM: Artificial Sequence
<220> FEATURE:
<223> OTHER INFORMATION: Primer

<400> SEQUENCE: 191
tacggtgaat acgttcccgg g 21

<210> SEQ ID NO 192
<211> LENGTH: 15
<212> TYPE: DNA
<213> ORGANISM: Artificial Sequence
<220> FEATURE:
<223> OTHER INFORMATION: Primer

<400> SEQUENCE: 192
tacagagttt gcgac 15

<210> SEQ ID NO 193
<211> LENGTH: 23
<212> TYPE: DNA
<213> ORGANISM: Artificial Sequence
<220> FEATURE:
<223> OTHER INFORMATION: Primer

<400> SEQUENCE: 193
tactacttca agccgaactt ccg 23

-continued

<210> SEQ ID NO 194
<211> LENGTH: 28
<212> TYPE: DNA
<213> ORGANISM: Artificial Sequence
<220> FEATURE:
<223> OTHER INFORMATION: Primer

<400> SEQUENCE: 194
tactagcggt aagcttaaac aagattgc 28

<210> SEQ ID NO 195
<211> LENGTH: 22
<212> TYPE: DNA
<213> ORGANISM: Artificial Sequence
<220> FEATURE:
<223> OTHER INFORMATION: Primer

<400> SEQUENCE: 195
tactctcggt ggagaagctc gc 22

<210> SEQ ID NO 196
<211> LENGTH: 22
<212> TYPE: DNA
<213> ORGANISM: Artificial Sequence
<220> FEATURE:
<223> OTHER INFORMATION: Primer

<400> SEQUENCE: 196
tactggaaca aagtctgcga cc 22

<210> SEQ ID NO 197
<211> LENGTH: 27
<212> TYPE: DNA
<213> ORGANISM: Artificial Sequence
<220> FEATURE:
<223> OTHER INFORMATION: Primer

<400> SEQUENCE: 197
tacttactac ttcaagccga acttccg 27

<210> SEQ ID NO 198
<211> LENGTH: 28
<212> TYPE: DNA
<213> ORGANISM: Artificial Sequence
<220> FEATURE:
<223> OTHER INFORMATION: Primer

<400> SEQUENCE: 198
tacttacttg agaatccaca agctgcaa 28

<210> SEQ ID NO 199
<211> LENGTH: 28
<212> TYPE: DNA
<213> ORGANISM: Artificial Sequence
<220> FEATURE:
<223> OTHER INFORMATION: Primer

<400> SEQUENCE: 199
tacttggtaa ataccaccca catggtga 28

<210> SEQ ID NO 200
<211> LENGTH: 32
<212> TYPE: DNA
<213> ORGANISM: Artificial Sequence
<220> FEATURE:
<223> OTHER INFORMATION: Primer

<400> SEQUENCE: 200
tactttttta aaactaggga tgcgtttgaa gc 32

<210> SEQ ID NO 201
<211> LENGTH: 27
<212> TYPE: DNA
<213> ORGANISM: Artificial Sequence
<220> FEATURE:
<223> OTHER INFORMATION: Primer

<400> SEQUENCE: 201
tagaaatcaa ggtgatagtg gcaatga 27

<210> SEQ ID NO 202
<211> LENGTH: 21
<212> TYPE: DNA
<213> ORGANISM: Artificial Sequence
<220> FEATURE:
<223> OTHER INFORMATION: Primer

<400> SEQUENCE: 202
tagaacaccg atggcgaagg c 21

<210> SEQ ID NO 203
<211> LENGTH: 22
<212> TYPE: DNA
<213> ORGANISM: Artificial Sequence
<220> FEATURE:
<223> OTHER INFORMATION: Primer

<400> SEQUENCE: 203
tagaacgtcg cgagacagtt cg 22

<210> SEQ ID NO 204
<211> LENGTH: 21
<212> TYPE: DNA
<213> ORGANISM: Artificial Sequence
<220> FEATURE:
<223> OTHER INFORMATION: Primer

<400> SEQUENCE: 204
tagactgccc aggacacgct g 21

<210> SEQ ID NO 205
<211> LENGTH: 29
<212> TYPE: DNA
<213> ORGANISM: Artificial Sequence
<220> FEATURE:
<223> OTHER INFORMATION: Primer

<400> SEQUENCE: 205
tagataattg ggctctttct cgcttaaac 29

<210> SEQ ID NO 206
<211> LENGTH: 22
<212> TYPE: DNA
<213> ORGANISM: Artificial Sequence
<220> FEATURE:
<223> OTHER INFORMATION: Primer

<400> SEQUENCE: 206
tagataccct ggtagtccac gc 22

<210> SEQ ID NO 207
<211> LENGTH: 28
<212> TYPE: DNA

<213> ORGANISM: Artificial Sequence
<220> FEATURE:
<223> OTHER INFORMATION: Primer

<400> SEQUENCE: 207
tagatgaaaa aggcgaagtg gctaatgg 28

<210> SEQ ID NO 208
<211> LENGTH: 28
<212> TYPE: DNA
<213> ORGANISM: Artificial Sequence
<220> FEATURE:
<223> OTHER INFORMATION: Primer

<400> SEQUENCE: 208
tagatgaaaa gggcgaagtg gctaatgg 28

<210> SEQ ID NO 209
<211> LENGTH: 30
<212> TYPE: DNA
<213> ORGANISM: Artificial Sequence
<220> FEATURE:
<223> OTHER INFORMATION: Primer

<400> SEQUENCE: 209
tagcaacaaa tatatctgaa gcagcgtact 30

<210> SEQ ID NO 210
<211> LENGTH: 29
<212> TYPE: DNA
<213> ORGANISM: Artificial Sequence
<220> FEATURE:
<223> OTHER INFORMATION: Primer

<400> SEQUENCE: 210
tagcaggtgg tgaaatcggc cacatgatt 29

<210> SEQ ID NO 211
<211> LENGTH: 26
<212> TYPE: DNA
<213> ORGANISM: Artificial Sequence
<220> FEATURE:
<223> OTHER INFORMATION: Primer

<400> SEQUENCE: 211
tagcatcaga actgttgttc cgctag 26

<210> SEQ ID NO 212
<211> LENGTH: 24
<212> TYPE: DNA
<213> ORGANISM: Artificial Sequence
<220> FEATURE:
<223> OTHER INFORMATION: Primer

<400> SEQUENCE: 212
tagcccagca caatttgtga ttca 24

<210> SEQ ID NO 213
<211> LENGTH: 34
<212> TYPE: DNA
<213> ORGANISM: Artificial Sequence
<220> FEATURE:
<223> OTHER INFORMATION: Primer

<400> SEQUENCE: 213
tagcctttaa cgaaaatgta aaaatgcgtt ttga 34

<210> SEQ ID NO 214
<211> LENGTH: 27
<212> TYPE: DNA
<213> ORGANISM: Artificial Sequence
<220> FEATURE:
<223> OTHER INFORMATION: Primer

<400> SEQUENCE: 214
tagcgaatgt ggctttactt cacaatt 27

<210> SEQ ID NO 215
<211> LENGTH: 19
<212> TYPE: DNA
<213> ORGANISM: Artificial Sequence
<220> FEATURE:
<223> OTHER INFORMATION: Primer

<400> SEQUENCE: 215
tagcgtaaag gtgaacctt 19

<210> SEQ ID NO 216
<211> LENGTH: 20
<212> TYPE: DNA
<213> ORGANISM: Artificial Sequence
<220> FEATURE:
<223> OTHER INFORMATION: Primer

<400> SEQUENCE: 216
tagctaatgg tcaggcagcc 20

<210> SEQ ID NO 217
<211> LENGTH: 30
<212> TYPE: DNA
<213> ORGANISM: Artificial Sequence
<220> FEATURE:
<223> OTHER INFORMATION: Primer

<400> SEQUENCE: 217
tagctatctt atcgttgaga agggatttgc 30

<210> SEQ ID NO 218
<211> LENGTH: 22
<212> TYPE: DNA
<213> ORGANISM: Artificial Sequence
<220> FEATURE:
<223> OTHER INFORMATION: Primer

<400> SEQUENCE: 218
tagctggcgc gaaattaggt gt 22

<210> SEQ ID NO 219
<211> LENGTH: 26
<212> TYPE: DNA
<213> ORGANISM: Artificial Sequence
<220> FEATURE:
<223> OTHER INFORMATION: Primer

<400> SEQUENCE: 219
tagctggcgg tatggagaat atgtct 26

<210> SEQ ID NO 220
<211> LENGTH: 27
<212> TYPE: DNA
<213> ORGANISM: Artificial Sequence
<220> FEATURE:
<223> OTHER INFORMATION: Primer

<400> SEQUENCE: 220
tagcttttgc atattatatc gagccac 27

<210> SEQ ID NO 221
<211> LENGTH: 29
<212> TYPE: DNA
<213> ORGANISM: Artificial Sequence
<220> FEATURE:
<223> OTHER INFORMATION: Primer

<400> SEQUENCE: 221
taggaattac ggctgataaa gcgtataaa 29

<210> SEQ ID NO 222
<211> LENGTH: 35
<212> TYPE: DNA
<213> ORGANISM: Artificial Sequence
<220> FEATURE:
<223> OTHER INFORMATION: Primer

<400> SEQUENCE: 222
taggcgaaga tatacaaaga gtattagaag ctaga 35

<210> SEQ ID NO 223
<211> LENGTH: 25
<212> TYPE: DNA
<213> ORGANISM: Artificial Sequence
<220> FEATURE:
<223> OTHER INFORMATION: Primer

<400> SEQUENCE: 223
taggcgtgaa agcaagctac cgttt 25

<210> SEQ ID NO 224
<211> LENGTH: 25
<212> TYPE: DNA
<213> ORGANISM: Artificial Sequence
<220> FEATURE:
<223> OTHER INFORMATION: Primer

<400> SEQUENCE: 224
taggtgctgg ttacgcagat caaga 25

<210> SEQ ID NO 225
<211> LENGTH: 30
<212> TYPE: DNA
<213> ORGANISM: Artificial Sequence
<220> FEATURE:
<223> OTHER INFORMATION: Primer

<400> SEQUENCE: 225
taggtttacg tcagtatggc gtgattatgg 30

<210> SEQ ID NO 226
<211> LENGTH: 23
<212> TYPE: DNA
<213> ORGANISM: Artificial Sequence
<220> FEATURE:
<223> OTHER INFORMATION: Primer

<400> SEQUENCE: 226
tagtaccgaa gctggtcata cga 23

<210> SEQ ID NO 227
<211> LENGTH: 17
<212> TYPE: DNA

<213> ORGANISM: Artificial Sequence
<220> FEATURE:
<223> OTHER INFORMATION: Primer

<400> SEQUENCE: 227
tagtacgaga ggaccgg 17

<210> SEQ ID NO 228
<211> LENGTH: 18
<212> TYPE: DNA
<213> ORGANISM: Artificial Sequence
<220> FEATURE:
<223> OTHER INFORMATION: Primer

<400> SEQUENCE: 228
tagtcccgca acgagcgc 18

<210> SEQ ID NO 229
<211> LENGTH: 27
<212> TYPE: DNA
<213> ORGANISM: Artificial Sequence
<220> FEATURE:
<223> OTHER INFORMATION: Primer

<400> SEQUENCE: 229
tagtgataga actgtaggca caatcgt 27

<210> SEQ ID NO 230
<211> LENGTH: 22
<212> TYPE: DNA
<213> ORGANISM: Artificial Sequence
<220> FEATURE:
<223> OTHER INFORMATION: Primer

<400> SEQUENCE: 230
tagttgctca aacagctggg ct 22

<210> SEQ ID NO 231
<211> LENGTH: 29
<212> TYPE: DNA
<213> ORGANISM: Artificial Sequence
<220> FEATURE:
<223> OTHER INFORMATION: Primer

<400> SEQUENCE: 231
tataagtggg taaaccgtga atatcgtgt 29

<210> SEQ ID NO 232
<211> LENGTH: 24
<212> TYPE: DNA
<213> ORGANISM: Artificial Sequence
<220> FEATURE:
<223> OTHER INFORMATION: Primer

<400> SEQUENCE: 232
tatacttcaa cgcctgctgc tttc 24

<210> SEQ ID NO 233
<211> LENGTH: 22
<212> TYPE: DNA
<213> ORGANISM: Artificial Sequence
<220> FEATURE:
<223> OTHER INFORMATION: Primer

<400> SEQUENCE: 233
tatcgctcag gcgaactcca ac 22

<210> SEQ ID NO 234
<211> LENGTH: 23
<212> TYPE: DNA
<213> ORGANISM: Artificial Sequence
<220> FEATURE:
<223> OTHER INFORMATION: Primer

<400> SEQUENCE: 234
tatgaccaaa ctcatcagac gag 23

<210> SEQ ID NO 235
<211> LENGTH: 30
<212> TYPE: DNA
<213> ORGANISM: Artificial Sequence
<220> FEATURE:
<223> OTHER INFORMATION: Primer

<400> SEQUENCE: 235
tatgattaca attcaagaag gtcgtcacgc 30

<210> SEQ ID NO 236
<211> LENGTH: 27
<212> TYPE: DNA
<213> ORGANISM: Artificial Sequence
<220> FEATURE:
<223> OTHER INFORMATION: Primer

<400> SEQUENCE: 236
tatgcagtgg aacgatggtt tccaaga 27

<210> SEQ ID NO 237
<211> LENGTH: 24
<212> TYPE: DNA
<213> ORGANISM: Artificial Sequence
<220> FEATURE:
<223> OTHER INFORMATION: Primer

<400> SEQUENCE: 237
tatgctgacc gaccagtggt acgt 24

<210> SEQ ID NO 238
<211> LENGTH: 21
<212> TYPE: DNA
<213> ORGANISM: Artificial Sequence
<220> FEATURE:
<223> OTHER INFORMATION: Primer

<400> SEQUENCE: 238
tatggccatg gcagaagctc a 21

<210> SEQ ID NO 239
<211> LENGTH: 15
<212> TYPE: DNA
<213> ORGANISM: Artificial Sequence
<220> FEATURE:
<223> OTHER INFORMATION: Primer

<400> SEQUENCE: 239
tatggctcta ctcaa 15

<210> SEQ ID NO 240
<211> LENGTH: 31
<212> TYPE: DNA
<213> ORGANISM: Artificial Sequence
<220> FEATURE:
<223> OTHER INFORMATION: Primer

<400> SEQUENCE: 240
tatgtccaag aagcatagca aaaaaagcaa t 31

<210> SEQ ID NO 241
<211> LENGTH: 27
<212> TYPE: DNA
<213> ORGANISM: Artificial Sequence
<220> FEATURE:
<223> OTHER INFORMATION: Primer

<400> SEQUENCE: 241
tattcaaggt ggtcctttga tgcatgt 27

<210> SEQ ID NO 242
<211> LENGTH: 22
<212> TYPE: DNA
<213> ORGANISM: Artificial Sequence
<220> FEATURE:
<223> OTHER INFORMATION: Primer

<400> SEQUENCE: 242
tattggacaa cggtcgtcgc gg 22

<210> SEQ ID NO 243
<211> LENGTH: 30
<212> TYPE: DNA
<213> ORGANISM: Artificial Sequence
<220> FEATURE:
<223> OTHER INFORMATION: Primer

<400> SEQUENCE: 243
tattgtttca aatgtacaag gtgaagtgcg 30

<210> SEQ ID NO 244
<211> LENGTH: 30
<212> TYPE: DNA
<213> ORGANISM: Artificial Sequence
<220> FEATURE:
<223> OTHER INFORMATION: Primer

<400> SEQUENCE: 244
tatttcacat gtaattttga tattcgcact 30

<210> SEQ ID NO 245
<211> LENGTH: 32
<212> TYPE: DNA
<213> ORGANISM: Artificial Sequence
<220> FEATURE:
<223> OTHER INFORMATION: Primer

<400> SEQUENCE: 245
tcaaaaagcc ctaggtaaag agattccata tc 32

<210> SEQ ID NO 246
<211> LENGTH: 29
<212> TYPE: DNA
<213> ORGANISM: Artificial Sequence
<220> FEATURE:
<223> OTHER INFORMATION: Primer

<400> SEQUENCE: 246
tcaaactggg caatcggaac tggtaaatc 29

<210> SEQ ID NO 247
<211> LENGTH: 26
<212> TYPE: DNA

<213> ORGANISM: Artificial Sequence
<220> FEATURE:
<223> OTHER INFORMATION: Primer

<400> SEQUENCE: 247
tcaaatgtac aaggtgaagt gcgtga 26

<210> SEQ ID NO 248
<211> LENGTH: 29
<212> TYPE: DNA
<213> ORGANISM: Artificial Sequence
<220> FEATURE:
<223> OTHER INFORMATION: Primer

<400> SEQUENCE: 248
tcaacaacct cttggaggta aagctcagt 29

<210> SEQ ID NO 249
<211> LENGTH: 19
<212> TYPE: DNA
<213> ORGANISM: Artificial Sequence
<220> FEATURE:
<223> OTHER INFORMATION: Primer

<400> SEQUENCE: 249
tcaacctcgg cccgaacca 19

<210> SEQ ID NO 250
<211> LENGTH: 25
<212> TYPE: DNA
<213> ORGANISM: Artificial Sequence
<220> FEATURE:
<223> OTHER INFORMATION: Primer

<400> SEQUENCE: 250
tcaacctgac tgcgtgaatg gttgt 25

<210> SEQ ID NO 251
<211> LENGTH: 27
<212> TYPE: DNA
<213> ORGANISM: Artificial Sequence
<220> FEATURE:
<223> OTHER INFORMATION: Primer

<400> SEQUENCE: 251
tcaacgaagg taaaaaccat ctcaacg 27

<210> SEQ ID NO 252
<211> LENGTH: 27
<212> TYPE: DNA
<213> ORGANISM: Artificial Sequence
<220> FEATURE:
<223> OTHER INFORMATION: Primer

<400> SEQUENCE: 252
tcaacggtaa cttctatgtt acttctg 27

<210> SEQ ID NO 253
<211> LENGTH: 26
<212> TYPE: DNA
<213> ORGANISM: Artificial Sequence
<220> FEATURE:
<223> OTHER INFORMATION: Primer

<400> SEQUENCE: 253
tcaactcgaa ttttcaacag gtacca 26

<210> SEQ ID NO 254
<211> LENGTH: 17
<212> TYPE: DNA
<213> ORGANISM: Artificial Sequence
<220> FEATURE:
<223> OTHER INFORMATION: Primer

<400> SEQUENCE: 254
tcaagaagaa aaagagc 17

<210> SEQ ID NO 255
<211> LENGTH: 24
<212> TYPE: DNA
<213> ORGANISM: Artificial Sequence
<220> FEATURE:
<223> OTHER INFORMATION: Primer

<400> SEQUENCE: 255
tcaagcaaac gcacaatcag aagc 24

<210> SEQ ID NO 256
<211> LENGTH: 27
<212> TYPE: DNA
<213> ORGANISM: Artificial Sequence
<220> FEATURE:
<223> OTHER INFORMATION: Primer

<400> SEQUENCE: 256
tcaagcagaa gctttggaag aagaagg 27

<210> SEQ ID NO 257
<211> LENGTH: 27
<212> TYPE: DNA
<213> ORGANISM: Artificial Sequence
<220> FEATURE:
<223> OTHER INFORMATION: Primer

<400> SEQUENCE: 257
tcaagccgta cgtattatta ggtgctg 27

<210> SEQ ID NO 258
<211> LENGTH: 27
<212> TYPE: DNA
<213> ORGANISM: Artificial Sequence
<220> FEATURE:
<223> OTHER INFORMATION: Primer

<400> SEQUENCE: 258
tcaataccgc aacagcggtg gcttggg 27

<210> SEQ ID NO 259
<211> LENGTH: 28
<212> TYPE: DNA
<213> ORGANISM: Artificial Sequence
<220> FEATURE:
<223> OTHER INFORMATION: Primer

<400> SEQUENCE: 259
tcaatgaacg accaacaagt gattgatg 28

<210> SEQ ID NO 260
<211> LENGTH: 28
<212> TYPE: DNA
<213> ORGANISM: Artificial Sequence
<220> FEATURE:
<223> OTHER INFORMATION: Primer

<400> SEQUENCE: 260
tcaatgaacg atcaacaagt gattgatg 28

<210> SEQ ID NO 261
<211> LENGTH: 24
<212> TYPE: DNA
<213> ORGANISM: Artificial Sequence
<220> FEATURE:
<223> OTHER INFORMATION: Primer

<400> SEQUENCE: 261
tcacatatcg tgagcaatga actg 24

<210> SEQ ID NO 262
<211> LENGTH: 30
<212> TYPE: DNA
<213> ORGANISM: Artificial Sequence
<220> FEATURE:
<223> OTHER INFORMATION: Primer

<400> SEQUENCE: 262
tcaccaggtt caactcaaaa aatattaaca 30

<210> SEQ ID NO 263
<211> LENGTH: 25
<212> TYPE: DNA
<213> ORGANISM: Artificial Sequence
<220> FEATURE:
<223> OTHER INFORMATION: Primer

<400> SEQUENCE: 263
tcaccagttt gccacgtatc ttcaa 25

<210> SEQ ID NO 264
<211> LENGTH: 28
<212> TYPE: DNA
<213> ORGANISM: Artificial Sequence
<220> FEATURE:
<223> OTHER INFORMATION: Primer

<400> SEQUENCE: 264
tcaccctcat ggtgactcat ctatttat 28

<210> SEQ ID NO 265
<211> LENGTH: 28
<212> TYPE: DNA
<213> ORGANISM: Artificial Sequence
<220> FEATURE:
<223> OTHER INFORMATION: Primer

<400> SEQUENCE: 265
tcaccctcat ggtgattcag ctgtttat 28

<210> SEQ ID NO 266
<211> LENGTH: 25
<212> TYPE: DNA
<213> ORGANISM: Artificial Sequence
<220> FEATURE:
<223> OTHER INFORMATION: Primer

<400> SEQUENCE: 266
tcaccgatat catggcttac cacgg 25

<210> SEQ ID NO 267
<211> LENGTH: 23
<212> TYPE: DNA

<213> ORGANISM: Artificial Sequence
<220> FEATURE:
<223> OTHER INFORMATION: Primer

<400> SEQUENCE: 267
tcaccgtgcc gttcaaggaa gag 23

<210> SEQ ID NO 268
<211> LENGTH: 29
<212> TYPE: DNA
<213> ORGANISM: Artificial Sequence
<220> FEATURE:
<223> OTHER INFORMATION: Primer

<400> SEQUENCE: 268
tcacctccaa gtttagatca cttgagaga 29

<210> SEQ ID NO 269
<211> LENGTH: 26
<212> TYPE: DNA
<213> ORGANISM: Artificial Sequence
<220> FEATURE:
<223> OTHER INFORMATION: Primer

<400> SEQUENCE: 269
tcacgataag aaaaccggtc aagagg 26

<210> SEQ ID NO 270
<211> LENGTH: 27
<212> TYPE: DNA
<213> ORGANISM: Artificial Sequence
<220> FEATURE:
<223> OTHER INFORMATION: Primer

<400> SEQUENCE: 270
tcactcttac atataaggaa ggcgctc 27

<210> SEQ ID NO 271
<211> LENGTH: 25
<212> TYPE: DNA
<213> ORGANISM: Artificial Sequence
<220> FEATURE:
<223> OTHER INFORMATION: Primer

<400> SEQUENCE: 271
tcagaccatg ctcgcagaga aactt 25

<210> SEQ ID NO 272
<211> LENGTH: 25
<212> TYPE: DNA
<213> ORGANISM: Artificial Sequence
<220> FEATURE:
<223> OTHER INFORMATION: Primer

<400> SEQUENCE: 272
tcagagaccg ttttatccta tcagc 25

<210> SEQ ID NO 273
<211> LENGTH: 26
<212> TYPE: DNA
<213> ORGANISM: Artificial Sequence
<220> FEATURE:
<223> OTHER INFORMATION: Primer

<400> SEQUENCE: 273
tcagcaaatg catcacaaac agataa 26

<210> SEQ ID NO 274
<211> LENGTH: 25
<212> TYPE: DNA
<213> ORGANISM: Artificial Sequence
<220> FEATURE:
<223> OTHER INFORMATION: Primer

<400> SEQUENCE: 274
tcagcatatg cacatggaac acctc 25

<210> SEQ ID NO 275
<211> LENGTH: 26
<212> TYPE: DNA
<213> ORGANISM: Artificial Sequence
<220> FEATURE:
<223> OTHER INFORMATION: Primer

<400> SEQUENCE: 275
tcagcatatg cacatggaac acctca 26

<210> SEQ ID NO 276
<211> LENGTH: 22
<212> TYPE: DNA
<213> ORGANISM: Artificial Sequence
<220> FEATURE:
<223> OTHER INFORMATION: Primer

<400> SEQUENCE: 276
tcagccatca aagcagctat tg 22

<210> SEQ ID NO 277
<211> LENGTH: 21
<212> TYPE: DNA
<213> ORGANISM: Artificial Sequence
<220> FEATURE:
<223> OTHER INFORMATION: Primer

<400> SEQUENCE: 277
tcagcgcgta cagtgggtga t 21

<210> SEQ ID NO 278
<211> LENGTH: 25
<212> TYPE: DNA
<213> ORGANISM: Artificial Sequence
<220> FEATURE:
<223> OTHER INFORMATION: Primer

<400> SEQUENCE: 278
tcagcgtatg cacatggaac tcctc 25

<210> SEQ ID NO 279
<211> LENGTH: 23
<212> TYPE: DNA
<213> ORGANISM: Artificial Sequence
<220> FEATURE:
<223> OTHER INFORMATION: Primer

<400> SEQUENCE: 279
tcagctacat cgactatgcg atg 23

<210> SEQ ID NO 280
<211> LENGTH: 30
<212> TYPE: DNA
<213> ORGANISM: Artificial Sequence
<220> FEATURE:
<223> OTHER INFORMATION: Primer

<400> SEQUENCE: 280
tcagctagac cttttaggta aagctaagct 30

<210> SEQ ID NO 281
<211> LENGTH: 29
<212> TYPE: DNA
<213> ORGANISM: Artificial Sequence
<220> FEATURE:
<223> OTHER INFORMATION: Primer

<400> SEQUENCE: 281
tcagctattt ttccaggtat ccaaggtgg 29

<210> SEQ ID NO 282
<211> LENGTH: 23
<212> TYPE: DNA
<213> ORGANISM: Artificial Sequence
<220> FEATURE:
<223> OTHER INFORMATION: Primer

<400> SEQUENCE: 282
tcagctgtcg cagttcatgg acc 23

<210> SEQ ID NO 283
<211> LENGTH: 25
<212> TYPE: DNA
<213> ORGANISM: Artificial Sequence
<220> FEATURE:
<223> OTHER INFORMATION: Primer

<400> SEQUENCE: 283
tcaggaaaag ggcattttac ccttg 25

<210> SEQ ID NO 284
<211> LENGTH: 30
<212> TYPE: DNA
<213> ORGANISM: Artificial Sequence
<220> FEATURE:
<223> OTHER INFORMATION: Primer

<400> SEQUENCE: 284
tcaggagtcg ttcaactcga tctacatgat 30

<210> SEQ ID NO 285
<211> LENGTH: 31
<212> TYPE: DNA
<213> ORGANISM: Artificial Sequence
<220> FEATURE:
<223> OTHER INFORMATION: Primer

<400> SEQUENCE: 285
tcaggagtcg ttcaactcga tctacatgat g 31

<210> SEQ ID NO 286
<211> LENGTH: 30
<212> TYPE: DNA
<213> ORGANISM: Artificial Sequence
<220> FEATURE:
<223> OTHER INFORMATION: Primer

<400> SEQUENCE: 286
tcaggatgga aataaccacc aattcactac 30

<210> SEQ ID NO 287
<211> LENGTH: 23
<212> TYPE: DNA

-continued

<213> ORGANISM: Artificial Sequence
<220> FEATURE:
<223> OTHER INFORMATION: Primer

<400> SEQUENCE: 287
tcaggcattg cggttgggat ggc 23

<210> SEQ ID NO 288
<211> LENGTH: 24
<212> TYPE: DNA
<213> ORGANISM: Artificial Sequence
<220> FEATURE:
<223> OTHER INFORMATION: Primer

<400> SEQUENCE: 288
tcaggtactg ctatccaccc tcaa 24

<210> SEQ ID NO 289
<211> LENGTH: 22
<212> TYPE: DNA
<213> ORGANISM: Artificial Sequence
<220> FEATURE:
<223> OTHER INFORMATION: Primer

<400> SEQUENCE: 289
tcaggtggct tacacggcgt ag 22

<210> SEQ ID NO 290
<211> LENGTH: 26
<212> TYPE: DNA
<213> ORGANISM: Artificial Sequence
<220> FEATURE:
<223> OTHER INFORMATION: Primer

<400> SEQUENCE: 290
tcagtatgta tccaccgtag ccagtc 26

<210> SEQ ID NO 291
<211> LENGTH: 23
<212> TYPE: DNA
<213> ORGANISM: Artificial Sequence
<220> FEATURE:
<223> OTHER INFORMATION: Primer

<400> SEQUENCE: 291
tcagttccgt tatcgccatt gca 23

<210> SEQ ID NO 292
<211> LENGTH: 24
<212> TYPE: DNA
<213> ORGANISM: Artificial Sequence
<220> FEATURE:
<223> OTHER INFORMATION: Primer

<400> SEQUENCE: 292
tcagttccgt tatcgccatt gcat 24

<210> SEQ ID NO 293
<211> LENGTH: 25
<212> TYPE: DNA
<213> ORGANISM: Artificial Sequence
<220> FEATURE:
<223> OTHER INFORMATION: Primer

<400> SEQUENCE: 293
tcagttccgt tatcgccatt gcatt 25

<210> SEQ ID NO 294
<211> LENGTH: 24
<212> TYPE: DNA
<213> ORGANISM: Artificial Sequence
<220> FEATURE:
<223> OTHER INFORMATION: Primer

<400> SEQUENCE: 294
tcagttcggc ggtcagcgct tcgg 24

<210> SEQ ID NO 295
<211> LENGTH: 34
<212> TYPE: DNA
<213> ORGANISM: Artificial Sequence
<220> FEATURE:
<223> OTHER INFORMATION: Primer

<400> SEQUENCE: 295
tcagttttaa tgtctcgtat gatcgaatca aaag 34

<210> SEQ ID NO 296
<211> LENGTH: 24
<212> TYPE: DNA
<213> ORGANISM: Artificial Sequence
<220> FEATURE:
<223> OTHER INFORMATION: Primer

<400> SEQUENCE: 296
tcatccacac ggtggtggtg aagg 24

<210> SEQ ID NO 297
<211> LENGTH: 28
<212> TYPE: DNA
<213> ORGANISM: Artificial Sequence
<220> FEATURE:
<223> OTHER INFORMATION: Primer

<400> SEQUENCE: 297
tcatcctaag ccaagtgtag actctgta 28

<210> SEQ ID NO 298
<211> LENGTH: 31
<212> TYPE: DNA
<213> ORGANISM: Artificial Sequence
<220> FEATURE:
<223> OTHER INFORMATION: Primer

<400> SEQUENCE: 298
tcatgataat atctttgaaa tcggctcagg a 31

<210> SEQ ID NO 299
<211> LENGTH: 33
<212> TYPE: DNA
<213> ORGANISM: Artificial Sequence
<220> FEATURE:
<223> OTHER INFORMATION: Primer

<400> SEQUENCE: 299
tcatgttgag cttaaaccta tagaagtaaa agc 33

<210> SEQ ID NO 300
<211> LENGTH: 27
<212> TYPE: DNA
<213> ORGANISM: Artificial Sequence
<220> FEATURE:
<223> OTHER INFORMATION: Primer

<400> SEQUENCE: 300
tcattatcat gcgccaatga gtgcaga 27

<210> SEQ ID NO 301
<211> LENGTH: 28
<212> TYPE: DNA
<213> ORGANISM: Artificial Sequence
<220> FEATURE:
<223> OTHER INFORMATION: Primer

<400> SEQUENCE: 301
tcattcaaga actagatctt caggcaag 28

<210> SEQ ID NO 302
<211> LENGTH: 26
<212> TYPE: DNA
<213> ORGANISM: Artificial Sequence
<220> FEATURE:
<223> OTHER INFORMATION: Primer

<400> SEQUENCE: 302
tccaaaaaaa tcagcgcgta cagtgg 26

<210> SEQ ID NO 303
<211> LENGTH: 29
<212> TYPE: DNA
<213> ORGANISM: Artificial Sequence
<220> FEATURE:
<223> OTHER INFORMATION: Primer

<400> SEQUENCE: 303
tccaaaccag gtgtatcaag aacatcagg 29

<210> SEQ ID NO 304
<211> LENGTH: 29
<212> TYPE: DNA
<213> ORGANISM: Artificial Sequence
<220> FEATURE:
<223> OTHER INFORMATION: Primer

<400> SEQUENCE: 304
tccaaataag tggcgttaca aatactgaa 29

<210> SEQ ID NO 305
<211> LENGTH: 32
<212> TYPE: DNA
<213> ORGANISM: Artificial Sequence
<220> FEATURE:
<223> OTHER INFORMATION: Primer

<400> SEQUENCE: 305
tccaacgaag tacaatacaa gacaaaagaa gg 32

<210> SEQ ID NO 306
<211> LENGTH: 32
<212> TYPE: DNA
<213> ORGANISM: Artificial Sequence
<220> FEATURE:
<223> OTHER INFORMATION: Primer

<400> SEQUENCE: 306
tccaaggtac actaaactta cttgagctaa tg 32

<210> SEQ ID NO 307
<211> LENGTH: 24
<212> TYPE: DNA

<213> ORGANISM: Artificial Sequence
<220> FEATURE:
<223> OTHER INFORMATION: Primer

<400> SEQUENCE: 307
tccaatgcca caaactcgtg aaca 24

<210> SEQ ID NO 308
<211> LENGTH: 24
<212> TYPE: DNA
<213> ORGANISM: Artificial Sequence
<220> FEATURE:
<223> OTHER INFORMATION: Primer

<400> SEQUENCE: 308
tccacacgcc gttcttcaac aact 24

<210> SEQ ID NO 309
<211> LENGTH: 21
<212> TYPE: DNA
<213> ORGANISM: Artificial Sequence
<220> FEATURE:
<223> OTHER INFORMATION: Primer

<400> SEQUENCE: 309
tccacacggt ggtggtgaag g 21

<210> SEQ ID NO 310
<211> LENGTH: 26
<212> TYPE: DNA
<213> ORGANISM: Artificial Sequence
<220> FEATURE:
<223> OTHER INFORMATION: Primer

<400> SEQUENCE: 310
tccaccaaga gcaagatcaa ataggc 26

<210> SEQ ID NO 311
<211> LENGTH: 20
<212> TYPE: DNA
<213> ORGANISM: Artificial Sequence
<220> FEATURE:
<223> OTHER INFORMATION: Primer

<400> SEQUENCE: 311
tccacggtca tggagcgcta 20

<210> SEQ ID NO 312
<211> LENGTH: 30
<212> TYPE: DNA
<213> ORGANISM: Artificial Sequence
<220> FEATURE:
<223> OTHER INFORMATION: Primer

<400> SEQUENCE: 312
tccacttatc gcaaatggaa aattaagcaa 30

<210> SEQ ID NO 313
<211> LENGTH: 33
<212> TYPE: DNA
<213> ORGANISM: Artificial Sequence
<220> FEATURE:
<223> OTHER INFORMATION: Primer

<400> SEQUENCE: 313
tccagatgga caaattttct tagaaactga ttt 33

<210> SEQ ID NO 314
<211> LENGTH: 26
<212> TYPE: DNA
<213> ORGANISM: Artificial Sequence
<220> FEATURE:
<223> OTHER INFORMATION: Primer

<400> SEQUENCE: 314
tccagcacga attgctgcta tgaaag 26

<210> SEQ ID NO 315
<211> LENGTH: 33
<212> TYPE: DNA
<213> ORGANISM: Artificial Sequence
<220> FEATURE:
<223> OTHER INFORMATION: Primer

<400> SEQUENCE: 315
tccaggacaa atgtatgaaa aatgtccaag aag 33

<210> SEQ ID NO 316
<211> LENGTH: 25
<212> TYPE: DNA
<213> ORGANISM: Artificial Sequence
<220> FEATURE:
<223> OTHER INFORMATION: Primer

<400> SEQUENCE: 316
tccattgttc gtatggctca agact 25

<210> SEQ ID NO 317
<211> LENGTH: 31
<212> TYPE: DNA
<213> ORGANISM: Artificial Sequence
<220> FEATURE:
<223> OTHER INFORMATION: Primer

<400> SEQUENCE: 317
tcccaattaa ttctgccatt tttccaggta t 31

<210> SEQ ID NO 318
<211> LENGTH: 34
<212> TYPE: DNA
<213> ORGANISM: Artificial Sequence
<220> FEATURE:
<223> OTHER INFORMATION: Primer

<400> SEQUENCE: 318
tcccacgaaa cagatgaaga aattaacaaa aaag 34

<210> SEQ ID NO 319
<211> LENGTH: 30
<212> TYPE: DNA
<213> ORGANISM: Artificial Sequence
<220> FEATURE:
<223> OTHER INFORMATION: Primer

<400> SEQUENCE: 319
tcccagctag accttttagg taaagctaag 30

<210> SEQ ID NO 320
<211> LENGTH: 26
<212> TYPE: DNA
<213> ORGANISM: Artificial Sequence
<220> FEATURE:
<223> OTHER INFORMATION: Primer

<400> SEQUENCE: 320
tcccaggtga cgatgtacct gtaatc 26

<210> SEQ ID NO 321
<211> LENGTH: 26
<212> TYPE: DNA
<213> ORGANISM: Artificial Sequence
<220> FEATURE:
<223> OTHER INFORMATION: Primer

<400> SEQUENCE: 321
tccccaggac accctgaaat ttcaac 26

<210> SEQ ID NO 322
<211> LENGTH: 34
<212> TYPE: DNA
<213> ORGANISM: Artificial Sequence
<220> FEATURE:
<223> OTHER INFORMATION: Primer

<400> SEQUENCE: 322
tcccccacgc tttaattgtt tatgatgatt tgag 34

<210> SEQ ID NO 323
<211> LENGTH: 31
<212> TYPE: DNA
<213> ORGANISM: Artificial Sequence
<220> FEATURE:
<223> OTHER INFORMATION: Primer

<400> SEQUENCE: 323
tcccggactt aatatcaatg aaaattgtgg a 31

<210> SEQ ID NO 324
<211> LENGTH: 28
<212> TYPE: DNA
<213> ORGANISM: Artificial Sequence
<220> FEATURE:
<223> OTHER INFORMATION: Primer

<400> SEQUENCE: 324
tcccggagct tttatgacta aagcagat 28

<210> SEQ ID NO 325
<211> LENGTH: 19
<212> TYPE: DNA
<213> ORGANISM: Artificial Sequence
<220> FEATURE:
<223> OTHER INFORMATION: Primer

<400> SEQUENCE: 325
tccgcggagt tgactgggt 19

<210> SEQ ID NO 326
<211> LENGTH: 20
<212> TYPE: DNA
<213> ORGANISM: Artificial Sequence
<220> FEATURE:
<223> OTHER INFORMATION: Primer

<400> SEQUENCE: 326
tccgctgaat ctgtcgccgc 20

<210> SEQ ID NO 327
<211> LENGTH: 23
<212> TYPE: DNA

<213> ORGANISM: Artificial Sequence
<220> FEATURE:
<223> OTHER INFORMATION: Primer

<400> SEQUENCE: 327
tccggctcac gttattatgg tac 23

<210> SEQ ID NO 328
<211> LENGTH: 27
<212> TYPE: DNA
<213> ORGANISM: Artificial Sequence
<220> FEATURE:
<223> OTHER INFORMATION: Primer

<400> SEQUENCE: 328
tccgtacgta ttattaggtg ctggtca 27

<210> SEQ ID NO 329
<211> LENGTH: 30
<212> TYPE: DNA
<213> ORGANISM: Artificial Sequence
<220> FEATURE:
<223> OTHER INFORMATION: Primer

<400> SEQUENCE: 329
tccgttatcg ccattgcatt atttggaact 30

<210> SEQ ID NO 330
<211> LENGTH: 33
<212> TYPE: DNA
<213> ORGANISM: Artificial Sequence
<220> FEATURE:
<223> OTHER INFORMATION: Primer

<400> SEQUENCE: 330
tccgttctta caaatagcaa tagaacttga agc 33

<210> SEQ ID NO 331
<211> LENGTH: 36
<212> TYPE: DNA
<213> ORGANISM: Artificial Sequence
<220> FEATURE:
<223> OTHER INFORMATION: Primer

<400> SEQUENCE: 331
tccgttgatt attgttatcc tgttatgcca tttgag 36

<210> SEQ ID NO 332
<211> LENGTH: 34
<212> TYPE: DNA
<213> ORGANISM: Artificial Sequence
<220> FEATURE:
<223> OTHER INFORMATION: Primer

<400> SEQUENCE: 332
tcctaatgga cttaatatca atgaaaattg tgga 34

<210> SEQ ID NO 333
<211> LENGTH: 22
<212> TYPE: DNA
<213> ORGANISM: Artificial Sequence
<220> FEATURE:
<223> OTHER INFORMATION: Primer

<400> SEQUENCE: 333
tcctagagga atggctgcca cg 22

<210> SEQ ID NO 334
<211> LENGTH: 30
<212> TYPE: DNA
<213> ORGANISM: Artificial Sequence
<220> FEATURE:
<223> OTHER INFORMATION: Primer

<400> SEQUENCE: 334
tcctatatta atcgtttaca gaaactggct 30

<210> SEQ ID NO 335
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (15)...(15)
<223> OTHER INFORMATION: I

<400> SEQUENCE: 335
tcctcaatga acgatcaaca agtgattgat g 31

<210> SEQ ID NO 336
<211> LENGTH: 31
<212> TYPE: DNA
<213> ORGANISM: Artificial Sequence
<220> FEATURE:
<223> OTHER INFORMATION: Primer

<400> SEQUENCE: 336
tcctcaatga atgatcaaca agtgattgat g 31

<210> SEQ ID NO 337
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (15)...(15)
<223> OTHER INFORMATION: I
<220> FEATURE:
<221> NAME/KEY: modified_base
<222> LOCATION: (24)...(24)
<223> OTHER INFORMATION: I

<400> SEQUENCE: 337
tcctcgatga acgatcaaca agtgattgat g 31

<210> SEQ ID NO 338
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (15)...(15)
<223> OTHER INFORMATION: I
<220> FEATURE:
<221> NAME/KEY: modified_base
<222> LOCATION: (24)...(24)
<223> OTHER INFORMATION: I

<400> SEQUENCE: 338
tcctcgatga atgatcaaca agtgattgat g 31

<210> SEQ ID NO 339
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)...(6)
<223> OTHER INFORMATION: I
<220> FEATURE:
<221> NAME/KEY: modified_base
<222> LOCATION: (15)...(15)
<223> OTHER INFORMATION: I

<400> SEQUENCE: 339
tcctcgatga acgatcaaca agtgattgat g 31

<210> SEQ ID NO 340
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)...(6)
<223> OTHER INFORMATION: I
<220> FEATURE:
<221> NAME/KEY: modified_base
<222> LOCATION: (12)...(12)
<223> OTHER INFORMATION: I
<220> FEATURE:
<221> NAME/KEY: modified_base
<222> LOCATION: (15)...(15)
<223> OTHER INFORMATION: I
<220> FEATURE:
<221> NAME/KEY: modified_base
<222> LOCATION: (24)...(24)
<223> OTHER INFORMATION: I

<400> SEQUENCE: 340
tcctcgatga acgatcaaca agtgattgat g 31

<210> SEQ ID NO 341
<211> LENGTH: 20
<212> TYPE: DNA
<213> ORGANISM: Artificial Sequence
<220> FEATURE:
<223> OTHER INFORMATION: Primer

<400> SEQUENCE: 341
tcctgaaaaa tggagcacgg 20

<210> SEQ ID NO 342
<211> LENGTH: 23
<212> TYPE: DNA
<213> ORGANISM: Artificial Sequence
<220> FEATURE:
<223> OTHER INFORMATION: Primer

<400> SEQUENCE: 342
tcctgaagca agtgcattta cga 23

<210> SEQ ID NO 343
<211> LENGTH: 28
<212> TYPE: DNA
<213> ORGANISM: Artificial Sequence
<220> FEATURE:
<223> OTHER INFORMATION: Primer

<400> SEQUENCE: 343
tcctgaccga cccattattc cctttatc 28

<210> SEQ ID NO 344
<211> LENGTH: 33
<212> TYPE: DNA
<213> ORGANISM: Artificial Sequence
<220> FEATURE:
<223> OTHER INFORMATION: Primer

<400> SEQUENCE: 344
tcctgatgct caaagtgctt ttttagatcc ttt 33

<210> SEQ ID NO 345
<211> LENGTH: 34
<212> TYPE: DNA
<213> ORGANISM: Artificial Sequence
<220> FEATURE:
<223> OTHER INFORMATION: Primer

<400> SEQUENCE: 345
tcctgttatc cctgaagtag ttaatcaagt ttgt 34

<210> SEQ ID NO 346
<211> LENGTH: 35
<212> TYPE: DNA
<213> ORGANISM: Artificial Sequence
<220> FEATURE:
<223> OTHER INFORMATION: Primer

<400> SEQUENCE: 346
tcctgttatc cctgaagtag ttaatcaagt ttgtt 35

<210> SEQ ID NO 347
<211> LENGTH: 36
<212> TYPE: DNA
<213> ORGANISM: Artificial Sequence
<220> FEATURE:
<223> OTHER INFORMATION: Primer

<400> SEQUENCE: 347
tcctgttatt cctgaagtag ttaatcaagt ttgtta 36

<210> SEQ ID NO 348
<211> LENGTH: 31
<212> TYPE: DNA
<213> ORGANISM: Artificial Sequence
<220> FEATURE:
<223> OTHER INFORMATION: Primer

<400> SEQUENCE: 348
tccttacttc gaactatgaa tcttttggaa g 31

<210> SEQ ID NO 349
<211> LENGTH: 29
<212> TYPE: DNA
<213> ORGANISM: Artificial Sequence
<220> FEATURE:
<223> OTHER INFORMATION: Primer

<400> SEQUENCE: 349
tccttatagg gatggctatc agtaatgtt 29

<210> SEQ ID NO 350
<211> LENGTH: 22
<212> TYPE: DNA

<213> ORGANISM: Artificial Sequence
<220> FEATURE:
<223> OTHER INFORMATION: Primer

<400> SEQUENCE: 350
tccttgaccg cctttccgat ac 22

<210> SEQ ID NO 351
<211> LENGTH: 33
<212> TYPE: DNA
<213> ORGANISM: Artificial Sequence
<220> FEATURE:
<223> OTHER INFORMATION: Primer

<400> SEQUENCE: 351
tccttgcttt agttttaagt gcatgtaatt caa 33

<210> SEQ ID NO 352
<211> LENGTH: 32
<212> TYPE: DNA
<213> ORGANISM: Artificial Sequence
<220> FEATURE:
<223> OTHER INFORMATION: Primer

<400> SEQUENCE: 352
tcctttgata tattatgcga tggaaggttg gt 32

<210> SEQ ID NO 353
<211> LENGTH: 30
<212> TYPE: DNA
<213> ORGANISM: Artificial Sequence
<220> FEATURE:
<223> OTHER INFORMATION: Primer

<400> SEQUENCE: 353
tcctttgatg catgtaattg ctgcaaaagc 30

<210> SEQ ID NO 354
<211> LENGTH: 31
<212> TYPE: DNA
<213> ORGANISM: Artificial Sequence
<220> FEATURE:
<223> OTHER INFORMATION: Primer

<400> SEQUENCE: 354
tcgaaagctt ttgcatatta tatcgagcca c 31

<210> SEQ ID NO 355
<211> LENGTH: 28
<212> TYPE: DNA
<213> ORGANISM: Artificial Sequence
<220> FEATURE:
<223> OTHER INFORMATION: Primer

<400> SEQUENCE: 355
tcgaagtaca atacaagaca aaagaagg 28

<210> SEQ ID NO 356
<211> LENGTH: 28
<212> TYPE: DNA
<213> ORGANISM: Artificial Sequence
<220> FEATURE:
<223> OTHER INFORMATION: Primer

<400> SEQUENCE: 356
tcgacaacac cattatctat ggtgtgaa 28

<210> SEQ ID NO 357
<211> LENGTH: 23
<212> TYPE: DNA
<213> ORGANISM: Artificial Sequence
<220> FEATURE:
<223> OTHER INFORMATION: Primer

<400> SEQUENCE: 357
tcgacctttg gcaggaacta gac 23

<210> SEQ ID NO 358
<211> LENGTH: 17
<212> TYPE: DNA
<213> ORGANISM: Artificial Sequence
<220> FEATURE:
<223> OTHER INFORMATION: Primer

<400> SEQUENCE: 358
tcgagcaggc gctgccg 17

<210> SEQ ID NO 359
<211> LENGTH: 31
<212> TYPE: DNA
<213> ORGANISM: Artificial Sequence
<220> FEATURE:
<223> OTHER INFORMATION: Primer

<400> SEQUENCE: 359
tcgagtatag ctaaaaaaat agtttatgac a 31

<210> SEQ ID NO 360
<211> LENGTH: 26
<212> TYPE: DNA
<213> ORGANISM: Artificial Sequence
<220> FEATURE:
<223> OTHER INFORMATION: Primer

<400> SEQUENCE: 360
tcgatctggt ttcatgctgt ttcagt 26

<210> SEQ ID NO 361
<211> LENGTH: 28
<212> TYPE: DNA
<213> ORGANISM: Artificial Sequence
<220> FEATURE:
<223> OTHER INFORMATION: Primer

<400> SEQUENCE: 361
tcgatgaacg accaacaagt gattgatg 28

<210> SEQ ID NO 362
<211> LENGTH: 24
<212> TYPE: DNA
<213> ORGANISM: Artificial Sequence
<220> FEATURE:
<223> OTHER INFORMATION: Primer

<400> SEQUENCE: 362
tcgattaggc agcaacgaaa gccg 24

<210> SEQ ID NO 363
<211> LENGTH: 24
<212> TYPE: DNA
<213> ORGANISM: Artificial Sequence
<220> FEATURE:
<223> OTHER INFORMATION: Primer

<400> SEQUENCE: 363
tcgcaaaaaa atccagctat tagc 24

<210> SEQ ID NO 364
<211> LENGTH: 26
<212> TYPE: DNA
<213> ORGANISM: Artificial Sequence
<220> FEATURE:
<223> OTHER INFORMATION: Primer

<400> SEQUENCE: 364
tcgccaatca aaactaaggg aatggc 26

<210> SEQ ID NO 365
<211> LENGTH: 19
<212> TYPE: DNA
<213> ORGANISM: Artificial Sequence
<220> FEATURE:
<223> OTHER INFORMATION: Primer

<400> SEQUENCE: 365
tcgccatcgt caccaaccg 19

<210> SEQ ID NO 366
<211> LENGTH: 16
<212> TYPE: DNA
<213> ORGANISM: Artificial Sequence
<220> FEATURE:
<223> OTHER INFORMATION: Primer

<400> SEQUENCE: 366
tcgcccgcga ggacgt 16

<210> SEQ ID NO 367
<211> LENGTH: 21
<212> TYPE: DNA
<213> ORGANISM: Artificial Sequence
<220> FEATURE:
<223> OTHER INFORMATION: Primer

<400> SEQUENCE: 367
tcgccgactt cgacggtgac c 21

<210> SEQ ID NO 368
<211> LENGTH: 22
<212> TYPE: DNA
<213> ORGANISM: Artificial Sequence
<220> FEATURE:
<223> OTHER INFORMATION: Primer

<400> SEQUENCE: 368
tcgccggcaa tgccattgga ta 22

<210> SEQ ID NO 369
<211> LENGTH: 23
<212> TYPE: DNA
<213> ORGANISM: Artificial Sequence
<220> FEATURE:
<223> OTHER INFORMATION: Primer

<400> SEQUENCE: 369
tcgccgtgga aaaatcctac gct 23

<210> SEQ ID NO 370
<211> LENGTH: 31
<212> TYPE: DNA

<213> ORGANISM: Artificial Sequence
<220> FEATURE:
<223> OTHER INFORMATION: Primer

<400> SEQUENCE: 370
tcgcgttgca acaaaacttt ctaaagtatg t 31

<210> SEQ ID NO 371
<211> LENGTH: 24
<212> TYPE: DNA
<213> ORGANISM: Artificial Sequence
<220> FEATURE:
<223> OTHER INFORMATION: Primer

<400> SEQUENCE: 371
tcgctacagg ccctttagga caag 24

<210> SEQ ID NO 372
<211> LENGTH: 27
<212> TYPE: DNA
<213> ORGANISM: Artificial Sequence
<220> FEATURE:
<223> OTHER INFORMATION: Primer

<400> SEQUENCE: 372
tcgctatctt atcgttgaga agggatt 27

<210> SEQ ID NO 373
<211> LENGTH: 24
<212> TYPE: DNA
<213> ORGANISM: Artificial Sequence
<220> FEATURE:
<223> OTHER INFORMATION: Primer

<400> SEQUENCE: 373
tcggaatctg atgttgcagt tgtt 24

<210> SEQ ID NO 374
<211> LENGTH: 22
<212> TYPE: DNA
<213> ORGANISM: Artificial Sequence
<220> FEATURE:
<223> OTHER INFORMATION: Primer

<400> SEQUENCE: 374
tcggccgcac cttcatcgaa gt 22

<210> SEQ ID NO 375
<211> LENGTH: 28
<212> TYPE: DNA
<213> ORGANISM: Artificial Sequence
<220> FEATURE:
<223> OTHER INFORMATION: Primer

<400> SEQUENCE: 375
tcggcgaaat ccgtattcct gaaaatga 28

<210> SEQ ID NO 376
<211> LENGTH: 18
<212> TYPE: DNA
<213> ORGANISM: Artificial Sequence
<220> FEATURE:
<223> OTHER INFORMATION: Primer

<400> SEQUENCE: 376
tcggcgcctg cctgatga 18

<210> SEQ ID NO 377
<211> LENGTH: 23
<212> TYPE: DNA
<213> ORGANISM: Artificial Sequence
<220> FEATURE:
<223> OTHER INFORMATION: Primer

<400> SEQUENCE: 377
tcgggtgatg atgcgcgtga agg 23

<210> SEQ ID NO 378
<211> LENGTH: 31
<212> TYPE: DNA
<213> ORGANISM: Artificial Sequence
<220> FEATURE:
<223> OTHER INFORMATION: Primer

<400> SEQUENCE: 378
tcggtttagt aaaagaacgt attgctcaac c 31

<210> SEQ ID NO 379
<211> LENGTH: 28
<212> TYPE: DNA
<213> ORGANISM: Artificial Sequence
<220> FEATURE:
<223> OTHER INFORMATION: Primer

<400> SEQUENCE: 379
tcgtacgtat tattaggtgc tggtcact 28

<210> SEQ ID NO 380
<211> LENGTH: 21
<212> TYPE: DNA
<213> ORGANISM: Artificial Sequence
<220> FEATURE:
<223> OTHER INFORMATION: Primer

<400> SEQUENCE: 380
tcgtatggct caatggtgga g 21

<210> SEQ ID NO 381
<211> LENGTH: 30
<212> TYPE: DNA
<213> ORGANISM: Artificial Sequence
<220> FEATURE:
<223> OTHER INFORMATION: Primer

<400> SEQUENCE: 381
tcgtcttttt gattctttcc ctgataatgc 30

<210> SEQ ID NO 382
<211> LENGTH: 32
<212> TYPE: DNA
<213> ORGANISM: Artificial Sequence
<220> FEATURE:
<223> OTHER INFORMATION: Primer

<400> SEQUENCE: 382
tcgtcttttt gattctttcc ctgataatgc tc 32

<210> SEQ ID NO 383
<211> LENGTH: 25
<212> TYPE: DNA
<213> ORGANISM: Artificial Sequence
<220> FEATURE:
<223> OTHER INFORMATION: Primer

<400> SEQUENCE: 383
tcgtgattat ggatggcaac gtgaa 25

<210> SEQ ID NO 384
<211> LENGTH: 24
<212> TYPE: DNA
<213> ORGANISM: Artificial Sequence
<220> FEATURE:
<223> OTHER INFORMATION: Primer

<400> SEQUENCE: 384
tcgtgcccgc aatttgcata aagc 24

<210> SEQ ID NO 385
<211> LENGTH: 21
<212> TYPE: DNA
<213> ORGANISM: Artificial Sequence
<220> FEATURE:
<223> OTHER INFORMATION: Primer

<400> SEQUENCE: 385
tcgtggcggc gtggttatcg a 21

<210> SEQ ID NO 386
<211> LENGTH: 27
<212> TYPE: DNA
<213> ORGANISM: Artificial Sequence
<220> FEATURE:
<223> OTHER INFORMATION: Primer

<400> SEQUENCE: 386
tcgtgttgaa cgtggtcaaa tcaaagt 27

<210> SEQ ID NO 387
<211> LENGTH: 23
<212> TYPE: DNA
<213> ORGANISM: Artificial Sequence
<220> FEATURE:
<223> OTHER INFORMATION: Primer

<400> SEQUENCE: 387
tcgttcctgg aacacgatga cgc 23

<210> SEQ ID NO 388
<211> LENGTH: 27
<212> TYPE: DNA
<213> ORGANISM: Artificial Sequence
<220> FEATURE:
<223> OTHER INFORMATION: Primer

<400> SEQUENCE: 388
tcgtttggtg gtggtagatg aaaaagg 27

<210> SEQ ID NO 389
<211> LENGTH: 11
<212> TYPE: DNA
<213> ORGANISM: Artificial Sequence
<220> FEATURE:
<223> OTHER INFORMATION: Primer

<400> SEQUENCE: 389
tccaccctca a 11

<210> SEQ ID NO 390
<211> LENGTH: 25
<212> TYPE: DNA

<213> ORGANISM: Artificial Sequence
<220> FEATURE:
<223> OTHER INFORMATION: Primer

<400> SEQUENCE: 390
tctaaaacac caggtcaccc agaag 25

<210> SEQ ID NO 391
<211> LENGTH: 24
<212> TYPE: DNA
<213> ORGANISM: Artificial Sequence
<220> FEATURE:
<223> OTHER INFORMATION: Primer

<400> SEQUENCE: 391
tctaaatggt cgtgcagttg cgtg 24

<210> SEQ ID NO 392
<211> LENGTH: 30
<212> TYPE: DNA
<213> ORGANISM: Artificial Sequence
<220> FEATURE:
<223> OTHER INFORMATION: Primer

<400> SEQUENCE: 392
tctactgatt ttggtaatct tgcagcacag 30

<210> SEQ ID NO 393
<211> LENGTH: 24
<212> TYPE: DNA
<213> ORGANISM: Artificial Sequence
<220> FEATURE:
<223> OTHER INFORMATION: Primer

<400> SEQUENCE: 393
tctagtaata ataggaccct cagc 24

<210> SEQ ID NO 394
<211> LENGTH: 31
<212> TYPE: DNA
<213> ORGANISM: Artificial Sequence
<220> FEATURE:
<223> OTHER INFORMATION: Primer

<400> SEQUENCE: 394
tctcaaggtg atattggtgt aggtaactta a 31

<210> SEQ ID NO 395
<211> LENGTH: 24
<212> TYPE: DNA
<213> ORGANISM: Artificial Sequence
<220> FEATURE:
<223> OTHER INFORMATION: Primer

<400> SEQUENCE: 395
tctcattacg ttgcatcgga aaca 24

<210> SEQ ID NO 396
<211> LENGTH: 30
<212> TYPE: DNA
<213> ORGANISM: Artificial Sequence
<220> FEATURE:
<223> OTHER INFORMATION: Primer

<400> SEQUENCE: 396
tctcgatgaa cgaccaacaa gtgattgatg 30

<210> SEQ ID NO 397
<211> LENGTH: 28
<212> TYPE: DNA
<213> ORGANISM: Artificial Sequence
<220> FEATURE:
<223> OTHER INFORMATION: Primer

<400> SEQUENCE: 397
tctcgtggtg cacaagtaac ggatatta 28

<210> SEQ ID NO 398
<211> LENGTH: 32
<212> TYPE: DNA
<213> ORGANISM: Artificial Sequence
<220> FEATURE:
<223> OTHER INFORMATION: Primer

<400> SEQUENCE: 398
tctgaaatga atagtgatag aactgtaggc ac 32

<210> SEQ ID NO 399
<211> LENGTH: 32
<212> TYPE: DNA
<213> ORGANISM: Artificial Sequence
<220> FEATURE:
<223> OTHER INFORMATION: Primer

<400> SEQUENCE: 399
tctgaacatg ataatatctt tgaaatcggc tc 32

<210> SEQ ID NO 400
<211> LENGTH: 30
<212> TYPE: DNA
<213> ORGANISM: Artificial Sequence
<220> FEATURE:
<223> OTHER INFORMATION: Primer

<400> SEQUENCE: 400
tctgaatgtc tatatggagg tacaacacta 30

<210> SEQ ID NO 401
<211> LENGTH: 19
<212> TYPE: DNA
<213> ORGANISM: Artificial Sequence
<220> FEATURE:
<223> OTHER INFORMATION: Primer

<400> SEQUENCE: 401
tctgacacct gcccggtgc 19

<210> SEQ ID NO 402
<211> LENGTH: 20
<212> TYPE: DNA
<213> ORGANISM: Artificial Sequence
<220> FEATURE:
<223> OTHER INFORMATION: Primer

<400> SEQUENCE: 402
tctgcccgtg tcgttggtga 20

<210> SEQ ID NO 403
<211> LENGTH: 24
<212> TYPE: DNA
<213> ORGANISM: Artificial Sequence
<220> FEATURE:
<223> OTHER INFORMATION: Primer

<400> SEQUENCE: 403
tctggaggca caccaaataa aaca 24

<210> SEQ ID NO 404
<211> LENGTH: 21
<212> TYPE: DNA
<213> ORGANISM: Artificial Sequence
<220> FEATURE:
<223> OTHER INFORMATION: Primer

<400> SEQUENCE: 404
tctggataac ggtcgtcgcg g 21

<210> SEQ ID NO 405
<211> LENGTH: 25
<212> TYPE: DNA
<213> ORGANISM: Artificial Sequence
<220> FEATURE:
<223> OTHER INFORMATION: Primer

<400> SEQUENCE: 405
tctggcaggt atgcgtggtc tgatg 25

<210> SEQ ID NO 406
<211> LENGTH: 24
<212> TYPE: DNA
<213> ORGANISM: Artificial Sequence
<220> FEATURE:
<223> OTHER INFORMATION: Primer

<400> SEQUENCE: 406
tctggctaaa actttggcaa cggt 24

<210> SEQ ID NO 407
<211> LENGTH: 29
<212> TYPE: DNA
<213> ORGANISM: Artificial Sequence
<220> FEATURE:
<223> OTHER INFORMATION: Primer

<400> SEQUENCE: 407
tctggtccaa caaaaggaac gattacagg 29

<210> SEQ ID NO 408
<211> LENGTH: 25
<212> TYPE: DNA
<213> ORGANISM: Artificial Sequence
<220> FEATURE:
<223> OTHER INFORMATION: Primer

<400> SEQUENCE: 408
tctgtcccta gtacgagagg accgg 25

<210> SEQ ID NO 409
<211> LENGTH: 23
<212> TYPE: DNA
<213> ORGANISM: Artificial Sequence
<220> FEATURE:
<223> OTHER INFORMATION: Primer

<400> SEQUENCE: 409
tctgttctta gtacgagagg acc 23

<210> SEQ ID NO 410
<211> LENGTH: 26
<212> TYPE: DNA

<213> ORGANISM: Artificial Sequence
<220> FEATURE:
<223> OTHER INFORMATION: Primer

<400> SEQUENCE: 410
tcttatgcca agaggacaga gtgagt 26

<210> SEQ ID NO 411
<211> LENGTH: 29
<212> TYPE: DNA
<213> ORGANISM: Artificial Sequence
<220> FEATURE:
<223> OTHER INFORMATION: Primer

<400> SEQUENCE: 411
tcttatgcca agaggacaga gtgagtact 29

<210> SEQ ID NO 412
<211> LENGTH: 31
<212> TYPE: DNA
<213> ORGANISM: Artificial Sequence
<220> FEATURE:
<223> OTHER INFORMATION: Primer

<400> SEQUENCE: 412
tcttattcca acttcaaacc gaactatgac g 31

<210> SEQ ID NO 413
<211> LENGTH: 29
<212> TYPE: DNA
<213> ORGANISM: Artificial Sequence
<220> FEATURE:
<223> OTHER INFORMATION: Primer

<400> SEQUENCE: 413
tcttctcatc ctatggctat tatgcttgc 29

<210> SEQ ID NO 414
<211> LENGTH: 33
<212> TYPE: DNA
<213> ORGANISM: Artificial Sequence
<220> FEATURE:
<223> OTHER INFORMATION: Primer

<400> SEQUENCE: 414
tcttgatact tgtaatgtgg gcgataaata tgt 33

<210> SEQ ID NO 415
<211> LENGTH: 32
<212> TYPE: DNA
<213> ORGANISM: Artificial Sequence
<220> FEATURE:
<223> OTHER INFORMATION: Primer

<400> SEQUENCE: 415
tcttgcagca gtttatttga tgaacctaaa gt 32

<210> SEQ ID NO 416
<211> LENGTH: 28
<212> TYPE: DNA
<213> ORGANISM: Artificial Sequence
<220> FEATURE:
<223> OTHER INFORMATION: Primer

<400> SEQUENCE: 416
tcttgctctt tcgtgagttc agtaaatg 28

-continued

<210> SEQ ID NO 417
<211> LENGTH: 31
<212> TYPE: DNA
<213> ORGANISM: Artificial Sequence
<220> FEATURE:
<223> OTHER INFORMATION: Primer

<400> SEQUENCE: 417
tcttgtactt gtggctcaca cggctgtttg g 31

<210> SEQ ID NO 418
<211> LENGTH: 27
<212> TYPE: DNA
<213> ORGANISM: Artificial Sequence
<220> FEATURE:
<223> OTHER INFORMATION: Primer

<400> SEQUENCE: 418
tcttgtttat gctggtaaag cagatgg 27

<210> SEQ ID NO 419
<211> LENGTH: 28
<212> TYPE: DNA
<213> ORGANISM: Artificial Sequence
<220> FEATURE:
<223> OTHER INFORMATION: Primer

<400> SEQUENCE: 419
tctttatggt ggagatgact gaaaccga 28

<210> SEQ ID NO 420
<211> LENGTH: 28
<212> TYPE: DNA
<213> ORGANISM: Artificial Sequence
<220> FEATURE:
<223> OTHER INFORMATION: Primer

<400> SEQUENCE: 420
tctttcttga atgctggtgt acgtatcg 28

<210> SEQ ID NO 421
<211> LENGTH: 25
<212> TYPE: DNA
<213> ORGANISM: Artificial Sequence
<220> FEATURE:
<223> OTHER INFORMATION: Primer

<400> SEQUENCE: 421
tctttgaaat cggctcagga aaagg 25

<210> SEQ ID NO 422
<211> LENGTH: 26
<212> TYPE: DNA
<213> ORGANISM: Artificial Sequence
<220> FEATURE:
<223> OTHER INFORMATION: Primer

<400> SEQUENCE: 422
tctttgccat tgaagatgac ttaagc 26

<210> SEQ ID NO 423
<211> LENGTH: 29
<212> TYPE: DNA
<213> ORGANISM: Artificial Sequence
<220> FEATURE:
<223> OTHER INFORMATION: Primer

<400> SEQUENCE: 423
tcttttacaa aaggggaaaa agttgactt 29

<210> SEQ ID NO 424
<211> LENGTH: 34
<212> TYPE: DNA
<213> ORGANISM: Artificial Sequence
<220> FEATURE:
<223> OTHER INFORMATION: Primer

<400> SEQUENCE: 424
tgaaaaatgt ccaagaagca tagcaaaaaa agca 34

<210> SEQ ID NO 425
<211> LENGTH: 30
<212> TYPE: DNA
<213> ORGANISM: Artificial Sequence
<220> FEATURE:
<223> OTHER INFORMATION: Primer

<400> SEQUENCE: 425
tgaaaagggt gaagtagcaa atggagatag 30

<210> SEQ ID NO 426
<211> LENGTH: 32
<212> TYPE: DNA
<213> ORGANISM: Artificial Sequence
<220> FEATURE:
<223> OTHER INFORMATION: Primer

<400> SEQUENCE: 426
tgaaaagtat ggatttgaac aactcgtgaa ta 32

<210> SEQ ID NO 427
<211> LENGTH: 27
<212> TYPE: DNA
<213> ORGANISM: Artificial Sequence
<220> FEATURE:
<223> OTHER INFORMATION: Primer

<400> SEQUENCE: 427
tgaaatctca ttacgttgca tcggaaa 27

<210> SEQ ID NO 428
<211> LENGTH: 30
<212> TYPE: DNA
<213> ORGANISM: Artificial Sequence
<220> FEATURE:
<223> OTHER INFORMATION: Primer

<400> SEQUENCE: 428
tgaaattgct acaggccctt taggacaagg 30

<210> SEQ ID NO 429
<211> LENGTH: 25
<212> TYPE: DNA
<213> ORGANISM: Artificial Sequence
<220> FEATURE:
<223> OTHER INFORMATION: Primer

<400> SEQUENCE: 429
tgaacgctgg tggcatgctt aacac 25

<210> SEQ ID NO 430
<211> LENGTH: 30
<212> TYPE: DNA

<213> ORGANISM: Artificial Sequence
<220> FEATURE:
<223> OTHER INFORMATION: Primer

<400> SEQUENCE: 430
tgaacgtggt caaatcaaag ttggtgaaga 30

<210> SEQ ID NO 431
<211> LENGTH: 31
<212> TYPE: DNA
<213> ORGANISM: Artificial Sequence
<220> FEATURE:
<223> OTHER INFORMATION: Primer

<400> SEQUENCE: 431
tgaacgtggt caaatcaaag ttggtgaaga a 31

<210> SEQ ID NO 432
<211> LENGTH: 27
<212> TYPE: DNA
<213> ORGANISM: Artificial Sequence
<220> FEATURE:
<223> OTHER INFORMATION: Primer

<400> SEQUENCE: 432
tgaagcttgt tctttagcag gacttca 27

<210> SEQ ID NO 433
<211> LENGTH: 28
<212> TYPE: DNA
<213> ORGANISM: Artificial Sequence
<220> FEATURE:
<223> OTHER INFORMATION: Primer

<400> SEQUENCE: 433
tgaaggtgga cgtcacactc cattcttc 28

<210> SEQ ID NO 434
<211> LENGTH: 26
<212> TYPE: DNA
<213> ORGANISM: Artificial Sequence
<220> FEATURE:
<223> OTHER INFORMATION: Primer

<400> SEQUENCE: 434
tgaagtagaa atgactgaac gtccga 26

<210> SEQ ID NO 435
<211> LENGTH: 28
<212> TYPE: DNA
<213> ORGANISM: Artificial Sequence
<220> FEATURE:
<223> OTHER INFORMATION: Primer

<400> SEQUENCE: 435
tgaagtagaa ggtgcaaagc aagttaga 28

<210> SEQ ID NO 436
<211> LENGTH: 34
<212> TYPE: DNA
<213> ORGANISM: Artificial Sequence
<220> FEATURE:
<223> OTHER INFORMATION: Primer

<400> SEQUENCE: 436
tgaagtgcgt gatgatatcg atgcacttga tgta 34

<210> SEQ ID NO 437
<211> LENGTH: 31
<212> TYPE: DNA
<213> ORGANISM: Artificial Sequence
<220> FEATURE:
<223> OTHER INFORMATION: Primer

<400> SEQUENCE: 437
tgaatagtga tagaactgta ggcacaatcg t 31

<210> SEQ ID NO 438
<211> LENGTH: 31
<212> TYPE: DNA
<213> ORGANISM: Artificial Sequence
<220> FEATURE:
<223> OTHER INFORMATION: Primer

<400> SEQUENCE: 438
tgaatgctta tttacctgca ctcccacaac t 31

<210> SEQ ID NO 439
<211> LENGTH: 31
<212> TYPE: DNA
<213> ORGANISM: Artificial Sequence
<220> FEATURE:
<223> OTHER INFORMATION: Primer

<400> SEQUENCE: 439
tgaattagtt caatcatttg ttgaacgacg t 31

<210> SEQ ID NO 440
<211> LENGTH: 26
<212> TYPE: DNA
<213> ORGANISM: Artificial Sequence
<220> FEATURE:
<223> OTHER INFORMATION: Primer

<400> SEQUENCE: 440
tgaattgctg ctatgaaagg tggctt 26

<210> SEQ ID NO 441
<211> LENGTH: 27
<212> TYPE: DNA
<213> ORGANISM: Artificial Sequence
<220> FEATURE:
<223> OTHER INFORMATION: Primer

<400> SEQUENCE: 441
tgacagcgaa gaaggttaga cttgtcc 27

<210> SEQ ID NO 442
<211> LENGTH: 26
<212> TYPE: DNA
<213> ORGANISM: Artificial Sequence
<220> FEATURE:
<223> OTHER INFORMATION: Primer

<400> SEQUENCE: 442
tgacatccgg ctcacgttat tatggt 26

<210> SEQ ID NO 443
<211> LENGTH: 27
<212> TYPE: DNA
<213> ORGANISM: Artificial Sequence
<220> FEATURE:
<223> OTHER INFORMATION: Primer

<400> SEQUENCE: 443
tgacatccgg ctcacgttat tatggta 27

<210> SEQ ID NO 444
<211> LENGTH: 28
<212> TYPE: DNA
<213> ORGANISM: Artificial Sequence
<220> FEATURE:
<223> OTHER INFORMATION: Primer

<400> SEQUENCE: 444
tgacatccgg ctcacgttat tatggtac 28

<210> SEQ ID NO 445
<211> LENGTH: 29
<212> TYPE: DNA
<213> ORGANISM: Artificial Sequence
<220> FEATURE:
<223> OTHER INFORMATION: Primer

<400> SEQUENCE: 445
tgacatgata ataaccgatt gaccgaaga 29

<210> SEQ ID NO 446
<211> LENGTH: 22
<212> TYPE: DNA
<213> ORGANISM: Artificial Sequence
<220> FEATURE:
<223> OTHER INFORMATION: Primer

<400> SEQUENCE: 446
tgacatgctt gtccgttcag gc 22

<210> SEQ ID NO 447
<211> LENGTH: 31
<212> TYPE: DNA
<213> ORGANISM: Artificial Sequence
<220> FEATURE:
<223> OTHER INFORMATION: Primer

<400> SEQUENCE: 447
tgacatggac tccccctata taactcttga g 31

<210> SEQ ID NO 448
<211> LENGTH: 23
<212> TYPE: DNA
<213> ORGANISM: Artificial Sequence
<220> FEATURE:
<223> OTHER INFORMATION: Primer

<400> SEQUENCE: 448
tgaccaggtg atggccatgt tcg 23

<210> SEQ ID NO 449
<211> LENGTH: 31
<212> TYPE: DNA
<213> ORGANISM: Artificial Sequence
<220> FEATURE:
<223> OTHER INFORMATION: Primer

<400> SEQUENCE: 449
tgacctacag taagaggttc tgtaatgaac c 31

<210> SEQ ID NO 450
<211> LENGTH: 23
<212> TYPE: DNA

<213> ORGANISM: Artificial Sequence
<220> FEATURE:
<223> OTHER INFORMATION: Primer

<400> SEQUENCE: 450
tgacgatctt cgcggtgact agt 23

<210> SEQ ID NO 451
<211> LENGTH: 26
<212> TYPE: DNA
<213> ORGANISM: Artificial Sequence
<220> FEATURE:
<223> OTHER INFORMATION: Primer

<400> SEQUENCE: 451
tgacggccta tacggtgttg gtttct 26

<210> SEQ ID NO 452
<211> LENGTH: 24
<212> TYPE: DNA
<213> ORGANISM: Artificial Sequence
<220> FEATURE:
<223> OTHER INFORMATION: Primer

<400> SEQUENCE: 452
tgacgtcatc ggtaagtacc accc 24

<210> SEQ ID NO 453
<211> LENGTH: 27
<212> TYPE: DNA
<213> ORGANISM: Artificial Sequence
<220> FEATURE:
<223> OTHER INFORMATION: Primer

<400> SEQUENCE: 453
tgagatggat ttaaacctgt tcaccgc 27

<210> SEQ ID NO 454
<211> LENGTH: 30
<212> TYPE: DNA
<213> ORGANISM: Artificial Sequence
<220> FEATURE:
<223> OTHER INFORMATION: Primer

<400> SEQUENCE: 454
tgagattgct gaacatttaa tgctgattga 30

<210> SEQ ID NO 455
<211> LENGTH: 32
<212> TYPE: DNA
<213> ORGANISM: Artificial Sequence
<220> FEATURE:
<223> OTHER INFORMATION: Primer

<400> SEQUENCE: 455
tgagcaatgg ggctttgaaa gaatttttaa at 32

<210> SEQ ID NO 456
<211> LENGTH: 26
<212> TYPE: DNA
<213> ORGANISM: Artificial Sequence
<220> FEATURE:
<223> OTHER INFORMATION: Primer

<400> SEQUENCE: 456
tgagctgcat caactgtatt ggatag 26

<210> SEQ ID NO 457
<211> LENGTH: 28
<212> TYPE: DNA
<213> ORGANISM: Artificial Sequence
<220> FEATURE:
<223> OTHER INFORMATION: Primer

<400> SEQUENCE: 457
tgagctttta gttgactttt tcaacagc 28

<210> SEQ ID NO 458
<211> LENGTH: 20
<212> TYPE: DNA
<213> ORGANISM: Artificial Sequence
<220> FEATURE:
<223> OTHER INFORMATION: Primer

<400> SEQUENCE: 458
tgaggaccgt gtcgcgctca 20

<210> SEQ ID NO 459
<211> LENGTH: 35
<212> TYPE: DNA
<213> ORGANISM: Artificial Sequence
<220> FEATURE:
<223> OTHER INFORMATION: Primer

<400> SEQUENCE: 459
tgagggtttt atgcttaaag ttggttttat tggtt 35

<210> SEQ ID NO 460
<211> LENGTH: 30
<212> TYPE: DNA
<213> ORGANISM: Artificial Sequence
<220> FEATURE:
<223> OTHER INFORMATION: Primer

<400> SEQUENCE: 460
tgaggtggtg gataactcaa ttgatgaagc 30

<210> SEQ ID NO 461
<211> LENGTH: 29
<212> TYPE: DNA
<213> ORGANISM: Artificial Sequence
<220> FEATURE:
<223> OTHER INFORMATION: Primer

<400> SEQUENCE: 461
tgagtaacat ccatatttct gccatacgt 29

<210> SEQ ID NO 462
<211> LENGTH: 22
<212> TYPE: DNA
<213> ORGANISM: Artificial Sequence
<220> FEATURE:
<223> OTHER INFORMATION: Primer

<400> SEQUENCE: 462
tgagtaagtt ccacccgcac gg 22

<210> SEQ ID NO 463
<211> LENGTH: 30
<212> TYPE: DNA
<213> ORGANISM: Artificial Sequence
<220> FEATURE:
<223> OTHER INFORMATION: Primer

<400> SEQUENCE: 463
tgagtcactt gaagttgata caaatcctct 30

<210> SEQ ID NO 464
<211> LENGTH: 28
<212> TYPE: DNA
<213> ORGANISM: Artificial Sequence
<220> FEATURE:
<223> OTHER INFORMATION: Primer

<400> SEQUENCE: 464
tgagtgatga aggccttagg gttgtaaa 28

<210> SEQ ID NO 465
<211> LENGTH: 27
<212> TYPE: DNA
<213> ORGANISM: Artificial Sequence
<220> FEATURE:
<223> OTHER INFORMATION: Primer

<400> SEQUENCE: 465
tgagtgccaa catatcagtg ctgaaga 27

<210> SEQ ID NO 466
<211> LENGTH: 30
<212> TYPE: DNA
<213> ORGANISM: Artificial Sequence
<220> FEATURE:
<223> OTHER INFORMATION: Primer

<400> SEQUENCE: 466
tgagtttaac agttcaccat atgaaacagg 30

<210> SEQ ID NO 467
<211> LENGTH: 25
<212> TYPE: DNA
<213> ORGANISM: Artificial Sequence
<220> FEATURE:
<223> OTHER INFORMATION: Primer

<400> SEQUENCE: 467
tgatacttca acgcctgctg ctttc 25

<210> SEQ ID NO 468
<211> LENGTH: 25
<212> TYPE: DNA
<213> ORGANISM: Artificial Sequence
<220> FEATURE:
<223> OTHER INFORMATION: Primer

<400> SEQUENCE: 468
tgatcactgg tgctgctcag atgga 25

<210> SEQ ID NO 469
<211> LENGTH: 30
<212> TYPE: DNA
<213> ORGANISM: Artificial Sequence
<220> FEATURE:
<223> OTHER INFORMATION: Primer

<400> SEQUENCE: 469
tgatcatccg tggtataacg atttattagt 30

<210> SEQ ID NO 470
<211> LENGTH: 29
<212> TYPE: DNA

<213> ORGANISM: Artificial Sequence
<220> FEATURE:
<223> OTHER INFORMATION: Primer

<400> SEQUENCE: 470
tgatcgttga gaagggattt gcgaaaaga 29

<210> SEQ ID NO 471
<211> LENGTH: 29
<212> TYPE: DNA
<213> ORGANISM: Artificial Sequence
<220> FEATURE:
<223> OTHER INFORMATION: Primer

<400> SEQUENCE: 471
tgatctcaga atctaataat tgggacgaa 29

<210> SEQ ID NO 472
<211> LENGTH: 30
<212> TYPE: DNA
<213> ORGANISM: Artificial Sequence
<220> FEATURE:
<223> OTHER INFORMATION: Primer

<400> SEQUENCE: 472
tgatcttaaa aatttccgcc aacttcattc 30

<210> SEQ ID NO 473
<211> LENGTH: 30
<212> TYPE: DNA
<213> ORGANISM: Artificial Sequence
<220> FEATURE:
<223> OTHER INFORMATION: Primer

<400> SEQUENCE: 473
tgatgacttt ttagctaatg gtcaggcagc 30

<210> SEQ ID NO 474
<211> LENGTH: 29
<212> TYPE: DNA
<213> ORGANISM: Artificial Sequence
<220> FEATURE:
<223> OTHER INFORMATION: Primer

<400> SEQUENCE: 474
tgatggcaag tggatagggt ataatacag 29

<210> SEQ ID NO 475
<211> LENGTH: 24
<212> TYPE: DNA
<213> ORGANISM: Artificial Sequence
<220> FEATURE:
<223> OTHER INFORMATION: Primer

<400> SEQUENCE: 475
tgattaccat gagtggcaag caag 24

<210> SEQ ID NO 476
<211> LENGTH: 31
<212> TYPE: DNA
<213> ORGANISM: Artificial Sequence
<220> FEATURE:
<223> OTHER INFORMATION: Primer

<400> SEQUENCE: 476
tgattattgt tatcctgtta tgccatttga g 31

<210> SEQ ID NO 477
<211> LENGTH: 19
<212> TYPE: DNA
<213> ORGANISM: Artificial Sequence
<220> FEATURE:
<223> OTHER INFORMATION: Primer

<400> SEQUENCE: 477
tgattccggt gcccgtggt 19

<210> SEQ ID NO 478
<211> LENGTH: 19
<212> TYPE: DNA
<213> ORGANISM: Artificial Sequence
<220> FEATURE:
<223> OTHER INFORMATION: Primer

<400> SEQUENCE: 478
tgattctggt gcccgtggt 19

<210> SEQ ID NO 479
<211> LENGTH: 34
<212> TYPE: DNA
<213> ORGANISM: Artificial Sequence
<220> FEATURE:
<223> OTHER INFORMATION: Primer

<400> SEQUENCE: 479
tgattttgct aaatttagag aaattgcgga tgaa 34

<210> SEQ ID NO 480
<211> LENGTH: 24
<212> TYPE: DNA
<213> ORGANISM: Artificial Sequence
<220> FEATURE:
<223> OTHER INFORMATION: Primer

<400> SEQUENCE: 480
tgcaaaatct gcaacgagct ttgg 24

<210> SEQ ID NO 481
<211> LENGTH: 23
<212> TYPE: DNA
<213> ORGANISM: Artificial Sequence
<220> FEATURE:
<223> OTHER INFORMATION: Primer

<400> SEQUENCE: 481
tgcaaaggag gtactcagac cat 23

<210> SEQ ID NO 482
<211> LENGTH: 25
<212> TYPE: DNA
<213> ORGANISM: Artificial Sequence
<220> FEATURE:
<223> OTHER INFORMATION: Primer

<400> SEQUENCE: 482
tgcaagcaaa cgcacaatca gaagc 25

<210> SEQ ID NO 483
<211> LENGTH: 20
<212> TYPE: DNA
<213> ORGANISM: Artificial Sequence
<220> FEATURE:
<223> OTHER INFORMATION: Primer

<400> SEQUENCE: 483
tgcaagcgcg accacatacg 20

<210> SEQ ID NO 484
<211> LENGTH: 23
<212> TYPE: DNA
<213> ORGANISM: Artificial Sequence
<220> FEATURE:
<223> OTHER INFORMATION: Primer

<400> SEQUENCE: 484
tgcaagcttc tggtgctagc att 23

<210> SEQ ID NO 485
<211> LENGTH: 24
<212> TYPE: DNA
<213> ORGANISM: Artificial Sequence
<220> FEATURE:
<223> OTHER INFORMATION: Primer

<400> SEQUENCE: 485
tgcaagtggt acttcaacat gggg 24

<210> SEQ ID NO 486
<211> LENGTH: 30
<212> TYPE: DNA
<213> ORGANISM: Artificial Sequence
<220> FEATURE:
<223> OTHER INFORMATION: Primer

<400> SEQUENCE: 486
tgcaagttaa gaaagctgtt gcaggtttat 30

<210> SEQ ID NO 487
<211> LENGTH: 33
<212> TYPE: DNA
<213> ORGANISM: Artificial Sequence
<220> FEATURE:
<223> OTHER INFORMATION: Primer

<400> SEQUENCE: 487
tgcaattgct ttagttttaa gtgcatgtaa ttc 33

<210> SEQ ID NO 488
<211> LENGTH: 31
<212> TYPE: DNA
<213> ORGANISM: Artificial Sequence
<220> FEATURE:
<223> OTHER INFORMATION: Primer

<400> SEQUENCE: 488
tgcacaatca gaagctaaga aagcgcaagc t 31

<210> SEQ ID NO 489
<211> LENGTH: 24
<212> TYPE: DNA
<213> ORGANISM: Artificial Sequence
<220> FEATURE:
<223> OTHER INFORMATION: Primer

<400> SEQUENCE: 489
tgcacacgcc gttcttcaac aact 24

<210> SEQ ID NO 490
<211> LENGTH: 22
<212> TYPE: DNA

<213> ORGANISM: Artificial Sequence
<220> FEATURE:
<223> OTHER INFORMATION: Primer

<400> SEQUENCE: 490
tgcacatcgt gtccaacgtc ac 22

<210> SEQ ID NO 491
<211> LENGTH: 32
<212> TYPE: DNA
<213> ORGANISM: Artificial Sequence
<220> FEATURE:
<223> OTHER INFORMATION: Primer

<400> SEQUENCE: 491
tgcaccggct attaagaatt actttgccaa ct 32

<210> SEQ ID NO 492
<211> LENGTH: 23
<212> TYPE: DNA
<213> ORGANISM: Artificial Sequence
<220> FEATURE:
<223> OTHER INFORMATION: Primer

<400> SEQUENCE: 492
tgcacgatgc ggaatggttc aca 23

<210> SEQ ID NO 493
<211> LENGTH: 28
<212> TYPE: DNA
<213> ORGANISM: Artificial Sequence
<220> FEATURE:
<223> OTHER INFORMATION: Primer

<400> SEQUENCE: 493
tgcacgccga ctatgttaag aacatgat 28

<210> SEQ ID NO 494
<211> LENGTH: 30
<212> TYPE: DNA
<213> ORGANISM: Artificial Sequence
<220> FEATURE:
<223> OTHER INFORMATION: Primer

<400> SEQUENCE: 494
tgcacttatc gcaaatggaa aattaagcaa 30

<210> SEQ ID NO 495
<211> LENGTH: 21
<212> TYPE: DNA
<213> ORGANISM: Artificial Sequence
<220> FEATURE:
<223> OTHER INFORMATION: Primer

<400> SEQUENCE: 495
tgcagggaac agctttaggc a 21

<210> SEQ ID NO 496
<211> LENGTH: 22
<212> TYPE: DNA
<213> ORGANISM: Artificial Sequence
<220> FEATURE:
<223> OTHER INFORMATION: Primer

<400> SEQUENCE: 496
tgcatacaaa cagtcggagc ct 22

<210> SEQ ID NO 497
<211> LENGTH: 23
<212> TYPE: DNA
<213> ORGANISM: Artificial Sequence
<220> FEATURE:
<223> OTHER INFORMATION: Primer

<400> SEQUENCE: 497
tgcataccgg taagttggca aca 23

<210> SEQ ID NO 498
<211> LENGTH: 27
<212> TYPE: DNA
<213> ORGANISM: Artificial Sequence
<220> FEATURE:
<223> OTHER INFORMATION: Primer

<400> SEQUENCE: 498
tgcatattat atcgagccac agcatcg 27

<210> SEQ ID NO 499
<211> LENGTH: 33
<212> TYPE: DNA
<213> ORGANISM: Artificial Sequence
<220> FEATURE:
<223> OTHER INFORMATION: Primer

<400> SEQUENCE: 499
tgcattattt ggaactattg caactgctaa tgc 33

<210> SEQ ID NO 500
<211> LENGTH: 28
<212> TYPE: DNA
<213> ORGANISM: Artificial Sequence
<220> FEATURE:
<223> OTHER INFORMATION: Primer

<400> SEQUENCE: 500
tgccaagagg acagagtgag tactttga 28

<210> SEQ ID NO 501
<211> LENGTH: 31
<212> TYPE: DNA
<213> ORGANISM: Artificial Sequence
<220> FEATURE:
<223> OTHER INFORMATION: Primer

<400> SEQUENCE: 501
tgccggacaa ttacgattca tcgagtatta a 31

<210> SEQ ID NO 502
<211> LENGTH: 33
<212> TYPE: DNA
<213> ORGANISM: Artificial Sequence
<220> FEATURE:
<223> OTHER INFORMATION: Primer

<400> SEQUENCE: 502
tgccgtaatg ataggtgaag atatacaaag agt 33

<210> SEQ ID NO 503
<211> LENGTH: 23
<212> TYPE: DNA
<213> ORGANISM: Artificial Sequence
<220> FEATURE:
<223> OTHER INFORMATION: Primer

<400> SEQUENCE: 503
tgccgtgttg aacgtggtca aat 23

<210> SEQ ID NO 504
<211> LENGTH: 33
<212> TYPE: DNA
<213> ORGANISM: Artificial Sequence
<220> FEATURE:
<223> OTHER INFORMATION: Primer

<400> SEQUENCE: 504
tgcctagaag atcttaaaaa tttccgccaa ctt 33

<210> SEQ ID NO 505
<211> LENGTH: 33
<212> TYPE: DNA
<213> ORGANISM: Artificial Sequence
<220> FEATURE:
<223> OTHER INFORMATION: Primer

<400> SEQUENCE: 505
tgcctatctt tttgctgata tagcacatat tgc 33

<210> SEQ ID NO 506
<211> LENGTH: 27
<212> TYPE: DNA
<213> ORGANISM: Artificial Sequence
<220> FEATURE:
<223> OTHER INFORMATION: Primer

<400> SEQUENCE: 506
tgcctcgaag ctgaatataa ccaagtt 27

<210> SEQ ID NO 507
<211> LENGTH: 22
<212> TYPE: DNA
<213> ORGANISM: Artificial Sequence
<220> FEATURE:
<223> OTHER INFORMATION: Primer

<400> SEQUENCE: 507
tgcctgtagg gaatcctgct ga 22

<210> SEQ ID NO 508
<211> LENGTH: 25
<212> TYPE: DNA
<213> ORGANISM: Artificial Sequence
<220> FEATURE:
<223> OTHER INFORMATION: Primer

<400> SEQUENCE: 508
tgcctgttct tagtacgaga ggacc 25

<210> SEQ ID NO 509
<211> LENGTH: 23
<212> TYPE: DNA
<213> ORGANISM: Artificial Sequence
<220> FEATURE:
<223> OTHER INFORMATION: Primer

<400> SEQUENCE: 509
tgcgcagctc ttggtatcga gtt 23

<210> SEQ ID NO 510
<211> LENGTH: 20
<212> TYPE: DNA

-continued

<213> ORGANISM: Artificial Sequence
<220> FEATURE:
<223> OTHER INFORMATION: Primer

<400> SEQUENCE: 510
tgcgcggaag atgtaacggg 20

<210> SEQ ID NO 511
<211> LENGTH: 30
<212> TYPE: DNA
<213> ORGANISM: Artificial Sequence
<220> FEATURE:
<223> OTHER INFORMATION: Primer

<400> SEQUENCE: 511
tgcggatcgt ttggtggttg tagatgaaaa 30

<210> SEQ ID NO 512
<211> LENGTH: 20
<212> TYPE: DNA
<213> ORGANISM: Artificial Sequence
<220> FEATURE:
<223> OTHER INFORMATION: Primer

<400> SEQUENCE: 512
tgcgggtagg gagcttgagc 20

<210> SEQ ID NO 513
<211> LENGTH: 31
<212> TYPE: DNA
<213> ORGANISM: Artificial Sequence
<220> FEATURE:
<223> OTHER INFORMATION: Primer

<400> SEQUENCE: 513
tgcgtacaat acgctttatg aaattttaac a 31

<210> SEQ ID NO 514
<211> LENGTH: 27
<212> TYPE: DNA
<213> ORGANISM: Artificial Sequence
<220> FEATURE:
<223> OTHER INFORMATION: Primer

<400> SEQUENCE: 514
tgcgtataaa aaacacagat ggcagca 27

<210> SEQ ID NO 515
<211> LENGTH: 21
<212> TYPE: DNA
<213> ORGANISM: Artificial Sequence
<220> FEATURE:
<223> OTHER INFORMATION: Primer

<400> SEQUENCE: 515
tgcgtttacc gcaatgcgtg c 21

<210> SEQ ID NO 516
<211> LENGTH: 29
<212> TYPE: DNA
<213> ORGANISM: Artificial Sequence
<220> FEATURE:
<223> OTHER INFORMATION: Primer

<400> SEQUENCE: 516
tgctacggta ggatctcctt atcctattg 29

<210> SEQ ID NO 517
<211> LENGTH: 30
<212> TYPE: DNA
<213> ORGANISM: Artificial Sequence
<220> FEATURE:
<223> OTHER INFORMATION: Primer

<400> SEQUENCE: 517
tgctagtcaa tctatcattc cggttgatac 30

<210> SEQ ID NO 518
<211> LENGTH: 27
<212> TYPE: DNA
<213> ORGANISM: Artificial Sequence
<220> FEATURE:
<223> OTHER INFORMATION: Primer

<400> SEQUENCE: 518
tgctagttat ggtacagagt ttgcgac 27

<210> SEQ ID NO 519
<211> LENGTH: 26
<212> TYPE: DNA
<213> ORGANISM: Artificial Sequence
<220> FEATURE:
<223> OTHER INFORMATION: Primer

<400> SEQUENCE: 519
tgctatggtg ttaccttccc tatgca 26

<210> SEQ ID NO 520
<211> LENGTH: 27
<212> TYPE: DNA
<213> ORGANISM: Artificial Sequence
<220> FEATURE:
<223> OTHER INFORMATION: Primer

<400> SEQUENCE: 520
tgctcaaccc gatcctaaat tagacga 27

<210> SEQ ID NO 521
<211> LENGTH: 27
<212> TYPE: DNA
<213> ORGANISM: Artificial Sequence
<220> FEATURE:
<223> OTHER INFORMATION: Primer

<400> SEQUENCE: 521
tgctcaatct aaacctaaag tcgaaga 27

<210> SEQ ID NO 522
<211> LENGTH: 33
<212> TYPE: DNA
<213> ORGANISM: Artificial Sequence
<220> FEATURE:
<223> OTHER INFORMATION: Primer

<400> SEQUENCE: 522
tgctcgagtg attgactttg ctaaatttag aga 33

<210> SEQ ID NO 523
<211> LENGTH: 24
<212> TYPE: DNA
<213> ORGANISM: Artificial Sequence
<220> FEATURE:
<223> OTHER INFORMATION: Primer

<400> SEQUENCE: 523
tgctcgtaag ggtctggcgg atac 24

<210> SEQ ID NO 524
<211> LENGTH: 29
<212> TYPE: DNA
<213> ORGANISM: Artificial Sequence
<220> FEATURE:
<223> OTHER INFORMATION: Primer

<400> SEQUENCE: 524
tgctcgtggt gcacaagtaa cggatatta 29

<210> SEQ ID NO 525
<211> LENGTH: 26
<212> TYPE: DNA
<213> ORGANISM: Artificial Sequence
<220> FEATURE:
<223> OTHER INFORMATION: Primer

<400> SEQUENCE: 525
tgctgaggcc tggaccgatt atttac 26

<210> SEQ ID NO 526
<211> LENGTH: 27
<212> TYPE: DNA
<213> ORGANISM: Artificial Sequence
<220> FEATURE:
<223> OTHER INFORMATION: Primer

<400> SEQUENCE: 526
tgctggtaac agagccttat aggcgca 27

<210> SEQ ID NO 527
<211> LENGTH: 19
<212> TYPE: DNA
<213> ORGANISM: Artificial Sequence
<220> FEATURE:
<223> OTHER INFORMATION: Primer

<400> SEQUENCE: 527
tgctggtacg ggtcgagga 19

<210> SEQ ID NO 528
<211> LENGTH: 31
<212> TYPE: DNA
<213> ORGANISM: Artificial Sequence
<220> FEATURE:
<223> OTHER INFORMATION: Primer

<400> SEQUENCE: 528
tgctggtgaa aataacccag atgtcgtctt c 31

<210> SEQ ID NO 529
<211> LENGTH: 32
<212> TYPE: DNA
<213> ORGANISM: Artificial Sequence
<220> FEATURE:
<223> OTHER INFORMATION: Primer

<400> SEQUENCE: 529
tgctgtagct tatcgcgaaa tgtctttgat tt 32

<210> SEQ ID NO 530
<211> LENGTH: 28
<212> TYPE: DNA

<213> ORGANISM: Artificial Sequence
<220> FEATURE:
<223> OTHER INFORMATION: Primer

<400> SEQUENCE: 530
tgcttattta cctgcactcc cacaactg 28

<210> SEQ ID NO 531
<211> LENGTH: 26
<212> TYPE: DNA
<213> ORGANISM: Artificial Sequence
<220> FEATURE:
<223> OTHER INFORMATION: Primer

<400> SEQUENCE: 531
tgcttcagga atcaatgatg gagcag 26

<210> SEQ ID NO 532
<211> LENGTH: 27
<212> TYPE: DNA
<213> ORGANISM: Artificial Sequence
<220> FEATURE:
<223> OTHER INFORMATION: Primer

<400> SEQUENCE: 532
tgcttcggat ccagcagcac ttcaata 27

<210> SEQ ID NO 533
<211> LENGTH: 19
<212> TYPE: DNA
<213> ORGANISM: Artificial Sequence
<220> FEATURE:
<223> OTHER INFORMATION: Primer

<400> SEQUENCE: 533
tgcttctggt gctagcatt 19

<210> SEQ ID NO 534
<211> LENGTH: 32
<212> TYPE: DNA
<213> ORGANISM: Artificial Sequence
<220> FEATURE:
<223> OTHER INFORMATION: Primer

<400> SEQUENCE: 534
tgctttccta tggcttatcc aaatttagat cg 32

<210> SEQ ID NO 535
<211> LENGTH: 29
<212> TYPE: DNA
<213> ORGANISM: Artificial Sequence
<220> FEATURE:
<223> OTHER INFORMATION: Primer

<400> SEQUENCE: 535
tgcttttgat ggtgatgcag atcgtttgg 29

<210> SEQ ID NO 536
<211> LENGTH: 24
<212> TYPE: DNA
<213> ORGANISM: Artificial Sequence
<220> FEATURE:
<223> OTHER INFORMATION: Primer

<400> SEQUENCE: 536
tggaaagcca tgcgtctgac atct 24

<210> SEQ ID NO 537
<211> LENGTH: 23
<212> TYPE: DNA
<213> ORGANISM: Artificial Sequence
<220> FEATURE:
<223> OTHER INFORMATION: Primer

<400> SEQUENCE: 537
tggaaaggtg ttgcagctac tca 23

<210> SEQ ID NO 538
<211> LENGTH: 31
<212> TYPE: DNA
<213> ORGANISM: Artificial Sequence
<220> FEATURE:
<223> OTHER INFORMATION: Primer

<400> SEQUENCE: 538
tggaaatggc agctagaata gtagctaaaa t 31

<210> SEQ ID NO 539
<211> LENGTH: 30
<212> TYPE: DNA
<213> ORGANISM: Artificial Sequence
<220> FEATURE:
<223> OTHER INFORMATION: Primer

<400> SEQUENCE: 539
tggaacaaaa tagtctctcg gattttgact 30

<210> SEQ ID NO 540
<211> LENGTH: 33
<212> TYPE: DNA
<213> ORGANISM: Artificial Sequence
<220> FEATURE:
<223> OTHER INFORMATION: Primer

<400> SEQUENCE: 540
tggaacagga attaattctc atcctgatta tcc 33

<210> SEQ ID NO 541
<211> LENGTH: 30
<212> TYPE: DNA
<213> ORGANISM: Artificial Sequence
<220> FEATURE:
<223> OTHER INFORMATION: Primer

<400> SEQUENCE: 541
tggaacgtta tcaggtgccc caaaaattcg 30

<210> SEQ ID NO 542
<211> LENGTH: 23
<212> TYPE: DNA
<213> ORGANISM: Artificial Sequence
<220> FEATURE:
<223> OTHER INFORMATION: Primer

<400> SEQUENCE: 542
tggaactatt gcaactgcta atg 23

<210> SEQ ID NO 543
<211> LENGTH: 30
<212> TYPE: DNA
<213> ORGANISM: Artificial Sequence
<220> FEATURE:
<223> OTHER INFORMATION: Primer

<400> SEQUENCE: 543
tggaacttga agctctcgct cttaaagatg 30

<210> SEQ ID NO 544
<211> LENGTH: 19
<212> TYPE: DNA
<213> ORGANISM: Artificial Sequence
<220> FEATURE:
<223> OTHER INFORMATION: Primer

<400> SEQUENCE: 544
tggaagatct gggtcaggc 19

<210> SEQ ID NO 545
<211> LENGTH: 22
<212> TYPE: DNA
<213> ORGANISM: Artificial Sequence
<220> FEATURE:
<223> OTHER INFORMATION: Primer

<400> SEQUENCE: 545
tggaagtcat caagcgcctg gc 22

<210> SEQ ID NO 546
<211> LENGTH: 30
<212> TYPE: DNA
<213> ORGANISM: Artificial Sequence
<220> FEATURE:
<223> OTHER INFORMATION: Primer

<400> SEQUENCE: 546
tggaataaca aaacatgaag gaaaccactt 30

<210> SEQ ID NO 547
<211> LENGTH: 32
<212> TYPE: DNA
<213> ORGANISM: Artificial Sequence
<220> FEATURE:
<223> OTHER INFORMATION: Primer

<400> SEQUENCE: 547
tggaatgatg ataaagattt cgcagatagc ta 32

<210> SEQ ID NO 548
<211> LENGTH: 29
<212> TYPE: DNA
<213> ORGANISM: Artificial Sequence
<220> FEATURE:
<223> OTHER INFORMATION: Primer

<400> SEQUENCE: 548
tggacaatag acaatcactt ggatttaca 29

<210> SEQ ID NO 549
<211> LENGTH: 28
<212> TYPE: DNA
<213> ORGANISM: Artificial Sequence
<220> FEATURE:
<223> OTHER INFORMATION: Primer

<400> SEQUENCE: 549
tggacacata tcgtgagcaa tgaactga 28

<210> SEQ ID NO 550
<211> LENGTH: 23
<212> TYPE: DNA

<213> ORGANISM: Artificial Sequence
<220> FEATURE:
<223> OTHER INFORMATION: Primer

<400> SEQUENCE: 550
tggacggcat cacgattctc tac 23

<210> SEQ ID NO 551
<211> LENGTH: 19
<212> TYPE: DNA
<213> ORGANISM: Artificial Sequence
<220> FEATURE:
<223> OTHER INFORMATION: Primer

<400> SEQUENCE: 551
tggactcctc ggtggtcgc 19

<210> SEQ ID NO 552
<211> LENGTH: 19
<212> TYPE: DNA
<213> ORGANISM: Artificial Sequence
<220> FEATURE:
<223> OTHER INFORMATION: Primer

<400> SEQUENCE: 552
tggagcacgg cttctgatc 19

<210> SEQ ID NO 553
<211> LENGTH: 30
<212> TYPE: DNA
<213> ORGANISM: Artificial Sequence
<220> FEATURE:
<223> OTHER INFORMATION: Primer

<400> SEQUENCE: 553
tggagcttga agctatcgct cttaaagatg 30

<210> SEQ ID NO 554
<211> LENGTH: 22
<212> TYPE: DNA
<213> ORGANISM: Artificial Sequence
<220> FEATURE:
<223> OTHER INFORMATION: Primer

<400> SEQUENCE: 554
tggaggtgtc actccacacg aa 22

<210> SEQ ID NO 555
<211> LENGTH: 25
<212> TYPE: DNA
<213> ORGANISM: Artificial Sequence
<220> FEATURE:
<223> OTHER INFORMATION: Primer

<400> SEQUENCE: 555
tggaggttgt tgtatgtatg gtggt 25

<210> SEQ ID NO 556
<211> LENGTH: 26
<212> TYPE: DNA
<213> ORGANISM: Artificial Sequence
<220> FEATURE:
<223> OTHER INFORMATION: Primer

<400> SEQUENCE: 556
tggatattca ccgaacacta gggttg 26

<210> SEQ ID NO 557
<211> LENGTH: 27
<212> TYPE: DNA
<213> ORGANISM: Artificial Sequence
<220> FEATURE:
<223> OTHER INFORMATION: Primer

<400> SEQUENCE: 557
tggatggcat ggtgaaatgg atatgtc 27

<210> SEQ ID NO 558
<211> LENGTH: 25
<212> TYPE: DNA
<213> ORGANISM: Artificial Sequence
<220> FEATURE:
<223> OTHER INFORMATION: Primer

<400> SEQUENCE: 558
tggatgggga ttagcggtta caatg 25

<210> SEQ ID NO 559
<211> LENGTH: 26
<212> TYPE: DNA
<213> ORGANISM: Artificial Sequence
<220> FEATURE:
<223> OTHER INFORMATION: Primer

<400> SEQUENCE: 559
tggatgttaa gggtgatttt cccgaa 26

<210> SEQ ID NO 560
<211> LENGTH: 23
<212> TYPE: DNA
<213> ORGANISM: Artificial Sequence
<220> FEATURE:
<223> OTHER INFORMATION: Primer

<400> SEQUENCE: 560
tggattagag accctggtag tcc 23

<210> SEQ ID NO 561
<211> LENGTH: 19
<212> TYPE: DNA
<213> ORGANISM: Artificial Sequence
<220> FEATURE:
<223> OTHER INFORMATION: Primer

<400> SEQUENCE: 561
tggcacggcc atctccgtg 19

<210> SEQ ID NO 562
<211> LENGTH: 34
<212> TYPE: DNA
<213> ORGANISM: Artificial Sequence
<220> FEATURE:
<223> OTHER INFORMATION: Primer

<400> SEQUENCE: 562
tggcactctt gcctttaata ttagtaaact atca 34

<210> SEQ ID NO 563
<211> LENGTH: 31
<212> TYPE: DNA
<213> ORGANISM: Artificial Sequence
<220> FEATURE:
<223> OTHER INFORMATION: Primer

<400> SEQUENCE: 563
tggcagctag aatagtagct aaaatcccta c 31

<210> SEQ ID NO 564
<211> LENGTH: 28
<212> TYPE: DNA
<213> ORGANISM: Artificial Sequence
<220> FEATURE:
<223> OTHER INFORMATION: Primer

<400> SEQUENCE: 564
tggcagtttt acaaggtgct gtttcatc 28

<210> SEQ ID NO 565
<211> LENGTH: 31
<212> TYPE: DNA
<213> ORGANISM: Artificial Sequence
<220> FEATURE:
<223> OTHER INFORMATION: Primer

<400> SEQUENCE: 565
tggcatttct tatgaagctt gttctttagc a 31

<210> SEQ ID NO 566
<211> LENGTH: 24
<212> TYPE: DNA
<213> ORGANISM: Artificial Sequence
<220> FEATURE:
<223> OTHER INFORMATION: Primer

<400> SEQUENCE: 566
tggccagcgc ttcggtgaaa tgga 24

<210> SEQ ID NO 567
<211> LENGTH: 21
<212> TYPE: DNA
<213> ORGANISM: Artificial Sequence
<220> FEATURE:
<223> OTHER INFORMATION: Primer

<400> SEQUENCE: 567
tggcccgaaa gaagctgagc g 21

<210> SEQ ID NO 568
<211> LENGTH: 32
<212> TYPE: DNA
<213> ORGANISM: Artificial Sequence
<220> FEATURE:
<223> OTHER INFORMATION: Primer

<400> SEQUENCE: 568
tggcctaatg ggcttaatat caatgaaaat tg 32

<210> SEQ ID NO 569
<211> LENGTH: 22
<212> TYPE: DNA
<213> ORGANISM: Artificial Sequence
<220> FEATURE:
<223> OTHER INFORMATION: Primer

<400> SEQUENCE: 569
tggcgaacct ggtgaacgaa gc 22

<210> SEQ ID NO 570
<211> LENGTH: 26
<212> TYPE: DNA

<213> ORGANISM: Artificial Sequence
<220> FEATURE:
<223> OTHER INFORMATION: Primer

<400> SEQUENCE: 570
tggcgagtgg atagggtata atacag 26

<210> SEQ ID NO 571
<211> LENGTH: 27
<212> TYPE: DNA
<213> ORGANISM: Artificial Sequence
<220> FEATURE:
<223> OTHER INFORMATION: Primer

<400> SEQUENCE: 571
tggcgtagta gagctattta cagacac 27

<210> SEQ ID NO 572
<211> LENGTH: 26
<212> TYPE: DNA
<213> ORGANISM: Artificial Sequence
<220> FEATURE:
<223> OTHER INFORMATION: Primer

<400> SEQUENCE: 572
tggcaagtgg atagggtata atacag 26

<210> SEQ ID NO 573
<211> LENGTH: 25
<212> TYPE: DNA
<213> ORGANISM: Artificial Sequence
<220> FEATURE:
<223> OTHER INFORMATION: Primer

<400> SEQUENCE: 573
tggctccttg gtatgactct gcttc 25

<210> SEQ ID NO 574
<211> LENGTH: 25
<212> TYPE: DNA
<213> ORGANISM: Artificial Sequence
<220> FEATURE:
<223> OTHER INFORMATION: Primer

<400> SEQUENCE: 574
tggctgacat cctacatgac tgtga 25

<210> SEQ ID NO 575
<211> LENGTH: 31
<212> TYPE: DNA
<213> ORGANISM: Artificial Sequence
<220> FEATURE:
<223> OTHER INFORMATION: Primer

<400> SEQUENCE: 575
tggcttatcc aaatttagat cgtggtttta c 31

<210> SEQ ID NO 576
<211> LENGTH: 30
<212> TYPE: DNA
<213> ORGANISM: Artificial Sequence
<220> FEATURE:
<223> OTHER INFORMATION: Primer

<400> SEQUENCE: 576
tgggacttga agctatcgct cttaaagatg 30

<210> SEQ ID NO 577
<211> LENGTH: 30
<212> TYPE: DNA
<213> ORGANISM: Artificial Sequence
<220> FEATURE:
<223> OTHER INFORMATION: Primer

<400> SEQUENCE: 577
tgggatgaaa aagcgttctt ttatccatga 30

<210> SEQ ID NO 578
<211> LENGTH: 34
<212> TYPE: DNA
<213> ORGANISM: Artificial Sequence
<220> FEATURE:
<223> OTHER INFORMATION: Primer

<400> SEQUENCE: 578
tgggattatt gttatcctgt tatgccattt gaga 34

<210> SEQ ID NO 579
<211> LENGTH: 32
<212> TYPE: DNA
<213> ORGANISM: Artificial Sequence
<220> FEATURE:
<223> OTHER INFORMATION: Primer

<400> SEQUENCE: 579
tgggatttta aaaaacattg gtaacatcgc ag 32

<210> SEQ ID NO 580
<211> LENGTH: 30
<212> TYPE: DNA
<213> ORGANISM: Artificial Sequence
<220> FEATURE:
<223> OTHER INFORMATION: Primer

<400> SEQUENCE: 580
tgggcaacag cagcggattg cgattgcgcg 30

<210> SEQ ID NO 581
<211> LENGTH: 24
<212> TYPE: DNA
<213> ORGANISM: Artificial Sequence
<220> FEATURE:
<223> OTHER INFORMATION: Primer

<400> SEQUENCE: 581
tgggcagcgt ttcggcgaaa tgga 24

<210> SEQ ID NO 582
<211> LENGTH: 33
<212> TYPE: DNA
<213> ORGANISM: Artificial Sequence
<220> FEATURE:
<223> OTHER INFORMATION: Primer

<400> SEQUENCE: 582
tgggcctaat gggcttaata tcaatgaaaa ttg 33

<210> SEQ ID NO 583
<211> LENGTH: 28
<212> TYPE: DNA
<213> ORGANISM: Artificial Sequence
<220> FEATURE:
<223> OTHER INFORMATION: Primer -continued

<400> SEQUENCE: 583
tgggcgatgc tgcgaaatgg ttaaaaga					28

<210> SEQ ID NO 584
<211> LENGTH: 27
<212> TYPE: DNA
<213> ORGANISM: Artificial Sequence
<220> FEATURE:
<223> OTHER INFORMATION: Primer

<400> SEQUENCE: 584
tgggcgtgag caatgaactg attatac					27

<210> SEQ ID NO 585
<211> LENGTH: 18
<212> TYPE: DNA
<213> ORGANISM: Artificial Sequence
<220> FEATURE:
<223> OTHER INFORMATION: Primer

<400> SEQUENCE: 585
tgggcgtgga acgtccac					18

<210> SEQ ID NO 586
<211> LENGTH: 24
<212> TYPE: DNA
<213> ORGANISM: Artificial Sequence
<220> FEATURE:
<223> OTHER INFORMATION: Primer

<400> SEQUENCE: 586
tgggctcttt ctcgcttaaa cacc					24

<210> SEQ ID NO 587
<211> LENGTH: 25
<212> TYPE: DNA
<213> ORGANISM: Artificial Sequence
<220> FEATURE:
<223> OTHER INFORMATION: Primer

<400> SEQUENCE: 587
tgggctcttt ctcgcttaaa cacct					25

<210> SEQ ID NO 588
<211> LENGTH: 31
<212> TYPE: DNA
<213> ORGANISM: Artificial Sequence
<220> FEATURE:
<223> OTHER INFORMATION: Primer

<400> SEQUENCE: 588
tggggattca gccatcaaag cagctattga c					31

<210> SEQ ID NO 589
<211> LENGTH: 28
<212> TYPE: DNA
<213> ORGANISM: Artificial Sequence
<220> FEATURE:
<223> OTHER INFORMATION: Primer

<400> SEQUENCE: 589
tggggattga tatcaccgat aagaagaa					28

<210> SEQ ID NO 590
<211> LENGTH: 33
<212> TYPE: DNA

<213> ORGANISM: Artificial Sequence
<220> FEATURE:
<223> OTHER INFORMATION: Primer

<400> SEQUENCE: 590
tggggcttta aatattccaa ttgaagattt tca 33

<210> SEQ ID NO 591
<211> LENGTH: 33
<212> TYPE: DNA
<213> ORGANISM: Artificial Sequence
<220> FEATURE:
<223> OTHER INFORMATION: Primer

<400> SEQUENCE: 591
tggggctttg ctttatagtt ttttacattt aag 33

<210> SEQ ID NO 592
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)...(5)
<223> OTHER INFORMATION: I
<220> FEATURE:
<221> NAME/KEY: modified_base
<222> LOCATION: (14)...(14)
<223> OTHER INFORMATION: I

<400> SEQUENCE: 592
tgggtgatgc tgctaaatgg ttaaaaga 28

<210> SEQ ID NO 593
<211> LENGTH: 35
<212> TYPE: DNA
<213> ORGANISM: Artificial Sequence
<220> FEATURE:
<223> OTHER INFORMATION: Primer

<400> SEQUENCE: 593
tgggtcgtgg ttttacagaa aatttcttat atatg 35

<210> SEQ ID NO 594
<211> LENGTH: 28
<212> TYPE: DNA
<213> ORGANISM: Artificial Sequence
<220> FEATURE:
<223> OTHER INFORMATION: Primer

<400> SEQUENCE: 594
tgggtgacat tcatcaattt catcgttc 28

<210> SEQ ID NO 595
<211> LENGTH: 32
<212> TYPE: DNA
<213> ORGANISM: Artificial Sequence
<220> FEATURE:
<223> OTHER INFORMATION: Primer

<400> SEQUENCE: 595
tgggtttaca catatcgtga gcaatgaact ga 32

<210> SEQ ID NO 596
<211> LENGTH: 25
<212> TYPE: DNA

<213> ORGANISM: Artificial Sequence
<220> FEATURE:
<223> OTHER INFORMATION: Primer

<400> SEQUENCE: 596
tggtaaatac cacccacatg gtgac 25

<210> SEQ ID NO 597
<211> LENGTH: 24
<212> TYPE: DNA
<213> ORGANISM: Artificial Sequence
<220> FEATURE:
<223> OTHER INFORMATION: Primer

<400> SEQUENCE: 597
tggtaacaga gccttatagg cgca 24

<210> SEQ ID NO 598
<211> LENGTH: 28
<212> TYPE: DNA
<213> ORGANISM: Artificial Sequence
<220> FEATURE:
<223> OTHER INFORMATION: Primer

<400> SEQUENCE: 598
tggtaacaga gccttatagg cgcatatg 28

<210> SEQ ID NO 599
<211> LENGTH: 30
<212> TYPE: DNA
<213> ORGANISM: Artificial Sequence
<220> FEATURE:
<223> OTHER INFORMATION: Primer

<400> SEQUENCE: 599
tggtaagagc gcaccggtaa gttggtaaca 30

<210> SEQ ID NO 600
<211> LENGTH: 18
<212> TYPE: DNA
<213> ORGANISM: Artificial Sequence
<220> FEATURE:
<223> OTHER INFORMATION: Primer

<400> SEQUENCE: 600
tggtacagag tttgcgac 18

<210> SEQ ID NO 601
<211> LENGTH: 26
<212> TYPE: DNA
<213> ORGANISM: Artificial Sequence
<220> FEATURE:
<223> OTHER INFORMATION: Primer

<400> SEQUENCE: 601
tggtacatgt gccttcattg atgctg 26

<210> SEQ ID NO 602
<211> LENGTH: 18
<212> TYPE: DNA
<213> ORGANISM: Artificial Sequence
<220> FEATURE:
<223> OTHER INFORMATION: Primer

<400> SEQUENCE: 602
tggtacagag tttgcgac 18

<210> SEQ ID NO 603
<211> LENGTH: 24
<212> TYPE: DNA
<213> ORGANISM: Artificial Sequence
<220> FEATURE:
<223> OTHER INFORMATION: Primer

<400> SEQUENCE: 603
tggtactcac ttagcgggtt tccg 24

<210> SEQ ID NO 604
<211> LENGTH: 24
<212> TYPE: DNA
<213> ORGANISM: Artificial Sequence
<220> FEATURE:
<223> OTHER INFORMATION: Primer

<400> SEQUENCE: 604
tggtatgata tgatgcctgc acca 24

<210> SEQ ID NO 605
<211> LENGTH: 21
<212> TYPE: DNA
<213> ORGANISM: Artificial Sequence
<220> FEATURE:
<223> OTHER INFORMATION: Primer

<400> SEQUENCE: 605
tggtatgcgt ggtctgatgg c 21

<210> SEQ ID NO 606
<211> LENGTH: 31
<212> TYPE: DNA
<213> ORGANISM: Artificial Sequence
<220> FEATURE:
<223> OTHER INFORMATION: Primer

<400> SEQUENCE: 606
tggtattcta ttttgctgat aatgacctcg c 31

<210> SEQ ID NO 607
<211> LENGTH: 25
<212> TYPE: DNA
<213> ORGANISM: Artificial Sequence
<220> FEATURE:
<223> OTHER INFORMATION: Primer

<400> SEQUENCE: 607
tggtcaaatc aaagttggtg aagaa 25

<210> SEQ ID NO 608
<211> LENGTH: 29
<212> TYPE: DNA
<213> ORGANISM: Artificial Sequence
<220> FEATURE:
<223> OTHER INFORMATION: Primer

<400> SEQUENCE: 608
tggtcttatg ccaagaggac agagtgagt 29

<210> SEQ ID NO 609
<211> LENGTH: 24
<212> TYPE: DNA
<213> ORGANISM: Artificial Sequence
<220> FEATURE:
<223> OTHER INFORMATION: Primer

<400> SEQUENCE: 609
tggtgactcg gcatgttatg aagc 24

<210> SEQ ID NO 610
<211> LENGTH: 30
<212> TYPE: DNA
<213> ORGANISM: Artificial Sequence
<220> FEATURE:
<223> OTHER INFORMATION: Primer

<400> SEQUENCE: 610
tggtgacttc ataatggatg aagttgaagt 30

<210> SEQ ID NO 611
<211> LENGTH: 27
<212> TYPE: DNA
<213> ORGANISM: Artificial Sequence
<220> FEATURE:
<223> OTHER INFORMATION: Primer

<400> SEQUENCE: 611
tggtgcgagt gcttatgctc gtattat 27

<210> SEQ ID NO 612
<211> LENGTH: 13
<212> TYPE: DNA
<213> ORGANISM: Artificial Sequence
<220> FEATURE:
<223> OTHER INFORMATION: Primer

<400> SEQUENCE: 612
tggtgctagc att 13

<210> SEQ ID NO 613
<211> LENGTH: 24
<212> TYPE: DNA
<213> ORGANISM: Artificial Sequence
<220> FEATURE:
<223> OTHER INFORMATION: Primer

<400> SEQUENCE: 613
tggtgctttc tggcgcttaa acga 24

<210> SEQ ID NO 614
<211> LENGTH: 27
<212> TYPE: DNA
<213> ORGANISM: Artificial Sequence
<220> FEATURE:
<223> OTHER INFORMATION: Primer

<400> SEQUENCE: 614
tggtggacat ttaacacatg gtgcaaa 27

<210> SEQ ID NO 615
<211> LENGTH: 26
<212> TYPE: DNA
<213> ORGANISM: Artificial Sequence
<220> FEATURE:
<223> OTHER INFORMATION: Primer

<400> SEQUENCE: 615
tggtggtgaa atagatagga ctgctt 26

<210> SEQ ID NO 616
<211> LENGTH: 13
<212> TYPE: DNA

<213> ORGANISM: Artificial Sequence
<220> FEATURE:
<223> OTHER INFORMATION: Primer

<400> SEQUENCE: 616
tggtgctagc att 13

<210> SEQ ID NO 617
<211> LENGTH: 26
<212> TYPE: DNA
<213> ORGANISM: Artificial Sequence
<220> FEATURE:
<223> OTHER INFORMATION: Primer

<400> SEQUENCE: 617
tggttatcgc tcaggcgaac tccaac 26

<210> SEQ ID NO 618
<211> LENGTH: 33
<212> TYPE: DNA
<213> ORGANISM: Artificial Sequence
<220> FEATURE:
<223> OTHER INFORMATION: Primer

<400> SEQUENCE: 618
tggttatgta ccaaatactt tgtctgaaga tgg 33

<210> SEQ ID NO 619
<211> LENGTH: 31
<212> TYPE: DNA
<213> ORGANISM: Artificial Sequence
<220> FEATURE:
<223> OTHER INFORMATION: Primer

<400> SEQUENCE: 619
tggtttagat aattccttag gatctatgcg t 31

<210> SEQ ID NO 620
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (3)...(3)
<223> OTHER INFORMATION: I
<220> FEATURE:
<221> NAME/KEY: modified_base
<222> LOCATION: (6)...(6)
<223> OTHER INFORMATION: I
<220> FEATURE:
<221> NAME/KEY: modified_base
<222> LOCATION: (9)...(9)
<223> OTHER INFORMATION: I
<220> FEATURE:
<221> NAME/KEY: modified_base
<222> LOCATION: (12)...(13)
<223> OTHER INFORMATION: I
<220> FEATURE:
<221> NAME/KEY: modified_base
<222> LOCATION: (15)...(15)
<223> OTHER INFORMATION: I

<400> SEQUENCE: 620
tgtcctactg tttgtggttc tgtaatgaac c 31

<210> SEQ ID NO 621
<211> LENGTH: 24
<212> TYPE: DNA

<213> ORGANISM: Artificial Sequence
<220> FEATURE:
<223> OTHER INFORMATION: Primer

<400> SEQUENCE: 621
tgtaactatc acccgcacgg tgat 24

<210> SEQ ID NO 622
<211> LENGTH: 30
<212> TYPE: DNA
<213> ORGANISM: Artificial Sequence
<220> FEATURE:
<223> OTHER INFORMATION: Primer

<400> SEQUENCE: 622
tgtaagctct acaacccaca aaaccttacg 30

<210> SEQ ID NO 623
<211> LENGTH: 30
<212> TYPE: DNA
<213> ORGANISM: Artificial Sequence
<220> FEATURE:
<223> OTHER INFORMATION: Primer

<400> SEQUENCE: 623
tgtaatgaac cctaatgacc atccacacgg 30

<210> SEQ ID NO 624
<211> LENGTH: 31
<212> TYPE: DNA
<213> ORGANISM: Artificial Sequence
<220> FEATURE:
<223> OTHER INFORMATION: Primer

<400> SEQUENCE: 624
tgtacccgct gaattaacga atttatacga c 31

<210> SEQ ID NO 625
<211> LENGTH: 24
<212> TYPE: DNA
<213> ORGANISM: Artificial Sequence
<220> FEATURE:
<223> OTHER INFORMATION: Primer

<400> SEQUENCE: 625
tgtactcggt aagtatcacc cgca 24

<210> SEQ ID NO 626
<211> LENGTH: 21
<212> TYPE: DNA
<213> ORGANISM: Artificial Sequence
<220> FEATURE:
<223> OTHER INFORMATION: Primer

<400> SEQUENCE: 626
tgtactgcta tccaccctca a 21

<210> SEQ ID NO 627
<211> LENGTH: 24
<212> TYPE: DNA
<213> ORGANISM: Artificial Sequence
<220> FEATURE:
<223> OTHER INFORMATION: Primer

<400> SEQUENCE: 627
tgtagccgct aagcactacc atcc 24

<210> SEQ ID NO 628
<211> LENGTH: 30
<212> TYPE: DNA
<213> ORGANISM: Artificial Sequence
<220> FEATURE:
<223> OTHER INFORMATION: Primer

<400> SEQUENCE: 628
tgtagcttat cgcgaaatgt ctttgatttt 30

<210> SEQ ID NO 629
<211> LENGTH: 33
<212> TYPE: DNA
<213> ORGANISM: Artificial Sequence
<220> FEATURE:
<223> OTHER INFORMATION: Primer

<400> SEQUENCE: 629
tgtatggtgg tgtaacgtta catgataata atc 33

<210> SEQ ID NO 630
<211> LENGTH: 27
<212> TYPE: DNA
<213> ORGANISM: Artificial Sequence
<220> FEATURE:
<223> OTHER INFORMATION: Primer

<400> SEQUENCE: 630
tgtattaggg gcatacagtc ctcatcc 27

<210> SEQ ID NO 631
<211> LENGTH: 24
<212> TYPE: DNA
<213> ORGANISM: Artificial Sequence
<220> FEATURE:
<223> OTHER INFORMATION: Primer

<400> SEQUENCE: 631
tgtcaaagtg gcacgtttac tggc 24

<210> SEQ ID NO 632
<211> LENGTH: 24
<212> TYPE: DNA
<213> ORGANISM: Artificial Sequence
<220> FEATURE:
<223> OTHER INFORMATION: Primer

<400> SEQUENCE: 632
tgtcatgggt aaatatcacc ctca 24

<210> SEQ ID NO 633
<211> LENGTH: 28
<212> TYPE: DNA
<213> ORGANISM: Artificial Sequence
<220> FEATURE:
<223> OTHER INFORMATION: Primer

<400> SEQUENCE: 633
tgtccaagaa gcatagcaaa aaaagcaa 28

<210> SEQ ID NO 634
<211> LENGTH: 23
<212> TYPE: DNA
<213> ORGANISM: Artificial Sequence
<220> FEATURE:
<223> OTHER INFORMATION: Primer

<400> SEQUENCE: 634
tgtcgatgca acgcgaagaa cct 23

<210> SEQ ID NO 635
<211> LENGTH: 25
<212> TYPE: DNA
<213> ORGANISM: Artificial Sequence
<220> FEATURE:
<223> OTHER INFORMATION: Primer

<400> SEQUENCE: 635
tgtcggtaca cgatattctt cacga 25

<210> SEQ ID NO 636
<211> LENGTH: 27
<212> TYPE: DNA
<213> ORGANISM: Artificial Sequence
<220> FEATURE:
<223> OTHER INFORMATION: Primer

<400> SEQUENCE: 636
tgtgaataaa tcacgattga ttgagca 27

<210> SEQ ID NO 637
<211> LENGTH: 26
<212> TYPE: DNA
<213> ORGANISM: Artificial Sequence
<220> FEATURE:
<223> OTHER INFORMATION: Primer

<400> SEQUENCE: 637
tgtggagtaa cactgcatga aaacaa 26

<210> SEQ ID NO 638
<211> LENGTH: 27
<212> TYPE: DNA
<213> ORGANISM: Artificial Sequence
<220> FEATURE:
<223> OTHER INFORMATION: Primer

<400> SEQUENCE: 638
tgtggtcaaa tcaaagttgg tgaagaa 27

<210> SEQ ID NO 639
<211> LENGTH: 25
<212> TYPE: DNA
<213> ORGANISM: Artificial Sequence
<220> FEATURE:
<223> OTHER INFORMATION: Primer

<400> SEQUENCE: 639
tgttcaagag ctagatcttc aggca 25

<210> SEQ ID NO 640
<211> LENGTH: 26
<212> TYPE: DNA
<213> ORGANISM: Artificial Sequence
<220> FEATURE:
<223> OTHER INFORMATION: Primer

<400> SEQUENCE: 640
tgttcaagag ctagatcttc aggcaa 26

<210> SEQ ID NO 641
<211> LENGTH: 28
<212> TYPE: DNA

<213> ORGANISM: Artificial Sequence
<220> FEATURE:
<223> OTHER INFORMATION: Primer

<400> SEQUENCE: 641
tgttcgctgt ttcacaaaca acattcca 28

<210> SEQ ID NO 642
<211> LENGTH: 32
<212> TYPE: DNA
<213> ORGANISM: Artificial Sequence
<220> FEATURE:
<223> OTHER INFORMATION: Primer

<400> SEQUENCE: 642
tgttctttag caggacttca caaacttgat aa 32

<210> SEQ ID NO 643
<211> LENGTH: 29
<212> TYPE: DNA
<213> ORGANISM: Artificial Sequence
<220> FEATURE:
<223> OTHER INFORMATION: Primer

<400> SEQUENCE: 643
tgttgaacgt ggtcaaatca aagttggtg 29

<210> SEQ ID NO 644
<211> LENGTH: 31
<212> TYPE: DNA
<213> ORGANISM: Artificial Sequence
<220> FEATURE:
<223> OTHER INFORMATION: Primer

<400> SEQUENCE: 644
tgttgggagt attccttacc atttaagcac a 31

<210> SEQ ID NO 645
<211> LENGTH: 23
<212> TYPE: DNA
<213> ORGANISM: Artificial Sequence
<220> FEATURE:
<223> OTHER INFORMATION: Primer

<400> SEQUENCE: 645
tgttggtgct ttctggcgct taa 23

<210> SEQ ID NO 646
<211> LENGTH: 38
<212> TYPE: DNA
<213> ORGANISM: Artificial Sequence
<220> FEATURE:
<223> OTHER INFORMATION: Primer

<400> SEQUENCE: 646
tccttgttgt cctactgttt gtggttctgt aatgaacc 38

<210> SEQ ID NO 647
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (7)...(7)
<223> OTHER INFORMATION: I
<220> FEATURE:

<221> NAME/KEY: modified_base
<222> LOCATION: (10)...(10)
<223> OTHER INFORMATION: I
<220> FEATURE:
<221> NAME/KEY: modified_base
<222> LOCATION: (13)...(13)
<223> OTHER INFORMATION: I
<220> FEATURE:
<221> NAME/KEY: modified_base
<222> LOCATION: (16)...(16)
<223> OTHER INFORMATION: I
<220> FEATURE:
<221> NAME/KEY: modified_base
<222> LOCATION: (19)...(20)
<223> OTHER INFORMATION: I
<220> FEATURE:
<221> NAME/KEY: modified_base
<222> LOCATION: (22)...(22)
<223> OTHER INFORMATION: I

<400> SEQUENCE: 647
ttaaagttgg ttttattggt tggcgcgga 29

<210> SEQ ID NO 648
<211> LENGTH: 30
<212> TYPE: DNA
<213> ORGANISM: Artificial Sequence
<220> FEATURE:
<223> OTHER INFORMATION: Primer

<400> SEQUENCE: 648
ttaacatgaa ggaaaccact ttgataatgg 30

<210> SEQ ID NO 649
<211> LENGTH: 26
<212> TYPE: DNA
<213> ORGANISM: Artificial Sequence
<220> FEATURE:
<223> OTHER INFORMATION: Primer

<400> SEQUENCE: 649
ttaacggtta tcatggccca gatggg 26

<210> SEQ ID NO 650
<211> LENGTH: 22
<212> TYPE: DNA
<213> ORGANISM: Artificial Sequence
<220> FEATURE:
<223> OTHER INFORMATION: Primer

<400> SEQUENCE: 650
ttaagtcccg caacgagcgc aa 22

<210> SEQ ID NO 651
<211> LENGTH: 22
<212> TYPE: DNA
<213> ORGANISM: Artificial Sequence
<220> FEATURE:
<223> OTHER INFORMATION: Primer

<400> SEQUENCE: 651
ttaagtcccg caacgatcgc aa 22

<210> SEQ ID NO 652
<211> LENGTH: 28
<212> TYPE: DNA
<213> ORGANISM: Artificial Sequence
<220> FEATURE:
<223> OTHER INFORMATION: Primer

<400> SEQUENCE: 652
ttaatttgcc aaaaatgcaa ccaggtag 28

<210> SEQ ID NO 653
<211> LENGTH: 27
<212> TYPE: DNA
<213> ORGANISM: Artificial Sequence
<220> FEATURE:
<223> OTHER INFORMATION: Primer

<400> SEQUENCE: 653
ttacacatat cgtgagcaat gaactga 27

<210> SEQ ID NO 654
<211> LENGTH: 31
<212> TYPE: DNA
<213> ORGANISM: Artificial Sequence
<220> FEATURE:
<223> OTHER INFORMATION: Primer

<400> SEQUENCE: 654
ttacaggaag tttaggtggt aatctaaaag g 31

<210> SEQ ID NO 655
<211> LENGTH: 30
<212> TYPE: DNA
<213> ORGANISM: Artificial Sequence
<220> FEATURE:
<223> OTHER INFORMATION: Primer

<400> SEQUENCE: 655
ttactccatt attgcttggt tacactttcc 30

<210> SEQ ID NO 656
<211> LENGTH: 35
<212> TYPE: DNA
<213> ORGANISM: Artificial Sequence
<220> FEATURE:
<223> OTHER INFORMATION: Primer

<400> SEQUENCE: 656
ttataactta ctgcaatcta ttcagttgct tggtg 35

<210> SEQ ID NO 657
<211> LENGTH: 26
<212> TYPE: DNA
<213> ORGANISM: Artificial Sequence
<220> FEATURE:
<223> OTHER INFORMATION: Primer

<400> SEQUENCE: 657
ttataccgga aacttcccga aaggag 26

<210> SEQ ID NO 658
<211> LENGTH: 32
<212> TYPE: DNA
<213> ORGANISM: Artificial Sequence
<220> FEATURE:
<223> OTHER INFORMATION: Primer

<400> SEQUENCE: 658
ttatcagcta gaccttttag gtaaagctaa gc 32

<210> SEQ ID NO 659
<211> LENGTH: 23
<212> TYPE: DNA

<213> ORGANISM: Artificial Sequence
<220> FEATURE:
<223> OTHER INFORMATION: Primer

<400> SEQUENCE: 659
ttatcgctca ggcgaactcc aac 23

<210> SEQ ID NO 660
<211> LENGTH: 28
<212> TYPE: DNA
<213> ORGANISM: Artificial Sequence
<220> FEATURE:
<223> OTHER INFORMATION: Primer

<400> SEQUENCE: 660
ttatcgtttg tggagctagt gcttatgc 28

<210> SEQ ID NO 661
<211> LENGTH: 30
<212> TYPE: DNA
<213> ORGANISM: Artificial Sequence
<220> FEATURE:
<223> OTHER INFORMATION: Primer

<400> SEQUENCE: 661
ttatgaagcg tgttctttag caggacttca 30

<210> SEQ ID NO 662
<211> LENGTH: 25
<212> TYPE: DNA
<213> ORGANISM: Artificial Sequence
<220> FEATURE:
<223> OTHER INFORMATION: Primer

<400> SEQUENCE: 662
ttatggatgg caacgtgaaa cgcgt 25

<210> SEQ ID NO 663
<211> LENGTH: 21
<212> TYPE: DNA
<213> ORGANISM: Artificial Sequence
<220> FEATURE:
<223> OTHER INFORMATION: Primer

<400> SEQUENCE: 663
ttattgttat cctgttatgc c 21

<210> SEQ ID NO 664
<211> LENGTH: 25
<212> TYPE: DNA
<213> ORGANISM: Artificial Sequence
<220> FEATURE:
<223> OTHER INFORMATION: Primer

<400> SEQUENCE: 664
ttatttacct gcactcccac aactg 25

<210> SEQ ID NO 665
<211> LENGTH: 33
<212> TYPE: DNA
<213> ORGANISM: Artificial Sequence
<220> FEATURE:
<223> OTHER INFORMATION: Primer

<400> SEQUENCE: 665
ttcaaaaact ccaggccatc ctgaaatttc aac 33

<210> SEQ ID NO 666
<211> LENGTH: 28
<212> TYPE: DNA
<213> ORGANISM: Artificial Sequence
<220> FEATURE:
<223> OTHER INFORMATION: Primer

<400> SEQUENCE: 666
ttcaacaggt accaatgatt tgatctca 28

<210> SEQ ID NO 667
<211> LENGTH: 28
<212> TYPE: DNA
<213> ORGANISM: Artificial Sequence
<220> FEATURE:
<223> OTHER INFORMATION: Primer

<400> SEQUENCE: 667
ttcccaccga tatcatggct taccacgg 28

<210> SEQ ID NO 668
<211> LENGTH: 25
<212> TYPE: DNA
<213> ORGANISM: Artificial Sequence
<220> FEATURE:
<223> OTHER INFORMATION: Primer

<400> SEQUENCE: 668
ttccgtaagt cggctaaaac agtcg 25

<210> SEQ ID NO 669
<211> LENGTH: 24
<212> TYPE: DNA
<213> ORGANISM: Artificial Sequence
<220> FEATURE:
<223> OTHER INFORMATION: Primer

<400> SEQUENCE: 669
ttcctccttt tgaaagcgac ggtt 24

<210> SEQ ID NO 670
<211> LENGTH: 17
<212> TYPE: DNA
<213> ORGANISM: Artificial Sequence
<220> FEATURE:
<223> OTHER INFORMATION: Primer

<400> SEQUENCE: 670
ttcctcggcc gcctggc 17

<210> SEQ ID NO 671
<211> LENGTH: 29
<212> TYPE: DNA
<213> ORGANISM: Artificial Sequence
<220> FEATURE:
<223> OTHER INFORMATION: Primer

<400> SEQUENCE: 671
ttcctgaccg acccattatt ccctttatc 29

<210> SEQ ID NO 672
<211> LENGTH: 22
<212> TYPE: DNA
<213> ORGANISM: Artificial Sequence
<220> FEATURE:
<223> OTHER INFORMATION: Primer

<400> SEQUENCE: 672
ttcgatgcaa cgcgaagaac ct 22

<210> SEQ ID NO 673
<211> LENGTH: 27
<212> TYPE: DNA
<213> ORGANISM: Artificial Sequence
<220> FEATURE:
<223> OTHER INFORMATION: Primer

<400> SEQUENCE: 673
ttcgccaatc aaaactaagg gaatggc 27

<210> SEQ ID NO 674
<211> LENGTH: 20
<212> TYPE: DNA
<213> ORGANISM: Artificial Sequence
<220> FEATURE:
<223> OTHER INFORMATION: Primer

<400> SEQUENCE: 674
ttcggcggtc agcgcttcgg 20

<210> SEQ ID NO 675
<211> LENGTH: 26
<212> TYPE: DNA
<213> ORGANISM: Artificial Sequence
<220> FEATURE:
<223> OTHER INFORMATION: Primer

<400> SEQUENCE: 675
ttctaaaaca ccaggtcacc cagaag 26

<210> SEQ ID NO 676
<211> LENGTH: 27
<212> TYPE: DNA
<213> ORGANISM: Artificial Sequence
<220> FEATURE:
<223> OTHER INFORMATION: Primer

<400> SEQUENCE: 676
ttctatctcg ttggtttatt cggagtt 27

<210> SEQ ID NO 677
<211> LENGTH: 30
<212> TYPE: DNA
<213> ORGANISM: Artificial Sequence
<220> FEATURE:
<223> OTHER INFORMATION: Primer

<400> SEQUENCE: 677
ttctgaatgt ctatatggag gtacaacact 30

<210> SEQ ID NO 678
<211> LENGTH: 21
<212> TYPE: DNA
<213> ORGANISM: Artificial Sequence
<220> FEATURE:
<223> OTHER INFORMATION: Primer

<400> SEQUENCE: 678
ttgactgccc aggtcacgct g 21

<210> SEQ ID NO 679
<211> LENGTH: 22
<212> TYPE: DNA

<213> ORGANISM: Artificial Sequence
<220> FEATURE:
<223> OTHER INFORMATION: Primer

<400> SEQUENCE: 679
ttgactgcgg cacaacacgg at 22

<210> SEQ ID NO 680
<211> LENGTH: 33
<212> TYPE: DNA
<213> ORGANISM: Artificial Sequence
<220> FEATURE:
<223> OTHER INFORMATION: Primer

<400> SEQUENCE: 680
ttgagaagac atccggctca cgttattatg gta 33

<210> SEQ ID NO 681
<211> LENGTH: 31
<212> TYPE: DNA
<213> ORGANISM: Artificial Sequence
<220> FEATURE:
<223> OTHER INFORMATION: Primer

<400> SEQUENCE: 681
ttgagggtat gcaccgtctt tttgattctt t 31

<210> SEQ ID NO 682
<211> LENGTH: 24
<212> TYPE: DNA
<213> ORGANISM: Artificial Sequence
<220> FEATURE:
<223> OTHER INFORMATION: Primer

<400> SEQUENCE: 682
ttgcaactgc tgatttagct caga 24

<210> SEQ ID NO 683
<211> LENGTH: 22
<212> TYPE: DNA
<213> ORGANISM: Artificial Sequence
<220> FEATURE:
<223> OTHER INFORMATION: Primer

<400> SEQUENCE: 683
ttgcacaagc aaggcgctat tt 22

<210> SEQ ID NO 684
<211> LENGTH: 28
<212> TYPE: DNA
<213> ORGANISM: Artificial Sequence
<220> FEATURE:
<223> OTHER INFORMATION: Primer

<400> SEQUENCE: 684
ttgccaatga tattcgttgg ttagcaag 28

<210> SEQ ID NO 685
<211> LENGTH: 31
<212> TYPE: DNA
<213> ORGANISM: Artificial Sequence
<220> FEATURE:
<223> OTHER INFORMATION: Primer

<400> SEQUENCE: 685
ttgcccgcgg tgcggaagta accgatatta c 31

-continued

<210> SEQ ID NO 686
<211> LENGTH: 23
<212> TYPE: DNA
<213> ORGANISM: Artificial Sequence
<220> FEATURE:
<223> OTHER INFORMATION: Primer

<400> SEQUENCE: 686
ttgcgaatag aacgatggct cgt 23

<210> SEQ ID NO 687
<211> LENGTH: 30
<212> TYPE: DNA
<213> ORGANISM: Artificial Sequence
<220> FEATURE:
<223> OTHER INFORMATION: Primer

<400> SEQUENCE: 687
ttgctcgtgg tgcacaagta acggatatta 30

<210> SEQ ID NO 688
<211> LENGTH: 31
<212> TYPE: DNA
<213> ORGANISM: Artificial Sequence
<220> FEATURE:
<223> OTHER INFORMATION: Primer

<400> SEQUENCE: 688
ttgctcgtgg tgcacaagta acggatatta c 31

<210> SEQ ID NO 689
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (15)...(15)
<223> OTHER INFORMATION: I
<220> FEATURE:
<221> NAME/KEY: modified_base
<222> LOCATION: (29)...(29)
<223> OTHER INFORMATION: I

<400> SEQUENCE: 689
ttgctcgtgg tgcacaagta acggatatta c 31

<210> SEQ ID NO 690
<211> LENGTH: 29
<212> TYPE: DNA
<213> ORGANISM: Artificial Sequence
<220> FEATURE:
<223> OTHER INFORMATION: Primer

<400> SEQUENCE: 690
ttgcttaaag ttggttttat tggttggcg 29

<210> SEQ ID NO 691
<211> LENGTH: 32
<212> TYPE: DNA
<213> ORGANISM: Artificial Sequence
<220> FEATURE:
<223> OTHER INFORMATION: Primer

<400> SEQUENCE: 691
ttggtccttt ttatacgaaa gaagaagttg aa 32

<210> SEQ ID NO 692
<211> LENGTH: 25
<212> TYPE: DNA
<213> ORGANISM: Artificial Sequence
<220> FEATURE:
<223> OTHER INFORMATION: Primer

<400> SEQUENCE: 692
ttgtaaatgc cggtgcttca gatcc 25

<210> SEQ ID NO 693
<211> LENGTH: 22
<212> TYPE: DNA
<213> ORGANISM: Artificial Sequence
<220> FEATURE:
<223> OTHER INFORMATION: Primer

<400> SEQUENCE: 693
ttgtacacac cgcccgtcat ac 22

<210> SEQ ID NO 694
<211> LENGTH: 31
<212> TYPE: DNA
<213> ORGANISM: Artificial Sequence
<220> FEATURE:
<223> OTHER INFORMATION: Primer

<400> SEQUENCE: 694
ttgtagcaca gcaaggcaaa tttcctgaaa c 31

<210> SEQ ID NO 695
<211> LENGTH: 30
<212> TYPE: DNA
<213> ORGANISM: Artificial Sequence
<220> FEATURE:
<223> OTHER INFORMATION: Primer

<400> SEQUENCE: 695
ttgtatgtat ggtggtgtaa cgttacatga 30

<210> SEQ ID NO 696
<211> LENGTH: 27
<212> TYPE: DNA
<213> ORGANISM: Artificial Sequence
<220> FEATURE:
<223> OTHER INFORMATION: Primer

<400> SEQUENCE: 696
ttgtatgtat ggtggtgtaa ctgagca 27

<210> SEQ ID NO 697
<211> LENGTH: 23
<212> TYPE: DNA
<213> ORGANISM: Artificial Sequence
<220> FEATURE:
<223> OTHER INFORMATION: Primer

<400> SEQUENCE: 697
tttaagtccc gcaacgagcg caa 23

<210> SEQ ID NO 698
<211> LENGTH: 28
<212> TYPE: DNA
<213> ORGANISM: Artificial Sequence
<220> FEATURE:
<223> OTHER INFORMATION: Primer

<400> SEQUENCE: 698
tttacacata tcgtgagcaa tgaactga 28

<210> SEQ ID NO 699
<211> LENGTH: 30
<212> TYPE: DNA
<213> ORGANISM: Artificial Sequence
<220> FEATURE:
<223> OTHER INFORMATION: Primer

<400> SEQUENCE: 699
tttacactac ttttattcat tgccctaacg 30

<210> SEQ ID NO 700
<211> LENGTH: 19
<212> TYPE: DNA
<213> ORGANISM: Artificial Sequence
<220> FEATURE:
<223> OTHER INFORMATION: Primer

<400> SEQUENCE: 700
tttacagctt tatgcaccg 19

<210> SEQ ID NO 701
<211> LENGTH: 29
<212> TYPE: DNA
<213> ORGANISM: Artificial Sequence
<220> FEATURE:
<223> OTHER INFORMATION: Primer

<400> SEQUENCE: 701
tttcacacag cgtgtttata gttctacca 29

<210> SEQ ID NO 702
<211> LENGTH: 30
<212> TYPE: DNA
<213> ORGANISM: Artificial Sequence
<220> FEATURE:
<223> OTHER INFORMATION: Primer

<400> SEQUENCE: 702
tttcacatgt aattttgata ttcgcactga 30

<210> SEQ ID NO 703
<211> LENGTH: 28
<212> TYPE: DNA
<213> ORGANISM: Artificial Sequence
<220> FEATURE:
<223> OTHER INFORMATION: Primer

<400> SEQUENCE: 703
tttcatctta tcgaggaccc gaaatcga 28

<210> SEQ ID NO 704
<211> LENGTH: 25
<212> TYPE: DNA
<213> ORGANISM: Artificial Sequence
<220> FEATURE:
<223> OTHER INFORMATION: Primer

<400> SEQUENCE: 704
tttcctcctt ttgaaagcga cggtt 25

<210> SEQ ID NO 705
<211> LENGTH: 22
<212> TYPE: DNA

<213> ORGANISM: Artificial Sequence
<220> FEATURE:
<223> OTHER INFORMATION: Primer

<400> SEQUENCE: 705
tttcgaaggg cctttcgacc tg 22

<210> SEQ ID NO 706
<211> LENGTH: 23
<212> TYPE: DNA
<213> ORGANISM: Artificial Sequence
<220> FEATURE:
<223> OTHER INFORMATION: Primer

<400> SEQUENCE: 706
tttcgatgca acgcgaagaa cct 23

<210> SEQ ID NO 707
<211> LENGTH: 27
<212> TYPE: DNA
<213> ORGANISM: Artificial Sequence
<220> FEATURE:
<223> OTHER INFORMATION: Primer

<400> SEQUENCE: 707
tttgatttta cgccgtcctc caggtcg 27

<210> SEQ ID NO 708
<211> LENGTH: 32
<212> TYPE: DNA
<213> ORGANISM: Artificial Sequence
<220> FEATURE:
<223> OTHER INFORMATION: Primer

<400> SEQUENCE: 708
tttgcggatg aagtaggtgc ctatcttttt gc 32

<210> SEQ ID NO 709
<211> LENGTH: 32
<212> TYPE: DNA
<213> ORGANISM: Artificial Sequence
<220> FEATURE:
<223> OTHER INFORMATION: Primer

<400> SEQUENCE: 709
ttttatgctt aaagttggtt ttattggttg gc 32

<210> SEQ ID NO 710
<211> LENGTH: 24
<212> TYPE: DNA
<213> ORGANISM: Artificial Sequence
<220> FEATURE:
<223> OTHER INFORMATION: Primer

<400> SEQUENCE: 710
ttttgaaggt gatccgtgcc aacg 24

<210> SEQ ID NO 711
<211> LENGTH: 29
<212> TYPE: DNA
<213> ORGANISM: Artificial Sequence
<220> FEATURE:
<223> OTHER INFORMATION: Primer

<400> SEQUENCE: 711
aaactatttt tttagctata ctcgaacac 29

<210> SEQ ID NO 712
<211> LENGTH: 19
<212> TYPE: DNA
<213> ORGANISM: Artificial Sequence
<220> FEATURE:
<223> OTHER INFORMATION: Primer

<400> SEQUENCE: 712
aacatagcct tctccgtcc 19

<210> SEQ ID NO 713
<211> LENGTH: 21
<212> TYPE: DNA
<213> ORGANISM: Artificial Sequence
<220> FEATURE:
<223> OTHER INFORMATION: Primer

<400> SEQUENCE: 713
aacttcgcct tcggtcatgt t 21

<210> SEQ ID NO 714
<211> LENGTH: 17
<212> TYPE: DNA
<213> ORGANISM: Artificial Sequence
<220> FEATURE:
<223> OTHER INFORMATION: Primer

<400> SEQUENCE: 714
aaggaggtga tccagcc 17

<210> SEQ ID NO 715
<211> LENGTH: 29
<212> TYPE: DNA
<213> ORGANISM: Artificial Sequence
<220> FEATURE:
<223> OTHER INFORMATION: Primer

<400> SEQUENCE: 715
aatcgacgac catcttggaa agatttctc 29

<210> SEQ ID NO 716
<211> LENGTH: 21
<212> TYPE: DNA
<213> ORGANISM: Artificial Sequence
<220> FEATURE:
<223> OTHER INFORMATION: Primer

<400> SEQUENCE: 716
acaaaaggca cgccatcacc c 21

<210> SEQ ID NO 717
<211> LENGTH: 21
<212> TYPE: DNA
<213> ORGANISM: Artificial Sequence
<220> FEATURE:
<223> OTHER INFORMATION: Primer

<400> SEQUENCE: 717
acaaaaggta cgccgtcacc c 21

<210> SEQ ID NO 718
<211> LENGTH: 18
<212> TYPE: DNA
<213> ORGANISM: Artificial Sequence
<220> FEATURE:
<223> OTHER INFORMATION: Primer
<220> FEATURE:

<221> NAME/KEY: modified_base
<222> LOCATION: (12)...(12)
<223> OTHER INFORMATION: I

<400> SEQUENCE: 718
acaacacgag ctgacgac 18

<210> SEQ ID NO 719
<211> LENGTH: 18
<212> TYPE: DNA
<213> ORGANISM: Artificial Sequence
<220> FEATURE:
<223> OTHER INFORMATION: Primer

<400> SEQUENCE: 719
acaacacgag ctgacgac 18

<210> SEQ ID NO 720
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (16)...(16)
<223> OTHER INFORMATION: I

<400> SEQUENCE: 720
acaacacgag ctgacgac 18

<210> SEQ ID NO 721
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (14)...(14)
<223> OTHER INFORMATION: I

<400> SEQUENCE: 721
acaacacgag ctgacgac 18

<210> SEQ ID NO 722
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (11)...(11)
<223> OTHER INFORMATION: I

<400> SEQUENCE: 722
acaacacgag ctgacgac 18

<210> SEQ ID NO 723
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (10)...(10)
<223> OTHER INFORMATION: I
<220> FEATURE:

<221> NAME/KEY: modified_base
<222> LOCATION: (13)...(13)
<223> OTHER INFORMATION: I

<400> SEQUENCE: 723
acaacacgag ctgacgac 18

<210> SEQ ID NO 724
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (8)...(8)
<223> OTHER INFORMATION: I
<220> FEATURE:
<221> NAME/KEY: modified_base
<222> LOCATION: (10)...(10)
<223> OTHER INFORMATION: I
<220> FEATURE:
<221> NAME/KEY: modified_base
<222> LOCATION: (13)...(13)
<223> OTHER INFORMATION: I

<400> SEQUENCE: 724
acaacacgag ctgacgac 18

<210> SEQ ID NO 725
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (8)...(8)
<223> OTHER INFORMATION: I
<220> FEATURE:
<221> NAME/KEY: modified_base
<222> LOCATION: (10)...(10)
<223> OTHER INFORMATION: I
<220> FEATURE:
<221> NAME/KEY: modified_base
<222> LOCATION: (13)...(13)
<223> OTHER INFORMATION: I
<220> FEATURE:
<221> NAME/KEY: modified_base
<222> LOCATION: (16)...(16)
<223> OTHER INFORMATION: I

<400> SEQUENCE: 725
acaacacgag ctgacgac 18

<210> SEQ ID NO 726
<211> LENGTH: 20
<212> TYPE: DNA
<213> ORGANISM: Artificial Sequence
<220> FEATURE:
<223> OTHER INFORMATION: Primer

<400> SEQUENCE: 726
acaaccatgc accacctgtc 20

<210> SEQ ID NO 727
<211> LENGTH: 12
<212> TYPE: DNA
<213> ORGANISM: Artificial Sequence
<220> FEATURE:
<223> OTHER INFORMATION: Primer

<400> SEQUENCE: 727
acacgagctg ac 12

<210> SEQ ID NO 728
<211> LENGTH: 28
<212> TYPE: DNA
<213> ORGANISM: Artificial Sequence
<220> FEATURE:
<223> OTHER INFORMATION: Primer

<400> SEQUENCE: 728
accactttta ataaggtttg tagctaac 28

<210> SEQ ID NO 729
<211> LENGTH: 27
<212> TYPE: DNA
<213> ORGANISM: Artificial Sequence
<220> FEATURE:
<223> OTHER INFORMATION: Primer

<400> SEQUENCE: 729
acctgcaata tctaatgcac tcttacg 27

<210> SEQ ID NO 730
<211> LENGTH: 24
<212> TYPE: DNA
<213> ORGANISM: Artificial Sequence
<220> FEATURE:
<223> OTHER INFORMATION: Primer

<400> SEQUENCE: 730
acctgcatcc ctaaacgtac ttgc 24

<210> SEQ ID NO 731
<211> LENGTH: 22
<212> TYPE: DNA
<213> ORGANISM: Artificial Sequence
<220> FEATURE:
<223> OTHER INFORMATION: Primer

<400> SEQUENCE: 731
accttgttac gacttcaccc ca 22

<210> SEQ ID NO 732
<211> LENGTH: 20
<212> TYPE: DNA
<213> ORGANISM: Artificial Sequence
<220> FEATURE:
<223> OTHER INFORMATION: Primer

<400> SEQUENCE: 732
acgaactgga tgtcgccgtt 20

<210> SEQ ID NO 733
<211> LENGTH: 18
<212> TYPE: DNA
<213> ORGANISM: Artificial Sequence
<220> FEATURE:
<223> OTHER INFORMATION: Primer

<400> SEQUENCE: 733
acgacacgag ctgacgac 18

<210> SEQ ID NO 734
<211> LENGTH: 18
<212> TYPE: DNA

<213> ORGANISM: Artificial Sequence
<220> FEATURE:
<223> OTHER INFORMATION: Primer

<400> SEQUENCE: 734
acgacacgag ctgacgac 18

<210> SEQ ID NO 735
<211> LENGTH: 20
<212> TYPE: DNA
<213> ORGANISM: Artificial Sequence
<220> FEATURE:
<223> OTHER INFORMATION: Primer

<400> SEQUENCE: 735
acgagctgac gacagccatg 20

<210> SEQ ID NO 736
<211> LENGTH: 19
<212> TYPE: DNA
<213> ORGANISM: Artificial Sequence
<220> FEATURE:
<223> OTHER INFORMATION: Primer

<400> SEQUENCE: 736
acgccatcag gccacgcat 19

<210> SEQ ID NO 737
<211> LENGTH: 21
<212> TYPE: DNA
<213> ORGANISM: Artificial Sequence
<220> FEATURE:
<223> OTHER INFORMATION: Primer

<400> SEQUENCE: 737
acgcgggcat gcagagatgc c 21

<210> SEQ ID NO 738
<211> LENGTH: 18
<212> TYPE: DNA
<213> ORGANISM: Artificial Sequence
<220> FEATURE:
<223> OTHER INFORMATION: Primer

<400> SEQUENCE: 738
acggcacgag gtagtcgc 18

<210> SEQ ID NO 739
<211> LENGTH: 20
<212> TYPE: DNA
<213> ORGANISM: Artificial Sequence
<220> FEATURE:
<223> OTHER INFORMATION: Primer

<400> SEQUENCE: 739
acggttacct tgttacgact 20

<210> SEQ ID NO 740
<211> LENGTH: 20
<212> TYPE: DNA
<213> ORGANISM: Artificial Sequence
<220> FEATURE:
<223> OTHER INFORMATION: Primer

<400> SEQUENCE: 740
acgtccttca tcgcctctga 20

<210> SEQ ID NO 741
<211> LENGTH: 27
<212> TYPE: DNA
<213> ORGANISM: Artificial Sequence
<220> FEATURE:
<223> OTHER INFORMATION: Primer

<400> SEQUENCE: 741
acgtttttcg ttttgaacga taatgct 27

<210> SEQ ID NO 742
<211> LENGTH: 17
<212> TYPE: DNA
<213> ORGANISM: Artificial Sequence
<220> FEATURE:
<223> OTHER INFORMATION: Primer

<400> SEQUENCE: 742
actgctgcct cccgtag 17

<210> SEQ ID NO 743
<211> LENGTH: 20
<212> TYPE: DNA
<213> ORGANISM: Artificial Sequence
<220> FEATURE:
<223> OTHER INFORMATION: Primer

<400> SEQUENCE: 743
acttagatgc tttcagcggt 20

<210> SEQ ID NO 744
<211> LENGTH: 20
<212> TYPE: DNA
<213> ORGANISM: Artificial Sequence
<220> FEATURE:
<223> OTHER INFORMATION: Primer

<400> SEQUENCE: 744
agacctcctg cgtgcaaagc 20

<210> SEQ ID NO 745
<211> LENGTH: 31
<212> TYPE: DNA
<213> ORGANISM: Artificial Sequence
<220> FEATURE:
<223> OTHER INFORMATION: Primer

<400> SEQUENCE: 745
agataaagaa tcacgaatat caatttgtag c 31

<210> SEQ ID NO 746
<211> LENGTH: 22
<212> TYPE: DNA
<213> ORGANISM: Artificial Sequence
<220> FEATURE:
<223> OTHER INFORMATION: Primer

<400> SEQUENCE: 746
agccgacatc gaggtgccaa ac 22

<210> SEQ ID NO 747
<211> LENGTH: 28
<212> TYPE: DNA
<213> ORGANISM: Artificial Sequence
<220> FEATURE:
<223> OTHER INFORMATION: Primer

<400> SEQUENCE: 747
agctgctaga tgagcttctg ccatggcc 28

<210> SEQ ID NO 748
<211> LENGTH: 23
<212> TYPE: DNA
<213> ORGANISM: Artificial Sequence
<220> FEATURE:
<223> OTHER INFORMATION: Primer

<400> SEQUENCE: 748
aggatagatt tatttcttgt tcg 23

<210> SEQ ID NO 749
<211> LENGTH: 20
<212> TYPE: DNA
<213> ORGANISM: Artificial Sequence
<220> FEATURE:
<223> OTHER INFORMATION: Primer

<400> SEQUENCE: 749
agtccatccc ggtcctctcg 20

<210> SEQ ID NO 750
<211> LENGTH: 22
<212> TYPE: DNA
<213> ORGANISM: Artificial Sequence
<220> FEATURE:
<223> OTHER INFORMATION: Primer

<400> SEQUENCE: 750
ataagccatg ttctgttcca tc 22

<210> SEQ ID NO 751
<211> LENGTH: 18
<212> TYPE: DNA
<213> ORGANISM: Artificial Sequence
<220> FEATURE:
<223> OTHER INFORMATION: Primer

<400> SEQUENCE: 751
ataagccggg ttctgtcg 18

<210> SEQ ID NO 752
<211> LENGTH: 26
<212> TYPE: DNA
<213> ORGANISM: Artificial Sequence
<220> FEATURE:
<223> OTHER INFORMATION: Primer

<400> SEQUENCE: 752
atatgattat cattgaactg cggccg 26

<210> SEQ ID NO 753
<211> LENGTH: 19
<212> TYPE: DNA
<213> ORGANISM: Artificial Sequence
<220> FEATURE:
<223> OTHER INFORMATION: Primer

<400> SEQUENCE: 753
atcccctgct tctgctgcc 19

<210> SEQ ID NO 754
<211> LENGTH: 30
<212> TYPE: DNA

<213> ORGANISM: Artificial Sequence
<220> FEATURE:
<223> OTHER INFORMATION: Primer

<400> SEQUENCE: 754
attcaagagc catttctttt ggtaaaccac 30

<210> SEQ ID NO 755
<211> LENGTH: 22
<212> TYPE: DNA
<213> ORGANISM: Artificial Sequence
<220> FEATURE:
<223> OTHER INFORMATION: Primer

<400> SEQUENCE: 755
attgcccaga aatcaaatca tc 22

<210> SEQ ID NO 756
<211> LENGTH: 33
<212> TYPE: DNA
<213> ORGANISM: Artificial Sequence
<220> FEATURE:
<223> OTHER INFORMATION: Primer

<400> SEQUENCE: 756
attgcttctt acttgcttag cataaatttt cca 33

<210> SEQ ID NO 757
<211> LENGTH: 21
<212> TYPE: DNA
<213> ORGANISM: Artificial Sequence
<220> FEATURE:
<223> OTHER INFORMATION: Primer

<400> SEQUENCE: 757
attgtagcac gtgtgtagcc c 21

<210> SEQ ID NO 758
<211> LENGTH: 24
<212> TYPE: DNA
<213> ORGANISM: Artificial Sequence
<220> FEATURE:
<223> OTHER INFORMATION: Primer

<400> SEQUENCE: 758
caagcggttt gcctcaaata gtca 24

<210> SEQ ID NO 759
<211> LENGTH: 22
<212> TYPE: DNA
<213> ORGANISM: Artificial Sequence
<220> FEATURE:
<223> OTHER INFORMATION: Primer

<400> SEQUENCE: 759
caatctgctg acggatctga gc 22

<210> SEQ ID NO 760
<211> LENGTH: 15
<212> TYPE: DNA
<213> ORGANISM: Artificial Sequence
<220> FEATURE:
<223> OTHER INFORMATION: Primer

<400> SEQUENCE: 760
caccgggcag gcgtc 15

<210> SEQ ID NO 761
<211> LENGTH: 20
<212> TYPE: DNA
<213> ORGANISM: Artificial Sequence
<220> FEATURE:
<223> OTHER INFORMATION: Primer

<400> SEQUENCE: 761
cacggctacc ttgttacgac 20

<210> SEQ ID NO 762
<211> LENGTH: 20
<212> TYPE: DNA
<213> ORGANISM: Artificial Sequence
<220> FEATURE:
<223> OTHER INFORMATION: Primer

<400> SEQUENCE: 762
cagataaaga atcgctccag 20

<210> SEQ ID NO 763
<211> LENGTH: 25
<212> TYPE: DNA
<213> ORGANISM: Artificial Sequence
<220> FEATURE:
<223> OTHER INFORMATION: Primer

<400> SEQUENCE: 763
catgacagcc aagacctcac ccacc 25

<210> SEQ ID NO 764
<211> LENGTH: 18
<212> TYPE: DNA
<213> ORGANISM: Artificial Sequence
<220> FEATURE:
<223> OTHER INFORMATION: Primer

<400> SEQUENCE: 764
catgatggtc acaaccgg 18

<210> SEQ ID NO 765
<211> LENGTH: 20
<212> TYPE: DNA
<213> ORGANISM: Artificial Sequence
<220> FEATURE:
<223> OTHER INFORMATION: Primer

<400> SEQUENCE: 765
ccaaacaccg ccgtcgatat 20

<210> SEQ ID NO 766
<211> LENGTH: 26
<212> TYPE: DNA
<213> ORGANISM: Artificial Sequence
<220> FEATURE:
<223> OTHER INFORMATION: Primer

<400> SEQUENCE: 766
ccaacctttt ccacaacaga atcagc 26

<210> SEQ ID NO 767
<211> LENGTH: 27
<212> TYPE: DNA
<213> ORGANISM: Artificial Sequence
<220> FEATURE:
<223> OTHER INFORMATION: Primer

<400> SEQUENCE: 767
ccaagtgctg gtttacccca tggagta 27

<210> SEQ ID NO 768
<211> LENGTH: 23
<212> TYPE: DNA
<213> ORGANISM: Artificial Sequence
<220> FEATURE:
<223> OTHER INFORMATION: Primer

<400> SEQUENCE: 768
ccacttttaa taaggtttgt agc 23

<210> SEQ ID NO 769
<211> LENGTH: 27
<212> TYPE: DNA
<213> ORGANISM: Artificial Sequence
<220> FEATURE:
<223> OTHER INFORMATION: Primer

<400> SEQUENCE: 769
ccagcagtta ctgtcccctc atctttg 27

<210> SEQ ID NO 770
<211> LENGTH: 28
<212> TYPE: DNA
<213> ORGANISM: Artificial Sequence
<220> FEATURE:
<223> OTHER INFORMATION: Primer

<400> SEQUENCE: 770
ccataaggtc accgtcacca ttcaaagc 28

<210> SEQ ID NO 771
<211> LENGTH: 18
<212> TYPE: DNA
<213> ORGANISM: Artificial Sequence
<220> FEATURE:
<223> OTHER INFORMATION: Primer

<400> SEQUENCE: 771
ccatgcagca cctgtctc 18

<210> SEQ ID NO 772
<211> LENGTH: 29
<212> TYPE: DNA
<213> ORGANISM: Artificial Sequence
<220> FEATURE:
<223> OTHER INFORMATION: Primer

<400> SEQUENCE: 772
cccatttttt cacgcatgct gaaaatatc 29

<210> SEQ ID NO 773
<211> LENGTH: 21
<212> TYPE: DNA
<213> ORGANISM: Artificial Sequence
<220> FEATURE:
<223> OTHER INFORMATION: Primer

<400> SEQUENCE: 773
cccccgtcaa ttcctttgag t 21

<210> SEQ ID NO 774
<211> LENGTH: 24
<212> TYPE: DNA

<213> ORGANISM: Artificial Sequence
<220> FEATURE:
<223> OTHER INFORMATION: Primer

<400> SEQUENCE: 774
ccctgtagta gaagaggtaa ccac 24

<210> SEQ ID NO 775
<211> LENGTH: 21
<212> TYPE: DNA
<213> ORGANISM: Artificial Sequence
<220> FEATURE:
<223> OTHER INFORMATION: Primer

<400> SEQUENCE: 775
ccgacaagga atttcgctac c 21

<210> SEQ ID NO 776
<211> LENGTH: 23
<212> TYPE: DNA
<213> ORGANISM: Artificial Sequence
<220> FEATURE:
<223> OTHER INFORMATION: Primer

<400> SEQUENCE: 776
ccgcggtcga attgcatgcc ttc 23

<210> SEQ ID NO 777
<211> LENGTH: 17
<212> TYPE: DNA
<213> ORGANISM: Artificial Sequence
<220> FEATURE:
<223> OTHER INFORMATION: Primer

<400> SEQUENCE: 777
ccggtcctct cgtacta 17

<210> SEQ ID NO 778
<211> LENGTH: 18
<212> TYPE: DNA
<213> ORGANISM: Artificial Sequence
<220> FEATURE:
<223> OTHER INFORMATION: Primer

<400> SEQUENCE: 778
ccgtgctcca tttttcag 18

<210> SEQ ID NO 779
<211> LENGTH: 25
<212> TYPE: DNA
<213> ORGANISM: Artificial Sequence
<220> FEATURE:
<223> OTHER INFORMATION: Primer

<400> SEQUENCE: 779
cctacccaac gttcaccaag ggcag 25

<210> SEQ ID NO 780
<211> LENGTH: 17
<212> TYPE: DNA
<213> ORGANISM: Artificial Sequence
<220> FEATURE:
<223> OTHER INFORMATION: Primer

<400> SEQUENCE: 780
cctcctgcgt gcaaagc 17

<210> SEQ ID NO 781
<211> LENGTH: 20
<212> TYPE: DNA
<213> ORGANISM: Artificial Sequence
<220> FEATURE:
<223> OTHER INFORMATION: Primer

<400> SEQUENCE: 781
cctgtagtag aagaggtaac 20

<210> SEQ ID NO 782
<211> LENGTH: 18
<212> TYPE: DNA
<213> ORGANISM: Artificial Sequence
<220> FEATURE:
<223> OTHER INFORMATION: Primer

<400> SEQUENCE: 782
ccttctcccg aagttacg 18

<210> SEQ ID NO 783
<211> LENGTH: 20
<212> TYPE: DNA
<213> ORGANISM: Artificial Sequence
<220> FEATURE:
<223> OTHER INFORMATION: Primer

<400> SEQUENCE: 783
ccttgttacg acttcacccc 20

<210> SEQ ID NO 784
<211> LENGTH: 24
<212> TYPE: DNA
<213> ORGANISM: Artificial Sequence
<220> FEATURE:
<223> OTHER INFORMATION: Primer

<400> SEQUENCE: 784
cgaacggcca gagtagtcaa cacg 24

<210> SEQ ID NO 785
<211> LENGTH: 24
<212> TYPE: DNA
<213> ORGANISM: Artificial Sequence
<220> FEATURE:
<223> OTHER INFORMATION: Primer

<400> SEQUENCE: 785
cgaacggcct gagtagtcaa cacg 24

<210> SEQ ID NO 786
<211> LENGTH: 24
<212> TYPE: DNA
<213> ORGANISM: Artificial Sequence
<220> FEATURE:
<223> OTHER INFORMATION: Primer

<400> SEQUENCE: 786
cgacttgacg gttaacattt cctg 24

<210> SEQ ID NO 787
<211> LENGTH: 21
<212> TYPE: DNA
<213> ORGANISM: Artificial Sequence
<220> FEATURE:
<223> OTHER INFORMATION: Primer

<400> SEQUENCE: 787
cgagttgcag actgcgatcc g 21

<210> SEQ ID NO 788
<211> LENGTH: 21
<212> TYPE: DNA
<213> ORGANISM: Artificial Sequence
<220> FEATURE:
<223> OTHER INFORMATION: Primer

<400> SEQUENCE: 788
cgagttgcag actgcgatcc g 21

<210> SEQ ID NO 789
<211> LENGTH: 25
<212> TYPE: DNA
<213> ORGANISM: Artificial Sequence
<220> FEATURE:
<223> OTHER INFORMATION: Primer

<400> SEQUENCE: 789
cgcaccatgc gtagagatga agtac 25

<210> SEQ ID NO 790
<211> LENGTH: 25
<212> TYPE: DNA
<213> ORGANISM: Artificial Sequence
<220> FEATURE:
<223> OTHER INFORMATION: Primer

<400> SEQUENCE: 790
cgcaccgtgg gttgagatga agtac 25

<210> SEQ ID NO 791
<211> LENGTH: 18
<212> TYPE: DNA
<213> ORGANISM: Artificial Sequence
<220> FEATURE:
<223> OTHER INFORMATION: Primer

<400> SEQUENCE: 791
cgcatttcac cgctacac 18

<210> SEQ ID NO 792
<211> LENGTH: 20
<212> TYPE: DNA
<213> ORGANISM: Artificial Sequence
<220> FEATURE:
<223> OTHER INFORMATION: Primer

<400> SEQUENCE: 792
cgcggtcggc tcgttgatga 20

<210> SEQ ID NO 793
<211> LENGTH: 21
<212> TYPE: DNA
<213> ORGANISM: Artificial Sequence
<220> FEATURE:
<223> OTHER INFORMATION: Primer

<400> SEQUENCE: 793
cggctgctgg cacgaagtta g 21

<210> SEQ ID NO 794
<211> LENGTH: 15
<212> TYPE: DNA

<213> ORGANISM: Artificial Sequence
<220> FEATURE:
<223> OTHER INFORMATION: Primer

<400> SEQUENCE: 794
cggcttcaag acccc 15

<210> SEQ ID NO 795
<211> LENGTH: 24
<212> TYPE: DNA
<213> ORGANISM: Artificial Sequence
<220> FEATURE:
<223> OTHER INFORMATION: Primer

<400> SEQUENCE: 795
cggtacgaac tggatgtcgc cgtt 24

<210> SEQ ID NO 796
<211> LENGTH: 15
<212> TYPE: DNA
<213> ORGANISM: Artificial Sequence
<220> FEATURE:
<223> OTHER INFORMATION: Primer

<400> SEQUENCE: 796
cgtactcccc aggcg 15

<210> SEQ ID NO 797
<211> LENGTH: 30
<212> TYPE: DNA
<213> ORGANISM: Artificial Sequence
<220> FEATURE:
<223> OTHER INFORMATION: Primer

<400> SEQUENCE: 797
cgtataagct gcaccataag cttgtaatgc 30

<210> SEQ ID NO 798
<211> LENGTH: 21
<212> TYPE: DNA
<213> ORGANISM: Artificial Sequence
<220> FEATURE:
<223> OTHER INFORMATION: Primer

<400> SEQUENCE: 798
cgtggactac cagggtatct a 21

<210> SEQ ID NO 799
<211> LENGTH: 21
<212> TYPE: DNA
<213> ORGANISM: Artificial Sequence
<220> FEATURE:
<223> OTHER INFORMATION: Primer

<400> SEQUENCE: 799
ctatcggtca gtcaggagta t 21

<210> SEQ ID NO 800
<211> LENGTH: 22
<212> TYPE: DNA
<213> ORGANISM: Artificial Sequence
<220> FEATURE:
<223> OTHER INFORMATION: Primer

<400> SEQUENCE: 800
cttctacatt tttagccatc ac 22

<210> SEQ ID NO 801
<211> LENGTH: 20
<212> TYPE: DNA
<213> ORGANISM: Artificial Sequence
<220> FEATURE:
<223> OTHER INFORMATION: Primer

<400> SEQUENCE: 801
ctttacgccc agtaattccg 20

<210> SEQ ID NO 802
<211> LENGTH: 25
<212> TYPE: DNA
<213> ORGANISM: Artificial Sequence
<220> FEATURE:
<223> OTHER INFORMATION: Primer

<400> SEQUENCE: 802
ctttcgcttt ctcgaactca accat 25

<210> SEQ ID NO 803
<211> LENGTH: 17
<212> TYPE: DNA
<213> ORGANISM: Artificial Sequence
<220> FEATURE:
<223> OTHER INFORMATION: Primer

<400> SEQUENCE: 803
gaatatcaat ttgtagc 17

<210> SEQ ID NO 804
<211> LENGTH: 27
<212> TYPE: DNA
<213> ORGANISM: Artificial Sequence
<220> FEATURE:
<223> OTHER INFORMATION: Primer

<400> SEQUENCE: 804
gaccccaacc tggccttttg tcgttga 27

<210> SEQ ID NO 805
<211> LENGTH: 19
<212> TYPE: DNA
<213> ORGANISM: Artificial Sequence
<220> FEATURE:
<223> OTHER INFORMATION: Primer

<400> SEQUENCE: 805
gaccgttata gttacggcc 19

<210> SEQ ID NO 806
<211> LENGTH: 19
<212> TYPE: DNA
<213> ORGANISM: Artificial Sequence
<220> FEATURE:
<223> OTHER INFORMATION: Primer

<400> SEQUENCE: 806
gacgggcggt gtgtacaag 19

<210> SEQ ID NO 807
<211> LENGTH: 19
<212> TYPE: DNA
<213> ORGANISM: Artificial Sequence
<220> FEATURE:
<223> OTHER INFORMATION: Primer

<400> SEQUENCE: 807
gacgggcggt gtgtacaag 19

<210> SEQ ID NO 808
<211> LENGTH: 19
<212> TYPE: DNA
<213> ORGANISM: Artificial Sequence
<220> FEATURE:
<223> OTHER INFORMATION: Primer

<400> SEQUENCE: 808
gacgggcggt gtgtacaag 19

<210> SEQ ID NO 809
<211> LENGTH: 21
<212> TYPE: DNA
<213> ORGANISM: Artificial Sequence
<220> FEATURE:
<223> OTHER INFORMATION: Primer

<400> SEQUENCE: 809
gacgtcatcc ccaccttcct c 21

<210> SEQ ID NO 810
<211> LENGTH: 22
<212> TYPE: DNA
<213> ORGANISM: Artificial Sequence
<220> FEATURE:
<223> OTHER INFORMATION: Primer

<400> SEQUENCE: 810
gacgtcatcc ccaccttcct cc 22

<210> SEQ ID NO 811
<211> LENGTH: 19
<212> TYPE: DNA
<213> ORGANISM: Artificial Sequence
<220> FEATURE:
<223> OTHER INFORMATION: Primer

<400> SEQUENCE: 811
gagcatcagc gtgcgtgct 19

<210> SEQ ID NO 812
<211> LENGTH: 25
<212> TYPE: DNA
<213> ORGANISM: Artificial Sequence
<220> FEATURE:
<223> OTHER INFORMATION: Primer

<400> SEQUENCE: 812
gagctgcgcc aacgaataaa tcgtc 25

<210> SEQ ID NO 813
<211> LENGTH: 29
<212> TYPE: DNA
<213> ORGANISM: Artificial Sequence
<220> FEATURE:
<223> OTHER INFORMATION: Primer

<400> SEQUENCE: 813
gattggcgat aaagtgatat tttctaaaa 29

<210> SEQ ID NO 814
<211> LENGTH: 26
<212> TYPE: DNA

<213> ORGANISM: Artificial Sequence
<220> FEATURE:
<223> OTHER INFORMATION: Primer

<400> SEQUENCE: 814
gcccaccaga aagactagca ggataa 26

<210> SEQ ID NO 815
<211> LENGTH: 21
<212> TYPE: DNA
<213> ORGANISM: Artificial Sequence
<220> FEATURE:
<223> OTHER INFORMATION: Primer

<400> SEQUENCE: 815
gccgtccatc tgagcagcac c 21

<210> SEQ ID NO 816
<211> LENGTH: 21
<212> TYPE: DNA
<213> ORGANISM: Artificial Sequence
<220> FEATURE:
<223> OTHER INFORMATION: Primer

<400> SEQUENCE: 816
gccgtccatt tgagcagcac c 21

<210> SEQ ID NO 817
<211> LENGTH: 19
<212> TYPE: DNA
<213> ORGANISM: Artificial Sequence
<220> FEATURE:
<223> OTHER INFORMATION: Primer

<400> SEQUENCE: 817
gccttgcgac cgtactccc 19

<210> SEQ ID NO 818
<211> LENGTH: 18
<212> TYPE: DNA
<213> ORGANISM: Artificial Sequence
<220> FEATURE:
<223> OTHER INFORMATION: Primer

<400> SEQUENCE: 818
gcgaccgtac tccccagg 18

<210> SEQ ID NO 819
<211> LENGTH: 19
<212> TYPE: DNA
<213> ORGANISM: Artificial Sequence
<220> FEATURE:
<223> OTHER INFORMATION: Primer

<400> SEQUENCE: 819
gcgctccacg tcttcacgc 19

<210> SEQ ID NO 820
<211> LENGTH: 19
<212> TYPE: DNA
<213> ORGANISM: Artificial Sequence
<220> FEATURE:
<223> OTHER INFORMATION: Primer

<400> SEQUENCE: 820
gcgtgacagg caggtattc 19

<210> SEQ ID NO 821
<211> LENGTH: 28
<212> TYPE: DNA
<213> ORGANISM: Artificial Sequence
<220> FEATURE:
<223> OTHER INFORMATION: Primer

<400> SEQUENCE: 821
gcgtgacgac cttcttgaat tgtaatca 28

<210> SEQ ID NO 822
<211> LENGTH: 24
<212> TYPE: DNA
<213> ORGANISM: Artificial Sequence
<220> FEATURE:
<223> OTHER INFORMATION: Primer

<400> SEQUENCE: 822
gcgttccaca gcttgttgca gaag 24

<210> SEQ ID NO 823
<211> LENGTH: 18
<212> TYPE: DNA
<213> ORGANISM: Artificial Sequence
<220> FEATURE:
<223> OTHER INFORMATION: Primer

<400> SEQUENCE: 823
gctgctggca cggagtta 18

<210> SEQ ID NO 824
<211> LENGTH: 26
<212> TYPE: DNA
<213> ORGANISM: Artificial Sequence
<220> FEATURE:
<223> OTHER INFORMATION: Primer

<400> SEQUENCE: 824
gctgctttga tggctgaatc cccttc 26

<210> SEQ ID NO 825
<211> LENGTH: 21
<212> TYPE: DNA
<213> ORGANISM: Artificial Sequence
<220> FEATURE:
<223> OTHER INFORMATION: Primer

<400> SEQUENCE: 825
gctggattcg cctttgctac g 21

<210> SEQ ID NO 826
<211> LENGTH: 20
<212> TYPE: DNA
<213> ORGANISM: Artificial Sequence
<220> FEATURE:
<223> OTHER INFORMATION: Primer

<400> SEQUENCE: 826
gcttacacac ccggcctatc 20

<210> SEQ ID NO 827
<211> LENGTH: 23
<212> TYPE: DNA
<213> ORGANISM: Artificial Sequence
<220> FEATURE:
<223> OTHER INFORMATION: Primer

<400> SEQUENCE: 827
ggaatttacc agcgatagac acc 23

<210> SEQ ID NO 828
<211> LENGTH: 30
<212> TYPE: DNA
<213> ORGANISM: Artificial Sequence
<220> FEATURE:
<223> OTHER INFORMATION: Primer

<400> SEQUENCE: 828
ggataattgg tcgtaacaag ggatagtgag 30

<210> SEQ ID NO 829
<211> LENGTH: 25
<212> TYPE: DNA
<213> ORGANISM: Artificial Sequence
<220> FEATURE:
<223> OTHER INFORMATION: Primer

<400> SEQUENCE: 829
ggcatcacca tttccttgtc cttcg 25

<210> SEQ ID NO 830
<211> LENGTH: 18
<212> TYPE: DNA
<213> ORGANISM: Artificial Sequence
<220> FEATURE:
<223> OTHER INFORMATION: Primer

<400> SEQUENCE: 830
ggccgtactc cccaggcg 18

<210> SEQ ID NO 831
<211> LENGTH: 20
<212> TYPE: DNA
<213> ORGANISM: Artificial Sequence
<220> FEATURE:
<223> OTHER INFORMATION: Primer

<400> SEQUENCE: 831
ggcgcttgta cttaccgcac 20

<210> SEQ ID NO 832
<211> LENGTH: 25
<212> TYPE: DNA
<213> ORGANISM: Artificial Sequence
<220> FEATURE:
<223> OTHER INFORMATION: Primer

<400> SEQUENCE: 832
gggtctacac ctgcacttgc ataac 25

<210> SEQ ID NO 833
<211> LENGTH: 16
<212> TYPE: DNA
<213> ORGANISM: Artificial Sequence
<220> FEATURE:
<223> OTHER INFORMATION: Primer

<400> SEQUENCE: 833
gggtttcccc attcgg 16

<210> SEQ ID NO 834
<211> LENGTH: 20
<212> TYPE: DNA

<213> ORGANISM: Artificial Sequence
<220> FEATURE:
<223> OTHER INFORMATION: Primer

<400> SEQUENCE: 834
ggtaaccctt gtctttgaat 20

<210> SEQ ID NO 835
<211> LENGTH: 19
<212> TYPE: DNA
<213> ORGANISM: Artificial Sequence
<220> FEATURE:
<223> OTHER INFORMATION: Primer

<400> SEQUENCE: 835
ggtaaggttc ttcgcgttg 19

<210> SEQ ID NO 836
<211> LENGTH: 28
<212> TYPE: DNA
<213> ORGANISM: Artificial Sequence
<220> FEATURE:
<223> OTHER INFORMATION: Primer

<400> SEQUENCE: 836
ggtataacgc atcgcagcaa aagattta 28

<210> SEQ ID NO 837
<211> LENGTH: 28
<212> TYPE: DNA
<213> ORGANISM: Artificial Sequence
<220> FEATURE:
<223> OTHER INFORMATION: Primer

<400> SEQUENCE: 837
gtaacccttg tctttgaatt gtatttgc 28

<210> SEQ ID NO 838
<211> LENGTH: 22
<212> TYPE: DNA
<213> ORGANISM: Artificial Sequence
<220> FEATURE:
<223> OTHER INFORMATION: Primer

<400> SEQUENCE: 838
gtaagccatg ttttgttcca tc 22

<210> SEQ ID NO 839
<211> LENGTH: 22
<212> TYPE: DNA
<213> ORGANISM: Artificial Sequence
<220> FEATURE:
<223> OTHER INFORMATION: Primer

<400> SEQUENCE: 839
gtatctaatc ctgtttgctc cc 22

<210> SEQ ID NO 840
<211> LENGTH: 27
<212> TYPE: DNA
<213> ORGANISM: Artificial Sequence
<220> FEATURE:
<223> OTHER INFORMATION: Primer

<400> SEQUENCE: 840
gtccgacttg acggtcaaca tttcctg 27

<210> SEQ ID NO 841
<211> LENGTH: 18
<212> TYPE: DNA
<213> ORGANISM: Artificial Sequence
<220> FEATURE:
<223> OTHER INFORMATION: Primer

<400> SEQUENCE: 841
gtgcgccctt tctaactt 18

<210> SEQ ID NO 842
<211> LENGTH: 22
<212> TYPE: DNA
<213> ORGANISM: Artificial Sequence
<220> FEATURE:
<223> OTHER INFORMATION: Primer

<400> SEQUENCE: 842
gtgctggttt accccatgga gt 22

<210> SEQ ID NO 843
<211> LENGTH: 21
<212> TYPE: DNA
<213> ORGANISM: Artificial Sequence
<220> FEATURE:
<223> OTHER INFORMATION: Primer

<400> SEQUENCE: 843
gttcaaatgc ctggataccc a 21

<210> SEQ ID NO 844
<211> LENGTH: 24
<212> TYPE: DNA
<213> ORGANISM: Artificial Sequence
<220> FEATURE:
<223> OTHER INFORMATION: Primer

<400> SEQUENCE: 844
gttgtcacca ggcattacca tttc 24

<210> SEQ ID NO 845
<211> LENGTH: 24
<212> TYPE: DNA
<213> ORGANISM: Artificial Sequence
<220> FEATURE:
<223> OTHER INFORMATION: Primer

<400> SEQUENCE: 845
gttgtcgcca ggcataacca tttc 24

<210> SEQ ID NO 846
<211> LENGTH: 24
<212> TYPE: DNA
<213> ORGANISM: Artificial Sequence
<220> FEATURE:
<223> OTHER INFORMATION: Primer

<400> SEQUENCE: 846
gtttcatgct tagatgcttt cagc 24

<210> SEQ ID NO 847
<211> LENGTH: 25
<212> TYPE: DNA
<213> ORGANISM: Artificial Sequence
<220> FEATURE:
<223> OTHER INFORMATION: Primer

<400> SEQUENCE: 847
gtttttcgtt gcgtacgatg atgtc 25

<210> SEQ ID NO 848
<211> LENGTH: 27
<212> TYPE: DNA
<213> ORGANISM: Artificial Sequence
<220> FEATURE:
<223> OTHER INFORMATION: Primer

<400> SEQUENCE: 848
taaacgtccg ataccaatgg ttcgctc 27

<210> SEQ ID NO 849
<211> LENGTH: 30
<212> TYPE: DNA
<213> ORGANISM: Artificial Sequence
<220> FEATURE:
<223> OTHER INFORMATION: Primer

<400> SEQUENCE: 849
taaactattt ttttagctat actcgaacac 30

<210> SEQ ID NO 850
<211> LENGTH: 28
<212> TYPE: DNA
<213> ORGANISM: Artificial Sequence
<220> FEATURE:
<223> OTHER INFORMATION: Primer

<400> SEQUENCE: 850
taaagacacc gctgggttta aatgtgca 28

<210> SEQ ID NO 851
<211> LENGTH: 27
<212> TYPE: DNA
<213> ORGANISM: Artificial Sequence
<220> FEATURE:
<223> OTHER INFORMATION: Primer

<400> SEQUENCE: 851
taaagagacg tttggtagtt catttgc 27

<210> SEQ ID NO 852
<211> LENGTH: 33
<212> TYPE: DNA
<213> ORGANISM: Artificial Sequence
<220> FEATURE:
<223> OTHER INFORMATION: Primer

<400> SEQUENCE: 852
taaaggatag cggtaactaa atggctgagc cat 33

<210> SEQ ID NO 853
<211> LENGTH: 26
<212> TYPE: DNA
<213> ORGANISM: Artificial Sequence
<220> FEATURE:
<223> OTHER INFORMATION: Primer

<400> SEQUENCE: 853
taaatgcact tgcttcaggg ccatat 26

<210> SEQ ID NO 854
<211> LENGTH: 31
<212> TYPE: DNA

<213> ORGANISM: Artificial Sequence
<220> FEATURE:
<223> OTHER INFORMATION: Primer

<400> SEQUENCE: 854
taaattccgc aaagactttg gcattaggtg t 31

<210> SEQ ID NO 855
<211> LENGTH: 29
<212> TYPE: DNA
<213> ORGANISM: Artificial Sequence
<220> FEATURE:
<223> OTHER INFORMATION: Primer

<400> SEQUENCE: 855
taacaaatcc cgtctgagtt cctcttgca 29

<210> SEQ ID NO 856
<211> LENGTH: 28
<212> TYPE: DNA
<213> ORGANISM: Artificial Sequence
<220> FEATURE:
<223> OTHER INFORMATION: Primer

<400> SEQUENCE: 856
taacaacgtt accttcgcga tccactaa 28

<210> SEQ ID NO 857
<211> LENGTH: 23
<212> TYPE: DNA
<213> ORGANISM: Artificial Sequence
<220> FEATURE:
<223> OTHER INFORMATION: Primer

<400> SEQUENCE: 857
taaccatttc gcgtaagatt caa 23

<210> SEQ ID NO 858
<211> LENGTH: 29
<212> TYPE: DNA
<213> ORGANISM: Artificial Sequence
<220> FEATURE:
<223> OTHER INFORMATION: Primer

<400> SEQUENCE: 858
taaccacccc aagatttatc tttttgcca 29

<210> SEQ ID NO 859
<211> LENGTH: 23
<212> TYPE: DNA
<213> ORGANISM: Artificial Sequence
<220> FEATURE:
<223> OTHER INFORMATION: Primer

<400> SEQUENCE: 859
taaccatttc gcgtaagatt caa 23

<210> SEQ ID NO 860
<211> LENGTH: 39
<212> TYPE: DNA
<213> ORGANISM: Artificial Sequence
<220> FEATURE:
<223> OTHER INFORMATION: Primer

<400> SEQUENCE: 860
taacccttgt ctttgaattg tatttgcaat taatcctgg 39

<210> SEQ ID NO 861
<211> LENGTH: 29
<212> TYPE: DNA
<213> ORGANISM: Artificial Sequence
<220> FEATURE:
<223> OTHER INFORMATION: Primer

<400> SEQUENCE: 861
taaccgtttc caaaggtact gtattttgt 29

<210> SEQ ID NO 862
<211> LENGTH: 34
<212> TYPE: DNA
<213> ORGANISM: Artificial Sequence
<220> FEATURE:
<223> OTHER INFORMATION: Primer

<400> SEQUENCE: 862
taaccgtttc caaaggtact gtattttgtt tacc 34

<210> SEQ ID NO 863
<211> LENGTH: 26
<212> TYPE: DNA
<213> ORGANISM: Artificial Sequence
<220> FEATURE:
<223> OTHER INFORMATION: Primer

<400> SEQUENCE: 863
taactcctct tccttcaaca ggtgga 26

<210> SEQ ID NO 864
<211> LENGTH: 29
<212> TYPE: DNA
<213> ORGANISM: Artificial Sequence
<220> FEATURE:
<223> OTHER INFORMATION: Primer

<400> SEQUENCE: 864
taactgaccc aaagctgaaa gctttactg 29

<210> SEQ ID NO 865
<211> LENGTH: 33
<212> TYPE: DNA
<213> ORGANISM: Artificial Sequence
<220> FEATURE:
<223> OTHER INFORMATION: Primer

<400> SEQUENCE: 865
taagacaagg ttttgtggat tttttagctt gtt 33

<210> SEQ ID NO 866
<211> LENGTH: 26
<212> TYPE: DNA
<213> ORGANISM: Artificial Sequence
<220> FEATURE:
<223> OTHER INFORMATION: Primer

<400> SEQUENCE: 866
taagagtgat gcgggctggt tcaaca 26

<210> SEQ ID NO 867
<211> LENGTH: 25
<212> TYPE: DNA
<213> ORGANISM: Artificial Sequence
<220> FEATURE:
<223> OTHER INFORMATION: Primer

<400> SEQUENCE: 867
taagcaatac ctttacttgc accac 25

<210> SEQ ID NO 868
<211> LENGTH: 27
<212> TYPE: DNA
<213> ORGANISM: Artificial Sequence
<220> FEATURE:
<223> OTHER INFORMATION: Primer

<400> SEQUENCE: 868
taagcaatac ctttacttgc accacct 27

<210> SEQ ID NO 869
<211> LENGTH: 28
<212> TYPE: DNA
<213> ORGANISM: Artificial Sequence
<220> FEATURE:
<223> OTHER INFORMATION: Primer

<400> SEQUENCE: 869
taagcaatac ctttacttgc accacctg 28

<210> SEQ ID NO 870
<211> LENGTH: 31
<212> TYPE: DNA
<213> ORGANISM: Artificial Sequence
<220> FEATURE:
<223> OTHER INFORMATION: Primer

<400> SEQUENCE: 870
taagcaccat ataagtctac ttttttccct t 31

<210> SEQ ID NO 871
<211> LENGTH: 27
<212> TYPE: DNA
<213> ORGANISM: Artificial Sequence
<220> FEATURE:
<223> OTHER INFORMATION: Primer

<400> SEQUENCE: 871
taagccagca agagctgtat agttcca 27

<210> SEQ ID NO 872
<211> LENGTH: 26
<212> TYPE: DNA
<213> ORGANISM: Artificial Sequence
<220> FEATURE:
<223> OTHER INFORMATION: Primer

<400> SEQUENCE: 872
taagctcccg tatcttgagt cgcctc 26

<210> SEQ ID NO 873
<211> LENGTH: 23
<212> TYPE: DNA
<213> ORGANISM: Artificial Sequence
<220> FEATURE:
<223> OTHER INFORMATION: Primer

<400> SEQUENCE: 873
taagttacct tgcccgtcaa cca 23

<210> SEQ ID NO 874
<211> LENGTH: 27
<212> TYPE: DNA

<213> ORGANISM: Artificial Sequence
<220> FEATURE:
<223> OTHER INFORMATION: Primer

<400> SEQUENCE: 874
taagttcctt cgctagtatg ttggctt 27

<210> SEQ ID NO 875
<211> LENGTH: 30
<212> TYPE: DNA
<213> ORGANISM: Artificial Sequence
<220> FEATURE:
<223> OTHER INFORMATION: Primer

<400> SEQUENCE: 875
taatcgacga ccatcttgga aagatttctc 30

<210> SEQ ID NO 876
<211> LENGTH: 23
<212> TYPE: DNA
<213> ORGANISM: Artificial Sequence
<220> FEATURE:
<223> OTHER INFORMATION: Primer

<400> SEQUENCE: 876
taatctggct gcggaagtga aat 23

<210> SEQ ID NO 877
<211> LENGTH: 25
<212> TYPE: DNA
<213> ORGANISM: Artificial Sequence
<220> FEATURE:
<223> OTHER INFORMATION: Primer

<400> SEQUENCE: 877
taatctggct gcggaagtga aatcg 25

<210> SEQ ID NO 878
<211> LENGTH: 31
<212> TYPE: DNA
<213> ORGANISM: Artificial Sequence
<220> FEATURE:
<223> OTHER INFORMATION: Primer

<400> SEQUENCE: 878
taatgccggg tagtgcaatc cattcttcta g 31

<210> SEQ ID NO 879
<211> LENGTH: 24
<212> TYPE: DNA
<213> ORGANISM: Artificial Sequence
<220> FEATURE:
<223> OTHER INFORMATION: Primer

<400> SEQUENCE: 879
taatgcgata ctggcctgca agtc 24

<210> SEQ ID NO 880
<211> LENGTH: 33
<212> TYPE: DNA
<213> ORGANISM: Artificial Sequence
<220> FEATURE:
<223> OTHER INFORMATION: Primer

<400> SEQUENCE: 880
tacaaccttc ggataatcag gatgagaatt aat 33

<210> SEQ ID NO 881
<211> LENGTH: 27
<212> TYPE: DNA
<213> ORGANISM: Artificial Sequence
<220> FEATURE:
<223> OTHER INFORMATION: Primer

<400> SEQUENCE: 881
tacaacgtga taaacacgac cagaagc 27

<210> SEQ ID NO 882
<211> LENGTH: 35
<212> TYPE: DNA
<213> ORGANISM: Artificial Sequence
<220> FEATURE:
<223> OTHER INFORMATION: Primer

<400> SEQUENCE: 882
tacaactggt tcaaaaacat taagctgtaa ttgtc 35

<210> SEQ ID NO 883
<211> LENGTH: 32
<212> TYPE: DNA
<213> ORGANISM: Artificial Sequence
<220> FEATURE:
<223> OTHER INFORMATION: Primer

<400> SEQUENCE: 883
tacagcttta aagccagcaa aatgaattac ag 32

<210> SEQ ID NO 884
<211> LENGTH: 22
<212> TYPE: DNA
<213> ORGANISM: Artificial Sequence
<220> FEATURE:
<223> OTHER INFORMATION: Primer

<400> SEQUENCE: 884
tacaggagca gcaggcttca ag 22

<210> SEQ ID NO 885
<211> LENGTH: 26
<212> TYPE: DNA
<213> ORGANISM: Artificial Sequence
<220> FEATURE:
<223> OTHER INFORMATION: Primer

<400> SEQUENCE: 885
tacatcgttt cgcccaagat caatca 26

<210> SEQ ID NO 886
<211> LENGTH: 33
<212> TYPE: DNA
<213> ORGANISM: Artificial Sequence
<220> FEATURE:
<223> OTHER INFORMATION: Primer

<400> SEQUENCE: 886
tacatctcct tcgatagaaa tttcattgct atc 33

<210> SEQ ID NO 887
<211> LENGTH: 25
<212> TYPE: DNA
<213> ORGANISM: Artificial Sequence
<220> FEATURE:
<223> OTHER INFORMATION: Primer

<400> SEQUENCE: 887
taccaaagcg tgcacgatag ttgag 25

<210> SEQ ID NO 888
<211> LENGTH: 27
<212> TYPE: DNA
<213> ORGANISM: Artificial Sequence
<220> FEATURE:
<223> OTHER INFORMATION: Primer

<400> SEQUENCE: 888
taccatctac ccaaacatta gcaccaa 27

<210> SEQ ID NO 889
<211> LENGTH: 22
<212> TYPE: DNA
<213> ORGANISM: Artificial Sequence
<220> FEATURE:
<223> OTHER INFORMATION: Primer

<400> SEQUENCE: 889
taccccagtt cccctgacct tc 22

<210> SEQ ID NO 890
<211> LENGTH: 27
<212> TYPE: DNA
<213> ORGANISM: Artificial Sequence
<220> FEATURE:
<223> OTHER INFORMATION: Primer

<400> SEQUENCE: 890
taccggaagc accagcgaca ttaatag 27

<210> SEQ ID NO 891
<211> LENGTH: 27
<212> TYPE: DNA
<213> ORGANISM: Artificial Sequence
<220> FEATURE:
<223> OTHER INFORMATION: Primer

<400> SEQUENCE: 891
tacctgcatt aatcgcttgt tcatcaa 27

<210> SEQ ID NO 892
<211> LENGTH: 22
<212> TYPE: DNA
<213> ORGANISM: Artificial Sequence
<220> FEATURE:
<223> OTHER INFORMATION: Primer

<400> SEQUENCE: 892
taccttaccg ccaaagctgt ct 22

<210> SEQ ID NO 893
<211> LENGTH: 24
<212> TYPE: DNA
<213> ORGANISM: Artificial Sequence
<220> FEATURE:
<223> OTHER INFORMATION: Primer

<400> SEQUENCE: 893
taccttagga ccgttatagt tacg 24

<210> SEQ ID NO 894
<211> LENGTH: 24
<212> TYPE: DNA

<213> ORGANISM: Artificial Sequence
<220> FEATURE:
<223> OTHER INFORMATION: Primer

<400> SEQUENCE: 894 tacctttcc acaacagaat cagc 24

<210> SEQ ID NO 895
<211> LENGTH: 21
<212> TYPE: DNA
<213> ORGANISM: Artificial Sequence
<220> FEATURE:
<223> OTHER INFORMATION: Primer

<400> SEQUENCE: 895
tacgagctga cgacagccat g 21

<210> SEQ ID NO 896
<211> LENGTH: 23
<212> TYPE: DNA
<213> ORGANISM: Artificial Sequence
<220> FEATURE:
<223> OTHER INFORMATION: Primer

<400> SEQUENCE: 896
tacgagctga cgacagccat gca 23

<210> SEQ ID NO 897
<211> LENGTH: 22
<212> TYPE: DNA
<213> ORGANISM: Artificial Sequence
<220> FEATURE:
<223> OTHER INFORMATION: Primer

<400> SEQUENCE: 897
tacgcattac tcacccgtcc gc 22

<210> SEQ ID NO 898
<211> LENGTH: 20
<212> TYPE: DNA
<213> ORGANISM: Artificial Sequence
<220> FEATURE:
<223> OTHER INFORMATION: Primer

<400> SEQUENCE: 898
tacgccatca ggccacgcat 20

<210> SEQ ID NO 899
<211> LENGTH: 27
<212> TYPE: DNA
<213> ORGANISM: Artificial Sequence
<220> FEATURE:
<223> OTHER INFORMATION: Primer

<400> SEQUENCE: 899
tacgctaagc cacgtccata tttatca 27

<210> SEQ ID NO 900
<211> LENGTH: 35
<212> TYPE: DNA
<213> ORGANISM: Artificial Sequence
<220> FEATURE:
<223> OTHER INFORMATION: Primer

<400> SEQUENCE: 900
tacgtatgta aattccgcaa agactttggc attag 35

<210> SEQ ID NO 901
<211> LENGTH: 30
<212> TYPE: DNA
<213> ORGANISM: Artificial Sequence
<220> FEATURE:
<223> OTHER INFORMATION: Primer

<400> SEQUENCE: 901
tacgtcgcct ttaacttggt tatattcagc 30

<210> SEQ ID NO 902
<211> LENGTH: 31
<212> TYPE: DNA
<213> ORGANISM: Artificial Sequence
<220> FEATURE:
<223> OTHER INFORMATION: Primer

<400> SEQUENCE: 902
tacgttctac gatttcttca tcaggtacat c 31

<210> SEQ ID NO 903
<211> LENGTH: 24
<212> TYPE: DNA
<213> ORGANISM: Artificial Sequence
<220> FEATURE:
<223> OTHER INFORMATION: Primer

<400> SEQUENCE: 903
tacgtttgta tcttctgcag aacc 24

<210> SEQ ID NO 904
<211> LENGTH: 29
<212> TYPE: DNA
<213> ORGANISM: Artificial Sequence
<220> FEATURE:
<223> OTHER INFORMATION: Primer

<400> SEQUENCE: 904
tacacctggt ttcgttttga tgatttgta 29

<210> SEQ ID NO 905
<211> LENGTH: 24
<212> TYPE: DNA
<213> ORGANISM: Artificial Sequence
<220> FEATURE:
<223> OTHER INFORMATION: Primer

<400> SEQUENCE: 905
tactagacga cgggtcaggt aacc 24

<210> SEQ ID NO 906
<211> LENGTH: 32
<212> TYPE: DNA
<213> ORGANISM: Artificial Sequence
<220> FEATURE:
<223> OTHER INFORMATION: Primer

<400> SEQUENCE: 906
tacttcagct tcgtccaata aaaaatcaca at 32

<210> SEQ ID NO 907
<211> LENGTH: 31
<212> TYPE: DNA
<213> ORGANISM: Artificial Sequence
<220> FEATURE:
<223> OTHER INFORMATION: Primer

```
<400> SEQUENCE: 907

tactttaagg ggctatcttt accatgaacc t                               31

<210> SEQ ID NO 908
<211> LENGTH: 27
<212> TYPE: DNA
<213> ORGANISM: Artificial Sequence
<220> FEATURE:
<223> OTHER INFORMATION: Primer

<400> SEQUENCE: 908

tagagagtag ccatcttcac cgttgtc                                    27

<210> SEQ ID NO 909
<211> LENGTH: 23
<212> TYPE: DNA
<213> ORGANISM: Artificial Sequence
<220> FEATURE:
<223> OTHER INFORMATION: Primer

<400> SEQUENCE: 909

tagcaccaat caccctttcc tgt                                        23

<210> SEQ ID NO 910
<211> LENGTH: 28
<212> TYPE: DNA
<213> ORGANISM: Artificial Sequence
<220> FEATURE:
<223> OTHER INFORMATION: Primer

<400> SEQUENCE: 910

tagcagcaaa agttatcaca cctgcagt                                   28

<210> SEQ ID NO 911
<211> LENGTH: 25
<212> TYPE: DNA
<213> ORGANISM: Artificial Sequence
<220> FEATURE:
<223> OTHER INFORMATION: Primer

<400> SEQUENCE: 911

tagcagctag ctcgtaacca gtgta                                      25

<210> SEQ ID NO 912
<211> LENGTH: 31
<212> TYPE: DNA
<213> ORGANISM: Artificial Sequence
<220> FEATURE:
<223> OTHER INFORMATION: Primer

<400> SEQUENCE: 912

tagccatacg taccattgct tcataaatag a                               31

<210> SEQ ID NO 913
<211> LENGTH: 22
<212> TYPE: DNA
<213> ORGANISM: Artificial Sequence
<220> FEATURE:
<223> OTHER INFORMATION: Primer

<400> SEQUENCE: 913

tagcccagct gtttgagcaa ct                                         22

<210> SEQ ID NO 914
<211> LENGTH: 20
<212> TYPE: DNA
```

-continued

<213> ORGANISM: Artificial Sequence
<220> FEATURE:
<223> OTHER INFORMATION: Primer

<400> SEQUENCE: 914
tagccgcggt cgaattgcat 20

<210> SEQ ID NO 915
<211> LENGTH: 25
<212> TYPE: DNA
<213> ORGANISM: Artificial Sequence
<220> FEATURE:
<223> OTHER INFORMATION: Primer

<400> SEQUENCE: 915
tagccttggc aacatcagca aaact 25

<210> SEQ ID NO 916
<211> LENGTH: 24
<212> TYPE: DNA
<213> ORGANISM: Artificial Sequence
<220> FEATURE:
<223> OTHER INFORMATION: Primer

<400> SEQUENCE: 916
tagccttttc tccggcgtag atct 24

<210> SEQ ID NO 917
<211> LENGTH: 34
<212> TYPE: DNA
<213> ORGANISM: Artificial Sequence
<220> FEATURE:
<223> OTHER INFORMATION: Primer

<400> SEQUENCE: 917
tagcgatttc tactcctaga gttgaaattt cagg 34

<210> SEQ ID NO 918
<211> LENGTH: 29
<212> TYPE: DNA
<213> ORGANISM: Artificial Sequence
<220> FEATURE:
<223> OTHER INFORMATION: Primer

<400> SEQUENCE: 918
tagctgctag atgagcttct gccatggcc 29

<210> SEQ ID NO 919
<211> LENGTH: 23
<212> TYPE: DNA
<213> ORGANISM: Artificial Sequence
<220> FEATURE:
<223> OTHER INFORMATION: Primer

<400> SEQUENCE: 919
taggatgaaa gcattccgct ggc 23

<210> SEQ ID NO 920
<211> LENGTH: 28
<212> TYPE: DNA
<213> ORGANISM: Artificial Sequence
<220> FEATURE:
<223> OTHER INFORMATION: Primer

<400> SEQUENCE: 920
taggatgagc attatcaggg aaagaatc 28

<210> SEQ ID NO 921
<211> LENGTH: 23
<212> TYPE: DNA
<213> ORGANISM: Artificial Sequence
<220> FEATURE:
<223> OTHER INFORMATION: Primer

<400> SEQUENCE: 921
taggattttt ccacggcggc atc 23

<210> SEQ ID NO 922
<211> LENGTH: 31
<212> TYPE: DNA
<213> ORGANISM: Artificial Sequence
<220> FEATURE:
<223> OTHER INFORMATION: Primer

<400> SEQUENCE: 922
taggcataac catttcagta ccttctggta a 31

<210> SEQ ID NO 923
<211> LENGTH: 28
<212> TYPE: DNA
<213> ORGANISM: Artificial Sequence
<220> FEATURE:
<223> OTHER INFORMATION: Primer

<400> SEQUENCE: 923
tagtatcacc acgtacaccc ggatcagt 28

<210> SEQ ID NO 924
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (17)...(17)
<223> OTHER INFORMATION: I
<220> FEATURE:
<221> NAME/KEY: modified_base
<222> LOCATION: (20)...(20)
<223> OTHER INFORMATION: I

<400> SEQUENCE: 924
tagtatcacc acgtacaccc ggatcagt 28

<210> SEQ ID NO 925
<211> LENGTH: 32
<212> TYPE: DNA
<213> ORGANISM: Artificial Sequence
<220> FEATURE:
<223> OTHER INFORMATION: Primer

<400> SEQUENCE: 925
tagtcctttc tgaattttac catcaaaggt ac 32

<210> SEQ ID NO 926
<211> LENGTH: 32
<212> TYPE: DNA
<213> ORGANISM: Artificial Sequence
<220> FEATURE:
<223> OTHER INFORMATION: Primer

<400> SEQUENCE: 926
tagtcttttg gaacaccgtc tttaattaaa gt 32

<210> SEQ ID NO 927
<211> LENGTH: 30
<212> TYPE: DNA
<213> ORGANISM: Artificial Sequence
<220> FEATURE:
<223> OTHER INFORMATION: Primer

<400> SEQUENCE: 927
tagtgttgta cctccatata gacattcaga 30

<210> SEQ ID NO 928
<211> LENGTH: 29
<212> TYPE: DNA
<213> ORGANISM: Artificial Sequence
<220> FEATURE:
<223> OTHER INFORMATION: Primer

<400> SEQUENCE: 928
tagttgaagt tgcactatat actgttgga 29

<210> SEQ ID NO 929
<211> LENGTH: 23
<212> TYPE: DNA
<213> ORGANISM: Artificial Sequence
<220> FEATURE:
<223> OTHER INFORMATION: Primer

<400> SEQUENCE: 929
tataacgcac atcgtcaggg tga 23

<210> SEQ ID NO 930
<211> LENGTH: 26
<212> TYPE: DNA
<213> ORGANISM: Artificial Sequence
<220> FEATURE:
<223> OTHER INFORMATION: Primer

<400> SEQUENCE: 930
tatagcacca tccatctgag cggcac 26

<210> SEQ ID NO 931
<211> LENGTH: 29
<212> TYPE: DNA
<213> ORGANISM: Artificial Sequence
<220> FEATURE:
<223> OTHER INFORMATION: Primer

<400> SEQUENCE: 931
tatatgaaca ataccagttc cttctgagt 29

<210> SEQ ID NO 932
<211> LENGTH: 27
<212> TYPE: DNA
<213> ORGANISM: Artificial Sequence
<220> FEATURE:
<223> OTHER INFORMATION: Primer

<400> SEQUENCE: 932
tatatgatta tcattgaact gcggccg 27

<210> SEQ ID NO 933
<211> LENGTH: 28
<212> TYPE: DNA
<213> ORGANISM: Artificial Sequence
<220> FEATURE:
<223> OTHER INFORMATION: Primer

<400> SEQUENCE: 933
tatccattga accaaagtta ccttggcc 28

<210> SEQ ID NO 934
<211> LENGTH: 20
<212> TYPE: DNA
<213> ORGANISM: Artificial Sequence
<220> FEATURE:
<223> OTHER INFORMATION: Primer

<400> SEQUENCE: 934
tatcccctgc ttctgctgcc 20

<210> SEQ ID NO 935
<211> LENGTH: 28
<212> TYPE: DNA
<213> ORGANISM: Artificial Sequence
<220> FEATURE:
<223> OTHER INFORMATION: Primer

<400> SEQUENCE: 935
tatcgacaga tccaaagtta ccatgccc 28

<210> SEQ ID NO 936
<211> LENGTH: 27
<212> TYPE: DNA
<213> ORGANISM: Artificial Sequence
<220> FEATURE:
<223> OTHER INFORMATION: Primer

<400> SEQUENCE: 936
tatggtctat ttcaatggca gttacga 27

<210> SEQ ID NO 937
<211> LENGTH: 24
<212> TYPE: DNA
<213> ORGANISM: Artificial Sequence
<220> FEATURE:
<223> OTHER INFORMATION: Primer

<400> SEQUENCE: 937
tatgtgctca cgagtttgcg gcat 24

<210> SEQ ID NO 938
<211> LENGTH: 28
<212> TYPE: DNA
<213> ORGANISM: Artificial Sequence
<220> FEATURE:
<223> OTHER INFORMATION: Primer

<400> SEQUENCE: 938
tatgtgtagt tgagcttact acatgagc 28

<210> SEQ ID NO 939
<211> LENGTH: 25
<212> TYPE: DNA
<213> ORGANISM: Artificial Sequence
<220> FEATURE:
<223> OTHER INFORMATION: Primer

<400> SEQUENCE: 939
tattcttcgt tactcatgcc ataca 25

<210> SEQ ID NO 940
<211> LENGTH: 23
<212> TYPE: DNA

-continued

<213> ORGANISM: Artificial Sequence
<220> FEATURE:
<223> OTHER INFORMATION: Primer

<400> SEQUENCE: 940
tattgcccag aaatcaaatc atc 23

<210> SEQ ID NO 941
<211> LENGTH: 30
<212> TYPE: DNA
<213> ORGANISM: Artificial Sequence
<220> FEATURE:
<223> OTHER INFORMATION: Primer

<400> SEQUENCE: 941
tattgcggat caccatgatg atattcttgc 30

<210> SEQ ID NO 942
<211> LENGTH: 31
<212> TYPE: DNA
<213> ORGANISM: Artificial Sequence
<220> FEATURE:
<223> OTHER INFORMATION: Primer

<400> SEQUENCE: 942
tattgctttt tttgctatgc ttcttggaca t 31

<210> SEQ ID NO 943
<211> LENGTH: 24
<212> TYPE: DNA
<213> ORGANISM: Artificial Sequence
<220> FEATURE:
<223> OTHER INFORMATION: Primer

<400> SEQUENCE: 943
tattggaaat accggcagca tctc 24

<210> SEQ ID NO 944
<211> LENGTH: 30
<212> TYPE: DNA
<213> ORGANISM: Artificial Sequence
<220> FEATURE:
<223> OTHER INFORMATION: Primer

<400> SEQUENCE: 944
tatttgggtt tcattccact cagattctgg 30

<210> SEQ ID NO 945
<211> LENGTH: 32
<212> TYPE: DNA
<213> ORGANISM: Artificial Sequence
<220> FEATURE:
<223> OTHER INFORMATION: Primer

<400> SEQUENCE: 945
tcaaaaacaa agaattcatt ttctggtcca aa 32

<210> SEQ ID NO 946
<211> LENGTH: 34
<212> TYPE: DNA
<213> ORGANISM: Artificial Sequence
<220> FEATURE:
<223> OTHER INFORMATION: Primer

<400> SEQUENCE: 946
tcaaaacgca tttttacatc ttcgttaaag gcta 34

-continued

<210> SEQ ID NO 947
<211> LENGTH: 29
<212> TYPE: DNA
<213> ORGANISM: Artificial Sequence
<220> FEATURE:
<223> OTHER INFORMATION: Primer

<400> SEQUENCE: 947
tcaaaacttg ctctagacca tttaactcc 29

<210> SEQ ID NO 948
<211> LENGTH: 30
<212> TYPE: DNA
<213> ORGANISM: Artificial Sequence
<220> FEATURE:
<223> OTHER INFORMATION: Primer

<400> SEQUENCE: 948
tcaaaatctt ttgattcgat catacgagac 30

<210> SEQ ID NO 949
<211> LENGTH: 27
<212> TYPE: DNA
<213> ORGANISM: Artificial Sequence
<220> FEATURE:
<223> OTHER INFORMATION: Primer

<400> SEQUENCE: 949
tcaaacgatc cgcatcacca tcaaaag 27

<210> SEQ ID NO 950
<211> LENGTH: 30
<212> TYPE: DNA
<213> ORGANISM: Artificial Sequence
<220> FEATURE:
<223> OTHER INFORMATION: Primer

<400> SEQUENCE: 950
tcaaagaacc agcacctaat tcatcattta 30

<210> SEQ ID NO 951
<211> LENGTH: 30
<212> TYPE: DNA
<213> ORGANISM: Artificial Sequence
<220> FEATURE:
<223> OTHER INFORMATION: Primer

<400> SEQUENCE: 951
tcaaagaacc cgcacctaat tcatcattta 30

<210> SEQ ID NO 952
<211> LENGTH: 26
<212> TYPE: DNA
<213> ORGANISM: Artificial Sequence
<220> FEATURE:
<223> OTHER INFORMATION: Primer

<400> SEQUENCE: 952
tcaacaacac ctccttattc ccactc 26

<210> SEQ ID NO 953
<211> LENGTH: 29
<212> TYPE: DNA
<213> ORGANISM: Artificial Sequence
<220> FEATURE:
<223> OTHER INFORMATION: Primer

<400> SEQUENCE: 953
tcaacaatca gatagatgtc agacgcatg 29

<210> SEQ ID NO 954
<211> LENGTH: 28
<212> TYPE: DNA
<213> ORGANISM: Artificial Sequence
<220> FEATURE:
<223> OTHER INFORMATION: Primer

<400> SEQUENCE: 954
tcaacaccag cgttacctaa agtacctt 28

<210> SEQ ID NO 955
<211> LENGTH: 35
<212> TYPE: DNA
<213> ORGANISM: Artificial Sequence
<220> FEATURE:
<223> OTHER INFORMATION: Primer

<400> SEQUENCE: 955
tcaactggtt caaaaacatt aagttgtaat tgtcc 35

<210> SEQ ID NO 956
<211> LENGTH: 28
<212> TYPE: DNA
<213> ORGANISM: Artificial Sequence
<220> FEATURE:
<223> OTHER INFORMATION: Primer

<400> SEQUENCE: 956
tcaacttctg ccattaaaag taatgcca 28

<210> SEQ ID NO 957
<211> LENGTH: 24
<212> TYPE: DNA
<213> ORGANISM: Artificial Sequence
<220> FEATURE:
<223> OTHER INFORMATION: Primer

<400> SEQUENCE: 957
tcaagcgatc tacccgcatt acaa 24

<210> SEQ ID NO 958
<211> LENGTH: 30
<212> TYPE: DNA
<213> ORGANISM: Artificial Sequence
<220> FEATURE:
<223> OTHER INFORMATION: Primer

<400> SEQUENCE: 958
tcaagcgcca tctctttcgg taatccacat 30

<210> SEQ ID NO 959
<211> LENGTH: 30
<212> TYPE: DNA
<213> ORGANISM: Artificial Sequence
<220> FEATURE:
<223> OTHER INFORMATION: Primer

<400> SEQUENCE: 959
tcaagcgcca tttcttttgg taaaccacat 30

<210> SEQ ID NO 960
<211> LENGTH: 31
<212> TYPE: DNA

<213> ORGANISM: Artificial Sequence
<220> FEATURE:
<223> OTHER INFORMATION: Primer

<400> SEQUENCE: 960
tcaagctata tgctacaact ggttcaaaaa c 31

<210> SEQ ID NO 961
<211> LENGTH: 30
<212> TYPE: DNA
<213> ORGANISM: Artificial Sequence
<220> FEATURE:
<223> OTHER INFORMATION: Primer

<400> SEQUENCE: 961
tcaagctcta caccataaaa aaagctctca 30

<210> SEQ ID NO 962
<211> LENGTH: 28
<212> TYPE: DNA
<213> ORGANISM: Artificial Sequence
<220> FEATURE:
<223> OTHER INFORMATION: Primer

<400> SEQUENCE: 962
tcaaggttct caccgtttac cttaggag 28

<210> SEQ ID NO 963
<211> LENGTH: 32
<212> TYPE: DNA
<213> ORGANISM: Artificial Sequence
<220> FEATURE:
<223> OTHER INFORMATION: Primer

<400> SEQUENCE: 963
tcaagtgctt ttacttctat aggtttaagc tc 32

<210> SEQ ID NO 964
<211> LENGTH: 30
<212> TYPE: DNA
<213> ORGANISM: Artificial Sequence
<220> FEATURE:
<223> OTHER INFORMATION: Primer

<400> SEQUENCE: 964
tcaatacaga gtctacactt ggcttaggat 30

<210> SEQ ID NO 965
<211> LENGTH: 25
<212> TYPE: DNA
<213> ORGANISM: Artificial Sequence
<220> FEATURE:
<223> OTHER INFORMATION: Primer

<400> SEQUENCE: 965
tcaatctcga ctttttgtgc cggta 25

<210> SEQ ID NO 966
<211> LENGTH: 28
<212> TYPE: DNA
<213> ORGANISM: Artificial Sequence
<220> FEATURE:
<223> OTHER INFORMATION: Primer

<400> SEQUENCE: 966
tcacaaggac cattataatc aatgccaa 28

<210> SEQ ID NO 967
<211> LENGTH: 23
<212> TYPE: DNA
<213> ORGANISM: Artificial Sequence
<220> FEATURE:
<223> OTHER INFORMATION: Primer

<400> SEQUENCE: 967
tcacaccaag tagtgcaagg atc 23

<210> SEQ ID NO 968
<211> LENGTH: 29
<212> TYPE: DNA
<213> ORGANISM: Artificial Sequence
<220> FEATURE:
<223> OTHER INFORMATION: Primer

<400> SEQUENCE: 968
tcacacctgt aagtgagaaa aaggttgat 29

<210> SEQ ID NO 969
<211> LENGTH: 34
<212> TYPE: DNA
<213> ORGANISM: Artificial Sequence
<220> FEATURE:
<223> OTHER INFORMATION: Primer

<400> SEQUENCE: 969
tcacaggttc tacttcatca ataatttcca ttgc 34

<210> SEQ ID NO 970
<211> LENGTH: 34
<212> TYPE: DNA
<213> ORGANISM: Artificial Sequence
<220> FEATURE:
<223> OTHER INFORMATION: Primer

<400> SEQUENCE: 970
tcaccagctt cagcgtagtc taataattta cgga 34

<210> SEQ ID NO 971
<211> LENGTH: 22
<212> TYPE: DNA
<213> ORGANISM: Artificial Sequence
<220> FEATURE:
<223> OTHER INFORMATION: Primer

<400> SEQUENCE: 971
tcaccatgcg cccgttcaca ta 22

<210> SEQ ID NO 972
<211> LENGTH: 37
<212> TYPE: DNA
<213> ORGANISM: Artificial Sequence
<220> FEATURE:
<223> OTHER INFORMATION: Primer

<400> SEQUENCE: 972
tcaccgataa ataaaatacc taaagttaat gccattg 37

<210> SEQ ID NO 973
<211> LENGTH: 29
<212> TYPE: DNA
<213> ORGANISM: Artificial Sequence
<220> FEATURE:
<223> OTHER INFORMATION: Primer

<400> SEQUENCE: 973
tcacctacag ctttaaagcc agcaaaatg 29

<210> SEQ ID NO 974
<211> LENGTH: 28
<212> TYPE: DNA
<213> ORGANISM: Artificial Sequence
<220> FEATURE:
<223> OTHER INFORMATION: Primer

<400> SEQUENCE: 974
tcacgatacc tgcatcatca aattggtt 28

<210> SEQ ID NO 975
<211> LENGTH: 32
<212> TYPE: DNA
<213> ORGANISM: Artificial Sequence
<220> FEATURE:
<223> OTHER INFORMATION: Primer

<400> SEQUENCE: 975
tcacgatcta aatttggata agccatagga aa 32

<210> SEQ ID NO 976
<211> LENGTH: 24
<212> TYPE: DNA
<213> ORGANISM: Artificial Sequence
<220> FEATURE:
<223> OTHER INFORMATION: Primer

<400> SEQUENCE: 976
tcacgcgacg agtgccatcc attg 24

<210> SEQ ID NO 977
<211> LENGTH: 22
<212> TYPE: DNA
<213> ORGANISM: Artificial Sequence
<220> FEATURE:
<223> OTHER INFORMATION: Primer

<400> SEQUENCE: 977
tcacgcgcat catcaccagt ca 22

<210> SEQ ID NO 978
<211> LENGTH: 18
<212> TYPE: DNA
<213> ORGANISM: Artificial Sequence
<220> FEATURE:
<223> OTHER INFORMATION: Primer

<400> SEQUENCE: 978
tcacgggcca gctcgtct 18

<210> SEQ ID NO 979
<211> LENGTH: 28
<212> TYPE: DNA
<213> ORGANISM: Artificial Sequence
<220> FEATURE:
<223> OTHER INFORMATION: Primer

<400> SEQUENCE: 979
tcacgtcgtc cgacttcacg gtcagcat 28

<210> SEQ ID NO 980
<211> LENGTH: 26
<212> TYPE: DNA

<213> ORGANISM: Artificial Sequence
<220> FEATURE:
<223> OTHER INFORMATION: Primer

<400> SEQUENCE: 980
tcagaatcga tgccaaatgc gtcatc 26

<210> SEQ ID NO 981
<211> LENGTH: 30
<212> TYPE: DNA
<213> ORGANISM: Artificial Sequence
<220> FEATURE:
<223> OTHER INFORMATION: Primer

<400> SEQUENCE: 981
tcagatataa atggaacaaa tggagccact 30

<210> SEQ ID NO 982
<211> LENGTH: 32
<212> TYPE: DNA
<213> ORGANISM: Artificial Sequence
<220> FEATURE:
<223> OTHER INFORMATION: Primer

<400> SEQUENCE: 982
tcagcgtagt ctaataattt acggaacatt tc 32

<210> SEQ ID NO 983
<211> LENGTH: 25
<212> TYPE: DNA
<213> ORGANISM: Artificial Sequence
<220> FEATURE:
<223> OTHER INFORMATION: Primer

<400> SEQUENCE: 983
tcagctgtta acggcttcaa gaccc 25

<210> SEQ ID NO 984
<211> LENGTH: 29
<212> TYPE: DNA
<213> ORGANISM: Artificial Sequence
<220> FEATURE:
<223> OTHER INFORMATION: Primer

<400> SEQUENCE: 984
tcaggtatga aacacgatta gtcctttct 29

<210> SEQ ID NO 985
<211> LENGTH: 29
<212> TYPE: DNA
<213> ORGANISM: Artificial Sequence
<220> FEATURE:
<223> OTHER INFORMATION: Primer

<400> SEQUENCE: 985
tcagtttgca cttcaaaaga aattgtgtt 29

<210> SEQ ID NO 986
<211> LENGTH: 29
<212> TYPE: DNA
<213> ORGANISM: Artificial Sequence
<220> FEATURE:
<223> OTHER INFORMATION: Primer

<400> SEQUENCE: 986
tcataactag catttgtgct ttgaatgct 29

<210> SEQ ID NO 987
<211> LENGTH: 31
<212> TYPE: DNA
<213> ORGANISM: Artificial Sequence
<220> FEATURE:
<223> OTHER INFORMATION: Primer

<400> SEQUENCE: 987
tcataagggt tgcgttgcag attatcttta c 31

<210> SEQ ID NO 988
<211> LENGTH: 26
<212> TYPE: DNA
<213> ORGANISM: Artificial Sequence
<220> FEATURE:
<223> OTHER INFORMATION: Primer

<400> SEQUENCE: 988
tcatctggtt taggatctgg ttgact 26

<210> SEQ ID NO 989
<211> LENGTH: 25
<212> TYPE: DNA
<213> ORGANISM: Artificial Sequence
<220> FEATURE:
<223> OTHER INFORMATION: Primer

<400> SEQUENCE: 989
tcatctgtgg tatggcgggt aagtt 25

<210> SEQ ID NO 990
<211> LENGTH: 26
<212> TYPE: DNA
<213> ORGANISM: Artificial Sequence
<220> FEATURE:
<223> OTHER INFORMATION: Primer

<400> SEQUENCE: 990
tcatgacagc caagacctca cccacc 26

<210> SEQ ID NO 991
<211> LENGTH: 31
<212> TYPE: DNA
<213> ORGANISM: Artificial Sequence
<220> FEATURE:
<223> OTHER INFORMATION: Primer

<400> SEQUENCE: 991
tcatgataga actacctggt tgcatttttg g 31

<210> SEQ ID NO 992
<211> LENGTH: 28
<212> TYPE: DNA
<213> ORGANISM: Artificial Sequence
<220> FEATURE:
<223> OTHER INFORMATION: Primer

<400> SEQUENCE: 992
tcatgtgcta atgttactgc tggatctg 28

<210> SEQ ID NO 993
<211> LENGTH: 31
<212> TYPE: DNA
<213> ORGANISM: Artificial Sequence
<220> FEATURE:
<223> OTHER INFORMATION: Primer

<400> SEQUENCE: 993
tcattaggta aaatgtctgg acatgatcca a 31

<210> SEQ ID NO 994
<211> LENGTH: 28
<212> TYPE: DNA
<213> ORGANISM: Artificial Sequence
<220> FEATURE:
<223> OTHER INFORMATION: Primer

<400> SEQUENCE: 994
tcatttattt cttcgctttt ctcgctac 28

<210> SEQ ID NO 995
<211> LENGTH: 20
<212> TYPE: DNA
<213> ORGANISM: Artificial Sequence
<220> FEATURE:
<223> OTHER INFORMATION: Primer

<400> SEQUENCE: 995
tcatttgtgc tttgaatgct 20

<210> SEQ ID NO 996
<211> LENGTH: 28
<212> TYPE: DNA
<213> ORGANISM: Artificial Sequence
<220> FEATURE:
<223> OTHER INFORMATION: Primer

<400> SEQUENCE: 996
tccaaacgat ctgcatcacc atcaaaag 28

<210> SEQ ID NO 997
<211> LENGTH: 29
<212> TYPE: DNA
<213> ORGANISM: Artificial Sequence
<220> FEATURE:
<223> OTHER INFORMATION: Primer

<400> SEQUENCE: 997
tccaacccag aaccacatac tttattcac 29

<210> SEQ ID NO 998
<211> LENGTH: 27
<212> TYPE: DNA
<213> ORGANISM: Artificial Sequence
<220> FEATURE:
<223> OTHER INFORMATION: Primer

<400> SEQUENCE: 998
tccaaccttt tccacaacag aatcagc 27

<210> SEQ ID NO 999
<211> LENGTH: 24
<212> TYPE: DNA
<213> ORGANISM: Artificial Sequence
<220> FEATURE:
<223> OTHER INFORMATION: Primer

<400> SEQUENCE: 999
tccaagtgct ggtttacccc atgg 24

<210> SEQ ID NO 1000
<211> LENGTH: 26
<212> TYPE: DNA

<213> ORGANISM: Artificial Sequence
<220> FEATURE:
<223> OTHER INFORMATION: Primer

<400> SEQUENCE: 1000
tccaagtgct ggtttacccc atggag 26

<210> SEQ ID NO 1001
<211> LENGTH: 28
<212> TYPE: DNA
<213> ORGANISM: Artificial Sequence
<220> FEATURE:
<223> OTHER INFORMATION: Primer

<400> SEQUENCE: 1001
tccaagtttg acttaaacgt accatcgc 28

<210> SEQ ID NO 1002
<211> LENGTH: 32
<212> TYPE: DNA
<213> ORGANISM: Artificial Sequence
<220> FEATURE:
<223> OTHER INFORMATION: Primer

<400> SEQUENCE: 1002
tccacactgg attgtaattt accttgttct tt 32

<210> SEQ ID NO 1003
<211> LENGTH: 26
<212> TYPE: DNA
<213> ORGANISM: Artificial Sequence
<220> FEATURE:
<223> OTHER INFORMATION: Primer

<400> SEQUENCE: 1003
tccaccacct caaagaccat gtggtg 26

<210> SEQ ID NO 1004
<211> LENGTH: 23
<212> TYPE: DNA
<213> ORGANISM: Artificial Sequence
<220> FEATURE:
<223> OTHER INFORMATION: Primer

<400> SEQUENCE: 1004
tccagcaggt tctgacggaa acg 23

<210> SEQ ID NO 1005
<211> LENGTH: 28
<212> TYPE: DNA
<213> ORGANISM: Artificial Sequence
<220> FEATURE:
<223> OTHER INFORMATION: Primer

<400> SEQUENCE: 1005
tccagcagtt actgtcccct catctttg 28

<210> SEQ ID NO 1006
<211> LENGTH: 30
<212> TYPE: DNA
<213> ORGANISM: Artificial Sequence
<220> FEATURE:
<223> OTHER INFORMATION: Primer

<400> SEQUENCE: 1006
tccaggcatt accatttcta ctccttctgg 30

-continued

<210> SEQ ID NO 1007
<211> LENGTH: 29
<212> TYPE: DNA
<213> ORGANISM: Artificial Sequence
<220> FEATURE:
<223> OTHER INFORMATION: Primer

<400> SEQUENCE: 1007
tccataaggt caccgtcacc attcaaagc 29

<210> SEQ ID NO 1008
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (21)...(21)
<223> OTHER INFORMATION: I
<220> FEATURE:
<221> NAME/KEY: modified_base
<222> LOCATION: (30)...(30)
<223> OTHER INFORMATION: I

<400> SEQUENCE: 1008
tccatacctt tatgcaactt tgtatcaact ggaat 35

<210> SEQ ID NO 1009
<211> LENGTH: 28
<212> TYPE: DNA
<213> ORGANISM: Artificial Sequence
<220> FEATURE:
<223> OTHER INFORMATION: Primer

<400> SEQUENCE: 1009
tccatattgt tgcataaaac ctgttggc 28

<210> SEQ ID NO 1010
<211> LENGTH: 27
<212> TYPE: DNA
<213> ORGANISM: Artificial Sequence
<220> FEATURE:
<223> OTHER INFORMATION: Primer

<400> SEQUENCE: 1010
tccatccata gaaccaaagt taccttg 27

<210> SEQ ID NO 1011
<211> LENGTH: 26
<212> TYPE: DNA
<213> ORGANISM: Artificial Sequence
<220> FEATURE:
<223> OTHER INFORMATION: Primer

<400> SEQUENCE: 1011
tccatcgcag tcacgtttac tgttgg 26

<210> SEQ ID NO 1012
<211> LENGTH: 32
<212> TYPE: DNA
<213> ORGANISM: Artificial Sequence
<220> FEATURE:
<223> OTHER INFORMATION: Primer

<400> SEQUENCE: 1012
tccatcgcca gtttttgcat aatcgctaaa aa 32

-continued

<210> SEQ ID NO 1013
<211> LENGTH: 33
<212> TYPE: DNA
<213> ORGANISM: Artificial Sequence
<220> FEATURE:
<223> OTHER INFORMATION: Primer

<400> SEQUENCE: 1013
tccatctgtt aaaccatcat ataccatgct atc 33

<210> SEQ ID NO 1014
<211> LENGTH: 26
<212> TYPE: DNA
<213> ORGANISM: Artificial Sequence
<220> FEATURE:
<223> OTHER INFORMATION: Primer

<400> SEQUENCE: 1014
tccatttccg acacgtcgtt gatcac 26

<210> SEQ ID NO 1015
<211> LENGTH: 27
<212> TYPE: DNA
<213> ORGANISM: Artificial Sequence
<220> FEATURE:
<223> OTHER INFORMATION: Primer

<400> SEQUENCE: 1015
tcccaatcta acttccacat accatct 27

<210> SEQ ID NO 1016
<211> LENGTH: 29
<212> TYPE: DNA
<213> ORGANISM: Artificial Sequence
<220> FEATURE:
<223> OTHER INFORMATION: Primer

<400> SEQUENCE: 1016
tcccaatctt ttgattcgat catacgaga 29

<210> SEQ ID NO 1017
<211> LENGTH: 27
<212> TYPE: DNA
<213> ORGANISM: Artificial Sequence
<220> FEATURE:
<223> OTHER INFORMATION: Primer

<400> SEQUENCE: 1017
tcccatacct atggcgataa ctgtcat 27

<210> SEQ ID NO 1018
<211> LENGTH: 30
<212> TYPE: DNA
<213> ORGANISM: Artificial Sequence
<220> FEATURE:
<223> OTHER INFORMATION: Primer

<400> SEQUENCE: 1018
tcccattttt tcacgcatgc tgaaaatatc 30

<210> SEQ ID NO 1019
<211> LENGTH: 15
<212> TYPE: DNA
<213> ORGANISM: Artificial Sequence
<220> FEATURE:
<223> OTHER INFORMATION: Primer -continued

<400> SEQUENCE: 1019
tccccacctt cctcc 15

<210> SEQ ID NO 1020
<211> LENGTH: 25
<212> TYPE: DNA
<213> ORGANISM: Artificial Sequence
<220> FEATURE:
<223> OTHER INFORMATION: Primer

<400> SEQUENCE: 1020
tccccatctc cgcaaagaca ataaa 25

<210> SEQ ID NO 1021
<211> LENGTH: 33
<212> TYPE: DNA
<213> ORGANISM: Artificial Sequence
<220> FEATURE:
<223> OTHER INFORMATION: Primer

<400> SEQUENCE: 1021
tccccattta ataattccac ctactatcac act 33

<210> SEQ ID NO 1022
<211> LENGTH: 33
<212> TYPE: DNA
<213> ORGANISM: Artificial Sequence
<220> FEATURE:
<223> OTHER INFORMATION: Primer

<400> SEQUENCE: 1022
tcccctcatg tttaaatgat caggataaaa agc 33

<210> SEQ ID NO 1023
<211> LENGTH: 31
<212> TYPE: DNA
<213> ORGANISM: Artificial Sequence
<220> FEATURE:
<223> OTHER INFORMATION: Primer

<400> SEQUENCE: 1023
tcccctttaa agcaccatta ctcattatag t 31

<210> SEQ ID NO 1024
<211> LENGTH: 33
<212> TYPE: DNA
<213> ORGANISM: Artificial Sequence
<220> FEATURE:
<223> OTHER INFORMATION: Primer

<400> SEQUENCE: 1024
tcccgaacaa tgagttgtat caactatttt tac 33

<210> SEQ ID NO 1025
<211> LENGTH: 21
<212> TYPE: DNA
<213> ORGANISM: Artificial Sequence
<220> FEATURE:
<223> OTHER INFORMATION: Primer

<400> SEQUENCE: 1025
tcccgctggc aaataaactc g 21

<210> SEQ ID NO 1026
<211> LENGTH: 25
<212> TYPE: DNA

<213> ORGANISM: Artificial Sequence
<220> FEATURE:
<223> OTHER INFORMATION: Primer

<400> SEQUENCE: 1026
tcccggctag agattctgta tacga 25

<210> SEQ ID NO 1027
<211> LENGTH: 28
<212> TYPE: DNA
<213> ORGANISM: Artificial Sequence
<220> FEATURE:
<223> OTHER INFORMATION: Primer

<400> SEQUENCE: 1027
tcccgtctga gttcctcttg catgatca 28

<210> SEQ ID NO 1028
<211> LENGTH: 32
<212> TYPE: DNA
<213> ORGANISM: Artificial Sequence
<220> FEATURE:
<223> OTHER INFORMATION: Primer

<400> SEQUENCE: 1028
tccctaatag tagaaataac tgcatcagta gc 32

<210> SEQ ID NO 1029
<211> LENGTH: 34
<212> TYPE: DNA
<213> ORGANISM: Artificial Sequence
<220> FEATURE:
<223> OTHER INFORMATION: Primer

<400> SEQUENCE: 1029
tcccttattt ttctttctac taccttcgga taat 34

<210> SEQ ID NO 1030
<211> LENGTH: 30
<212> TYPE: DNA
<213> ORGANISM: Artificial Sequence
<220> FEATURE:
<223> OTHER INFORMATION: Primer

<400> SEQUENCE: 1030
tcccttcctt aatatgagaa ggaaaccact 30

<210> SEQ ID NO 1031
<211> LENGTH: 32
<212> TYPE: DNA
<213> ORGANISM: Artificial Sequence
<220> FEATURE:
<223> OTHER INFORMATION: Primer

<400> SEQUENCE: 1031
tccgaaactt gttttgtagc tttaatttga gc 32

<210> SEQ ID NO 1032
<211> LENGTH: 21
<212> TYPE: DNA
<213> ORGANISM: Artificial Sequence
<220> FEATURE:
<223> OTHER INFORMATION: Primer

<400> SEQUENCE: 1032
tccgaagttg ccctggccgt c 21

<210> SEQ ID NO 1033
<211> LENGTH: 24
<212> TYPE: DNA
<213> ORGANISM: Artificial Sequence
<220> FEATURE:
<223> OTHER INFORMATION: Primer

<400> SEQUENCE: 1033
tccgagacca gcgtaggtgt aacg 24

<210> SEQ ID NO 1034
<211> LENGTH: 22
<212> TYPE: DNA
<213> ORGANISM: Artificial Sequence
<220> FEATURE:
<223> OTHER INFORMATION: Primer

<400> SEQUENCE: 1034
tccgataagc cggattctgt gc 22

<210> SEQ ID NO 1035
<211> LENGTH: 28
<212> TYPE: DNA
<213> ORGANISM: Artificial Sequence
<220> FEATURE:
<223> OTHER INFORMATION: Primer

<400> SEQUENCE: 1035
tccgcaaaga ctttggcatt aggtgtga 28

<210> SEQ ID NO 1036
<211> LENGTH: 27
<212> TYPE: DNA
<213> ORGANISM: Artificial Sequence
<220> FEATURE:
<223> OTHER INFORMATION: Primer

<400> SEQUENCE: 1036
tccgccaaaa actccccttt tcacagg 27

<210> SEQ ID NO 1037
<211> LENGTH: 24
<212> TYPE: DNA
<213> ORGANISM: Artificial Sequence
<220> FEATURE:
<223> OTHER INFORMATION: Primer

<400> SEQUENCE: 1037
tccgccttca aaatggtggc gagt 24

<210> SEQ ID NO 1038
<211> LENGTH: 31
<212> TYPE: DNA
<213> ORGANISM: Artificial Sequence
<220> FEATURE:
<223> OTHER INFORMATION: Primer

<400> SEQUENCE: 1038
tccggctaga gattctgtat acgaaaatat c 31

<210> SEQ ID NO 1039
<211> LENGTH: 31
<212> TYPE: DNA
<213> ORGANISM: Artificial Sequence
<220> FEATURE:
<223> OTHER INFORMATION: Primer

<400> SEQUENCE: 1039
tccggctaga gattctgtat acgacaatat c 31

<210> SEQ ID NO 1040
<211> LENGTH: 23
<212> TYPE: DNA
<213> ORGANISM: Artificial Sequence
<220> FEATURE:
<223> OTHER INFORMATION: Primer

<400> SEQUENCE: 1040
tccggtaact gggtcagctc gaa 23

<210> SEQ ID NO 1041
<211> LENGTH: 34
<212> TYPE: DNA
<213> ORGANISM: Artificial Sequence
<220> FEATURE:
<223> OTHER INFORMATION: Primer

<400> SEQUENCE: 1041
tccgtagttt tgcataattt atggtctatt tcaa 34

<210> SEQ ID NO 1042
<211> LENGTH: 27
<212> TYPE: DNA
<213> ORGANISM: Artificial Sequence
<220> FEATURE:
<223> OTHER INFORMATION: Primer

<400> SEQUENCE: 1042
tccgtcatcg ctgacagaaa ctgagtt 27

<210> SEQ ID NO 1043
<211> LENGTH: 28
<212> TYPE: DNA
<213> ORGANISM: Artificial Sequence
<220> FEATURE:
<223> OTHER INFORMATION: Primer

<400> SEQUENCE: 1043
tccgtctatc cacaagttaa ttggtact 28

<210> SEQ ID NO 1044
<211> LENGTH: 26
<212> TYPE: DNA
<213> ORGANISM: Artificial Sequence
<220> FEATURE:
<223> OTHER INFORMATION: Primer

<400> SEQUENCE: 1044
tcctacccaa cgttcaccaa gggcag 26

<210> SEQ ID NO 1045
<211> LENGTH: 29
<212> TYPE: DNA
<213> ORGANISM: Artificial Sequence
<220> FEATURE:
<223> OTHER INFORMATION: Primer

<400> SEQUENCE: 1045
tcctccttgt gcctcaaaac gcattttta 29

<210> SEQ ID NO 1046
<211> LENGTH: 30
<212> TYPE: DNA

<213> ORGANISM: Artificial Sequence
<220> FEATURE:
<223> OTHER INFORMATION: Primer

<400> SEQUENCE: 1046
tcctctatgc aacttagtat caacaggaat 30

<210> SEQ ID NO 1047
<211> LENGTH: 24
<212> TYPE: DNA
<213> ORGANISM: Artificial Sequence
<220> FEATURE:
<223> OTHER INFORMATION: Primer

<400> SEQUENCE: 1047
tcctcttggg ccacgcaaag tttt 24

<210> SEQ ID NO 1048
<211> LENGTH: 27
<212> TYPE: DNA
<213> ORGANISM: Artificial Sequence
<220> FEATURE:
<223> OTHER INFORMATION: Primer

<400> SEQUENCE: 1048
tcctcttttc acaggctcta cttcatc 27

<210> SEQ ID NO 1049
<211> LENGTH: 30
<212> TYPE: DNA
<213> ORGANISM: Artificial Sequence
<220> FEATURE:
<223> OTHER INFORMATION: Primer

<400> SEQUENCE: 1049
tcctgaagat ctagttcttg aatggttact 30

<210> SEQ ID NO 1050
<211> LENGTH: 27
<212> TYPE: DNA
<213> ORGANISM: Artificial Sequence
<220> FEATURE:
<223> OTHER INFORMATION: Primer

<400> SEQUENCE: 1050
tcctgcaata tctaatgcac tcttacg 27

<210> SEQ ID NO 1051
<211> LENGTH: 25
<212> TYPE: DNA
<213> ORGANISM: Artificial Sequence
<220> FEATURE:
<223> OTHER INFORMATION: Primer

<400> SEQUENCE: 1051
tcctgcagct ctacctgctc catta 25

<210> SEQ ID NO 1052
<211> LENGTH: 20
<212> TYPE: DNA
<213> ORGANISM: Artificial Sequence
<220> FEATURE:
<223> OTHER INFORMATION: Primer

<400> SEQUENCE: 1052
tcctggccat cctgcaggat 20

<210> SEQ ID NO 1053
<211> LENGTH: 27
<212> TYPE: DNA
<213> ORGANISM: Artificial Sequence
<220> FEATURE:
<223> OTHER INFORMATION: Primer

<400> SEQUENCE: 1053
tcctgtttta tagccgccaa gagtaag 27

<210> SEQ ID NO 1054
<211> LENGTH: 21
<212> TYPE: DNA
<213> ORGANISM: Artificial Sequence
<220> FEATURE:
<223> OTHER INFORMATION: Primer

<400> SEQUENCE: 1054
tccttcacgc gcatcatcac c 21

<210> SEQ ID NO 1055
<211> LENGTH: 27
<212> TYPE: DNA
<213> ORGANISM: Artificial Sequence
<220> FEATURE:
<223> OTHER INFORMATION: Primer

<400> SEQUENCE: 1055
tccttctgat gcctgatgga ccaggag 27

<210> SEQ ID NO 1056
<211> LENGTH: 26
<212> TYPE: DNA
<213> ORGANISM: Artificial Sequence
<220> FEATURE:
<223> OTHER INFORMATION: Primer

<400> SEQUENCE: 1056
tccttggcat acatcatgtc gtagca 26

<210> SEQ ID NO 1057
<211> LENGTH: 33
<212> TYPE: DNA
<213> ORGANISM: Artificial Sequence
<220> FEATURE:
<223> OTHER INFORMATION: Primer

<400> SEQUENCE: 1057
tccttgtgct tcaaaacgca tttttacatt ttc 33

<210> SEQ ID NO 1058
<211> LENGTH: 28
<212> TYPE: DNA
<213> ORGANISM: Artificial Sequence
<220> FEATURE:
<223> OTHER INFORMATION: Primer

<400> SEQUENCE: 1058
tcctttaaaa taaccgctag tagctcct 28

<210> SEQ ID NO 1059
<211> LENGTH: 30
<212> TYPE: DNA
<213> ORGANISM: Artificial Sequence
<220> FEATURE:
<223> OTHER INFORMATION: Primer

<400> SEQUENCE: 1059
tcctttatgc aacttagtat caaccggaat 30

<210> SEQ ID NO 1060
<211> LENGTH: 30
<212> TYPE: DNA
<213> ORGANISM: Artificial Sequence
<220> FEATURE:
<223> OTHER INFORMATION: Primer

<400> SEQUENCE: 1060
tcctttatgc aacttggtat caacaggaat 30

<210> SEQ ID NO 1061
<211> LENGTH: 30
<212> TYPE: DNA
<213> ORGANISM: Artificial Sequence
<220> FEATURE:
<223> OTHER INFORMATION: Primer

<400> SEQUENCE: 1061
tcctttatgc aacttggtat caaccggaat 30

<210> SEQ ID NO 1062
<211> LENGTH: 29
<212> TYPE: DNA
<213> ORGANISM: Artificial Sequence
<220> FEATURE:
<223> OTHER INFORMATION: Primer

<400> SEQUENCE: 1062
tcctttcaat gttacagaaa actctacag 29

<210> SEQ ID NO 1063
<211> LENGTH: 24
<212> TYPE: DNA
<213> ORGANISM: Artificial Sequence
<220> FEATURE:
<223> OTHER INFORMATION: Primer

<400> SEQUENCE: 1063
tcgaaccgaa gttaccctga ccat 24

<210> SEQ ID NO 1064
<211> LENGTH: 30
<212> TYPE: DNA
<213> ORGANISM: Artificial Sequence
<220> FEATURE:
<223> OTHER INFORMATION: Primer

<400> SEQUENCE: 1064
tcgaattcag ctaaatactt ttcagcatct 30

<210> SEQ ID NO 1065
<211> LENGTH: 26
<212> TYPE: DNA
<213> ORGANISM: Artificial Sequence
<220> FEATURE:
<223> OTHER INFORMATION: Primer

<400> SEQUENCE: 1065
tcgacctgga ggacgacgta aaatca 26

<210> SEQ ID NO 1066
<211> LENGTH: 25
<212> TYPE: DNA

<213> ORGANISM: Artificial Sequence
<220> FEATURE:
<223> OTHER INFORMATION: Primer

<400> SEQUENCE: 1066
tcgacgacca tcttggaaag atttc 25

<210> SEQ ID NO 1067
<211> LENGTH: 25
<212> TYPE: DNA
<213> ORGANISM: Artificial Sequence
<220> FEATURE:
<223> OTHER INFORMATION: Primer

<400> SEQUENCE: 1067
tcgagccgaa gttaccctgt ccgtc 25

<210> SEQ ID NO 1068
<211> LENGTH: 27
<212> TYPE: DNA
<213> ORGANISM: Artificial Sequence
<220> FEATURE:
<223> OTHER INFORMATION: Primer

<400> SEQUENCE: 1068
tcgatccgca tcaccatcaa aagcaaa 27

<210> SEQ ID NO 1069
<211> LENGTH: 26
<212> TYPE: DNA
<213> ORGANISM: Artificial Sequence
<220> FEATURE:
<223> OTHER INFORMATION: Primer

<400> SEQUENCE: 1069
tcgatcgaac cgaagttacc ctgacc 26

<210> SEQ ID NO 1070
<211> LENGTH: 28
<212> TYPE: DNA
<213> ORGANISM: Artificial Sequence
<220> FEATURE:
<223> OTHER INFORMATION: Primer

<400> SEQUENCE: 1070
tcgatcgtga ctctctttat tttcagtt 28

<210> SEQ ID NO 1071
<211> LENGTH: 20
<212> TYPE: DNA
<213> ORGANISM: Artificial Sequence
<220> FEATURE:
<223> OTHER INFORMATION: Primer

<400> SEQUENCE: 1071
tcgatctcct tggcgtccga 20

<210> SEQ ID NO 1072
<211> LENGTH: 26
<212> TYPE: DNA
<213> ORGANISM: Artificial Sequence
<220> FEATURE:
<223> OTHER INFORMATION: Primer

<400> SEQUENCE: 1072
tcgcaccgtg ggttgagatg aagtac 26

<210> SEQ ID NO 1073
<211> LENGTH: 18
<212> TYPE: DNA
<213> ORGANISM: Artificial Sequence
<220> FEATURE:
<223> OTHER INFORMATION: Primer

<400> SEQUENCE: 1073
tcgcagcgtg cgtggcac 18

<210> SEQ ID NO 1074
<211> LENGTH: 26
<212> TYPE: DNA
<213> ORGANISM: Artificial Sequence
<220> FEATURE:
<223> OTHER INFORMATION: Primer

<400> SEQUENCE: 1074
tcgcaggctt acagaacgct ctccta 26

<210> SEQ ID NO 1075
<211> LENGTH: 23
<212> TYPE: DNA
<213> ORGANISM: Artificial Sequence
<220> FEATURE:
<223> OTHER INFORMATION: Primer

<400> SEQUENCE: 1075
tcgcagttca tcagcacgaa gcg 23

<210> SEQ ID NO 1076
<211> LENGTH: 26
<212> TYPE: DNA
<213> ORGANISM: Artificial Sequence
<220> FEATURE:
<223> OTHER INFORMATION: Primer

<400> SEQUENCE: 1076
tcgccagcta gcacgatgtc attttc 26

<210> SEQ ID NO 1077
<211> LENGTH: 31
<212> TYPE: DNA
<213> ORGANISM: Artificial Sequence
<220> FEATURE:
<223> OTHER INFORMATION: Primer

<400> SEQUENCE: 1077
tcgccatagc taagttgttt attgtttcca t 31

<210> SEQ ID NO 1078
<211> LENGTH: 22
<212> TYPE: DNA
<213> ORGANISM: Artificial Sequence
<220> FEATURE:
<223> OTHER INFORMATION: Primer

<400> SEQUENCE: 1078
tcgcctggtg caggcatcat at 22

<210> SEQ ID NO 1079
<211> LENGTH: 24
<212> TYPE: DNA
<213> ORGANISM: Artificial Sequence
<220> FEATURE:
<223> OTHER INFORMATION: Primer

<400> SEQUENCE: 1079
tcgcgctgta tttttcctcc gaga 24

<210> SEQ ID NO 1080
<211> LENGTH: 18
<212> TYPE: DNA
<213> ORGANISM: Artificial Sequence
<220> FEATURE:
<223> OTHER INFORMATION: Primer

<400> SEQUENCE: 1080
tcgctacctt aggaccgt 18

<210> SEQ ID NO 1081
<211> LENGTH: 29
<212> TYPE: DNA
<213> ORGANISM: Artificial Sequence
<220> FEATURE:
<223> OTHER INFORMATION: Primer

<400> SEQUENCE: 1081
tcgctcagca ataattcact ataagccga 29

<210> SEQ ID NO 1082
<211> LENGTH: 29
<212> TYPE: DNA
<213> ORGANISM: Artificial Sequence
<220> FEATURE:
<223> OTHER INFORMATION: Primer

<400> SEQUENCE: 1082
tcgctctctc aagtgatcta aacttggag 29

<210> SEQ ID NO 1083
<211> LENGTH: 25
<212> TYPE: DNA
<213> ORGANISM: Artificial Sequence
<220> FEATURE:
<223> OTHER INFORMATION: Primer

<400> SEQUENCE: 1083
tcgcttgagt gtagtcatga ttgcg 25

<210> SEQ ID NO 1084
<211> LENGTH: 32
<212> TYPE: DNA
<213> ORGANISM: Artificial Sequence
<220> FEATURE:
<223> OTHER INFORMATION: Primer

<400> SEQUENCE: 1084
tcggaaacaa agaattcatt ttctggtcca aa 32

<210> SEQ ID NO 1085
<211> LENGTH: 33
<212> TYPE: DNA
<213> ORGANISM: Artificial Sequence
<220> FEATURE:
<223> OTHER INFORMATION: Primer

<400> SEQUENCE: 1085
tcggaaatat tctttcaata cctttatgca act 33

<210> SEQ ID NO 1086
<211> LENGTH: 34
<212> TYPE: DNA

<213> ORGANISM: Artificial Sequence
<220> FEATURE:
<223> OTHER INFORMATION: Primer

<400> SEQUENCE: 1086
tcggaaatat tctttcaata cctttatgca actt 34

<210> SEQ ID NO 1087
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (20)...(20)
<223> OTHER INFORMATION: I
<220> FEATURE:
<221> NAME/KEY: modified_base
<222> LOCATION: (26)...(26)
<223> OTHER INFORMATION: I

<400> SEQUENCE: 1087
tcggaaatat tctttcaata cctttatgca actt 34

<210> SEQ ID NO 1088
<211> LENGTH: 20
<212> TYPE: DNA
<213> ORGANISM: Artificial Sequence
<220> FEATURE:
<223> OTHER INFORMATION: Primer

<400> SEQUENCE: 1088
tcggactcgc tttcgctacg 20

<210> SEQ ID NO 1089
<211> LENGTH: 20
<212> TYPE: DNA
<213> ORGANISM: Artificial Sequence
<220> FEATURE:
<223> OTHER INFORMATION: Primer

<400> SEQUENCE: 1089
tcggataagc tgccacaagg 20

<210> SEQ ID NO 1090
<211> LENGTH: 19
<212> TYPE: DNA
<213> ORGANISM: Artificial Sequence
<220> FEATURE:
<223> OTHER INFORMATION: Primer

<400> SEQUENCE: 1090
tcggcatcac gccgtcgtc 19

<210> SEQ ID NO 1091
<211> LENGTH: 20
<212> TYPE: DNA
<213> ORGANISM: Artificial Sequence
<220> FEATURE:
<223> OTHER INFORMATION: Primer

<400> SEQUENCE: 1091
tcggcgaaca tggccatcac 20

<210> SEQ ID NO 1092
<211> LENGTH: 33
<212> TYPE: DNA

<213> ORGANISM: Artificial Sequence
<220> FEATURE:
<223> OTHER INFORMATION: Primer

<400> SEQUENCE: 1092
tcgggcgtag tttttagtaa ttaaatcaga agt 33

<210> SEQ ID NO 1093
<211> LENGTH: 25
<212> TYPE: DNA
<213> ORGANISM: Artificial Sequence
<220> FEATURE:
<223> OTHER INFORMATION: Primer

<400> SEQUENCE: 1093
tcggtacgaa ctggatgtcg ccgtt 25

<210> SEQ ID NO 1094
<211> LENGTH: 24
<212> TYPE: DNA
<213> ORGANISM: Artificial Sequence
<220> FEATURE:
<223> OTHER INFORMATION: Primer

<400> SEQUENCE: 1094
tcggtcagca aaacggtagc ttgc 24

<210> SEQ ID NO 1095
<211> LENGTH: 21
<212> TYPE: DNA
<213> ORGANISM: Artificial Sequence
<220> FEATURE:
<223> OTHER INFORMATION: Primer

<400> SEQUENCE: 1095
tcggtggtgg tagccgatct c 21

<210> SEQ ID NO 1096
<211> LENGTH: 31
<212> TYPE: DNA
<213> ORGANISM: Artificial Sequence
<220> FEATURE:
<223> OTHER INFORMATION: Primer

<400> SEQUENCE: 1096
tcggtttaag ctctacatga tcgtaaggat a 31

<210> SEQ ID NO 1097
<211> LENGTH: 29
<212> TYPE: DNA
<213> ORGANISM: Artificial Sequence
<220> FEATURE:
<223> OTHER INFORMATION: Primer

<400> SEQUENCE: 1097
tcggtttcag tcatctccac cataaaggt 29

<210> SEQ ID NO 1098
<211> LENGTH: 26
<212> TYPE: DNA
<213> ORGANISM: Artificial Sequence
<220> FEATURE:
<223> OTHER INFORMATION: Primer

<400> SEQUENCE: 1098
tcgtatgacc agcttcggta ctacta 26

<210> SEQ ID NO 1099
<211> LENGTH: 32
<212> TYPE: DNA
<213> ORGANISM: Artificial Sequence
<220> FEATURE:
<223> OTHER INFORMATION: Primer

<400> SEQUENCE: 1099
tcgtcaacac taccattatt accatgcatc tc 32

<210> SEQ ID NO 1100
<211> LENGTH: 26
<212> TYPE: DNA
<213> ORGANISM: Artificial Sequence
<220> FEATURE:
<223> OTHER INFORMATION: Primer

<400> SEQUENCE: 1100
tcgtccgact taacggtcag catttc 26

<210> SEQ ID NO 1101
<211> LENGTH: 29
<212> TYPE: DNA
<213> ORGANISM: Artificial Sequence
<220> FEATURE:
<223> OTHER INFORMATION: Primer

<400> SEQUENCE: 1101
tcgtccgact taacggtcag catttcctg 29

<210> SEQ ID NO 1102
<211> LENGTH: 31
<212> TYPE: DNA
<213> ORGANISM: Artificial Sequence
<220> FEATURE:
<223> OTHER INFORMATION: Primer

<400> SEQUENCE: 1102
tcgtccgact taacggtcag catttcctgc a 31

<210> SEQ ID NO 1103
<211> LENGTH: 26
<212> TYPE: DNA
<213> ORGANISM: Artificial Sequence
<220> FEATURE:
<223> OTHER INFORMATION: Primer

<400> SEQUENCE: 1103
tcgtcctctc gaatctccga tatacc 26

<210> SEQ ID NO 1104
<211> LENGTH: 20
<212> TYPE: DNA
<213> ORGANISM: Artificial Sequence
<220> FEATURE:
<223> OTHER INFORMATION: Primer

<400> SEQUENCE: 1104
tcgtcgcgga cttcgaagcc 20

<210> SEQ ID NO 1105
<211> LENGTH: 26
<212> TYPE: DNA
<213> ORGANISM: Artificial Sequence
<220> FEATURE:
<223> OTHER INFORMATION: Primer

<400> SEQUENCE: 1105
tcgtcggact taacggtcag catttc 26

<210> SEQ ID NO 1106
<211> LENGTH: 29
<212> TYPE: DNA
<213> ORGANISM: Artificial Sequence
<220> FEATURE:
<223> OTHER INFORMATION: Primer

<400> SEQUENCE: 1106
tcgtcggact taacggtcag catttcctg 29

<210> SEQ ID NO 1107
<211> LENGTH: 31
<212> TYPE: DNA
<213> ORGANISM: Artificial Sequence
<220> FEATURE:
<223> OTHER INFORMATION: Primer

<400> SEQUENCE: 1107
tcgtcggact taacggtcag catttcctgc a 31

<210> SEQ ID NO 1108
<211> LENGTH: 28
<212> TYPE: DNA
<213> ORGANISM: Artificial Sequence
<220> FEATURE:
<223> OTHER INFORMATION: Primer

<400> SEQUENCE: 1108
tcgtcgtatt tatagtgacc agcaccta 28

<210> SEQ ID NO 1109
<211> LENGTH: 28
<212> TYPE: DNA
<213> ORGANISM: Artificial Sequence
<220> FEATURE:
<223> OTHER INFORMATION: Primer

<400> SEQUENCE: 1109
tcgtgcctaa caaatcccgt ctgagttc 28

<210> SEQ ID NO 1110
<211> LENGTH: 22
<212> TYPE: DNA
<213> ORGANISM: Artificial Sequence
<220> FEATURE:
<223> OTHER INFORMATION: Primer

<400> SEQUENCE: 1110
tcgtggacta ccagggtatc ta 22

<210> SEQ ID NO 1111
<211> LENGTH: 17
<212> TYPE: DNA
<213> ORGANISM: Artificial Sequence
<220> FEATURE:
<223> OTHER INFORMATION: Primer

<400> SEQUENCE: 1111
tcgtgggcct tgccggt 17

<210> SEQ ID NO 1112
<211> LENGTH: 28
<212> TYPE: DNA

<213> ORGANISM: Artificial Sequence
<220> FEATURE:
<223> OTHER INFORMATION: Primer

<400> SEQUENCE: 1112
tcgttaatta atctggctgc ggaagtga 28

<210> SEQ ID NO 1113
<211> LENGTH: 27
<212> TYPE: DNA
<213> ORGANISM: Artificial Sequence
<220> FEATURE:
<223> OTHER INFORMATION: Primer

<400> SEQUENCE: 1113
tcgttgagat ggtttttacc ttcgttg 27

<210> SEQ ID NO 1114
<211> LENGTH: 25
<212> TYPE: DNA
<213> ORGANISM: Artificial Sequence
<220> FEATURE:
<223> OTHER INFORMATION: Primer

<400> SEQUENCE: 1114
tcgtttaagc gccagaaagc accaa 25

<210> SEQ ID NO 1115
<211> LENGTH: 21
<212> TYPE: DNA
<213> ORGANISM: Artificial Sequence
<220> FEATURE:
<223> OTHER INFORMATION: Primer

<400> SEQUENCE: 1115
tcgtttcacc ctgtcatgcc g 21

<210> SEQ ID NO 1116
<211> LENGTH: 26
<212> TYPE: DNA
<213> ORGANISM: Artificial Sequence
<220> FEATURE:
<223> OTHER INFORMATION: Primer

<400> SEQUENCE: 1116
tctttcgtat aaaaaggacc aattgg 26

<210> SEQ ID NO 1117
<211> LENGTH: 35
<212> TYPE: DNA
<213> ORGANISM: Artificial Sequence
<220> FEATURE:
<223> OTHER INFORMATION: Primer

<400> SEQUENCE: 1117
tctacaacac ttgattgtaa tttgccttgt tcttt 35

<210> SEQ ID NO 1118
<211> LENGTH: 24
<212> TYPE: DNA
<213> ORGANISM: Artificial Sequence
<220> FEATURE:
<223> OTHER INFORMATION: Primer

<400> SEQUENCE: 1118
tctagcggaa caacagttct gatg 24

<210> SEQ ID NO 1119
<211> LENGTH: 27
<212> TYPE: DNA
<213> ORGANISM: Artificial Sequence
<220> FEATURE:
<223> OTHER INFORMATION: Primer

<400> SEQUENCE: 1119
tctatagagt ccggactttc ctcgtga 27

<210> SEQ ID NO 1120
<211> LENGTH: 30
<212> TYPE: DNA
<213> ORGANISM: Artificial Sequence
<220> FEATURE:
<223> OTHER INFORMATION: Primer

<400> SEQUENCE: 1120
tctataggta ctgtagtttg ttttccgtct 30

<210> SEQ ID NO 1121
<211> LENGTH: 27
<212> TYPE: DNA
<213> ORGANISM: Artificial Sequence
<220> FEATURE:
<223> OTHER INFORMATION: Primer

<400> SEQUENCE: 1121
tctcacctac agctttaaag ccagcaa 27

<210> SEQ ID NO 1122
<211> LENGTH: 31
<212> TYPE: DNA
<213> ORGANISM: Artificial Sequence
<220> FEATURE:
<223> OTHER INFORMATION: Primer

<400> SEQUENCE: 1122
tctcacctac agctttaaag ccagcaaaat g 31

<210> SEQ ID NO 1123
<211> LENGTH: 25
<212> TYPE: DNA
<213> ORGANISM: Artificial Sequence
<220> FEATURE:
<223> OTHER INFORMATION: Primer

<400> SEQUENCE: 1123
tctcatcccg atattaccgc catga 25

<210> SEQ ID NO 1124
<211> LENGTH: 29
<212> TYPE: DNA
<213> ORGANISM: Artificial Sequence
<220> FEATURE:
<223> OTHER INFORMATION: Primer

<400> SEQUENCE: 1124
tctcatgaaa aaggctcagg agatacaag 29

<210> SEQ ID NO 1125
<211> LENGTH: 27
<212> TYPE: DNA
<213> ORGANISM: Artificial Sequence
<220> FEATURE:
<223> OTHER INFORMATION: Primer

<400> SEQUENCE: 1125
tctcttaccc caccctttca cccttac 27

<210> SEQ ID NO 1126
<211> LENGTH: 31
<212> TYPE: DNA
<213> ORGANISM: Artificial Sequence
<220> FEATURE:
<223> OTHER INFORMATION: Primer

<400> SEQUENCE: 1126
tctctttcaa agcaccattg ctcattatag t 31

<210> SEQ ID NO 1127
<211> LENGTH: 24
<212> TYPE: DNA
<213> ORGANISM: Artificial Sequence
<220> FEATURE:
<223> OTHER INFORMATION: Primer

<400> SEQUENCE: 1127
tctgcatttt tgcgagcctg tcta 24

<210> SEQ ID NO 1128
<211> LENGTH: 28
<212> TYPE: DNA
<213> ORGANISM: Artificial Sequence
<220> FEATURE:
<223> OTHER INFORMATION: Primer

<400> SEQUENCE: 1128
tctgcctgag atgtcgaaaa aaacgttg 28

<210> SEQ ID NO 1129
<211> LENGTH: 26
<212> TYPE: DNA
<213> ORGANISM: Artificial Sequence
<220> FEATURE:
<223> OTHER INFORMATION: Primer

<400> SEQUENCE: 1129
tctggcccct ccatacatgt atttag 26

<210> SEQ ID NO 1130
<211> LENGTH: 23
<212> TYPE: DNA
<213> ORGANISM: Artificial Sequence
<220> FEATURE:
<223> OTHER INFORMATION: Primer

<400> SEQUENCE: 1130
tctggctgcg gaagtgaaat cgt 23

<210> SEQ ID NO 1131
<211> LENGTH: 23
<212> TYPE: DNA
<213> ORGANISM: Artificial Sequence
<220> FEATURE:
<223> OTHER INFORMATION: Primer

<400> SEQUENCE: 1131
tctgggtgac ctggtgtttt aga 23

<210> SEQ ID NO 1132
<211> LENGTH: 20
<212> TYPE: DNA

<213> ORGANISM: Artificial Sequence
<220> FEATURE:
<223> OTHER INFORMATION: Primer

<400> SEQUENCE: 1132
tctgtttcag ttgcaaattc 20

<210> SEQ ID NO 1133
<211> LENGTH: 34
<212> TYPE: DNA
<213> ORGANISM: Artificial Sequence
<220> FEATURE:
<223> OTHER INFORMATION: Primer

<400> SEQUENCE: 1133
tcttcacact tttagaatca accgttttat tgtc 34

<210> SEQ ID NO 1134
<211> LENGTH: 35
<212> TYPE: DNA
<213> ORGANISM: Artificial Sequence
<220> FEATURE:
<223> OTHER INFORMATION: Primer

<400> SEQUENCE: 1134
tcttcagcgt agtctaataa tttacggaac atttc 35

<210> SEQ ID NO 1135
<211> LENGTH: 30
<212> TYPE: DNA
<213> ORGANISM: Artificial Sequence
<220> FEATURE:
<223> OTHER INFORMATION: Primer

<400> SEQUENCE: 1135
tcttccaagg atagatttat ttcttgttcg 30

<210> SEQ ID NO 1136
<211> LENGTH: 33
<212> TYPE: DNA
<213> ORGANISM: Artificial Sequence
<220> FEATURE:
<223> OTHER INFORMATION: Primer

<400> SEQUENCE: 1136
tcttctgtaa agggtggttt attattcatc cca 33

<210> SEQ ID NO 1137
<211> LENGTH: 32
<212> TYPE: DNA
<213> ORGANISM: Artificial Sequence
<220> FEATURE:
<223> OTHER INFORMATION: Primer

<400> SEQUENCE: 1137
tcttcttctt tcgtataaaa aggaccaatt gg 32

<210> SEQ ID NO 1138
<211> LENGTH: 28
<212> TYPE: DNA
<213> ORGANISM: Artificial Sequence
<220> FEATURE:
<223> OTHER INFORMATION: Primer

<400> SEQUENCE: 1138
tcttcttgaa aaattgttgt cccgaaac 28

<210> SEQ ID NO 1139
<211> LENGTH: 31
<212> TYPE: DNA
<213> ORGANISM: Artificial Sequence
<220> FEATURE:
<223> OTHER INFORMATION: Primer

<400> SEQUENCE: 1139
tcttctttcg tataaaaagg accaattggt t 31

<210> SEQ ID NO 1140
<211> LENGTH: 18
<212> TYPE: DNA
<213> ORGANISM: Artificial Sequence
<220> FEATURE:
<223> OTHER INFORMATION: Primer

<400> SEQUENCE: 1140
tcttgacagc atccgttg 18

<210> SEQ ID NO 1141
<211> LENGTH: 32
<212> TYPE: DNA
<213> ORGANISM: Artificial Sequence
<220> FEATURE:
<223> OTHER INFORMATION: Primer

<400> SEQUENCE: 1141
tcttgagcat tggttcttac ttgttttgca ta 32

<210> SEQ ID NO 1142
<211> LENGTH: 23
<212> TYPE: DNA
<213> ORGANISM: Artificial Sequence
<220> FEATURE:
<223> OTHER INFORMATION: Primer

<400> SEQUENCE: 1142
tcttgagcca tacgtaccat tgc 23

<210> SEQ ID NO 1143
<211> LENGTH: 32
<212> TYPE: DNA
<213> ORGANISM: Artificial Sequence
<220> FEATURE:
<223> OTHER INFORMATION: Primer

<400> SEQUENCE: 1143
tcttggctta ggatgaaaat atagtggtgg ta 32

<210> SEQ ID NO 1144
<211> LENGTH: 39
<212> TYPE: DNA
<213> ORGANISM: Artificial Sequence
<220> FEATURE:
<223> OTHER INFORMATION: Primer

<400> SEQUENCE: 1144
tctttaagtt cttccaagga tagatttatt tcttgttcg 39

<210> SEQ ID NO 1145
<211> LENGTH: 31
<212> TYPE: DNA
<213> ORGANISM: Artificial Sequence
<220> FEATURE:
<223> OTHER INFORMATION: Primer

<400> SEQUENCE: 1145
tcttttcttt gcttaatttt ccatttgcga t 31

<210> SEQ ID NO 1146
<211> LENGTH: 14
<212> TYPE: DNA
<213> ORGANISM: Artificial Sequence
<220> FEATURE:
<223> OTHER INFORMATION: Primer

<400> SEQUENCE: 1146
tgttactgct ggat 14

<210> SEQ ID NO 1147
<211> LENGTH: 25
<212> TYPE: DNA
<213> ORGANISM: Artificial Sequence
<220> FEATURE:
<223> OTHER INFORMATION: Primer

<400> SEQUENCE: 1147
tgaacatttg cgacggtata cccat 25

<210> SEQ ID NO 1148
<211> LENGTH: 31
<212> TYPE: DNA
<213> ORGANISM: Artificial Sequence
<220> FEATURE:
<223> OTHER INFORMATION: Primer

<400> SEQUENCE: 1148
tgaatatgta atgcaaacca gtctttgtca t 31

<210> SEQ ID NO 1149
<211> LENGTH: 21
<212> TYPE: DNA
<213> ORGANISM: Artificial Sequence
<220> FEATURE:
<223> OTHER INFORMATION: Primer

<400> SEQUENCE: 1149
tgaatcttga aacaccatac g 21

<210> SEQ ID NO 1150
<211> LENGTH: 26
<212> TYPE: DNA
<213> ORGANISM: Artificial Sequence
<220> FEATURE:
<223> OTHER INFORMATION: Primer

<400> SEQUENCE: 1150
tgaatcttga aacaccatac gtaacg 26

<210> SEQ ID NO 1151
<211> LENGTH: 34
<212> TYPE: DNA
<213> ORGANISM: Artificial Sequence
<220> FEATURE:
<223> OTHER INFORMATION: Primer

<400> SEQUENCE: 1151
tgaattatgc aagaagtgat caattttctc acga 34

<210> SEQ ID NO 1152
<211> LENGTH: 34
<212> TYPE: DNA

<213> ORGANISM: Artificial Sequence
<220> FEATURE:
<223> OTHER INFORMATION: Primer

<400> SEQUENCE: 1152
tgaattcttt caaagcacca ttgctcatta tagt 34

<210> SEQ ID NO 1153
<211> LENGTH: 30
<212> TYPE: DNA
<213> ORGANISM: Artificial Sequence
<220> FEATURE:
<223> OTHER INFORMATION: Primer

<400> SEQUENCE: 1153
tgacaggaca caatctgcat gaagtctgag 30

<210> SEQ ID NO 1154
<211> LENGTH: 25
<212> TYPE: DNA
<213> ORGANISM: Artificial Sequence
<220> FEATURE:
<223> OTHER INFORMATION: Primer

<400> SEQUENCE: 1154
tgacccaaag ctgaaagctt tactg 25

<210> SEQ ID NO 1155
<211> LENGTH: 28
<212> TYPE: DNA
<213> ORGANISM: Artificial Sequence
<220> FEATURE:
<223> OTHER INFORMATION: Primer

<400> SEQUENCE: 1155
tgaccccaac ctggcctttt gtcgttga 28

<210> SEQ ID NO 1156
<211> LENGTH: 20
<212> TYPE: DNA
<213> ORGANISM: Artificial Sequence
<220> FEATURE:
<223> OTHER INFORMATION: Primer

<400> SEQUENCE: 1156
tgaccgttat agttacggcc 20

<210> SEQ ID NO 1157
<211> LENGTH: 22
<212> TYPE: DNA
<213> ORGANISM: Artificial Sequence
<220> FEATURE:
<223> OTHER INFORMATION: Primer

<400> SEQUENCE: 1157
tgacggcatc gataccaccg tc 22

<210> SEQ ID NO 1158
<211> LENGTH: 20
<212> TYPE: DNA
<213> ORGANISM: Artificial Sequence
<220> FEATURE:
<223> OTHER INFORMATION: Primer

<400> SEQUENCE: 1158
tgacgtcatc cccaccttcc 20

<210> SEQ ID NO 1159
<211> LENGTH: 22
<212> TYPE: DNA
<213> ORGANISM: Artificial Sequence
<220> FEATURE:
<223> OTHER INFORMATION: Primer

<400> SEQUENCE: 1159
tgacgtcatc cccaccttcc tc                                             22

<210> SEQ ID NO 1160
<211> LENGTH: 20
<212> TYPE: DNA
<213> ORGANISM: Artificial Sequence
<220> FEATURE:
<223> OTHER INFORMATION: Primer

<400> SEQUENCE: 1160
tgacgtcatg cccaccttcc                                                20

<210> SEQ ID NO 1161
<211> LENGTH: 20
<212> TYPE: DNA
<213> ORGANISM: Artificial Sequence
<220> FEATURE:
<223> OTHER INFORMATION: Primer

<400> SEQUENCE: 1161
tgacgtcatg gccaccttcc                                                20

<210> SEQ ID NO 1162
<211> LENGTH: 32
<212> TYPE: DNA
<213> ORGANISM: Artificial Sequence
<220> FEATURE:
<223> OTHER INFORMATION: Primer

<400> SEQUENCE: 1162
tgacttaaac gtaccatcgc ttcatataca ga                                  32

<210> SEQ ID NO 1163
<211> LENGTH: 27
<212> TYPE: DNA
<213> ORGANISM: Artificial Sequence
<220> FEATURE:
<223> OTHER INFORMATION: Primer

<400> SEQUENCE: 1163
tgactttcct cccccttatc agtctcc                                        27

<210> SEQ ID NO 1164
<211> LENGTH: 31
<212> TYPE: DNA
<213> ORGANISM: Artificial Sequence
<220> FEATURE:
<223> OTHER INFORMATION: Primer

<400> SEQUENCE: 1164
tgagatgtcg aaaaaaacgt tggcaaaata c                                   31

<210> SEQ ID NO 1165
<211> LENGTH: 31
<212> TYPE: DNA
<213> ORGANISM: Artificial Sequence
<220> FEATURE:
<223> OTHER INFORMATION: Primer

<400> SEQUENCE: 1165
tgagatgttg atgatttacc agttccgatt g 31

<210> SEQ ID NO 1166
<211> LENGTH: 20
<212> TYPE: DNA
<213> ORGANISM: Artificial Sequence
<220> FEATURE:
<223> OTHER INFORMATION: Primer

<400> SEQUENCE: 1166
tgagcatcag cgtgcgtgct 20

<210> SEQ ID NO 1167
<211> LENGTH: 28
<212> TYPE: DNA
<213> ORGANISM: Artificial Sequence
<220> FEATURE:
<223> OTHER INFORMATION: Primer

<400> SEQUENCE: 1167
tgagcatttt tatatccatc tccaccat 28

<210> SEQ ID NO 1168
<211> LENGTH: 32
<212> TYPE: DNA
<213> ORGANISM: Artificial Sequence
<220> FEATURE:
<223> OTHER INFORMATION: Primer

<400> SEQUENCE: 1168
tgagccatac gaacaatggt ttcataaaca gc 32

<210> SEQ ID NO 1169
<211> LENGTH: 32
<212> TYPE: DNA
<213> ORGANISM: Artificial Sequence
<220> FEATURE:
<223> OTHER INFORMATION: Primer

<400> SEQUENCE: 1169
tgagccatga gtaccatggc ttcataacat gc 32

<210> SEQ ID NO 1170
<211> LENGTH: 26
<212> TYPE: DNA
<213> ORGANISM: Artificial Sequence
<220> FEATURE:
<223> OTHER INFORMATION: Primer

<400> SEQUENCE: 1170
tgagcgtgtg gaaaaggact tggatg 26

<210> SEQ ID NO 1171
<211> LENGTH: 29
<212> TYPE: DNA
<213> ORGANISM: Artificial Sequence
<220> FEATURE:
<223> OTHER INFORMATION: Primer

<400> SEQUENCE: 1171
tgagctggtg ctatatgaac aataccagt 29

<210> SEQ ID NO 1172
<211> LENGTH: 30
<212> TYPE: DNA

<213> ORGANISM: Artificial Sequence
<220> FEATURE:
<223> OTHER INFORMATION: Primer

<400> SEQUENCE: 1172
tgagtcaccc tccacaatgt atagttcaga 30

<210> SEQ ID NO 1173
<211> LENGTH: 25
<212> TYPE: DNA
<213> ORGANISM: Artificial Sequence
<220> FEATURE:
<223> OTHER INFORMATION: Primer

<400> SEQUENCE: 1173
tgagtcgggt tcactttacc tggca 25

<210> SEQ ID NO 1174
<211> LENGTH: 27
<212> TYPE: DNA
<213> ORGANISM: Artificial Sequence
<220> FEATURE:
<223> OTHER INFORMATION: Primer

<400> SEQUENCE: 1174
tgagtctaca cttggcttag gatgaaa 27

<210> SEQ ID NO 1175
<211> LENGTH: 32
<212> TYPE: DNA
<213> ORGANISM: Artificial Sequence
<220> FEATURE:
<223> OTHER INFORMATION: Primer

<400> SEQUENCE: 1175
tgagttaaaa tgcgattgat ttcagtttcc aa 32

<210> SEQ ID NO 1176
<211> LENGTH: 32
<212> TYPE: DNA
<213> ORGANISM: Artificial Sequence
<220> FEATURE:
<223> OTHER INFORMATION: Primer

<400> SEQUENCE: 1176
tgagtttgaa ccatttcaga gcgaatatct ac 32

<210> SEQ ID NO 1177
<211> LENGTH: 28
<212> TYPE: DNA
<213> ORGANISM: Artificial Sequence
<220> FEATURE:
<223> OTHER INFORMATION: Primer

<400> SEQUENCE: 1177
tgagtttgca cttcaaaaga aattgtgt 28

<210> SEQ ID NO 1178
<211> LENGTH: 29
<212> TYPE: DNA
<213> ORGANISM: Artificial Sequence
<220> FEATURE:
<223> OTHER INFORMATION: Primer

<400> SEQUENCE: 1178
tgataaaaag cactaagcga tgaaacagc 29

<210> SEQ ID NO 1179
<211> LENGTH: 27
<212> TYPE: DNA
<213> ORGANISM: Artificial Sequence
<220> FEATURE:
<223> OTHER INFORMATION: Primer

<400> SEQUENCE: 1179
tgataatgaa gggaaacctt tttcacg 27

<210> SEQ ID NO 1180
<211> LENGTH: 32
<212> TYPE: DNA
<213> ORGANISM: Artificial Sequence
<220> FEATURE:
<223> OTHER INFORMATION: Primer

<400> SEQUENCE: 1180
tgatattgaa ctggtgtacc ataatagttg cc 32

<210> SEQ ID NO 1181
<211> LENGTH: 30
<212> TYPE: DNA
<213> ORGANISM: Artificial Sequence
<220> FEATURE:
<223> OTHER INFORMATION: Primer

<400> SEQUENCE: 1181
tgatcctgaa tgtttatatc tttaacgcct 30

<210> SEQ ID NO 1182
<211> LENGTH: 22
<212> TYPE: DNA
<213> ORGANISM: Artificial Sequence
<220> FEATURE:
<223> OTHER INFORMATION: Primer

<400> SEQUENCE: 1182
tgatctccat ggcgcggatc tt 22

<210> SEQ ID NO 1183
<211> LENGTH: 19
<212> TYPE: DNA
<213> ORGANISM: Artificial Sequence
<220> FEATURE:
<223> OTHER INFORMATION: Primer

<400> SEQUENCE: 1183
tgatgcgggc tggttcaac 19

<210> SEQ ID NO 1184
<211> LENGTH: 24
<212> TYPE: DNA
<213> ORGANISM: Artificial Sequence
<220> FEATURE:
<223> OTHER INFORMATION: Primer

<400> SEQUENCE: 1184
tgatgcgggc tggttcaaca agag 24

<210> SEQ ID NO 1185
<211> LENGTH: 30
<212> TYPE: DNA
<213> ORGANISM: Artificial Sequence
<220> FEATURE:
<223> OTHER INFORMATION: Primer

<400> SEQUENCE: 1185
tgatggtcta tttcaatggc agttacgaaa 30

<210> SEQ ID NO 1186
<211> LENGTH: 19
<212> TYPE: DNA
<213> ORGANISM: Artificial Sequence
<220> FEATURE:
<223> OTHER INFORMATION: Primer

<400> SEQUENCE: 1186
tgattatcag cggaagtag 19

<210> SEQ ID NO 1187
<211> LENGTH: 28
<212> TYPE: DNA
<213> ORGANISM: Artificial Sequence
<220> FEATURE:
<223> OTHER INFORMATION: Primer

<400> SEQUENCE: 1187
tgattcaaat gcagaaccat caaactcg 28

<210> SEQ ID NO 1188
<211> LENGTH: 31
<212> TYPE: DNA
<213> ORGANISM: Artificial Sequence
<220> FEATURE:
<223> OTHER INFORMATION: Primer

<400> SEQUENCE: 1188
tgattcgatc atacgagaca ttaaaactga g 31

<210> SEQ ID NO 1189
<211> LENGTH: 30
<212> TYPE: DNA
<213> ORGANISM: Artificial Sequence
<220> FEATURE:
<223> OTHER INFORMATION: Primer

<400> SEQUENCE: 1189
tgattggcga taaagtgata ttttctaaaa 30

<210> SEQ ID NO 1190
<211> LENGTH: 22
<212> TYPE: DNA
<213> ORGANISM: Artificial Sequence
<220> FEATURE:
<223> OTHER INFORMATION: Primer

<400> SEQUENCE: 1190
tgattgtttt gcagctgatt gt 22

<210> SEQ ID NO 1191
<211> LENGTH: 22
<212> TYPE: DNA
<213> ORGANISM: Artificial Sequence
<220> FEATURE:
<223> OTHER INFORMATION: Primer

<400> SEQUENCE: 1191
tgattgtttt gcagctgatt gt 22

<210> SEQ ID NO 1192
<211> LENGTH: 30
<212> TYPE: DNA

<213> ORGANISM: Artificial Sequence
<220> FEATURE:
<223> OTHER INFORMATION: Primer

<400> SEQUENCE: 1192
tgcaaaagta acggttacat ctgctccaat 30

<210> SEQ ID NO 1193
<211> LENGTH: 33
<212> TYPE: DNA
<213> ORGANISM: Artificial Sequence
<220> FEATURE:
<223> OTHER INFORMATION: Primer

<400> SEQUENCE: 1193
tgcaacaatt aatgctccga caattaaagg att 33

<210> SEQ ID NO 1194
<211> LENGTH: 24
<212> TYPE: DNA
<213> ORGANISM: Artificial Sequence
<220> FEATURE:
<223> OTHER INFORMATION: Primer

<400> SEQUENCE: 1194
tgcaactcat ctggtttagg atct 24

<210> SEQ ID NO 1195
<211> LENGTH: 32
<212> TYPE: DNA
<213> ORGANISM: Artificial Sequence
<220> FEATURE:
<223> OTHER INFORMATION: Primer

<400> SEQUENCE: 1195
tgcaactgaa tagattgcag taagttataa gc 32

<210> SEQ ID NO 1196
<211> LENGTH: 23
<212> TYPE: DNA
<213> ORGANISM: Artificial Sequence
<220> FEATURE:
<223> OTHER INFORMATION: Primer

<400> SEQUENCE: 1196
tgcaagagca accctagtgt tcg 23

<210> SEQ ID NO 1197
<211> LENGTH: 29
<212> TYPE: DNA
<213> ORGANISM: Artificial Sequence
<220> FEATURE:
<223> OTHER INFORMATION: Primer

<400> SEQUENCE: 1197
tgcaagggaa acctagaatt acaaaccct 29

<210> SEQ ID NO 1198
<211> LENGTH: 29
<212> TYPE: DNA
<213> ORGANISM: Artificial Sequence
<220> FEATURE:
<223> OTHER INFORMATION: Primer

<400> SEQUENCE: 1198
tgcaatgtgt gctatgtcag caaaaagat 29

<210> SEQ ID NO 1199
<211> LENGTH: 18
<212> TYPE: DNA
<213> ORGANISM: Artificial Sequence
<220> FEATURE:
<223> OTHER INFORMATION: Primer

<400> SEQUENCE: 1199
tgcacctgcg gtcgagcg 18

<210> SEQ ID NO 1200
<211> LENGTH: 24
<212> TYPE: DNA
<213> ORGANISM: Artificial Sequence
<220> FEATURE:
<223> OTHER INFORMATION: Primer

<400> SEQUENCE: 1200
tgcacgcaaa cgctttactt cagc 24

<210> SEQ ID NO 1201
<211> LENGTH: 26
<212> TYPE: DNA
<213> ORGANISM: Artificial Sequence
<220> FEATURE:
<223> OTHER INFORMATION: Primer

<400> SEQUENCE: 1201
tgcacgtctg tttcagttgc aaattc 26

<210> SEQ ID NO 1202
<211> LENGTH: 13
<212> TYPE: DNA
<213> ORGANISM: Artificial Sequence
<220> FEATURE:
<223> OTHER INFORMATION: Primer

<400> SEQUENCE: 1202
tgcagctgat tgt 13

<210> SEQ ID NO 1203
<211> LENGTH: 26
<212> TYPE: DNA
<213> ORGANISM: Artificial Sequence
<220> FEATURE:
<223> OTHER INFORMATION: Primer

<400> SEQUENCE: 1203
tgcataggga aggtaacacc atagtt 26

<210> SEQ ID NO 1204
<211> LENGTH: 25
<212> TYPE: DNA
<213> ORGANISM: Artificial Sequence
<220> FEATURE:
<223> OTHER INFORMATION: Primer

<400> SEQUENCE: 1204
tgcatcacca tttccttgtc cttcg 25

<210> SEQ ID NO 1205
<211> LENGTH: 35
<212> TYPE: DNA
<213> ORGANISM: Artificial Sequence
<220> FEATURE:
<223> OTHER INFORMATION: Primer

<400> SEQUENCE: 1205
tgcatgaagc ataaaaactg tatcaagtgc tttta 35

<210> SEQ ID NO 1206
<211> LENGTH: 36
<212> TYPE: DNA
<213> ORGANISM: Artificial Sequence
<220> FEATURE:
<223> OTHER INFORMATION: Primer

<400> SEQUENCE: 1206
tgcatgctta ctcaaatcat cataaacaat taaagc 36

<210> SEQ ID NO 1207
<211> LENGTH: 29
<212> TYPE: DNA
<213> ORGANISM: Artificial Sequence
<220> FEATURE:
<223> OTHER INFORMATION: Primer

<400> SEQUENCE: 1207
tgcattgtac cgaagtagtt cacattgtt 29

<210> SEQ ID NO 1208
<211> LENGTH: 25
<212> TYPE: DNA
<213> ORGANISM: Artificial Sequence
<220> FEATURE:
<223> OTHER INFORMATION: Primer

<400> SEQUENCE: 1208
tgccaagtgc tggtttaccc catgg 25

<210> SEQ ID NO 1209
<211> LENGTH: 26
<212> TYPE: DNA
<213> ORGANISM: Artificial Sequence
<220> FEATURE:
<223> OTHER INFORMATION: Primer

<400> SEQUENCE: 1209
tgccactttg acaactcctg ttgctg 26

<210> SEQ ID NO 1210
<211> LENGTH: 21
<212> TYPE: DNA
<213> ORGANISM: Artificial Sequence
<220> FEATURE:
<223> OTHER INFORMATION: Primer

<400> SEQUENCE: 1210
tgccagcgac agaccatcgt a 21

<210> SEQ ID NO 1211
<211> LENGTH: 24
<212> TYPE: DNA
<213> ORGANISM: Artificial Sequence
<220> FEATURE:
<223> OTHER INFORMATION: Primer

<400> SEQUENCE: 1211
tgccagctta gtcatacgga cttc 24

<210> SEQ ID NO 1212
<211> LENGTH: 27
<212> TYPE: DNA

-continued

<213> ORGANISM: Artificial Sequence
<220> FEATURE:
<223> OTHER INFORMATION: Primer

<400> SEQUENCE: 1212
tgccagtttc cacatttcac gttcgtg 27

<210> SEQ ID NO 1213
<211> LENGTH: 30
<212> TYPE: DNA
<213> ORGANISM: Artificial Sequence
<220> FEATURE:
<223> OTHER INFORMATION: Primer

<400> SEQUENCE: 1213
tgccatacgt accatcgttt cataaacagc 30

<210> SEQ ID NO 1214
<211> LENGTH: 24
<212> TYPE: DNA
<213> ORGANISM: Artificial Sequence
<220> FEATURE:
<223> OTHER INFORMATION: Primer

<400> SEQUENCE: 1214
tgccatagca aagcctacag catt 24

<210> SEQ ID NO 1215
<211> LENGTH: 28
<212> TYPE: DNA
<213> ORGANISM: Artificial Sequence
<220> FEATURE:
<223> OTHER INFORMATION: Primer

<400> SEQUENCE: 1215
tgccatccat aatcacgcca tactgacg 28

<210> SEQ ID NO 1216
<211> LENGTH: 30
<212> TYPE: DNA
<213> ORGANISM: Artificial Sequence
<220> FEATURE:
<223> OTHER INFORMATION: Primer

<400> SEQUENCE: 1216
tgccatttcc atgtactctt ctctaacatt 30

<210> SEQ ID NO 1217
<211> LENGTH: 27
<212> TYPE: DNA
<213> ORGANISM: Artificial Sequence
<220> FEATURE:
<223> OTHER INFORMATION: Primer

<400> SEQUENCE: 1217
tgcccaccag aaagactagc aggataa 27

<210> SEQ ID NO 1218
<211> LENGTH: 20
<212> TYPE: DNA
<213> ORGANISM: Artificial Sequence
<220> FEATURE:
<223> OTHER INFORMATION: Primer

<400> SEQUENCE: 1218
tgcccaggta caacctgcat 20

<210> SEQ ID NO 1219
<211> LENGTH: 27
<212> TYPE: DNA
<213> ORGANISM: Artificial Sequence
<220> FEATURE:
<223> OTHER INFORMATION: Primer

<400> SEQUENCE: 1219
tgccccattg ctcatgatag tagctac 27

<210> SEQ ID NO 1220
<211> LENGTH: 30
<212> TYPE: DNA
<213> ORGANISM: Artificial Sequence
<220> FEATURE:
<223> OTHER INFORMATION: Primer

<400> SEQUENCE: 1220
tgccctttct aaaagtcttg agtgaagata 30

<210> SEQ ID NO 1221
<211> LENGTH: 25
<212> TYPE: DNA
<213> ORGANISM: Artificial Sequence
<220> FEATURE:
<223> OTHER INFORMATION: Primer

<400> SEQUENCE: 1221
tgcccttttg taaaagcagg gctat 25

<210> SEQ ID NO 1222
<211> LENGTH: 23
<212> TYPE: DNA
<213> ORGANISM: Artificial Sequence
<220> FEATURE:
<223> OTHER INFORMATION: Primer

<400> SEQUENCE: 1222
tgccgataag ccggattctg tgc 23

<210> SEQ ID NO 1223
<211> LENGTH: 28
<212> TYPE: DNA
<213> ORGANISM: Artificial Sequence
<220> FEATURE:
<223> OTHER INFORMATION: Primer

<400> SEQUENCE: 1223
tgccgtaaca tagaagttac cgttgatt 28

<210> SEQ ID NO 1224
<211> LENGTH: 33
<212> TYPE: DNA
<213> ORGANISM: Artificial Sequence
<220> FEATURE:
<223> OTHER INFORMATION: Primer

<400> SEQUENCE: 1224
tgccgtaact aacataagag aattatgcaa gaa 33

<210> SEQ ID NO 1225
<211> LENGTH: 33
<212> TYPE: DNA
<213> ORGANISM: Artificial Sequence
<220> FEATURE:
<223> OTHER INFORMATION: Primer

<400> SEQUENCE: 1225
tgccgtatac gaaaatatct tatcatttag cgt 33

<210> SEQ ID NO 1226
<211> LENGTH: 25
<212> TYPE: DNA
<213> ORGANISM: Artificial Sequence
<220> FEATURE:
<223> OTHER INFORMATION: Primer

<400> SEQUENCE: 1226
tgcctaacaa atcccgtctg agttc 25

<210> SEQ ID NO 1227
<211> LENGTH: 20
<212> TYPE: DNA
<213> ORGANISM: Artificial Sequence
<220> FEATURE:
<223> OTHER INFORMATION: Primer

<400> SEQUENCE: 1227
tgcctcgcgc aacctacccg 20

<210> SEQ ID NO 1228
<211> LENGTH: 20
<212> TYPE: DNA
<213> ORGANISM: Artificial Sequence
<220> FEATURE:
<223> OTHER INFORMATION: Primer

<400> SEQUENCE: 1228
tgcctcgtgc aacccacccg 20

<210> SEQ ID NO 1229
<211> LENGTH: 22
<212> TYPE: DNA
<213> ORGANISM: Artificial Sequence
<220> FEATURE:
<223> OTHER INFORMATION: Primer

<400> SEQUENCE: 1229
tgcgaggaac ttcacgtcct gc 22

<210> SEQ ID NO 1230
<211> LENGTH: 30
<212> TYPE: DNA
<213> ORGANISM: Artificial Sequence
<220> FEATURE:
<223> OTHER INFORMATION: Primer

<400> SEQUENCE: 1230
tgcgatggta ggtatcttag caatcattct 30

<210> SEQ ID NO 1231
<211> LENGTH: 24
<212> TYPE: DNA
<213> ORGANISM: Artificial Sequence
<220> FEATURE:
<223> OTHER INFORMATION: Primer

<400> SEQUENCE: 1231
tgcgcgagct tttatttggg tttc 24

<210> SEQ ID NO 1232
<211> LENGTH: 29
<212> TYPE: DNA

<213> ORGANISM: Artificial Sequence
<220> FEATURE:
<223> OTHER INFORMATION: Primer

<400> SEQUENCE: 1232
tgcgctaatt cttcaacttc ttctttcgt 29

<210> SEQ ID NO 1233
<211> LENGTH: 32
<212> TYPE: DNA
<213> ORGANISM: Artificial Sequence
<220> FEATURE:
<223> OTHER INFORMATION: Primer

<400> SEQUENCE: 1233
tgcgctatca acgattttga caatatatgt ga 32

<210> SEQ ID NO 1234
<211> LENGTH: 23
<212> TYPE: DNA
<213> ORGANISM: Artificial Sequence
<220> FEATURE:
<223> OTHER INFORMATION: Primer

<400> SEQUENCE: 1234
tgcggcagca ctatcaccat cca 23

<210> SEQ ID NO 1235
<211> LENGTH: 21
<212> TYPE: DNA
<213> ORGANISM: Artificial Sequence
<220> FEATURE:
<223> OTHER INFORMATION: Primer

<400> SEQUENCE: 1235
tgcgggctgg ttcaacaaga g 21

<210> SEQ ID NO 1236
<211> LENGTH: 23
<212> TYPE: DNA
<213> ORGANISM: Artificial Sequence
<220> FEATURE:
<223> OTHER INFORMATION: Primer

<400> SEQUENCE: 1236
tgcgggtgat acttaccgag tac 23

<210> SEQ ID NO 1237
<211> LENGTH: 22
<212> TYPE: DNA
<213> ORGANISM: Artificial Sequence
<220> FEATURE:
<223> OTHER INFORMATION: Primer

<400> SEQUENCE: 1237
tgcggtctgg cgcatatagg ta 22

<210> SEQ ID NO 1238
<211> LENGTH: 30
<212> TYPE: DNA
<213> ORGANISM: Artificial Sequence
<220> FEATURE:
<223> OTHER INFORMATION: Primer

<400> SEQUENCE: 1238
tgcgtagtct aataatttac ggaacatttc 30

-continued

<210> SEQ ID NO 1239
<211> LENGTH: 29
<212> TYPE: DNA
<213> ORGANISM: Artificial Sequence
<220> FEATURE:
<223> OTHER INFORMATION: Primer

<400> SEQUENCE: 1239
tgcgtgacga ccttcttgaa ttgtaatca 29

<210> SEQ ID NO 1240
<211> LENGTH: 23
<212> TYPE: DNA
<213> ORGANISM: Artificial Sequence
<220> FEATURE:
<223> OTHER INFORMATION: Primer

<400> SEQUENCE: 1240
tgcgtggact accagggtat cta 23

<210> SEQ ID NO 1241
<211> LENGTH: 13
<212> TYPE: DNA
<213> ORGANISM: Artificial Sequence
<220> FEATURE:
<223> OTHER INFORMATION: Primer

<400> SEQUENCE: 1241
tgcagctgat tgt 13

<210> SEQ ID NO 1242
<211> LENGTH: 30
<212> TYPE: DNA
<213> ORGANISM: Artificial Sequence
<220> FEATURE:
<223> OTHER INFORMATION: Primer

<400> SEQUENCE: 1242
tgctaaagtc ttgagccata cgaacaatgg 30

<210> SEQ ID NO 1243
<211> LENGTH: 24
<212> TYPE: DNA
<213> ORGANISM: Artificial Sequence
<220> FEATURE:
<223> OTHER INFORMATION: Primer

<400> SEQUENCE: 1243
tgctagacct ttacgtgcac cgtg 24

<210> SEQ ID NO 1244
<211> LENGTH: 23
<212> TYPE: DNA
<213> ORGANISM: Artificial Sequence
<220> FEATURE:
<223> OTHER INFORMATION: Primer

<400> SEQUENCE: 1244
tgctaggcca tcaggccacg cat 23

<210> SEQ ID NO 1245
<211> LENGTH: 34
<212> TYPE: DNA
<213> ORGANISM: Artificial Sequence
<220> FEATURE:
<223> OTHER INFORMATION: Primer

<400> SEQUENCE: 1245
tgctatatgc tacaactggt tcaaaaacat taag 34

<210> SEQ ID NO 1246
<211> LENGTH: 29
<212> TYPE: DNA
<213> ORGANISM: Artificial Sequence
<220> FEATURE:
<223> OTHER INFORMATION: Primer

<400> SEQUENCE: 1246
tgctcacctg ctacaacaag tccagcaat 29

<210> SEQ ID NO 1247
<211> LENGTH: 29
<212> TYPE: DNA
<213> ORGANISM: Artificial Sequence
<220> FEATURE:
<223> OTHER INFORMATION: Primer

<400> SEQUENCE: 1247
tgctcttacc tcaccgttcc acccttacc 29

<210> SEQ ID NO 1248
<211> LENGTH: 29
<212> TYPE: DNA
<213> ORGANISM: Artificial Sequence
<220> FEATURE:
<223> OTHER INFORMATION: Primer

<400> SEQUENCE: 1248
tgctgctttc gcatggttaa ttgcttcaa 29

<210> SEQ ID NO 1249
<211> LENGTH: 27
<212> TYPE: DNA
<213> ORGANISM: Artificial Sequence
<220> FEATURE:
<223> OTHER INFORMATION: Primer

<400> SEQUENCE: 1249
tgctgctttg atggctgaat ccccttc 27

<210> SEQ ID NO 1250
<211> LENGTH: 22
<212> TYPE: DNA
<213> ORGANISM: Artificial Sequence
<220> FEATURE:
<223> OTHER INFORMATION: Primer

<400> SEQUENCE: 1250
tgctggattc gcctttgcta cg 22

<210> SEQ ID NO 1251
<211> LENGTH: 21
<212> TYPE: DNA
<213> ORGANISM: Artificial Sequence
<220> FEATURE:
<223> OTHER INFORMATION: Primer

<400> SEQUENCE: 1251
tgctgtaggg aaatcagggc c 21

<210> SEQ ID NO 1252
<211> LENGTH: 18
<212> TYPE: DNA

<213> ORGANISM: Artificial Sequence
<220> FEATURE:
<223> OTHER INFORMATION: Primer

<400> SEQUENCE: 1252
tgcttagatg ctttcagc 18

<210> SEQ ID NO 1253
<211> LENGTH: 34
<212> TYPE: DNA
<213> ORGANISM: Artificial Sequence
<220> FEATURE:
<223> OTHER INFORMATION: Primer

<400> SEQUENCE: 1253
tgcttcaaaa cgcattttta cattttcgtt aaag 34

<210> SEQ ID NO 1254
<211> LENGTH: 27
<212> TYPE: DNA
<213> ORGANISM: Artificial Sequence
<220> FEATURE:
<223> OTHER INFORMATION: Primer

<400> SEQUENCE: 1254
tgcttcagca cggccaccaa cttctag 27

<210> SEQ ID NO 1255
<211> LENGTH: 31
<212> TYPE: DNA
<213> ORGANISM: Artificial Sequence
<220> FEATURE:
<223> OTHER INFORMATION: Primer

<400> SEQUENCE: 1255
tgcttcagcg tagtctaata atttacggaa c 31

<210> SEQ ID NO 1256
<211> LENGTH: 20
<212> TYPE: DNA
<213> ORGANISM: Artificial Sequence
<220> FEATURE:
<223> OTHER INFORMATION: Primer

<400> SEQUENCE: 1256
tgcttctctt ccgggtcggc 20

<210> SEQ ID NO 1257
<211> LENGTH: 32
<212> TYPE: DNA
<213> ORGANISM: Artificial Sequence
<220> FEATURE:
<223> OTHER INFORMATION: Primer

<400> SEQUENCE: 1257
tgcttgctca aatcatcata aacaattaaa gc 32

<210> SEQ ID NO 1258
<211> LENGTH: 31
<212> TYPE: DNA
<213> ORGANISM: Artificial Sequence
<220> FEATURE:
<223> OTHER INFORMATION: Primer

<400> SEQUENCE: 1258
tgcttgctct ttcaagcagt cttgaatgaa g 31

<210> SEQ ID NO 1259
<211> LENGTH: 23
<212> TYPE: DNA
<213> ORGANISM: Artificial Sequence
<220> FEATURE:
<223> OTHER INFORMATION: Primer

<400> SEQUENCE: 1259
tgcttggtgg cttcttcgtc gaa 23

<210> SEQ ID NO 1260
<211> LENGTH: 32
<212> TYPE: DNA
<213> ORGANISM: Artificial Sequence
<220> FEATURE:
<223> OTHER INFORMATION: Primer

<400> SEQUENCE: 1260
tgctttgtaa tctagttcct gaatagtaac ca 32

<210> SEQ ID NO 1261
<211> LENGTH: 30
<212> TYPE: DNA
<213> ORGANISM: Artificial Sequence
<220> FEATURE:
<223> OTHER INFORMATION: Primer

<400> SEQUENCE: 1261
tggaaaactc atgaaattaa agtgaaagga 30

<210> SEQ ID NO 1262
<211> LENGTH: 29
<212> TYPE: DNA
<213> ORGANISM: Artificial Sequence
<220> FEATURE:
<223> OTHER INFORMATION: Primer

<400> SEQUENCE: 1262
tggaaaccgg ctaagtgagt accaccatc 29

<210> SEQ ID NO 1263
<211> LENGTH: 30
<212> TYPE: DNA
<213> ORGANISM: Artificial Sequence
<220> FEATURE:
<223> OTHER INFORMATION: Primer

<400> SEQUENCE: 1263
tggaacaccg tctttaatta aagtatctcc 30

<210> SEQ ID NO 1264
<211> LENGTH: 24
<212> TYPE: DNA
<213> ORGANISM: Artificial Sequence
<220> FEATURE:
<223> OTHER INFORMATION: Primer

<400> SEQUENCE: 1264
tggaatttac cagcgataga cacc 24

<210> SEQ ID NO 1265
<211> LENGTH: 20
<212> TYPE: DNA
<213> ORGANISM: Artificial Sequence
<220> FEATURE:
<223> OTHER INFORMATION: Primer

<400> SEQUENCE: 1265
tggaccacgc cgaagaacgg 20

<210> SEQ ID NO 1266
<211> LENGTH: 30
<212> TYPE: DNA
<213> ORGANISM: Artificial Sequence
<220> FEATURE:
<223> OTHER INFORMATION: Primer

<400> SEQUENCE: 1266
tggacgatat tcacggttta cccacttata 30

<210> SEQ ID NO 1267
<211> LENGTH: 31
<212> TYPE: DNA
<213> ORGANISM: Artificial Sequence
<220> FEATURE:
<223> OTHER INFORMATION: Primer

<400> SEQUENCE: 1267
tggactaata acaatgagct cattgtactg a 31

<210> SEQ ID NO 1268
<211> LENGTH: 31
<212> TYPE: DNA
<213> ORGANISM: Artificial Sequence
<220> FEATURE:
<223> OTHER INFORMATION: Primer

<400> SEQUENCE: 1268
tggataattg gtcgtaacaa gggatagtga g 31

<210> SEQ ID NO 1269
<211> LENGTH: 27
<212> TYPE: DNA
<213> ORGANISM: Artificial Sequence
<220> FEATURE:
<223> OTHER INFORMATION: Primer

<400> SEQUENCE: 1269
tggatagacg tcatatgaag gtgtgct 27

<210> SEQ ID NO 1270
<211> LENGTH: 27
<212> TYPE: DNA
<213> ORGANISM: Artificial Sequence
<220> FEATURE:
<223> OTHER INFORMATION: Primer

<400> SEQUENCE: 1270
tggatcactg cttacgaact cagcttc 27

<210> SEQ ID NO 1271
<211> LENGTH: 26
<212> TYPE: DNA
<213> ORGANISM: Artificial Sequence
<220> FEATURE:
<223> OTHER INFORMATION: Primer

<400> SEQUENCE: 1271
tggatgtgct cacgagtctg tggcat 26

<210> SEQ ID NO 1272
<211> LENGTH: 23
<212> TYPE: DNA

<213> ORGANISM: Artificial Sequence
<220> FEATURE:
<223> OTHER INFORMATION: Primer

<400> SEQUENCE: 1272
tggcaacagc tcaacacctt tgg 23

<210> SEQ ID NO 1273
<211> LENGTH: 26
<212> TYPE: DNA
<213> ORGANISM: Artificial Sequence
<220> FEATURE:
<223> OTHER INFORMATION: Primer

<400> SEQUENCE: 1273
tggcaccgtg ggttgagatg aagtac 26

<210> SEQ ID NO 1274
<211> LENGTH: 19
<212> TYPE: DNA
<213> ORGANISM: Artificial Sequence
<220> FEATURE:
<223> OTHER INFORMATION: Primer

<400> SEQUENCE: 1274
tggcacgagc ctgacctgt 19

<210> SEQ ID NO 1275
<211> LENGTH: 34
<212> TYPE: DNA
<213> ORGANISM: Artificial Sequence
<220> FEATURE:
<223> OTHER INFORMATION: Primer

<400> SEQUENCE: 1275
tggcagcaat agtttgacgt acaaatgcac acat 34

<210> SEQ ID NO 1276
<211> LENGTH: 26
<212> TYPE: DNA
<213> ORGANISM: Artificial Sequence
<220> FEATURE:
<223> OTHER INFORMATION: Primer

<400> SEQUENCE: 1276
tggcatcacc atttccttgt ccttcg 26

<210> SEQ ID NO 1277
<211> LENGTH: 29
<212> TYPE: DNA
<213> ORGANISM: Artificial Sequence
<220> FEATURE:
<223> OTHER INFORMATION: Primer

<400> SEQUENCE: 1277
tggccacttt tatcagcaac cttacagtc 29

<210> SEQ ID NO 1278
<211> LENGTH: 19
<212> TYPE: DNA
<213> ORGANISM: Artificial Sequence
<220> FEATURE:
<223> OTHER INFORMATION: Primer

<400> SEQUENCE: 1278
tggccgtact ccccaggcg 19

<210> SEQ ID NO 1279
<211> LENGTH: 20
<212> TYPE: DNA
<213> ORGANISM: Artificial Sequence
<220> FEATURE:
<223> OTHER INFORMATION: Primer

<400> SEQUENCE: 1279
tggcgatgca ctggcttgag 20

<210> SEQ ID NO 1280
<211> LENGTH: 24
<212> TYPE: DNA
<213> ORGANISM: Artificial Sequence
<220> FEATURE:
<223> OTHER INFORMATION: Primer

<400> SEQUENCE: 1280
tggctcataa gacgcgcttg taga 24

<210> SEQ ID NO 1281
<211> LENGTH: 22
<212> TYPE: DNA
<213> ORGANISM: Artificial Sequence
<220> FEATURE:
<223> OTHER INFORMATION: Primer

<400> SEQUENCE: 1281
tggctgcgga agtgaaatcg ta 22

<210> SEQ ID NO 1282
<211> LENGTH: 19
<212> TYPE: DNA
<213> ORGANISM: Artificial Sequence
<220> FEATURE:
<223> OTHER INFORMATION: Primer

<400> SEQUENCE: 1282
tggctgcttc taagccaac 19

<210> SEQ ID NO 1283
<211> LENGTH: 26
<212> TYPE: DNA
<213> ORGANISM: Artificial Sequence
<220> FEATURE:
<223> OTHER INFORMATION: Primer

<400> SEQUENCE: 1283
tggcttgaga atttaggatc cggcac 26

<210> SEQ ID NO 1284
<211> LENGTH: 30
<212> TYPE: DNA
<213> ORGANISM: Artificial Sequence
<220> FEATURE:
<223> OTHER INFORMATION: Primer

<400> SEQUENCE: 1284
tgggacgtaa tcgtataaat tcatcatttc 30

<210> SEQ ID NO 1285
<211> LENGTH: 36
<212> TYPE: DNA
<213> ORGANISM: Artificial Sequence
<220> FEATURE:
<223> OTHER INFORMATION: Primer

<400> SEQUENCE: 1285
tgggataaca ttggttggaa tataagcaga aacatc 36

<210> SEQ ID NO 1286
<211> LENGTH: 30
<212> TYPE: DNA
<213> ORGANISM: Artificial Sequence
<220> FEATURE:
<223> OTHER INFORMATION: Primer

<400> SEQUENCE: 1286
tgggatggag gtgtagaagg tgttatcatc 30

<210> SEQ ID NO 1287
<211> LENGTH: 30
<212> TYPE: DNA
<213> ORGANISM: Artificial Sequence
<220> FEATURE:
<223> OTHER INFORMATION: Primer

<400> SEQUENCE: 1287
tgggatggag gtgtagaagg tgttatcatc 30

<210> SEQ ID NO 1288
<211> LENGTH: 32
<212> TYPE: DNA
<213> ORGANISM: Artificial Sequence
<220> FEATURE:
<223> OTHER INFORMATION: Primer

<400> SEQUENCE: 1288
tgggcaccat ttatccacaa attgattggt at 32

<210> SEQ ID NO 1289
<211> LENGTH: 31
<212> TYPE: DNA
<213> ORGANISM: Artificial Sequence
<220> FEATURE:
<223> OTHER INFORMATION: Primer

<400> SEQUENCE: 1289
tggggacttc cttaccactt ttagtatcta a 31

<210> SEQ ID NO 1290
<211> LENGTH: 33
<212> TYPE: DNA
<213> ORGANISM: Artificial Sequence
<220> FEATURE:
<223> OTHER INFORMATION: Primer

<400> SEQUENCE: 1290
tggggatatg gaggtgtaga aggtgttatc atc 33

<210> SEQ ID NO 1291
<211> LENGTH: 27
<212> TYPE: DNA
<213> ORGANISM: Artificial Sequence
<220> FEATURE:
<223> OTHER INFORMATION: Primer

<400> SEQUENCE: 1291
tggggtaaga cgcggctagc atgtatt 27

<210> SEQ ID NO 1292
<211> LENGTH: 25
<212> TYPE: DNA

<213> ORGANISM: Artificial Sequence
<220> FEATURE:
<223> OTHER INFORMATION: Primer

<400> SEQUENCE: 1292
tgggtacgaa ctggatgtcg ccgtt 25

<210> SEQ ID NO 1293
<211> LENGTH: 27
<212> TYPE: DNA
<213> ORGANISM: Artificial Sequence
<220> FEATURE:
<223> OTHER INFORMATION: Primer

<400> SEQUENCE: 1293
tgggtaggtt tttatctgtg acgcctt 27

<210> SEQ ID NO 1294
<211> LENGTH: 26
<212> TYPE: DNA
<213> ORGANISM: Artificial Sequence
<220> FEATURE:
<223> OTHER INFORMATION: Primer

<400> SEQUENCE: 1294
tgggtctaca cctgcacttg cataac 26

<210> SEQ ID NO 1295
<211> LENGTH: 24
<212> TYPE: DNA
<213> ORGANISM: Artificial Sequence
<220> FEATURE:
<223> OTHER INFORMATION: Primer

<400> SEQUENCE: 1295
tgggtgctgg tttaccccat ggag 24

<210> SEQ ID NO 1296
<211> LENGTH: 29
<212> TYPE: DNA
<213> ORGANISM: Artificial Sequence
<220> FEATURE:
<223> OTHER INFORMATION: Primer

<400> SEQUENCE: 1296
tgggttgcgt tgcagattat ctttaccaa 29

<210> SEQ ID NO 1297
<211> LENGTH: 25
<212> TYPE: DNA
<213> ORGANISM: Artificial Sequence
<220> FEATURE:
<223> OTHER INFORMATION: Primer

<400> SEQUENCE: 1297
tgggtttcgc gcttagatgc tttca 25

<210> SEQ ID NO 1298
<211> LENGTH: 18
<212> TYPE: DNA
<213> ORGANISM: Artificial Sequence
<220> FEATURE:
<223> OTHER INFORMATION: Primer

<400> SEQUENCE: 1298
tggtaaccct tgtctttg 18

<210> SEQ ID NO 1299
<211> LENGTH: 31
<212> TYPE: DNA
<213> ORGANISM: Artificial Sequence
<220> FEATURE:
<223> OTHER INFORMATION: Primer

<400> SEQUENCE: 1299
tggtaaccct tgtctttgaa ttgtatttgc a 31

<210> SEQ ID NO 1300
<211> LENGTH: 33
<212> TYPE: DNA
<213> ORGANISM: Artificial Sequence
<220> FEATURE:
<223> OTHER INFORMATION: Primer

<400> SEQUENCE: 1300
tggtacaaca tcgttagctt taccactttc acg 33

<210> SEQ ID NO 1301
<211> LENGTH: 32
<212> TYPE: DNA
<213> ORGANISM: Artificial Sequence
<220> FEATURE:
<223> OTHER INFORMATION: Primer

<400> SEQUENCE: 1301
tggtacacct ggtttcgttt tgatgatttg ta 32

<210> SEQ ID NO 1302
<211> LENGTH: 30
<212> TYPE: DNA
<213> ORGANISM: Artificial Sequence
<220> FEATURE:
<223> OTHER INFORMATION: Primer

<400> SEQUENCE: 1302
tggtacttca acttcatcca ttatgaagtc 30

<210> SEQ ID NO 1303
<211> LENGTH: 31
<212> TYPE: DNA
<213> ORGANISM: Artificial Sequence
<220> FEATURE:
<223> OTHER INFORMATION: Primer

<400> SEQUENCE: 1303
tggtatattc gttaattaat ctggctgcgg a 31

<210> SEQ ID NO 1304
<211> LENGTH: 21
<212> TYPE: DNA
<213> ORGANISM: Artificial Sequence
<220> FEATURE:
<223> OTHER INFORMATION: Primer

<400> SEQUENCE: 1304
tggtctgagt acctcctttg c 21

<210> SEQ ID NO 1305
<211> LENGTH: 31
<212> TYPE: DNA
<213> ORGANISM: Artificial Sequence
<220> FEATURE:
<223> OTHER INFORMATION: Primer

<400> SEQUENCE: 1305
tggtgggtat cttagcaatc attctaatag c 31

<210> SEQ ID NO 1306
<211> LENGTH: 32
<212> TYPE: DNA
<213> ORGANISM: Artificial Sequence
<220> FEATURE:
<223> OTHER INFORMATION: Primer

<400> SEQUENCE: 1306
tggtgttcta gtatagattg aggtagtggt ga 32

<210> SEQ ID NO 1307
<211> LENGTH: 24
<212> TYPE: DNA
<213> ORGANISM: Artificial Sequence
<220> FEATURE:
<223> OTHER INFORMATION: Primer

<400> SEQUENCE: 1307
tggttagaag tcgtaacgtg gacc 24

<210> SEQ ID NO 1308
<211> LENGTH: 25
<212> TYPE: DNA
<213> ORGANISM: Artificial Sequence
<220> FEATURE:
<223> OTHER INFORMATION: Primer

<400> SEQUENCE: 1308
tggttcaaca agagttgccg ttgca 25

<210> SEQ ID NO 1309
<211> LENGTH: 31
<212> TYPE: DNA
<213> ORGANISM: Artificial Sequence
<220> FEATURE:
<223> OTHER INFORMATION: Primer

<400> SEQUENCE: 1309
tggttcttac ttgctttgca taaactttcc a 31

<210> SEQ ID NO 1310
<211> LENGTH: 31
<212> TYPE: DNA
<213> ORGANISM: Artificial Sequence
<220> FEATURE:
<223> OTHER INFORMATION: Primer

<400> SEQUENCE: 1310
tggttgtagt tcctgtagtt gttgcattaa c 31

<210> SEQ ID NO 1311
<211> LENGTH: 30
<212> TYPE: DNA
<213> ORGANISM: Artificial Sequence
<220> FEATURE:
<223> OTHER INFORMATION: Primer

<400> SEQUENCE: 1311
tggtttgtca gaatcacgtt ctggagttgg 30

<210> SEQ ID NO 1312
<211> LENGTH: 28
<212> TYPE: DNA

<213> ORGANISM: Artificial Sequence
<220> FEATURE:
<223> OTHER INFORMATION: Primer

<400> SEQUENCE: 1312
tgtaaaagca gggctataat aaggactc 28

<210> SEQ ID NO 1313
<211> LENGTH: 29
<212> TYPE: DNA
<213> ORGANISM: Artificial Sequence
<220> FEATURE:
<223> OTHER INFORMATION: Primer

<400> SEQUENCE: 1313
tgtaaattcc gcaaagactt tggcattag 29

<210> SEQ ID NO 1314
<211> LENGTH: 29
<212> TYPE: DNA
<213> ORGANISM: Artificial Sequence
<220> FEATURE:
<223> OTHER INFORMATION: Primer

<400> SEQUENCE: 1314
tgtaaccctt gtctttgaat tgtatttgc 29

<210> SEQ ID NO 1315
<211> LENGTH: 31
<212> TYPE: DNA
<213> ORGANISM: Artificial Sequence
<220> FEATURE:
<223> OTHER INFORMATION: Primer

<400> SEQUENCE: 1315
tgtaattaac cgaaggttct gtagaagtat g 31

<210> SEQ ID NO 1316
<211> LENGTH: 28
<212> TYPE: DNA
<213> ORGANISM: Artificial Sequence
<220> FEATURE:
<223> OTHER INFORMATION: Primer

<400> SEQUENCE: 1316
tgtacaagga ccattataat caatgcca 28

<210> SEQ ID NO 1317
<211> LENGTH: 31
<212> TYPE: DNA
<213> ORGANISM: Artificial Sequence
<220> FEATURE:
<223> OTHER INFORMATION: Primer

<400> SEQUENCE: 1317
tgtacaataa ggagtcacct tatgtccctt a 31

<210> SEQ ID NO 1318
<211> LENGTH: 30
<212> TYPE: DNA
<213> ORGANISM: Artificial Sequence
<220> FEATURE:
<223> OTHER INFORMATION: Primer

<400> SEQUENCE: 1318
tgtacaccat ttatccacaa attgattggt 30

<210> SEQ ID NO 1319
<211> LENGTH: 29
<212> TYPE: DNA
<213> ORGANISM: Artificial Sequence
<220> FEATURE:
<223> OTHER INFORMATION: Primer

<400> SEQUENCE: 1319
tgtaggcaag tgcataagaa attgataca 29

<210> SEQ ID NO 1320
<211> LENGTH: 27
<212> TYPE: DNA
<213> ORGANISM: Artificial Sequence
<220> FEATURE:
<223> OTHER INFORMATION: Primer

<400> SEQUENCE: 1320
tgtcaatatg aaggtgctct gtggata 27

<210> SEQ ID NO 1321
<211> LENGTH: 28
<212> TYPE: DNA
<213> ORGANISM: Artificial Sequence
<220> FEATURE:
<223> OTHER INFORMATION: Primer

<400> SEQUENCE: 1321
tgtcaccagc ttcagcgtag tctaataa 28

<210> SEQ ID NO 1322
<211> LENGTH: 19
<212> TYPE: DNA
<213> ORGANISM: Artificial Sequence
<220> FEATURE:
<223> OTHER INFORMATION: Primer

<400> SEQUENCE: 1322
tgtcactccc gacacgcca 19

<210> SEQ ID NO 1323
<211> LENGTH: 29
<212> TYPE: DNA
<213> ORGANISM: Artificial Sequence
<220> FEATURE:
<223> OTHER INFORMATION: Primer

<400> SEQUENCE: 1323
tgtcagctaa gctaataacg tttgtagag 29

<210> SEQ ID NO 1324
<211> LENGTH: 26
<212> TYPE: DNA
<213> ORGANISM: Artificial Sequence
<220> FEATURE:
<223> OTHER INFORMATION: Primer

<400> SEQUENCE: 1324
tgtcatcaag caccccaaaa tgaact 26

<210> SEQ ID NO 1325
<211> LENGTH: 28
<212> TYPE: DNA
<213> ORGANISM: Artificial Sequence
<220> FEATURE:
<223> OTHER INFORMATION: Primer

<400> SEQUENCE: 1325
tgtccgactt gacggtcaac atttcctg 28

<210> SEQ ID NO 1326
<211> LENGTH: 28
<212> TYPE: DNA
<213> ORGANISM: Artificial Sequence
<220> FEATURE:
<223> OTHER INFORMATION: Primer

<400> SEQUENCE: 1326
tgtccgactt gacggtcagc atttcctg 28

<210> SEQ ID NO 1327
<211> LENGTH: 28
<212> TYPE: DNA
<213> ORGANISM: Artificial Sequence
<220> FEATURE:
<223> OTHER INFORMATION: Primer

<400> SEQUENCE: 1327
tgtccgactt gacggttagc atttcctg 28

<210> SEQ ID NO 1328
<211> LENGTH: 21
<212> TYPE: DNA
<213> ORGANISM: Artificial Sequence
<220> FEATURE:
<223> OTHER INFORMATION: Primer

<400> SEQUENCE: 1328
tgtcgcagca tctgttcctg c 21

<210> SEQ ID NO 1329
<211> LENGTH: 29
<212> TYPE: DNA
<213> ORGANISM: Artificial Sequence
<220> FEATURE:
<223> OTHER INFORMATION: Primer

<400> SEQUENCE: 1329
tgtctattgt cgattgttac ctgtacagt 29

<210> SEQ ID NO 1330
<211> LENGTH: 27
<212> TYPE: DNA
<213> ORGANISM: Artificial Sequence
<220> FEATURE:
<223> OTHER INFORMATION: Primer

<400> SEQUENCE: 1330
tgtgaacatt tgcgacggta tacccat 27

<210> SEQ ID NO 1331
<211> LENGTH: 29
<212> TYPE: DNA
<213> ORGANISM: Artificial Sequence
<220> FEATURE:
<223> OTHER INFORMATION: Primer

<400> SEQUENCE: 1331
tgtgaagaac tttcaaatct gtgaatcca 29

<210> SEQ ID NO 1332
<211> LENGTH: 24
<212> TYPE: DNA

<213> ORGANISM: Artificial Sequence
<220> FEATURE:
<223> OTHER INFORMATION: Primer

<400> SEQUENCE: 1332
tgtgatatgg aggtgtagaa ggtg 24

<210> SEQ ID NO 1333
<211> LENGTH: 27
<212> TYPE: DNA
<213> ORGANISM: Artificial Sequence
<220> FEATURE:
<223> OTHER INFORMATION: Primer

<400> SEQUENCE: 1333
tgtgatatgg aggtgtagaa ggtgtta 27

<210> SEQ ID NO 1334
<211> LENGTH: 24
<212> TYPE: DNA
<213> ORGANISM: Artificial Sequence
<220> FEATURE:
<223> OTHER INFORMATION: Primer

<400> SEQUENCE: 1334
tgtgcaggca tcatgtcata ccaa 24

<210> SEQ ID NO 1335
<211> LENGTH: 31
<212> TYPE: DNA
<213> ORGANISM: Artificial Sequence
<220> FEATURE:
<223> OTHER INFORMATION: Primer

<400> SEQUENCE: 1335
tgtgctgctt tcgcatggtt aattgcttca a 31

<210> SEQ ID NO 1336
<211> LENGTH: 22
<212> TYPE: DNA
<213> ORGANISM: Artificial Sequence
<220> FEATURE:
<223> OTHER INFORMATION: Primer

<400> SEQUENCE: 1336
tgtgctggtt taccccatgg ag 22

<210> SEQ ID NO 1337
<211> LENGTH: 23
<212> TYPE: DNA
<213> ORGANISM: Artificial Sequence
<220> FEATURE:
<223> OTHER INFORMATION: Primer

<400> SEQUENCE: 1337
tgtgctggtt taccccatgg agt 23

<210> SEQ ID NO 1338
<211> LENGTH: 15
<212> TYPE: DNA
<213> ORGANISM: Artificial Sequence
<220> FEATURE:
<223> OTHER INFORMATION: Primer

<400> SEQUENCE: 1338
tgtgctttga atgct 15

<210> SEQ ID NO 1339
<211> LENGTH: 28
<212> TYPE: DNA
<213> ORGANISM: Artificial Sequence
<220> FEATURE:
<223> OTHER INFORMATION: Primer

<400> SEQUENCE: 1339
tgtgcttttt ttgctgccat agcaaagc 28

<210> SEQ ID NO 1340
<211> LENGTH: 26
<212> TYPE: DNA
<213> ORGANISM: Artificial Sequence
<220> FEATURE:
<223> OTHER INFORMATION: Primer

<400> SEQUENCE: 1340
tgtggccgat ttcaccacct gctcct 26

<210> SEQ ID NO 1341
<211> LENGTH: 18
<212> TYPE: DNA
<213> ORGANISM: Artificial Sequence
<220> FEATURE:
<223> OTHER INFORMATION: Primer

<400> SEQUENCE: 1341
tgtgttgtcg ccgcgcag 18

<210> SEQ ID NO 1342
<211> LENGTH: 20
<212> TYPE: DNA
<213> ORGANISM: Artificial Sequence
<220> FEATURE:
<223> OTHER INFORMATION: Primer

<400> SEQUENCE: 1342
tgttaacggc ttcaagaccc 20

<210> SEQ ID NO 1343
<211> LENGTH: 28
<212> TYPE: DNA
<213> ORGANISM: Artificial Sequence
<220> FEATURE:
<223> OTHER INFORMATION: Primer

<400> SEQUENCE: 1343
tgttaagtgt gttgcggctg tctttatt 28

<210> SEQ ID NO 1344
<211> LENGTH: 36
<212> TYPE: DNA
<213> ORGANISM: Artificial Sequence
<220> FEATURE:
<223> OTHER INFORMATION: Primer

<400> SEQUENCE: 1344
tgttaatggt aacccttgtc tttgaattgt atttgc 36

<210> SEQ ID NO 1345
<211> LENGTH: 22
<212> TYPE: DNA
<213> ORGANISM: Artificial Sequence
<220> FEATURE:
<223> OTHER INFORMATION: Primer

<400> SEQUENCE: 1345
tgttactcac ccgtctgcca ct 22

<210> SEQ ID NO 1346
<211> LENGTH: 14
<212> TYPE: DNA
<213> ORGANISM: Artificial Sequence
<220> FEATURE:
<223> OTHER INFORMATION: Primer

<400> SEQUENCE: 1346
tgttactgct ggat 14

<210> SEQ ID NO 1347
<211> LENGTH: 34
<212> TYPE: DNA
<213> ORGANISM: Artificial Sequence
<220> FEATURE:
<223> OTHER INFORMATION: Primer

<400> SEQUENCE: 1347
tgttcatgtt taaatgatca ggataaaaag cact 34

<210> SEQ ID NO 1348
<211> LENGTH: 30
<212> TYPE: DNA
<213> ORGANISM: Artificial Sequence
<220> FEATURE:
<223> OTHER INFORMATION: Primer

<400> SEQUENCE: 1348
tgttccaata gcagttccgc ccaaattgat 30

<210> SEQ ID NO 1349
<211> LENGTH: 30
<212> TYPE: DNA
<213> ORGANISM: Artificial Sequence
<220> FEATURE:
<223> OTHER INFORMATION: Primer

<400> SEQUENCE: 1349
tgttctggat tgattgcaca atcaccaaag 30

<210> SEQ ID NO 1350
<211> LENGTH: 30
<212> TYPE: DNA
<213> ORGANISM: Artificial Sequence
<220> FEATURE:
<223> OTHER INFORMATION: Primer

<400> SEQUENCE: 1350
tgttcttgat acacctggtt tcgttttgat 30

<210> SEQ ID NO 1351
<211> LENGTH: 30
<212> TYPE: DNA
<213> ORGANISM: Artificial Sequence
<220> FEATURE:
<223> OTHER INFORMATION: Primer

<400> SEQUENCE: 1351
tgttgaagct gtacttgacc tgattttacg 30

<210> SEQ ID NO 1352
<211> LENGTH: 19
<212> TYPE: DNA

<213> ORGANISM: Artificial Sequence
<220> FEATURE:
<223> OTHER INFORMATION: Primer

<400> SEQUENCE: 1352
tgttgaccat gcttcttag 19

<210> SEQ ID NO 1353
<211> LENGTH: 28
<212> TYPE: DNA
<213> ORGANISM: Artificial Sequence
<220> FEATURE:
<223> OTHER INFORMATION: Primer

<400> SEQUENCE: 1353
tgttgtgccg cagtcaaata tctaaata 28

<210> SEQ ID NO 1354
<211> LENGTH: 25
<212> TYPE: DNA
<213> ORGANISM: Artificial Sequence
<220> FEATURE:
<223> OTHER INFORMATION: Primer

<400> SEQUENCE: 1354
tgtttgtgat gcatttgctg agcta 25

<210> SEQ ID NO 1355
<211> LENGTH: 33
<212> TYPE: DNA
<213> ORGANISM: Artificial Sequence
<220> FEATURE:
<223> OTHER INFORMATION: Primer

<400> SEQUENCE: 1355
tgttttatgt gtagttgagc ttactacatg agc 33

<210> SEQ ID NO 1356
<211> LENGTH: 29
<212> TYPE: DNA
<213> ORGANISM: Artificial Sequence
<220> FEATURE:
<223> OTHER INFORMATION: Primer

<400> SEQUENCE: 1356
tgttttgtat ccaagtgctg gtttacccc 29

<210> SEQ ID NO 1357
<211> LENGTH: 11
<212> TYPE: DNA
<213> ORGANISM: Artificial Sequence
<220> FEATURE:
<223> OTHER INFORMATION: Primer

<400> SEQUENCE: 1357
tactcatgcc a 11

<210> SEQ ID NO 1358
<211> LENGTH: 11
<212> TYPE: DNA
<213> ORGANISM: Artificial Sequence
<220> FEATURE:
<223> OTHER INFORMATION: Primer

<400> SEQUENCE: 1358
tattcttcgt t 11

<210> SEQ ID NO 1359
<211> LENGTH: 17
<212> TYPE: DNA
<213> ORGANISM: Artificial Sequence
<220> FEATURE:
<223> OTHER INFORMATION: Primer

<400> SEQUENCE: 1359
ttacttctaa cccactc 17

<210> SEQ ID NO 1360
<211> LENGTH: 27
<212> TYPE: DNA
<213> ORGANISM: Artificial Sequence
<220> FEATURE:
<223> OTHER INFORMATION: Primer

<400> SEQUENCE: 1360
ttaatctggc tgcggaagtg aaatcgt 27

<210> SEQ ID NO 1361
<211> LENGTH: 28
<212> TYPE: DNA
<213> ORGANISM: Artificial Sequence
<220> FEATURE:
<223> OTHER INFORMATION: Primer

<400> SEQUENCE: 1361
ttaccatctt caaatacccg aacagtaa 28

<210> SEQ ID NO 1362
<211> LENGTH: 26
<212> TYPE: DNA
<213> ORGANISM: Artificial Sequence
<220> FEATURE:
<223> OTHER INFORMATION: Primer

<400> SEQUENCE: 1362
ttaccgagca ggttctgacg gaaacg 26

<210> SEQ ID NO 1363
<211> LENGTH: 20
<212> TYPE: DNA
<213> ORGANISM: Artificial Sequence
<220> FEATURE:
<223> OTHER INFORMATION: Primer

<400> SEQUENCE: 1363
ttacgccatc aggccacgca 20

<210> SEQ ID NO 1364
<211> LENGTH: 17
<212> TYPE: DNA
<213> ORGANISM: Artificial Sequence
<220> FEATURE:
<223> OTHER INFORMATION: Primer

<400> SEQUENCE: 1364
ttactcaccc gtccgcc 17

<210> SEQ ID NO 1365
<211> LENGTH: 20
<212> TYPE: DNA
<213> ORGANISM: Artificial Sequence
<220> FEATURE:
<223> OTHER INFORMATION: Primer

<400> SEQUENCE: 1365
ttactcaccc gtccgccgct 20

<210> SEQ ID NO 1366
<211> LENGTH: 34
<212> TYPE: DNA
<213> ORGANISM: Artificial Sequence
<220> FEATURE:
<223> OTHER INFORMATION: Primer

<400> SEQUENCE: 1366
ttacttcctt accactttta gtatctaaag cata 34

<210> SEQ ID NO 1367
<211> LENGTH: 17
<212> TYPE: DNA
<213> ORGANISM: Artificial Sequence
<220> FEATURE:
<223> OTHER INFORMATION: Primer

<400> SEQUENCE: 1367
ttacttctaa cccactc 17

<210> SEQ ID NO 1368
<211> LENGTH: 21
<212> TYPE: DNA
<213> ORGANISM: Artificial Sequence
<220> FEATURE:
<223> OTHER INFORMATION: Primer

<400> SEQUENCE: 1368
ttagaagtcg taacgtggac c 21

<210> SEQ ID NO 1369
<211> LENGTH: 22
<212> TYPE: DNA
<213> ORGANISM: Artificial Sequence
<220> FEATURE:
<223> OTHER INFORMATION: Primer

<400> SEQUENCE: 1369
ttagatgctt tcagcactta tc 22

<210> SEQ ID NO 1370
<211> LENGTH: 26
<212> TYPE: DNA
<213> ORGANISM: Artificial Sequence
<220> FEATURE:
<223> OTHER INFORMATION: Primer

<400> SEQUENCE: 1370
ttcaaaacct tgctctcgcc aaacaa 26

<210> SEQ ID NO 1371
<211> LENGTH: 24
<212> TYPE: DNA
<213> ORGANISM: Artificial Sequence
<220> FEATURE:
<223> OTHER INFORMATION: Primer

<400> SEQUENCE: 1371
ttcaaaagtt gctcgagacc attg 24

<210> SEQ ID NO 1372
<211> LENGTH: 23
<212> TYPE: DNA

<213> ORGANISM: Artificial Sequence
<220> FEATURE:
<223> OTHER INFORMATION: Primer

<400> SEQUENCE: 1372
ttcaaaatgc ggaggcgtat gtg 23

<210> SEQ ID NO 1373
<211> LENGTH: 22
<212> TYPE: DNA
<213> ORGANISM: Artificial Sequence
<220> FEATURE:
<223> OTHER INFORMATION: Primer

<400> SEQUENCE: 1373
ttcaacaaga gttgccgttg ca 22

<210> SEQ ID NO 1374
<211> LENGTH: 28
<212> TYPE: DNA
<213> ORGANISM: Artificial Sequence
<220> FEATURE:
<223> OTHER INFORMATION: Primer

<400> SEQUENCE: 1374
ttcaacactc tcacctacag ctttaaag 28

<210> SEQ ID NO 1375
<211> LENGTH: 24
<212> TYPE: DNA
<213> ORGANISM: Artificial Sequence
<220> FEATURE:
<223> OTHER INFORMATION: Primer

<400> SEQUENCE: 1375
ttcaagtgct tgctcaccat tgtc 24

<210> SEQ ID NO 1376
<211> LENGTH: 26
<212> TYPE: DNA
<213> ORGANISM: Artificial Sequence
<220> FEATURE:
<223> OTHER INFORMATION: Primer

<400> SEQUENCE: 1376
ttcaggtaca gcaggtggtt caggat 26

<210> SEQ ID NO 1377
<211> LENGTH: 23
<212> TYPE: DNA
<213> ORGANISM: Artificial Sequence
<220> FEATURE:
<223> OTHER INFORMATION: Primer

<400> SEQUENCE: 1377
ttcaggtcca tcgggttcat gcc 23

<210> SEQ ID NO 1378
<211> LENGTH: 29
<212> TYPE: DNA
<213> ORGANISM: Artificial Sequence
<220> FEATURE:
<223> OTHER INFORMATION: Primer

<400> SEQUENCE: 1378
ttcataagca atacctttac ttgcaccac 29

<210> SEQ ID NO 1379
<211> LENGTH: 30
<212> TYPE: DNA
<213> ORGANISM: Artificial Sequence
<220> FEATURE:
<223> OTHER INFORMATION: Primer

<400> SEQUENCE: 1379
ttcattttct ggtccaaagt aagcagtatc 30

<210> SEQ ID NO 1380
<211> LENGTH: 25
<212> TYPE: DNA
<213> ORGANISM: Artificial Sequence
<220> FEATURE:
<223> OTHER INFORMATION: Primer

<400> SEQUENCE: 1380
ttccaagtgc tggtttaccc catgg 25

<210> SEQ ID NO 1381
<211> LENGTH: 33
<212> TYPE: DNA
<213> ORGANISM: Artificial Sequence
<220> FEATURE:
<223> OTHER INFORMATION: Primer

<400> SEQUENCE: 1381
ttccaccttg gatacctgga aaaatagctg aat 33

<210> SEQ ID NO 1382
<211> LENGTH: 36
<212> TYPE: DNA
<213> ORGANISM: Artificial Sequence
<220> FEATURE:
<223> OTHER INFORMATION: Primer

<400> SEQUENCE: 1382
ttccatttca actaattcta ataattcttc atcgtc 36

<210> SEQ ID NO 1383
<211> LENGTH: 28
<212> TYPE: DNA
<213> ORGANISM: Artificial Sequence
<220> FEATURE:
<223> OTHER INFORMATION: Primer

<400> SEQUENCE: 1383
ttcccctgac cttcgattaa aggatagc 28

<210> SEQ ID NO 1384
<211> LENGTH: 27
<212> TYPE: DNA
<213> ORGANISM: Artificial Sequence
<220> FEATURE:
<223> OTHER INFORMATION: Primer

<400> SEQUENCE: 1384
ttcgcgcatc caggagaagt acatgtt 27

<210> SEQ ID NO 1385
<211> LENGTH: 15
<212> TYPE: DNA
<213> ORGANISM: Artificial Sequence
<220> FEATURE:
<223> OTHER INFORMATION: Primer

<400> SEQUENCE: 1385
ttcgctcgcc gctac 15

<210> SEQ ID NO 1386
<211> LENGTH: 18
<212> TYPE: DNA
<213> ORGANISM: Artificial Sequence
<220> FEATURE:
<223> OTHER INFORMATION: Primer

<400> SEQUENCE: 1386
ttcgctctcg gcctggcc 18

<210> SEQ ID NO 1387
<211> LENGTH: 22
<212> TYPE: DNA
<213> ORGANISM: Artificial Sequence
<220> FEATURE:
<223> OTHER INFORMATION: Primer

<400> SEQUENCE: 1387
ttcggtataa cgcatcgcag ca 22

<210> SEQ ID NO 1388
<211> LENGTH: 26
<212> TYPE: DNA
<213> ORGANISM: Artificial Sequence
<220> FEATURE:
<223> OTHER INFORMATION: Primer

<400> SEQUENCE: 1388
ttcgtgctgg attttgtcct tgtcct 26

<210> SEQ ID NO 1389
<211> LENGTH: 21
<212> TYPE: DNA
<213> ORGANISM: Artificial Sequence
<220> FEATURE:
<223> OTHER INFORMATION: Primer

<400> SEQUENCE: 1389
ttcgtgctta gatgctttca g 21

<210> SEQ ID NO 1390
<211> LENGTH: 24
<212> TYPE: DNA
<213> ORGANISM: Artificial Sequence
<220> FEATURE:
<223> OTHER INFORMATION: Primer

<400> SEQUENCE: 1390
ttctgagcta aatcagcagt tgca 24

<210> SEQ ID NO 1391
<211> LENGTH: 23
<212> TYPE: DNA
<213> ORGANISM: Artificial Sequence
<220> FEATURE:
<223> OTHER INFORMATION: Primer

<400> SEQUENCE: 1391
ttctgcgaat caatcgcacg ctg 23

<210> SEQ ID NO 1392
<211> LENGTH: 24
<212> TYPE: DNA

<213> ORGANISM: Artificial Sequence
<220> FEATURE:
<223> OTHER INFORMATION: Primer

<400> SEQUENCE: 1392
ttctgcttga ggaatagtgc gtgg 24

<210> SEQ ID NO 1393
<211> LENGTH: 24
<212> TYPE: DNA
<213> ORGANISM: Artificial Sequence
<220> FEATURE:
<223> OTHER INFORMATION: Primer

<400> SEQUENCE: 1393
ttctgggtga cctggtgttt taga 24

<210> SEQ ID NO 1394
<211> LENGTH: 31
<212> TYPE: DNA
<213> ORGANISM: Artificial Sequence
<220> FEATURE:
<223> OTHER INFORMATION: Primer

<400> SEQUENCE: 1394
ttcttccaag gatagattta tttcttgttc g 31

<210> SEQ ID NO 1395
<211> LENGTH: 24
<212> TYPE: DNA
<213> ORGANISM: Artificial Sequence
<220> FEATURE:
<223> OTHER INFORMATION: Primer

<400> SEQUENCE: 1395
ttcttgaacg cgaggtttcg attg 24

<210> SEQ ID NO 1396
<211> LENGTH: 22
<212> TYPE: DNA
<213> ORGANISM: Artificial Sequence
<220> FEATURE:
<223> OTHER INFORMATION: Primer

<400> SEQUENCE: 1396
ttgacatcgt ccctcttcac ag 22

<210> SEQ ID NO 1397
<211> LENGTH: 26
<212> TYPE: DNA
<213> ORGANISM: Artificial Sequence
<220> FEATURE:
<223> OTHER INFORMATION: Primer

<400> SEQUENCE: 1397
ttgacatttg catgcttcaa agcctg 26

<210> SEQ ID NO 1398
<211> LENGTH: 23
<212> TYPE: DNA
<213> ORGANISM: Artificial Sequence
<220> FEATURE:
<223> OTHER INFORMATION: Primer

<400> SEQUENCE: 1398
ttgacgtcat ccccaccttc ctc 23

<210> SEQ ID NO 1399
<211> LENGTH: 24
<212> TYPE: DNA
<213> ORGANISM: Artificial Sequence
<220> FEATURE:
<223> OTHER INFORMATION: Primer

<400> SEQUENCE: 1399
ttgacgttgc atgttcgagc ccat 24

<210> SEQ ID NO 1400
<211> LENGTH: 30
<212> TYPE: DNA
<213> ORGANISM: Artificial Sequence
<220> FEATURE:
<223> OTHER INFORMATION: Primer

<400> SEQUENCE: 1400
ttgcaatcga catatccatt tcaccatgcc 30

<210> SEQ ID NO 1401
<211> LENGTH: 27
<212> TYPE: DNA
<213> ORGANISM: Artificial Sequence
<220> FEATURE:
<223> OTHER INFORMATION: Primer

<400> SEQUENCE: 1401
ttgcacgtct gtttcagttg caaattc 27

<210> SEQ ID NO 1402
<211> LENGTH: 27
<212> TYPE: DNA
<213> ORGANISM: Artificial Sequence
<220> FEATURE:
<223> OTHER INFORMATION: Primer

<400> SEQUENCE: 1402
ttgcacgtct gtttcagttg caaattc 27

<210> SEQ ID NO 1403
<211> LENGTH: 20
<212> TYPE: DNA
<213> ORGANISM: Artificial Sequence
<220> FEATURE:
<223> OTHER INFORMATION: Primer

<400> SEQUENCE: 1403
ttgcatcggg ttggtaagtc 20

<210> SEQ ID NO 1404
<211> LENGTH: 27
<212> TYPE: DNA
<213> ORGANISM: Artificial Sequence
<220> FEATURE:
<223> OTHER INFORMATION: Primer

<400> SEQUENCE: 1404
ttgccacttt gacaactcct gttgctg 27

<210> SEQ ID NO 1405
<211> LENGTH: 25
<212> TYPE: DNA
<213> ORGANISM: Artificial Sequence
<220> FEATURE:
<223> OTHER INFORMATION: Primer

<400> SEQUENCE: 1405
ttgccatagc aaagcctaca gcatt 25

<210> SEQ ID NO 1406
<211> LENGTH: 30
<212> TYPE: DNA
<213> ORGANISM: Artificial Sequence
<220> FEATURE:
<223> OTHER INFORMATION: Primer

<400> SEQUENCE: 1406
ttgccattca tggtatttaa gtgtagcaga 30

<210> SEQ ID NO 1407
<211> LENGTH: 21
<212> TYPE: DNA
<213> ORGANISM: Artificial Sequence
<220> FEATURE:
<223> OTHER INFORMATION: Primer

<400> SEQUENCE: 1407
ttgcgccata cgtaccatcg t 21

<210> SEQ ID NO 1408
<211> LENGTH: 25
<212> TYPE: DNA
<213> ORGANISM: Artificial Sequence
<220> FEATURE:
<223> OTHER INFORMATION: Primer

<400> SEQUENCE: 1408
ttgcgttgca gattatcttt accaa 25

<210> SEQ ID NO 1409
<211> LENGTH: 25
<212> TYPE: DNA
<213> ORGANISM: Artificial Sequence
<220> FEATURE:
<223> OTHER INFORMATION: Primer

<400> SEQUENCE: 1409
ttgctgccat agcaaagcct acagc 25

<210> SEQ ID NO 1410
<211> LENGTH: 30
<212> TYPE: DNA
<213> ORGANISM: Artificial Sequence
<220> FEATURE:
<223> OTHER INFORMATION: Primer

<400> SEQUENCE: 1410
ttgctgcttt cgcatggtta atcgcttcaa 30

<210> SEQ ID NO 1411
<211> LENGTH: 30
<212> TYPE: DNA
<213> ORGANISM: Artificial Sequence
<220> FEATURE:
<223> OTHER INFORMATION: Primer

<400> SEQUENCE: 1411
ttgctgcttt cgcatggtta attgcttcaa 30

<210> SEQ ID NO 1412
<211> LENGTH: 27
<212> TYPE: DNA

<213> ORGANISM: Artificial Sequence
<220> FEATURE:
<223> OTHER INFORMATION: Primer

<400> SEQUENCE: 1412
ttggacctgt aatcagctga atactgg 27

<210> SEQ ID NO 1413
<211> LENGTH: 22
<212> TYPE: DNA
<213> ORGANISM: Artificial Sequence
<220> FEATURE:
<223> OTHER INFORMATION: Primer

<400> SEQUENCE: 1413
ttggccatca gaccacgcat ac 22

<210> SEQ ID NO 1414
<211> LENGTH: 22
<212> TYPE: DNA
<213> ORGANISM: Artificial Sequence
<220> FEATURE:
<223> OTHER INFORMATION: Primer

<400> SEQUENCE: 1414
ttggccatca ggccacgcat ac 22

<210> SEQ ID NO 1415
<211> LENGTH: 28
<212> TYPE: DNA
<213> ORGANISM: Artificial Sequence
<220> FEATURE:
<223> OTHER INFORMATION: Primer

<400> SEQUENCE: 1415
ttggcgacgg tatacccata gctttata 28

<210> SEQ ID NO 1416
<211> LENGTH: 17
<212> TYPE: DNA
<213> ORGANISM: Artificial Sequence
<220> FEATURE:
<223> OTHER INFORMATION: Primer

<400> SEQUENCE: 1416
ttggtgcgct tggcgta 17

<210> SEQ ID NO 1417
<211> LENGTH: 32
<212> TYPE: DNA
<213> ORGANISM: Artificial Sequence
<220> FEATURE:
<223> OTHER INFORMATION: Primer

<400> SEQUENCE: 1417
ttggttctta cttgttttgc ataaactttc ca 32

<210> SEQ ID NO 1418
<211> LENGTH: 35
<212> TYPE: DNA
<213> ORGANISM: Artificial Sequence
<220> FEATURE:
<223> OTHER INFORMATION: Primer

<400> SEQUENCE: 1418
ttgtacattt gaaacaatat gcatgacatg tgaat 35

<210> SEQ ID NO 1419
<211> LENGTH: 23
<212> TYPE: DNA
<213> ORGANISM: Artificial Sequence
<220> FEATURE:
<223> OTHER INFORMATION: Primer

<400> SEQUENCE: 1419
ttgtcagact catcgcgaac atc 23

<210> SEQ ID NO 1420
<211> LENGTH: 28
<212> TYPE: DNA
<213> ORGANISM: Artificial Sequence
<220> FEATURE:
<223> OTHER INFORMATION: Primer

<400> SEQUENCE: 1420
ttgtgatatg gaggtgtaga aggtgtta 28

<210> SEQ ID NO 1421
<211> LENGTH: 26
<212> TYPE: DNA
<213> ORGANISM: Artificial Sequence
<220> FEATURE:
<223> OTHER INFORMATION: Primer

<400> SEQUENCE: 1421
ttgtgattgt tttgcagctg attgtg 26

<210> SEQ ID NO 1422
<211> LENGTH: 27
<212> TYPE: DNA
<213> ORGANISM: Artificial Sequence
<220> FEATURE:
<223> OTHER INFORMATION: Primer

<400> SEQUENCE: 1422
ttgtggccga tttcaccacc tgctcct 27

<210> SEQ ID NO 1423
<211> LENGTH: 21
<212> TYPE: DNA
<213> ORGANISM: Artificial Sequence
<220> FEATURE:
<223> OTHER INFORMATION: Primer

<400> SEQUENCE: 1423
ttgttaacgg cttcaagacc c 21

<210> SEQ ID NO 1424
<211> LENGTH: 32
<212> TYPE: DNA
<213> ORGANISM: Artificial Sequence
<220> FEATURE:
<223> OTHER INFORMATION: Primer

<400> SEQUENCE: 1424
ttgtttattg tttccatatg ctacacactt tc 32

<210> SEQ ID NO 1425
<211> LENGTH: 23
<212> TYPE: DNA
<213> ORGANISM: Artificial Sequence
<220> FEATURE:
<223> OTHER INFORMATION: Primer

<400> SEQUENCE: 1425
tttaagcgcc agaaagcacc aac 23

<210> SEQ ID NO 1426
<211> LENGTH: 25
<212> TYPE: DNA
<213> ORGANISM: Artificial Sequence
<220> FEATURE:
<223> OTHER INFORMATION: Primer

<400> SEQUENCE: 1426
tttacctcgc ctttccaccc ttacc 25

<210> SEQ ID NO 1427
<211> LENGTH: 29
<212> TYPE: DNA
<213> ORGANISM: Artificial Sequence
<220> FEATURE:
<223> OTHER INFORMATION: Primer

<400> SEQUENCE: 1427
tttagctact attctagctg ccatttcca 29

<210> SEQ ID NO 1428
<211> LENGTH: 27
<212> TYPE: DNA
<213> ORGANISM: Artificial Sequence
<220> FEATURE:
<223> OTHER INFORMATION: Primer

<400> SEQUENCE: 1428
tttatgacca gcttcggtac tactaaa 27

<210> SEQ ID NO 1429
<211> LENGTH: 30
<212> TYPE: DNA
<213> ORGANISM: Artificial Sequence
<220> FEATURE:
<223> OTHER INFORMATION: Primer

<400> SEQUENCE: 1429
tttatggtct atttcaatgg cagttacgaa 30

<210> SEQ ID NO 1430
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (23)...(23)
<223> OTHER INFORMATION: I
<220> FEATURE:
<221> NAME/KEY: modified_base
<222> LOCATION: (32)...(32)
<223> OTHER INFORMATION: I

<400> SEQUENCE: 1430
tttcaatacc tttatgcaac tttgtatcaa ctggaat 37

<210> SEQ ID NO 1431
<211> LENGTH: 30
<212> TYPE: DNA
<213> ORGANISM: Artificial Sequence
<220> FEATURE:
<223> OTHER INFORMATION: Primer

<400> SEQUENCE: 1431
tttcacagca tgcacgtctg tttcagttgc 30

<210> SEQ ID NO 1432
<211> LENGTH: 35
<212> TYPE: DNA
<213> ORGANISM: Artificial Sequence
<220> FEATURE:
<223> OTHER INFORMATION: Primer

<400> SEQUENCE: 1432
tttccccgat ctaaatttgg ataagccata ggaaa 35

<210> SEQ ID NO 1433
<211> LENGTH: 27
<212> TYPE: DNA
<213> ORGANISM: Artificial Sequence
<220> FEATURE:
<223> OTHER INFORMATION: Primer

<400> SEQUENCE: 1433
tttccgatgc aacgtaatga gatttca 27

<210> SEQ ID NO 1434
<211> LENGTH: 22
<212> TYPE: DNA
<213> ORGANISM: Artificial Sequence
<220> FEATURE:
<223> OTHER INFORMATION: Primer

<400> SEQUENCE: 1434
tttcgtgctt agatgctttc ag 22

<210> SEQ ID NO 1435
<211> LENGTH: 30
<212> TYPE: DNA
<213> ORGANISM: Artificial Sequence
<220> FEATURE:
<223> OTHER INFORMATION: Primer

<400> SEQUENCE: 1435
tttcttgaag agtatgagct gctccgtaag 30

<210> SEQ ID NO 1436
<211> LENGTH: 22
<212> TYPE: DNA
<213> ORGANISM: Artificial Sequence
<220> FEATURE:
<223> OTHER INFORMATION: Primer

<400> SEQUENCE: 1436
tttgcacctt accgccaaag ct 22

<210> SEQ ID NO 1437
<211> LENGTH: 28
<212> TYPE: DNA
<213> ORGANISM: Artificial Sequence
<220> FEATURE:
<223> OTHER INFORMATION: Primer

<400> SEQUENCE: 1437
tttgctcatg atctgcatga agcataaa 28

<210> SEQ ID NO 1438
<211> LENGTH: 24
<212> TYPE: DNA

<213> ORGANISM: Artificial Sequence
<220> FEATURE:
<223> OTHER INFORMATION: Primer

<400> SEQUENCE: 1438
tttgctctcc gccaaagttt ccac 24

<210> SEQ ID NO 1439
<211> LENGTH: 28
<212> TYPE: DNA
<213> ORGANISM: Artificial Sequence
<220> FEATURE:
<223> OTHER INFORMATION: Primer

<400> SEQUENCE: 1439
tttggacctg taatcagctg aatactgg 28

<210> SEQ ID NO 1440
<211> LENGTH: 29
<212> TYPE: DNA
<213> ORGANISM: Artificial Sequence
<220> FEATURE:
<223> OTHER INFORMATION: Primer

<400> SEQUENCE: 1440
tttgtgaaac agcgaacatt ttcttggta 29

<210> SEQ ID NO 1441
<211> LENGTH: 20
<212> TYPE: DNA
<213> ORGANISM: Artificial Sequence
<220> FEATURE:
<223> OTHER INFORMATION: Primer

<400> SEQUENCE: 1441
ttttccagcc atgcagcgac 20

<210> SEQ ID NO 1442
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (29)...(29)
<223> OTHER INFORMATION: I

<400> SEQUENCE: 1442
ttttcccttt atgcaactta gtatcaactg gaat 34

<210> SEQ ID NO 1443
<211> LENGTH: 29
<212> TYPE: DNA
<213> ORGANISM: Artificial Sequence
<220> FEATURE:
<223> OTHER INFORMATION: Primer

<400> SEQUENCE: 1443
ttttgctcat gatctgcatg aagcataaa 29

<210> SEQ ID NO 1444
<211> LENGTH: 2118
<212> TYPE: DNA
<213> ORGANISM: Artificial Sequence
<220> FEATURE:
<223> OTHER INFORMATION: Concatenation of A. baumannii genes
<220> FEATURE:

-continued

<221> NAME/KEY: misc_feature
<222> LOCATION: 447-486, 778-817, 1162-1201, 1495-1534, 1928-1967,
      2115-2118
<223> OTHER INFORMATION: n = A,T,C or G

<400> SEQUENCE: 1444

```
cgcgcggtaa aactaaagaa gaagatatag cattagaaaa agatttgctg tctgatgaaa     60

aagagattgc tgaacattta atgctgattg atcttgggcg aaacgatgta gggcgtgtat    120

cgaaaatagg taaagtccaa gtcacggatc aaatggtgat cgagcgttat tcacatgtca    180

tgcatattgt ttcaaatgta caaggtgaag tgcgtgatga tatcgatgca cttgatgtat    240

ttaaagccac ctttccagca ggaacgttat caggtgcccc aaaaaattcgt gcaatggaaa    300

ttattgatga agtagaacct gtgaaaaggg gagtttttgg cggggctgtt ggttatttgg    360

gatggcatgg tgaaatggat atgtcgattg caatccgtac ttgtgttatc cgtgataaaa    420

aggtgtatgt acaggctggt gcagggnnnn nnnnnnnnnn nnnnnnnnnn nnnnnnnnnn    480

nnnnnnggaa tctggcggtt tagtttcaga tgaactcatt atcggtttag taaaagaacg    540

tattgctcaa cctgactgcg tgaatggttg tattttcgac ggcttcccac gcactattcc    600

tcaagcagaa gctttggaaa aagaagggat cagcattgat catgtaattg aaattgatgt    660

acctgatgaa gaaatcgtaa aacgtctttc tggtcgtcgt cagcatcctg cttctggtcg    720

tgtttatcac gttgtataca atccacctaa agtggaaggt aaagatgatg tcacaggnnn    780

nnnnnnnnnn nnnnnnnnnn nnnnnnnnnn nnnnnnncgt tcaaccgtgt aaaattacgt    840

aaccttaaaa ctggtaaagt tttagaaaaa acttttaaat ctggtgatac tttagaagct    900

gctgacatcg tagaagtaga aatgaactac ctatacaacg atggcgaaat gtggcacttc    960

atggacccag aaagcttcga acaaattgca gctgacaaaa ctgcaatggg tgatgctgct   1020

aaatggttaa aagacgactc aaatgaaaca tgtacaatca tgttattcaa cggcgttcct   1080

ttaaacgtaa atgcacctaa cttcgttgta ttgaaagttg ttgaaactga tccgggcgta   1140

cgtggtgata cttctggtgg tnnnnnnnnn nnnnnnnnnn nnnnnnnnnn nnnnnnnnnn   1200

ntcgtgcccg yaatttgcat aaagctgccg gccttgtagc acagcaaggc aaatttcctg   1260

aaactctaga agaatggatt gcactacccg gcattggtcg ctcgaccgca ggtgcactca   1320

tgtctttagg tttacgtcag tatggcgtga ttatggatgg caacgtgaaa cgcgttttag   1380

cccgtttctt tgccattgaa gatgacttaa gcaaaccaca gcacgaacgt gaaatgtgga   1440

aactggctga agagctttgt cccacccaac gcaatcatga ctacactcaa gcgannnnnn   1500

nnnnnnnnnn nnnnnnnnnn nnnnnnnnnn nnnnttaaaa acactagcgg taagcttaaa   1560

caagattgcc aatgatattc gttggttagc aagtggtcca cgttgcggct tcggcgaaat   1620

ccgtattcct gaaaatgaac ctggttcaag tatcatgcca ggtaaagtga acccgactca   1680

aagtgaagcc atgaccatgg ttgttgctca agtacttggc aacgatacca ctattaatgt   1740

cgctggtgct tctggtaact tcgagctcaa tgtatttatg ccagtgattg cttataactt   1800

actgcaatct attcagttgc ttggtgatgc atgtaatagt tttaatgatc actgtgcagt   1860

agggatcgag ccaaatcgtg agaaaattga tcatttcttg cataattctc ttatgttagt   1920

tacggcannn nnnnnnnnnn nnnnnnnnnn nnnnnnnnnn nnnnnnnccc ggttatgtac   1980

caaatacttt gtctgaagat ggtgacccat tagacgtact tgttgtaact ccacatcctg   2040

ttgctgccgg ttctgtaatt cgttgccgcc cagtgggcaa attaaacatg gaagacgacg   2100

gtggtatcga tgccnnnn                                                 2118
```

<210> SEQ ID NO 1445
<211> LENGTH: 102
<212> TYPE: DNA
<213> ORGANISM: Artificial Sequence
<220> FEATURE:
<223> OTHER INFORMATION: Calibration Polynucleotide

<400> SEQUENCE: 1445
tttaagtccc gcaacgagcg caacccttga tcttagttgt ttagttgggc actctaaggt 60
gactgccggt gacaaaccgg aggaaggtgg ggatgacgtc aa 102

<210> SEQ ID NO 1446
<211> LENGTH: 94
<212> TYPE: DNA
<213> ORGANISM: Artificial Sequence
<220> FEATURE:
<223> OTHER INFORMATION: Calibration Polynucleotide

<400> SEQUENCE: 1446
tagaacaccg atggcgaagg cgactttctg gtctgtaact gacactgaga aagcgtgggg 60
agcaaacagg attagatacc ctggtagtcc acga 94

<210> SEQ ID NO 1447
<211> LENGTH: 108
<212> TYPE: DNA
<213> ORGANISM: Artificial Sequence
<220> FEATURE:
<223> OTHER INFORMATION: Calibration Polynucleotide

<400> SEQUENCE: 1447
tggattagag accctggtag tccacgccgt aaacgatgag tgctaagtgt tagaggcctt 60
tagtgctgaa gttaacgcat taagcactcc gcctggggag tacggcca 108

<210> SEQ ID NO 1448
<211> LENGTH: 108
<212> TYPE: DNA
<213> ORGANISM: Artificial Sequence
<220> FEATURE:
<223> OTHER INFORMATION: Calibration Polynucleotide

<400> SEQUENCE: 1448
tttcgatgca acgcgaagaa ccttaccagg tcttgacatc ctctgacaac cctagcttct 60
ccttcgggag cagagtgaca ggtggtgcat ggctgtcgtc agctcgta 108

<210> SEQ ID NO 1449
<211> LENGTH: 95
<212> TYPE: DNA
<213> ORGANISM: Artificial Sequence
<220> FEATURE:
<223> OTHER INFORMATION: Calibration Polynucleotide

<400> SEQUENCE: 1449
tctgacacct gcccggtgct ggaaggttaa ggagaggggt tagcgtaact ctgaactgaa 60
gccccagtaa acggcggccg taactataac ggtca 95

<210> SEQ ID NO 1450
<211> LENGTH: 117
<212> TYPE: DNA
<213> ORGANISM: Artificial Sequence
<220> FEATURE:
<223> OTHER INFORMATION: Calibration Polynucleotide

<400> SEQUENCE: 1450
tctgttctta gtacgagagg accgggatgg acgcaccggt accagttgtt ctgccaaggg 60
catagctggg tagctatgtg cggaagggat aagtgctgaa agcatctaag cacgaaa 117

<210> SEQ ID NO 1451
<211> LENGTH: 100
<212> TYPE: DNA
<213> ORGANISM: Artificial Sequence
<220> FEATURE:
<223> OTHER INFORMATION: Calibration Polynucleotide

<400> SEQUENCE: 1451
tgattattgt tatcctgtta tgccatttga gatttttgag tggtattgga gttattgttc 60
caggattaat tgcaaataca attcaaagac aagggttaca 100

<210> SEQ ID NO 1452
<211> LENGTH: 112
<212> TYPE: DNA
<213> ORGANISM: Artificial Sequence
<220> FEATURE:
<223> OTHER INFORMATION: Calibration Polynucleotide

<400> SEQUENCE: 1452
tcgaagtaca atacaagaca aaagaaggta aaattactgt tttaggggaa aaattcaaga 60
aatatagaag tgatggctaa aaatgtagaa ggggtcttga agccgttaac aa 112

<210> SEQ ID NO 1453
<211> LENGTH: 100
<212> TYPE: DNA
<213> ORGANISM: Artificial Sequence
<220> FEATURE:
<223> OTHER INFORMATION: Calibration Polynucleotide

<400> SEQUENCE: 1453
ttgctcgtgg tgcacaagta acggatatta caatcattgt tgttgcagct gatgacggcg 60
taataaacag ttgaagcaat taaccatgcg aaagcagcaa 100

<210> SEQ ID NO 1454
<211> LENGTH: 114
<212> TYPE: DNA
<213> ORGANISM: Artificial Sequence
<220> FEATURE:
<223> OTHER INFORMATION: Calibration Polynucleotide

<400> SEQUENCE: 1454
tagcttttgc atattatatc gagccacagc atcgtgatgt tttacagctt tatgcaccgg 60
aagcttttaa tggataaatt taacgaacaa gaaataaatc tatccttgga agaa 114

<210> SEQ ID NO 1455
<211> LENGTH: 116
<212> TYPE: DNA
<213> ORGANISM: Artificial Sequence
<220> FEATURE:
<223> OTHER INFORMATION: Calibration Polynucleotide

<400> SEQUENCE: 1455
tgacctacag taagaggttc tgtaatgaac cctaatgacc atccacacgg tggtggtgaa 60
ggtagatctc ctatcggaaa gtccacgtac tccatggggt aaaccagcac ttggaa 116

<210> SEQ ID NO 1456
<211> LENGTH: 70
<212> TYPE: DNA
<213> ORGANISM: Artificial Sequence
<220> FEATURE:
<223> OTHER INFORMATION: Calibration Polynucleotide

<400> SEQUENCE: 1456
tccacacggt ggtggtgaag gtagatctcc tatcggaaag tccacgtact ccatggggta 60
aaccagcaca 70

<210> SEQ ID NO 1457
<211> LENGTH: 82
<212> TYPE: DNA
<213> ORGANISM: Artificial Sequence
<220> FEATURE:
<223> OTHER INFORMATION: Calibration Polynucleotide

<400> SEQUENCE: 1457
ttatcgctca ggcgaactcc aacctggatg atgaaggccg ctttttagaa ggtgacttgt 60
cgtagcaaag gcgaatccag ca 82

<210> SEQ ID NO 1458
<211> LENGTH: 87
<212> TYPE: DNA
<213> ORGANISM: Artificial Sequence
<220> FEATURE:
<223> OTHER INFORMATION: Calibration Polynucleotide

<400> SEQUENCE: 1458
tgggcagcgt ttcggcgaaa tggaagtggc tcgaagcgta tggcgcttcg tacgtgctgc 60
aggaaatgtt gaccgtcaag tcggaca 87

<210> SEQ ID NO 1459
<211> LENGTH: 97
<212> TYPE: DNA
<213> ORGANISM: Artificial Sequence
<220> FEATURE:
<223> OTHER INFORMATION: Calibration Polynucleotide

<400> SEQUENCE: 1459
tcaggagtcg ttcaactcga tctacatgat ggccgaccgc ccggggttcg gcggtgcaga 60
ttcgtcagct ggccggcatg cgtggcctga tggcgta 97

<210> SEQ ID NO 1460
<211> LENGTH: 117
<212> TYPE: DNA
<213> ORGANISM: Artificial Sequence
<220> FEATURE:
<223> OTHER INFORMATION: Calibration Polynucleotide

<400> SEQUENCE: 1460
tctggcaggt atgcgtggtc tgatggccaa tccatctggt cgtatcatcg aacttccaat 60
caagtttccg tgaaggttta acagtacttg agtacttcat ctcaacccac ggtgcga 117

<210> SEQ ID NO 1461
<211> LENGTH: 98
<212> TYPE: DNA
<213> ORGANISM: Artificial Sequence
<220> FEATURE:
<223> OTHER INFORMATION: Calibration Polynucleotide

<400> SEQUENCE: 1461
tcaagcaaac gcacaatcag aagctaagaa agcgcaagct tctggaaagc acaaatgcta 60
gttatggtac agaatttgca actgaaacag acgtgcaa 98

<210> SEQ ID NO 1462
<211> LENGTH: 99

<212> TYPE: DNA
<213> ORGANISM: Artificial Sequence
<220> FEATURE:
<223> OTHER INFORMATION: Calibration Polynucleotide

<400> SEQUENCE: 1462
tccacacgcc gttcttcaac aactaccgtg ttctacttcc gtacgacgga cgtgacgggc 60
tcgatcgagc tgccgaagga caaggaaatg gtgatgcca 99

<210> SEQ ID NO 1463
<211> LENGTH: 111
<212> TYPE: DNA
<213> ORGANISM: Artificial Sequence
<220> FEATURE:
<223> OTHER INFORMATION: Calibration Sequence

<400> SEQUENCE: 1463
tcgtggcggc gtggttatcg aacccatgct gaccgatcaa tggtacgtgc acaccgcccc 60
ccaaagtcgc gattgaagcc gtagagaacg gcgacatcca gttcgtaccg a 111

<210> SEQ ID NO 1464
<211> LENGTH: 2100
<212> TYPE: DNA
<213> ORGANISM: Artificial Sequence
<220> FEATURE:
<223> OTHER INFORMATION: Combination Calibration Polynucleotide

<400> SEQUENCE: 1464
gaagtagaga tatggaggaa caccagtggc gaaggcgact ttctggtctg taactgacac 60
tgagaaagcg tggggagcaa acaggattag ataccctggt agtccacgcc gtaaacgatg 120
agtgctaagt gttagaggcc tttagtgctg aagttaacgc attaagcact ccgcctgggg 180
agtacggccg caaggctgaa actcaaagga attgacgggg cacaagcggt ggagcatgtg 240
gtttaattcg aagcaacgcg aagaacctta ccaggtcttg acatcctctg acaaccctag 300
cttctccttc gggagcagag tgacaggtgg tgcatggttg tcgtcagctc gtgtcgtgag 360
atgttgggtt aagtcccgca acgagcgcaa cccttgatct tagttgttta gttgggcact 420
ctaaggtgac tgccggtgac aaaccggagg aaggtgggga tgacgtcaaa tcatcatgcc 480
ccagtaccgt gagggaaagg tgaaaagcac ccccggaaggg gagtgaaaga gatcctgaaa 540
ccgtgtgcca tagtcagagc ccgttaacgg gtgatggcgt gccttttgta gaatgaaccg 600
gcgagttata agatccgtag tcaaaaggga aacagcccag accgccagct aaggtcccaa 660
agtgtgtatt gaaaaggatg tggagttgct tagacaacta ggatgttggc ttagaagcag 720
ccaccattta aagagtatag ggggtgacac ctgcccggtg ctggaaggtt aaggagaggg 780
gttagcgtaa ctctgaactg aagccccagt aaacggcggc cgtaactata acggtcctaa 840
ggtagcgaaa gaaatttgag aggagctgtc cttagtacga gaggaccggg atggacgcac 900
cggtaccagt tgttctgcca agggcatagc tgggtagcta tgtgcggaag ggataagtgc 960
tgaaagcatc taagcatgaa gcccccctca agatgagagc agtaaaacaa gcaaacgcac 1020
aatcagaagc taagaaagcg caagcttctg gaaagcacaa atgctagtta tggtacagaa 1080
tttgcaactg aaacagacgt gcatgctgtg aaatttgcga aagcttttgc atattatatc 1140
gagccacagc atcgtgatgt tttacagctt tatgcaccgg aagcttttaa tggataaatt 1200
taacgaacaa gaaataaatc tatccttgga agaacttaaa gatcaacgga tgctggcaag 1260
atatgaaaaa taagataaaa cagcactatc aacactggag cgattcttta tctgaagaag 1320
gaagagcgat gaaaacaacg aagtacaata caagacaaaa gaaggtaaaa ttactgtttt 1380

-continued

```
aggggaaaaa ttcaagaaat atagaagtga tggctaaaaa tgtagaaggg gtcttgaagc   1440

cgttaacagc tgttatggcg accgtggcgg cgtggttatc gaacccatgc tgaccgatca   1500

atggtacgtg cacaccgccc cccaaagtcg cgattgaagc cgtagagaac ggcgagatcc   1560

agttcgtccc taaacagtac ggcaacttcg ttatcgctca ggcgaactcc aacctggatg   1620

atgaaggccg ctttttagaa ggtgacttgt cgtagcaaag gcgaatcaag cctgtttagc   1680

cacaactatg cgtgctcgtg gtgcacaagt aacggatatt acaatcattg ttgttgcagc   1740

tgatgacggc gtaataaaca gttgaagcga ttaaccatgc gaaagcagca ggagtaccaa   1800

ctttactcag cttgctggta tgcgtggtct gatggccaat ccatctggtc gtatcatcga   1860

acttccaatc aagtttccgt gaaggtttaa cagtacttga gtacttcatc tctacgcatg   1920

gtgcgcgtaa aggtcatggg agtaagacct acagtaagag gttctgtaat gaaccctaat   1980

gaccatccac acggtggtgg tgaaggtaga tctcctatcg gaaagtccac gtactccatg   2040

gggtaaacca gcacttggat acaaaacaag cgcagttcgg cggccagcgc ttcggtgaaa   2100
```

COMPOSITIONS FOR USE IN IDENTIFICATION OF BACTERIA

RELATED APPLICATIONS

This application is a continuation of U.S. application Ser. No. 11/409,535, filed Apr. 21, 2006, which is a continuation-in-part of U.S. application Ser. No. 11/060,135, filed Feb. 17, 2005 which claims the benefit of priority to U.S. Provisional Application Ser. No. 60/545,425 filed Feb. 18, 2004; U.S. Provisional Application Ser. No. 60/559,754, filed Apr. 5, 2004; U.S. Provisional Application Ser. No. 60/632,862, filed Dec. 3, 2004; U.S. Provisional Application Ser. No. 60/639,068, filed Dec. 22, 2004; and U.S. Provisional Application Ser. No. 60/648,188, filed Jan. 28, 2005. U.S. application Ser. No. 11/409,535 is a also continuation-in-part of U.S. application Ser. No. 10/728,486, filed Dec. 5, 2003 which claims the benefit of priority to U.S. Provisional Application Ser. No. 60/501,926, filed Sep. 11, 2003. U.S. application Ser. No. 11/409,535 also claims the benefit of priority to: U.S. Provisional Application Ser. No. 60/674,118, filed Apr. 21, 2005; U.S. Provisional Application Ser. No. 60/705,631, filed Aug. 3, 2005; U.S. Provisional Application Ser. No. 60/732,539, filed Nov. 1, 2005; and U.S. Provisional Application Ser. No. 60/773,124, filed Feb. 13, 2006. Each of the above-referenced U.S. Applications is incorporated herein by reference in its entirety. Methods disclosed in U.S. application Ser. Nos. 09/891,793, 10/156,608, 10/405,756, 10/418,514, 10/660,122, 10/660,996, 10/660,997, 10/660,998, 10/728,486, 11/060,135, and 11/073,362, are commonly owned and incorporated herein by reference in their entirety for any purpose.

SEQUENCE LISTING

The present application is being filed along with a Sequence Listing in electronic format. The Sequence Listing is provided as a file entitled DIBIS0083USC2SEQ.txt, created on Mar. 6, 2007 which is 252 Kb in size. The information in the electronic format of the sequence listing is incorporated herein by reference in its entirety.

STATEMENT OF GOVERNMENT SUPPORT

This invention was made with United States Government support under CDC contract RO1 CI000099-01. The United States Government has certain rights in the invention.

FIELD OF THE INVENTION

The present invention provides compositions, kits and methods for rapid identification and quantification of bacteria by molecular mass and base composition analysis.

BACKGROUND OF THE INVENTION

A problem in determining the cause of a natural infectious outbreak or a bioterrorist attack is the sheer variety of organisms that can cause human disease. There are over 1400 organisms infectious to humans; many of these have the potential to emerge suddenly in a natural epidemic or to be used in a malicious attack by bioterrorists (Taylor et al. Philos. Trans. R. Soc. London B. Biol. Sci., 2001, 356, 983-989). This number does not include numerous strain variants, bioengineered versions, or pathogens that infect plants or animals.

Much of the new technology being developed for detection of biological weapons incorporates a polymerase chain reaction (PCR) step based upon the use of highly specific primers and probes designed to selectively detect certain pathogenic organisms. Although this approach is appropriate for the most obvious bioterrorist organisms, like smallpox and anthrax, experience has shown that it is very difficult to predict which of hundreds of possible pathogenic organisms might be employed in a terrorist attack. Likewise, naturally emerging human disease that has caused devastating consequence in public health has come from unexpected families of bacteria, viruses, fungi, or protozoa. Plants and animals also have their natural burden of infectious disease agents and there are equally important biosafety and security concerns for agriculture.

A major conundrum in public health protection, biodefense, and agricultural safety and security is that these disciplines need to be able to rapidly identify and characterize infectious agents, while there is no existing technology with the breadth of function to meet this need. Currently used methods for identification of bacteria rely upon culturing the bacterium to effect isolation from other organisms and to obtain sufficient quantities of nucleic acid followed by sequencing of the nucleic acid, both processes which are time and labor intensive.

Mass spectrometry provides detailed information about the molecules being analyzed, including high mass accuracy. It is also a process that can be easily automated. DNA chips with specific probes can only determine the presence or absence of specifically anticipated organisms. Because there are hundreds of thousands of species of benign bacteria, some very similar in sequence to threat organisms, even arrays with 10,000 probes lack the breadth needed to identify a particular organism.

The present invention provides oligonucleotide primers and compositions and kits containing the oligonucleotide primers, which define bacterial bioagent identifying amplicons and, upon amplification, produce corresponding amplification products whose molecular masses provide the means to identify bacteria, for example, at and below the species taxonomic level.

SUMMARY OF THE INVENTION

The present invention provides compositions, kits and methods for rapid identification and quantification of bacteria by molecular mass and base composition analysis.

One embodiment is an oligonucleotide primer 14 to 35 nucleobases in length having at least 70% sequence identity with SEQ ID NO: 456.

Another embodiment is an oligonucleotide primer 14 to 35 nucleobases in length having at least 70% sequence identity with SEQ ID NO: 1261.

Another embodiment is an oligonucleotide primer pair including an oligonucleotide primer 14 to 35 nucleobases in length having at least 70% sequence identity with SEQ ID NO: 456 and an oligonucleotide primer 14 to 35 nucleobases in length having at least 70% sequence identity with SEQ ID NO: 1261.

One embodiment is an oligonucleotide primer 14 to 35 nucleobases in length having at least 70% sequence identity with SEQ ID NO: 288.

Another embodiment is an oligonucleotide primer 14 to 35 nucleobases in length having at least 70% sequence identity with SEQ ID NO: 1269.

Another embodiment is an oligonucleotide primer pair including an oligonucleotide primer 14 to 35 nucleobases in length having at least 70% sequence identity with SEQ ID NO: 288 and an oligonucleotide primer 14 to 35 nucleobases in length having at least 70% sequence identity with SEQ ID NO: 1269.

One embodiment is an oligonucleotide primer 14 to 35 nucleobases in length having at least 70% sequence identity with SEQ ID NO: 698.

Another embodiment is an oligonucleotide primer 14 to 35 nucleobases in length having at least 70% sequence identity with SEQ ID NO: 1420.

Another embodiment is an oligonucleotide primer pair including an oligonucleotide primer 14 to 35 nucleobases in length having at least 70% sequence identity with SEQ ID NO: 698 and an oligonucleotide primer 14 to 35 nucleobases in length having at least 70% sequence identity with SEQ ID NO: 1420.

One embodiment is an oligonucleotide primer 14 to 35 nucleobases in length having at least 70% sequence identity with SEQ ID NO: 217.

Another embodiment is an oligonucleotide primer 14 to 35 nucleobases in length having at least 70% sequence identity with SEQ ID NO: 1167

Another embodiment is an oligonucleotide primer pair including an oligonucleotide primer 14 to 35 nucleobases in length having at least 70% sequence identity with SEQ ID NO: 217 and an oligonucleotide primer 14 to 35 nucleobases in length having at least 70% sequence identity with SEQ ID NO: 1167.

One embodiment is an oligonucleotide primer 14 to 35 nucleobases in length having at least 70% sequence identity with SEQ ID NO: 399.

Another embodiment is an oligonucleotide primer 14 to 35 nucleobases in length having at least 70% sequence identity with SEQ ID NO: 1041.

Another embodiment is an oligonucleotide primer pair including an oligonucleotide primer 14 to 35 nucleobases in length having at least 70% sequence identity with SEQ ID NO: 399 and an oligonucleotide primer 14 to 35 nucleobases in length having at least 70% sequence identity with SEQ ID NO: 1041.

One embodiment is an oligonucleotide primer 14 to 35 nucleobases in length having at least 70% sequence identity with SEQ ID NO: 430.

Another embodiment is an oligonucleotide primer 14 to 35 nucleobases in length having at least 70% sequence identity with SEQ ID NO: 1321.

Another embodiment is an oligonucleotide primer pair including an oligonucleotide primer 14 to 35 nucleobases in length having at least 70% sequence identity with SEQ ID NO: 430 and an oligonucleotide primer 14 to 35 nucleobases in length having at least 70% sequence identity with SEQ ID NO: 1321.

One embodiment is an oligonucleotide primer 14 to 35 nucleobases in length having at least 70% sequence identity with SEQ ID NO: 174.

Another embodiment is an oligonucleotide primer 14 to 35 nucleobases in length having at least 70% sequence identity with SEQ ID NO: 853.

Another embodiment is an oligonucleotide primer pair including an oligonucleotide primer 14 to 35 nucleobases in length having at least 70% sequence identity with SEQ ID NO: 174 and an oligonucleotide primer 14 to 35 nucleobases in length having at least 70% sequence identity with SEQ ID NO: 853.

One embodiment is an oligonucleotide primer 14 to 35 nucleobases in length having at least 70% sequence identity with SEQ ID NO: 172.

Another embodiment is an oligonucleotide primer 14 to 35 nucleobases in length having at least 70% sequence identity with SEQ ID NO: 1360.

Another embodiment is an oligonucleotide primer pair including an oligonucleotide primer 14 to 35 nucleobases in length having at least 70% sequence identity with SEQ ID NO: 172 and an oligonucleotide primer 14 to 35 nucleobases in length having at least 70% sequence identity with SEQ ID NO: 1360.

Another embodiment is a kit comprising an oligonucleotide primer pair including an oligonucleotide primer 14 to 35 nucleobases in length having at least 70% sequence identity with SEQ ID NO: 456 and an oligonucleotide primer 14 to 35 nucleobases in length having at least 70% sequence identity with SEQ ID NO: 1261.

Another embodiment is a kit comprising an oligonucleotide primer pair including an oligonucleotide primer 14 to 35 nucleobases in length having at least 70% sequence identity with SEQ ID NO: 456 and an oligonucleotide primer 14 to 35 nucleobases in length having at least 70% sequence identity with SEQ ID NO: 1261 and further comprising one or more primer pairs wherein each member of said one or more primer pairs is of a length of 14 to 35 nucleobases and has 70% to 100% sequence identity with the corresponding member from the group of primer pairs represented by SEQ ID NOs: 288:1269, 698:1420, 217:1167, 399:1041, 430:1321, 174:853, and 172:1360.

One embodiment is an oligonucleotide primer 14 to 35 nucleobases in length having at least 70% sequence identity with SEQ ID NO: 681.

Another embodiment is an oligonucleotide primer 14 to 35 nucleobases in length having at least 70% sequence identity with SEQ ID NO: 1022.

Another embodiment is an oligonucleotide primer pair including an oligonucleotide primer 14 to 35 nucleobases in length having at least 70% sequence identity with SEQ ID NO: 681 and an oligonucleotide primer 14 to 35 nucleobases in length having at least 70% sequence identity with SEQ ID NO: 1022.

One embodiment is an oligonucleotide primer 14 to 35 nucleobases in length having at least 70% sequence identity with SEQ ID NO: 315.

Another embodiment is an oligonucleotide primer 14 to 35 nucleobases in length having at least 70% sequence identity with SEQ ID NO: 1379.

Another embodiment is an oligonucleotide primer pair including an oligonucleotide primer 14 to 35 nucleobases in length having at least 70% sequence identity with SEQ ID NO: 315 and an oligonucleotide primer 14 to 35 nucleobases in length having at least 70% sequence identity with SEQ ID NO: 1379.

One embodiment is an oligonucleotide primer 14 to 35 nucleobases in length having at least 70% sequence identity with SEQ ID NO: 346.

Another embodiment is an oligonucleotide primer 14 to 35 nucleobases in length having at least 70% sequence identity with SEQ ID NO: 955.

Another embodiment is an oligonucleotide primer pair including an oligonucleotide primer 14 to 35 nucleobases in length having at least 70% sequence identity with SEQ ID NO: 346 and an oligonucleotide primer 14 to 35 nucleobases in length having at least 70% sequence identity with SEQ ID NO: 955.

One embodiment is an oligonucleotide primer 14 to 35 nucleobases in length having at least 70% sequence identity with SEQ ID NO: 504.

Another embodiment is an oligonucleotide primer 14 to 35 nucleobases in length having at least 70% sequence identity with SEQ ID NO: 1409.

Another embodiment is an oligonucleotide primer pair including an oligonucleotide primer 14 to 35 nucleobases in length having at least 70% sequence identity with SEQ ID NO: 504 and an oligonucleotide primer 14 to 35 nucleobases in length having at least 70% sequence identity with SEQ ID NO: 1409.

One embodiment is an oligonucleotide primer 14 to 35 nucleobases in length having at least 70% sequence identity with SEQ ID NO: 323.

Another embodiment is an oligonucleotide primer 14 to 35 nucleobases in length having at least 70% sequence identity with SEQ ID NO: 1068.

Another embodiment is an oligonucleotide primer pair including an oligonucleotide primer 14 to 35 nucleobases in length having at least 70% sequence identity with SEQ ID NO: 323 and an oligonucleotide primer 14 to 35 nucleobases in length having at least 70% sequence identity with SEQ ID NO: 1068.

One embodiment is an oligonucleotide primer 14 to 35 nucleobases in length having at least 70% sequence identity with SEQ ID NO: 479.

Another embodiment is an oligonucleotide primer 14 to 35 nucleobases in length having at least 70% sequence identity with SEQ ID NO: 938.

Another embodiment is an oligonucleotide primer pair including an oligonucleotide primer 14 to 35 nucleobases in length having at least 70% sequence identity with SEQ ID NO: 479 and an oligonucleotide primer 14 to 35 nucleobases in length having at least 70% sequence identity with SEQ ID NO: 938.

Another embodiment is a kit comprising an oligonucleotide primer pair including an oligonucleotide primer 14 to 35 nucleobases in length having at least 70% sequence identity with SEQ ID NO: 681 and an oligonucleotide primer 14 to 35 nucleobases in length having at least 70% sequence identity with SEQ ID NO: 1022.

Another embodiment is a kit comprising an oligonucleotide primer pair including an oligonucleotide primer 14 to 35 nucleobases in length having at least 70% sequence identity with SEQ ID NO: 681 and an oligonucleotide primer 14 to 35 nucleobases in length having at least 70% sequence identity with SEQ ID NO: 1022 and further comprising one or more primer pairs wherein each member of said one or more primer pairs is of a length of 14 to 35 nucleobases and has 70% to 100% sequence identity with the corresponding member from the group of primer pairs represented by SEQ ID NOs: 315:1379, 346:955, 504:1409, 323:1068, 479:938.

One embodiment is an oligonucleotide primer 14 to 35 nucleobases in length having at least 70% sequence identity with SEQ ID NO: 583.

Another embodiment is an oligonucleotide primer 14 to 35 nucleobases in length having at least 70% sequence identity with SEQ ID NO: 923.

Another embodiment is a kit comprising an oligonucleotide primer pair including an oligonucleotide primer 14 to 35 nucleobases in length having at least 70% sequence identity with SEQ ID NO: 583 and an oligonucleotide primer 14 to 35 nucleobases in length having at least 70% sequence identity with SEQ ID NO: 923.

One embodiment is an oligonucleotide primer 14 to 35 nucleobases in length having at least 70% sequence identity with SEQ ID NO: 454.

Another embodiment is an oligonucleotide primer 14 to 35 nucleobases in length having at least 70% sequence identity with SEQ ID NO: 1418.

Another embodiment is a kit comprising an oligonucleotide primer pair including an oligonucleotide primer 14 to 35 nucleobases in length having at least 70% sequence identity with SEQ ID NO: 454 and an oligonucleotide primer 14 to 35 nucleobases in length having at least 70% sequence identity with SEQ ID NO: 1418.

One embodiment is an oligonucleotide primer 14 to 35 nucleobases in length having at least 70% sequence identity with SEQ ID NO: 250.

Another embodiment is an oligonucleotide primer 14 to 35 nucleobases in length having at least 70% sequence identity with SEQ ID NO: 902.

Another embodiment is a kit comprising an oligonucleotide primer pair including an oligonucleotide primer 14 to 35 nucleobases in length having at least 70% sequence identity with SEQ ID NO: 250 and an oligonucleotide primer 14 to 35 nucleobases in length having at least 70% sequence identity with SEQ ID NO: 902.

One embodiment is an oligonucleotide primer 14 to 35 nucleobases in length having at least 70% sequence identity with SEQ ID NO: 384.

Another embodiment is an oligonucleotide primer 14 to 35 nucleobases in length having at least 70% sequence identity with SEQ ID NO: 878.

Another embodiment is a kit comprising an oligonucleotide primer pair including an oligonucleotide primer 14 to 35 nucleobases in length having at least 70% sequence identity with SEQ ID NO: 384 and an oligonucleotide primer 14 to 35 nucleobases in length having at least 70% sequence identity with SEQ ID NO: 878.

One embodiment is an oligonucleotide primer 14 to 35 nucleobases in length having at least 70% sequence identity with SEQ ID NO: 694.

Another embodiment is an oligonucleotide primer 14 to 35 nucleobases in length having at least 70% sequence identity with SEQ ID NO: 1215.

Another embodiment is a kit comprising an oligonucleotide primer pair including an oligonucleotide primer 14 to 35 nucleobases in length having at least 70% sequence identity with SEQ ID NO: 694 and an oligonucleotide primer 14 to 35 nucleobases in length having at least 70% sequence identity with SEQ ID NO: 1215.

One embodiment is an oligonucleotide primer 14 to 35 nucleobases in length having at least 70% sequence identity with SEQ ID NO: 194.

Another embodiment is an oligonucleotide primer 14 to 35 nucleobases in length having at least 70% sequence identity with SEQ ID NO: 1173.

Another embodiment is a kit comprising an oligonucleotide primer pair including an oligonucleotide primer 14 to 35 nucleobases in length having at least 70% sequence identity with SEQ ID NO: 194 and an oligonucleotide primer 14 to 35 nucleobases in length having at least 70% sequence identity with SEQ ID NO: 1173.

One embodiment is an oligonucleotide primer 14 to 35 nucleobases in length having at least 70% sequence identity with SEQ ID NO: 375.

Another embodiment is an oligonucleotide primer 14 to 35 nucleobases in length having at least 70% sequence identity with SEQ ID NO: 890.

Another embodiment is a kit comprising an oligonucleotide primer pair including an oligonucleotide primer 14 to 35 nucleobases in length having at least 70% sequence identity with SEQ ID NO: 375 and an oligonucleotide primer 14 to 35 nucleobases in length having at least 70% sequence identity with SEQ ID NO: 890.

One embodiment is an oligonucleotide primer 14 to 35 nucleobases in length having at least 70% sequence identity with SEQ ID NO: 656.

Another embodiment is an oligonucleotide primer 14 to 35 nucleobases in length having at least 70% sequence identity with SEQ ID NO: 1224.

Another embodiment is a kit comprising an oligonucleotide primer pair including an oligonucleotide primer 14 to 35 nucleobases in length having at least 70% sequence identity with SEQ ID NO: 656 and an oligonucleotide primer 14 to 35 nucleobases in length having at least 70% sequence identity with SEQ ID NO: 1224.

One embodiment is an oligonucleotide primer 14 to 35 nucleobases in length having at least 70% sequence identity with SEQ ID NO: 618.

Another embodiment is an oligonucleotide primer 14 to 35 nucleobases in length having at least 70% sequence identity with SEQ ID NO: 1157.

Another embodiment is a kit comprising an oligonucleotide primer pair including an oligonucleotide primer 14 to 35 nucleobases in length having at least 70% sequence identity with SEQ ID NO: 618 and an oligonucleotide primer 14 to 35 nucleobases in length having at least 70% sequence identity with SEQ ID NO: 1157.

One embodiment is an oligonucleotide primer 14 to 35 nucleobases in length having at least 70% sequence identity with SEQ ID NO: 302.

Another embodiment is an oligonucleotide primer 14 to 35 nucleobases in length having at least 70% sequence identity with SEQ ID NO: 852.

Another embodiment is a kit comprising an oligonucleotide primer pair including an oligonucleotide primer 14 to 35 nucleobases in length having at least 70% sequence identity with SEQ ID NO: 302 and an oligonucleotide primer 14 to 35 nucleobases in length having at least 70% sequence identity with SEQ ID NO: 852.

One embodiment is an oligonucleotide primer 14 to 35 nucleobases in length having at least 70% sequence identity with SEQ ID NO: 199.

Another embodiment is an oligonucleotide primer 14 to 35 nucleobases in length having at least 70% sequence identity with SEQ ID NO: 889.

Another embodiment is a kit comprising an oligonucleotide primer pair including an oligonucleotide primer 14 to 35 nucleobases in length having at least 70% sequence identity with SEQ ID NO: 199 and an oligonucleotide primer 14 to 35 nucleobases in length having at least 70% sequence identity with SEQ ID NO: 889.

One embodiment is an oligonucleotide primer 14 to 35 nucleobases in length having at least 70% sequence identity with SEQ ID NO: 596.

Another embodiment is an oligonucleotide primer 14 to 35 nucleobases in length having at least 70% sequence identity with SEQ ID NO: 1169.

Another embodiment is a kit comprising an oligonucleotide primer pair including an oligonucleotide primer 14 to 35 nucleobases in length having at least 70% sequence identity with SEQ ID NO: 596 and an oligonucleotide primer 14 to 35 nucleobases in length having at least 70% sequence identity with SEQ ID NO: 1169.

One embodiment is an oligonucleotide primer 14 to 35 nucleobases in length having at least 70% sequence identity with SEQ ID NO: 150.

Another embodiment is an oligonucleotide primer 14 to 35 nucleobases in length having at least 70% sequence identity with SEQ ID NO: 1242.

Another embodiment is a kit comprising an oligonucleotide primer pair including an oligonucleotide primer 14 to 35 nucleobases in length having at least 70% sequence identity with SEQ ID NO: 150 and an oligonucleotide primer 14 to 35 nucleobases in length having at least 70% sequence identity with SEQ ID NO: 1242.

One embodiment is an oligonucleotide primer 14 to 35 nucleobases in length having at least 70% sequence identity with SEQ ID NO: 166.

Another embodiment is an oligonucleotide primer 14 to 35 nucleobases in length having at least 70% sequence identity with SEQ ID NO: 1069.

Another embodiment is a kit comprising an oligonucleotide primer pair including an oligonucleotide primer 14 to 35 nucleobases in length having at least 70% sequence identity with SEQ ID NO: 166 and an oligonucleotide primer 14 to 35 nucleobases in length having at least 70% sequence identity with SEQ ID NO: 1069.

One embodiment is an oligonucleotide primer 14 to 35 nucleobases in length having at least 70% sequence identity with SEQ ID NO: 166.

Another embodiment is an oligonucleotide primer 14 to 35 nucleobases in length having at least 70% sequence identity with SEQ ID NO: 1168.

Another embodiment is a kit comprising an oligonucleotide primer pair including an oligonucleotide primer 14 to 35 nucleobases in length having at least 70% sequence identity with SEQ ID NO: 166 and an oligonucleotide primer 14 to 35 nucleobases in length having at least 70% sequence identity with SEQ ID NO: 1168.

Another embodiment is a kit comprising an oligonucleotide primer pair including an oligonucleotide primer 14 to 35 nucleobases in length having at least 70% sequence identity with SEQ ID NO: 583 and an oligonucleotide primer 14 to 35 nucleobases in length having at least 70% sequence identity with SEQ ID NO: 923 and further comprising one or more primer pairs wherein each member of said one or more primer pairs is of a length of 14 to 35 nucleobases and has 70% to 100% sequence identity with the corresponding member from the group of primer pairs represented by SEQ ID NOs: 454:1418, 250:902, 384:878, 694:1215, 194:1173, 375:890, 656:1224, 618:1157, 302:852, 199:889, 596:1169, 150:1242, 166:1069 and 166:1168.

One embodiment is an oligonucleotide primer 14 to 35 nucleobases in length having at least 70% sequence identity with SEQ ID NO: 437.

Another embodiment is an oligonucleotide primer 14 to 35 nucleobases in length having at least 70% sequence identity with SEQ ID NO: 1137.

Another embodiment is a kit comprising an oligonucleotide primer pair including an oligonucleotide primer 14 to 35 nucleobases in length having at least 70% sequence identity with SEQ ID NO: 437 and an oligonucleotide primer 14 to 35 nucleobases in length having at least 70% sequence identity with SEQ ID NO: 1137.

One embodiment is an oligonucleotide primer 14 to 35 nucleobases in length having at least 70% sequence identity with SEQ ID NO: 530.

Another embodiment is an oligonucleotide primer 14 to 35 nucleobases in length having at least 70% sequence identity with SEQ ID NO: 891.

Another embodiment is a kit comprising an oligonucleotide primer pair including an oligonucleotide primer 14 to 35 nucleobases in length having at least 70% sequence identity with SEQ ID NO: 530 and an oligonucleotide primer 14 to 35 nucleobases in length having at least 70% sequence identity with SEQ ID NO: 891.

One embodiment is an oligonucleotide primer 14 to 35 nucleobases in length having at least 70% sequence identity with SEQ ID NO: 474.

Another embodiment is an oligonucleotide primer 14 to 35 nucleobases in length having at least 70% sequence identity with SEQ ID NO: 869.

Another embodiment is a kit comprising an oligonucleotide primer pair including an oligonucleotide primer 14 to 35 nucleobases in length having at least 70% sequence identity with SEQ ID NO: 474 and an oligonucleotide primer 14 to 35 nucleobases in length having at least 70% sequence identity with SEQ ID NO: 869.

One embodiment is an oligonucleotide primer 14 to 35 nucleobases in length having at least 70% sequence identity with SEQ ID NO: 268.

Another embodiment is an oligonucleotide primer 14 to 35 nucleobases in length having at least 70% sequence identity with SEQ ID NO: 1284.

Another embodiment is a kit comprising an oligonucleotide primer pair including an oligonucleotide primer 14 to 35 nucleobases in length having at least 70% sequence identity with SEQ ID NO: 268 and an oligonucleotide primer 14 to 35 nucleobases in length having at least 70% sequence identity with SEQ ID NO: 1284.

One embodiment is an oligonucleotide primer 14 to 35 nucleobases in length having at least 70% sequence identity with SEQ ID NO: 418.

Another embodiment is an oligonucleotide primer 14 to 35 nucleobases in length having at least 70% sequence identity with SEQ ID NO: 1301.

Another embodiment is a kit comprising an oligonucleotide primer pair including an oligonucleotide primer 14 to 35 nucleobases in length having at least 70% sequence identity with SEQ ID NO: 418 and an oligonucleotide primer 14 to 35 nucleobases in length having at least 70% sequence identity with SEQ ID NO: 1301.

One embodiment is an oligonucleotide primer 14 to 35 nucleobases in length having at least 70% sequence identity with SEQ ID NO: 318.

Another embodiment is an oligonucleotide primer 14 to 35 nucleobases in length having at least 70% sequence identity with SEQ ID NO: 1300.

Another embodiment is a kit comprising an oligonucleotide primer pair including an oligonucleotide primer 14 to 35 nucleobases in length having at least 70% sequence identity with SEQ ID NO: 318 and an oligonucleotide primer 14 to 35 nucleobases in length having at least 70% sequence identity with SEQ ID NO: 1300.

One embodiment is an oligonucleotide primer 14 to 35 nucleobases in length having at least 70% sequence identity with SEQ ID NO: 440.

Another embodiment is an oligonucleotide primer 14 to 35 nucleobases in length having at least 70% sequence identity with SEQ ID NO: 1076.

Another embodiment is a kit comprising an oligonucleotide primer pair including an oligonucleotide primer 14 to 35 nucleobases in length having at least 70% sequence identity with SEQ ID NO: 440 and an oligonucleotide primer 14 to 35 nucleobases in length having at least 70% sequence identity with SEQ ID NO: 1076.

One embodiment is an oligonucleotide primer 14 to 35 nucleobases in length having at least 70% sequence identity with SEQ ID NO: 219.

Another embodiment is an oligonucleotide primer 14 to 35 nucleobases in length having at least 70% sequence identity with SEQ ID NO: 1013.

Another embodiment is a kit comprising an oligonucleotide primer pair including an oligonucleotide primer 14 to 35 nucleobases in length having at least 70% sequence identity with SEQ ID NO: 219 and an oligonucleotide primer 14 to 35 nucleobases in length having at least 70% sequence identity with SEQ ID NO: 1013.

Another embodiment is a kit comprising an oligonucleotide primer pair including an oligonucleotide primer 14 to 35 nucleobases in length having at least 70% sequence identity with SEQ ID NO: 437 and an oligonucleotide primer 14 to 35 nucleobases in length having at least 70% sequence identity with SEQ ID NO: 1137 and further comprising one or more primer pairs wherein each member of said one or more primer pairs is of a length of 14 to 35 nucleobases and has 70% to 100% sequence identity with the corresponding member from the group of primer pairs represented by SEQ ID NOs: 530:891, 474:869, 268:1284, 418:1301, 318:1300, 440:1076 and 219:1013.

One embodiment is an oligonucleotide primer 14 to 35 nucleobases in length having at least 70% sequence identity with SEQ ID NO: 325.

Another embodiment is an oligonucleotide primer 14 to 35 nucleobases in length having at least 70% sequence identity with SEQ ID NO: 1163.

Another embodiment is a kit comprising an oligonucleotide primer pair including an oligonucleotide primer 14 to 35 nucleobases in length having at least 70% sequence identity with SEQ ID NO: 325 and an oligonucleotide primer 14 to 35 nucleobases in length having at least 70% sequence identity with SEQ ID NO: 1163.

One embodiment is an oligonucleotide primer 14 to 35 nucleobases in length having at least 70% sequence identity with SEQ ID NO: 278.

Another embodiment is an oligonucleotide primer 14 to 35 nucleobases in length having at least 70% sequence identity with SEQ ID NO: 1039.

Another embodiment is a kit comprising an oligonucleotide primer pair including an oligonucleotide primer 14 to 35 nucleobases in length having at least 70% sequence identity with SEQ ID NO: 278 and an oligonucleotide primer 14 to 35 nucleobases in length having at least 70% sequence identity with SEQ ID NO: 1039.

One embodiment is an oligonucleotide primer 14 to 35 nucleobases in length having at least 70% sequence identity with SEQ ID NO: 465.

Another embodiment is an oligonucleotide primer 14 to 35 nucleobases in length having at least 70% sequence identity with SEQ ID NO: 1037.

Another embodiment is a kit comprising an oligonucleotide primer pair including an oligonucleotide primer 14 to 35 nucleobases in length having at least 70% sequence identity with SEQ ID NO: 465 and an oligonucleotide primer 14 to 35 nucleobases in length having at least 70% sequence identity with SEQ ID NO: 1037.

One embodiment is an oligonucleotide primer 14 to 35 nucleobases in length having at least 70% sequence identity with SEQ ID NO: 148.

Another embodiment is an oligonucleotide primer 14 to 35 nucleobases in length having at least 70% sequence identity with SEQ ID NO: 1172.

Another embodiment is a kit comprising an oligonucleotide primer pair including an oligonucleotide primer 14 to 35 nucleobases in length having at least 70% sequence identity with SEQ ID NO: 148 and an oligonucleotide primer 14 to 35 nucleobases in length having at least 70% sequence identity with SEQ ID NO: 1172.

One embodiment is an oligonucleotide primer 14 to 35 nucleobases in length having at least 70% sequence identity with SEQ ID NO: 190.

Another embodiment is an oligonucleotide primer 14 to 35 nucleobases in length having at least 70% sequence identity with SEQ ID NO: 1254.

Another embodiment is a kit comprising an oligonucleotide primer pair including an oligonucleotide primer 14 to 35 nucleobases in length having at least 70% sequence identity with SEQ ID NO: 190 and an oligonucleotide primer 14 to 35 nucleobases in length having at least 70% sequence identity with SEQ ID NO: 1254.

One embodiment is an oligonucleotide primer 14 to 35 nucleobases in length having at least 70% sequence identity with SEQ ID NO: 266.

Another embodiment is an oligonucleotide primer 14 to 35 nucleobases in length having at least 70% sequence identity with SEQ ID NO: 1094.

Another embodiment is a kit comprising an oligonucleotide primer pair including an oligonucleotide primer 14 to 35 nucleobases in length having at least 70% sequence identity with SEQ ID NO: 266 and an oligonucleotide primer 14 to 35 nucleobases in length having at least 70% sequence identity with SEQ ID NO: 1094.

One embodiment is an oligonucleotide primer 14 to 35 nucleobases in length having at least 70% sequence identity with SEQ ID NO: 508.

Another embodiment is an oligonucleotide primer 14 to 35 nucleobases in length having at least 70% sequence identity with SEQ ID NO: 1297.

Another embodiment is a kit comprising an oligonucleotide primer pair including an oligonucleotide primer 14 to 35 nucleobases in length having at least 70% sequence identity with SEQ ID NO: 508 and an oligonucleotide primer 14 to 35 nucleobases in length having at least 70% sequence identity with SEQ ID NO: 1297.

One embodiment is an oligonucleotide primer 14 to 35 nucleobases in length having at least 70% sequence identity with SEQ ID NO: 259.

Another embodiment is an oligonucleotide primer 14 to 35 nucleobases in length having at least 70% sequence identity with SEQ ID NO: 1060.

Another embodiment is a kit comprising an oligonucleotide primer pair including an oligonucleotide primer 14 to 35 nucleobases in length having at least 70% sequence identity with SEQ ID NO: 259 and an oligonucleotide primer 14 to 35 nucleobases in length having at least 70% sequence identity with SEQ ID NO: 1060.

Another embodiment is a kit comprising an oligonucleotide primer pair including an oligonucleotide primer 14 to 35 nucleobases in length having at least 70% sequence identity with SEQ ID NO: 325 and an oligonucleotide primer 14 to 35 nucleobases in length having at least 70% sequence identity with SEQ ID NO: 1163 and further comprising one or more primer pairs wherein each member of said one or more primer pairs is of a length of 14 to 35 nucleobases and has 70% to 100% sequence identity with the corresponding member from the group of primer pairs represented by SEQ ID NOs: 278:1039: 465:1037, 148:1172, 190:1254, 266:1094, 508:1297 and 259:1060.

One embodiment is an oligonucleotide primer 14 to 35 nucleobases in length having at least 70% sequence identity with SEQ ID NO: 376.

Another embodiment is an oligonucleotide primer 14 to 35 nucleobases in length having at least 70% sequence identity with SEQ ID NO: 1265.

Another embodiment is a kit comprising an oligonucleotide primer pair including an oligonucleotide primer 14 to 35 nucleobases in length having at least 70% sequence identity with SEQ ID NO: 376 and an oligonucleotide primer 14 to 35 nucleobases in length having at least 70% sequence identity with SEQ ID NO: 1265.

One embodiment is an oligonucleotide primer 14 to 35 nucleobases in length having at least 70% sequence identity with SEQ ID NO: 267.

Another embodiment is an oligonucleotide primer 14 to 35 nucleobases in length having at least 70% sequence identity with SEQ ID NO: 1341.

Another embodiment is a kit comprising an oligonucleotide primer pair including an oligonucleotide primer 14 to 35 nucleobases in length having at least 70% sequence identity with SEQ ID NO: 267 and an oligonucleotide primer 14 to 35 nucleobases in length having at least 70% sequence identity with SEQ ID NO: 1341.

One embodiment is an oligonucleotide primer 14 to 35 nucleobases in length having at least 70% sequence identity with SEQ ID NO: 705.

Another embodiment is an oligonucleotide primer 14 to 35 nucleobases in length having at least 70% sequence identity with SEQ ID NO: 1056.

Another embodiment is a kit comprising an oligonucleotide primer pair including an oligonucleotide primer 14 to 35 nucleobases in length having at least 70% sequence identity with SEQ ID NO: 705 and an oligonucleotide primer 14 to 35 nucleobases in length having at least 70% sequence identity with SEQ ID NO: 1056.

One embodiment is an oligonucleotide primer 14 to 35 nucleobases in length having at least 70% sequence identity with SEQ ID NO: 710.

Another embodiment is an oligonucleotide primer 14 to 35 nucleobases in length having at least 70% sequence identity with SEQ ID NO: 1259.

Another embodiment is a kit comprising an oligonucleotide primer pair including an oligonucleotide primer 14 to 35 nucleobases in length having at least 70% sequence identity with SEQ ID NO: 710 and an oligonucleotide primer 14 to 35 nucleobases in length having at least 70% sequence identity with SEQ ID NO: 1259.

One embodiment is an oligonucleotide primer 14 to 35 nucleobases in length having at least 70% sequence identity with SEQ ID NO: 374.

Another embodiment is an oligonucleotide primer 14 to 35 nucleobases in length having at least 70% sequence identity with SEQ ID NO: 1111.

Another embodiment is a kit comprising an oligonucleotide primer pair including an oligonucleotide primer 14 to 35 nucleobases in length having at least 70% sequence identity with SEQ ID NO: 374 and an oligonucleotide primer 14 to 35 nucleobases in length having at least 70% sequence identity with SEQ ID NO: 1111.

One embodiment is an oligonucleotide primer 14 to 35 nucleobases in length having at least 70% sequence identity with SEQ ID NO: 545.

Another embodiment is an oligonucleotide primer 14 to 35 nucleobases in length having at least 70% sequence identity with SEQ ID NO: 978.

Another embodiment is a kit comprising an oligonucleotide primer pair including an oligonucleotide primer 14 to 35 nucleobases in length having at least 70% sequence identity with SEQ ID NO: 545 and an oligonucleotide primer 14 to 35 nucleobases in length having at least 70% sequence identity with SEQ ID NO: 978.

One embodiment is an oligonucleotide primer 14 to 35 nucleobases in length having at least 70% sequence identity with SEQ ID NO: 249.

Another embodiment is an oligonucleotide primer 14 to 35 nucleobases in length having at least 70% sequence identity with SEQ ID NO: 1095.

Another embodiment is a kit comprising an oligonucleotide primer pair including an oligonucleotide primer 14 to 35 nucleobases in length having at least 70% sequence identity with SEQ ID NO: 249 and an oligonucleotide primer 14 to 35 nucleobases in length having at least 70% sequence identity with SEQ ID NO: 1095.

One embodiment is an oligonucleotide primer 14 to 35 nucleobases in length having at least 70% sequence identity with SEQ ID NO: 195.

Another embodiment is an oligonucleotide primer 14 to 35 nucleobases in length having at least 70% sequence identity with SEQ ID NO: 1376.

Another embodiment is a kit comprising an oligonucleotide primer pair including an oligonucleotide primer 14 to 35 nucleobases in length having at least 70% sequence identity with SEQ ID NO: 195 and an oligonucleotide primer 14 to 35 nucleobases in length having at least 70% sequence identity with SEQ ID NO: 1376.

One embodiment is an oligonucleotide primer 14 to 35 nucleobases in length having at least 70% sequence identity with SEQ ID NO: 311.

Another embodiment is an oligonucleotide primer 14 to 35 nucleobases in length having at least 70% sequence identity with SEQ ID NO: 1014.

Another embodiment is a kit comprising an oligonucleotide primer pair including an oligonucleotide primer 14 to 35 nucleobases in length having at least 70% sequence identity with SEQ ID NO: 311 and an oligonucleotide primer 14 to 35 nucleobases in length having at least 70% sequence identity with SEQ ID NO: 1014.

One embodiment is an oligonucleotide primer 14 to 35 nucleobases in length having at least 70% sequence identity with SEQ ID NO: 365.

Another embodiment is an oligonucleotide primer 14 to 35 nucleobases in length having at least 70% sequence identity with SEQ ID NO: 1052.

Another embodiment is a kit comprising an oligonucleotide primer pair including an oligonucleotide primer 14 to 35 nucleobases in length having at least 70% sequence identity with SEQ ID NO: 365 and an oligonucleotide primer 14 to 35 nucleobases in length having at least 70% sequence identity with SEQ ID NO: 1052.

One embodiment is an oligonucleotide primer 14 to 35 nucleobases in length having at least 70% sequence identity with SEQ ID NO: 527.

Another embodiment is an oligonucleotide primer 14 to 35 nucleobases in length having at least 70% sequence identity with SEQ ID NO: 1071.

Another embodiment is a kit comprising an oligonucleotide primer pair including an oligonucleotide primer 14 to 35 nucleobases in length having at least 70% sequence identity with SEQ ID NO: 527 and an oligonucleotide primer 14 to 35 nucleobases in length having at least 70% sequence identity with SEQ ID NO: 1071.

One embodiment is an oligonucleotide primer 14 to 35 nucleobases in length having at least 70% sequence identity with SEQ ID NO: 490.

Another embodiment is an oligonucleotide primer 14 to 35 nucleobases in length having at least 70% sequence identity with SEQ ID NO: 1182.

Another embodiment is a kit comprising an oligonucleotide primer pair including an oligonucleotide primer 14 to 35 nucleobases in length having at least 70% sequence identity with SEQ ID NO: 490 and an oligonucleotide primer 14 to 35 nucleobases in length having at least 70% sequence identity with SEQ ID NO: 1182.

Another embodiment is a kit comprising an oligonucleotide primer pair including an oligonucleotide primer 14 to 35 nucleobases in length having at least 70% sequence identity with SEQ ID NO: 376 and an oligonucleotide primer 14 to 35 nucleobases in length having at least 70% sequence identity with SEQ ID NO: 1265 and further comprising one or more primer pairs wherein each member of said one or more primer pairs is of a length of 14 to 35 nucleobases and has 70% to 100% sequence identity with the corresponding member from the group of primer pairs represented by SEQ ID NOs: 267:1341, 705:1056, 710:1259, 374:1111, 545:978, 249:1095, 195:1376, 311:1014, 365:1052, 527:1071 and 490:1182.

In some embodiments, either or both of the primers of a primer pair composition contain at least one modified nucleobase such as 5-propynyluracil or 5-propynylcytosine for example.

In some embodiments, either or both of the primers of the primer pair comprises at least one universal nucleobase such as inosine for example.

In some embodiments, either or both of the primers of the primer pair comprises at least one non-templated T residue on the 5'-end.

In some embodiments, either or both of the primers of the primer pair comprises at least one non-template tag.

In some embodiments, either or both of the primers of the primer pair comprises at least one molecular mass modifying tag.

In some embodiments, the present invention provides primers and compositions comprising pairs of primers, and kits containing the same, and methods for use in identification of bacteria. The primers are designed to produce amplification products of DNA encoding genes that have conserved and variable regions across different subgroups and genotypes of bacteria.

Some embodiments are kits that contain one or more of the primer pair compositions. In some embodiments, each member of the one or more primer pairs of the kit is of a length of 14 to 35 nucleobases and has 70% to 100% sequence identity with the corresponding member from any of the primer pairs listed in Table 2.

Some embodiments of the kits contain at least one calibration polynucleotide for use in quantitation of bacteria in a given sample, and also for use as a positive control for amplification.

Some embodiments of the kits contain at least one anion exchange functional group linked to a magnetic bead.

In some embodiments, the present invention also provides methods for identification of bacteria. Nucleic acid from the bacterium is amplified using the primers described above to obtain an amplification product. The molecular mass of the amplification product is measured. Optionally, the base composition of the amplification product is determined from the molecular mass. The molecular mass or base composition is compared with a plurality of molecular masses or base compositions of known analogous bacterial identifying amplicons, wherein a match between the molecular mass or base composition and a member of the plurality of molecular masses or base compositions identifies the bacterium. In some embodiments, the molecular mass is measured by mass spectrometry in a modality such as electrospray ionization (ESI) time of flight (TOF) mass spectrometry or ESI Fourier transform ion cyclotron resonance (FTICR) mass spectrometry, for example. Other mass spectrometry techniques can also be used to measure the molecular mass of bacterial bioagent identifying amplicons.

In some embodiments, the present invention is also directed to a method for determining the presence or absence of a bacterium in a sample. Nucleic acid from the sample is amplified using the composition described above to obtain an amplification product. The molecular mass of the amplification product is determined. Optionally, the base composition of the amplification product is determined from the molecular mass. The molecular mass or base composition of the amplification product is compared with the known molecular masses or base compositions of one or more known analogous bacterial bioagent identifying amplicons, wherein a match between the molecular mass or base composition of the amplification product and the molecular mass or base composition of one or more known bacterial bioagent identifying amplicons indicates the presence of the bacterium in the sample. In some embodiments, the molecular mass is measured by mass spectrometry.

In some embodiments, the present invention also provides methods for determination of the quantity of an unknown bacterium in a sample. The sample is contacted with the composition described above and a known quantity of a calibration polynucleotide comprising a calibration sequence. Nucleic acid from the unknown bacterium in the sample is concurrently amplified with the composition described above and nucleic acid from the calibration polynucleotide in the sample is concurrently amplified with the composition described above to obtain a first amplification product comprising a bacterial bioagent identifying amplicon and a second amplification product comprising a calibration amplicon. The molecular masses and abundances for the bacterial bioagent identifying amplicon and the calibration amplicon are determined. The bacterial bioagent identifying amplicon is distinguished from the calibration amplicon based on molecular mass and comparison of bacterial bioagent identifying amplicon abundance and calibration amplicon abundance indicates the quantity of bacterium in the sample. In some embodiments, the base composition of the bacterial bioagent identifying amplicon is determined.

In some embodiments, the present invention provides methods for detecting or quantifying bacteria by combining a nucleic acid amplification process with a mass determination process. In some embodiments, such methods identify or otherwise analyze the bacterium by comparing mass information from an amplification product with a calibration or control product. Such methods can be carried out in a highly multiplexed and/or parallel manner allowing for the analysis of as many as 300 samples per 24 hours on a single mass measurement platform. The accuracy of the mass determination methods in some embodiments of the present invention permits allows for the ability to discriminate between different bacteria such as, for example, various genotypes and drug resistant strains of *Staphylococcus aureus.*

BRIEF DESCRIPTION OF THE DRAWINGS

The foregoing summary of the invention, as well as the following detailed description of the invention, is better understood when read in conjunction with the accompanying drawings which are included by way of example and not by way of limitation.

DEFINITIONS

Figure 1:
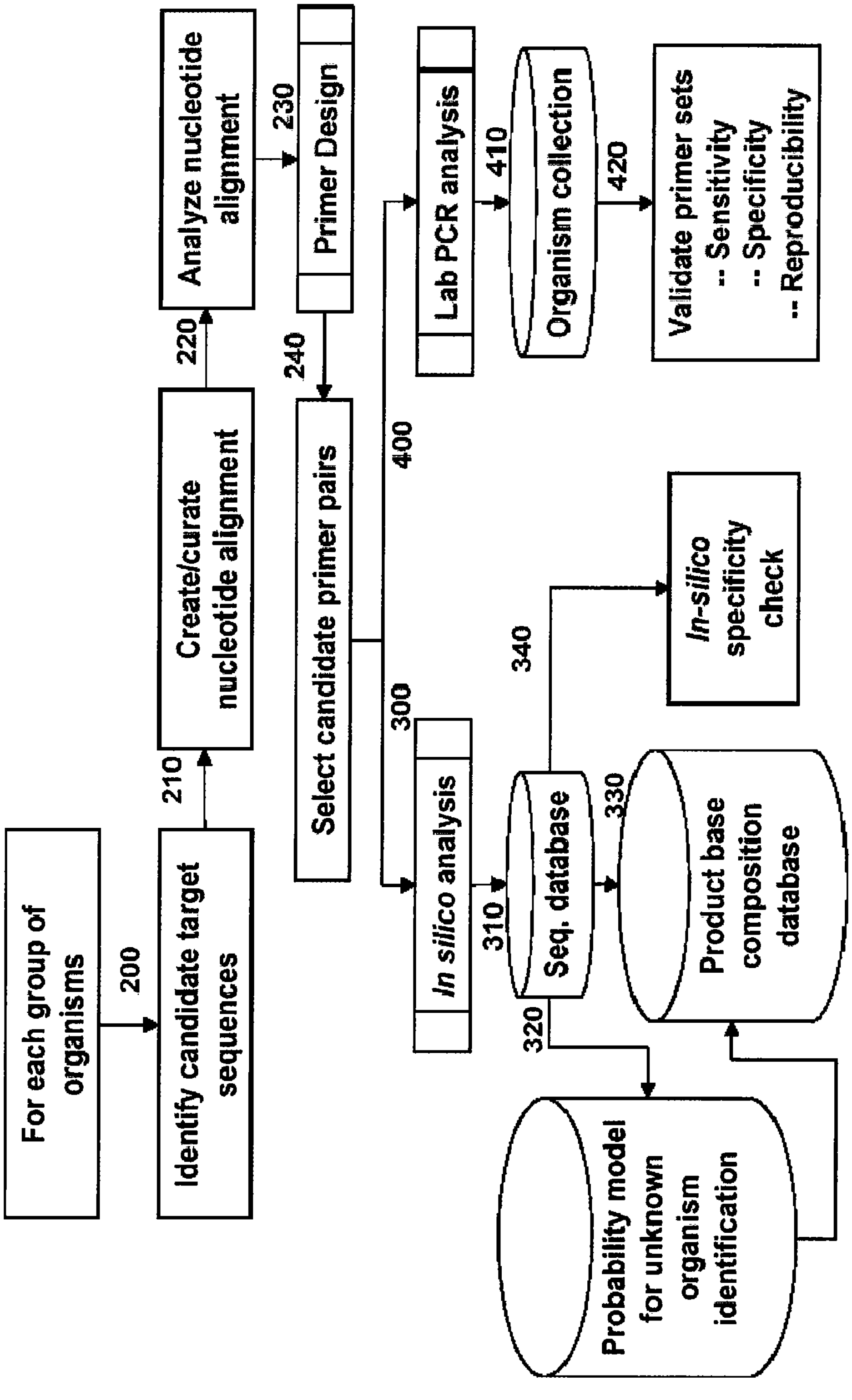
FIG. 1: process diagram illustrating a representative primer pair selection process.

As used herein, the term "abundance" refers to an amount. The amount may be described in terms of concentration which are common in molecular biology such as "copy number," "pfu or plate-forming unit" which are well known to those with ordinary skill. Concentration may be relative to a known standard or may be absolute.

As used herein, the term "amplifiable nucleic acid" is used in reference to nucleic acids that may be amplified by any amplification method. It is contemplated that "amplifiable nucleic acid" also comprises "sample template."

As used herein the term "amplification" refers to a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplification reagents" refers to those reagents (deoxyribonucleotide triphosphates, buffer, etc.), needed for amplification, excluding primers, nucleic acid template, and the amplification enzyme. Typically, amplification reagents along with other reaction components are placed and contained in a reaction vessel (test tube, microwell, etc.).

As used herein, the term "analogous" when used in context of comparison of bioagent identifying amplicons indicates that the bioagent identifying amplicons being compared are produced with the same pair of primers. For example, bioagent identifying amplicon "A" and bioagent identifying amplicon "B", produced with the same pair of primers are analogous with respect to each other. Bioagent identifying amplicon "C", produced with a different pair of primers is not analogous to either bioagent identifying amplicon "A" or bioagent identifying amplicon "B".

As used herein, the term "anion exchange functional group" refers to a positively charged functional group capable of binding an anion through an electrostatic interaction. The most well known anion exchange functional groups are the amines, including primary, secondary, tertiary and quaternary amines.

The term "bacteria" or "bacterium" refers to any member of the groups of eubacteria and archaebacteria.

As used herein, a "base composition" is the exact number of each nucleobase (for example, A, T, C and G) in a segment of nucleic acid. For example, amplification of nucleic acid of *Staphylococcus aureus* strain carrying the lukS-PV gene with primer pair number 2095 (SEQ ID NOs: 456:1261) produces an amplification product 117 nucleobases in length from nucleic acid of the lukS-PV gene that has a base composition of A35 G17 C19 T46 (by convention—with reference to the sense strand of the amplification product). Because the molecular masses of each of the four natural nucleotides and chemical modifications thereof are known (if applicable), a measured molecular mass can be deconvoluted to a list of possible base compositions. Identification of a base composition of a sense strand which is complementary to the corresponding antisense strand in terms of base composition provides a confirmation of the true base composition of an unknown amplification product. For example, the base composition of the antisense strand of the 139 nucleobase amplification product described above is A46 G19 C17 T35.

As used herein, a "base composition probability cloud" is a representation of the diversity in base composition resulting from a variation in sequence that occurs among different isolates of a given species. The "base composition probability cloud" represents the base composition constraints for each species and is typically visualized using a pseudo four-dimensional plot.

In the context of this invention, a "bioagent" is any organism, cell, or virus, living or dead, or a nucleic acid derived from such an organism, cell or virus. Examples of bioagents include, but are not limited, to cells, (including but not limited to human clinical samples, bacterial cells and other pathogens), viruses, fungi, protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

As used herein, a "bioagent division" is defined as group of bioagents above the species level and includes but is not limited to, orders, families, classes, clades, genera or other such groupings of bioagents above the species level.

As used herein, the term "bioagent identifying amplicon" refers to a polynucleotide that is amplified from a bioagent in an amplification reaction and which 1) provides sufficient variability to distinguish among bioagents from whose nucleic acid the bioagent identifying amplicon is produced and 2) whose molecular mass is amenable to a rapid and convenient molecular mass determination modality such as mass spectrometry, for example.

As used herein, the term "biological product" refers to any product originating from an organism. Biological products are often products of processes of biotechnology. Examples of biological products include, but are not limited to: cultured cell lines, cellular components, antibodies, proteins and other cell-derived biomolecules, growth media, growth harvest fluids, natural products and bio-pharmaceutical products.

The terms "biowarfare agent" and "bioweapon" are synonymous and refer to a bacterium, virus, fungus or protozoan that could be deployed as a weapon to cause bodily harm to individuals. Military or terrorist groups may be implicated in deployment of biowarfare agents.

In context of this invention, the term "broad range survey primer pair" refers to a primer pair designed to produce bioagent identifying amplicons across different broad groupings of bioagents. For example, the ribosomal RNA-targeted primer pairs are broad range survey primer pairs which have the capability of producing bacterial bioagent identifying amplicons for essentially all known bacteria. With respect to broad range primer pairs employed for identification of bacteria, a broad range survey primer pair for bacteria such as 16S rRNA primer pair number 346 (SEQ ID NOs: 202:1110) for example, will produce an bacterial bioagent identifying amplicon for essentially all known bacteria.

The term "calibration amplicon" refers to a nucleic acid segment representing an amplification product obtained by amplification of a calibration sequence with a pair of primers designed to produce a bioagent identifying amplicon.

The term "calibration sequence" refers to a polynucleotide sequence to which a given pair of primers hybridizes for the purpose of producing an internal (i.e: included in the reaction) calibration standard amplification product for use in determining the quantity of a bioagent in a sample. The calibration sequence may be expressly added to an amplification reaction, or may already be present in the sample prior to analysis.

The term "clade primer pair" refers to a primer pair designed to produce bioagent identifying amplicons for species belonging to a clade group. A clade primer pair may also be considered as a "speciating" primer pair which is useful for distinguishing among closely related species.

The term "codon" refers to a set of three adjoined nucleotides (triplet) that codes for an amino acid or a termination signal.

In context of this invention, the term "codon base composition analysis," refers to determination of the base composition of an individual codon by obtaining a bioagent identifying amplicon that includes the codon. The bioagent identifying amplicon will at least include regions of the target nucleic acid sequence to which the primers hybridize for generation of the bioagent identifying amplicon as well as the codon being analyzed, located between the two primer hybridization regions.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "complement of a nucleic acid sequence" as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Where a first oligonucleotide is complementary to a region of a target nucleic acid and a second oligonucleotide has complementary to the same region (or a portion of this region) a "region of overlap" exists along the target nucleic acid. The degree of overlap will vary depending upon the extent of the complementarity.

In context of this invention, the term "division-wide primer pair" refers to a primer pair designed to produce bioagent identifying amplicons within sections of a broader spectrum of bioagents For example, primer pair number 352 (SEQ ID NOs: 687:1411), a division-wide primer pair, is designed to produce bacterial bioagent identifying amplicons for members of the *Bacillus* group of bacteria which comprises, for example, members of the genera *Streptococci, Enterococci*, and *Staphylococci*. Other division-wide primer pairs may be used to produce bacterial bioagent identifying amplicons for other groups of bacterial bioagents.

As used herein, the term "concurrently amplifying" used with respect to more than one amplification reaction refers to the act of simultaneously amplifying more than one nucleic acid in a single reaction mixture.

As used herein, the term "drill-down primer pair" refers to a primer pair designed to produce bioagent identifying amplicons for identification of sub-species characteristics or confirmation of a species assignment. For example, primer pair number 2146 (SEQ ID NOs: 437:1137), a drill-down *Staphylococcus aureus* genotyping primer pair, is designed to produce *Staphylococcus aureus* genotyping amplicons. Other drill-down primer pairs may be used to produce bioagent identifying amplicons for *Staphylococcus aureus* and other bacterial species.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

As used herein, the term "etiology" refers to the causes or origins, of diseases or abnormal physiological conditions.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. In context of the present invention, sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers of the present invention, sequence identity is properly determined when the alignment is designated as Plus/Plus. Sequence identity may also encompass alternate or modified nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "housekeeping gene" refers to a gene encoding a protein or RNA involved in basic functions required for survival and reproduction of a bioagent. Housekeeping genes include, but are not limited to genes encoding RNA or proteins involved in translation, replication, recombination and repair, transcription, nucleotide metabolism, amino acid metabolism, lipid metabolism, energy generation, uptake, secretion and the like.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$, of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modem biology.

The term "in silico" refers to processes taking place via computer calculations. For example, electronic PCR (ePCR) is a process analogous to ordinary PCR except that it is carried out using nucleic acid sequences and primer pair sequences stored on a computer formatted medium.

As used herein, "intelligent primers" are primers that are designed to bind to highly conserved sequence regions of a bioagent identifying amplicon that flank an intervening variable region and, upon amplification, yield amplification products which ideally provide enough variability to distinguish individual bioagents, and which are amenable to molecular mass analysis. By the term "highly conserved," it is meant that the sequence regions exhibit between about 80-100%, or between about 90-100%, or between about 95-100% identity among all, or at least 70%, at least 80%, at least 90%, at least 95%, or at least 99% of species or strains.

The "ligase chain reaction" (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. However, because the four oligonucleotides used in this assay can pair to form two short ligatable fragments, there is the potential for the generation of target-independent background signal. The use of LCR for mutant screening is limited to the examination of specific nucleic acid positions.

The term "locked nucleic acid" or "LNA" refers to a nucleic acid analogue containing one or more 2'-O, 4'-C-methylene-β-D-ribofuranosyl nucleotide monomers in an RNA mimicking sugar conformation. LNA oligonucleotides display unprecedented hybridization affinity toward complementary single-stranded RNA and complementary single- or double-stranded DNA. LNA oligonucleotides induce A-type (RNA-like) duplex conformations. The primers of the present invention may contain LNA modifications.

As used herein, the term "mass-modifying tag" refers to any modification to a given nucleotide which results in an increase in mass relative to the analogous non-mass modified nucleotide. Mass-modifying tags can include heavy isotopes of one or more elements included in the nucleotide such as carbon-13 for example. Other possible modifications include addition of substituents such as iodine or bromine at the 5 position of the nucleobase for example.

The term "mass spectrometry" refers to measurement of the mass of atoms or molecules. The molecules are first converted to ions, which are separated using electric or magnetic fields according to the ratio of their mass to electric charge. The measured masses are used to identity the molecules.

The term "microorganism" as used herein means an organism too small to be observed with the unaided eye and includes, but is not limited to bacteria, virus, protozoans, fungi; and ciliates.

The term "multi-drug resistant" or multiple-drug resistant" refers to a microorganism which is resistant to more than one of the antibiotics or antimicrobial agents used in the treatment of said microorganism.

The term "multiplex PCR" refers to a PCR reaction where more than one primer set is included in the reaction pool allowing 2 or more different DNA targets to be amplified by PCR in a single reaction tube.

The term "non-template tag" refers to a stretch of at least three guanine or cytosine nucleobases of a primer used to produce a bioagent identifying amplicon which are not complementary to the template. A non-template tag is incorporated into a primer for the purpose of increasing the primer-duplex stability of later cycles of amplification by incorporation of extra G-C pairs which each have one additional hydrogen bond relative to an A-T pair.

The term "nucleic acid sequence" as used herein refers to the linear composition of the nucleic acid residues A, T, C or G or any modifications thereof, within an oligonucleotide, nucleotide or polynucleotide, and fragments or portions thereof, and to DNA or RNA of genomic or synthetic origin which may be single or double stranded, and represent the sense or antisense strand As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

The term "nucleotide analog" as used herein refers to modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

The term "oligonucleotide" as used herein is defined as a molecule comprising two or more deoxyribonucleotides or ribonucleotides, preferably at least 5 nucleotides, more preferably at least about 13 to 35 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof. Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5'-end" if its 5' phosphate is not linked to the 3' oxygen of a mononucleotide pentose ring and as the "3'-end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. All oligonucleotide primers disclosed herein are understood to be presented in the 5' to 3' direction when reading left to right. When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

In the context of this invention, a "pathogen" is a bioagent which causes a disease or disorder.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "peptide nucleic acid" ("PNA") as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen, et al. Anticancer Drug Des. 8:53 63). The primers of the present invention may comprise PNAs.

The term "polymerase" refers to an enzyme having the ability to synthesize a complementary strand of nucleic acid from a starting template nucleic acid strand and free dNTPs.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing; the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The term "polymerization means" or "polymerization agent" refers to any agent capable of facilitating the addition of nucleoside triphosphates to an oligonucleotide. Preferred polymerization means comprise DNA and RNA polymerases.

As used herein, the terms "pair of primers," or "primer pair" are synonymous. A primer pair is used for amplification of a nucleic acid sequence. A pair of primers comprises a forward primer and a reverse primer. The forward primer hybridizes to a sense strand of a target gene sequence to be amplified and primes synthesis of an antisense strand (complementary to the sense strand) using the target sequence as a template. A reverse primer hybridizes to the antisense strand of a target gene sequence to be amplified and primes synthesis of a sense strand (complementary to the antisense strand) using the target sequence as a template.

The primers are designed to bind to highly conserved sequence regions of a bioagent identifying amplicon that flank an intervening variable region and yield amplification products which ideally provide enough variability to distinguish each individual bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the bioagent from which it was obtained, due to the variability of the variable region. Thus design of the primers requires selection of a variable region with appropriate variability to resolve the identity of a given bioagent. Bioagent identifying amplicons are ideally specific to the identity of the bioagent.

Properties of the primers may include any number of properties related to structure including, but not limited to: nucleobase length which may be contiguous (linked together) or non-contiguous (for example, two or more contiguous segments which are joined by a linker or loop moiety), modified or universal nucleobases (used for specific purposes such as for example, increasing hybridization affinity, preventing non-templated adenylation and modifying molecular mass) percent complementarity to a given target sequences.

Properties of the primers also include functional features including, but not limited to, orientation of hybridization (forward or reverse) relative to a nucleic acid template. The coding or sense strand is the strand to which the forward priming primer hybridizes (forward priming orientation) while the reverse priming primer hybridizes to the non-coding or antisense strand (reverse priming orientation). The functional properties of a given primer pair also include the generic template nucleic acid to which the primer pair hybridizes. For example, identification of bioagents can be accomplished at different levels using primers suited to resolution of each individual level of identification. Broad range survey primers are designed with the objective of identifying a bioagent as a member of a particular division (e.g., an order, family, genus or other such grouping of bioagents above the species level of bioagents). In some embodiments, broad range survey intelligent primers are capable of identification of bioagents at the species or sub-species level. Other primers may have the functionality of producing bioagent identifying amplicons for members of a given taxonomic genus, clade, species, sub-species or genotype (including genetic variants which may include presence of virulence genes or antibiotic resistance genes or mutations). Additional functional properties of primer pairs include the functionality of performing amplification either singly (single primer pair per amplification reaction vessel) or in a multiplex fashion (multiple primer pairs and multiple amplification reactions within a single reaction vessel).

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "reverse transcriptase" refers to an enzyme having the ability to transcribe DNA from an RNA template. This enzymatic activity is known as reverse transcriptase activity. Reverse transcriptase activity is desirable in order to obtain DNA from RNA viruses which can then be amplified and analyzed by the methods of the present invention.

The term "ribosomal RNA" or "rRNA" refers to the primary ribonucleic acid constituent of ribosomes. Ribosomes are the protein-manufacturing organelles of cells and exist in the cytoplasm. Ribosomal RNAs are transcribed from the DNA genes encoding them.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc. Environmental samples include environmental material such as surface matter, soil, water, air and industrial samples, as well as samples obtained from food and dairy processing instruments, apparatus, equipment, utensils, disposable and non-disposable items. These examples are not to be construed as limiting the sample types applicable to the present invention. The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is often a contaminant. It may be the result of carryover, or it may be due to the presence of nucleic acid contaminants sought to be purified away from the sample. For example, nucleic acids from organisms other than those to be detected may be present as background in a test sample.

A "segment" is defined herein as a region of nucleic acid within a target sequence.

The "self-sustained sequence replication reaction" (3SR) (Guatelli et al., Proc. Natl. Acad. Sci., 87:1874-1878 [1990], with an erratum at Proc. Natl. Acad. Sci., 87:7797 [1990]) is a transcription-based in vitro amplification system (Kwok et al., Proc. Natl. Acad. Sci., 86:1173-1177 [1989]) that can exponentially amplify RNA sequences at a uniform temperature. The amplified RNA can then be utilized for mutation detection (Fahy et al., PCR Meth. Appl., 1:25-33 [1991]). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo- and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

As used herein, the term ""sequence alignment"" refers to a listing of multiple DNA or amino acid sequences and aligns them to highlight their similarities. The listings can be made using bioinformatics computer programs.

In context of this invention, the term "speciating primer pair" refers to a primer pair designed to produce a bioagent identifying amplicon with the diagnostic capability of identifying species members of a group of genera or a particular genus of bioagents. Primer pair number 2249 (SEQ ID NOs: 430:1321), for example, is a speciating primer pair used to distinguish *Staphylococcus aureus* from other species of the genus *Staphylococcus.*

As used herein, a "sub-species characteristic" is a genetic characteristic that provides the means to distinguish two members of the same bioagent species. For example, one viral strain could be distinguished from another viral strain of the same species by possessing a genetic change (e.g., for example, a nucleotide deletion, addition or substitution) in one of the viral genes, such as the RNA-dependent RNA polymerase. Sub-species characteristics such as virulence genes and drug-are responsible for the phenotypic differences among the different strains of bacteria.

As used herein, the term "target" is used in a broad sense to indicate the gene or genomic region being amplified by the primers. Because the present invention provides a plurality of amplification products from any given primer pair (depending on the bioagent being analyzed), multiple amplification products from different specific nucleic acid sequences may be obtained. Thus, the term "target" is not used to refer to a single specific nucleic acid sequence. The "target" is sought to be sorted out from other nucleic acid sequences and contains a sequence that has at least partial complementarity with an oligonucleotide primer. The target nucleic acid may comprise single- or double-stranded DNA or RNA. A "segment" is defined as a region of nucleic acid within the target sequence.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m$=81.5+0.41(% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G. T mismatches in DNA. Biochemistry 36, 10581-94 (1997) include more sophisticated computations which take structural and environmental, as well as sequence characteristics into account for the calculation of $T_m$.

The term "triangulation genotyping analysis" refers to a method of genotyping a bioagent by measurement of molecular masses or base compositions of amplification products, corresponding to bioagent identifying amplicons, obtained by amplification of regions of more than one gene. In this sense, the term "triangulation" refers to a method of establishing the accuracy of information by comparing three or more types of independent points of view bearing on the same findings. Triangulation genotyping analysis carried out with a plurality of triangulation genotyping analysis primers yields a plurality of base compositions that then provide a pattern or "barcode" from which a species type can be assigned. The species type may represent a previously known sub-species or strain, or may be a previously unknown strain having a specific and previously unobserved base composition barcode indicating the existence of a previously unknown genotype.

As used herein, the term "triangulation genotyping analysis primer pair" is a primer pair designed to produce bioagent identifying amplicons for determining species types in a triangulation genotyping analysis.

The employment of more than one bioagent identifying amplicon for identification of a bioagent is herein referred to as "triangulation identification." Triangulation identification is pursued by analyzing a plurality of bioagent identifying amplicons produced with different primer pairs. This process is used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In the context of this invention, the term "unknown bioagent" may mean either: (i) a bioagent whose existence is known (such as the well known bacterial species *Staphylococcus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

The term "variable sequence" as used herein refers to differences in nucleic acid sequence between two nucleic acids. For example, the genes of two different bacterial species may vary in sequence by the presence of single base substitutions and/or deletions or insertions of one or more nucleotides. These two forms of the structural gene are said to vary in sequence from one another. In the context of the present invention, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

The term "virus" refers to obligate, ultramicroscopic, parasites that are incapable of autonomous replication (i.e., replication requires the use of the host cell's machinery). Viruses can survive outside of a host cell but cannot replicate.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, a "wobble base" is a variation in a codon found at the third nucleotide position of a DNA triplet. Variations in conserved regions of sequence are often found at the third nucleotide position due to redundancy in the amino acid code.

DETAILED DESCRIPTION OF EMBODIMENTS

A. Bioagent Identifying Amplicons

The present invention provides methods for detection and identification of unknown bioagents using bioagent identifying amplicons. Primers are selected to hybridize to conserved sequence regions of nucleic acids derived from a bioagent, and which bracket variable sequence regions to yield a bioagent identifying amplicon, which can be amplified and which is amenable to molecular mass determination. The molecular mass then provides a means to uniquely identify the bioagent without a requirement for prior knowledge of the possible identity of the bioagent. The molecular mass or corresponding base composition signature of the amplification product is then matched against a database of molecular masses or base composition signatures. A match is obtained when an experimentally-determined molecular mass or base composition of an analyzed amplification product is compared with known molecular masses or base compositions of known bioagent identifying amplicons and the experimentally determined molecular mass or base composition is the same as the molecular mass or base composition of one of the known bioagent identifying amplicons. Alternatively, the experimentally-determined molecular mass or base composition may be within experimental error of the molecular mass or base composition of a known bioagent identifying amplicon and still be classified as a match. In some cases, the match may also be classified using a probability of match model such as the models described in U.S. Ser. No. 11/073,362, which is commonly owned and incorporated herein by reference in entirety. Furthermore, the method can be applied to rapid parallel multiplex analyses, the results of which can be employed in a triangulation identification strategy. The present method provides rapid throughput and does not require nucleic acid sequencing of the amplified target sequence for bioagent detection and identification.

Despite enormous biological diversity, all forms of life on earth share sets of essential, common features in their genomes. Since genetic data provide the underlying basis for identification of bioagents by the methods of the present invention, it is necessary to select segments of nucleic acids which ideally provide enough variability to distinguish each individual bioagent and whose molecular mass is amenable to molecular mass determination.

Unlike bacterial genomes, which exhibit conservation of numerous genes (i.e. housekeeping genes) across all organisms, viruses do not share a gene that is essential and conserved among all virus families. Therefore, viral identification is achieved within smaller groups of related viruses, such as members of a particular virus family or genus. For example, RNA-dependent RNA polymerase is present in all single-stranded RNA viruses and can be used for broad priming as well as resolution within the virus family.

In some embodiments of the present invention, at least one bacterial nucleic acid segment is amplified in the process of identifying the bacterial bioagent. Thus, the nucleic acid segments that can be amplified by the primers disclosed herein and that provide enough variability to distinguish each individual bioagent and whose molecular masses are amenable to molecular mass determination are herein described as bioagent identifying amplicons.

In some embodiments of the present invention, bioagent identifying amplicons comprise from about 45 to about 150 nucleobases (i.e. from about 45 to about 200 linked nucleosides), although both longer and short regions may be used. One of ordinary skill in the art will appreciate that the invention embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nucleobases in length, or any range therewithin.

It is the combination of the portions of the bioagent nucleic acid segment to which the primers hybridize (hybridization sites) and the variable region between the primer hybridization sites that comprises the bioagent identifying amplicon. Thus, it can be said that a given bioagent identifying amplicon is "defined by" a given pair of primers.

In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with chemical reagents, restriction enzymes or cleavage primers, for example. Thus, in some embodiments, bioagent identifying amplicons are larger than 150 nucleobases and are amenable to molecular mass determination following restriction digestion. Methods of using restriction enzymes and cleavage primers are well known to those with ordinary skill in the art.

In some embodiments, amplification products corresponding to bioagent identifying amplicons are obtained using the polymerase chain reaction (PCR) that is a routine method to those with ordinary skill in the molecular biology arts. Other amplification methods may be used such as ligase chain reaction (LCR), low-stringency single primer PCR, and multiple strand displacement amplification (MDA). These methods are also known to those with ordinary skill.

B. Primers and Primer Pairs

In some embodiments, the primers are designed to bind to conserved sequence regions of a bioagent identifying amplicon that flank an intervening variable region and yield amplification products which provide variability sufficient to distinguish each individual bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the bioagent from which it was obtained, due to the variability of the variable region. Thus, design of the primers involves selection of a variable region with sufficient variability to resolve the identity of a given bioagent. In some embodiments, bioagent identifying amplicons are specific to the identity of the bioagent.

In some embodiments, identification of bioagents is accomplished at different levels using primers suited to resolution of each individual level of identification. Broad range survey primers are designed with the objective of identifying a bioagent as a member of a particular division (e.g., an order, family, genus or other such grouping of bioagents above the species level of bioagents). In some embodiments, broad range survey intelligent primers are capable of identification of bioagents at the species or sub-species level. Examples of broad range survey primers include, but are not limited to: primer pair numbers: 346 (SEQ ID NOs: 202:1110), 347 (SEQ ID NOs: 560:1278), 348 SEQ ID NOs: 706:895), and 361 (SEQ ID NOs: 697:1398) which target DNA encoding 16S rRNA, and primer pair numbers 349 (SEQ ID NOs: 401:1156) and 360 (SEQ ID NOs: 409:1434) which target DNA encoding 23S rRNA.

In some embodiments, drill-down primers are designed with the objective of identifying a bioagent at the sub-species level (including strains, subtypes, variants and isolates) based on sub-species characteristics which may, for example, include single nucleotide polymorphisms (SNPs), variable number tandem repeats (VNTRs), deletions, drug resistance mutations or any other modification of a nucleic acid sequence of a bioagent relative to other members of a species having different sub-species characteristics. Drill-down intelligent primers are not always required for identification at the sub-species level because broad range survey intelligent primers may, in some cases provide sufficient identification resolution to accomplishing this identification objective. Examples of drill-down primers include, but are not limited to: confirmation primer pairs such as primer pair numbers 351 (SEQ ID NOs: 355:1423) and 353 (SEQ ID NOs: 220:1394), which target the pX01 virulence plasmid of *Bacillus anthracis*. Other examples of drill-down primer pairs are found in sets of triangulation genotyping primer pairs such as, for example, the primer pair number 2146 (SEQ ID NOs: 437:1137) which targets the arcC gene (encoding carmabate kinase) and is included in an 8 primer pair panel or kit for use in genotyping *Staphylococcus aureus*, or in other panels or kits of primer pairs used for determining drug-resistant bacterial strains, such as, for example, primer pair number 2095 (SEQ ID NOs: 456:1261) which targets the pv-luk gene (encoding Panton-Valentine leukocidin) and is included in an 8 primer pair panel or kit for use in identification of drug resistant strains of *Staphylococcus aureus*.

A representative process flow diagram used for primer selection and validation process is outlined in FIG. 1. For each group of organisms, candidate target sequences are identified (200) from which nucleotide alignments are created (210) and analyzed (220). Primers are then designed by selecting appropriate priming regions (230) to facilitate the selection of candidate primer pairs (240). The primer pairs are then subjected to in silico analysis by electronic PCR (ePCR) (300) wherein bioagent identifying amplicons are obtained from sequence databases such as GenBank or other sequence collections (310) and checked for specificity in silico (320). Bioagent identifying amplicons obtained from GenBank sequences (310) can also be analyzed by a probability model which predicts the capability of a given amplicon to identify unknown bioagents such that the base compositions of amplicons with favorable probability scores are then stored in a base composition database (325). Alternatively, base compositions of the bioagent identifying amplicons obtained from the primers and GenBank sequences can be directly entered into the base composition database (330). Candidate primer pairs (240) are validated by testing their ability to hybridize to target nucleic acid by an in vitro amplification by a method such as PCR analysis (400) of nucleic acid from a collection of organisms (410). Amplification products thus obtained are analyzed by gel electrophoresis or by mass spectrometry to confirm the sensitivity, specificity and reproducibility of the primers used to obtain the amplification products (420).

Many of the important pathogens, including the organisms of greatest concern as biowarfare agents, have been completely sequenced. This effort has greatly facilitated the design of primers for the detection of unknown bioagents. The combination of broad-range priming with division-wide and drill-down priming has been used very successfully in several applications of the technology, including environmental surveillance for biowarfare threat agents and clinical sample analysis for medically important pathogens.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

In some embodiments primers are employed as compositions for use in methods for identification of bacterial bioagents as follows: a primer pair composition is contacted with nucleic acid (such as, for example, bacterial DNA or DNA reverse transcribed from the rRNA) of an unknown bacterial bioagent. The nucleic acid is then amplified by a nucleic acid amplification technique, such as PCR for example, to obtain an amplification product that represents a bioagent identifying amplicon. The molecular mass of each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known viral bioagents. A match between the molecular mass or base composition of the amplification product and the molecular mass or base composition of an analogous bioagent identifying amplicon for a known viral bioagent indicates the identity of the unknown bioagent. In some embodiments, the primer pair used is one of the primer pairs of Table 2. In some embodiments, the method is repeated using one or more different primer pairs to resolve possible ambiguities in the identification process or to improve the confidence level for the identification assignment.

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR). Adaptation of this amplification method in order to produce bioagent identifying amplicons can be accomplished by one with ordinary skill in the art without undue experimentation.

In some embodiments, the oligonucleotide primers are broad range survey primers which hybridize to conserved regions of nucleic acid encoding the hexon gene of all (or between 80% and 100%, between 85% and 100%, between 90% and 100% or between 95% and 100%) known bacteria and produce bacterial bioagent identifying amplicons.

In some cases, the molecular mass or base composition of a bacterial bioagent identifying amplicon defined by a broad range survey primer pair does not provide enough resolution to unambiguously identify a bacterial bioagent at or below the species level. These cases benefit from further analysis of one or more bacterial bioagent identifying amplicons generated from at least one additional broad range survey primer pair or from at least one additional division-wide primer pair. The employment of more than one bioagent identifying amplicon for identification of a bioagent is herein referred to as triangulation identification.

In other embodiments, the oligonucleotide primers are division-wide primers which hybridize to nucleic acid encoding genes of species within a genus of bacteria. In other embodiments, the oligonucleotide primers are drill-down primers which enable the identification of sub-species characteristics. Drill down primers provide the functionality of producing bioagent identifying amplicons for drill-down analyses such as strain typing when contacted with nucleic acid under amplification conditions. Identification of such sub-species characteristics is often critical for determining proper clinical treatment of viral infections. In some embodiments, sub-species characteristics are identified using only broad range survey primers and division-wide and drill-down primers are not used.

In some embodiments, the primers used for amplification hybridize to and amplify genomic DNA, and DNA of bacterial plasmids.

In some embodiments, various computer software programs may be used to aid in design of primers for amplification reactions such as Primer Premier 5 (Premier Biosoft, Palo Alto, Calif.) or OLIGO Primer Analysis Software (Molecular Biology Insights, Cascade, Colo.). These programs allow the user to input desired hybridization conditions such as melting temperature of a primer-template duplex for example. In some embodiments, an in silico PCR search algorithm, such as (ePCR) is used to analyze primer specificity across a plurality of template sequences which can be readily obtained from public sequence databases such as GenBank for example. An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs. In some embodiments, the hybridization conditions applied to the algorithm can limit the results of primer specificity obtained from the algorithm. In some embodiments, the melting temperature threshold for the primer template duplex is specified to be 35° C. or a higher temperature. In some embodiments the number of acceptable mismatches is specified to be seven mismatches or less. In some embodiments, the buffer components and concentrations and primer concentrations may be specified and incorporated into the algorithm, for example, an appropriate primer concentration is about 250 nM and appropriate buffer components are 50 mM sodium or potassium and 1.5 mM $Mg^{2+}$.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g., for example, a loop structure or a hairpin structure). The primers of the present invention may comprise at least 70%, at least 75%, at least 80%, at least 85%, at least 90%, at least 95% or at least 99% sequence identity with any of the primers listed in Table 2. Thus, in some embodiments of the present invention, an extent of variation of 70% to 100%, or any range therewithin, of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer.

Percent homology, sequence identity or complementarity, can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid is between about 70% and about 75% 80%. In other embodiments, homology, sequence identity or complementarity, is between about 75% and about 80%. In yet other embodiments, homology, sequence identity or complementarity, is at least 85%, at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range therewithin) sequence identity with the primer sequences specifically disclosed herein.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In one embodiment, the primers are at least 13 nucleobases in length. In another embodiment, the primers are less than 36 nucleobases in length.

In some embodiments of the present invention, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin. The present invention contemplates using both longer and shorter primers. Furthermore, the primers may also be linked to one or more other desired moieties, including, but not limited to, affinity groups, ligands, regions of nucleic acid that are not complementary to the nucleic acid to be amplified, labels, etc. Primers may also form hairpin structures. For example, hairpin primers may be used to amplify short target nucleic acid molecules. The presence of the hairpin may stabilize the amplification complex (see e.g., TAQMAN MicroRNA Assays, Applied Biosystems, Foster City, Calif.).

In some embodiments, any oligonucleotide primer pair may have one or both primers with less then 70% sequence homology with a corresponding member of any of the primer pairs of Table 2 if the primer pair has the capability of producing an amplification product corresponding to a bioagent identifying amplicon. In other embodiments, any oligonucleotide primer pair may have one or both primers with a length greater than 35 nucleobases if the primer pair has the capability of producing an amplification product corresponding to a bioagent identifying amplicon.

In some embodiments, the function of a given primer may be substituted by a combination of two or more primers segments that hybridize adjacent to each other or that are linked by a nucleic acid loop structure or linker which allows a polymerase to extend the two or more primers in an amplification reaction.

In some embodiments, the primer pairs used for obtaining bioagent identifying amplicons are the primer pairs of Table 2. In other embodiments, other combinations of primer pairs are possible by combining certain members of the forward primers with certain members of the reverse primers. An example can be seen in Table 2 for two primer pair combinations of forward primer 16S_EC__789__810_F (SEQ ID NO: 206), with the reverse primers 16S_EC__880__894_R (SEQ ID NO: 796), or 16S_EC__882__899_R or (SEQ ID NO: 818). Arriving at a favorable alternate combination of primers in a primer pair depends upon the properties of the primer pair, most notably the size of the bioagent identifying amplicon that would be produced by the primer pair, which preferably is between about 45 to about 150 nucleobases in length. Alternatively, a bioagent identifying amplicon longer than 150 nucleobases in length could be cleaved into smaller segments by cleavage reagents such as chemical reagents, or restriction enzymes, for example.

In some embodiments, the primers are configured to amplify nucleic acid of a bioagent to produce amplification products that can be measured by mass spectrometry and from whose molecular masses candidate base compositions can be readily calculated.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated adenosine residues as a result of the non-specific enzyme activity of Taq polymerase (Magnuson et al., Biotechniques, 1996, 21, 700-709), an occurrence which may lead to ambiguous results arising from molecular mass analysis.

In some embodiments of the present invention, primers may contain one or more universal bases. Because any variation (due to codon wobble in the $3^{rd}$ position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In some embodiments, to compensate for the somewhat weaker binding by the wobble base, the oligonucleotide primers are designed such that the first and second positions of each triplet are occupied by nucleotide analogs that bind with greater affinity than the unmodified nucleotide. Examples of these analogs include, but are not limited to, 2,6-diaminopurine which binds to thymine, 5-propynyluracil (also known as propynylated thymine) which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S Pre-Grant Publication No. 2003-0170682, which is also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, primer hybridization is enhanced using primers containing 5-propynyl deoxy-cytidine and deoxy-thymidine nucleotides. These modified primers offer increased affinity and base pairing selectivity.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon from its molecular mass.

In some embodiments of the present invention, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$.

In some embodiments, multiplex amplification is performed where multiple bioagent identifying amplicons are amplified with a plurality of primer pairs. The advantages of multiplexing are that fewer reaction containers (for example, wells of a 96- or 384-well plate) are needed for each molecular mass measurement, providing time, resource and cost savings because additional bioagent identification data can be obtained within a single analysis. Multiplex amplification methods are well known to those with ordinary skill and can be developed without undue experimentation. However, in some embodiments, one useful and non-obvious step in selecting a plurality candidate bioagent identifying amplicons for multiplex amplification is to ensure that each strand of each amplification product will be sufficiently different in molecular mass that mass spectral signals will not overlap and lead to ambiguous analysis results. In some embodiments, a 10 Da difference in mass of two strands of one or more amplification products is sufficient to avoid overlap of mass spectral peaks.

In some embodiments, as an alternative to multiplex amplification, single amplification reactions can be pooled before analysis by mass spectrometry. In these embodiments, as for multiplex amplification embodiments, it is useful to select a plurality of candidate bioagent identifying amplicons to ensure that each strand of each amplification product will be sufficiently different in molecular mass that mass spectral signals will not overlap and lead to ambiguous analysis results.

C Determination of Molecular Mass of Bioagent Identifying Amplicons

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), time of flight (TOF), ion trap, quadrupole, magnetic sector, Q-TOF, and triple quadrupole.

D. Base Compositions of Bioagent Identifying Amplicons

Although the molecular mass of amplification products obtained using intelligent primers provides a means for identification of bioagents, conversion of molecular mass data to a base composition signature is useful for certain analyses. As used herein, "base composition" is the exact number of each nucleobase (A, T, C and G) determined from the molecular mass of a bioagent identifying amplicon. In some embodiments, a base composition provides an index of a specific organism. Base compositions can be calculated from known sequences of known bioagent identifying amplicons and can be experimentally determined by measuring the molecular mass of a given bioagent identifying amplicon, followed by determination of all possible base compositions which are consistent with the measured molecular mass within acceptable experimental error. The following example illustrates determination of base composition from an experimentally obtained molecular mass of a 46-mer amplification product originating at position 1337 of the 16S rRNA of *Bacillus anthracis*. The forward and reverse strands of the amplification product have measured molecular masses of 14208 and 14079 Da, respectively. The possible base compositions derived from the molecular masses of the forward and reverse strands for the *B. anthracis* products are listed in Table 1.

TABLE 1

Possible Base Compositions for *B. anthracis* 46mer Amplification Product

| Calc. Mass Forward Strand | Mass Error Forward Strand | Base Composition of Forward Strand | Calc. Mass Reverse Strand | Mass Error Reverse Strand | Base Composition of Reverse Strand |
|---|---|---|---|---|---|
| 14208.2935 | 0.079520 | A1 G17 C10 T18 | 14079.2624 | 0.080600 | A0 G14 C13 T19 |
| 14208.3160 | 0.056980 | A1 G20 C15 T10 | 14079.2849 | 0.058060 | A0 G17 C18 T11 |
| 14208.3386 | 0.034440 | A1 G23 C20 T2 | 14079.3075 | 0.035520 | A0 G20 C23 T3 |
| 14208.3074 | 0.065560 | A6 G11 C3 T26 | 14079.2538 | 0.089180 | A5 G5 C1 T35 |
| 14208.3300 | 0.043020 | A6 G14 C8 T18 | 14079.2764 | 0.066640 | A5 G8 C6 T27 |
| 14208.3525 | 0.020480 | A6 G17 C13 T10 | 14079.2989 | 0.044100 | A5 G11 C11 T19 |
| 14208.3751 | 0.002060 | A6 G20 C18 T2 | 14079.3214 | 0.021560 | A5 G14 C16 T11 |
| 14208.3439 | 0.029060 | A11 G8 C1 T26 | 14079.3440 | 0.000980 | A5 G17 C21 T3 |
| 14208.3665 | 0.006520 | A11 G11 C6 T18 | 14079.3129 | 0.030140 | A10 G5 C4 T27 |
| **14208.3890** | **0.016020** | **A11 G14 C11 T10** | 14079.3354 | 0.007600 | A10 G8 C9 T19 |
| 14208.4116 | 0.038560 | A11 G17 C16 T2 | **14079.3579** | **0.014940** | **A10 G11 C14 T11** |
| 14208.4030 | 0.029980 | A16 G8 C4 T18 | 14079.3805 | 0.037480 | A10 G14 C19 T3 |
| 14208.4255 | 0.052520 | A16 G11 C9 T10 | 14079.3494 | 0.006360 | A15 G2 C2 T27 |
| 14208.4481 | 0.075060 | A16 G14 C14 T2 | 14079.3719 | 0.028900 | A15 G5 C7 T19 |
| 14208.4395 | 0.066480 | A21 G5 C2 T18 | 14079.3944 | 0.051440 | A15 G8 C12 T11 |

TABLE 1-continued

| Possible Base Compositions for *B. anthracis* 46mer Amplification Product | | | | | |
|---|---|---|---|---|---|
| Calc. Mass Forward Strand | Mass Error Forward Strand | Base Composition of Forward Strand | Calc. Mass Reverse Strand | Mass Error Reverse Strand | Base Composition of Reverse Strand |
| 14208.4620 | 0.089020 | A21 G8 C7 T10 | 14079.4170 | 0.073980 | A15 G11 C17 T3 |
| — | — | — | 14079.4084 | 0.065400 | A20 G2 C5 T19 |
| — | — | — | 14079.4309 | 0.087940 | A20 G5 C10 T13 |

Among the 16 possible base compositions for the forward strand and the 18 possible base compositions for the reverse strand that were calculated, only one pair (shown in bold) are complementary base compositions, which indicates the true base composition of the amplification product. It should be recognized that this logic is applicable for determination of base compositions of any bioagent identifying amplicon, regardless of the class of bioagent from which the corresponding amplification product was obtained.

In some embodiments, assignment of previously unobserved base compositions (also known as "true unknown base compositions") to a given phylogeny can be accomplished via the use of pattern classifier model algorithms. Base compositions, like sequences, vary slightly from strain to strain within species, for example. In some embodiments, the pattern classifier model is the mutational probability model. On other embodiments, the pattern classifier is the polytope model. The mutational probability model and polytope model are both commonly owned and described in U.S. patent application Ser. No. 11/073,362 which is incorporated herein by reference in entirety.

In one embodiment, it is possible to manage this diversity by building "base composition probability clouds" around the composition constraints for each species. This permits identification of organisms in a fashion similar to sequence analysis. A "pseudo four-dimensional plot" can be used to visualize the concept of base composition probability clouds. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

The present invention provides bioagent classifying information similar to DNA sequencing and phylogenetic analysis at a level sufficient to identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more BCS indexes become available in base composition databases.

E. Triangulation Identification

In some cases, a molecular mass of a single bioagent identifying amplicon alone does not provide enough resolution to unambiguously identify a given bioagent. The employment of more than one bioagent identifying amplicon for identification of a bioagent is herein referred to as "triangulation identification." Triangulation identification is pursued by determining the molecular masses of a plurality of bioagent identifying amplicons selected within a plurality of housekeeping genes. This process is used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well. PCR methods are well known to those with ordinary skill in the arts of rapid throughput amplification of nucleic acids. In other related embodiments, one PCR reaction per well or container may be carried out, followed by an amplicon pooling step wherein the amplification products of different wells are combined in a single well or container which is then subjected to molecular mass analysis. The combination of pooled amplicons can be chosen such that the expected ranges of molecular masses of individual amplicons are not overlapping and thus will not complicate identification of signals.

F. Codon Base Composition Analysis

In some embodiments of the present invention, one or more nucleotide substitutions within a codon of a gene of an infectious organism confer drug resistance upon an organism which can be determined by codon base composition analysis. The organism can be a bacterium, virus, fungus or protozoan.

In some embodiments, the amplification product containing the codon being analyzed is of a length of about 35 to about 200 nucleobases. The primers employed in obtaining the amplification product can hybridize to upstream and downstream sequences directly adjacent to the codon, or can hybridize to upstream and downstream sequences one or more sequence positions away from the codon. The primers may have between about 70% to 100% sequence complementarity with the sequence of the gene containing the codon being analyzed.

In some embodiments, the codon base composition analysis is undertaken

In some embodiments, the codon analysis is undertaken for the purpose of investigating genetic disease in an individual. In other embodiments, the codon analysis is undertaken for the purpose of investigating a drug resistance mutation or any other deleterious mutation in an infectious organism such as a bacterium, virus, fungus or protozoan. In some embodiments, the bioagent is a bacterium identified in a biological product.

In some embodiments, the molecular mass of an amplification product containing the codon being analyzed is measured by mass spectrometry. The mass spectrometry can be either electrospray (ESI) mass spectrometry or matrix-assisted laser desorption ionization (MALDI) mass spectrometry. Time-of-flight (TOF) is an example of one mode of mass spectrometry compatible with the analyses of the present invention.

The methods of the present invention can also be employed to determine the relative abundance of drug resistant strains of the organism being analyzed. Relative abundances can be calculated from amplitudes of mass spectral signals with relation to internal calibrants. In some embodiments, known quantities of internal amplification calibrants can be included in the amplification reactions and abundances of analyte amplification product estimated in relation to the known quantities of the calibrants.

In some embodiments, upon identification of one or more drug-resistant strains of an infectious organism infecting an individual, one or more alternative treatments can be devised to treat the individual.

G. Determination of the Quantity of a Bioagent

Figure 2:
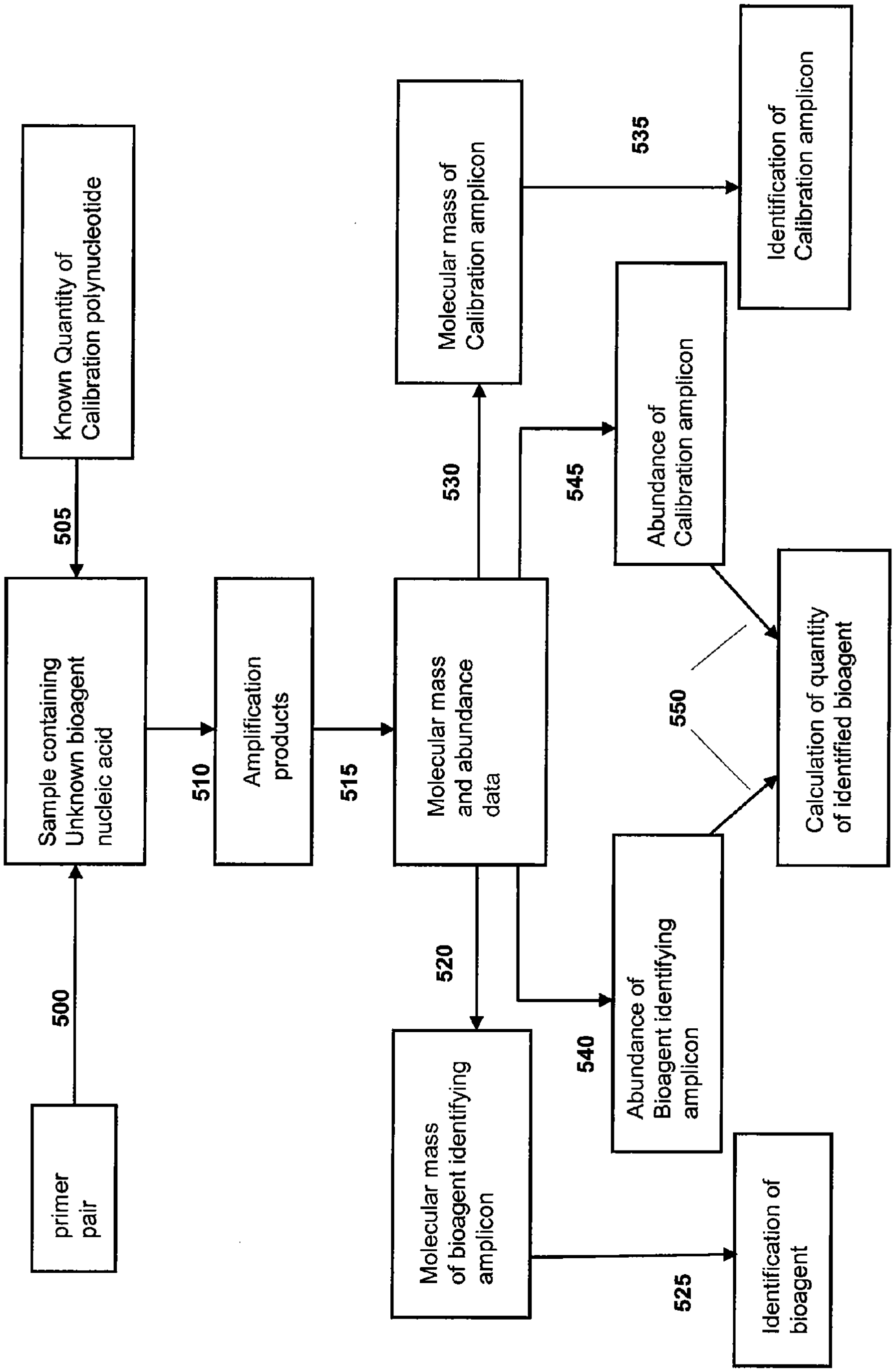
FIG. 2: process diagram illustrating an embodiment of the calibration method.

In some embodiments, the identity and quantity of an unknown bioagent can be determined using the process illustrated in FIG. 2. Primers (500) and a known quantity of a calibration polynucleotide (505) are added to a sample containing nucleic acid of an unknown bioagent. The total nucleic acid in the sample is then subjected to an amplification reaction (510) to obtain amplification products. The molecular masses of amplification products are determined (515) from which are obtained molecular mass and abundance data. The molecular mass of the bioagent identifying amplicon (520) provides the means for its identification (525) and the molecular mass of the calibration amplicon obtained from the calibration polynucleotide (530) provides the means for its identification (535). The abundance data of the bioagent identifying amplicon is recorded (540) and the abundance data for the calibration data is recorded (545), both of which are used in a calculation (550) which determines the quantity of unknown bioagent in the sample.

A sample comprising an unknown bioagent is contacted with a pair of primers that provide the means for amplification of nucleic acid from the bioagent, and a known quantity of a polynucleotide that comprises a calibration sequence. The nucleic acids of the bioagent and of the calibration sequence are amplified and the rate of amplification is reasonably assumed to be similar for the nucleic acid of the bioagent and of the calibration sequence. The amplification reaction then produces two amplification products: a bioagent identifying amplicon and a calibration amplicon. The bioagent identifying amplicon and the calibration amplicon should be distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample.

In some embodiments, construction of a standard curve where the amount of calibration polynucleotide spiked into the sample is varied provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single vector which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide should give rise to a calibration amplicon. Failure to produce a measurable calibration amplicon indicates a failure of amplification or subsequent analysis step such as amplicon purification or molecular mass determination. Reaching a conclusion that such failures have occurred is in itself, a useful event.

In some embodiments, the calibration sequence is comprised of DNA. In some embodiments, the calibration sequence is comprised of RNA.

In some embodiments, the calibration sequence is inserted into a vector that itself functions as the calibration polynucleotide. In some embodiments, more than one calibration sequence is inserted into the vector that functions as the calibration polynucleotide. Such a calibration polynucleotide is herein termed a "combination calibration polynucleotide." The process of inserting polynucleotides into vectors is routine to those skilled in the art and can be accomplished without undue experimentation. Thus, it should be recognized that the calibration method should not be limited to the embodiments described herein. The calibration method can be applied for determination of the quantity of any bioagent identifying amplicon when an appropriate standard calibrant polynucleotide sequence is designed and used. The process of choosing an appropriate vector for insertion of a calibrant is also a routine operation that can be accomplished by one with ordinary skill without undue experimentation.

H. Identification of Bacteria

In other embodiments of the present invention, the primer pairs produce bioagent identifying amplicons within stable and highly conserved regions of bacteria. The advantage to characterization of an amplicon defined by priming regions that fall within a highly conserved region is that there is a low probability that the region will evolve past the point of primer recognition, in which case, the primer hybridization of the amplification step would fail. Such a primer set is thus useful as a broad range survey-type primer. In another embodiment of the present invention, the intelligent primers produce bioagent identifying amplicons including a region which evolves more quickly than the stable region described above. The advantage of characterization bioagent identifying amplicon corresponding to an evolving genomic region is that it is useful for distinguishing emerging strain variants or the presence of virulence genes, drug resistance genes, or codon mutations that induce drug resistance.

The present invention also has significant advantages as a platform for identification of diseases caused by emerging bacterial strains such as, for example, drug-resistant strains of *Staphylococcus aureus*. The present invention eliminates the need for prior knowledge of bioagent sequence to generate hybridization probes. This is possible because the methods are not confounded by naturally occurring evolutionary variations occurring in the sequence acting as the template for production of the bioagent identifying amplicon. Measurement of molecular mass and determination of base composition is accomplished in an unbiased manner without sequence prejudice.

Another embodiment of the present invention also provides a means of tracking the spread of a bacterium, such as a particular drug-resistant strain when a plurality of samples obtained from different locations are analyzed by the methods described above in an epidemiological setting. In one embodiment, a plurality of samples from a plurality of different locations is analyzed with primer pairs which produce bioagent identifying amplicons, a subset of which contains a specific drug-resistant bacterial strain. The corresponding locations of the members of the drug-resistant strain subset indicate the spread of the specific drug-resistant strain to the corresponding locations.

I. Kits

The present invention also provides kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pairs recited in Table 2.

In some embodiments, the kit comprises one or more broad range survey primer(s), division wide primer(s), or drill-down primer(s), or any combination thereof. If a given problem involves identification of a specific bioagent, the solution to the problem may require the selection of a particular combination of primers to provide the solution to the problem. A kit may be designed so as to comprise particular primer pairs for identification of a particular bioagent. A drill-down kit may be used, for example, to distinguish different genotypes or strains, drug-resistant, or otherwise. In some embodiments, the primer pair components of any of these kits may be additionally combined to comprise additional combinations of broad range survey primers and division-wide primers so as to be able to identify a bacterium.

In some embodiments, the kit contains standardized calibration polynucleotides for use as internal amplification calibrants. Internal calibrants are described in commonly owned U.S. Patent Application Ser. No. 60/545,425 which is incorporated herein by reference in its entirety.

In some embodiments, the kit comprises a sufficient quantity of reverse transcriptase (if RNA is to be analyzed for example), a DNA polymerase, suitable nucleoside triphosphates (including alternative dNTPs such as inosine or modified dNTPs such as the 5-propynyl pyrimidines or any dNTP containing molecular mass-modifying tags such as those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

Some embodiments are kits that contain one or more survey bacterial primer pairs represented by primer pair compositions wherein each member of each pair of primers has 70% to 100% sequence identity with the corresponding member from the group of primer pairs represented by any of the primer pairs of Table 5. The survey primer pairs may include broad range primer pairs which hybridize to ribosomal RNA, and may also include division-wide primer pairs which hybridize to housekeeping genes such as rplB, tufB, rpoB, rpoC, valS, and infB, for example.

In some embodiments, a kit may contain one or more survey bacterial primer pairs and one or more triangulation genotyping analysis primer pairs such as the primer pairs of Tables 8, 12, 14, 19, 21, 23, or 24. In some embodiments, the kit may represent a less expansive genotyping analysis but include triangulation genotyping analysis primer pairs for more than one genus or species of bacteria. For example, a kit for surveying nosocomial infections at a health care facility may include, for example, one or more broad range survey primer pairs, one or more division wide primer pairs, one or more *Acinetobacter baumannii* triangulation genotyping analysis primer pairs and one or more *Staphylococcus aureus* triangulation genotyping analysis primer pairs. One with ordinary skill will be capable of analyzing in silico amplification data to determine which primer pairs will be able to provide optimal identification resolution for the bacterial bioagents of interest.

In some embodiments, a kit may be assembled for identification of strains of bacteria involved in contamination of food. An example of such a kit embodiment is a kit comprising one or more bacterial survey primer pairs of Table 5 with one or more triangulation genotyping analysis primer pairs of Table 12 which provide strain resolving capabilities for identification of specific strains of *Campylobacter jejuni.*

Some embodiments of the kits are 96-well or 384-well plates with a plurality of wells containing any or all of the following components: dNTPs, buffer salts, $Mg^{2+}$, betaine, and primer pairs. In some embodiments, a polymerase is also included in the plurality of wells of the 96-well or 384-well plates.

Some embodiments of the kit contain instructions for PCR and mass spectrometry analysis of amplification products obtained using the primer pairs of the kits.

Some embodiments of the kit include a barcode which uniquely identifies the kit and the components contained therein according to production lots and may also include any other information relative to the components such as concentrations, storage temperatures, etc. The barcode may also include analysis information to be read by optical barcode readers and sent to a computer controlling amplification, purification and mass spectrometric measurements. In some embodiments, the barcode provides access to a subset of base compositions in a base composition database which is in digital communication with base composition analysis software such that a base composition measured with primer pairs from a given kit can be compared with known base compositions of bioagent identifying amplicons defined by the primer pairs of that kit.

In some embodiments, the kit contains a database of base compositions of bioagent identifying amplicons defined by the primer pairs of the kit. The database is stored on a convenient computer readable medium such as a compact disk or USB drive, for example.

In some embodiments, the kit includes a computer program stored on a computer formatted medium (such as a compact disk or portable USB disk drive, for example) comprising instructions which direct a processor to analyze data obtained from the use of the primer pairs of the present invention. The instructions of the software transform data related to amplification products into a molecular mass or base composition which is a useful concrete and tangible result used in identification and/or classification of bioagents. In some embodiments, the kits of the present invention contain all of the reagents sufficient to carry out one or more of the methods described herein.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLES

Example 1

Design and Validation of Primers that Define Bioagent Identifying Amplicons for Identification of Bacteria For design of primers that define bacterial bioagent identifying amplicons, a series of bacterial genome segment sequences were obtained, aligned and scanned for regions where pairs of PCR primers would amplify products of about 45 to about 150 nucleotides in length and distinguish subgroups and/or individual strains from each other by their molecular masses or base compositions. A typical process shown in FIG. 1 is employed for this type of analysis.

A database of expected base compositions for each primer region was generated using an in silico PCR search algorithm, such as (ePCR). An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs.

Table 2 represents a collection of primers (sorted by primer pair number) designed to identify bacteria using the methods described herein. The primer pair number is an in-house database index number. Primer sites were identified on segments of genes, such as, for example, the 16S rRNA gene. The forward or reverse primer name shown in Table 2 indicates the gene region of the bacterial genome to which the primer hybridizes relative to a reference sequence. In Table 2, for example, the forward primer name 16 S_EC__1077__1106_F indicates that the forward primer (_F) hybridizes to residues 1077-1106 of the reference sequence represented by a sequence extraction of coordinates 4033120.4034661 from GenBank gi number 16127994 (as indicated in Table 3). As an additional example: the forward primer name BONTA_X52066__450__473 indicates that the primer hybridizes to residues 450-437 of the gene encoding *Clostridium botulinum* neurotoxin type A (BoNT/A) represented by GenBank Accession No. X52066 (primer pair name codes appearing in Table 2 are defined in Table 3. One with ordinary skill knows how to obtain individual gene sequences or portions thereof from genomic sequences present in GenBank. In Table 2, Tp=5-propynyluracil; Cp=5-propynylcytosine; *=phosphorothioate linkage; I=inosine. T. GenBank Accession Numbers for reference sequences of bacteria are shown in Table 3 (below). In some cases, the reference sequences are extractions from bacterial genomic sequences or complements thereof.

TABLE 2

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1 | 16S_EC_1077_1106_F | GTGAGATGTTGGGTTAAGTCCCGTAA CGAG | 134 | 16S_EC_1175_1195_R | GACGTCATCCCCACCTTCCTC | 809 |
| 2 | 16S_EC_1082_1106_F | ATGTTGGGTTAAGTCCCGCAACGAG | 38 | 16S_EC_1175_1197_R | TTGACGTCATCCCCACCTTCCTC | 1398 |
| 3 | 16S_EC_1090_1111_F | TTAAGTCCCGCAACGATCGCAA | 651 | 16S_EC_1175_1196_R | TGACGTCATCCCCACCTTCCTC | 1159 |
| 4 | 16S_EC_1222_1241_F | GCTACACACGTGCTACAATG | 114 | 16S_EC_1303_1323_R | CGAGTTGCAGACTGCGATCCG | 787 |
| 5 | 16S_EC_1332_1353_F | AAGTCGGAATCGCTAGTAATCG | 10 | 16S_EC_1389_1407_R | GACGGGCGGTGTGTACAAG | 806 |
| 6 | 16S_EC_30_54_F | TGAACGCTGGTGGCATGCTTAACAC | 429 | 16S_EC_105_126_R | TACGCATTACTCACCCGTCCGC | 897 |
| 7 | 168_EC_38_64_F | GTGGCATGCCTAATACATGCAAGTCG | 136 | 16S_EC_101_120_R | TTACTCACCCGTCCGCCGCT | 1365 |
| 8 | 16S_EC_49_68_F | TAACACATGCAAGTCGAACG | 152 | 16S_EC_104_120_R | TTACTCACCCGTCCGCC | 1364 |
| 9 | 16S_EC_683_700_F | GTGTAGCGGTGAAATGCG | 137 | 16S_EC_774_795_R | GTATCTAATCCTGTTTGCTCCC | 839 |
| 10 | 16S_EC_713_732_F | AGAACACCGATGGCGAAGGC | 21 | 16S_EC_789_809_R | CGTGGACTACCAGGGTATCTA | 798 |
| 11 | 16S_EC_785_806_F | GGATTAGAGACCCTGGTAGTCC | 118 | 16S_EC_880_897_R | GGCCGTACTCCCCAGGCG | 830 |
| 12 | 16S_EC_785_810_F | GGATTAGATACCCTGGTAGTCCACGC | 119 | 16S_EC_880_897_2_R | GGCCGTACTCCCCAGGCG | 830 |
| 13 | 16S_EC_789_810_F | TAGATACCCTGGTAGTCCACGC | 206 | 16S_EC_880_894_R | CGTACTCCCCAGGCG | 796 |
| 14 | 16S_EC_960_981_F | TTCGATGCAACGCGAAGAACCT | 672 | 16S_EC_1054_1073_R | ACGAGCTGACGACAGCCATG | 735 |
| 15 | 16S_EC_969_985_F | ACGCGAAGAACCTTACC | 19 | 16S_EC_1061_1078_R | ACGACACGAGCTGACGAC | 734 |
| 16 | 23S_EC_1826_1843_F | CTGACACCTGCCCGGTGC | 80 | 23S_EC_1906_1924_R | GACCGTTATAGTTACGGCC | 805 |
| 17 | 23S_EC_2645_2669_F | TCTGTCCCTAGTACGAGAGGACCGG | 408 | 23S_EC_2744_2761_R | TGCTTAGATGCTTTCAGC | 1252 |
| 18 | 23S_EC_2645_2669_2_F | CTGTCCCTAGTACGAGAGGACCGG | 83 | 23S_EC_2751_2767_R | GTTTCATGCTTAGATGCTTTCAGC | 846 |
| 19 | 23S_EC_493_518_F | GGGGAGTGAAAGAGATCCTGAAACCG | 125 | 23S_EC_551_571_R | ACAAAAGGTACGCCGTCACCC | 717 |
| 20 | 23S_EC_493_518_2_F | GGGGAGTGAAAGAGATCCTGAAACCG | 125 | 23S_EC_551_571_2_R | ACAAAAGGCACGCCATCACCC | 716 |
| 21 | 23S_EC_971_992_F | CGAGAGGGAAACAACCCAGACC | 66 | 23S_EC_1059_1077_R | TGGCTGCTTCTAAGCCAAC | 1282 |
| 22 | CAPC_BA_104_131_F | GTTATTTAGCACTCGTTTTTAATCAG CC | 139 | CAPC_BA_180_205_R | TGAATCTTGAAACACCATACGTAACG | 1150 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 23 | CAPC_BA_114_133_F | ACTCGTTTTTAATCAGCCCG | 20 | CAPC_BA_185_205_R | TGAATCTTGAAACACCATACG | 1149 |
| 24 | CAPC_BA_274_303_F | GATTATTGTTATCCTGTTATGCCATTTGAG | 109 | CAPC_BA_349_376_R | GTAACCCTTGTCTTTGAATTGTATTTGC | 837 |
| 25 | CAPC_BA_276_296_F | TTATTGTTATCCTGTTATGCC | 663 | CAPC_BA_358_377_R | GGTAACCCTTGTCTTTGAAT | 834 |
| 26 | CAPC_BA_281_301_F | GTTATCCTGTTATGCCATTTG | 138 | CAPC_BA_361_378_R | TGGTAACCCTTGTCTTTG | 1298 |
| 27 | CAPC_BA_315_334_F | CCGTGGTATTGGAGTTATTG | 59 | CAPC_BA_361_378_R | TGGTAACCCTTGTCTTTG | 1298 |
| 28 | CYA_BA_1055_1072_F | GAAAGAGTTCGGATTGGG | 92 | CYA_BA_1112_1130_R | TGTTGACCATGCTTCTTAG | 1352 |
| 29 | CYA_BA_1349_1370_F | ACAACGAAGTACAATACAAGAC | 12 | CYA_BA_1447_1426_R | CTTCTACATTTTTAGCCATCAC | 800 |
| 30 | CYA_BA_1353_1379_F | CGAAGTACAATACAAGACAAAAGAAGG | 64 | CYA_BA_1448_1467_R | TGTTAACGGCTTCAAGACCC | 1342 |
| 31 | CYA_BA_1359_1379_F | ACAATACAAGACAAAAGAAGG | 13 | CYA_BA_1447_1461_R | CGGCTTCAAGACCCC | 794 |
| 32 | CYA_BA_914_937_F | CAGGTTTAGTACCAGAACATGCAG | 53 | CYA_BA_999_1026_R | ACCACTTTTAATAAGGTTTGTAGCTAAC | 728 |
| 33 | CYA_BA_916_935_F | GGTTTAGTACCAGAACATGC | 131 | CYA_BA_1003_1025_R | CCACTTTTAATAAGGTTTGTAGC | 768 |
| 34 | INFB_EC_1365_1393_F | TGCTCGTGGTGCACAAGTAACGGATATTA | 524 | INFB_EC_1439_1467_R | TGCTGCTTTCGCATGGTTAATTGCTTCAA | 1248 |
| 35 | LEF_BA_1033_1052_F | TCAAGAAGAAAAAGAGC | 254 | LEF_BA_1119_1135_R | GAATATCAATTTGTAGC | 803 |
| 36 | LEF_BA_1036_1066_F | CAAGAAGAAAAAGAGCTTCTAAAAAGAATAC | 44 | LEF_BA_1119_1149_R | AGATAAAGAATCACGAATATCAATTTGTAGC | 745 |
| 37 | LEF_BA_756_781_F | AGCTTTTGCATATTATATCGAGCCAC | 26 | LEF_BA_843_872_R | TCTTCCAAGGATAGATTTATTTCTTGTTCG | 1135 |
| 38 | LEF_BA_758_778_F | CTTTTGCATATTATATCGAGC | 90 | LEF_BA_843_865_R | AGGATAGATTTATTTCTTGTTCG | 748 |
| 39 | LEF_BA_795_813_F | TTTACAGCTTTATGCACCG | 700 | LEF_BA_883_900_R | TCTTGACAGCATCCGTTG | 1140 |
| 40 | LEF_BA_883_899_F | CAACGGATGCTGGCAAG | 43 | LEF_BA_939_958_R | CAGATAAAGAATCGCTCCAG | 762 |
| 41 | PAG_BA_122_142_F | CAGAATCAAGTTCCCAGGGG | 49 | PAG_BA_190_209_R | CCTGTAGTAGAAGAGGTAAC | 781 |
| 42 | PAG_BA_123_145_F | AGAATCAAGTTCCCAGGGGTTAC | 22 | PAG_BA_187_210_R | CCCTGTAGTAGAAGAGGTAACCAC | 774 |
| 43 | PAG_BA_269_287_F | AATCTGCTATTTGGTCAGG | 11 | PAG_BA_326_344_R | TGATTATCAGCGGAAGTAG | 1186 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 44 | PAG_BA_655_675_F | GAAGGATATACGGTTGATGTC | 93 | PAG_BA_755_772_R | CCGTGCTCCATTTTTCAG | 778 |
| 45 | PAG_BA_753_772_F | TCCTGAAAAATGGAGCACGG | 341 | PAG_BA_849_868_R | TCGGATAAGCTGCCACAAGG | 1089 |
| 46 | PAG_BA_763_781_F | TGGAGCACGGCTTCTGATC | 552 | PAG_BA_849_868_R | TCGGATAAGCTGCCACAAGG | 1089 |
| 47 | RPOC_EC_1018_1045_F | CAAAACTTATTAGGTAAGCGTGTTGA CT | 39 | RPOC_EC_1095_1124_R | TCAAGCGCCATTTCTTTTGGTAAACCAC AT | 959 |
| 48 | RPOC_EC_1018_1045_2_F | CAAAACTTATTAGGTAAGCGTGTTGA CT | 39 | RPOC_EC_1095_1124_2_R | TCAAGCGCCATCTCTTTCGGTAATCCAC AT | 958 |
| 49 | RPOC_EC_114_140_F | TAAGAAGCCGGAAACCATCAACTACC G | 158 | RPOC_EC_213_232_R | GGCGCTTGTACTTACCGCAC | 831 |
| 50 | RPOC_EC_2178_2196_F | TGATTCTGGTGCCCGTGGT | 478 | RPOC_EC_2225_2246_R | TTGGCCATCAGGCCACGCATAC | 1414 |
| 51 | RPOC_EC_2178_2196_2_F | TGATTCCGGTGCCCGTGGT | 477 | RPOC_EC_2225_2246_2_R | TTGGCCATCAGACCACGCATAC | 1413 |
| 52 | RPOC_EC_2218_2241_F | CTGGCAGGTATGCGTGGTCTGATG | 81 | RPOC_EC_2313_2337_R | CGCACCGTGGGTTGAGATGAAGTAC | 790 |
| 53 | RPOC_EC_2218_2241_2_F | CTTGCTGGTATGCGTGGTCTGATG | 86 | RPOC_EC_2313_2337_2_R | CGCACCATGCGTAGAGATGAAGTAC | 789 |
| 54 | RPOC_EC_808_833_F | CGTCGGGTGATTAACCGTAACAACCG | 75 | RPOC_EC_865_889_R | GTTTTTCGTTGCGTACGATGATGTC | 847 |
| 55 | RPOC_EC_808_833_2_F | CGTCGTGTAATTAACCGTAACAACCG | 76 | RPOC_EC_865_891_R | ACGTTTTTCGTTTTGAACGATAATGCT | 741 |
| 56 | RPOC_EC_993_1019_F | CAAAGGTAAGCAAGGTCGTTTCCGTCA | 41 | RPOC_EC_1036_1059_R | CGAACGGCCAGAGTAGTCAACACG | 785 |
| 57 | RPOC_EC_993_1019_2_F | CAAAGGTAAGCAAGGACGTTTCCGTCA | 40 | RPOC_EC_1036_1059_2_R | CGAACGGCCAGAGTAGTCAACACG | 784 |
| 58 | SSPE_BA_115_137_F | CAAGCAAACGCACAATCAGAAGC | 45 | SSPE_BA_197_222_R | TGCACGTCTGTTTCAGTTGCAAATTC | 1201 |
| 59 | TUFB_EC_239_259_F | TAGACTGCCCAGGACACGCTG | 204 | TUFB_EC_283_303_R | GCCGTCCATCTGAGCAGCACC | 815 |
| 60 | TUFB_EC_239_259_2_F | TTGACTGCCCAGGTCACGCTG | 678 | TUFB_EC_283_303_2_R | GCCGTCCATTTGAGCAGCACC | 816 |
| 61 | TUFB_EC_976_1000_F | AACTACCGTCCGCAGTTCTACTTCC | 4 | TUFB_EC_1045_1068_R | GTTGTCGCCAGGCATAACCATTTC | 845 |
| 62 | TUFB_EC_976_1000_2_F | AACTACCGTCCTCAGTTCTACTTCC | 5 | TUFB_EC_1045_1068_2_R | GTTGTCACCAGGCATTACCATTTC | 844 |
| 63 | TUFB_EC_985_1012_F | CCACAGTTCTACTTCCGTACTACTGA CG | 56 | TUFB_EC_1033_1062_R | TCCAGGCATTACCATTTCTACTCCTTCT GG | 1006 |
| 66 | RPLB_EC_650_679_F | GACCTACAGTAAGAGGTTCTGTAATG AACC | 98 | RPLB_EC_739_762_R | TCCAAGTGCTGGTTTACCCCATGG | 999 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 67 | RPLB_EC_688_710_F | CATCCACACGGTGGTGGTGAAGG | 54 | RPLB_EC_736_757_R | GTGCTGGTTTACCCCATGGAGT | 842 |
| 68 | RPOC_EC_1036_1060_F | CGTGTTGACTATTCGGGGCGTTCAG | 78 | RPOC_EC_1097_1126_R | ATTCAAGAGCCATTTCTTTTGGTAAACC AC | 754 |
| 69 | RPOB_EC_3762_3790_F | TCAACAACCTCTTGGAGGTAAAGCTC AGT | 248 | RPOB_EC_3836_3865_R | TTTCTTGAAGAGTATGAGCTGCTCCGTA AG | 1435 |
| 70 | RPLB_EC_688_710_F | CATCCACACGGTGGTGGTGAAGG | 54 | RPLB_EC_743_771_R | TGTTTTGTATCCAAGTGCTGGTTTACCC C | 1356 |
| 71 | VALS_EC_1105_1124_F | CGTGGCGGCGTGGTTATCGA | 77 | VALS_EC_1195_1218_R | CGGTACGAACTGGATGTCGCCGTT | 795 |
| 72 | RPOB_EC_1845_1866_F | TATCGCTCAGGCGAACTCCAAC | 233 | RPOB_EC_1909_1929_R | GCTGGATTCGCCTTTGCTACG | 825 |
| 73 | RPLB_EC_669_698_F | TGTAATGAACCCTAATGACCATCCAC ACGG | 623 | RPLB_EC_735_761_R | CCAAGTGCTGGTTTACCCCATGGAGTA | 767 |
| 74 | RPLB_EC_671_700_F | TAATGAACCCTAATGACCATCCACAC GGTG | 169 | RPLB_EC_737_762_R | TCCAAGTGCTGGTTTACCCCATGGAG | 1000 |
| 75 | SP101_SPET11_1_29_F | AACCTTAATTGGAAAGAAACCCAAGA AGT | 2 | SP101_SPET11_92_116_R | CCTACCCAACGTTCACCAAGGGCAG | 779 |
| 76 | SP101_SPET11_118_147_F | GCTGGTGAAAATAACCCAGATGTCGT CTTC | 115 | SP101_SPET11_213_238_R | TGTGGCCGATTTCACCACCTGCTCCT | 1340 |
| 77 | SP101_SPET11_216_243_F | AGCAGGTGGTGAAATCGGCCACATGA TT | 24 | SP101_SPET11_308_333_R | TGCCACTTTGACAACTCCTGTTGCTG | 1209 |
| 78 | SP101_SPET11_266_295_F | CTTGTACTTGTGGCTCACACGGCTGT TTGG | 89 | SP101_SPET11_355_380_R | GCTGCTTTGATGGCTGAATCCCCTTC | 824 |
| 79 | SP101_SPET11_322_344_F | GTCAAAGTGGCACGTTTACTGGC | 132 | SP101_SPET11_423_441_R | ATCCCCTGCTTCTGCTGCC | 753 |
| 80 | SP101_SPET11_358_387_F | GGGGATTCAGCCATCAAAGCAGCTAT TGAC | 126 | SP101_SPET11_448_473_R | CCAACCTTTTCCACAACAGAATCAGC | 766 |
| 81 | SP101_SPET11_600_629_F | CCTTACTTCGAACTATGAATCTTTTG GAAG | 62 | SP101_SPET11_686_714_R | CCCATTTTTTCACGCATGCTGAAAATAT C | 772 |
| 82 | SP101_SPET11_658_684_F | GGGGATTGATATCACCGATAAGAAGA A | 127 | SP101_SPET11_756_784_R | GATTGGCGATAAAGTGATATTTTCTAAA A | 813 |
| 83 | SP101_SPET11_776_801_F | TCGCCAATCAAAACTAAGGGAATGGC | 364 | SP101_SPET11_871_896_R | GCCCACCAGAAAGACTAGCAGGATAA | 814 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 84 | SP101_SPET11_893_921_F | GGGCAACAGCAGCGGATTGCGATTGC GCG | 123 | SP101_SPET11_988_1012_R | CATGACAGCCAAGACCTCACCCACC | 763 |
| 85 | SP101_SPET11_1154_1179_F | CAATACCGCAACAGCGGTGGCTTGGG | 47 | SP101_SPET11_1251_1277_R | GACCCCAACCTGGCCTTTTGTCGTTGA | 804 |
| 86 | SP101_SPET11_1314_1336_F | CGCAAAAAAATCCAGCTATTAGC | 68 | SP101_SPET11_1403_1431_R | AAACTATTTTTTTAGCTATACTCGAACA C | 711 |
| 87 | SP101_SPET11_1408_1437_F | CGAGTATAGCTAAAAAAATAGTTTAT GACA | 67 | SP101_SPET11_1486_1515_R | GGATAATTGGTCGTAACAAGGGATAGTG AG | 828 |
| 88 | SP101_SPET11_1688_1716_F | CCTATATTAATCGTTTACAGAAACTG GCT | 60 | SP101_SPET11_1783_1808_R | ATATGATTATCATTGAACTGCGGCCG | 752 |
| 89 | SP101_SPET11_1711_1733_F | CTGGCTAAAACTTTGGCAACGGT | 82 | SP101_SPET11_1808_1835_R | GCGTGACGACCTTCTTGAATTGTAATCA | 821 |
| 90 | SP101_SPET11_1807_1835_F | ATGATTACAATTCAAGAAGGTCGTCA CGC | 33 | SP101_SPET11_1901_1927_R | TTGGACCTGTAATCAGCTGAATACTGG | 1412 |
| 91 | SP101_SPET11_1967_1991_F | TAACGGTTATCATGGCCCAGATGGG | 155 | SP101_SPET11_2062_2083_R | ATTGCCCAGAAATCAAATCATC | 755 |
| 92 | SP101_SPET11_2260_2283_F | CAGAGACCGTTTTATCCTATCAGC | 50 | SP101_SPET11_2375_2397_R | TCTGGGTGACCTGGTGTTTTAGA | 1131 |
| 93 | SP101_SPET11_2375_2399_F | TCTAAAACACCAGGTCACCCAGAAG | 390 | SP101_SPET11_2470_2497_R | AGCTGCTAGATGAGCTTCTGCCATGGCC | 747 |
| 94 | SP101_SPET11_2468_2487_F | ATGGCCATGGCAGAAGCTCA | 35 | SP101_SPET11_2543_2570_R | CCATAAGGTCACCGTCACCATTCAAAGC | 770 |
| 95 | SP101_SPET11_2961_2984_F | ACCATGACAGAAGGCATTTTGACA | 15 | SP101_SPET11_3023_3045_R | GGAATTTACCAGCGATAGACACC | 827 |
| 96 | SP101_SPET11_3075_3103_F | GATGACTTTTTAGCTAATGGTCAGGC AGC | 108 | SP101_SPET11_3168_3196_R | AATCGACGACCATCTTGGAAAGATTTCT C | 715 |
| 97 | SP101_SPET11_3386_3403_F | AGCGTAAAGGTGAACCTT | 25 | SP101_SPET11_3480_3506_R | CCAGCAGTTACTGTCCCCTCATCTTTG | 769 |
| 98 | SP101_SPET11_3511_3535_F | GCTTCAGGAATCAATGATGGAGCAG | 116 | SP101_SPET11_2470_2497_R | GGGTCTACACCTGCACTTGCATAAC | 832 |
| 111 | RPOB_EC_3775_3803_F | CTTGGAGGTAAGTCTCATTTTGGTGG GCA | 87 | RPOB_EC_3829_3858_R | CGTATAAGCTGCACCATAAGCTTGTAAT GC | 797 |
| 112 | VALS_EC_1833_1850_F | CGACGCGCTGCGCTTCAC | 65 | VALS_EC_1920_1943_R | GCGTTCCACAGCTTGTTGCAGAAG | 822 |
| 113 | RPOB_EC_1336_1353_F | GACCACCTCGGCAACCGT | 97 | RPOB_EC_1438_1455_R | TTCGCTCTCGGCCTGGCC | 1386 |
| 114 | TUFB_EC_225_251_F | GCACTATGCACACGTAGATTGTCCTG G | 111 | TUFB_EC_284_309_R | TATAGCACCATCCATCTGAGCGGCAC | 930 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| Primer Pairs for Identification of Bacteria | | | | | | |
| 115 | DNAK_EC_428_449_F | CGGCGTACTTCAACGACAGCCA | 72 | DNAK_EC_503_522_R | CGCGGGTCGGCTCGTTGATGA | 792 |
| 116 | VALS_EC_1920_1943_F | CTTCTGCAACAAGCTGTGGAACGC | 85 | VALS_EC_1948_1970_R | TCGCAGTTCATCAGCACGAAGCG | 1075 |
| 117 | TUFB_EC_757_774_F | AAGACGACCTGCACGGGC | 6 | TUFB_EC_849_867_R | GCGCTCCACGTCTTCACGC | 819 |
| 118 | 23S_EC_2646_2667_F | CTGTTCTTAGTACGAGAGGACC | 84 | 23S_EC_2745_2765_R | TTCGTGCTTAGATGCTTTCAG | 1389 |
| 119 | 16S_EC_969_985_1P_F | ACGCGAAGAACCTTACpc | 19 | 16S_EC_1061_1078_2P_R | ACGACACGAGCpTpGACGAC | 733 |
| 120 | 16S_EC_972_985_2P_F | CGAAGAACpCpTTACC | 63 | 16S_EC_1064_1075_2P_R | ACACGAGCpTpGAC | 727 |
| 121 | 16S_EC_972_985_F | CGAAGAACCTTACC | 63 | 16S_EC_1064_1075_R | ACACGAGCTGAC | 727 |
| 122 | TRNA_ILE-RRNH_EC_32_50.2_F | CCTGATAAGGGTGAGGTCG | 61 | 23S_EC_40_59_R | ACGTCCTTCATCGCCTCTGA | 740 |
| 123 | 23S_EC_-7_15_F | GTTGTGAGGTTAAGCGACTAAG | 140 | 23S_EC_430_450_R | CTATCGGTCAGTCAGGAGTAT | 799 |
| 124 | 23S_EC_-7_15_F | GTTGTGAGGTTAAGCGACTAAG | 141 | 23S_EC_891_910_R | TTGCATCGGGTTGGTAAGTC | 1403 |
| 125 | 23S_EC_430_450_F | ATACTCCTGACTGACCGATAG | 30 | 23S_EC_1424_1442_R | AACATAGCCTTCTCCGTCC | 712 |
| 126 | 23S_EC_891_910_F | GACTTACCAACCCGATGCAA | 100 | 23S_EC_1908_1931_R | TACCTTAGGACCGTTATAGTTACG | 893 |
| 127 | 23S_EC_1424_1442_F | GGACGGAGAAGGCTATGTT | 117 | 23S_EC_2475_2494_R | CCAAACACCGCCGTCGATAT | 765 |
| 128 | 23S_EC_1908_1931_F | CGTAACTATAACGGTCCTAAGGTA | 73 | 23S_EC_2833_2852_R | GCTTACACACCCGGCCTATC | 826 |
| 129 | 23S_EC_2475_2494_F | ATATCGACGGCGGTGTTTGG | 31 | TRNA_ASP-RRNH_EC_23_41.2_R | GCGTGACAGGCAGGTATTC | 820 |
| 131 | 16S_EC_-60_-39_F | AGTCTCAAGAGTGAACACGTAA | 28 | 16S_EC_508_525_R | GCTGCTGGCACGGAGTTA | 823 |
| 132 | 16S_EC_326_345_F | GACACGGTCCAGACTCCTAC | 95 | 16S_EC_1041_1058_R | CCATGCAGCACCTGTCTC | 771 |
| 133 | 16S_EC_705_724_F | GATCTGGAGGAATACCGGTG | 107 | 16S_EC_1493_1512_R | ACGGTTACCTTGTTACGACT | 739 |
| 134 | 16S_EC_1268_1287_F | GAGAGCAAGCGGACCTCATA | 101 | TRNA_ALA-RRNH_EC_30_46.2_R | CCTCCTGCGTGCAAAGC | 780 |
| 135 | 16S_EC_969_985_F | ACGCGAAGAACCTTACC | 19 | 16S_EC_1061_1078.2_R | ACAACACGAGCTGACGAC | 719 |
| 137 | 16S_EC_969_985_F | ACGCGAAGAACCTTACC | 19 | 16S_EC_1061_1078.2_I14_R | ACAACACGAGCTGICGAC | 721 |
| 138 | 16S_EC_969_985_F | ACGCGAAGAACCTTACC | 19 | 16S_EC_1061_1078.2_I12_R | ACAACACGAGCIGACGAC | 718 |
| 139 | 16S_EC_969_985_F | ACGCGAAGAACCTTACC | 19 | 16S_EC_1061_1078.2_I11_R | ACAACACGAGITGACGAC | 722 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 140 | 16S_EC_969_985_F | ACGCGAAGAACCTTACC | 19 | 16S_EC_1061_1078.2_I16_R | ACAACACGAGCTGACIAC | 720 |
| 141 | 16S_EC_969_985_F | ACGCGAAGAACCTTACC | 19 | 16S_EC_1061_1078.2_2I_R | ACAACACGAICTIACGAC | 723 |
| 142 | 16S_EC_969_985_F | ACGCGAAGAACCTTACC | 19 | 16S_EC_1061_1078.2_3I_R | ACAACACIAICTIACGAC | 724 |
| 143 | 16S_EC_969_985_F | ACGCGAAGAACCTTACC | 19 | 16S_EC_1061_1078.2_4I_R | ACAACACIAICTIACIAC | 725 |
| 147 | 23S_EC_2652_2669_F | CTAGTACGAGAGGACCGG | 79 | 23S_EC_2741_2760_R | ACTTAGATGCTTTCAGCGGT | 743 |
| 158 | 16S_EC_683_700_F | GTGTAGCGGTGAAATGCG | 137 | 16S_EC_880_894_R | CGTACTCCCCAGGCG | 796 |
| 159 | 16S_EC_1100_1116_F | CAACGAGCGCAACCCTT | 42 | 16S_EC_1174_1188_R | TCCCCACCTTCCTCC | 1019 |
| 215 | SSPE_BA_121_137_F | AACGCACAATCAGAAGC | 3 | SSPE_BA_197_216_R | TCTGTTTCAGTTGCAAATTC | 1132 |
| 220 | GROL_EC_941_959_F | TGGAAGATCTGGGTCAGGC | 544 | GROL_EC_1039_1060_R | CAATCTGCTGACGGATCTGAGC | 759 |
| 221 | INFB_EC_1103_1124_F | GTCGTGAAAACGAGCTGGAAGA | 133 | INFB_EC_1174_1191_R | CATGATGGTCACAACCGG | 764 |
| 222 | HFLB_EC_1082_1102_F | TGGCGAACCTGGTGAACGAAGC | 569 | HFLB_EC_1144_1168_R | CTTTCGCTTTCTCGAACTCAACCAT | 802 |
| 223 | INFB_EC_1969_1994_F | CGTCAGGGTAAATTCCGTGAAGTTAA | 74 | INFB_EC_2038_2058_R | AACTTCGCCTTCGGTCATGTT | 713 |
| 224 | GROL_EC_219_242_F | GGTGAAAGAAGTTGCCTCTAAAGC | 128 | GROL_EC_328_350_R | TTCAGGTCCATCGGGTTCATGCC | 1377 |
| 225 | VALS_EC_1105_1124_F | CGTGGCGGCGTGGTTATCGA | 77 | VALS_EC_1195_1214_R | ACGAACTGGATGTCGCCGTT | 732 |
| 226 | 16S_EC_556_575_F | CGGAATTACTGGGCGTAAAG | 70 | 16S_EC_683_700_R | CGCATTTCACCGCTACAC | 791 |
| 227 | RPOC_EC_1256_1277_F | ACCCAGTGCTGCTGAACCGTGC | 16 | RPOC_EC_1295_1315_R | GTTCAAATGCCTGGATACCCA | 843 |
| 228 | 16S_EC_774_795_F | GGGAGCAAACAGGATTAGATAC | 122 | 16S_EC_880_894_R | CGTACTCCCCAGGCG | 796 |
| 229 | RPOC_EC_1584_1604_F | TGGCCCGAAAGAAGCTGAGCG | 567 | RPOC_EC_1623_1643_R | ACGCGGGCATGCAGAGATGCC | 737 |
| 230 | 16S_EC_1082_1100_F | ATGTTGGGTTAAGTCCCGC | 37 | 16S_EC_1177_1196_R | TGACGTCATCCCCACCTTCC | 1158 |
| 231 | 16S_EC_1389_1407_F | CTTGTACACACCGCCCGTC | 88 | 16S_EC_1525_1541_R | AAGGAGGTGATCCAGCC | 714 |
| 232 | 16S_EC_1303_1323_F | CGGATTGGAGTCTGCAACTCG | 71 | 16S_EC_1389_1407_R | GACGGGCGGTGTGTACAAG | 808 |
| 233 | 23S_EC_23_37_F | GGTGGATGCCTTGGC | 129 | 23S_EC_115_130_R | GGGTTTCCCCATTCGG | 833 |
| 234 | 23S_EC_187_207_F | GGGAACTGAAACATCTAAGTA | 121 | 23S_EC_242_256_R | TTCGCTCGCCGCTAC | 1385 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| Primer Pairs for Identification of Bacteria | | | | | | |
| 235 | 23S_EC_1602_1620_F | TACCCCAAACCGACACAGG | 184 | 23S_EC_1686_1703_R | CCTTCTCCCGAAGTTACG | 782 |
| 236 | 23S_EC_1685_1703_F | CCGTAACTTCGGGAGAAGG | 58 | 23S_EC_1828_1842_R | CACCGGGCAGGCGTC | 760 |
| 237 | 23S_EC_1827_1843_F | GACGCCTGCCCGGTGC | 99 | 23S_EC_1929_1949_R | CCGACAAGGAATTTCGCTACC | 775 |
| 238 | 23S_EC_2434_2456_F | AAGGTACTCCGGGGATAACAGGC | 9 | 23S_EC_2490_2511_R | AGCCGACATCGAGGTGCCAAAC | 746 |
| 239 | 23S_EC_2599_2616_F | GACAGTTCGGTCCCTATC | 96 | 23S_EC_2653_2669_R | CCGGTCCTCTCGTACTA | 777 |
| 240 | 23S_EC_2653_2669_F | TAGTACGAGAGGACCGG | 227 | 23S_EC_2737_2758_R | TTAGATGCTTTCAGCACTTATC | 1369 |
| 241 | 23S_BS_-68_-44_F | AAACTAGATAACAGTAGACATCAC | 1 | 23S_BS_5_21_R | GTGCGCCCTTTCTAACTT | 841 |
| 242 | 16S_EC_8_27_F | AGAGTTTGATCATGGCTCAG | 23 | 16S_EC_342_358_R | ACTGCTGCCTCCCGTAG | 742 |
| 243 | 16S_EC_314_332_F | CACTGGAACTGAGACACGG | 48 | 16S_EC_556_575_R | CTTTACGCCCAGTAATTCCG | 801 |
| 244 | 16S_EC_518_536_F | CCAGCAGCCGCGGTAATAC | 57 | 16S_EC_774_795_R | GTATCTAATCCTGTTTGCTCCC | 839 |
| 245 | 16S_EC_683_700_F | GTGTAGCGGTGAAATGCG | 137 | 16S_EC_967_985_R | GGTAAGGTTCTTCGCGTTG | 835 |
| 246 | 16S_EC_937_954_F | AAGCGGTGGAGCATGTGG | 7 | 16S_EC_1220_1240_R | ATTGTAGCACGTGTGTAGCCC | 757 |
| 247 | 16S_EC_1195_1213_F | CAAGTCATCATGGCCCTTA | 46 | 16S_EC_1525_1541_R | AAGGAGGTGATCCAGCC | 714 |
| 248 | 16S_EC_8_27_F | AGAGTTTGATCATGGCTCAG | 23 | 16S_EC_1525_1541_R | AAGGAGGTGATCCAGCC | 714 |
| 249 | 23S_EC_1831_1849_F | ACCTGCCCAGTGCTGGAAG | 18 | 23S_EC_1919_1936_R | TCGCTACCTTAGGACCGT | 1080 |
| 250 | 16S_EC_1387_1407_F | GCCTTGTACACACCTCCCGTC | 112 | 16S_EC_1494_1513_R | CACGGCTACCTTGTTACGAC | 761 |
| 251 | 16S_EC_1390_1411_F | TTGTACACACCGCCCGTCATAC | 693 | 16S_EC_1486_1505_R | CCTTGTTACGACTTCACCCC | 783 |
| 252 | 16S_EC_1367_1387_F | TACGGTGAATACGTTCCCGGG | 191 | 16S_EC_1485_1506_R | ACCTTGTTACGACTTCACCCCA | 731 |
| 253 | 16S_EC_804_822_F | ACCACGCCGTAAACGATGA | 14 | 16S_EC_909_929_R | CCCCCGTCAATTCCTTTGAGT | 773 |
| 254 | 16S_EC_791_812_F | GATACCCTGGTAGTCCACACCG | 106 | 16S_EC_886_904_R | GCCTTGCGACCGTACTCCC | 817 |
| 255 | 16S_EC_789_810_F | TAGATACCCTGGTAGTCCACGC | 206 | 16S_EC_882_899_R | GCGACCGTACTCCCCAGG | 818 |
| 256 | 16S_EC_1092_1109_F | TAGTCCCGCAACGAGCGC | 228 | 16S_EC_1174_1195_R | GACGTCATCCCCACCTTCCTCC | 810 |
| 257 | 23S_EC_2586_2607_F | TAGAACGTCGCGAGACAGTTCG | 203 | 23S_EC_2658_2677_R | AGTCCATCCCGGTCCTCTCG | 749 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| Primer Pairs for Identification of Bacteria | | | | | | |
| 258 | RNASEP_SA_31_49_F | GAGGAAAGTCCATGCTCAC | 103 | RNASEP_SA_358_379_R | ATAAGCCATGTTCTGTTCCATC | 750 |
| 258 | RNASEP_SA_31_49_F | GAGGAAAGTCCATGCTCAC | 103 | RNASEP_EC_345_362_R | ATAAGCCGGGTTCTGTCG | 751 |
| 258 | RNASEP_SA_31_49_F | GAGGAAAGTCCATGCTCAC | 103 | RNASEP_BS_363_384_R | GTAAGCCATGTTTTGTTCCATC | 838 |
| 258 | RNASEP_BS_43_61_F | GAGGAAAGTCCATGCTCGC | 104 | RNASEP_SA_358_379_R | ATAAGCCATGTTCTGTTCCATC | 750 |
| 258 | RNASEP_BS_43_61_F | GAGGAAAGTCCATGCTCGC | 104 | RNASEP_EC_345_362_R | ATAAGCCGGGTTCTGTCG | 751 |
| 258 | RNASEP_BS_43_61_F | GAGGAAAGTCCATGCTCGC | 104 | RNASEP_BS_363_384_R | GTAAGCCATGTTTTGTTCCATC | 838 |
| 258 | RNASEP_EC_61_77_F | GAGGAAAGTCCGGGCTC | 105 | RNASEP_SA_358_379_R | ATAAGCCATGTTCTGTTCCATC | 750 |
| 258 | RNASEP_EC_61_77_F | GAGGAAAGTCCGGGCTC | 105 | RNASEP_EC_345_362_R | ATAAGCCGGGTTCTGTCG | 751 |
| 258 | RNASEP_EC_61_77_F | GAGGAAAGTCCGGGCTC | 105 | RNASEP_BS_363_384_R | GTAAGCCATGTTTTGTTCCATC | 838 |
| 259 | RNASEP_BS_43_61_F | GAGGAAAGTCCATGCTCGC | 104 | RNASEP_BS_363_384_R | GTAAGCCATGTTTTGTTCCATC | 838 |
| 260 | RNASEP_EC_61_77_F | GAGGAAAGTCCGGGCTC | 105 | RNASEP_EC_345_362_R | ATAAGCCGGGTTCTGTCG | 751 |
| 262 | RNASEP_SA_31_49_F | GAGGAAAGTCCATGCTCAC | 103 | RNASEP_SA_358_379_R | ATAAGCCATGTTCTGTTCCATC | 750 |
| 263 | 16S_EC_1082_1100_F | ATGTTGGGTTAAGTCCCGC | 37 | 16S_EC_1525_1541_R | AAGGAGGTGATCCAGCC | 714 |
| 264 | 16S_EC_556_575_F | CGGAATTACTGGGCGTAAAG | 70 | 16S_EC_774_795_R | GTATCTAATCCTGTTTGCTCCC | 839 |
| 265 | 16S_EC_1082_1100_F | ATGTTGGGTTAAGTCCCGC | 37 | 16S_EC_1177_1196_10G_R | TGACGTCATGCCCACCTTCC | 1160 |
| 266 | 16S_EC_1082_1100_F | ATGTTGGGTTAAGTCCCGC | 37 | 16S_EC_1177_1196_10G_11G_R | TGACGTCATGGCCACCTTCC | 1161 |
| 268 | YAED_EC_513_532_F_MOD | GGTGTTAAATAGCCTGGCAG | 130 | TRNA_ALA-RRNH_EC_30_49_F_MOD | AGACCTCCTGCGTGCAAAGC | 744 |
| 269 | 16S_EC_1082_1100_F_MOD | ATGTTGGGTTAAGTCCCGC | 37 | 16S_EC_1177_1196_R_MOD | TGACGTCATCCCCACCTTCC | 1158 |
| 270 | 23S_EC_2586_2607_F_MOD | TAGAACGTCGCGAGACAGTTCG | 203 | 23S_EC_2658_2677_R_MOD | AGTCCATCCCGGTCCTCTCG | 749 |
| 272 | 16S_EC_969_985_F | ACGCGAAGAACCTTACC | 19 | 16S_EC_1389_1407_R | GACGGGCGGTGTGTACAAG | 807 |
| 273 | 16S_EC_683_700_F | GTGTAGCGGTGAAATGCG | 137 | 16S_EC_1303_1323_R | CGAGTTGCAGACTGCGATCCG | 788 |
| 274 | 16S_EC_49_68_F | TAACACATGCAAGTCGAACG | 152 | 16S_EC_880_894_R | CGTACTCCCCAGGCG | 796 |
| 275 | 16S_EC_49_68_F | TAACACATGCAAGTCGAACG | 152 | 16S_EC_1061_1078_R | ACGACACGAGCTGACGAC | 734 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 277 | CYA_BA_1349_1370_F | ACAACGAAGTACAATACAAGAC | 12 | CYA_BA_1426_1447_R | CTTCTACATTTTTAGCCATCAC | 800 |
| 278 | 16S_EC_1090_1111_2_F | TTAAGTCCCGCAACGAGCGCAA | 650 | 16S_EC_1175_1196_R | TGACGTCATCCCCACCTTCCTC | 1159 |
| 279 | 16S_EC_405_432_F | TGAGTGATGAAGGCCTTAGGGTTGTAAA | 464 | 16S_EC_507_527_R | CGGCTGCTGGCACGAAGTTAG | 793 |
| 280 | GROL_EC_496_518_F | ATGGACAAGGTTGGCAAGGAAGG | 34 | GROL_EC_577_596_R | TAGCCGCGGTCGAATTGCAT | 914 |
| 281 | GROL_EC_511_536_F | AAGGAAGGCGTGATCACCGTTGAAGA | 8 | GROL_EC_571_593_R | CCGCGGTCGAATTGCATGCCTTC | 776 |
| 288 | RPOB_EC_3802_3821_F | CAGCGTTTCGGCGAAATGGA | 51 | RPOB_EC_3862_3885_R | CGACTTGACGGTTAACATTTCCTG | 786 |
| 289 | RPOB_EC_3799_3821_F | GGGCAGCGTTTCGGCGAAATGGA | 124 | RPOB_EC_3862_3888_R | GTCCGACTTGACGGTCAACATTTCCTG | 840 |
| 290 | RPOC_EC_2146_2174_F | CAGGAGTCGTTCAACTCGATCTACATGAT | 52 | RPOC_EC_2227_2245_R | ACGCCATCAGGCCACGCAT | 736 |
| 291 | ASPS_EC_405_422_F | GCACAACCTGCGGCTGCG | 110 | ASPS_EC_521_538_R | ACGGCACGAGGTAGTCGC | 738 |
| 292 | RPOC_EC_1374_1393_F | CGCCGACTTCGACGGTGACC | 69 | RPOC_EC_1437_1455_R | GAGCATCAGCGTGCGTGCT | 811 |
| 293 | TUFB_EC_957_979_F | CCACACGCCGTTCTTCAACAACT | 55 | TUFB_EC_1034_1058_R | GGCATCACCATTTCCTTGTCCTTCG | 829 |
| 294 | 16S_EC_7_33_F | GAGAGTTTGATCCTGGCTCAGAACGAA | 102 | 16S_EC_101_122_R | TGTTACTCACCCGTCTGCCACT | 1345 |
| 295 | VALS_EC_610_649_F | ACCGAGCAAGGAGACCAGC | 17 | VALS_EC_705_727_R | TATAACGCACATCGTCAGGGTGA | 929 |
| 344 | 16S_EC_971_990_F | GCGAAGAACCTTACCAGGTC | 113 | 16S_EC_1043_1062_R | ACAACCATGCACCACCTGTC | 726 |
| 346 | 16S_EC_713_732_TMOD_F | TAGAACACCGATGGCGAAGGC | 202 | 16S_EC_789_809_TMOD_R | TCGTGGACTACCAGGGTATCTA | 1110 |
| 347 | 16S_EC_785_806_TMOD_F | TGGATTAGAGACCCTGGTAGTCC | 560 | 16S_EC_880_897_TMOD_R | TGGCCGTACTCCCCAGGCG | 1278 |
| 348 | 16S_EC_960_981_TMOD_F | TTTCGATGCAACGCGAAGAACCT | 706 | 16S_EC_1054_1073_TMOD_R | TACGAGCTGACGACAGCCATG | 895 |
| 349 | 23S_EC_1826_1843_TMOD_F | TCTGACACCTGCCCGGTGC | 401 | 23S_EC_1906_1924_TMOD_R | TGACCGTTATAGTTACGGCC | 1156 |
| 350 | CAPC_BA_274_303_TMOD_F | TGATTATTGTTATCCTGTTATGCCATTTGAG | 476 | CAPC_BA_349_376_TMOD_R | TGTAACCCTTGTCTTTGAATTGTATTTGC | 1314 |
| 351 | CYA_BA_1353_1379_TMOD_F | TCGAAGTACAATACAAGACAAAAGAAGG | 355 | CYA_BA_1448_1467_TMOD_R | TTGTTAACGGCTTCAAGACCC | 1423 |
| 352 | INFB_EC_1365_1393_TMOD_F | TTGCTCGTGGTGCACAAGTAACGGATATTA | 687 | INFB_EC_1439_1467_TMOD_R | TTGCTGCTTTCGCATGGTTAATTGCTTCAA | 1411 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 353 | LEF_BA_756_781_TMOD_F | TAGCTTTTGCATATTATATCGAGCCA C | 220 | LEF_BA_843_872_TMOD_R | TTCTTCCAAGGATAGATTTATTTCTTGT TCG | 1394 |
| 354 | RPOC_EC_2218_2241_TMOD_F | TCTGGCAGGTATGCGTGGTCTGATG | 405 | RPOC_EC_2313_2337_TMOD_R | TCGCACCGTGGGTTGAGATGAAGTAC | 1072 |
| 355 | SSPE_BA_115_137_TMOD_F | TCAAGCAAACGCACAATCAGAAGC | 255 | SSPE_BA_197_222_TMOD_R | TTGCACGTCTGTTTCAGTTGCAAATTC | 1402 |
| 356 | RPLB_EC_650_679_TMOD_F | TGACCTACAGTAAGAGGTTCTGTAAT GAACC | 449 | RPLB_EC_739_762_TMOD_R | TTCCAAGTGCTGGTTTACCCCATGG | 1380 |
| 357 | RPLB_EC_688_710_TMOD_F | TCATCCACACGGTGGTGGTGAAGG | 296 | RPLB_EC_736_757_TMOD_R | TGTGCTGGTTTACCCCATGGAGT | 1337 |
| 358 | VALS_EC_1105_1124_TMOD_F | TCGTGGCGGCGTGGTTATCGA | 385 | VALS_EC_1195_1218_TMOD_R | TCGGTACGAACTGGATGTCGCCGTT | 1093 |
| 359 | RPOB_EC_1845_1866_TMOD_F | TTATCGCTCAGGCGAACTCCAAC | 659 | RPOB_EC_1909_1929_TMOD_R | TGCTGGATTCGCCTTTGCTACG | 1250 |
| 360 | 23S_EC_2646_2667_TMOD_F | TCTGTTCTTAGTACGAGAGGACC | 409 | 23S_EC_2745_2765_TMOD_R | TTTCGTGCTTAGATGCTTTCAG | 1434 |
| 361 | 16S_EC_1090_1111_2_TMOD_F | TTTAAGTCCCGCAACGAGCGCAA | 697 | 16S_EC_1175_1196_TMOD_R | TTGACGTCATCCCCACCTTCCTC | 1398 |
| 362 | RPOB_EC_3799_3821_TMOD_F | TGGGCAGCGTTTCGGCGAAATGGA | 581 | RPOB_EC_3862_3888_TMOD_R | TGTCCGACTTGACGGTCAACATTTCCTG | 1325 |
| 363 | RPOC_EC_2146_2174_TMOD_F | TCAGGAGTCGTTCAACTCGATCTACA TGAT | 284 | RPOC_EC_2227_2245_TMOD_R | TACGCCATCAGGCCACGCAT | 898 |
| 364 | RPOC_EC_1374_1393_TMOD_F | TCGCCGACTTCGACGGTGACC | 367 | RPOC_EC_1437_1455_TMOD_R | TGAGCATCAGCGTGCGTGCT | 1166 |
| 367 | TUFB_EC_957_979_TMOD_F | TCCACACGCCGTTCTTCAACAACT | 308 | TUFB_BC_1034_1058_TMOD_R | TGGCATCACCATTTCCTTGTCCTTCG | 1276 |
| 423 | SP101_SPET11_893_ 921_TMOD_F | TGGGCAACAGCAGCGGATTGCGATTG CGCG | 580 | SP101_SPET11_988_1012_ TMOD_R | TCATGACAGCCAAGACCTCACCCACC | 990 |
| 424 | SP101_SPET11_1154_ 1179_TMOD_F | TCAATACCGCAACAGCGGTGGCTTGG G | 258 | SP101_SPET11_1251_1277_ TMOD_R | TGACCCCAACCTGGCCTTTTGTCGTTGA | 1155 |
| 425 | SP101_SPET11_118_ 147_TMOD_F | TGCTGGTGAAAATAACCCAGATGTCG TCTTC | 528 | SP101_SPET11_213_238_ TMOD_R | TTGTGGCCGATTTCACCACCTGCTCCT | 1422 |
| 426 | SP101_SPET11_1314_ 1336_TMOD_F | TCGCAAAAAAATCCAGCTATTAGC | 363 | SP101_SPET11_1403_1431_ TMOD_R | TAAACTATTTTTTTAGCTATACTCGAAC AC | 849 |
| 427 | SP101_SPET11_1408_ 1437_TMOD_F | TCGAGTATAGCTAAAAAAATAGTTTA TGACA | 359 | SP101_SPET11_1486_1515_ TMOD_R | TGGATAATTGGTCGTAACAAGGGATAGT GAG | 1268 |
| 428 | SP101_SPET11_1688_ 1716_TMOD_F | TCCTATATTAATCGTTTACAGAAACT GGCT | 334 | SP101_SPET11_1783_1808_ TMOD_R | TATATGATTATCATTGAACTGCGGCCG | 932 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 429 | SP101_SPET11_1711_1733_TMOD_F | TCTGGCTAAAACTTTGGCAACGGT | 406 | SP101_SPET11_1808_1835_TMOD_R | TGCGTGACGACCTTCTTGAATTGTAATCA | 1239 |
| 430 | SP101_SPET11_1807_1835_TMOD_F | TATGATTACAATTCAAGAAGGTCGTCACGC | 235 | SP101_SPET11_1901_1927_TMOD_R | TTTGGACCTGTAATCAGCTGAATACTGG | 1439 |
| 431 | SP101_SPET11_1967_1991_TMOD_F | TTAACGGTTATCATGGCCCAGATGGG | 649 | SP101_SPET11_2062_2083_TMOD_R | TATTGCCCAGAAATCAAATCATC | 940 |
| 432 | SP101_SPET11_216_243_TMOD_F | TAGCAGGTGGTGAAATCGGCCACATGATT | 210 | SP101_SPET11_308_333_TMOD_R | TTGCCACTTTGACAACTCCTGTTGCTG | 1404 |
| 433 | SP101_SPET11_2260_2283_TMOD_F | TCAGAGACCGTTTTATCCTATCAGC | 272 | SP101_SPET11_2375_2397_TMOD_R | TTCTGGGTGACCTGGTGTTTTAGA | 1393 |
| 434 | SP101_SPET11_2375_2399_TMOD_F | TTCTAAAACACCAGGTCACCCAGAAG | 675 | SP101_SPET11_2470_2497_TMOD_R | TAGCTGCTAGATGAGCTTCTGCCATGGCC | 918 |
| 435 | SP101_SPET11_2468_2487_TMOD_F | TATGGCCATGGCAGAAGCTCA | 238 | SP101_SPET11_2543_2570_TMOD_R | TCCATAAGGTCACCGTCACCATTCAAAGC | 1007 |
| 436 | SP101_SPET11_266_295_TMOD_F | TCTTGTACTTGTGGCTCACACGGCTGTTTGG | 417 | SP101_SPET11_355_380_TMOD_R | TGCTGCTTTGATGGCTGAATCCCCTTC | 1249 |
| 437 | SP101_SPET11_2961_2984_TMOD_F | TACCATGACAGAAGGCATTTTGACA | 183 | SP101_SPET11_3023_3045_TMOD_R | TGGAATTTACCAGCGATAGACACC | 1264 |
| 438 | SP101_SPET11_3075_3103_TMOD_F | TGATGACTTTTTAGCTAATGGTCAGGCAGC | 473 | SP101_SPET11_3168_3196_TMOD_R | TAATCGACGACCATCTTGGAAAGATTTCTC | 875 |
| 439 | SP101_SPET11_322_344_TMOD_F | TGTCAAAGTGGCACGTTTACTGGC | 631 | SP101_SPET11_423_441_TMOD_R | TATCCCCTGCTTCTGCTGCC | 934 |
| 440 | SP101_SPET11_3386_3403_TMOD_F | TAGCGTAAAGGTGAACCTT | 215 | SP101_SPET11_3480_3506_TMOD_R | TCCAGCAGTTACTGTCCCCTCATCTTTG | 1005 |
| 441 | SP101_SPET11_3511_3535_TMOD_F | TGCTTCAGGAATCAATGATGGAGCAG | 531 | SP101_SPET11_3605_3629_TMOD_R | TGGGTCTACACCTGCACTTGCATAAC | 1294 |
| 442 | SP101_SPET11_358_387_TMOD_F | TGGGGATTCAGCCATCAAAGCAGCTATTGAC | 588 | SP101_SPET11_448_473_TMOD_R | TCCAACCTTTTCCACAACAGAATCAGC | 998 |
| 443 | SP101_SPET11_600_629_TMOD_F | TCCTTACTTCGAACTATGAATCTTTTGGAAG | 348 | SP101_SPET11_686_714_TMOD_R | TCCCATTTTTTCACGCATGCTGAAAATATC | 1018 |
| 444 | SP101_SPET11_658_684_TMOD_F | TGGGGATTGATATCACCGATAAGAAGAA | 589 | SP101_SPET11_756_784_TMOD_R | TGATTGGCGATAAAGTGATATTTTCTAAAA | 1189 |
| 445 | SP101_SPET11_776_801_TMOD_F | TTCGCCAATCAAAACTAAGGGAATGGC | 673 | SP101_SPET11_871_896_TMOD_R | TGCCCACCAGAAAGACTAGCAGGATAA | 1217 |
| 446 | SP101_SPET11_1_29_TMOD_F | TAACCTTAATTGGAAAGAAACCCAAGAAGT | 154 | SP101_SPET11_92_116_TMOD_R | TCCTACCCAACGTTCACCAAGGGCAG | 1044 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| | | | Primer Pairs for Identification of Bacteria | | | |
| 447 | SP101_SPET11_364_385_F | TCAGCCATCAAAGCAGCTATTG | 276 | SP101_SPET11_448_471_R | TACCTTTTCCACAACAGAATCAGC | 894 |
| 448 | SP101_SPET11_3085_3104_F | TAGCTAATGGTCAGGCAGCC | 216 | SP101_SPET11_3170_3194_R | TCGACGACCATCTTGGAAAGATTTC | 1066 |
| 449 | RPLB_EC_690_710_F | TCCACACGGTGGTGGTGAAGG | 309 | RPLB_EC_737_758_R | TGTGCTGGTTTACCCCATGGAG | 1336 |
| 481 | BONTA_X52066_538_552_F | TATGGCTCTACTCAA | 239 | BONTA_X52066_647_660_R | TGTTACTGCTGGAT | 1346 |
| 482 | BONTA_X52066_538_552P_F | TA*TpGGC*Tp*Cp*TpA*Cp*Tp*CpAA | 143 | BONTA_X52066_647_660P_R | TG*Tp*TpA*Cp*TpG*Cp*TpGGAT | 1146 |
| 483 | BONTA_X52066_701_720_F | GAATAGCAATTAATCCAAAT | 94 | BONTA_X52066_759_775_R | TTACTTCTAACCCACTC | 1367 |
| 484 | BONTA_X52066_701_720P_F | GAA*TpAG*CpAA*Tp*TpAA*Tp*Cp*CpAAAT | 91 | BONTA_X52066_759_775P_R | TTA*Cp*Tp*Tp*Cp*TpAA*Cp*Cp*CpA*Cp*TpC | 1359 |
| 485 | BONTA_X52066_450_473_F | TCTAGTAATAATAGGACCCTCAGC | 393 | BONTA_X52066_517_539_R | TAACCATTTCGCGTAAGATTCAA | 859 |
| 486 | BONTA_X52066_450_473P_F | T*Cp*TpAGTAATAATAGGA*Cp*Cp*Cp*Tp*CpAGC | 142 | BONTA_X52066_517_539P_R | TAACCA*Tp*Tp*Tp*CpGCGTAAGA*Tp*Tp*CpAA | 857 |
| 487 | BONTA_X52066_591_620_F | TGAGTCACTTGAAGTTGATACAAATCCTCT | 463 | BONTA_X52066_644_671_R | TCATGTGCTAATGTTACTGCTGGATCTG | 992 |
| 608 | SSPE_BA_156_168P_F | TGGTpGCpTpAGCpATT | 616 | SSPE_BA_243_255P_R | TGCpAGCpTGATpTpGT | 1241 |
| 609 | SSPE_BA_75_89P_F | TACpAGAGTpTpTpGCpGAC | 192 | SSPE_BA_163_177P_R | TGTGCTpTpTpGAATpGCpT | 1338 |
| 610 | SSPE_BA_150_168P_F | TGCTTCTGGTpGCpTpAGCpATT | 533 | SSPE_BA_243_264P_R | TGATTGTTTTGCpAGCpTGATpTpGT | 1191 |
| 611 | SSPE_BA_72_89P_F | TGGTACpAGAGTpTpTpGCpGAC | 602 | SSPE_BA_163_182P_R | TCATTTGTGCTpTpTpGAATpGCpT | 995 |
| 612 | SSPE_BA_114_137P_F | TCAAGCAAACGCACAATpCpAGAAGC | 255 | SSPE_BA_196_222P_R | TTGCACGTCpTpGTTTCAGTTGCAAATTC | 1401 |
| 699 | SSPE_BA_123_153_F | TGCACAATCAGAAGCTAAGAAAGCGCAAGCT | 488 | SSPE_BA_202_231_R | TTTCACAGCATGCACGTCTGTTTCAGTTGC | 1431 |
| 700 | SSPE_BA_156_168_F | TGGTGCTAGCATT | 612 | SSPE_BA_243_255_R | TGCAGCTGATTGT | 1202 |
| 701 | SSPE_BA_75_89_F | TACAGAGTTTGCGAC | 179 | SSPE_BA_163_177_R | TGTGCTTTGAATGCT | 1338 |
| 702 | SSPE_BA_150_168_F | TGCTTCTGGTGCTAGCATT | 533 | SSPE_BA_243_264_R | TGATTGTTTTGCAGCTGATTGT | 1190 |
| 703 | SSPE_BA_72_89_F | TGGTACAGAGTTTGCGAC | 600 | SSPE_BA_163_182_R | TCATTTGTGCTTTGAATGCT | 995 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 704 | SSPE_BA_146_168_F | TGCAAGCTTCTGGTGCTAGCATT | 484 | SSPE_BA_242_267_R | TTGTGATTGTTTTGCAGCTGATTGTG | 1421 |
| 705 | SSPE_BA_63_89_F | TGCTAGTTATGGTACAGAGTTTGCGAC | 518 | SSPE_BA_163_191_R | TCATAACTAGCATTTGTGCTTTGAATGCT | 986 |
| 706 | SSPE_BA_114_137_F | TCAAGCAAACGCACAATCAGAAGC | 255 | SSPE_BA_196_222_R | TTGCACGTCTGTTTCAGTTGCAAATTC | 1402 |
| 770 | PLA_AF053945_7377_7402_F | TGACATCCGGCTCACGTTATTATGGT | 442 | PLA_AF053945_7434_7462_R | TGTAAATTCCGCAAAGACTTTGGCATTAG | 1313 |
| 771 | PLA_AF053945_7382_7404_F | TCCGGCTCACGTTATTATGGTAC | 327 | PLA_AF053945_7482_7502_R | TGGTCTGAGTACCTCCTTTGC | 1304 |
| 772 | PLA_AF053945_7481_7503_F | TGCAAAGGAGGTACTCAGACCAT | 481 | PLA_AF053945_7539_7562_R | TATTGGAAATACCGGCAGCATCTC | 943 |
| 773 | PLA_AF053945_7186_7211_F | TTATACCGGAAACTTCCCGAAAGGAG | 657 | PLA_AF053945_7257_7280_R | TAATGCGATACTGGCCTGCAAGTC | 879 |
| 774 | CAF1_AF053947_33407_33430_F | TCAGTTCCGTTATCGCCATTGCAT | 292 | CAF1_AF053947_33494_33514_R | TGCGGGCTGGTTCAACAAGAG | 1235 |
| 775 | CAF1_AF053947_33515_33541_F | TCACTCTTACATATAAGGAAGGCGCTC | 270 | CAF1_AF053947_33595_33621_R | TCCTGTTTTATAGCCGCCAAGAGTAAG | 1053 |
| 776 | CAF1_AF053947_33435_33457_F | TGGAACTATTGCAACTGCTAATG | 542 | CAF1_AF053947_33499_33517_R | TGATGCGGGCTGGTTCAAC | 1183 |
| 777 | CAF1_AF053947_33687_33716_F | TCAGGATGGAAATAACCACCAATTCACTAC | 286 | CAF1_AF053947_33755_33782_R | TCAAGGTTCTCACCGTTTACCTTAGGAG | 962 |
| 778 | INV_U22457_515_539_F | TGGCTCCTTGGTATGACTCTGCTTC | 573 | INV_U22457_571_598_R | TGTTAAGTGTGTTGCGGCTGTCTTTATT | 1343 |
| 779 | INV_U22457_699_724_F | TGCTGAGGCCTGGACCGATTATTTAC | 525 | INV_U22457_753_776_R | TCACGCGACGAGTGCCATCCATTG | 976 |
| 780 | INV_U22457_834_858_F | TTATTTACCTGCACTCCCACAACTG | 664 | INV_U22457_942_966_R | TGACCCAAAGCTGAAAGCTTTACTG | 1154 |
| 781 | INV_U22457_1558_1581_F | TGGTAACAGAGCCTTATAGGCGCA | 597 | INV_U22457_1619_1643_R | TTGCGTTGCAGATTATCTTTACCAA | 1408 |
| 782 | LL_NC003143_2366996_2367019_F | TGTAGCCGCTAAGCACTACCATCC | 627 | LL_NC003143_2367073_2367097_R | TCTCATCCCGATATTACCGCCATGA | 1123 |
| 783 | LL_NC003143_2367172_2367194_F | TGGACGGCATCACGATTCTCTAC | 550 | LL_NC003143_2367249_2367271_R | TGGCAACAGCTCAACACCTTTGG | 1272 |
| 874 | RPLB_EC_649_679_F | TGICCIACIGTIIGIGGTTCTGTAATGAACC | 620 | RPLB_EC_739_762_TMOD_R | TTCCAAGTGCTGGTTTACCCCATGG | 1380 |
| 875 | RPLB_EC_642_679P_F | TpCpCpTpTpGITpGICCIACIGTIIGIGGTTCTGTAATGAACC | 646 | RPLB_EC_739_762_TMOD_R | TTCCAAGTGCTGGTTTACCCCATGG | 1380 |
| 876 | MECIA_Y14051_3315_3341_F | TTACACATATCGTGAGCAATGAACTGA | 653 | MECIA_Y14051_3367_3393_R | TGTGATATGGAGGTGTAGAAGGTGTTA | 1333 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 877 | MECA_Y14051_3774_3802_F | TAAAACAAACTACGGTAACATTGATCGCA | 144 | MECA_Y14051_3828_3854_R | TCCCAATCTAACTTCCACATACCATCT | 1015 |
| 878 | MECA_Y14051_3645_3670_F | TGAAGTAGAAATGACTGAACGTCCGA | 434 | MECA_Y14051_3690_3719_R | TGATCCTGAATGTTTATATCTTTAACGCCT | 1181 |
| 879 | MECA_Y14051_4507_4530_F | TCAGGTACTGCTATCCACCCTCAA | 288 | MECA_Y14051_4555_4581_R | TGGATAGACGTCATATGAAGGTGTGCT | 1269 |
| 880 | MECA_Y14051_4510_4530_F | TGTACTGCTATCCACCCTCAA | 626 | MECA_Y14051_4586_4610_R | TATTCTTCGTTACTCATGCCATACA | 939 |
| 881 | MECA_Y14051_4669_4698_F | TCACCAGGTTCAACTCAAAAAATATTAACA | 262 | MECA_Y14051_4765_4793_R | TAACCACCCCAAGATTTATCTTTTTGCCA | 858 |
| 882 | MECA_Y14051_4520_4530P_F | TCpCpACpCpCpTpCpAA | 389 | MECA_Y14051_4590_4600P_R | TpACpTpCpATpGCpCpA | 1357 |
| 883 | MECA_Y14051_4520_4530P_F | TCpCpACpCpCpTpCpAA | 389 | MECA_Y14051_4600_4610P_R | TpATpTpCpTpTpCpGTpT | 1358 |
| 902 | TRPE_AY094355_1467_1491_F | ATGTCGATTGCAATCCGTACTTGTG | 36 | TRPE_AY094355_1569_1592_R | TGCGCGAGCTTTTATTTGGGTTTC | 1231 |
| 903 | TRPE_AY094355_1445_1471_F | TGGATGGCATGGTGAAATGGATATGTC | 557 | TRPE_AY094355_1551_1580_R | TATTTGGGTTTCATTCCACTCAGATTCTGG | 944 |
| 904 | TRPE_AY094355_1278_1303_F | TCAAATGTACAAGGTGAAGTGCGTGA | 247 | TRPE_AY094355_1392_1418_R | TCCTCTTTTCACAGGCTCTACTTCATC | 1048 |
| 905 | TRPE_AY094355_1064_1086_F | TCGACCTTTGGCAGGAACTAGAC | 357 | TRPE_AY094355_1171_1196_R | TACATCGTTTCGCCCAAGATCAATCA | 885 |
| 906 | TRPE_AY094355_666_688_F | GTGCATGCGGATACAGAGCAGAG | 135 | TRPE_AY094355_769_791_R | TTCAAAATGCGGAGGCGTATGTG | 1372 |
| 907 | TRPE_AY094355_757_776_F | TGCAAGCGCGACCACATACG | 483 | TRPE_AY094355_864_883_R | TGCCCAGGTACAACCTGCAT | 1218 |
| 908 | RECA_AF251469_43_68_F | TGGTACATGTGCCTTCATTGATGCTG | 601 | RECA_AF251469_140_163_R | TTCAAGTGCTTGCTCACCATTGTC | 1375 |
| 909 | RECA_AF251469_169_190_F | TGACATGCTTGTCCGTTCAGGC | 446 | RECA_AF251469_277_300_R | TGGCTCATAAGACGCGCTTGTAGA | 1280 |
| 910 | PARC_X95819_87_110_F | TGGTGACTCGGCATGTTATGAAGC | 609 | PARC_X95819_201_222_R | TTCGGTATAACGCATCGCAGCA | 1387 |
| 911 | PARC_X95819_87_110_F | TGGTGACTCGGCATGTTATGAAGC | 609 | PARC_X95819_192_219_R | GGTATAACGCATCGCAGCAAAAGATTTA | 836 |
| 912 | PARC_X95819_123_147_F | GGCTCAGCCATTTAGTTACCGCTAT | 120 | PARC_X95819_232_260_R | TCGCTCAGCAATAATTCACTATAAGCCGA | 1081 |
| 913 | PARC_X95819_43_63_F | TCAGCGCGTACAGTGGGTGAT | 277 | PARC_X95819_143_170_R | TTCCCCTGACCTTCGATTAAAGGATAGC | 1383 |
| 914 | OMPA_AY485227_272_301_F | TTACTCCATTATTGCTTGGTTACACTTTCC | 655 | OMPA_AY485227_364_388_R | GAGCTGCGCCAACGAATAAATCGTC | 812 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 915 | OMPA_AY485227_379_401_F | TGCGCAGCTCTTGGTATCGAGTT | 509 | OMPA_AY485227_492_519_R | TGCCGTAACATAGAAGTTACCGTTGATT | 1223 |
| 916 | OMPA_AY485227_311_335_F | TACACAACAATGGCGGTAAAGATGG | 178 | OMPA_AY485227_424_453_R | TACGTCGCCTTTAACTTGGTTATATTCAGC | 901 |
| 917 | OMPA_AY485227_415_441_F | TGCCTCGAAGCTGAATATAACCAAGTT | 506 | OMPA_AY485227_514_546_R | TCGGGCGTAGTTTTTAGTAATTAAATCAGAAGT | 1092 |
| 918 | OMPA_AY485227_494_520_F | TCAACGGTAACTTCTATGTTACTTCTG | 252 | OMPA_AY485227_569_596_R | TCGTCGTATTTATAGTGACCAGCACCTA | 1108 |
| 919 | OMPA_AY485227_551_577_F | TCAAGCCGTACGTATTATTAGGTGCTG | 257 | OMPA_AY485227_658_680_R | TTTAAGCGCCAGAAAGCACCAAC | 1425 |
| 920 | OMPA_AY485227_555_581_F | TCCGTACGTATTATTAGGTGCTGGTCA | 328 | OMPA_AY485227_635_662_R | TCAACACCAGCGTTACCTAAAGTACCTT | 954 |
| 921 | OMPA_AY485227_556_583_F | TCGTACGTATTATTAGGTGCTGGTCACT | 379 | OMPA_AY485227_659_683_R | TCGTTTAAGCGCCAGAAAGCACCAA | 1114 |
| 922 | OMPA_AY485227_657_679_F | TGTTGGTGCTTTCTGGCGCTTAA | 645 | OMPA_AY485227_739_765_R | TAAGCCAGCAAGAGCTGTATAGTTCCA | 871 |
| 923 | OMPA_AY485227_660_683_F | TGGTGCTTTCTGGCGCTTAAACGA | 613 | OMPA_AY485227_786_807_R | TACAGGAGCAGCAGGCTTCAAG | 884 |
| 924 | GYRA_AF100557_4_23_F | TCTGCCCGTGTCGTTGGTGA | 402 | GYRA_AF100557_119_142_R | TCGAACCGAAGTTACCCTGACCAT | 1063 |
| 925 | GYRA_AF100557_70_94_F | TCCATTGTTCGTATGGCTCAAGACT | 316 | GYRA_AF100557_178_201_R | TGCCAGCTTAGTCATACGGACTTC | 1211 |
| 926 | GYRB_AB008700_19_40_F | TCAGGTGGCTTACACGGCGTAG | 289 | GYRB_AB008700_111_140_R | TATTGCGGATCACCATGATGATATTCTTGC | 941 |
| 927 | GYRB_AB008700_265_292_F | TCTTTCTTGAATGCTGGTGTACGTATCG | 420 | GYRB_AB008700_369_395_R | TCGTTGAGATGGTTTTTACCTTCGTTG | 1113 |
| 928 | GYRB_AB008700_368_394_F | TCAACGAAGGTAAAAACCATCTCAACG | 251 | GYRB_AB008700_466_494_R | TTTGTGAAACAGCGAACATTTTCTTGGTA | 1440 |
| 929 | GYRB_AB008700_477_504_F | TGTTCGCTGTTTCACAAACAACATTCCA | 641 | GYRB_AB008700_611_632_R | TCACGCGCATCATCACCAGTCA | 977 |
| 930 | GYRB_AB008700_760_787_F | TACTTACTTGAGAATCCACAAGCTGCAA | 198 | GYRB_AB008700_862_888_R | ACCTGCAATATCTAATGCACTCTTACG | 729 |
| 931 | WAAA_Z96925_2_29_F | TCTTGCTCTTTCGTGAGTTCAGTAAATG | 416 | WAAA_Z96925_115_138_R | CAAGCGGTTTGCCTCAAATAGTCA | 758 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 932 | WAAA_Z96925_286_311_F | TCGATCTGGTTTCATGCTGTTTCAGT | 360 | WAAA_Z96925_394_412_R | TGGCACGAGCCTGACCTGT | 1274 |
| 939 | RPOB_EC_3798_3821_F | TGGGCAGCGTTTCGGCGAAATGGA | 581 | RPOB_EC_3862_3889_R | TGTCCGACTTGACGGTCAGCATTTCCTG | 1326 |
| 940 | RPOB_EC_3798_3821_F | TGGGCAGCGTTTCGGCGAAATGGA | 581 | RPOB_EC_3862_3889_2_R | TGTCCGACTTGACGGTTAGCATTTCCTG | 1327 |
| 941 | TUFB_EC_275_299_F | TGATCACTGGTGCTGCTCAGATGGA | 468 | TUFB_EC_337_362_R | TGGATGTGCTCACGAGTCTGTGGCAT | 1271 |
| 942 | TUFB_EC_251_278_F | TGCACGCCGACTATGTTAAGAACATG AT | 493 | TUFB_EC_337_360_R | TATGTGCTCACGAGTTTGCGGCAT | 937 |
| 949 | GYRB_AB008700_760_787_F | TACTTACTTGAGAATCCACAAGCTGC AA | 198 | GYRB_AB008700_862_888_2_R | TCCTGCAATATCTAATGCACTCTTACG | 1050 |
| 958 | RPOC_EC_2223_2243_F | TGGTATGCGTGGTCTGATGGC | 605 | RPOC_EC_2329_2352_R | TGCTAGACCTTTACGTGCACCGTG | 1243 |
| 959 | RPOC_EC_918_938_F | TCTGGATAACGGTCGTCGCGG | 404 | RPOC_EC_1009_1031_R | TCCAGCAGGTTCTGACGGAAACG | 1004 |
| 960 | RPOC_EC_2334_2357_F | TGCTCGTAAGGGTCTGGCGGATAC | 523 | RPOC_EC_2380_2403_R | TACTAGACGACGGGTCAGGTAACC | 905 |
| 961 | RPOC_EC_917_938_F | TATTGGACAACGGTCGTCGCGG | 242 | RPOC_EC_1009_1034_R | TTACCGAGCAGGTTCTGACGGAAACG | 1362 |
| 962 | RPOB_EC_2005_2027_F | TCGTTCCTGGAACACGATGACGC | 387 | RPOB_EC_2041_2064_R | TTGACGTTGCATGTTCGAGCCCAT | 1399 |
| 963 | RPOB_EC_1527_1549_F | TCAGCTGTCGCAGTTCATGGACC | 282 | RPOB_EC_1630_1649_R | TCGTCGCGGACTTCGAAGCC | 1104 |
| 964 | INFB_EC_1347_1367_F | TGCGTTTACCGCAATGCGTGC | 515 | INFB_EC_1414_1432_R | TCGGCATCACGCCGTCGTC | 1090 |
| 965 | VALS_EC_1128_1151_F | TATGCTGACCGACCAGTGGTACGT | 237 | VALS_EC_1231_1257_R | TTCGCGCATCCAGGAGAAGTACATGTT | 1384 |
| 978 | RPOC_EC_2145_2175_F | TCAGGAGTCGTTCAACTCGATCTACA TGATG | 285 | RPOC_EC_2228_2247_R | TTACGCCATCAGGCCACGCA | 1363 |
| 1045 | CJST_CJ_1668_1700_F | TGCTCGAGTGATTGACTTTGCTAAAT TTAGAGA | 522 | CJST_CJ_1774_1799_R | TGAGCGTGTGGAAAAGGACTTGGATG | 1170 |
| 1046 | CJST_CJ_2171_2197_F | TCGTTTGGTGGTGGTAGATGAAAAAG G | 388 | CJST_CJ_2283_2313_R | TCTCTTTCAAAGCACCATTGCTCATTAT AGT | 1126 |
| 1047 | CJST_CJ_584_616_F | TCCAGGACAAATGTATGAAAAATGTC CAAGAAG | 315 | CJST_CJ_663_692_R | TTCATTTTCTGGTCCAAAGTAAGCAGTA TC | 1379 |
| 1048 | CJST_CJ_360_394_F | TCCTGTTATCCCTGAAGTAGTTAATC AAGTTTGTT | 346 | CJST_CJ_442_476_R | TCAACTGGTTCAAAAACATTAAGTTGTA ATTGTCC | 955 |
| 1049 | CJST_CJ_2636_2668_F | TGCCTAGAAGATCTTAAAAATTTCCG CCAACTT | 504 | CJST_CJ_2753_2777_R | TTGCTGCCATAGCAAAGCCTACAGC | 1409 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1050 | CJST_CJ_1290_1320_F | TGGCTTATCCAAATTTAGATCGTGGTTTTAC | 575 | CJST_CJ_1406_1433_R | TTTGCTCATGATCTGCATGAAGCATAAA | 1437 |
| 1051 | CJST_CJ_3267_3293_F | TTTGATTTTACGCCGTCCTCCAGGTCG | 707 | CJST_CJ_3356_3385_R | TCAAAGAACCCGCACCTAATTCATCATTTA | 951 |
| 1052 | CJST_CJ_5_39_F | TAGGCGAAGATATACAAAGAGTATTAGAAGCTAGA | 222 | CJST_CJ_104_137_R | TCCCTTATTTTTCTTTCTACTACCTTCGGATAAT | 1029 |
| 1053 | CJST_CJ_1080_1110_F | TTGAGGGTATGCACCGTCTTTTTGATTCTTT | 681 | CJST_CJ_1166_1198_R | TCCCCTCATGTTTAAATGATCAGGATAAAAAGC | 1022 |
| 1054 | CJST_CJ_2060_2090_F | TCCCGGACTTAATATCAATGAAAATTGTGGA | 323 | CJST_CJ_2148_2174_R | TCGATCCGCATCACCATCAAAAGCAAA | 1068 |
| 1055 | CJST_CJ_2869_2895_F | TGAAGCTTGTTCTTTAGCAGGACTTCA | 432 | CJST_CJ_2979_3007_R | TCCTCCTTGTGCCTCAAAACGCATTTTTA | 1045 |
| 1056 | CJST_CJ_1880_1910_F | TCCCAATTAATTCTGCCATTTTTCCAGGTAT | 317 | CJST_CJ_1981_2011_R | TGGTTCTTACTTGCTTTGCATAAACTTTCCA | 1309 |
| 1057 | CJST_CJ_2185_2212_F | TAGATGAAAAGGGCGAAGTGGCTAATGG | 208 | CJST_CJ_2283_2316_R | TGAATTCTTTCAAAGCACCATTGCTCATTATAGT | 1152 |
| 1058 | CJST_CJ_1643_1670_F | TTATCGTTTGTGGAGCTAGTGCTTATGC | 660 | CJST_CJ_1724_1752_R | TGCAATGTGTGCTATGTCAGCAAAAAGAT | 1198 |
| 1059 | CJST_CJ_2165_2194_F | TGCGGATCGTTTGGTGGTTGTAGATGAAAA | 511 | CJST_CJ_2247_2278_R | TCCACACTGGATTGTAATTTACCTTGTTCTTT | 1002 |
| 1060 | CJST_CJ_599_632_F | TGAAAAATGTCCAAGAAGCATAGCAAAAAAAGCA | 424 | CJST_CJ_711_743_R | TCCCGAACAATGAGTTGTATCAACTATTTTTAC | 1024 |
| 1061 | CJST_CJ_360_393_F | TCCTGTTATCCCTGAAGTAGTTAATCAAGTTTGT | 345 | CJST_CJ_443_477_R | TACAACTGGTTCAAAAACATTAAGCTGTAATTGTC | 882 |
| 1062 | CJST_CJ_2678_2703_F | TCCCCAGGACACCCTGAAATTTCAAC | 321 | CJST_CJ_2760_2787_R | TGTGCTTTTTTTGCTGCCATAGCAAAGC | 1339 |
| 1063 | CJST_CJ_1268_1299_F | AGTTATAAACACGGCTTTCCTATGGCTTATCC | 29 | CJST_CJ_1349_1379_R | TCGGTTTAAGCTCTACATGATCGTAAGGATA | 1096 |
| 1064 | CJST_CJ_1680_1713_F | TGATTTTGCTAAATTTAGAGAAATTGCGGATGAA | 479 | CJST_CJ_1795_1822_R | TATGTGTAGTTGAGCTTACTACATGAGC | 938 |
| 1065 | CJST_CJ_2857_2887_F | TGGCATTTCTTATGAAGCTTGTTCTTTAGCA | 565 | CJST_CJ_2965_2998_R | TGCTTCAAAACGCATTTTTACATTTTCGTTAAAG | 1253 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1070 | RNASEP_BKM_580_599_F | TGCGGGTAGGGAGCTTGAGC | 512 | RNASEP_BKM_665_686_R | TCCGATAAGCCGGATTCTGTGC | 1034 |
| 1071 | RNASEP_BKM_616_637_F | TCCTAGAGGAATGGCTGCCACG | 333 | RNASEP_BKM 665_687_R | TGCCGATAAGCCGGATTCTGTGC | 1222 |
| 1072 | RNASEP_BDP_574_592_F | TGGCACGGCCATCTCCGTG | 561 | RNASEP_BDP 616_635_R | TCGTTTCACCCTGTCATGCCG | 1115 |
| 1073 | 23S_BRM_1110_1129_F | TGCGCGGAAGATGTAACGGG | 510 | 23S_BRM_1176_1201_R | TCGCAGGCTTACAGAACGCTCTCCTA | 1074 |
| 1074 | 23S_BRM_515_536_F | TGCATACAAACAGTCGGAGCCT | 496 | 23S_BRM_616_635_R | TCGGACTCGCTTTCGCTACG | 1088 |
| 1075 | RNASEP_CLB_459_487_F | TAAGGATAGTGCAACAGAGATATACC GCC | 162 | RNASEP_CLB_498_526_R | TGCTCTTACCTCACCGTTCCACCCTTAC C | 1247 |
| 1076 | RNASEP_CLB_459_487_F | TAAGGATAGTGCAACAGAGATATACC GCC | 162 | RNASEP_CLB_498_522_R | TTTACCTCGCCTTTCCACCCTTACC | 1426 |
| 1077 | ICD_CXB_93_120_F | TCCTGACCGACCCATTATTCCCTTTA TC | 343 | ICD_CXB_172_194_R | TAGGATTTTTCCACGGCGGCATC | 921 |
| 1078 | ICD_CXB_92_120_F | TTCCTGACCGACCCATTATTCCCTTT ATC | 671 | ICD_CXB_172_194_R | TAGGATTTTTCCACGGCGGCATC | 921 |
| 1079 | ICD_CXB_176_198_F | TCGCCGTGGAAAAATCCTACGCT | 369 | ICD_CXB_224_247_R | TAGCCTTTTCTCCGGCGTAGATCT | 916 |
| 1080 | IS1111A_NC002971_6866_6891_F | TCAGTATGTATCCACCGTAGCCAGTC | 290 | IS1111A_NC002971_6928_6954_R | TAAACGTCCGATACCAATGGTTCGCTC | 848 |
| 1081 | IS1111A_NC002971_7456_7483_F | TGGGTGACATTCATCAATTTCATCGT TC | 594 | IS1111A_NC002971_7529_7554_R | TCAACAACACCTCCTTATTCCCACTC | 952 |
| 1082 | RNASEP_RKP_419_448_F | TGGTAAGAGCGCACCGGTAAGTTGGT AACA | 599 | RNASEP_RKP_542_565_R | TCAAGCGATCTACCCGCATTACAA | 957 |
| 1083 | RNASEP_RKP_422_443_F | TAAGAGCGCACCGGTAAGTTGG | 159 | RNASEP_RKP_542_565_R | TCAAGCGATCTACCCGCATTACAA | 957 |
| 1084 | RNASEP_RKP_466_491_F | TCCACCAAGAGCAAGATCAAATAGGC | 310 | RNASEP_RKP_542_565_R | TCAAGCGATCTACCCGCATTACAA | 957 |
| 1085 | RNASEP_RKP_264_287_F | TCTAAATGGTCGTGCAGTTGCGTG | 391 | RNASEP_RKP_295_321_R | TCTATAGAGTCCGGACTTTCCTCGTGA | 1119 |
| 1086 | RNASEP_RKP_426_448_F | TGCATACCGGTAAGTTGGCAACA | 497 | RNASEP_RKP_542_565_R | TCAAGCGATCTACCCGCATTACAA | 957 |
| 1087 | OMPB_RKP_860_890_F | TTACAGGAAGTTTAGGTGGTAATCTA AAAGG | 654 | OMPB_RKP_972_996_R | TCCTGCAGCTCTACCTGCTCCATTA | 1051 |
| 1088 | OMPB_RKP_1192_1221_F | TCTACTGATTTTGGTAATCTTGCAGC ACAG | 392 | OMPB_RKP_1288_1315_R | TAGCAgCAAAAGTTATCACACCTGCAGT | 910 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1089 | OMPB_RKP_3417_3440_F | TGCAAGTGGTACTTCAACATGGGG | 485 | OMPB_RKP_3520_3550_R | TGGTTGTAGTTCCTGTAGTTGTTGCATTAAC | 1310 |
| 1090 | GLTA_RKP_1043_1072_F | TGGGACTTGAAGCTATCGCTCTTAAAGATG | 576 | GLTA_RKP_1138_1162_R | TGAACATTTGCGACGGTATACCCAT | 1147 |
| 1091 | GLTA_RKP_400_428_F | TCTTCTCATCCTATGGCTATTATGCTTGC | 413 | GLTA_RKP_499_529_R | TGGTGGGTATCTTAGCAATCATTCTAATAGC | 1305 |
| 1092 | GLTA_RKP_1023_1055_F | TCCGTTCTTACAAATAGCAATAGAACTTGAAGC | 330 | GLTA_RKP_1129_1156_R | TTGGCGACGGTATACCCATAGCTTTATA | 1415 |
| 1093 | GLTA_RKP_1043_1072_2_F | TGGAGCTTGAAGCTATCGCTCTTAAAGATG | 553 | GLTA_RKP_1138_1162_R | TGAACATTTGCGACGGTATACCCAT | 1147 |
| 1094 | GLTA_RKP_1043_1072_3_F | TGGAACTTGAAGCTCTCGCTCTTAAAGATG | 543 | GLTA_RKP_1138_1164_R | TGTGAACATTTGCGACGGTATACCCAT | 1330 |
| 1095 | GLTA_RKP_400_428_F | TCTTCTCATCCTATGGCTATTATGCTTGC | 413 | GLTA_RKP_505_534_R | TGCGATGGTAGGTATCTTAGCAATCATTCT | 1230 |
| 1096 | CTXA_VBC_117_142_F | TCTTATGCCAAGAGGACAGAGTGAGT | 410 | CTXA_VBC_194_218_R | TGCCTAACAAATCCCGTCTGAGTTC | 1226 |
| 1097 | CTXA_VBC_351_377_F | TGTATTAGGGGCATACAGTCCTCATCC | 630 | CTXA_VBC_441_466_R | TGTCATCAAGCACCCCAAAATGAACT | 1324 |
| 1098 | RNASEP_VBC_331_349_F | TCCGCGGAGTTGACTGGGT | 325 | RNASEP_VBC_388_414_R | TGACTTTCCTCCCCCTTATCAGTCTCC | 1163 |
| 1099 | TOXR_VBC_135_158_F | TCGATTAGGCAGCAACGAAAGCCG | 362 | TOXR_VBC_221_246_R | TTCAAAACCTTGCTCTCGCCAAACAA | 1370 |
| 1100 | ASD_FRT_1_29_F | TTGCTTAAAGTTGGTTTTATTGGTTGGCG | 690 | ASD_FRT_86_116_R | TGAGATGTCGAAAAAAACGTTGGCAAAATAC | 1164 |
| 1101 | ASD_FRT_43_76_F | TCAGTTTTAATGTCTCGTATGATCGAATCAAAAG | 295 | ASD_FRT_129_156_R | TCCATATTGTTGCATAAAACCTGTTGGC | 1009 |
| 1102 | GALE_FRT_168_199_F | TTATCAGCTAGACCTTTTAGGTAAAGCTAAGC | 658 | GALE_FRT_241_269_R | TCACCTACAGCTTTAAAGCCAGCAAAATG | 973 |
| 1103 | GALE_FRT_834_865_F | TCAAAAAGCCCTAGGTAAAGAGATTCCATATC | 245 | GALE_FRT_901_925_R | TAGCCTTGGCAACATCAGCAAAACT | 915 |
| 1104 | GALE_FRT_308_339_F | TCCAAGGTACACTAAACTTACTTGAGCTAATG | 306 | GALE_FRT_390_422_R | TCTTCTGTAAAGGGTGGTTTATTATTCATCCCA | 1136 |
| 1105 | IPAH_SGF_258_277_F | TGAGGACCGTGTCGCGCTCA | 458 | IPAH_SGF_301_327_R | TCCTTCTGATGCCTGATGGACCAGGAG | 1055 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1106 | IPAH_SGF_113_134_F | TCCTTGACCGCCTTTCCGATAC | 350 | IPAH_SGF_172_191_R | TTTTCCAGCCATGCAGCGAC | 1441 |
| 1107 | IPAH_SGF_462_486_F | TCAGACCATGCTCGCAGAGAAACTT | 271 | IPAH_SGF_522_540_R | TGTCACTCCCGACACGCCA | 1322 |
| 1111 | RNASEP_BRM_461_488_F | TAAACCCCATCGGGAGCAAGACCGAATA | 147 | RNASEP_BRM_542_561_R | TGCCTCGCGCAACCTACCCG | 1227 |
| 1112 | RNASEP_BRM_325_347_F | TACCCCAGGGAAAGTGCCACAGA | 185 | RNASEP_BRM_402_428_R | TCTCTTACCCCACCCTTTCACCCTTAC | 1125 |
| 1128 | HUPB_CJ_113_134_F | TAGTTGCTCAAACAGCTGGGCT | 230 | HUPB_CJ_157_188_R | TCCCTAATAGTAGAAATAACTGCATCAGTAGC | 1028 |
| 1129 | HUPB_CJ_76_102_F | TCCCGGAGCTTTTATGACTAAAGCAGAT | 324 | HUPB_CJ_157_188_R | TCCCTAATAGTAGAAATAACTGCATCAGTAGC | 1028 |
| 1130 | HUPB_CJ_76_102_F | TCCCGGAGCTTTTATGACTAAAGCAGAT | 324 | HUPB_CJ_114_135_R | TAGCCCAGCTGTTTGAGCAACT | 913 |
| 1151 | AB_MLST-11-OIF007_62_91_F | TGAGATTGCTGAACATTTAATGCTGATTGA | 454 | AB_MLST-11-OIF007_169_203_R | TTGTACATTTGAAACAATATGCATGACATGTGAAT | 1418 |
| 1152 | AB_MLST-11-OIF007_185_214_F | TATTGTTTCAAATGTACAAGGTGAAGTGCG | 243 | AB_MLST-11-OIF007_291_324_R | TCACAGGTTCTACTTCATCAATAATTTCCATTGC | 969 |
| 1153 | AB_MLST-11-OIF007_260_289_F | TGGAACGTTATCAGGTGCCCCAAAAATTCG | 541 | AB_MLST-11-OIF007_364_393_R | TTGCAATCGACATATCCATTTCACCATGCC | 1400 |
| 1154 | AB_MLST-11-OIF007_206_239_F | TGAAGTGCGTGATGATATCGATGCACTTGATGTA | 436 | AB_MLST-11-OIF007_318_344_R | TCCGCCAAAAACTCCCCTTTTCACAGG | 1036 |
| 1155 | AB_MLST-11-OIF007_522_552_F | TCGGTTTAGTAAAAGAACGTATTGCTCAACC | 378 | AB_MLST-11-OIF007_587_610_R | TTCTGCTTGAGGAATAGTGCGTGG | 1392 |
| 1156 | AB_MLST-11-OIF007_547_571_F | TCAACCTGACTGCGTGAATGGTTGT | 250 | AB_MLST-11-OIF007_656_686_R | TACGTTCTACGATTTCTTCATCAGGTACATC | 902 |
| 1157 | AB_MLST-11-OIF007_601_627_F | TCAAGCAGAAGCTTTGGAAGAAGAAGG | 256 | AB_MLST-11-OIF007_710_736_R | TACAACGTGATAAACACGACCAGAAGC | 881 |
| 1158 | AB_MLST-11-OIF007_1202_1225_F | TCGTGCCCGCAATTTGCATAAAGC | 384 | AB_MLST-11-OIF007_1266_1296_R | TAATGCCGGGTAGTGCAATCCATTCTTCTAG | 878 |
| 1159 | AB_MLST-11-OIF007_1202_1225_F | TCGTGCCCGCAATTTGCATAAAGC | 384 | AB_MLST-11-OIF007_1299_1316_R | TGCACCTGCGGTCGAGCG | 1199 |
| 1160 | AB_MLST-11-OIF007_1234_1264_F | TTGTAGCACAGCAAGGCAAATTTCCTGAAAC | 694 | AB_MLST-11-OIF007_1335_1362_R | TGCCATCCATAATCACGCCATACTGACG | 1215 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1161 | AB_MLST-11-OIF007_1327_1356_F | TAGGTTTACGTCAGTATGGCGTGATTATGG | 225 | AB_MLST-11-OIF007_1422_1448_R | TGCCAGTTTCCACATTTCACGTTCGTG | 1212 |
| 1162 | AB_MLST-11-OIF007_1345_1369_F | TCGTGATTATGGATGGCAACGTGAA | 383 | AB_MLST-11-OIF007_1470_1494_R | TCGCTTGAGTGTAGTCATGATTGCG | 1083 |
| 1163 | AB_MLST-11-OIF007_1351_1375_F | TTATGGATGGCAACGTGAAACGCGT | 662 | AB_MLST-11-OIF007_1470_1494_R | TCGCTTGAGTGTAGTCATGATTGCG | 1083 |
| 1164 | AB_MLST-11-OIF007_1387_1412_F | TCTTTGCCATTGAAGATGACTTAAGC | 422 | AB_MLST-11-OIF007_1470_1494_R | TCGCTTGAGTGTAGTCATGATTGCG | 1083 |
| 1165 | AB_MLST-11-OIF007_1542_1569_F | TACTAGCGGTAAGCTTAAACAAGATTGC | 194 | AB_MLST-11-OIF007_1656_1680_R | TGAGTCGGGTTCACTTTACCTGGCA | 1173 |
| 1166 | AB_MLST-11-OIF007_1566_1593_F | TTGCCAATGATATTCGTTGGTTAGCAAG | 684 | AB_MLST-11-OIF007_1656_1680_R | TGAGTCGGGTTCACTTTACCTGGCA | 1173 |
| 1167 | AB_MLST-11-OIF007_1611_1638_F | TCGGCGAAATCCGTATTCCTGAAAATGA | 375 | AB_MLST-11-OIF007_1731_1757_R | TACCGGAAGCACCAGCGACATTAATAG | 890 |
| 1168 | AB_MLST-11-OIF007_1726_1752_F | TACCACTATTAATGTCGCTGGTGCTTC | 182 | AB_MLST-11-OIF007_1790_1821_R | TGCAACTGAATAGATTGCAGTAAGTTATAAGC | 1195 |
| 1169 | AB_MLST-11-OIF007_1792_1826_F | TTATAACTTACTGCAATCTATTCAGTTGCTTGGTG | 656 | AB_MLST-11-OIF007_1876_1909_R | TGAATTATGCAAGAAGTGATCAATTTTCTCACGA | 1151 |
| 1170 | AB_MLST-11-OIF007_1792_1826_F | TTATAACTTACTGCAATCTATTCAGTTGCTTGGTG | 656 | AB_MLST-11-OIF007_1895_1927_R | TGCCGTAACTAACATAAGAGAATTATGCAAGAA | 1224 |
| 1171 | AB_MLST-11-OIF007_1970_2002_F | TGGTTATGTACCAAATACTTTGTCTGAAGATGG | 618 | AB_MLST-11-OIF007_2097_2118_R | TGACGGCATCGATACCACCGTC | 1157 |
| 1172 | RNASEP_BRM_461_488_F | TAAACCCCATCGGGAGCAAGACCGAATA | 147 | RNASEP_BRM_542_561_2_R | TGCCTCGTGCAACCCACCCG | 1228 |
| 2000 | CTXB_NC002505_46_70_F | TCAGCGTATGCACATGGAACTCCTC | 278 | CTXB_NC002505_132_162_R | TCCGGCTAGAGATTCTGTATACGACAATATC | 1039 |
| 2001 | FUR_NC002505_87_113_F | TGAGTGCCAACATATCAGTGCTGAAGA | 465 | FUR_NC002505_205_228_R | TCCGCCTTCAAAATGGTGGCGAGT | 1037 |
| 2002 | FUR_NC002505_87_113_F | TGAGTGCCAACATATCAGTGCTGAAGA | 465 | FUR_NC002505_178_205_R | TCACGATACCTGCATCATCAAATTGGTT | 974 |
| 2003 | GAPA_NC002505_533_560_F | TCGACAACACCATTATCTATGGTGTGAA | 356 | GAPA_NC002505_646_671_R | TCAGAATCGATGCCAAATGCGTCATC | 980 |
| 2004 | GAPA_NC002505_694_721_F | TCAATGAACGACCAACAAGTGATTGATG | 259 | GAPA_NC002505_769_798_R | TCCTCTATGCAACTTAGTATCAACAGGAAT | 1046 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2005 | GAPA_NC002505_753_782_F | TGCTAGTCAATCTATCATTCCGGTTGATAC | 517 | GAPA_NC002505_856_881_R | TCCATCGCAGTCACGTTTACTGTTGG | 1011 |
| 2006 | GYRB_NC002505_2_32_F | TGCCGGACAATTACGATTCATCGAGTATTAA | 501 | GYRB_NC002505_109_134_R | TCCACCACCTCAAAGACCATGTGGTG | 1003 |
| 2007 | GYRB_NC002505_123_152_F | TGAGGTGGTGGATAACTCAATTGATGAAGC | 460 | GYRB_NC002505_199_225_R | TCCGTCATCGCTGACAGAAACTGAGTT | 1042 |
| 2008 | GYRB_NC002505_768_794_F | TATGCAGTGGAACGATGGTTTCCAAGA | 236 | GYRB_NC002505_832_860_R | TGGAAACCGGCTAAGTGAGTACCACCATC | 1262 |
| 2009 | GYRB_NC002505_837_860_F | TGGTACTCACTTAGCGGGTTTCCG | 603 | GYRB_NC002505_937_957_R | TCCTTCACGCGCATCATCACC | 1054 |
| 2010 | GYRB_NC002505_934_956_F | TCGGGTGATGATGCGCGTGAAGG | 377 | GYRB_NC002505_982_1007_R | TGGCTTGAGAATTTAGGATCCGGCAC | 1283 |
| 2011 | GYRB_NC002505_1161_1190_F | TAAAGCCCGTGAAATGACTCGTCGTAAAGG | 148 | GYRB_NC002505_1255_1284_R | TGAGTCACCCTCCACAATGTATAGTTCAGA | 1172 |
| 2012 | OMPU_NC002505_85_110_F | TACGCTGACGGAATCAACCAAAGCGG | 190 | OMPU_NC002505_154_180_R | TGCTTCAGCACGGCCACCAACTTCTAG | 1254 |
| 2013 | OMPU_NC002505_258_283_F | TGACGGCCTATACGGTGTTGGTTTCT | 451 | OMPU_NC002505_346_369_R | TCCGAGACCAGCGTAGGTGTAACG | 1033 |
| 2014 | OMPU_NC002505_431_455_F | TCACCGATATCATGGCTTACCACGG | 266 | OMPU_NC002505_544_567_R | TCGGTCAGCAAAACGGTAGCTTGC | 1094 |
| 2015 | OMPU_NC002505_533_557_F | TAGGCGTGAAAGCAAGCTACCGTTT | 223 | OMPU_NC002505_625_651_R | TAGAGAGTAGCCATCTTCACCGTTGTC | 908 |
| 2016 | OMPU_NC002505_689_713_F | TAGGTGCTGGTTACGCAGATCAAGA | 224 | OMPU_NC002505_725_751_R | TGGGGTAAGACGCGGCTAGCATGTATT | 1291 |
| 2017 | OMPU_NC002505_727_747_F | TACATGCTAGCCGCGTCTTAC | 181 | OMPU_NC002505_811_835_R | TAGCAGCTAGCTCGTAACCAGTGTA | 911 |
| 2018 | OMPU_NC002505_931_953_F | TACTACTTCAAGCCGAACTTCCG | 193 | OMPU_NC002505_1033_1053_R | TTAGAAGTCGTAACGTGGACC | 1368 |
| 2019 | OMPU_NC002505_927_953_F | TACTTACTACTTCAAGCCGAACTTCCG | 197 | OMPU_NC002505_1033_1054_R | TGGTTAGAAGTCGTAACGTGGACC | 1307 |
| 2020 | TCPA_NC002505_48_73_F | TCACGATAAGAAAACCGGTCAAGAGG | 269 | TCPA_NC002505_148_170_R | TTCTGCGAATCAATCGCACGCTG | 1391 |
| 2021 | TDH_NC004605_265_289_F | TGGCTGACATCCTACATGACTGTGA | 574 | TDH_NC004605_357_386_R | TGTTGAAGCTGTACTTGACCTGATTTTACG | 1351 |
| 2022 | VVHA_NC004460_772_802_F | TCTTATTCCAACTTCAAACCGAACTATGACG | 412 | VVHA_NC004460_862_886_R | TACCAAAGCGTGCACGATAGTTGAG | 887 |
| 2023 | 23S_EC_2643_2667_F | TGCCTGTTCTTAGTACGAGAGGACC | 508 | 23S_EC_2746_2770_R | TGGGTTTCGCGCTTAGATGCTTTCA | 1297 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2024 | 16S_EC_713_732_TMOD_F | TAGAACACCGATGGCGAAGGC | 202 | 16S_EC_789_811_R | TGCGTGGACTACCAGGGTATCTA | 1240 |
| 2025 | 16S_EC_784_806_F | TGGATTAGAGACCCTGGTAGTCC | 560 | 16S_EC_880_897_TMOD_R | TGGCCGTACTCCCCAGGCG | 1278 |
| 2026 | 16S_EC_959_981_F | TGTCGATGCAACGCGAAGAACCT | 634 | 16S_EC_1052_1074_R | TACGAGCTGACGACAGCCATGCA | 896 |
| 2027 | TUFB_EC_956_979_F | TGCACACGCCGTTCTTCAACAACT | 489 | TUFB_EC_1034_1058_2_R | TGCATCACCATTTCCTTGTCCTTCG | 1204 |
| 2028 | RPOC_EC_2146_2174_TMOD_F | TCAGGAGTCGTTCAACTCGATCTACA TGAT | 284 | RPOC_EC_2227_2249_R | TGCTAGGCCATCAGGCCACGCAT | 1244 |
| 2029 | RPOB_EC_1841_1866_F | TGGTTATCGCTCAGGCGAACTCCAAC | 617 | RPOB_EC_1909_1929_TMOD_R | TGCTGGATTCGCCTTTGCTACG | 1250 |
| 2030 | RPLB_EC_650_679_TMOD_F | TGACCTACAGTAAGAGGTTCTGTAAT GAACC | 449 | RPLB_EC_739_763_R | TGCCAAGTGCTGGTTTACCCCATGG | 1208 |
| 2031 | RPLB_EC_690_710_F | TCCACACGGTGGTGGTGAAGG | 309 | RPLB_EC_737_760_R | TGGGTGCTGGTTTACCCCATGGAG | 1295 |
| 2032 | INFB_EC_1366_1393_F | TCTCGTGGTGCACAAGTAACGGATAT TA | 397 | INFB_EC_1439_1469_R | TGTGCTGCTTTCGCATGGTTAATTGCTT CAA | 1335 |
| 2033 | VALS_EC_1105_1124_TMOD_F | TCGTGGCGGCGTGGTTATCGA | 385 | VALS_EC_1195_1219_R | TGGGTACGAACTGGATGTCGCCGTT | 1292 |
| 2034 | SSPE_BA_113_137_F | TGCAAGCAAACGCACAATCAGAAGC | 482 | SSPE_BA_197_222_TMOD_R | TTGCACGTCTGTTTCAGTTGCAAATTC | 1402 |
| 2035 | RPOC_EC_2218_2241_TMOD_F | TCTGGCAGGTATGCGTGGTCTGATG | 405 | RPOC_EC_2313_2338_R | TGGCACCGTGGGTTGAGATGAAGTAC | 1273 |
| 2056 | MECI-R_NC003923-41798-41609_33_60_F | TTTACACATATCGTGAGCAATGAACT GA | 698 | MECI-R_NC003923-41798-41609_86_113_R | TTGTGATATGGAGGTGTAGAAGGTGTTA | 1420 |
| 2057 | AGR-III_NC003923-2108074-2109507_1_23_F | TCACCAGTTTGCCACGTATCTTCAA | 263 | AGR-III_NC003923-2108074-2109507_56_79_R | ACCTGCATCCCTAAACGTACTTGC | 730 |
| 2058 | AGR-III_NC003923-2108074-2109507_569_596_F | TGAGCTTTTAGTTGACTTTTTCAACA GC | 457 | AGR-III_NC003923-2108074-2109507_622_653_R | TACTTCAGCTTCGTCCAATAAAAAATCA CAAT | 906 |
| 2059 | AGR-III_NC003923-2108074-2109507_1024_1052_F | TTTCACACAGCGTGTTTATAGTTCTA CCA | 701 | AGR-III_NC003923-2108074-2109507_1070_1098_R | TGTAGGCAAGTGCATAAGAAATTGATAC A | 1319 |
| 2060 | AGR-I_AJ617706_622_651_F | TGGTGACTTCATAATGGATGAAGTTG AAGT | 610 | AGR-I_AJ617706_694_726_R | TCCCCATTTAATAATTCCACCTACTATC ACACT | 1021 |
| 2061 | AGR-I_AJ617706_580_611_F | TGGGATTTTAAAAAACATTGGTAACA TCGCAG | 579 | AGR-I_AJ617706_626_655_R | TGGTACTTCAACTTCATCCATTATGAAG TC | 1302 |
| 2062 | AGR-II_NC002745-2079448-2080879_620_651_F | TCTTGCAGCAGTTTATTTGATGAACC TAAAGT | 415 | AGR-II_NC002745-2079448-2080879_700_731_R | TTGTTTATTGTTTCCATATGCTACACAC TTTC | 1424 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2063 | AGR-II_NC002745-2079441-2080879_649_679_F | TGTACCCGCTGAATTAACGAATTTATACGAC | 624 | AGR-II_NC002745-2079448-2080879_715_745_R | TCGCCATAGCTAAGTTGTTTATTGTTTCCAT | 1077 |
| 2064 | AGR-IV_AJ617711_931_961_F | TGGTATTCTATTTTGCTGATAATGACCTCGC | 606 | AGR-IV_AJ617711_1004_1035_R | TGCGCTATCAACGATTTTGACAATATATGTGA | 1233 |
| 2065 | AGR-IV_AJ617711_250_283_F | TGGCACTCTTGCCTTTAATATTAGTAAACTATCA | 562 | AGR-IV_AJ617711_309_335_R | TCCCATACCTATGGCGATAACTGTCAT | 1017 |
| 2066 | BLAZ_NC002952(1913827..1914672)_68_68_F | TCCACTTATCGCAAATGGAAAATTAAGCAA | 312 | BLAZ_NC002952(1913827..1914672)_68_68_R | TGGCCACTTTTATCAGCAACCTTACAGTC | 1277 |
| 2067 | BLAZ_NC002952(1913827_..1914672)_68_68_2_F | TGCACTTATCGCAAATGGAAAATTAAGCAA | 494 | BLAZ_NC002952(1913827..1914672) 68_68_2_R | TAGTCTTTTGGAACACCGTCTTTAATTAAAGT | 926 |
| 2068 | BLAZ_NC002952(1913827..1914672)_68_683_F | TGATACTTCAACGCCTGCTGCTTTC | 467 | BLAZ_NC002952(1913827..1914672) 68_68_3_R | TGGAACACCGTCTTTAATTAAAGTATCTCC | 1263 |
| 2069 | BLAZ_NC002952(1913827..1914672)_68_68_4_F | TATACTTCAACGCCTGCTGCTTTC | 232 | BLAZ_NC002952(1913827..1914672)_68_68_4_R | TCTTTTCTTTGCTTAATTTTCCATTTGCGAT | 1145 |
| 2070 | BLAZ_NC002952_(1913827..1914672)_1_33_F | TGCAATTGCTTTAGTTTTAAGTGCATGTAATTC | 487 | BLAZ_NC002952(1913827..1914672)_34_67_R | TTACTTCCTTACCACTTTTAGTATCTAAAGCATA | 1366 |
| 2071 | BLAZ_NC002952(1913827..1914672)_3_34_F | TCCTTGCTTTAGTTTTAAGTGCATGTAATTCAA | 351 | BLAZ_NC002952(1913827..1914672)_40_68_R | TGGGGACTTCCTTACCACTTTTAGTATCTAA | 1289 |
| 2072 | BSA-A_NC003923-1304065-1303589_99_125_F | TAGCGAATGTGGCTTTACTTCACAATT | 214 | BSA-A_NC003923-1304065-1303589_165_193_R | TGCAAGGGAAACCTAGAATTACAAACCCT | 1197 |
| 2073 | BSA-A_NC003923-1304065-1303589_194_218_F | ATCAATTTGGTGGCCAAGAACCTGG | 32 | BSA-A_NC003923-1304065-1303589_253_278_R | TGCATAGGGAAGGTAACACCATAGTT | 1203 |
| 2074 | BSA-A_NC003923-1304065-1303589_328_349_F | TTGACTGCGGCACAACACGGAT | 679 | BSA-A_NC003923-1304065-1303589_388_415_R | TAACAACGTTACCTTCGCGATCCACTAA | 856 |
| 2075 | BSA-A_NC003923-1304065-1303589_253_278_F | TGCTATGGTGTTACCTTCCCTATGCA | 519 | BSA-A_NC003923-1304065-1303589_317_344_R | TGTTGTGCCGCAGTCAAATATCTAAATA | 1353 |
| 2076 | BSA-B_NC003923-1917149-1914156_953_982_F | TAGCAACAAATATATCTGAAGCAGCGTACT | 209 | BSA-B_NC003923-1917149-1914156_1011_1039_R | TGTGAAGAACTTTCAAATCTGTGAATCCA | 1331 |
| 2077 | BSA-B_NC003923-1917149-1914156_1050_1081_F | TGAAAAGTATGGATTTGAACAACTCGTGAATA | 426 | BSA-B_NC003923-1917149-1914156_1109_1136_R | TCTTCTTGAAAAATTGTTGTCCCGAAAC | 1138 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2078 | BSA-B_NC003923-1917149-1914156_1260_1286_F | TCATTATCATGCGCCAATGAGTGCAGA | 300 | BSA-B_NC003923-1917149-1914156_1323_1353_R | TGGACTAATAACAATGAGCTCATTGTACTGA | 1267 |
| 2079 | BSA-B_NC003923-1917149-1914156_2126_2153_F | TTTCATCTTATCGAGGACCCGAAATCGA | 703 | BSA-B_NC003923-1917149-1914156_2186_2216_R | TGAATATGTAATGCAAACCAGTCTTTGTCAT | 1148 |
| 2080 | ERMA_NC002952-55890-56621_366_392_F | TCGCTATCTTATCGTTGAGAAGGGATT | 372 | ERMA_NC002952-55890-56621_487_513_R | TGAGTCTACACTTGGCTTAGGATGAAA | 1174 |
| 2081 | ERMA_NC002952-55890-56621_366_395_F | TAGCTATCTTATCGTTGAGAAGGGATTTGC | 217 | ERMA_NC002952-55890-56621_438_465_R | TGAGCATTTTTATATCCATCTCCACCAT | 1167 |
| 2082 | ERMA_NC002952-55890-56621_374_402_F | TGATCGTTGAGAAGGGATTTGCGAAAAGA | 470 | ERMA_NC002952-55890-56621_473_504_R | TCTTGGCTTAGGATGAAAATATAGTGGTGGTA | 1143 |
| 2083 | ERMA_NC002952-55890-56621_404_427_F | TGCAAAATCTGCAACGAGCTTTGG | 480 | ERMA_NC002952-55890-56621_491_520_R | TCAATACAGAGTCTACACTTGGCTTAGGAT | 964 |
| 2084 | ERMA_NC002952-55891-56621_489_516_F | TCATCCTAAGCCAAGTGTAGACTCTGTA | 297 | ERMA_NC002952-55890-56621_586_615_R | TGGACGATATTCACGGTTTACCCACTTATA | 1266 |
| 2085 | ERMA_NC002952-55890-56621_586_614_F | TATAAGTGGGTAAACCGTGAATATCGTGT | 231 | ERMA_NC002952-55890-56621_640_665_R | TTGACATTTGCATGCTTCAAAGCCTG | 1397 |
| 2086 | ERMC_NC005908-2004-2738_85_116_F | TCTGAACATGATAATATCTTTGAAATCGGCTC | 399 | ERMC_NC005908-2004-2738_173_206_R | TCCGTAGTTTTGCATAATTTATGGTCTATTTCAA | 1041 |
| 2087 | ERMC_NC005908-2004-2738_90_120_F | TCATGATAATATCTTTGAAATCGGCTCAGGA | 298 | ERMC_NC005908-2004-2738_160_189_R | TTTATGGTCTATTTCAATGGCAGTTACGAA | 1429 |
| 2088 | ERMC_NC005908-2004-2738_115_139_F | TCAGGAAAAGGGCATTTTACCCTTG | 283 | ERMC_NC005908-2004-2738_161_187_R | TATGGTCTATTTCAATGGCAGTTACGA | 936 |
| 2089 | ERMC_N0005908-2004-2738_374_397_F | TAATCGTGGAATACGGGTTTGCTA | 168 | ERMC_NC005908-2004-2738_425_452_R | TCAACTTCTGCCATTAAAAGTAATGCCA | 956 |
| 2090 | ERMC_NC005908-2004-2738_101_125_F | TCTTTGAAATCGGCTCAGGAAAAGG | 421 | ERMC_NC005908-2004-2738_159_188_R | TGATGGTCTATTTCAATGGCAGTTACGAAA | 1185 |
| 2091 | ERMB_Y13600-625-1362_291_321_F | TGTTGGGAGTATTCCTTACCATTTAAGCACA | 644 | ERMB_Y13600-625-1362_352_380_R | TCAACAATCAGATAGATGTCAGACGCATG | 953 |
| 2092 | ERMB_Y13600-625-1362_344_367_F | TGGAAAGCCATGCGTCTGACATCT | 536 | ERMB_Y13600-625-1362_415_437_R | TGCAAGAGCAACCCTAGTGTTCG | 1196 |
| 2093 | ERMB_Y13600-625-1362_404_429_F | TGGATATTCACCGAACACTAGGGTTG | 556 | ERMB_Y13600-625-1362_471_493_R | TAGGATGAAAGCATTCCGCTGGC | 919 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2094 | ERMB_Y13600-625-1362_465_487_F | TAAGCTGCCAGCGGAATGCTTTC | 161 | ERMB_Y13600-625-1362_521_545_R | TCATCTGTGGTATGGCGGGTAAGTT | 989 |
| 2095 | PVLUK_NC003923-1529515-1531285_688_713_F | TGAGCTGCATCAACTGTATTGGATAG | 456 | PVLUK_NC003923-1529595-1531285_775_804_R | TGGAAAACTCATGAAATTAAAGTGAAAGGA | 1261 |
| 2096 | PVLUK_NC003923-1529515-1531285_1039_1068_F | TGGAACAAAATAGTCTCTCGGATTTTGACT | 539 | PVLUK NC003923-1529595-1531285_1095_1125_R | TCATTAGGTAAAATGTCTGGACATGATCCAA | 993 |
| 2097 | PVLUK_NC003923-1529595-1531285_908_936_F | TGAGTAACATCCATATTTCTGCCATACGT | 461 | PVLUK NC003923-1529595-1531285_950_978_R | TCTCATGAAAAAGGCTCAGGAGATACAAG | 1124 |
| 2098 | PVLUK_NC003923-15295/5-1531285_610_633_F | TCGGAATCTGATGTTGCAGTTGTT | 373 | PVLUK NC003923-1529595-1531285_654_682_R | TCACACCTGTAAGTGAGAAAAAGGTTGAT | 968 |
| 2099 | SA442_NC003923-2538556-2538831_11_35_F | TGTCGGTACACGATATTCTTCACGA | 635 | SA442_NC003923-2538576-2538831_98_124_R | TTTCCGATGCAACGTAATGAGATTTCA | 1433 |
| 2100 | SA442_NC003923-253856-2538831_98_124_F | TGAAATCTCATTACGTTGCATCGGAAA | 427 | SA442_NC003923-2538576-2538831_163_188_R | TCGTATGACCAGCTTCGGTACTACTA | 1098 |
| 2101 | SA442_NC003923-2538576-2538831_103_126_F | TCTCATTACGTTGCATCGGAAACA | 395 | SA442_NC003923-2538576-2538831_161_187_R | TTTATGACCAGCTTCGGTACTACTAAA | 1428 |
| 2102 | SA442_N003923-2538576-2538831_166_188_F | TAGTACCGAAGCTGGTCATACGA | 226 | SA442_NC003923-2538576-2538831_231_257_R | TGATAATGAAGGGAAACCTTTTTCACG | 1179 |
| 2103 | SEA_NC003923-2052219-2051456_115_135F | TGCAGGGAACAGCTTTAGGCA | 495 | SEA_NC003923-2052219-2051456_173_200_R | TCGATCGTGACTCTCTTTATTTTCAGTT | 1070 |
| 2104 | SEA_NC003923-2052219-2051456_572_598_F | TAACTCTGATGTTTTTGATGGGAAGGT | 156 | SEA_NC003923-2052219-2051456_621_651_R | TGTAATTAACCGAAGGTTCTGTAGAAGTATG | 1315 |
| 2105 | SEA_NC003923-2052219-2051456_382_414_F | TGTATGGTGGTGTAACGTTACATGATAATAATC | 629 | SEA_NC003923-2052219-2051456_464_492_R | TAACCGTTTCCAAAGGTACTGTATTTTGT | 861 |
| 2106 | SEA_NC003923-2052219-2051456_377_406_F | TTGTATGTATGGTGGTGTAACGTTACATGA | 695 | SEA_NC003923-2052219-2051456_459_492_R | TAACCGTTTCCAAAGGTACTGTATTTTGTTTACC | 862 |
| 2107 | SEB_NC002758-2135540-2135140_208_237_F | TTTCACATGTAATTTTGATATTCGCACTGA | 702 | SEB_NC002758-2135540-2135140_273_298_R | TCATCTGGTTTAGGATCTGGTTGACT | 988 |
| 2108 | SEB_NC002758-2135540-2135140_206_235_F | TATTTCACATGTAATTTTGATATTCGCACT | 244 | SEE_NC002758-2135540-2135140_281_304_R | TGCAACTCATCTGGTTTAGGATCT | 1194 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2109 | SEB_NC002758-2135540-2135140_402_402_F | TAACAACTCGCCTTATGAAACGGGATATA | 151 | SEB_NC002758-2135540-2135140_402_402_R | TGTGCAGGCATCATGTCATACCAA | 1334 |
| 2110 | SEB_NC002758-2135540-2135140_402_402_2_F | TTGTATGTATGGTGGTGTAACTGAGCA | 696 | SEE_NC002758-2135540-2135140_402_402_2_R | TTACCATCTTCAAATACCCGAACAGTAA | 1361 |
| 2111 | SEC_NC003923-851678-852768_546_575_F | TTAACATGAAGGAAACCACTTTGATAATGG | 648 | SEC_NC003923-851678-852768_620_647_R | TGAGTTTGCACTTCAAAAGAAATTGTGT | 1177 |
| 2112 | SEC_NC003923-851678-852768_537_566_F | TGGAATAACAAAACATGAAGGAAACCACTT | 546 | SEC_NC003923-851678-852768_619_647_R | TCAGTTTGCACTTCAAAAGAAATTGTGTT | 985 |
| 2113 | SEC_NC003923-851678-852768_720_749_F | TGAGTTTAACAGTTCACCATATGAAACAGG | 466 | SEC_NC003923-851678-852768_794_815_R | TCGCCTGGTGCAGGCATCATAT | 1078 |
| 2114 | SEC_NC003923-851678-852768_787_810_F | TGGTATGATATGATGCCTGCACCA | 604 | SEC_NC003923-851678-852768_853_886_R | TCTTCACACTTTTAGAATCAACCGTTTTATTGTC | 1133 |
| 2115 | SED_M28521_657_682_F | TGGTGGTGAAATAGATAGGACTGCTT | 615 | SED_M28521_741_770_R | TGTACACCATTTATCCACAAATTGATTGGT | 1318 |
| 2116 | SED_M28521_690_711_F | TGGAGGTGTCACTCCACACGAA | 554 | SED_M28521_739_770_R | TGGGCACCATTTATCCACAAATTGATTGGTAT | 1288 |
| 2117 | SED_M28521_833_854_F | TTGCACAAGCAAGGCGCTATTT | 683 | SED_M28521_888_911_R | TCGCGCTGTATTTTTCCTCCGAGA | 1079 |
| 2118 | SED_M28521_962_987_F | TGGATGTTAAGGGTGATTTTCCCGAA | 559 | SED_M28521_1022_1048_R | TGTCAATATGAAGGTGCTCTGTGGATA | 1320 |
| 2119 | SEA-SEE_NC002952-2131289-2130703_16_45_F | TTTACACTACTTTTATTCATTGCCCTAACG | 699 | SEA-SEE_NC002952-2131289-2130703_71_98_R | TCATTTATTTCTTCGCTTTTCTCGCTAC | 994 |
| 2120 | SEA-SEE_NC002952-2131289-2130703_249_278_F | TGATCATCCGTGGTATAACGATTTATTAGT | 469 | SEA-SEE_NC002952-2131289-2130703_314_344_R | TAAGCACCATATAAGTCTACTTTTTTCCCTT | 870 |
| 2121 | SEE_NC002952-2131289-2130703_409_437_F | TGACATGATAATAACCGATTGACCGAAGA | 445 | SEE_NC002952-2131289-2130703_465_494_R | TCTATAGGTACTGTAGTTTGTTTTCCGTCT | 1120 |
| 2122 | SEE_NC002952-2131289-2130703_525_550_F | TGTTCAAGAGCTAGATCTTCAGGCAA | 640 | SEE_NC002952-2131289-2130703_586_586_R | TTTGCACCTTACCGCCAAAGCT | 1436 |
| 2123 | SEE_NC002952-2131289-2130703_525_549_F | TGTTCAAGAGCTAGATCTTCAGGCA | 639 | SEE_NC002952-2131289-2130703_586_586_2_R | TACCTTACCGCCAAAGCTGTCT | 892 |
| 2124 | SEE_NC002952-2131289-2130703_361_384_F | TCTGGAGGCACACCAAATAAAACA | 403 | SEE_N0002952-2131289-2130703_444_471_R | TCCGTCTATCCACAAGTTAATTGGTACT | 1043 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2125 | SEG_NC002758-1955100-1954171_225_251_F | TGCTCAACCCGATCCTAAATTAGACGA | 520 | SEG_NC002758-1955100-1954171_321_346_R | TAACTCCTCTTCCTTCAACAGGTGGA | 863 |
| 2126 | SEG_NC002758-1955100-1954171_623_651_F | TGGACAATAGACAATCACTTGGATTTACA | 548 | SEG_NC002758-1955100-1954171_671_702_R | TGCTTTGTAATCTAGTTCCTGAATAGTAACCA | 1260 |
| 2127 | SEG_NC002758-1955100-1954171_540_564_F | TGGAGGTTGTTGTATGTATGGTGGT | 555 | SEG_NC002758-1955100-1954171_607_635_R | TGTCTATTGTCGATTGTTACCTGTACAGT | 1329 |
| 2128 | SEG_N0002758-1955100-1954171_694_718_F | TACAAAGCAAGACACTGGCTCACTA | 173 | SEG_NC002758-1955100-1954171_735_762_R | TGATTCAAATGCAGAACCATCAAACTCG | 1187 |
| 2129 | SEH_NC002953-60024-60977_449_472_F | TTGCAACTGCTGATTTAGCTCAGA | 682 | SEH_NC002953-60024-60977_547_576_R | TAGTGTTGTACCTCCATATAGACATTCAGA | 927 |
| 2130 | SEH_NC002953-60024-60977_408_434_F | TAGAAATCAAGGTGATAGTGGCAATGA | 201 | SEH_NC002953-60024-60977_450_473_R | TTCTGAGCTAAATCAGCAGTTGCA | 1390 |
| 2131 | SEH_NC002953-60024-60977_547_576_F | TCTGAATGTCTATATGGAGGTACAACACTA | 400 | SEH_NC002953-60024-60977_608_634_R | TACCATCTACCCAAACATTAGCACCAA | 888 |
| 2132 | SEH_NC002953-60024-60977_546_575_F | TTCTGAATGTCTATATGGAGGTACAACACT | 677 | SEH_NC002953-60024-60977_594_616_R | TAGCACCAATCACCCTTTCCTGT | 909 |
| 2133 | SEI_NC002758-1957830-1956949_324_349_F | TCAACTCGAATTTTCAACAGGTACCA | 253 | SEI_NC002758-1957830-1956949_419_446_R | TCACAAGGACCATTATAATCAATGCCAA | 966 |
| 2134 | SEI_NC002758-1957830-1956949_336_363_F | TTCAACAGGTACCAATGATTTGATCTCA | 666 | SEI_NC002758-1957830-1956949_420_447_R | TGTACAAGGACCATTATAATCAATGCCA | 1316 |
| 2135 | SEI_NC002758-1957830-1956949_356_384_F | TGATCTCAGAATCTAATAATTGGGACGAA | 471 | SEI_NC002758-1957830-1956949_449_474_R | TCTGGCCCCTCCATACATGTATTTAG | 1129 |
| 2136 | SEI_NC002758-1957830-1956949_223_253_F | TCTCAAGGTGATATTGGTGTAGGTAACTTAA | 394 | SEI_NC002758-1957830-1956949_290_316_R | TGGGTAGGTTTTTATCTGTGACGCCTT | 1293 |
| 2137 | SEJ_AF053140_1307_1332_F | TGTGGAGTAACACTGCATGAAAACAA | 637 | SEJ_AF053140_1381_1404_R | TCTAGCGGAACAACAGTTCTGATG | 1118 |
| 2138 | SEJ_AF053140_1378_1403_F | TAGCATCAGAACTGTTGTTCCGCTAG | 211 | SEJ_AF053140_1429_1458_R | TCCTGAAGATCTAGTTCTTGAATGGTTACT | 1049 |
| 2139 | SEJ_AF053140_1431_1459_F | TAACCATTCAAGAACTAGATCTTCAGGCA | 153 | SEJ_AF053140_1500_1531_R | TAGTCCTTTCTGAATTTTACCATCAAAGGTAC | 925 |
| 2140 | SEJ_AF053140_1434_1461_F | TCATTCAAGAACTAGATCTTCAGGCAAG | 301 | SEJ_AF053140_1521_1549_R | TCAGGTATGAAACACGATTAGTCCTTTCT | 984 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2141 | TSST_NC002758-2137564-2138293_206_236_F | TGGTTTAGATAATTCCTTAGGATCTATGCGT | 619 | TSST_NC002758-2137564-2138293_278_305_R | TGTAAAAGCAGGGCTATAATAAGGACTC | 1312 |
| 2142 | TSST_NC002758-2137564-2138293_232_258_F | TGCGTATAAAAAACACAGATGGCAGCA | 514 | TSST_NC002758-2137564-2138293_289_313_R | TGCCCTTTTGTAAAAGCAGGGCTAT | 1221 |
| 2143 | TSST_NC002758-2137564-2138293_382_410_F | TCCAAATAAGTGGCGTTACAAATACTGAA | 304 | TSST_NC002758-2137564-2138293_448_478_R | TACTTTAAGGGGCTATCTTTACCATGAACCT | 907 |
| 2144 | TSST_NC002758-2137564-2138293_297_325_F | TCTTTTACAAAAGGGGAAAAAGTTGACTT | 423 | TSST_NC002758-2137564-2138293_347_373_R | TAAGTTCCTTCGCTAGTATGTTGGCTT | 874 |
| 2145 | ARCC_NC003923-2725050-2724595_37_58_F | TCGCCGGCAATGCCATTGGATA | 368 | ARCC_NC003923-2725050-2724595_97_128_R | TGAGTTAAAATGCGATTGATTTCAGTTTCCAA | 1175 |
| 2146 | ARCC_NC003923-2725050-2724595_131_161_F | TGAATAGTGATAGAACTGTAGGCACAATCGT | 437 | ARCC_NC003923-2725050-2724595_214_245_R | TCTTCTTCTTTCGTATAAAAAGGACCAATTGG | 1137 |
| 2147 | ARCC_NC003923-2725050-2724595_218_249_F | TTGGTCCTTTTTATACGAAAGAAGAAGTTGAA | 691 | ARCC_NC003923-2725050-2724595_322_353_R | TGGTGTTCTAGTATAGATTGAGGTAGTGGTGA | 1306 |
| 2148 | AROE_NC003923-1674726-1674277_371_393_F | TTGCGAATAGAACGATGGCTCGT | 686 | AROE_NC003923-1674726-1674277_435_464_R | TCGAATTCAGCTAAATACTTTTCAGCATCT | 1064 |
| 2149 | AROE_NC003923-1674726-1674277_30_62_F | TGGGGCTTTAAATATTCCAATTGAAGATTTTCA | 590 | AROE_NC003923-1674726-1674277_155_181_R | TACCTGCATTAATCGCTTGTTCATCAA | 891 |
| 2150 | AROE_NC003923-1674726-1674277_204_232_F | TGATGGCAAGTGGATAGGGTATAATACAG | 474 | AROE_NC003923-1674726-1674277_308_335_R | TAAGCAATACCTTTACTTGCACCACCTG | 869 |
| 2151 | GLPF_NC003923-1296927-1297391_270_301_F | TGCACCGGCTATTAAGAATTACTTTGCCAACT | 491 | GLPF_NC003923-1296927-1297391_382_414_R | TGCAACAATTAATGCTCCGACAATTAAAGGATT | 1193 |
| 2152 | GLPF_NC003923-1296927-1297391_27_51_F | TGGATGGGGATTAGCGGTTACAATG | 558 | GLPF_NC003923-1296927-1297391_81_108_R | TAAAGACACCGCTGGGTTTAAATGTGCA | 850 |
| 2153 | GLPF_NC003923-1297391_239_260_F | TAGCTGGCGCGAAATTAGGTGT | 218 | GLPF_NC003923-1296927-1297391_323_359_R | TCACCGATAAATAAAATACCTAAAGTTAATGCCATTG | 972 |
| 2154 | GMK_NC003923-1190906-1191334_91_122_F | TACTTTTTTAAAACTAGGGATGCGTTTGAAGC | 200 | GMK_NC003923-1190906-1191334_166_197_R | TGATATTGAACTGGTGTACCATAATAGTTGCC | 1180 |
| 2155 | GMK_NC003923-1190906-1191334_240_267_F | TGAAGTAGAAGGTGCAAAGCAAGTTAGA | 435 | GMK_NC003923-1190906-1191334_305_333_R | TCGCTCTCTCAAGTGATCTAAACTTGGAG | 1082 |
| 2156 | GMK_NC003923-1190906-1191334_301_329_F | TCACCTCCAAGTTTAGATCACTTGAGAGA | 268 | GMK_NC003923-1190906-1191334_403_432_R | TGGGACGTAATCGTATAAATTCATCATTTC | 1284 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2157 | PTA_NC003923-628885-629355_237_263_F | TCTTGTTTATGCTGGTAAAGCAGATGG | 418 | PTA_NC003923-628885-629355_314_345_R | TGGTACACCTGGTTTCGTTTTGATGATTTGTA | 1301 |
| 2158 | PTA_NC003923-628885-629355_141_171_F | TGAATTAGTTCAATCATTTGTTGAACGACGT | 439 | PTA_NC003923-628885-629355_211_239_R | TGCATTGTACCGAAGTAGTTCACATTGTT | 1207 |
| 2159 | PTA_NC003923-628885-629355_328_356_F | TCCAAACCAGGTGTATCAAGAACATCAGG | 303 | PTA_NC003923-628885-629355_393_422_R | TGTTCTGGATTGATTGCACAATCACCAAAG | 1349 |
| 2160 | TPI_NC003923-83071-831072_131_160_F | TGCAAGTTAAGAAAGCTGTTGCAGGTTTAT | 486 | TPI_NC003923-830671-831072_209_239_R | TGAGATGTTGATGATTTACCAGTTCCGATTG | 1165 |
| 2161 | TPI_NC003923-830671-831072_1_34_F | TCCCACGAAACAGATGAAGAAATTAACAAAAAAG | 318 | TPI_NC003923-830671-831072_97_129_R | TGGTACAACATCGTTAGCTTTACCACTTTCACG | 1300 |
| 2162 | TPI_NC003923-830671-831072_199_227_F | TCAAACTGGGCAATCGGAACTGGTAAATC | 246 | TPI_NC003923-830671-831072_253_286_R | TGGCAGCAATAGTTTGACGTACAAATGCACACAT | 1275 |
| 2163 | YQI_NC003923-378916-379431_142_167_F | TGAATTGCTGCTATGAAAGGTGGCTT | 440 | YQI_NC003923-378916-379131_259_284_R | TCGCCAGCTAGCACGATGTCATTTTC | 1076 |
| 2164 | YQI_NC003923-378916-379431_44_77_F | TACAACATATTATTAAAGAGACGGGTTTGAATCC | 175 | YQI_NC003923-378916-379431_120_145_R | TTCGTGCTGGATTTTGTCCTTGTCCT | 1388 |
| 2165 | YQI_NC003923-378916-379431_135_160_F | TCCAGCACGAATTGCTGCTATGAAAG | 314 | YQI_NC003923-378916-379431_193_221_R | TCCAACCCAGAACCACATACTTTATTCAC | 997 |
| 2166 | YQI_NC003923-378916-379431_275_300_F | TAGCTGGCGGTATGGAGAATATGTCT | 219 | YQI_NC003923-378916-379431_364_396_R | TCCATCTGTTAAACCATCATATACCATGCTATC | 1013 |
| 2167 | BLAZ_(1913827..1914672)_546_575_F | TCCACTTATCGCAAATGGAAAATTAAGCAA | 312 | BLAZ_(1913827..1914672)_655_683_R | TGGCCACTTTTATCAGCAACCTTACAGTC | 1277 |
| 2168 | BLAZ_(1913827..1914672)_546_575_2_F | TGCACTTATCGCAAATGGAAAATTAAGCAA | 494 | BLAZ_(1913827..1914672)_628_659_R | TAGTCTTTTGGAACACCGTCTTTAATTAAAGT | 926 |
| 2169 | BLAZ_(1913827..1914672)_507_531_F | TGATACTTCAACGCCTGCTGCTTTC | 467 | BLAZ_(1913827..1914672)_622_651_R | TGGAACACCGTCTTTAATTAAAGTATCTCC | 1263 |
| 2170 | BLAZ_(1913827..1914672)_508_531_F | TATACTTCAACGCCTGCTGCTTTC | 232 | BLAZ_(1913827..1914672)_553_583_R | TCTTTTCTTTGCTTAATTTTCCATTTGCGAT | 1145 |
| 2171 | BLAZ_(1913827..1914672)_24_56_F | TGCAATTGCTTTAGTTTTAAGTGCATGTAATTC | 487 | BLAZ_(1913827..1914672)_121_154_R | TTACTTCCTTACCACTTTTAGTATCTAAAGCATA | 1366 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2172 | BLAZ_(1913827..1914672)_26_58_F | TCCTTGCTTTAGTTTTAAGTGCATGTAATTCAA | 351 | BLAZ_(1913827..1914672)_1_27_157_R | TGGGGACTTCCTTACCACTTTTAGTATCTAA | 1289 |
| 2173 | BLAZ_NC002952-1913827-1914672_546_575_F | TCCACTTATCGCAAATGGAAAATTAAGCAA | 312 | BLAZ_NC002952-1913827-1914672_655_683_R | TGGCCACTTTTATCAGCAACCTTACAGTC | 1277 |
| 2174 | BLAZ_NC002952-1913827-1914672_546_575_2_F | TGCACTTATCGCAAATGGAAAATTAAGCAA | 494 | BLAZ_NC002952-1913827-1914672_628_659_R | TAGTCTTTTGGAACACCGTCTTTAATTAAAGT | 926 |
| 2175 | BLAZ_NC002952-1913827-1914672_507_531_F | TGATACTTCAACGCCTGCTGCTTTC | 467 | BLAZ_NC002952-1913827-1914672_622_651_R | TGGAACACCGTCTTTAATTAAAGTATCTCC | 1263 |
| 2176 | BLAZ_NC002952-1913827-1914672_508_531_F | TATACTTCAACGCCTGCTGCTTTC | 232 | BLAZ_NC002952-1913827-1914672_553_583_R | TCTTTTCTTTGCTTAATTTTCCATTTGCGAT | 1145 |
| 2177 | BLAZ_NC002952-1913827-1914672_24_56_F | TGCAATTGCTTTAGTTTTAAGTGCATGTAATTC | 487 | BLAZ_NC002952-1913827-1914672_121_154_R | TTACTTCCTTACCACTTTTAGTATCTAAAGCATA | 1366 |
| 2178 | BLAZ_NC002952-1913827-1914672_26_58_F | TCCTTGCTTTAGTTTTAAGTGCATGTAATTCAA | 351 | BLAZ_NC002952-1913827-1914672_127_157_R | TGGGGACTTCCTTACCACTTTTAGTATCTAA | 1289 |
| 2247 | TUFB_NC002758-615058-616222_693_721_F | TGTTGAACGTGGTCAAATCAAAGTTGGTG | 643 | TUFB_NC002758-615038-616222_793_820_R | TGTCACCAGCTTCAGCGTAGTCTAATAA | 1321 |
| 2248 | TUFB_NC002758-615058-616222_690_716_F | TCGTGTTGAACGTGGTCAAATCAAAGT | 386 | TUFB_NC002758-615038-616222_793_820_R | TGTCACCAGCTTCAGCGTAGTCTAATAA | 1321 |
| 2249 | TUFB_NC002758-615038-616222_696_725_F | TGAACGTGGTCAAATCAAAGTTGGTGAAGA | 430 | TUFB_NC002758-615038-616222_793_820_R | TGTCACCAGCTTCAGCGTAGTCTAATAA | 1321 |
| 2250 | TUFB_NC002758-615038-616222_488_513_F | TCCCAGGTGACGATGTACCTGTAATC | 320 | TUFB_NC002758-615038-616222_601_630_R | TGGTTTGTCAGAATCACGTTCTGGAGTTGG | 1311 |
| 2251 | TUFB_NC002758-615038-616222_945_972_F | TGAAGGTGGACGTCACACTCCATTCTTC | 433 | TUFB_NC002758-615038-616222_1030_1060_R | TAGGCATAACCATTTCAGTACCTTCTGGTAA | 922 |
| 2252 | TUFB_N-6002758-615038-616222_333_356_F | TCCAATGCCACAAACTCGTGAACA | 307 | TUFB_NC002758-615038-616222_424_459_R | TTCCATTTCAACTAATTCTAATAATTCTTCATCGTC | 1382 |
| 2253 | NUC_N0002758-894288-894974_402_424_F | TCCTGAAGCAAGTGCATTTACGA | 342 | NUC_NC002758-894288-894974_483_509_R | TACGCTAAGCCACGTCCATATTTATCA | 899 |
| 2254 | NUC_NC002758-894288-894974_53_81_F | TCCTTATAGGGATGGCTATCAGTAATGTT | 349 | NUC_NC002758-894288-894974_165_189_R | TGTTTGTGATGCATTTGCTGAGCTA | 1354 |
| 2255 | NUC_NC002758-894288-894974_169_194_F | TCAGCAAATGCATCACAAACAGATAA | 273 | NUC_NC002758-894288-894974_222_250_R | TAGTTGAAGTTGCACTATATACTGTTGGA | 928 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2256 | NUC_NC002758-894288-894974_316_345_F | TACAAAGGTCAACCAATGACATTCAGACTA | 174 | NUC_NC002758-894288-894974_396_421_R | TAAATGCACTTGCTTCAGGGCCATAT | 853 |
| 2270 | RPOB_EC_3798_3821_1_F | TGGCCAGCGCTTCGGTGAAATGGA | 566 | RPOB_EC_3868_3895_R | TCACGTCGTCCGACTTCACGGTCAGCAT | 979 |
| 2271 | RPOB_EC_3789_3812_F | TCAGTTCGGCGGTCAGCGCTTCGG | 294 | RPOB_EC_3860_3890_R | TCGTCGGACTTAACGGTCAGCATTTCCTGCA | 1107 |
| 2272 | RPOB_EC_3789_3812_F | TCAGTTCGGCGGTCAGCGCTTCGG | 294 | RPOB_EC_3860_3890_2_R | TCGTCCGACTTAACGGTCAGCATTTCCTGCA | 1102 |
| 2273 | RPOB_EC_3789_3812_F | TCAGTTCGGCGGTCAGCGCTTCGG | 294 | RPOB_EC_3862_3890_R | TCGTCGGACTTAACGGTCAGCATTTCCTG | 1106 |
| 2274 | RPOB_EC_3789_3812_F | TCAGTTCGGCGGTCAGCGCTTCGG | 294 | RPOB_EC_3862_3890_2_R | TCGTCCGACTTAACGGTCAGCATTTCCTG | 1101 |
| 2275 | RPOB_EC_3793_3812_F | TTCGGCGGTCAGCGCTTCGG | 674 | RPOB_EC_3865_3890_R | TCGTCGGACTTAACGGTCAGCATTTC | 1105 |
| 2276 | RPOB_EC_3793_3812_F | TTCGGCGGTCAGCGCTTCGG | 674 | RPOB_EC_3865_3890_2_R | TCGTCCGACTTAACGGTCAGCATTTC | 1100 |
| 2309 | MUPR_X75439_1658_1689_F | TCCTTTGATATATTATGCGATGGAAGGTTGGT | 352 | MUPR_X75439_1744_1773_R | TCCCTTCCTTAATATGAGAAGGAAACCACT | 1030 |
| 2310 | MUPR_X75439_1330_1353_F | TTCCTCCTTTTGAAAGCGACGGTT | 669 | MUPR_X75439_1413_1441_R | TGAGCTGGTGCTATATGAACAATACCAGT | 1171 |
| 2312 | MUPR_X75439_1314_1338_F | TTTCCTCCTTTTGAAAGCGACGGTT | 704 | MUPR_X75439_1381_1409_R | TATATGAACAATACCAGTTCCTTCTGAGT | 931 |
| 2313 | MUPR_X75439_2486_2516_F | TAATTGGGCTCTTTCTCGCTTAAACACCTTA | 172 | MUPR_X75439_2548_2574_R | TTAATCTGGCTGCGGAAGTGAAATCGT | 1360 |
| 2314 | MUPR_X75439_2547_2572_F | TACGATTTCACTTCCGCAGCCAGATT | 188 | MUPR_X75439_2605_2630_R | TCGTCCTCTCGAATCTCCGATATACC | 1103 |
| 2315 | MUPR_X75439_2666_2696_F | TGCGTACAATACGCTTTATGAAATTTTAACA | 513 | MUPR_X75439_2711_2740_R | TCAGATATAAATGGAACAAATGGAGCCACT | 981 |
| 2316 | MUPR_X75439_2813_2843_F | TAATCAAGCATTGGAAGATGAAATGCATACC | 165 | MUPR_X75439_2867_2890_R | TCTGCATTTTTGCGAGCCTGTCTA | 1127 |
| 2317 | MUPR_X75439_884_914_F | TGACATGGACTCCCCCTATATAACTCTTGAG | 447 | MUPR_X75439_977_1007_R | TGTACAATAAGGAGTCACCTTATGTCCCTTA | 1317 |
| 2318 | CTXA_NC002505-1568114-1567341_114_142_F | TGGTCTTATGCCAAGAGGACAGAGTGAGT | 608 | CTXA_NC002505-1568114-1567341_194_221_R | TCGTGCCTAACAAATCCCGTCTGAGTTC | 1109 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2319 | CTXA_NC002505-1568114-1567341_117_145_F | TCTTATGCCAAGAGGACAGAGTGAGTACT | 411 | CTXA_NC002505-1568114-1567341_194_221_R | TCGTGCCTAACAAATCCCGTCTGAGTTC | 1109 |
| 2320 | CTXA_NC002505-1568114-1567341_114_142_F | TGGTCTTATGCCAAGAGGACAGAGTGAGT | 608 | CTXA_NC002505-1568114-1567341_186_214_R | TAACAAATCCCGTCTGAGTTCCTCTTGCA | 855 |
| 2321 | CTXA_NC002505-1568114-1567341_117_145_F | TCTTATGCCAAGAGGACAGAGTGAGTACT | 411 | CTXA_NC002505-1568114-1567341_186_214_R | TAACAAATCCCGTCTGAGTTCCTCTTGCA | 855 |
| 2322 | CTXA_NC002505-1568114-1567341_129_156_F | AGGACAGAGTGAGTACTTTGACCGAGGT | 27 | CTXA_NC002505-1568114-1567341_180_207_R | TCCCGTCTGAGTTCCTCTTGCATGATCA | 1027 |
| 2323 | CTXA_NC002505-1568114-1567341_122_149_F | TGCCAAGAGGACAGAGTGAGTACTTTGA | 500 | CTXA_NC002505-1568114-1567341_186_214_R | TAACAAATCCCGTCTGAGTTCCTCTTGCA | 855 |
| 2324 | INV_U22457-74-3772_831_858_F | TGCTTATTTACCTGCACTCCCACAACTG | 530 | INV_U22457-74-3772_942_966_R | TGACCCAAAGCTGAAAGCTTTACTG | 1154 |
| 2325 | INV_U22457-74-3772_827_857_F | TGAATGCTTATTTACCTGCACTCCCACAACT | 438 | INV_U22457-74-3772_942_970_R | TAACTGACCCAAAGCTGAAAGCTTTACTG | 864 |
| 2326 | INV_U22457-74-3772_1555_1581_F | TGCTGGTAACAGAGCCTTATAGGCGCA | 526 | INV_U22457-74-3772_1619_1647_R | TGGGTTGCGTTGCAGATTATCTTTACCA | 1296 |
| 2327 | INV_U22457-74-3772_1558_1585_F | TGGTAACAGAGCCTTATAGGCGCATATG | 598 | INV_U22457-74-3772_1622_1652_R | TCATAAGGGTTGCGTTGCAGATTATCTTTAC | 987 |
| 2328 | ASD_NC006570-439714-438608_3_37_F | TGAGGGTTTTATGCTTAAAGTTGGTTTTATTGGTT | 459 | ASD_NC006570-439714-438608_54_84_R | TGATTCGATCATACGAGACATTAAAACTGAG | 1188 |
| 2329 | ASD_NC006570-439714-438608_18_45_F | TAAAGTTGGTTTTATTGGTTGGCGCGGA | 149 | ASD_NC006570-439714-438608_66_95_R | TCAAAATCTTTTGATTCGATCATACGAGAC | 948 |
| 2330 | ASD_NC006570-439714-438608_17_45_F | TTAAAGTTGGTTTTATTGGTTGGCGCGGA | 647 | ASD_NC006570-439714-438608_67_95_R | TCCCAATCTTTTGATTCGATCATACGAGA | 1016 |
| 2331 | ASD_NC006570-439714-438608_9_40_F | TTTTATGCTTAAAGTTGGTTTTATTGGTTGGC | 709 | ASD_NC006570-439714-438608_107_134_R | TCTGCCTGAGATGTCGAAAAAAACGTTG | 1128 |
| 2332 | GALE_AF513299_171_200_F | TCAGCTAGACCTTTTAGGTAAAGCTAAGCT | 280 | GALE_AF513299_241_271_R | TCTCACCTACAGCTTTAAAGCCAGCAAATG | 1122 |
| 2333 | GALE_AF513299_168_199_F | TTATCAGCTAGACCTTTTAGGTAAAGCTAAGC | 658 | GALE_AF513299_245_271_R | TCTCACCTACAGCTTTAAAGCCAGCAA | 1121 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2334 | GALE_AF513299_168_199_F | TTATCAGCTAGACCTTTTAGGTAAAGCTAAGC | 658 | GALE_AF513299_233_264_R | TACAGCTTTAAAGCCAGCAAAATGAATTACAG | 883 |
| 2335 | GALE_AF513299_169_198_F | TCCCAGCTAGACCTTTTAGGTAAAGCTAAG | 319 | GALE_AF513299_252_279_R | TTCAACACTCTCACCTACAGCTTTAAAG | 1374 |
| 2336 | PLA_AF053945_7371_7403_F | TTGAGAAGACATCCGGCTCACGTTATTATGGTA | 680 | PLA_AF053945_7434_7468_R | TACGTATGTAAATTCCGCAAAGACTTTGGCATTAG | 900 |
| 2337 | PLA_AF053945_7377_7403_F | TGACATCCGGCTCACGTTATTATGGTA | 443 | PLA_AF053945_7428_7455_R | TCCGCAAAGACTTTGGCATTAGGTGTGA | 1035 |
| 2338 | PLA_AF053945_7377_7404_F | TGACATCCGGCTCACGTTATTATGGTAC | 444 | PLA_AF053945_7430_7460_R | TAAATTCCGCAAAGACTTTGGCATTAGGTGT | 854 |
| 2339 | CAF_AF053947_33412_33441_F | TCCGTTATCGCCATTGCATTATTTGGAACT | 329 | CAF_AF053947_33498_33523_R | TAAGAGTGATGCGGGCTGGTTCAACA | 866 |
| 2340 | CAF_AF053947_33426_33458_F | TGCATTATTTGGAACTATTGCAACTGCTAATGC | 499 | CAF_AF053947_33483_33507_R | TGGTTCAACAAGAGTTGCCGTTGCA | 1308 |
| 2341 | CAF_AF053947_33407_33429_F | TCAGTTCCGTTATCGCCATTGCA | 291 | CAF_AF053947_33483_33504_R | TTCAACAAGAGTTGCCGTTGCA | 1373 |
| 2342 | CAF_AF053947_33407_33431_F | TCAGTTCCGTTATCGCCATTGCATT | 293 | CAF_AF053947_33494_33517_R | TGATGCGGGCTGGTTCAACAAGAG | 1184 |
| 2344 | GAPA_NC_002505_1_28_F_1 | TCAATGAACGATCAACAAGTGATTGATG | 260 | GAPA_NC_002505_29_58_R_1 | TCCTTTATGCAACTTGGTATCAACAGGAAT | 1060 |
| 2472 | OMPA_NC000117_68_89_F | TGCCTGTAGGGAATCCTGCTGA | 507 | OMPA_NC000117_145_167_R | TCACACCAAGTAGTGCAAGGATC | 967 |
| 2473 | OMPA_NC000117_798_821_F | TGATTACCATGAGTGGCAAGCAAG | 475 | OMPA_NC000117_865_893_R | TCAAAACTTGCTCTAGACCATTTAACTCC | 947 |
| 2474 | OMPA_NC000117_645_671_F | TGCTCAATCTAAACCTAAAGTCGAAGA | 521 | OMPA_NC000117_757_777_R | TGTCGCAGCATCTGTTCCTGC | 1328 |
| 2475 | OMPA_NC000117_947_973_F | TAACTGCATGGAACCCTTCTTTACTAG | 157 | OMPA_NC000117_1011_1040_R | TGACAGGACACAATCTGCATGAAGTCTGAG | 1153 |
| 2476 | OMPA_NC000117_774_795_F | TACTGGAACAAAGTCTGCGACC | 196 | OMPA_NC000117_871_894_R | TTCAAAAGTTGCTCGAGACCATTG | 1371 |
| 2477 | OMPA_NC000117_457_483_F | TTCTATCTCGTTGGTTTATTCGGAGTT | 676 | OMPA_NC000117_511_534_R | TAAAGAGACGTTTGGTAGTTCATTTGC | 851 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2478 | OMPA_NC000117_687_710_F | TAGCCCAGCACAATTTGTGATTCA | 212 | OMPA_NC000117_787_816_R | TTGCCATTCATGGTATTTAAGTGTAGCAGA | 1406 |
| 2479 | OMPA_NC000117_540_566_F | TGGCGTAGTAGAGCTATTTACAGACAC | 571 | OMPA_NC000117_649_672_R | TTCTTGAACGCGAGGTTTCGATTG | 1395 |
| 2480 | OMPA_NC000117_338_360_F | TGCACGATGCGGAATGGTTCACA | 492 | OMPA_NC000117_417_444_R | TCCTTTAAAATAACCGCTAGTAGCTCCT | 1058 |
| 2481 | OMP2_NC000117_18_40_F | TATGACCAAACTCATCAGACGAG | 234 | OMP2_NC000117_71_91_R | TCCCGCTGGCAAATAAACTCG | 1025 |
| 2482 | OMP2_NC000117_354_382_F | TGCTACGGTAGGATCTCCTTATCCTATTG | 516 | OMP2_NC000117_445_471_R | TGGATCACTGCTTACGAACTCAGCTTC | 1270 |
| 2483 | OMP2_NC000117_1297_1319_F | TGGAAAGGTGTTGCAGCTACTCA | 537 | OMP2_NC000117_1396_1419_R | TACGTTTGTATCTTCTGCAGAACC | 903 |
| 2484 | OMP2_NC000117_1465_1493_F | TCTGGTCCAACAAAAGGAACGATTACAGG | 407 | OMP2_NC000117_1541_1569_R | TCCTTTCAATGTTACAGAAAACTCTACAG | 1062 |
| 2485 | OMP2_NC000117_44_66_F | TGACGATCTTCGCGGTGACTAGT | 450 | OMP2_NC000117_120_148_R | TGTCAGCTAAGCTAATAACGTTTGTAGAG | 1323 |
| 2486 | OMP2_NC000117_166_190_F | TGACAGCGAAGAAGGTTAGACTTGTCC | 441 | OMP2_NC000117_240_261_R | TTGACATCGTCCCTCTTCACAG | 1396 |
| 2487 | GYRA_NC000117_514_536_F | TCAGGCATTGCGGTTGGGATGGC | 287 | GYRA_NC000117_640_660_R | TGCTGTAGGGAAATCAGGGCC | 1251 |
| 2488 | GYRA_NC000117_801_827_F | TGTGAATAAATCACGATTGATTGAGCA | 636 | GYRA_NC000117_871_893_R | TTGTCAGACTCATCGCGAACATC | 1419 |
| 2489 | GYRA_NC002952_219_242_F | TGTCATGGGTAAATATCACCCTCA | 632 | GYRA_NC002952_319_345_R | TCCATCCATAGAACCAAAGTTACCTTG | 1010 |
| 2490 | GYRA_NC002952_964_983_F | TACAAGCACTCCCAGCTGCA | 176 | GYRA_NC002952_1024_1041_R | TCGCAGCGTGCGTGGCAC | 1073 |
| 2491 | GYRA_NC002952_1505_1520_F | TCGCCCGCGAGGACGT | 366 | GYRA_NC002952_1546_1562_R | TTGGTGCGCTTGGCGTA | 1416 |
| 2492 | GYRA_NC002952_59_81_F | TCAGCTACATCGACTATGCGATG | 279 | GYRA_NC002952_124_143_R | TGGCGATGCACTGGCTTGAG | 1279 |
| 2493 | GYRA_NC002952_216_239_F | TGACGTCATCGGTAAGTACCACCC | 452 | GYRA_NC002952_313_333_R | TCCGAAGTTGCCCTGGCCGTC | 1032 |
| 2494 | GYRA_NC002952_219_242_2_F | TGTACTCGGTAAGTATCACCCGCA | 625 | GYRA_NC002952_308_330_R | TAAGTTACCTTGCCCGTCAACCA | 873 |
| 2495 | GYRA_NC002952_115_141_F | TGAGATGGATTTAAACCTGTTCACCGC | 453 | GYRA_NC002952_220_242_R | TGCGGGTGATACTTACCGAGTAC | 1236 |
| 2496 | GYRA_NC002952_517_539_F | TCAGGCATTGCGGTTGGGATGGC | 287 | GYRA_NC002952_643_663_R | TGCTGTAGGGAAATCAGGGCC | 1251 |
| 2497 | GYRA_NC002952_273_293_F | TCGTATGGCTCAATGGTGGAG | 380 | GYRA_NC002952_338_360_R | TGCGGCAGCACTATCACCATCCA | 1234 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| | | Primer Pairs for Identification of Bacteria | | | | |
| 2498 | GYRA_NC000912_257_278_F | TGAGTAAGTTCCACCCGCACGG | 462 | GYRA_NC000912_346_370_R | TCGAGCCGAAGTTACCCTGTCCGTC | 1067 |
| 2504 | ARCC_NC003923-2725050-2724595_135_161P_F | TAGTpGATpAGAACpTpGTAGGCpACpAATpCpGT | 229 | ARCC_NC003923-2725050-2724595_214_239P_R | TCpTpTpTpCpGTATAAAAAGGACpCpAATpTpGG | 1116 |
| 2505 | PTA_NC003923-628885-629355_237_263P_F | TCTTGTpTpTpATGCpTpGGTAAAGCAGATGG | 417 | PTA_N0003923-628885-629355_314_342P_R | TACpACpCpTGGTpTpTpCpGTpTpTpTpGATGATpTpTpGTA | 904 |
| 2517 | CJMLST_ST1_1852_1883_F | TTTGCGGATGAAGTAGGTGCCTATCTTTTTGC | 708 | CJMLST_ST1_1945_1977_R | TGTTTTATGTGTAGTTGAGCTTACTACATGAGC | 1355 |
| 2518 | CJMLST_ST1_2963_2992_F | TGAAATTGCTACAGGCCCTTTAGGACAAGG | 428 | CJMLST_ST1_3073_3097_R | TCCCCATCTCCGCAAAGACAATAAA | 1020 |
| 2519 | CJMLST_ST1_2350_2378_F | TGCTTTTGATGGTGATGCAGATCGTTTGG | 535 | CJMLST_ST1_2447_2481_R | TCTACAACACTTGATTGTAATTTGCCTTGTTCTTT | 1117 |
| 2520 | CJMLST_ST1_654_684_F | TATGTCCAAGAAGCATAGCAAAAAAAGCAAT | 240 | CJMLST_ST1_725_756_R | TCGGAAACAAAGAATTCATTTTCTGGTCCAAA | 1084 |
| 2521 | CJMLST_ST1_360_395_F | TCCTGTTATTCCTGAAGTAGTTAATCAAGTTTGTTA | 347 | CJMLST_ST1_454_487_R | TGCTATATGCTACAACTGGTTCAAAAACATTAAG | 1245 |
| 2522 | CJMLST_ST1_1231_1258_F | TGGCAGTTTTACAAGGTGCTGTTTCATC | 564 | CJMLST_ST1_1312_1340_R | TTTAGCTACTATTCTAGCTGCCATTTCCA | 1427 |
| 2523 | CJMLST_ST1_3543_3574_F | TGCTGTAGCTTATCGCGAAATGTCTTTGATTT | 529 | CJMLST_ST1_3656_3685_R | TCAAAGAACCAGCACCTAATTCATCATTTA | 950 |
| 2524 | CJMLST_ST1_1_17_F | TAAAACTTTTGCCGTAATGATGGGTGAAGATAT | 145 | CJMLST_ST1_55_84_R | TGTTCCAATAGCAGTTCCGCCCAAATTGAT | 1348 |
| 2525 | CJMLST_ST1_1312_1342_F | TGGAAATGGCAGCTAGAATAGTAGCTAAAAT | 538 | CJMLST_ST1_1383_1417_R | TTTCCCCGATCTAAATTTGGATAAGCCATAGGAAA | 1432 |
| 2526 | CJMLST_ST1_2254_2286_F | TGGGCCTAATGGGCTTAATATCAATGAAAATTG | 582 | CJMLST_ST1_2352_2379_R | TCCAAACGATCTGCATCACCATCAAAAG | 996 |
| 2527 | CJMLST_ST1_1380_1411_F | TGCTTTCCTATGGCTTATCCAAATTTAGATCG | 534 | CJMLST_ST1_1486_1520_R | TGCATGAAGCATAAAAACTGTATCAAGTGCTTTTA | 1205 |
| 2528 | CJMLST_ST1_3413_3437_F | TTGTAAATGCCGGTGCTTCAGATCC | 692 | CJMLST_ST1_3511_3542_R | TGCTTGCTCAAATCATCATAAACAATTAAAGC | 1257 |
| 2529 | CJMLST_ST1_1130_1156_F | TACGCGTCTTGAAGCGTTTCGTTATGA | 189 | CJMLST_ST1_1203_1230_R | TAGGATGAGCATTATCAGGGAAAGAATC | 920 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2530 | CJMLST_ST1_2840_2872_F | TGGGGCTTTGCTTTATAGTTTTTTACATTTAAG | 591 | CJMLST_ST1_2940_2973_R | TAGCGATTTCTACTCCTAGAGTTGAAATTTCAGG | 917 |
| 2531 | CJMLST_ST1_2058_2084_F | TATTCAAGGTGGTCCTTTGATGCATGT | 241 | CJMLST_ST1_2131_2162_R | TTGGTTCTTACTTGTTTTGCATAAACTTTCCA | 1417 |
| 2532 | CJMLST_ST1_553_585_F | TCCTGATGCTCAAAGTGCTTTTTTAGATCCTTT | 344 | CJMLST_ST1_655_685_R | TATTGCTTTTTTTGCTATGCTTCTTGGACAT | 942 |
| 2564 | GLTA_NC002163-1604930-1604529_306_338_F | TCATGTTGAGCTTAAACCTATAGAAGTAAAAGC | 299 | GLTA_NC002163-1604930-1604529_352_380_R | TTTTGCTCATGATCTGCATGAAGCATAAA | 1443 |
| 2565 | UNCA_NC002163-112166-112647_80_113_F | TCCCCCACGCTTTAATTGTTTATGATGATTTGAG | 322 | UNCA_NC002163-112166-112647_146_171_R | TCGACCTGGAGGACGACGTAAAATCA | 1065 |
| 2566 | UNCA_NC002163-112166-112647_233_259_F | TAATGATGAATTAGGTGCGGGTTCTTT | 170 | UNCA_NC002163-112166-112647_294_329_R | TGGGATAACATTGGTTGGAATATAAGCAGAAACATC | 1285 |
| 2567 | PGM_NC002163-327773-328270_273_305_F | TCTTGATACTTGTAATGTGGGCGATAAATATGT | 414 | PGM_NC002163-327773-328270_365_396_R | TCCATCGCCAGTTTTTGCATAATCGCTAAAAA | 1012 |
| 2568 | TKT_NC002163-1569415-1569873_255_284_F | TTATGAAGCGTGTTCTTTAGCAGGACTTCA | 661 | TKT_NC002163-1569415-1569873_350_383_R | TCAAAACGCATTTTTACATCTTCGTTAAAGGCTA | 946 |
| 2570 | GLTA_NC002163-1604930-1604529_39_68_F | TCGTCTTTTTGATTCTTTCCCTGATAATGC | 381 | GLTA_NC002163-1604930-1604529_109_142_R | TGTTCATGTTTAAATGATCAGGATAAAAAGCACT | 1347 |
| 2571 | TKT_NC002163-1569415-1569903_33_62_F | TGATCTTAAAAATTTCCGCCAACTTCATTC | 472 | TKT_NC002163-1569415-1569903_139_162_R | TGCCATAGCAAAGCCTACAGCATT | 1214 |
| 2572 | TKT_NC002163-1569415-1569903_207_239_F | TAAGGTTTATTGTCTTTGTGGAGATGGGGATTT | 164 | TKT_NC002163-1569415-1569903_313_345_R | TACATCTCCTTCGATAGAAATTTCATTGCTATC | 886 |
| 2573 | TKT_NC002163-1569415-1569903_350_383_F | TAGCCTTTAACGAAAATGTAAAAATGCGTTTTGA | 213 | TKT_NC002163-1569415-1569903_449_481_R | TAAGACAAGGTTTTGTGGATTTTTTAGCTTGTT | 865 |
| 2574 | TKT_NC002163-1569415-1569903_60_92_F | TTCAAAAACTCCAGGCCATCCTGAAATTTCAAC | 665 | TKT_NC002163-1569415-1569903_139_163_R | TTGCCATAGCAAAGCCTACAGCATT | 1405 |
| 2575 | GLTA_NC002163-1604930-1604529_39_70_F | TCGTCTTTTTGATTCTTTCCCTGATAATGCTC | 382 | GLTA_NC002163-1604930-1604529_139_168_R | TGCCATTTCCATGTACTCTTCTCTAACATT | 1216 |
| 2576 | GLYA_NC002163-367572-368079_386_414_F | TCAGCTATTTTTCCAGGTATCCAAGGTGG | 281 | GLYA_NC002163-367572-368079_476_508_R | ATTGCTTCTTACTTGCTTAGCATAAATTTTCCA | 756 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2577 | GLYA_NC002163-367572-368079_148_174_F | TGGTGCGAGTGCTTATGCTCGTATTAT | 611 | GLYA_NC002163-367572-368079_242_270_R | TGCTCACCTGCTACAACAAGTCCAGCAAT | 1246 |
| 2578 | GLYA_NC002163-367572-368079_298_327_F | TGTAAGCTCTACAACCCACAAAACCTTACG | 622 | GLYA_NC002163-367572-368079_384_416_R | TTCCACCTTGGATACCTGGAAAAATAGCTGAAT | 1381 |
| 2579 | GLYA_NC002163-367572-368079_1_27_F | TGGTGGACATTTAACACATGGTGCAAA | 614 | GLYA_NC002163-367572-368079_52_81_R | TCAAGCTCTACACCATAAAAAAAGCTCTCA | 961 |
| 2580 | PGM_NC002163-327746-328270_254_285_F | TGAGCAATGGGGCTTTGAAAGAATTTTTAAAT | 455 | PGM_NC002163-327746-328270_356_379_R | TTTGCTCTCCGCCAAAGTTTCCAC | 1438 |
| 2581 | PGM_NC002163-327746-328270_153_182_F | TGAAAAGGGTGAAGTAGCAAATGGAGATAG | 425 | PGM_NC002163-327746-328270_241_267_R | TGCCCCATTGCTCATGATAGTAGCTAC | 1219 |
| 2582 | PGM_NC002163-327746-328270_19_50_F | TGGCCTAATGGGCTTAATATCAATGAAAATTG | 568 | PGM_N0002163-327746-328270_79_102_R | TGCACGCAAACGCTTTACTTCAGC | 1200 |
| 2583 | UNCA_NC002163-112166-112647_114_141_F | TAAGCATGCTGTGGCTTATCGTGAAATG | 160 | UNCA_NC002163-112166-112647_196_225_R | TGCCCTTTCTAAAAGTCTTGAGTGAAGATA | 1220 |
| 2584 | UNCA_NC002163-112166-112647_3_29_F | TGCTTCGGATCCAGCAGCACTTCAATA | 532 | UNCA_NC002163-112166-112647_88_123_R | TGCATGCTTACTCAAATCATCATAAACAATTAAAGC | 1206 |
| 2585 | ASPA_NC002163-96692-97166_308_335_F | TTAATTTGCCAAAAATGCAACCAGGTAG | 652 | ASPA_NC002163-96692-97166_403_432_R | TGCAAAAGTAACGGTTACATCTGCTCCAAT | 1192 |
| 2586 | ASPA_NC002163-96692-97166_228_258_F | TCGCGTTGCAACAAAACTTTCTAAAGTATGT | 370 | ASPA_NC002163-96692-97166_316_346_R | TCATGATAGAACTACCTGGTTGCATTTTTGG | 991 |
| 2587 | GLNA_NC002163-658085-657609_244_275_F | TGGAATGATGATAAAGATTTCGCAGATAGCTA | 547 | GLNA_NC002163-658085-657609_340_371_R | TGAGTTTGAACCATTTCAGAGCGAATATCTAC | 1176 |
| 2588 | TKT_NC002163-1569415-1569903_107_130_F | TCGCTACAGGCCCTTTAGGACAAG | 371 | TKT_NC002163-1569415-1569903_212_236_R | TCCCCATCTCCGCAAAGACAATAAA | 1020 |
| 2589 | TKT_NC002163-1569415-1569903_265_296_F | TGTTCTTTAGCAGGACTTCACAAACTTGATAA | 642 | TKT_NC002163-1569415-1569903_361_393_R | TCCTTGTGCTTCAAAACGCATTTTTACATTTTC | 1057 |
| 2590 | GLYA_NC002163-367572-368095_214_246_F | TGCCTATCTTTTTGCTGATATAGCACATATTGC | 505 | GLYA_NC002163-367572-368095_317_340_R | TCCTCTTGGGCCACGCAAAGTTTT | 1047 |
| 2591 | GLYA_NC002163-367572-368095_415_444_F | TCCTTTGATGCATGTAATTGCTGCAAAAGC | 353 | GLYA_NC002163-367572-368095_485_516_R | TCTTGAGCATTGGTTCTTACTTGTTTTGCATA | 1141 |
| 2592 | PGM_NC002163_21_54_F | TCCTAATGGACTTAATATCAATGAAAATTGTGGA | 332 | PGM_NC002163_116_142_R | TCAAACGATCCGCATCACCATCAAAAG | 949 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| Primer Pairs for Identification of Bacteria | | | | | | |
| 2593 | PGM_NC002163_149_176_F | TAGATGAAAAAGGCGAAGTGGCTAATGG | 207 | PGM_NC002163_247_277_R | TCCCCTTTAAAGCACCATTACTCATTATAGT | 1023 |
| 2594 | GLNA_NC002163-658085-657609_79_106_F | TGTCCAAGAAGCATAGCAAAAAAAGCAA | 633 | GLNA_NC002163-658085-657609_148_179_R | TCAAAAACAAAGAATTCATTTTCTGGTCCAAA | 945 |
| 2595 | ASPA_NC002163-96685-97196_367_402_F | TCCTGTTATTCCTGAAGTAGTTAATCAAGTTTGTTA | 347 | ASPA_NC002163-96685-97196_467_497_R | TCAAGCTATATGCTACAACTGGTTCAAAAAC | 960 |
| 2596 | ASPA_NC002163-96685-97196_1_33_F | TGCCGTAATGATAGGTGAAGATATACAAAGAGT | 502 | ASPA_NC002163-96685-97196_95_127_R | TACAACCTTCGGATAATCAGGATGAGAATTAAT | 880 |
| 2597 | ASPA_NC002163-96685-97196_85_117_F | TGGAACAGGAATTAATTCTCATCCTGATTATCC | 540 | ASPA_NC002163-96685-97196_185_210_R | TAAGCTCCCGTATCTTGAGTCGCCTC | 872 |
| 2598 | PGM_NC002163-327746-328270_165_195_F | TGGCAGCTAGAATAGTAGCTAAAATCCCTAC | 563 | PGM_N0002163-327746-328570_230_261_R | TCACGATCTAAATTTGGATAAGCCATAGGAAA | 975 |
| 2599 | PGM_NC002163-327746-328270_252_286_F | TGGGTCGTGGTTTTACAGAAAATTTCTTATATATG | 593 | PGM_NC002163-327746-328270_353_381_R | TTTTGCTCATGATCTGCATGAAGCATAAA | 1443 |
| 2600 | PGM_NC002163-327746-328270_1_30_F | TGGGATGAAAAAGCGTTCTTTTATCCATGA | 577 | PGM_NC002163-327746-328270_95_123_R | TGATAAAAAGCACTAAGCGATGAAACAGC | 1178 |
| 2601 | PGM_NC002163-327746-328270_220_250_F | TAAACACGGCTTTCCTATGGCTTATCCAAAT | 146 | PGM_NC002163-327746-328570_314_345_R | TCAAGTGCTTTTACTTCTATAGGTTTAAGCTC | 963 |
| 2602 | UNCA_NC002163-112166-112647_123_152_F | TGTAGCTTATCGCGAAATGTCTTTGATTTT | 628 | UNCA_NC002163-112166-112647_199_229_R | TGCTTGCTCTTTCAAGCAGTCTTGAATGAAG | 1258 |
| 2603 | UNCA_NC002163-112166-112647_333_365_F | TCCAGATGGACAAATTTTCTTAGAAACTGATTT | 313 | UNCA_NC002163-112166-112647_430_461_R | TCCGAAACTTGTTTTGTAGCTTTAATTTGAGC | 1031 |
| 2734 | GYRA_AY291534_237_264_F | TCACCCTCATGGTGATTCAGCTGTTTAT | 265 | GYRA_AY291534_268_288_R | TTGCGCCATACGTACCATCGT | 1407 |
| 2735 | GYRA_AY291534_224_252_F | TAATCGGTAAGTATCACCCTCATGGTGAT | 167 | GYRA_AY291534_256_285_R | TGCCATACGTACCATCGTTTCATAAACAGC | 1213 |
| 2736 | GYRA_AY291534_170_198_F | TAGGAATTACGGCTGATAAAGCGTATAAA | 221 | GYRA_AY291534_268_288_R | TTGCGCCATACGTACCATCGT | 1407 |
| 2737 | GYRA_AY291534_224_252_F | TAATCGGTAAGTATCACCCTCATGGTGAT | 167 | GYRA_AY291534_319_346_R | TATCGACAGATCCAAAGTTACCATGCCC | 935 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2738 | GYRA_NC002953-7005-9668_166_195_F | TAAGGTATGACACCGGATAAATCATATAAA | 163 | GYRA_NC002953-7005-9668_265_287_R | TCTTGAGCCATACGTACCATTGC | 1142 |
| 2739 | GYRA_NC002953-7005-9668_221_249_F | TAATGGGTAAATATCACCCTCATGGTGAC | 171 | GYRA_NC002953-7005-9668_316_343_R | TATCCATTGAACCAAAGTTACCTTGGCC | 933 |
| 2740 | GYRA_NC002953-7005-9668_221_249_F | TAATGGGTAAATATCACCCTCATGGTGAC | 171 | GYRA_NC002953-7005-9668_253_283_R | TAGCCATACGTACCATTGCTTCATAAATAGA | 912 |
| 2741 | GYRA_NC002953-7005-9668_234_261_F | TCACCCTCATGGTGACTCATCTATTTAT | 264 | GYRA_NC002953-7005-9668_265_287_R | TCTTGAGCCATACGTACCATTGC | 1142 |
| 2842 | CAPC_AF188935-56074-55628_271_304_F | TGGGATTATTGTTATCCTGTTATGCCATTTGAGA | 578 | CAPC_AF188935-56074-55628_348_378_R | TGGTAACCCTTGTCTTTGAATTGTATTTGCA | 1299 |
| 2843 | CAPC_AF188935-56074-55628_273_303P_F | TGATTATTGTTATCCTGTTATGCpCpATpTpTpGAG | 476 | CAPC_AF188935-56074-55628_349_377P_R | TGTAACCCTTGTCTTTGAATpTpGTATpTpTpGC | 1314 |
| 2844 | CAPC_AF188935-56074-55628_268_303_F | TCCGTTGATTATTGTTATCCTGTTATGCCATTTGAG | 331 | CAPC_AF188935-56074-55628_349_384_R | TGTTAATGGTAACCCTTGTCTTTGAATTGTATTTGC | 1344 |
| 2845 | CAPC_AF188935-56074-55628_268_303_F | TCCGTTGATTATTGTTATCCTGTTATGCCATTTGAG | 331 | CAPC_AF188935-56074-55628_337_375_R | TAACCCTTGTCTTTGAATTGTATTTGCAATTAATCCTGG | 860 |
| 2846 | PARC_X95819_33_58_F | TCCAAAAAAATCAGCGCGTACAGTGG | 302 | PARC_X95819_121_153_R | TAAAGGATAGCGGTAACTAAATGGCTGAGCCAT | 852 |
| 2847 | PARC_X95819_65_92_F | TACTTGGTAAATACCACCCACATGGTGA | 199 | PARC_X95819_157_178_R | TACCCCAGTTCCCCTGACCTTC | 889 |
| 2848 | PARC_X95819_69_93_F | TGGTAAATACCACCCACATGGTGAC | 596 | PARC_X95819_97_128_R | TGAGCCATGAGTACCATGGCTTCATAACATGC | 1169 |
| 2849 | PARC_NC003997-3362578-3365001_181_205_F | TTCCGTAAGTCGGCTAAAACAGTCG | 668 | PARC_NC003997-3362578-3365001_256_283_R | TCCAAGTTTGACTTAAACGTACCATCGC | 1001 |
| 2850 | PARC_NC003997-3362578-3365001_217_240_F | TGTAACTATCACCCGCACGGTGAT | 621 | PARC_NC003997-3362578-3365001_304_335_R | TCGTCAACACTACCATTATTACCATGCATCTC | 1099 |
| 2851 | PARC_NC003997-3362578-3365001_217_240_F | TGTAACTATCACCCGCACGGTGAT | 621 | PARC_NC003997-3362578-3365001_244_275_R | TGACTTAAACGTACCATCGCTTCATATACAGA | 1162 |
| 2852 | GYRA_AY642140_-1_24_F | TAAATCTGCCCGTGTCGTTGGTGAC | 150 | GYRA_AY642140_71_100_R | TGCTAAAGTCTTGAGCCATACGAACAATGG | 1242 |
| 2853 | GYRA_AY642140_26_54_F | TAATCGGTAAATATCACCCGCATGGTGAC | 166 | GYRA_AY642140_121_146_R | TCGATCGAACCGAAGTTACCCTGACC | 1069 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2854 | GYRA_AY642140_26_54_F | TAATCGGTAAATATCACCCGCATGGTGAC | 166 | GYRA_AY642140_58_89_R | TGAGCCATACGAACAATGGTTTCATAAACAGC | 1168 |
| 2860 | CYA_AF065404_1348_1379_F | TCCAACGAAGTACAATACAAGACAAAAGAAGG | 305 | CYA_AF065404_1448_1472_R | TCAGCTGTTAACGGCTTCAAGACCC | 983 |
| 2861 | LEF_BA_AF065404_751_781_F | TCGAAAGCTTTTGCATATTATATCGAGCCAC | 354 | LEF_BA_AF065404_843_881_R | TCTTTAAGTTCTTCCAAGGATAGATTTATTTCTTGTTCG | 1144 |
| 2862 | LEF_BA_AF065404_762_788_F | TGCATATTATATCGAGCCACAGCATCG | 498 | LEF_BA_AF065404_843_881_R | TCTTTAAGTTCTTCCAAGGATAGATTTATTTCTTGTTCG | 1144 |
| 2917 | MUTS_AY698802_106_125_F | TCCGCTGAATCTGTCGCCGC | 326 | MUTS_AY698802_172_193_R | TGCGGTCTGGCGCATATAGGTA | 1237 |
| 2918 | MUTS_AY698802_172_192_F | TACCTATATGCGCCAGACCGC | 187 | MUTS_AY698802_228_252_R | TCAATCTCGACTTTTTGTGCCGGTA | 965 |
| 2919 | MUTS_AY698802_228_252_F | TACCGGCGCAAAAAGTCGAGATTGG | 186 | MUTS_AY698802_314_342_R | TCGGTTTCAGTCATCTCCACCATAAAGGT | 1097 |
| 2920 | MUTS_AY698802_315_342_F | TCTTTATGGTGGAGATGACTGAAACCGA | 419 | MUTS_AY698802_413_433_R | TGCCAGCGACAGACCATCGTA | 1210 |
| 2921 | MUTS_AY698802_394_411_F | TGGGCGTGGAACGTCCAC | 585 | MUTS_AY698802_497_519_R | TCCGGTAACTGGGTCAGCTCGAA | 1040 |
| 2922 | AB_MLST-11-OIF007_991_1018_F | TGGGcGATGCTGCgAAATGGTTAAAAGA | 583 | AB_MLST-11-OIF007_1110_1137_R | TAGTATCACCACGTACACCCGGATCAGT | 923 |
| 2927 | GAPA_NC002505_694_721_F | TCAATGAACGACCAACAAGTGATTGATG | 259 | GAPA_NC_002505_29_58_R_1 | TCCTTTATGCAACTTGGTATCAACAGGAAT | 1060 |
| 2928 | GAPA_NC002505_694_721_2_F | TCGATGAACGACCAACAAGTGATTGATG | 361 | GAPA_NC002505_769_798_2_R | TCCTTTATGCAACTTGGTATCAACCGGAAT | 1061 |
| 2929 | GAPA_NC002505_694_721_2_F | TCGATGAACGACCAACAAGTGATTGATG | 361 | GAPA_NC002505_769_798_3_R | TCCTTTATGCAACTTAGTATCAACCGGAAT | 1059 |
| 2932 | INFB_EC_1364_1394_F | TTGCTCGTGGTGCACAAGTAACGGATATTAC | 688 | INFB_EC_1439_1468_R | TTGCTGCTTTCGCATGGTTAATCGCTTCAA | 1410 |
| 2933 | INFB_EC_1364_1394_2_F | TTGCTCGTGGTGCAIAAGTAACGGATATIAC | 689 | INFB_EC_1439_1468_R | TTGCTGCTTTCGCATGGTTAATCGCTTCAA | 1410 |
| 2934 | INFB_EC_80_110_F | TTGCCCGCGGTGCGGAAGTAACCGATATTAC | 685 | INFB_EC_1439_1468_R | TTGCTGCTTTCGCATGGTTAATCGCTTCAA | 1410 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2949 | ACS_NC002516-970624-971013_299_316_F | TCGGCGCCTGCCTGATGA | 376 | ACS_NC002516-970624-971013_364_383_R | TGGACCACGCCGAAGAACGG | 1265 |
| 2950 | ARO_NC002516-26883-27380_4_26_F | TCACCGTGCCGTTCAAGGAAGAG | 267 | ARO_NC002516-26883-27380_111_128_R | TGTGTTGTCGCCGCGCAG | 1341 |
| 2951 | ARO_NC002516-26883-27380_356_377_F | TTTCGAAGGGCCTTTCGACCTG | 705 | ARO_NC002516-26883-27380_459_484_R | TCCTTGGCATACATCATGTCGTAGCA | 1056 |
| 2952 | GUA_NC002516-4226546-4226174_23_41_F | TGGACTCCTCGGTGGTCGC | 551 | GUA_NC002516-4226546-4226174_127_146_R | TCGGCGAACATGGCCATCAC | 1091 |
| 2953 | GUA_NC002516-4226546-4226174_120_142_F | TGACCAGGTGATGGCCATGTTCG | 448 | GUA_NC002516-4226546-4226174_214_233_R | TGCTTCTCTTCCGGGTCGGC | 1256 |
| 2954 | GUA_NC002516-4226546-4226174_155_178_F | TTTTGAAGGTGATCCGTGCCAACG | 710 | GUA_NC002516-4226546-4226174_265_287_R | TGCTTGGTGGCTTCTTCGTCGAA | 1259 |
| 2955 | GUA_NC002516-4226546-4226174_190_206_F | TTCCTCGGCCGCCTGGC | 670 | GUA_NC002516-4226546-4226174_288_309_R | TGCGAGGAACTTCACGTCCTGC | 1229 |
| 2956 | GUA_NC002516-4226546-4226174_242_263_F | TCGGCCGCACCTTCATCGAAGT | 374 | GUA_NC002516-4226546-4226174_355_371_R | TCGTGGGCCTTGCCGGT | 1111 |
| 2957 | MUT_NC002516-5551158-5550717_5_26_F | TGGAAGTCATCAAGCGCCTGGC | 545 | MUT_NC002516-5551158-5550717_99_116_R | TCACGGGCCAGCTCGTCT | 978 |
| 2958 | MUT_NC002516-5551158-5550717_152_168_F | TCGAGCAGGCGCTGCCG | 358 | MUT_NC002516-5551158-5550717_256_277_R | TCACCATGCGCCCGTTCACATA | 971 |
| 2959 | NUO_NC002516-2984589-2984954_8_26_F | TCAACCTCGGCCCGAACCA | 249 | NUO_NC002516-2984589-2984954_97_117_R | TCGGTGGTGGTAGCCGATCTC | 1095 |
| 2960 | NUO_NC002516-2984589-2984954_218_239_F | TACTCTCGGTGGAGAAGCTCGC | 195 | NUO_NC002516-2984589-2984954_301_326_R | TTCAGGTACAGCAGGTGGTTCAGGAT | 1376 |
| 2961 | PPS_NC002516-1915014-1915383_44_63_F | TCCACGGTCATGGAGCGCTA | 311 | PPS_NC002516-1915014-1915383_140_165_R | TCCATTTCCGACACGTCGTTGATCAC | 1014 |
| 2962 | PPS_NC002516-1915014-1915383_240_258_F | TCGCCATCGTCACCAACCG | 365 | PPS_NC002516-1915014-1915383_341_360_R | TCCTGGCCATCCTGCAGGAT | 1052 |
| 2963 | TRP_NC002516-671831-672273_24_42_F | TGCTGGTACGGGTCGAGGA | 527 | TRP_NC002516-671831-672273_131_150_R | TCGATCTCCTTGGCGTCCGA | 1071 |
| 2964 | TRP_NC002516-671831-672273_261_282_F | TGCACATCGTGTCCAACGTCAC | 490 | TRP_N0002516-671831-672273_362_383_R | TGATCTCCATGGCGCGGATCTT | 1182 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2972 | AB_MLST-11-OIF007_1007_1034_F | TGGGIGATGCTGCIAAATGGTTAAAAGA | 592 | AB_MLST-11-OIF007_1126_1153_R | TAGTATCACCACGTACICCIGGATCAGT | 924 |
| 2993 | OMPU_NC002505-674828-675880_428_455_F | TTCCCACCGATATCATGGCTTACCACGG | 667 | OMPU_NC002505_544_567_R | TCGGTCAGCAAAACGGTAGCTTGC | 1094 |
| 2994 | GAPA_NC002505-506780-507937_691_721_F | TCCTCAATGAACGAICAACAAGTGATTGATG | 335 | GAPA_NC002505-506780-507937_769_802_R | TTTTCCCTTTATGCAACTTAGTATCAACIGGAAT | 1442 |
| 2995 | GAPA_NC002505-506780-507937_691_721_2_F | TCCTCIATGAACGAICAACAAGTGATTGATG | 339 | GAPA_NC002505-506780-507937_769_803_R | TCCATACCTTTATGCAACTTIGTATCAACIGGAAT | 1008 |
| 2996 | GAPA_NC002505-506780-507937_692_721_F | TCTCGATGAACGACCAACAAGTGATTGATG | 396 | GAPA_NC002505-506780-507937_785_817_R | TCGGAAATATTCTTTCAATACCTTTATGCAACT | 1085 |
| 2997 | GAPA_NC002505-506780-507937_691_721_3_F | TCCTCGATGAACGAICAACAAGTIATTGATG | 337 | GAPA_NC002505-506780-507937_785_817_R | TCGGAAATATTCTTTCAATACCTTTATGCAACT | 1085 |
| 2998 | GAPA_NC002505-506780-507937_691_721_4_F | TCCTCAATGAATGATCAACAAGTGATTGATG | 336 | GAPA_NC002505-506780-507937_784_817_R | TCGGAAATATTCTTTCAATICCTTTITGCAACTT | 1087 |
| 2999 | GAPA_NC002505-506780-507937_691_721_5_F | TCCTCIATGAAIGAICAACAAGTIATTGATG | 340 | GAPA_NC002505-506780-507937_784_817_2_R | TCGGAAATATTCTTTCAATACCTTTATGCAACTT | 1086 |
| 3000 | GAPA_NC002505-506780-507937_691_721_6_F | TCCTCGATGAATGAICAACAAGTIATTGATG | 338 | GAPA_NC002505-506780-507937_769_805_R | TTTCAATACCTTTATGCAACTTIGTATCAACIGGAAT | 1430 |
| 3001 | CTXB_NC002505-1566967-1567341_46_71_F | TCAGCATATGCACATGGAACACCTCA | 275 | CTXB_NC002505-1566967-1567341_139_163_R | TCCCGGCTAGAGATTCTGTATACGA | 1026 |
| 3002 | CTXB_NC002505-1566967-1567341_46_70_F | TCAGCATATGCACATGGAACACCTC | 274 | CTXB_NC002505-1566967-1567341_132_162_R | TCCGGCTAGAGATTCTGTATACGAAAATATC | 1038 |
| 3003 | CTXB_NC002505-1566967-1567341_46_70_F | TCAGCATATGCACATGGAACACCTC | 274 | CTXB_NC002505-1566967-1567341_118_150_R | TGCCGTATACGAAAATATCTTATCATTTAGCGT | 1225 |
| 3004 | TUFB_NC002758-61508-616222_684_704_F | TACAGGCCGTGTTGAACGTGG | 180 | TUFB_NC002758-615038-616222_778_809_R | TCAGCGTAGTCTAATAATTTACGGAACATTTC | 982 |
| 3005 | TUFB_NC002758-615038-616222_688_710_F | TGCCGTGTTGAACGTGGTCAAAT | 503 | TUFB_NC002758-615038-616222_783_813_R | TGCTTCAGCGTAGTCTAATAATTTACGGAAC | 1255 |
| 3006 | TUFB_NC002758-615038-616222_700_726_F | TGTGGTCAAATCAAAGTTGGTGAAGAA | 638 | TUFB_NC002758-615038-616222_778_807_R | TGCGTAGTCTAATAATTTACGGAACATTTC | 1238 |

TABLE 2-continued

Primer Pairs for Identification of Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 3007 | TUFB_NC002758-615308-616222_702_726_F | TGGTCAAATCAAAGTTGGTGAAGAA | 607 | TUFB_NC002758-615038-616222_778_807_R | TGCGTAGTCTAATAATTTACGGAACATTTC | 1238 |
| 3008 | TUFB_NC002758-615308-616222_696_726_F | TGAACGTGGTCAAATCAAAGTTGGTGAAGAA | 431 | TUFB_NC002758-615038-616222_785_818_R | TCACCAGCTTCAGCGTAGTCTAATAATTTACGGA | 970 |
| 3009 | TUFB_NC002758-615038-616222_690_716_F | TCGTGTTGAACGTGGTCAAATCAAAGT | 386 | TUFB_NC002758-615038-616222_778_812_R | TCTTCAGCGTAGTCTAATAATTTACGGAACATTTC | 1134 |
| 3010 | MECI-R_NC003923-41798-41609_36_59_F | TCACATATCGTGAGCAATGAACTG | 261 | MECI-R_NC003923-41798-41609_89_112_R | TGTGATATGGAGGTGTAGAAGGTG | 1332 |
| 3011 | MECI-R_NC003923-41798-41609_40_66_F | TGGGCGTGAGCAATGAACTGATTATAC | 584 | MECI-R_NC003923-41798-41609_81_110_R | TGGGATGGAGGTGTAGAAGGTGTTATCATC | 1287 |
| 3012 | MECI-R_NC003923-41798-41609_33_60_2_F | TGGACACATATCGTGAGCAATGAACTGA | 549 | MECI-R_NC003923-41798-41609_81_110_R | TGGGATGGAGGTGTAGAAGGTGTTATCATC | 1286 |
| 3013 | MECI-R_NC003923-41798-41609_29_60_F | TGGGTTTACACATATCGTGAGCAATGAACTGA | 595 | MECI-R_NC003923-41798-41609_81_113_R | TGGGGATATGGAGGTGTAGAAGGTGTTATCATC | 1290 |
| 3014 | MUPR_X75439_2490_2514_F | TGGGCTCTTTCTCGCTTAAACACCT | 587 | MUPR_X75439_2548_2570_R | TCTGGCTGCGGAAGTGAAATCGT | 1130 |
| 3015 | MUPR_X75439_2490_2513_F | TGGGCTCTTTCTCGCTTAAACACC | 586 | MUPR_X75439_2547_2568_R | TGGCTGCGGAAGTGAAATCGTA | 1281 |
| 3016 | MUPR_X75439_2482_2510_F | TAGATAATTGGGCTCTTTCTCGCTTAAAC | 205 | MUPR_X75439_2551_2573_R | TAATCTGGCTGCGGAAGTGAAAT | 876 |
| 3017 | MUPR_X75439_2490_2514_F | TGGGCTCTTTCTCGCTTAAACACCT | 587 | MUPR_X75439_2549_2573_R | TAATCTGGCTGCGGAAGTGAAATCG | 877 |
| 3018 | MUPR_X75439_2482_2510_F | TAGATAATTGGGCTCTTTCTCGCTTAAAC | 205 | MUPR_X75439_2559_2589_R | TGGTATATTCGTTAATTAATCTGGCTGCGGA | 1303 |
| 3019 | MUPR_X75439_2490_2514_F | TGGGCTCTTTCTCGCTTAAACACCT | 587 | MUPR_X75439_2554_2581_R | TCGTTAATTAATCTGGCTGCGGAAGTGA | 1112 |
| 3020 | AROE_NC003923-1674726-1674277_204_232_F | TGATGGCAAGTGGATAGGGTATAATACAG | 474 | AROE_NC003923-1674726-1674277_309_335_R | TAAGCAATACCTTTACTTGCACCACCT | 868 |
| 3021 | AROE_NC003923-1674726-1674277_207_232_F | TGGCGAGTGGATAGGGTATAATACAG | 570 | AROE_NC003923-1674726-1674277_311_339_R | TTCATAAGCAATACCTTTACTTGCACCAC | 1378 |
| 3022 | AROE_NC003923-1674726-1674277_207_232P_F | TGGCpAAGTpGGATpAGGGTpATpAATpACpAG | 572 | AROE_NC003923-1674726-1674277_311_335P_R | TAAGCAATACCpTpTpTpACTpTpGCpACpCpAC | 867 |
| 3023 | ARCC_NC003923-2725050-2724595_124_155_F | TCTGAAATGAATAGTGATAGAACTGTAGGCAC | 398 | ARCC_NC003923-2725050-2724595_214_245_R | TCTTCTTCTTTCGTATAAAAAGGACCAATTGG | 1137 |

TABLE 2-continued

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| Primer Pairs for Identification of Bacteria | | | | | | |
| 3024 | ARCC_NC003923-2725050-2724595_131_161_F | TGAATAGTGATAGAACTGTAGGCACAATCGT | 437 | ARCC_NC003923-2725050-2724595_212_242_R | TCTTCTTTCGTATAAAAAGGACCAATTGGTT | 1139 |
| 3025 | ARCC_NC003923-2725050-2724595_131_161_F | TGAATAGTGATAGAACTGTAGGCACAATCGT | 437 | ARCC_NC003923-2725050-2724595_232_260_R | TGCGCTAATTCTTCAACTTCTTCTTTCGT | 1232 |
| 3026 | PTA_NC003923-628885-629355_231_259_F | TACAATGCTTGTTTATGCTGGTAAAGCAG | 177 | PTA_NC003923-628885-629355_322_351_R | TGTTCTTGATACACCTGGTTTCGTTTTGAT | 1350 |
| 3027 | PTA_NC003923-628885-629355_231_259_F | TACAATGCTTGTTTATGCTGGTAAAGCAG | 177 | PTA_NC003923-628885-629355_314_345_R | TGGTACACCTGGTTTCGTTTTGATGATTTGTA | 1301 |
| 3028 | PTA_NC003923-628885-629355_237_263_F | TCTTGTTTATGCTGGTAAAGCAGATGG | 418 | PTA_NC003923-628885-629355_322_351_R | TGTTCTTGATACACCTGGTTTCGTTTTGAT | 1350 |

Primer pair name codes and reference sequences are shown in Table 3. The primer name code typically represents the gene to which the given primer pair is targeted. The primer pair name may include specific coordinates with respect to a reference sequence defined by an extraction of a section of sequence or defined by a GenBank gi number, or the corresponding complementary sequence of the extraction, or the entire GenBank gi number as indicated by the label "no extraction." Where "no extraction" is indicated for a reference sequence, the coordinates of a primer pair named to the reference sequence are with respect to the GenBank gi listing. Gene abbreviations are shown in bold type in the "Gene Name" column.

To determine the exact primer hybridization coordinates of a given pair of primers on a given bioagent nucleic acid sequence and to determine the sequences, molecular masses and base compositions of an amplification product to be obtained upon amplification of nucleic acid of a known bioagent with known sequence information in the region of interest with a given pair of primers, one with ordinary skill in bioinformatics is capable of obtaining alignments of the primers of the present invention with the GenBank gi number of the relevant nucleic acid sequence of the known bioagent. For example, the reference sequence GenBank gi numbers (Table 3) provide the identities of the sequences which can be obtained from GenBank. Alignments can be done using a bioinformatics tool such as BLASTn provided to the public by NCBI (Bethesda, Md.). Alternatively, a relevant GenBank sequence may be downloaded and imported into custom programmed or commercially available bioinformatics programs wherein the alignment can be carried out to determine the primer hybridization coordinates and the sequences, molecular masses and base compositions of the amplification product. For example, to obtain the hybridization coordinates of primer pair number 2095 (SEQ ID NOs: 456:1261), First the forward primer (SEQ ID NO: 456) is subjected to a BLASTn search on the publicly available NCBI BLAST website. "RefSeq_Genomic" is chosen as the BLAST database since the gi numbers refer to genomic sequences. The BLAST query is then performed. Among the top results returned is a match to GenBank gi number 21281729 (Accession Number NC_003923). The result shown below, indicates that the forward primer hybridizes to positions 1530282.1530307 of the genomic sequence of *Staphylococcus aureus* subsp. *aureus* MW2 (represented by gi number 21281729).

*Staphylococcus aureus* subsp. *aureus* MW2, complete genome Length=2820462

Features in this part of subject sequence:
Panton-Valentine leukocidin chain F precursor
Score=52.0 bits (26), Expect=2e-05
Identities=26/26 (100%), Gaps=0/26 (0%)
Strand=Plus/Plus

```
Query  1        TGAGCTGCATCAACTGTATTGGATAG  26
                ||||||||||||||||||||||||||
Sbjct  1530282  TGAGCTGCATCAACTGTATTGGATAG  1530307
```

The hybridization coordinates of the reverse primer (SEQ ID NO: 1261) can be determined in a similar manner and thus, the bioagent identifying amplicon can be defined in terms of genomic coordinates. The query/subject arrangement of the result would be presented in Strand=Plus/Minus format because the reverse strand hybridizes to the reverse complement of the genomic sequence. HThe preceding sequence analyses are well known to one with ordinary skill in bioinformatics and thus, Table 3 contains sufficient information to determine the primer hybridization coordinates of any of the primers of Table 2 to the applicable reference sequences described therein.

TABLE 3

Primer Name Codes and Reference Sequence

| Primer name code | Gene Name | *Organism* | Reference GenBank gi number |
|---|---|---|---|
| 16S_EC | **16S rRNA** (16S ribosomal RNA gene) | *Escherichia coli* | 16127994 |
| 23S_EC | **23S rRNA** (23S ribosomal RNA gene) | *Escherichia coli* | 16127994 |
| CAPC_BA | **capC** (capsule biosynthesis gene) | *Bacillus anthracis* | 6470151 |
| CYA_BA | **cya** (cyclic AMP gene) | *Bacillus anthracis* | 4894216 |
| DNAK_EC | **dnaK** (chaperone dnaK gene) | *Escherichia coli* | 16127994 |
| GROL_EC | **groL** (chaperonin groL) | *Escherichia coli* | 16127994 |
| HFLB_EC | **hflb** (cell division protein peptidase ftsH) | *Escherichia coli* | 16127994 |
| INFB_EC | **infB** (protein chain initiation factor infB gene) | *Escherichia coli* | 16127994 |
| LEF_BA | **lef** (lethal factor) | *Bacillus anthracis* | 21392688 |
| PAG_BA | **pag** (protective antigen) | *Bacillus anthracis* | 21392688 |
| RPLB_EC | **rp1B** (50S ribosomal protein L2) | *Escherichia coli* | 16127994 |
| RPOB_EC | **rpoB** (DNA-directed RNA polymerase beta chain) | *Escherichia coli* | 6127994 |
| RPOC_EC | **rpoC** (DNA-directed RNA polymerase beta' chain) | *Escherichia coli* | 16127994 |
| SP101ET_SPET_11 | Artificial Sequence Concatenation comprising:<br>**gki** (glucose kinase)<br>**gtr** (glutamine transporter protein)<br>**murI** (glutamate racemase)<br>**mutS** (DNA mismatch repair protein)<br>**xpt** (xanthine phosphoribosyl transferase)<br>**yqiL** (acetyl-CoA-acetyl transferase)<br>**tkt** (transketolase) | Artificial Sequence* - partial gene sequences of *Streptococcus pyogenes* | 15674250 |

TABLE 3-continued

Primer Name Codes and Reference Sequence

| Primer name code | Gene Name | *Organism* | Reference GenBank gi number |
|---|---|---|---|
| SSPE_BA | **sspE** (small acid-soluble spore protein) | *Bacillus anthracis* | 30253828 |
| TUFB_EC | **tufB** (Elongation factor Tu) | *Escherichia coli* | 16127994 |
| VALS_EC | **valS** (Valyl-tRNA synthetase) | *Escherichia coli* | 16127994 |
| ASPS_EC | **aspS** (Aspartyl-tRNA synthetase) | *Escherichia coli* | 16127994 |
| CAF1_AF053947 | **caf1** (capsular protein caf1) | *Yersinia pestis* | 2996286 |
| INV_U22457 | **inv** (invasin) | *Yersinia pestis* | 1256565 |
| LL_NC003143 | *Y. pestis* specific chromosomal genes - difference region | *Yersinia pestis* | 16120353 |
| BONTA_X52066 | **BoNT/A** (neurotoxin type A) | *Clostridium botulinum* | 40381 |
| MECA_Y14051 | **mecA** methicillin resistance gene | *Staphylococcus aureus* | 2791983 |
| TRPE_AY094355 | **trpE** (anthranilate synthase (large component)) | *Acinetobacter baumanii* | 20853695 |
| RECA_AF251469 | **recA** (recombinase A) | *Acinetobacter baumanii* | 9965210 |
| GYRA_AF100557 | **gyrA** (DNA gyrase subunit A) | *Acinetobacter baumanii* | 4240540 |
| GYRB_AB008700 | **gyrB** (DNA gyrase subunit B) | *Acinetobacter baumanii* | 4514436 |
| WAAA_Z96925 | **waaA** (3-deoxy-D-manno-octulosonic-acid transferase) | *Acinetobacter baumanii* | 2765828 |
| CJSTCJ | Artificial Sequence Concatenation comprising:<br>**tkt** (transketolase)<br>**glyA** (serine hydroxymethyltransferase)<br>**gltA** (citrate synthase)<br>**aspA** (aspartate ammonia lyase)<br>**glnA** (glutamine synthase)<br>**pgm** (phosphoglycerate mutase)<br>**uncA** (ATP synthetase alpha chain) | Artificial Sequence* - partial gene sequences of *Campylobacter jejuni* | 15791399 |
| RNASEP_BDP | **RNase** P (ribonuclease P) | *Bordetella pertussis* | 33591275 |
| RNASEP_BKM | **RNase** P (ribonuclease P) | *Burkholderia mallei* | 53723370 |
| RNASEP_BS | **RNase** P (ribonuclease P) | *Bacillus subtilis* | 16077068 |
| RNASEP_CLB | **RNase** P (ribonuclease P) | *Clostridium perfringens* | 18308982 |
| RNASEP_EC | **RNase** P (ribonuclease P) | *Escherichia coli* | 16127994 |
| RNASEP_RKP | **RNase** P (ribonuclease P) | *Rickettsia prowazekii* | 15603881 |
| RNASEP_SA | **RNase** P (ribonuclease P) | *Staphylococcus aureus* | 15922990 |
| RNASEP_VBC | **RNase** P (ribonuclease P) | *Vibrio cholerae* | 15640032 |
| ICD_CXB | **icd** (isocitrate dehydrogenase) | *Coxiella burnetii* | 29732244 |
| IS1111A | multi-locus IS1111A insertion element | *Acinetobacter baumannii* | 29732244 |
| OMPA_AY485227 | **ompA** (outer membrane protein A) | *Rickettsia prowazekii* | 40287451 |
| OMPB_RKP | **ompB** (outer membrane protein B) | *Rickettsia prowazekii* | 15603881 |
| GLTA_RKP | **gltA** (citrate synthase) | *Vibrio cholerae* | 15603881 |
| TOXR_VBC | **toxR** (transcription regulator toxR) | *Francisella tularensis* | 15640032 |
| ASD_FRT | **asd** (Aspartate semialdehyde dehydrogenase) | *Francisella tularensis* | 56707187 |
| GALE_FRT | **galE** (UDP-glucose 4-epimerase) | *Shigella flexneri* | 56707187 |
| IPAH_SGF | **ipaH** (invasion plasmid antigen) | *Campylobacter jejuni* | 30061571 |
| HUPB_CJ | **hupB** (DNA-binding protein Hu-beta) | *Coxiella burnetii* | |
| AB_MLST | Artificial Sequence Concatenation comprising:<br>**trpE** (anthranilate synthase component I))<br>**adk** (adenylate kinase)<br>**mutY** (adenine glycosylase)<br>**fumC** (fumarate hydratase)<br>**efp** (elongation factor p)<br>**ppa** (pyrophosphate phospho-hydratase | Artificial Sequence* - partial gene sequences of *Acinetobacter baumannii* | Sequenced in-house (SEQ ID NO: 1444) |
| MUPR_X75439 | **mupR** (mupriocin resistance gene) | *Staphylococcus aureus* | 438226 |

TABLE 3-continued

Primer Name Codes and Reference Sequence

| Primer name code | Gene Name | *Organism* | Reference GenBank gi number |
|---|---|---|---|
| PARC_X95819 | **parC** (topoisomerase IV) | *Acinetobacter baumannii* | 1212748 |
| SED_M28521 | **sed** (enterotoxin D) | *Staphylococcus aureus* | 1492109 |
| PLA_AF053945 | **pla** (plasminogen activator) | *Yersinia pestis* | 2996216 |
| SEJ_AF053140 | **sej** (enterotoxin J) | *Staphylococcus aureus* | 3372540 |
| GYRA_NC000912 | **gyrA** (DNA gyrase subunit A) | *Mycoplasma pneumoniae* | 13507739 |
| ACS_NC002516 | **acsA** (Acetyl CoA Synthase) | *Pseudomonas aeruginosa* | 15595198 |
| ARO_NC002516 | **aroE** (shikimate 5-dehydrogenase | *Pseudomonas aeruginosa* | 15595198 |
| GUA_NC002516 | **guaA** (GMP synthase) | *Pseudomonas aeruginosa* | 15595198 |
| MUT_NC002516 | **mutL** (DNA mismatch repair protein) | *Pseudomonas aeruginosa* | 15595198 |
| NUO_NC002516 | **nuoD** (NADH dehydrogenase I chain C, D) | *Pseudomonas aeruginosa* | 15595198 |
| PPS_NC002516 | **ppsA** (Phosphoenolpyruvate synthase) | *Pseudomonas aeruginosa* | 15595198 |
| TRP_NC002516 | **trpE** (Anthranilate synthetase component I) | *Pseudomonas aeruginosa* | 15595198 |
| OMP2_NC000117 | **ompB** (outer membrane protein B) | *Chlamydia trachomatis* | 15604717 |
| OMPA_NC000117 | **ompA** (outer membrane protein B) | *Chlamydia trachomatis* | 15604717 |
| GYRA_NC000117 | **gyrA** (DNA gyrase subunit A) | *Chlamydia trachomatis* | 15604717 |
| CTXA_NC002505 | **ctxA** (Cholera toxin A subunit) | *Vibrio cholerae* | 15640032 |
| CTXB_NC002505 | **ctxB** (Cholera toxin B subunit) | *Vibrio cholerae* | 15640032 |
| FUR_NC002505 | **fur** (ferric uptake regulator protein ) | *Vibrio cholerae* | 15640032 |
| GAPA_NC_002505 | **gapA** (glyceraldehyde-3-phosphate dehydrogenase) | *Vibrio cholerae* | 15640032 |
| GYRB_NC002505 | **gyrB** (DNA gyrase subunit B) | *Vibrio cholerae* | 15640032 |
| OMPU_NC002505 | **ompU** (outer membrane protein) | *Vibrio cholerae* | 15640032 |
| TCPA_NC002505 | **tcpA** (toxin-coregulated pilus) | *Vibrio cholerae* | 15640032 |
| ASPA_NC002163 | **aspA** (aspartate ammonia lyase) | *Campylobacter jejuni* | 15791399 |
| GLNA_NC002163 | **glnA** (glutamine synthetase) | *Campylobacter jejuni* | 15791399 |
| GLTA_NC002163 | **gltA** (glutamate synthase) | *Campylobacter jejuni* | 15791399 |
| GLYA_NC002163 | **glyA** (serine hydroxymethyltransferase) | *Campylobacter jejuni* | 15791399 |
| PGM_NC002163 | **pgm** (phosphoglyceromutase) | *Campylobacter jejuni* | 15791399 |
| TKT_NC002163 | **tkt** (transketolase) | *Campylobacter jejuni* | 15791399 |
| UNCA_NC002163 | **uncA** (ATP synthetase alpha chain) | *Campylobacter jejuni* | 15791399 |
| AGR-III_NC003923 | **agr-III** (accessory gene regulator-III) | *Staphylococcus aureus* | 21281729 |
| ARCC_NC003923 | **arcC** (carbamate kinase) | *Staphylococcus aureus* | 21281729 |
| AROE_NC003923 | **aroE** (shikimate 5-dehydrogenase | *Staphylococcus aureus* | 21281729 |
| BSA-A_NC003923 | **bsa-a** (glutathione peroxidase) | *Staphylococcus aureus* | 21281729 |
| BSA-B_NC003923 | **bsa-b** (epidermin biosynthesis protein EpiB) | *Staphylococcus aureus* | 21281729 |
| GLPF_NC003923 | **glpF** (glycerol transporter) | *Staphylococcus aureus* | 21281729 |
| GMK_NC003923 | **gmk** (guanylate kinase) | *Staphylococcus aureus* | 21281729 |
| MECI-R_NC003923 | **mecR1** (truncated methicillin resistance protein) | *Staphylococcus aureus* | 21281729 |
| PTA_NC003923 | **pta** (phosphate acetyltransferase) | *Staphylococcus aureus* | 21281729 |
| PVLUK_NC003923 | **pvluk** (Panton-Valentine leukocidin chain F precursor) | *Staphylococcus aureus* | 21281729 |
| SA442_NC003923 | **sa442 gene** | *Staphylococcus aureus* | 21281729 |

TABLE 3-continued

Primer Name Codes and Reference Sequence

| Primer name code | Gene Name | *Organism* | Reference GenBank gi number |
|---|---|---|---|
| SEA_NC003923 | **sea** (staphylococcal enterotoxin A precursor) | *Staphylococcus aureus* | 21281729 |
| SEC_NC003923 | **sec4** (enterotoxin type C precursor) | *Staphylococcus aureus* | 21281729 |
| TPI_NC003923 | **tpi** (triosephosphate isomerase) | *Staphylococcus aureus* | 21281729 |
| YQI_NC003923 | **yqi** (acetyl-CoA C-acetyltransferase homologue) | *Staphylococcus aureus* | 21281729 |
| GALE_AF513299 | **galE** (galactose epimerase) | *Francisella tularensis* | 23506418 |
| VVHA_NC004460 | **vVhA** (cytotoxin, cytolysin precursor) | *Vibrio vulnificus* | 27366463 |
| TDH_NC004605 | **tdh** (thermostable direct hemolysin A) | *Vibrio parahaemolyticus* | 28899855 |
| AGR-II_NC002745 | **agr-II** (accessory gene regulator-II) | *Staphylococcus aureus* | 29165615 |
| PARC_NC003997 | **parC** (topoisomerase IV) | *Bacillus anthracis* | 30260195 |
| GYRA_AY291534 | **gyrA** (DNA gyrase subunit A) | *Bacillus anthracis* | 31323274 |
| AGR-I_AJ617706 | **agr-I** (accessory gene regulator-I) | *Staphylococcus aureus* | 46019543 |
| AGR-IV_AJ617711 | **agr-IV** (accessory gene regulator-III) | *Staphylococcus aureus* | 46019563 |
| BLAZ_NC002952 | **blaZ** (beta lactamase III) | *Staphylococcus aureus* | 49482253 |
| ERMA_NC002952 | **ermA** (rRNA methyltransferase A) | *Staphylococcus aureus* | 49482253 |
| ERMB_Y13600 | **ermB** (rRNA methyltransferase B) | *Staphylococcus aureus* | 49482253 |
| SEA-SEE_NC002952 | **sea** (staphylococcal enterotoxin A precursor) | *Staphylococcus aureus* | 49482253 |
| SEA-SEE_NC002952 | **sea** (staphylococcal enterotoxin A precursor) | *Staphylococcus aureus* | 49482253 |
| SEE_NC002952 | **sea**(staphylococcal enterotoxin A precursor) | *Staphylococcus aureus* | 49482253 |
| SEH_NC002953 | **seh** (staphylococcal enterotoxin H) | *Staphylococcus aureus* | 49484912 |
| ERMC_NC005908 | **ermC** (rRNA methyltransferase C) | *Staphylococcus aureus* | 49489772 |
| MUTS_AY698802 | **mutS** (DNA mismatch repair protein) | *Shigella boydii* | 52698233 |
| NUC_NC002758 | **nuc** (staphylococcal nuclease) | *Staphylococcus aureus* | 57634611 |
| SEB_NC002758 | **seb** (enterotoxin type B precursor) | *Staphylococcus aureus* | 57634611 |
| SEG_NC002758 | **seg** (staphylococcal enterotoxin G) | *Staphylococcus aureus* | 57634611 |
| SEI_NC002758 | **sei** (staphylococcal enterotoxin I) | *Staphylococcus aureus* | 57634611 |
| TSST_NC002758 | **tsst** (toxic shock syndrome toxin-1) | *Staphylococcus aureus* | 57634611 |
| TUFB_NC002758 | **tufB** (Elongation factor Tu) | *Staphylococcus aureus* | 57634611 |

Note:
artificial reference sequences represent concatenations of partial gene extractions from the indicated reference gi number. Partial sequences were used to create the concatenated sequence because complete gene sequences were not necessary for primer design.

Example 2

Sample Preparation and PCR

Genomic DNA was prepared from samples using the DNeasy Tissue Kit (Qiagen, Valencia, Calif.) according to the manufacturer's protocols.

All PCR reactions were assembled in 50 μL reaction volumes in a 96-well microtiter plate format using a Packard MPII liquid handling robotic platform and M. J. Dyad thermocyclers (MJ research, Waltham, Mass.) or Eppendorf Mastercycler thermocyclers (Eppendorf, Westbury, N.Y.). The PCR reaction mixture consisted of 4 units of Amplitaq Gold, 1× buffer II (Applied Biosystems, Foster City, Calif.), 1.5 mM $MgCl_2$, 0.4 M betaine, 800 μM dNTP mixture and 250 nM of each primer. The following typical PCR conditions were used: 95° C. for 10 min followed by 8 cycles of 95° C. for 30 seconds, 48° C. for 30 seconds, and 72° C. 30 seconds with the 48° C. annealing temperature increasing 0.9° C. with each of the eight cycles. The PCR was then continued for 37 additional cycles of 95° C. for 15 seconds, 56° C. for 20 seconds, and 72° C. 20 seconds.

Example 3

Purification of PCR Products for Mass Spectrometry with Ion Exchange Resin-Magnetic Beads For solution capture of nucleic acids with ion exchange resin linked to magnetic beads, 25 μl of a 2.5 mg/mL suspension of BioClone amine terminated superparamagnetic beads were added to 25 to 50 μl of a PCR (or RT-PCR) reaction containing approximately 10 pM of a typical PCR amplification product. The above suspension was mixed for approximately 5 minutes by vortexing or pipetting, after which the liquid was removed after using a magnetic separator. The beads containing bound PCR amplification product were then washed three times with 50 mM ammonium bicarbonate/50% MeOH or 100 mM ammonium bicarbonate/50% MeOH, followed by three more washes with 50% MeOH. The bound PCR amplicon was eluted with a solution of 25 mM piperidine, 25 mM imidazole, 35% MeOH which included peptide calibration standards.

Example 4

Mass Spectrometry and Base Composition Analysis

The ESI-FTICR mass spectrometer is based on a Bruker Daltonics (Billerica, Mass.) Apex II 70e electrospray ionization Fourier transform ion cyclotron resonance mass spectrometer that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics, can operate in close proximity to the FTICR spectrometer. All aspects of pulse sequence control and data acquisition were performed on a 600 MHz Pentium II data station running Bruker's Xmass software under Windows NT 4.0 operating system. Sample aliquots, typically 15 μl, were extracted directly from 96-well microtiter plates using a CTC HTS PAL autosampler (LEAP Technologies, Carrboro, N.C.) triggered by the FTICR data station. Samples were injected directly into a 10 μl sample loop integrated with a fluidics handling system that supplies the 100 μl/hr flow rate to the ESI source. Ions were formed via electrospray ionization in a modified Analytica (Branford, Conn.) source employing an off axis, grounded electrospray probe positioned approximately 1.5 cm from the metalized terminus of a glass desolvation capillary. The atmospheric pressure end of the glass capillary was biased at 6000 V relative to the ESI needle during data acquisition. A counter-current flow of dry $N_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed. Ionization duty cycles greater than 99% were achieved by simultaneously accumulating ions in the external ion reservoir during ion detection. Each detection event consisted of 1M data points digitized over 2.3 s. To improve the signal-to-noise ratio (S/N), 32 scans were co-added for a total data acquisition time of 74 s.

The ESI-TOF mass spectrometer is based on a Bruker Daltonics MicroTOF™. Ions from the ESI source undergo orthogonal ion extraction and are focused in a reflectron prior to detection. The TOF and FTICR are equipped with the same automated sample handling and fluidics described above. Ions are formed in the standard MicroTOF™ ESI source that is equipped with the same off-axis sprayer and glass capillary as the FTICR ESI source. Consequently, source conditions were the same as those described above. External ion accumulation was also employed to improve ionization duty cycle during data acquisition. Each detection event on the TOF was comprised of 75,000 data points digitized over 75 μs.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer was injected at a high flow rate to rinse the transfer line and spray needle to avoid sample contamination/carryover. Following the rinse step, the autosampler injected the next sample and the flow rate was switched to low flow. Following a brief equilibration delay, data acquisition commenced. As spectra were co-added, the autosampler continued rinsing the syringe and picking up buffer to rinse the injector and sample transfer line. In general, two syringe rinses and one injector rinse were required to minimize sample carryover. During a routine screening protocol a new sample mixture was injected every 106 seconds. More recently a fast wash station for the syringe needle has been implemented which, when combined with shorter acquisition times, facilitates the acquisition of mass spectra at a rate of just under one spectrum/minute.

Raw mass spectra were post-calibrated with an internal mass standard and deconvoluted to monoisotopic molecular masses. Unambiguous base compositions were derived from the exact mass measurements of the complementary single-stranded oligonucleotides. Quantitative results are obtained by comparing the peak heights with an internal PCR calibration standard present in every PCR well at 500 molecules per well. Calibration methods are commonly owned and disclosed in U.S. Provisional Patent Application Ser. No. 60/545,425 which is incorporated herein by reference in entirety.

Example 5

De Novo Determination of Base Composition of Amplification Products using Molecular Mass Modified Deoxynucleotide Triphosphates Because the molecular masses of the four natural nucleobases have a relatively narrow molecular mass range (A=313.058, G=329.052, C=289.046, T=304.046—See Table 4), a persistent source of ambiguity in assignment of base composition can occur as follows: two nucleic acid strands having different base composition may have a difference of about 1 Da when the base composition difference between the two strands is G↔A (−15.994) combined with C↔T (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052. A 1 Da difference in molecular mass may be within the experimental error of a molecular mass measurement and thus, the relatively narrow molecular mass range of the four natural nucleobases imposes an uncertainty factor.

The present invention provides for a means for removing this theoretical 1 Da uncertainty factor through amplification of a nucleic acid with one mass-tagged nucleobase and three natural nucleobases. The term "nucleobase" as used herein is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

Addition of significant mass to one of the 4 nucleobases (dNTPs) in an amplification reaction, or in the primers themselves, will result in a significant difference in mass of the resulting amplification product (significantly greater than 1 Da) arising from ambiguities arising from the G↔A combined with C↔T event (Table 4). Thus, the same the G↔A (−15.994) event combined with 5-Iodo-C↔T (−110.900) event would result in a molecular mass difference of 126.894. If the molecular mass of the base composition $A_{27}G_{30}$5-Iodo-$C_{21}T_{21}$ (33422.958) is compared with $A_{26}G_{31}$5-Indo-$C_{22}T_{20}$, (33549.852) the theoretical molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 4

Molecular Masses of Natural Nucleobases and the Mass-Modified Nucleobase 5-Iodo-C and Molecular Mass Differences Resulting from Transitions

| Nucleobase | Molecular Mass | Transition | Δ Molecular Mass |
|---|---|---|---|
| A | 313.058 | A --> T | −9.012 |
| A | 313.058 | A --> C | −24.012 |
| A | 313.058 | A --> 5-Iodo-C | 101.888 |
| A | 313.058 | A --> G | 15.994 |
| T | 304.046 | T --> A | 9.012 |
| T | 304.046 | T --> C | −15.000 |
| T | 304.046 | T --> 5-Iodo-C | 110.900 |
| T | 304.046 | T --> G | 25.006 |
| C | 289.046 | C --> A | 24.012 |
| C | 289.046 | C --> T | 15.000 |
| C | 289.046 | C --> G | 40.006 |
| 5-Iodo-C | 414.946 | 5-Iodo-C --> A | −101.888 |
| 5-Iodo-C | 414.946 | 5-Iodo-C --> T | −110.900 |
| 5-Iodo-C | 414.946 | 5-Iodo-C --> G | −85.894 |
| G | 329.052 | G --> A | −15.994 |
| G | 329.052 | G --> T | −25.006 |
| G | 329.052 | G --> C | −40.006 |
| G | 329.052 | G --> 5-Iodo-C | 85.894 |

Mass spectra of bioagent-identifying amplicons were analyzed independently using a maximum-likelihood processor, such as is widely used in radar signal processing. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent-identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

Base count blurring can be carried out as follows. "Electronic PCR" can be conducted on nucleotide sequences of the desired bioagents to obtain the different expected base counts that could be obtained for each primer pair. See for example, ncbi.nlm.nih.gov/sutils/e-per/; Schuler, *Genome Res.* 7:541-50, 1997. In one illustrative embodiment, one or more spreadsheets, such as Microsoft Excel workbooks contain a plurality of worksheets. First in this example, there is a worksheet with a name similar to the workbook name; this worksheet contains the raw electronic PCR data. Second, there is a worksheet named "filtered bioagents base count" that contains bioagent name and base count; there is a separate record for each strain after removing sequences that are not identified with a genus and species and removing all sequences for bioagents with less than 10 strains. Third, there is a worksheet, "Sheet1" that contains the frequency of substitutions, insertions, or deletions for this primer pair. This data is generated by first creating a pivot table from the data in the "filtered bioagents base count" worksheet and then executing an Excel VBA macro. The macro creates a table of differences in base counts for bioagents of the same species, but different strains. One of ordinary skill in the art may understand additional pathways for obtaining similar table differences without undo experimentation.

Application of an exemplary script, involves the user defining a threshold that specifies the fraction of the strains that are represented by the reference set of base counts for each bioagent. The reference set of base counts for each bioagent may contain as many different base counts as are needed to meet or exceed the threshold. The set of reference base counts is defined by taking the most abundant strain's base type composition and adding it to the reference set and then the next most abundant strain's base type composition is added until the threshold is met or exceeded. The current set of data was obtained using a threshold of 55%, which was obtained empirically.

For each base count not included in the reference base count set for that bioagent, the script then proceeds to determine the manner in which the current base count differs from each of the base counts in the reference set. This difference may be represented as a combination of substitutions, Si=Xi, and insertions, Ii=Yi, or deletions, Di=Zi. If there is more than one reference base count, then the reported difference is chosen using rules that aim to minimize the number of changes and, in instances with the same number of changes, minimize the number of insertions or deletions. Therefore, the primary rule is to identify the difference with the minimum sum (Xi+Yi) or (Xi+Zi), e.g., one insertion rather than two substitutions. If there are two or more differences with the minimum sum, then the one that will be reported is the one that contains the most substitutions.

Differences between a base count and a reference composition are categorized as one, two, or more substitutions, one, two, or more insertions, one, two, or more deletions, and combinations of substitutions and insertions or deletions. The different classes of nucleobase changes and their probabilities of occurrence have been delineated in U.S. Patent Application Publication No. 2004209260 (U.S. application Ser. No. 10/418,514) which is incorporated herein by reference in entirety.

Example 6

Use of Broad Range Survey and Division Wide Primer Pairs for Identification of Bacteria in an Epidemic Surveillance Investigation This investigation employed a set of 16 primer pairs which is herein designated the "surveillance primer set" and comprises broad range survey primer pairs, division wide primer pairs and a single *Bacillus* clade primer pair. The surveillance primer set is shown in Table 5 and consists of primer pairs originally listed in Table 2. This surveillance set comprises primers with T modifications (note TMOD designation in primer names) which constitutes a functional improvement with regard to prevention of non-templated adenylation (vide supra) relative to originally selected primers which are displayed below in the same row. Primer pair 449 (non-T modified) has been modified twice. Its predecessors are primer pairs 70 and 357, displayed below in the same row. Primer pair 360 has also been modified twice and its predecessors are primer pairs 17 and 118.

TABLE 5

Bacterial Primer Pairs of the Surveillance Primer Set

| Primer Pair No. | Forward Primer Name | Forward Primer (SEQ ID NO:) | Reverse Primer Name | Reverse Primer (SEQ ID NO:) | Target Gene |
|---|---|---|---|---|---|
| 346 | 16S_EC_713_732_TMOD_F | 202 | 16S_EC_789_809_TMOD_R | 1110 | 16S rRNA |
| 10 | 16S_EC_713_732_F | 21 | 16S_EC_789_809 | 798 | 16S rRNA |
| 347 | 16S_EC_785_806_TMOD_F | 560 | 16S_EC_880_897_TMOD_R | 1278 | 16S rRNA |
| 11 | 16S_EC_785_806_F | 118 | 16S_EC_880_897_R | 830 | 16S rRNA |
| 348 | 16S_EC_960_981_TMOD_F | 706 | 16S_EC_1054_1073_TMOD_R | 895 | 16S rRNA |
| 14 | 16S_EC_960_981_F | 672 | 16S_EC_1054_1073_R | 735 | 16S rRNA |
| 349 | 23S_EC_1826_1843_TMOD_F | 401 | 23S_EC_1906_1924_TMOD_R | 1156 | 23S rRNA |
| 16 | 23S_EC_1826_1843_F | 80 | 23S_EC_1906_1924_R | 805 | 23S rRNA |
| 352 | INFB_EC_1365_1393_TMOD_F | 687 | INFB_EC_1439_1467_TMOD_R | 1411 | infB |
| 34 | INFB_EC_1365_1393_F | 524 | INFB_EC_1439_1467_R | 1248 | infB |
| 354 | RPOC_EC_2218_2241_TMOD_F | 405 | RPOC_EC_2313_2337_TMOD_R | 1072 | rpoC |
| 52 | RPOC_EC_2218_2241_F | 81 | RPOC_EC_2313_2337_R | 790 | rpoC |
| 355 | SSPE_BA_115_137_TMOD_F | 255 | SSPE_BA_197_222_TMOD_R | 1402 | sspE |
| 58 | SSPE_BA_115_137_F | 45 | SSPE_BA_197_222_R | 1201 | sspE |
| 356 | RPLB_EC_650_679_TMOD_F | 232 | RPLB_EC_739_762_TMOD_R | 592 | rp1B |
| 66 | RPLB_EC_650_679_F | 98 | RPLB_EC_739_762_R | 999 | rp1B |
| 358 | VALS_EC_1105_1124_TMOD_F | 385 | VALS_EC_1195_1218_TMOD_R | 1093 | valS |
| 71 | VALS_EC_1105_1124_F | 77 | VALS_EC_1195_1218_R | 795 | valS |
| 359 | RPOB_EC_1845_1866_TMOD_F | 659 | RPOB_EC_1909_1929_TMOD_R | 1250 | rpoB |
| 72 | RPOB_EC_1845_1866_F | 233 | RPOB_EC_1909_1929_R | 825 | rpoB |
| 360 | 23S_EC_2646_2667_TMOD_F | 409 | 23S_EC_2745_2765_TMOD_R | 1434 | 23S rRNA |
| 118 | 23S_EC_2646_2667_F | 84 | 23S_EC_2745_2765_R | 1389 | 23S rRNA |
| 17 | 23S_EC_2645_2669_F | 408 | 23S_EC_2744_2761_R | 1252 | 23S rRNA |
| 361 | 16S_EC_1090_1111_2_TMOD_F | 697 | 16S_EC_1175_1196_TMOD_R | 1398 | 16S rRNA |
| 3 | 16S_EC_1090_1111_2_F | 651 | 16S_EC_1175_1196_R | 1159 | 16S rRNA |
| 362 | RPOB_EC_3799_3821_TMOD_F | 581 | RPOB_EC_3862_3888_TMOD_R | 1325 | rpoB |
| 289 | RPOB_EC_3799_3821_F | 124 | RPOB_EC_3862_3888_R | 840 | rpoB |
| 363 | RPOC_EC_2146_2174_TMOD_F | 284 | RPOC_EC_2227_2245_TMOD_R | 898 | rpoC |
| 290 | RPOC_EC_2146_2174_F | 52 | RPOC_EC_2227_2245_R | 736 | rpoC |
| 367 | TUFB_EC_957_979_TMOD_F | 308 | TUFB_EC_1034_1058_TMOD_R | 1276 | tufB |
| 293 | TUFB_EC_957_979_F | 55 | TUFB_EC_1034_1058_R | 829 | tufB |
| 449 | RPLB_EC_690_710_F | 309 | RPLB_EC_737_758_R | 1336 | rp1B |
| 357 | RPLB_EC_688_710_TMOD_F | 296 | RPLB_EC_736_757_TMOD_R | 1337 | rp1B |
| 67 | RPLB_EC_688_710_F | 54 | RPLB_EC_736_757_R | 842 | rp1B |

The 16 primer pairs of the surveillance set are used to produce bioagent identifying amplicons whose base compositions are sufficiently different amongst all known bacteria at the species level to identify, at a reasonable confidence level, any given bacterium at the species level. As shown in Tables 6A-E, common respiratory bacterial pathogens can be distinguished by the base compositions of bioagent identifying amplicons obtained using the 16 primer pairs of the surveillance set. In some cases, triangulation identification improves the confidence level for species assignment. For example, nucleic acid from *Streptococcus pyogenes* can be amplified by nine of the sixteen surveillance primer pairs and *Streptococcus pneumoniae* can be amplified by ten of the sixteen surveillance primer pairs. The base compositions of the bioagent identifying amplicons are identical for only one of the analogous bioagent identifying amplicons and differ in all of the remaining analogous bioagent identifying amplicons by up to four bases per bioagent identifying amplicon. The resolving power of the surveillance set was confirmed by determination of base compositions for 120 isolates of respiratory pathogens representing 70 different bacterial species and the results indicated that natural variations (usually only one or two base substitutions per bioagent identifying amplicon) amongst multiple isolates of the same species did not prevent correct identification of major pathogenic organisms at the species level.

*Bacillus anthracis* is a well known biological warfare agent which has emerged in domestic terrorism in recent years. Since it was envisioned to produce bioagent identifying amplicons for identification of *Bacillus anthracis*, additional drill-down analysis primers were designed to target genes present on virulence plasmids of *Bacillus anthracis* so that additional confidence could be reached in positive identification of this pathogenic organism. Three drill-down analysis primers were designed and are listed in Tables 2 and 6. In Table 6, the drill-down set comprises primers with T modifications (note TMOD designation in primer names) which constitutes a functional improvement with regard to prevention of non-templated adenylation (vide supra) relative to originally selected primers which are displayed below in the same row.

TABLE 6

Drill-Down Primer Pairs for Confirmation of Identification of *Bacillus anthracis*

| Primer Pair No. | Forward Primer Name | Forward Primer (SEQ ID NO:) | Reverse Primer Name | Reverse Primer (SEQ NO:) | Target Gene ID |
|---|---|---|---|---|---|
| 350 | CAPC_BA_274_303_TMOD_F | 476 | CAPC_BA_349_376_TMOD_R | 1314 | capC |
| 24 | CAPC_BA_274_303_F | 109 | CAPC_BA_349_376_R | 837 | capC |
| 351 | CYA_BA_1353_1379_TMOD_F | 355 | CYA_BA_1448_1467_TMOD_R | 1423 | cyA |
| 30 | CYA_BA_1353_1379_F | 64 | CYA_BA_1448_1467_R | 1342 | cyA |
| 353 | LEF_BA_756_781_TMOD_F | 220 | LEF_BA_843_872_TMOD_R | 1394 | lef |
| 37 | LEF_BA_756_781_F | 26 | LEF_BA_843_872_R | 1135 | lef |

Figure 3:
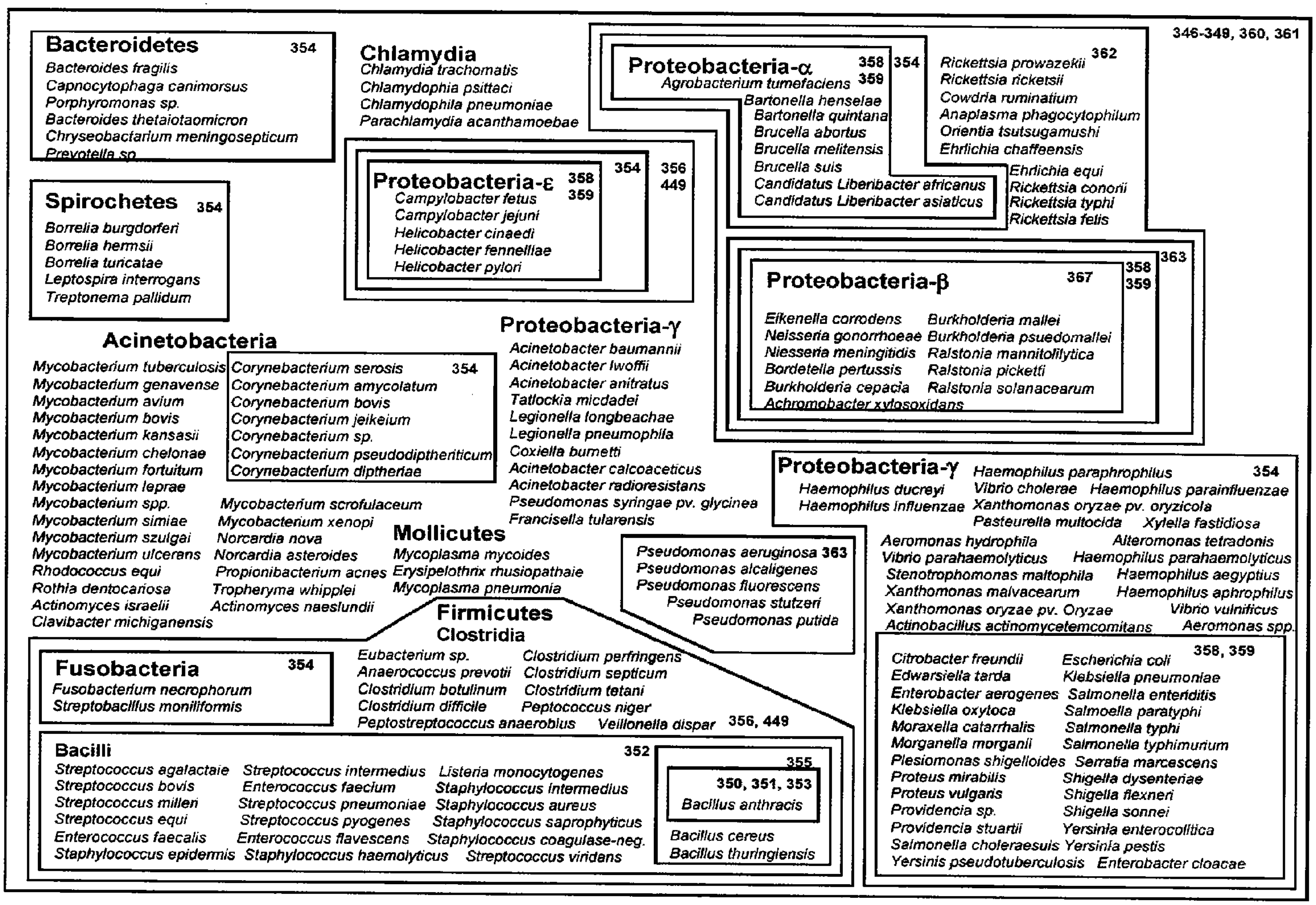
FIG. 3: common pathogenic bacteria and primer pair coverage. The primer pair number in the upper right hand corner of each polygon indicates that the primer pair can produce a bioagent identifying amplicon for all species within that polygon.

Phylogenetic coverage of bacterial space of the sixteen surveillance primers of Table 5 and the three *Bacillus anthracis* drill-down primers of Table 6 is shown in FIG. 3 which lists common pathogenic bacteria. FIG. 3 is not meant to be comprehensive in illustrating all species identified by the primers. Only pathogenic bacteria are listed as representative examples of the bacterial species that can be identified by the primers and methods of the present invention. Nucleic acid of groups of bacteria enclosed within the polygons of FIG. 3 can be amplified to obtain bioagent identifying amplicons using the primer pair numbers listed in the upper right hand corner of each polygon. Primer coverage for polygons within polygons is additive. As an illustrative example, bioagent identifying amplicons can be obtained for *Chlamydia trachomatis* by amplification with, for example, primer pairs 346-349, 360 and 361, but not with any of the remaining primers of the surveillance primer set. On the other hand, bioagent identifying amplicons can be obtained from nucleic acid originating from *Bacillus anthracis* (located within 5 successive polygons) using, for example, any of the following primer pairs: 346-349, 360, 361 (base polygon), 356, 449 (second polygon), 352 (third polygon), 355 (fourth polygon), 350, 351 and 353 (fifth polygon). Multiple coverage of a given organism with multiple primers provides for increased confidence level in identification of the organism as a result of enabling broad triangulation identification.

In Tables 7A-E, base compositions of respiratory pathogens for primer target regions are shown. Two entries in a cell, represent variation in ribosomal DNA operons. The most predominant base composition is shown first and the minor (frequently a single operon) is indicated by an asterisk (*). Entries with NO DATA mean that the primer would not be expected to prime this species due to mismatches between the primer and target region, as determined by theoretical PCR.

TABLE 7A

Base Compositions of Common Respiratory Pathogens for Bioagent Identifying Amplicons Corresponding to Primer Pair Nos: 346, 347 and 348

| Organism | Strain | Primer 346 [A G C T] | Primer 347 [A G C T] | Primer 348 [A G C T] |
|---|---|---|---|---|
| *Klebsiella pneumoniae* | MGH78578 | [29 32 25 13]<br>[29 31 25 13]* | [23 38 28 26]<br>[23 37 28 26]* | [26 32 28 30]<br>[26 31 28 30]* |
| *Yersinia pestis* | CO-92 Biovar Orientalis | [29 32 25 13] | [22 39 28 26] | [29 30 28 29]<br>[30 30 27 29]* |
| *Yersinia pestis* | KIM5 P12 (Biovar Mediaevalis) | [29 32 25 13] | [22 39 28 26] | [29 30 28 29] |
| *Yersinia pestis* | 91001 | [29 32 25 13] | [22 39 28 26] | [29 30 28 29]<br>[30 30 27 29]* |
| *Haemophilus influenzae* | KW20 | [28 31 23 17] | [24 37 25 27] | [29 30 28 29] |
| *Pseudomonas aeruginosa* | PAO1 | [30 31 23 15] | [26 36 29 24]<br>[27 36 29 23]* | [26 32 29 29] |
| *Pseudomonas fluorescens* | Pf0-1 | [30 31 23 15] | [26 35 29 25] | [28 31 28 29] |
| *Pseudomonas putida* | KT2440 | [30 31 23 15] | [28 33 27 27] | [27 32 29 28] |
| *Legionella pneumophila* | Philadelphia-1 | [30 30 24 15] | [33 33 23 27] | [29 28 28 31] |
| *Francisella tularensis* | schu 4 | [32 29 22 16] | [28 38 26 26] | [25 32 28 31] |
| *Bordetella pertussis* | Tohama I | [30 29 24 16] | [23 37 30 24] | [30 32 30 26] |
| *Burkholderia cepacia* | J2315 | [29 29 27 14] | [27 32 26 29] | [27 36 31 24]<br>[20 42 35 19]* |
| *Burkholderia pseudomallei* | K96243 | [29 29 27 14] | [27 32 26 29] | [27 36 31 24] |
| *Neisseria gonorrhoeae* | FA 1090, ATCC 700825 | [29 28 24 18] | [27 34 26 28] | [24 36 29 27] |
| *Neisseria meningitidis* | MC58 (serogroup B) | [29 28 26 16] | [27 34 27 27] | [25 35 30 26] |
| *Neisseria meningitidis* | serogroup C, FAM18 | [29 28 26 16] | [27 34 27 27] | [25 35 30 26] |

TABLE 7A-continued

Base Compositions of Common Respiratory Pathogens for Bioagent Identifying Amplicons Corresponding to Primer Pair Nos: 346, 347 and 348

| Organism | Strain | Primer 346 [A G C T] | Primer 347 [A G C T] | Primer 348 [A G C T] |
|---|---|---|---|---|
| *Neisseria meningitidis* | Z2491 (serogroup A) | [29 28 26 16] | [27 34 27 27] | [25 35 30 26] |
| *Chlamydophila pneumoniae* | TW-183 | [31 27 22 19] | NO DATA | [32 27 27 29] |
| *Chlamydophila pneumoniae* | AR39 | [31 27 22 19] | NO DATA | [32 27 27 29] |
| *Chlamydophila pneumoniae* | CWL029 | [31 27 22 19] | NO DATA | [32 27 27 29] |
| *Chlamydophila pneumoniae* | J138 | [31 27 22 19] | NO DATA | [32 27 27 29] |
| *Corynebacterium diphtheriae* | NCTC13129 | [29 34 21 15] | [22 38 31 25] | [22 33 25 34] |
| *Mycobacterium avium* | k10 | [27 36 21 15] | [22 37 30 28] | [21 36 27 30] |
| *Mycobacterium avium* | 104 | [27 36 21 15] | [22 37 30 28] | [21 36 27 30] |
| *Mycobacterium tuberculosis* | CSU#93 | [27 36 21 15] | [22 37 30 28] | [21 36 27 30] |
| *Mycobacterium tuberculosis* | CDC 1551 | [27 36 21 15] | [22 37 30 28] | [21 36 27 30] |
| *Mycobacterium tuberculosis* | H37Rv (lab strain) | [27 36 21 15] | [22 37 30 28] | [21 36 27 30] |
| *Mycoplasma pneumoniae* | M129 | [31 29 19 20] | NO DATA | NO DATA |
| *Staphylococcus aureus* | MRSA252 | [27 30 21 21] | [25 35 30 26] | [30 29 30 29] [29 31 30 29]* |
| *Staphylococcus aureus* | MSSA476 | [27 30 21 21] | [25 35 30 26] | [30 29 30 29] [30 29 29 30]* |
| *Staphylococcus aureus* | COL | [27 30 21 21] | [25 35 30 26] | [30 29 30 29] [30 29 29 30]* |
| *Staphylococcus aureus* | Mu50 | [27 30 21 21] | [25 35 30 26] | [30 29 30 29] [30 29 29 30]* |
| *Staphylococcus aureus* | MW2 | [27 30 21 21] | [25 35 30 26] | [30 29 30 29] [30 29 29 30]* |
| *Staphylococcus aureus* | N315 | [27 30 21 21] | [25 35 30 26] | [30 29 30 29] [30 29 29 30]* |
| *Staphylococcus aureus* | NCTC 8325 | [27 30 21 21] | [25 35 30 26] [25 35 31 26]* | [30 29 30 29] [30 29 29 30] |
| *Streptococcus agalactiae* | NEM316 | [26 32 23 18] | [24 36 31 25] [24 36 30 26]* | [25 32 29 30] |
| *Streptococcus equi* | NC_002955 | [26 32 23 18] | [23 37 31 25] | [29 30 25 32] |
| *Streptococcus pyogenes* | MGAS8232 | [26 32 23 18] | [24 37 30 25] | [25 31 29 31] |
| *Streptococcus pyogenes* | MGAS315 | [26 32 23 18] | [24 37 30 25] | [25 31 29 31] |
| *Streptococcus pyogenes* | SSI-1 | [26 32 23 18] | [24 37 30 25] | [25 31 29 31] |
| *Streptococcus pyogenes* | MGAS10394 | [26 32 23 18] | [24 37 30 25] | [25 31 29 31] |
| *Streptococcus pyogenes* | Manfredo (M5) | [26 32 23 18] | [24 37 30 25] | [25 31 29 31] |
| *Streptococcus pyogenes* | SF370 (M1) | [26 32 23 18] | [24 37 30 25] | [25 31 29 31] |
| *Streptococcus pneumoniae* | 670 | [26 32 23 18] | [25 35 28 28] | [25 32 29 30] |
| *Streptococcus pneumoniae* | R6 | [26 32 23 18] | [25 35 28 28] | [25 32 29 30] |
| *Streptococcus pneumoniae* | TIGR4 | [26 32 23 18] | [25 35 28 28] | [25 32 30 29] |
| *Streptococcus gordonii* | NCTC7868 | [25 33 23 18] | [24 36 31 25] | [25 31 29 31] |
| *Streptococcus mitis* | NCTC 12261 | [26 32 23 18] | [25 35 30 26] | [25 32 29 30] [24 31 35 29]* |
| *Streptococcus mutans* | UA159 | [24 32 24 19] | [25 37 30 24] | [28 31 26 31] |

TABLE 7B

Base Compositions of Common Respiratory Pathogens for Bioagent Identifying Amplicons Corresponding to Primer Pair Nos: 349, 360, and 356

| Organism | Strain | Primer 349 [A G C T] | Primer 360 [A G C T] | Primer 356 [A G C T] |
|---|---|---|---|---|
| *Klebsiella pneumoniae* | MGH78578 | [25 31 25 22] | [33 37 25 27] | NO DATA |
| *Yersinia pestis* | CO-92 Biovar Orientalis | [25 31 27 20] [25 32 26 20]* | [34 35 25 28] | NO DATA |
| *Yersinia pestis* | KIM5 P12 (Biovar Mediaevalis) | [25 31 27 20] [25 32 26 20]* | [34 35 25 28] | NO DATA |
| *Yersinia pestis* | 91001 | [25 31 27 20] | [34 35 25 28] | NO DATA |
| *Haemophilus influenzae* | KW20 | [28 28 25 20] | [32 38 25 27] | NO DATA |
| *Pseudomonas aeruginosa* | PAO1 | [24 31 26 20] | [31 36 27 27] [31 36 27 28]* | NO DATA |
| *Pseudomonas fluorescens* | Pf0-1 | NO DATA | [30 37 27 28] [30 37 27 28] | NO DATA |
| *Pseudomonas putida* | KT2440 | [24 31 26 20] | [30 37 27 28] | NO DATA |
| *Legionella pneumophila* | Philadelphia-1 | [23 30 25 23] | [30 39 29 24] | NO DATA |
| *Francisella tularensis* | schu 4 | [26 31 25 19] | [32 36 27 27] | NO DATA |
| *Bordetella pertussis* | Tohama I | [21 29 24 18] | [33 36 26 27] | NO DATA |
| *Burkholderia cepacia* | J2315 | [23 27 22 20] | [31 37 28 26] | NO DATA |
| *Burkholderia pseudomallei* | K96243 | [23 27 22 20] | [31 37 28 26] | NO DATA |
| *Neisseria gonorrhoeae* | FA 1090, ATCC 700825 | [24 27 24 17] | [34 37 25 26] | NO DATA |
| *Neisseria meningitidis* | MC58 (serogroup B) | [25 27 22 18] | [34 37 25 26] | NO DATA |
| *Neisseria meningitidis* | serogroup C, FAM18 | [25 26 23 18] | [34 37 25 26] | NO DATA |
| *Neisseria meningitidis* | Z2491 (serogroup A) | [25 26 23 18] | [34 37 25 26] | NO DATA |
| *Chlamydophila pneumoniae* | TW-183 | [30 28 27 18] | NO DATA | NO DATA |
| *Chlamydophila pneumoniae* | AR39 | [30 28 27 18] | NO DATA | NO DATA |
| *Chlamydophila pneumoniae* | CWL029 | [30 28 27 18] | NO DATA | NO DATA |
| *Chlamydophila pneumoniae* | J138 | [30 28 27 18] | NO DATA | NO DATA |
| *Corynebacterium diphtheriae* | NCTC13129 | NO DATA | [29 40 28 25] | NO DATA |
| *Mycobacterium avium* | k10 | NO DATA | [33 35 32 22] | NO DATA |
| *Mycobacterium avium* | 104 | NO DATA | [33 35 32 22] | NO DATA |
| *Mycobacterium tuberculosis* | CSU#93 | NO DATA | [30 36 34 22] | NO DATA |
| *Mycobacterium tuberculosis* | CDC 1551 | NO DATA | [30 36 34 22] | NO DATA |
| *Mycobacterium tuberculosis* | H37Rv (lab strain) | NO DATA | [30 36 34 22] | NO DATA |
| *Mycoplasma pneumoniae* | M129 | [28 30 24 19] | [34 31 29 28] | NO DATA |
| *Staphylococcus aureus* | MRSA252 | [26 30 25 20] | [31 38 24 29] | [33 30 31 27] |
| *Staphylococcus aureus* | MSSA476 | [26 30 25 20] | [31 38 24 29] | [33 30 31 27] |
| *Staphylococcus aureus* | COL | [26 30 25 20] | [31 38 24 29] | [33 30 31 27] |
| *Staphylococcus aureus* | Mu50 | [26 30 25 20] | [31 38 24 29] | [33 30 31 27] |
| *Staphylococcus aureus* | MW2 | [26 30 25 20] | [31 38 24 29] | [33 30 31 27] |
| *Staphylococcus aureus* | N315 | [26 30 25 20] | [31 38 24 29] | [33 30 31 27] |
| *Staphylococcus aureus* | NCTC 8325 | [26 30 25 20] | [31 38 24 29] | [33 30 31 27] |
| *Streptococcus agalactiae* | NEM316 | [28 31 22 20] | [33 37 24 28] | [37 30 28 26] |
| *Streptococcus equi* | NC_002955 | [28 31 23 19] | [33 38 24 27] | [37 31 28 25] |

TABLE 7B-continued

Base Compositions of Common Respiratory Pathogens for Bioagent Identifying Amplicons Corresponding to Primer Pair Nos: 349, 360, and 356

| Organism | Strain | Primer 349 [A G C T] | Primer 360 [A G C T] | Primer 356 [A G C T] |
|---|---|---|---|---|
| *Streptococcus pyogenes* | MGAS8232 | [28 31 23 19] | [33 37 24 28] | [38 31 29 23] |
| *Streptococcus pyogenes* | MGAS315 | [28 31 23 19] | [33 37 24 28] | [38 31 29 23] |
| *Streptococcus pyogenes* | SSI-1 | [28 31 23 19] | [33 37 24 28] | [38 31 29 23] |
| *Streptococcus pyogenes* | MGAS10394 | [28 31 23 19] | [33 37 24 28] | [38 31 29 23] |
| *Streptococcus pyogenes* | Manfredo (M5) | [28 31 23 19] | [33 37 24 28] | [38 31 29 23] |
| *Streptococcus pyogenes* | SF370 (M1) | [28 31 23 19] [28 31 22 20]* | [33 37 24 28] | [38 31 29 23] |
| *Streptococcus pneumoniae* | 670 | [28 31 22 20] | [34 36 24 28] | [37 30 29 25] |
| *Streptococcus pneumoniae* | R6 | [28 31 22 20] | [34 36 24 28] | [37 30 29 25] |
| *Streptococcus pneumoniae* | TIGR4 | [28 31 22 20] | [34 36 24 28] | [37 30 29 25] |
| *Streptococcus gordonii* | NCTC7868 | [28 32 23 20] | [34 36 24 28] | [36 31 29 25] |
| *Streptococcus mitis* | NCTC 12261 | [28 31 22 20] [29 30 22 20]* | [34 36 24 28] | [37 30 29 25] |
| *Streptococcus mutans* | UA159 | [26 32 23 22] | [34 37 24 27] | NO DATA |

TABLE 7C

Base Compositions of Common Respiratory Pathogens for Bioagent Identifying Amplicons Corresponding to Primer Pair Nos: 449, 354, and 352

| Organism | Strain | Primer 449 [A G C T] | Primer 354 [A G C T] | Primer 352 [A G C T] |
|---|---|---|---|---|
| *Klebsiella pneumoniae* | MGH78578 | NO DATA | [27 33 36 26] | NO DATA |
| *Yersinia pestis* | CO-92 Biovar Orientalis | NO DATA | [29 31 33 29] | [32 28 20 25] |
| *Yersinia pestis* | KIM5 P12 (Biovar Mediaevalis) | NO DATA | [29 31 33 29] | [32 28 20 25] |
| *Yersinia pestis* | 91001 | NO DATA | [29 31 33 29] | NO DATA |
| *Haemophilus influenzae* | KW20 | NO DATA | [30 29 31 32] | NO DATA |
| *Pseudomonas aeruginosa* | PAO1 | NO DATA | [26 33 39 24] | NO DATA |
| *Pseudomonas fluorescens* | Pf0-1 | NO DATA | [26 33 34 29] | NO DATA |
| *Pseudomonas putida* | KT2440 | NO DATA | [25 34 36 27] | NO DATA |
| *Legionella pneumophila* | Philadelphia-1 | NO DATA | NO DATA | NO DATA |
| *Francisella tularensis* | schu 4 | NO DATA | [33 32 25 32] | NO DATA |
| *Bordetella pertussis* | Tohama I | NO DATA | [26 33 39 24] | NO DATA |
| *Burkholderia cepacia* | J2315 | NO DATA | [25 37 33 27] | NO DATA |
| *Burkholderia pseudomallei* | K96243 | NO DATA | [25 37 34 26] | NO DATA |
| *Neisseria gonorrhoeae* | FA 1090, ATCC 700825 | [17 23 22 10] | [29 31 32 30] | NO DATA |
| *Neisseria meningitidis* | MC58 (serogroup B) | NO DATA | [29 30 32 31] | NO DATA |
| *Neisseria meningitidis* | serogroup C, FAM18 | NO DATA | [29 30 32 31] | NO DATA |
| *Neisseria meningitidis* | Z2491 (serogroup A) | NO DATA | [29 30 32 31] | NO DATA |
| *Chlamydophila pneumoniae* | TW-183 | NO DATA | NO DATA | NO DATA |
| *Chlamydophila pneumoniae* | AR39 | NO DATA | NO DATA | NO DATA |

TABLE 7C-continued

Base Compositions of Common Respiratory Pathogens for Bioagent Identifying Amplicons Corresponding to Primer Pair Nos: 449, 354, and 352

| Organism | Strain | Primer 449 [A G C T] | Primer 354 [A G C T] | Primer 352 [A G C T] |
|---|---|---|---|---|
| *Chlamydophila pneumoniae* | CWL029 | NO DATA | NO DATA | NO DATA |
| *Chlamydophila pneumoniae* | J138 | NO DATA | NO DATA | NO DATA |
| *Corynebacterium diphtheriae* | NCTC13129 | NO DATA | NO DATA | NO DATA |
| *Mycobacterium avium* | k10 | NO DATA | NO DATA | NO DATA |
| *Mycobacterium avium* | 104 | NO DATA | NO DATA | NO DATA |
| *Mycobacterium tuberculosis* | CSU#93 | NO DATA | NO DATA | NO DATA |
| *Mycobacterium tuberculosis* | CDC 1551 | NO DATA | NO DATA | NO DATA |
| *Mycobacterium tuberculosis* | H37Rv (lab strain) | NO DATA | NO DATA | NO DATA |
| *Mycoplasma pneumoniae* | M129 | NO DATA | NO DATA | NO DATA |
| *Staphylococcus aureus* | MRSA252 | [17 20 21 17] | [30 27 30 35] | [36 24 19 26] |
| *Staphylococcus aureus* | MSSA476 | [17 20 21 17] | [30 27 30 35] | [36 24 19 26] |
| *Staphylococcus aureus* | COL | [17 20 21 17] | [30 27 30 35] | [35 24 19 27] |
| *Staphylococcus aureus* | Mu50 | [17 20 21 17] | [30 27 30 35] | [36 24 19 26] |
| *Staphylococcus aureus* | MW2 | [17 20 21 17] | [30 27 30 35] | [36 24 19 26] |
| *Staphylococcus aureus* | N315 | [17 20 21 17] | [30 27 30 35] | [36 24 19 26] |
| *Staphylococcus aureus* | NCTC 8325 | [17 20 21 17] | [30 27 30 35] | [35 24 19 27] |
| *Streptococcus agalactiae* | NEM316 | [22 20 19 14] | [26 31 27 38] | [29 26 22 28] |
| *Streptococcus equi* | NC_002955 | [22 21 19 13] | NO DATA | NO DATA |
| *Streptococcus pyogenes* | MGAS8232 | [23 21 19 12] | [24 32 30 36] | NO DATA |
| *Streptococcus pyogenes* | MGAS315 | [23 21 19 12) | [24 32 30 36] | NO DATA |
| *Streptococcus pyogenes* | SSI-1 | [23 21 19 12] | [24 32 30 36] | NO DATA |
| *Streptococcus pyogenes* | MGAS10394 | [23 21 19 12] | [24 32 30 36] | NO DATA |
| *Streptococcus pyogenes* | Manfredo (M5) | [23 21 19 12] | [24 32 30 36] | NO DATA |
| *Streptococcus pyogenes* | SF370 (M1) | [23 21 19 12] | [24 32 30 36] | NO DATA |
| *Streptococcus pneumoniae* | 670 | [22 20 19 14] | [25 33 29 35] | [30 29 21 25] |
| *Streptococcus pneumoniae* | R6 | [22 20 19 14] | [25 33 29 35] | [30 29 21 25] |
| *Streptococcus pneumoniae* | TIGR4 | [22 20 19 14] | [25 33 29 35] | [30 29 21 25] |
| *Streptococcus gordonii* | NCTC7868 | [21 21 19 14] | NO DATA | [29 26 22 28] |
| *Streptococcus mitis* | NCTC 12261 | [22 20 19 14] | [26 30 32 34] | NO DATA |
| *Streptococcus mutans* | UA159 | NO DATA | NO DATA | NO DATA |

TABLE 7D

Base Compositions of Common Respiratory Pathogens for Bioagent Identifying Amplicons Corresponding to Primer Pair Nos: 355, 358, and 359

| Organism | Strain | Primer 355 [A G C T] | Primer 358 [A G C T] | Primer 359 [A G C T] |
|---|---|---|---|---|
| *Klebsiella pneumoniae* | MGH78578 | NO DATA | [24 39 33 20] | [25 21 24 17] |
| *Yersinia pestis* | CO-92 Biovar Orientalis | NO DATA | [26 34 35 21] | [23 23 19 22] |
| *Yersinia pestis* | KIM5 P12 (Biovar Mediaevalis) | NO DATA | [26 34 35 21] | [23 23 19 22] |
| *Yersinia pestis* | 91001 | NO DATA | [26 34 35 21] | [23 23 19 22] |
| *Haemophilus influenzae* | KW20 | NO DATA | NO DATA | NO DATA |
| *Pseudomonas aeruginosa* | PAO1 | NO DATA | NO DATA | NO DATA |
| *Pseudomonas fluorescens* | Pf0-1 | NO DATA | NO DATA | NO DATA |
| *Pseudomonas putida* | KT2440 | NO DATA | [21 37 37 21] | NO DATA |
| *Legionella pneumophila* | Philadelphia-1 | NO DATA | NO DATA | NO DATA |
| *Francisella tularensis* | schu 4 | NO DATA | NO DATA | NO DATA |
| *Bordetella pertussis* | Tohama I | NO DATA | NO DATA | NO DATA |
| *Burkholderia cepacia* | J2315 | NO DATA | NO DATA | NO DATA |
| *Burkholderia pseudomallei* | K96243 | NO DATA | NO DATA | NO DATA |
| *Neisseria gonorrhoeae* | FA 1090, ATCC 700825 | NO DATA | NO DATA | NO DATA |
| *Neisseria meningitidis* | MC58 (serogroup B) | NO DATA | NO DATA | NO DATA |
| *Neisseria meningitidis* | serogroup C, FAM18 | NO DATA | NO DATA | NO DATA |
| *Neisseria meningitidis* | Z2491 (serogroup A) | NO DATA | NO DATA | NO DATA |
| *Chlamydophila pneumoniae* | TW-183 | NO DATA | NO DATA | NO DATA |
| *Chlamydophila pneumoniae* | AR39 | NO DATA | NO DATA | NO DATA |
| *Chlamydophila pneumoniae* | CWL029 | NO DATA | NO DATA | NO DATA |
| *Chlamydophila pneumoniae* | J138 | NO DATA | NO DATA | NO DATA |
| *Corynebacterium diphtheriae* | NCTC13129 | NO DATA | NO DATA | NO DATA |
| *Mycobacterium avium* | k10 | NO DATA | NO DATA | NO DATA |
| *Mycobacterium avium* | 104 | NO DATA | NO DATA | NO DATA |
| *Mycobacterium tuberculosis* | CSU#93 | NO DATA | NO DATA | NO DATA |
| *Mycobacterium tuberculosis* | CDC 1551 | NO DATA | NO DATA | NO DATA |
| *Mycobacterium tuberculosis* | H37Rv (lab strain) | NO DATA | NO DATA | NO DATA |
| *Mycoplasma pneumoniae* | M129 | NO DATA | NO DATA | NO DATA |
| *Staphylococcus aureus* | MRSA252 | NO DATA | NO DATA | NO DATA |
| *Staphylococcus aureus* | MSSA476 | NO DATA | NO DATA | NO DATA |
| *Staphylococcus aureus* | COL | NO DATA | NO DATA | NO DATA |
| *Staphylococcus aureus* | Mu50 | NO DATA | NO DATA | NO DATA |
| *Staphylococcus aureus* | MW2 | NO DATA | NO DATA | NO DATA |
| *Staphylococcus aureus* | N315 | NO DATA | NO DATA | NO DATA |
| *Staphylococcus aureus* | NCTC 8325 | NO DATA | NO DATA | NO DATA |
| *Streptococcus agalactiae* | NEM316 | NO DATA | NO DATA | NO DATA |
| *Streptococcus equi* | NC_002955 | NO DATA | NO DATA | NO DATA |

TABLE 7D-continued

Base Compositions of Common Respiratory Pathogens for Bioagent Identifying Amplicons Corresponding to Primer Pair Nos: 355, 358, and 359

| Organism | Strain | Primer 355 [A G C T] | Primer 358 [A G C T] | Primer 359 [A G C T] |
|---|---|---|---|---|
| *Streptococcus pyogenes* | MGAS8232 | NO DATA | NO DATA | NO DATA |
| *Streptococcus pyogenes* | MGAS315 | NO DATA | NO DATA | NO DATA |
| *Streptococcus pyogenes* | SSI-1 | NO DATA | NO DATA | NO DATA |
| *Streptococcus pyogenes* | MGAS10394 | NO DATA | NO DATA | NO DATA |
| *Streptococcus pyogenes* | Manfredo (M5) | NO DATA | NO DATA | NO DATA |
| *Streptococcus pyogenes* | SF370 (M1) | NO DATA | NO DATA | NO DATA |
| *Streptococcus pneumoniae* | 670 | NO DATA | NO DATA | NO DATA |
| *Streptococcus pneumoniae* | R6 | NO DATA | NO DATA | NO DATA |
| *Streptococcus pneumoniae* | TIGR4 | NO DATA | NO DATA | NO DATA |
| *Streptococcus gordonii* | NCTC7868 | NO DATA | NO DATA | NO DATA |
| *Streptococcus mitis* | NCTC 12261 | NO DATA | NO DATA | NO DATA |
| *Streptococcus mutans* | UA159 | NO DATA | NO DATA | NO DATA |

TABLE 7E

Base Compositions of Common Respiratory Pathogens for Bioagent Identifying Amplicons Corresponding to Primer Pair Nos: 362, 363, and 367

| Organism | Strain | Primer 362 [A G C T] | Primer 363 [A G C T] | Primer 367 [A G C T] |
|---|---|---|---|---|
| *Klebsiella pneumoniae* | MGH78578 | [21 33 22 16] | [16 34 26 26] | NO DATA |
| *Yersinia pestis* | CO-92 Biovar Orientalis | [20 34 18 20] | NO DATA | NO DATA |
| *Yersinia pestis* | KIM5 P12 (Biovar Mediaevalis) | [20 34 18 20] | NO DATA | NO DATA |
| *Yersinia pestis* | 91001 | [20 34 18 20] | NO DATA | NO DATA |
| *Haemophilus influenzae* | KW20 | NO DATA | NO DATA | NO DATA |
| *Pseudomonas aeruginosa* | PAO1 | [19 35 21 17] | [16 36 28 22] | NO DATA |
| *Pseudomonas fluorescens* | Pf0-1 | NO DATA | [18 35 26 23] | NO DATA |
| *Pseudomonas putida* | KT2440 | NO DATA | [16 35 28 23] | NO DATA |
| *Legionella pneumophila* | Philadelphia-1 | NO DATA | NO DATA | NO DATA |
| *Francisella tularensis* | schu 4 | NO DATA | NO DATA | NO DATA |
| *Bordetella pertussis* | Tohama I | [20 31 24 17] | [15 34 32 21] | [26 25 34 19] |
| *Burkholderia cepacia* | J2315 | [20 33 21 18] | [15 36 26 25] | [25 27 32 20] |
| *Burkholderia pseudomallei* | K96243 | [19 34 19 20] | [15 37 28 22] | [25 27 32 20] |
| *Neisseria gonorrhoeae* | FA 1090, ATCC 700825 | NO DATA | NO DATA | NO DATA |
| *Neisseria meningitidis* | MC58 (serogroup B) | NO DATA | NO DATA | NO DATA |
| *Neisseria meningitidis* | serogroup C, FAM18 | NO DATA | NO DATA | NO DATA |
| *Neisseria meningitidis* | Z2491 (serogroup A) | NO DATA | NO DATA | NO DATA |
| *Chlamydophila pneumoniae* | TW-183 | NO DATA | NO DATA | NO DATA |
| *Chlamydophila pneumoniae* | AR39 | NO DATA | NO DATA | NO DATA |

TABLE 7E-continued

Base Compositions of Common Respiratory Pathogens for Bioagent Identifying Amplicons Corresponding to Primer Pair Nos: 362, 363, and 367

| Organism | Strain | Primer 362 [A G C T] | Primer 363 [A G C T] | Primer 367 [A G C T] |
|---|---|---|---|---|
| *Chlamydophila pneumoniae* | CWL029 | NO DATA | NO DATA | NO DATA |
| *Chlamydophila pneumoniae* | J138 | NO DATA | NO DATA | NO DATA |
| *Corynebacterium diphtheriae* | NCTC13129 | NO DATA | NO DATA | NO DATA |
| *Mycobacterium avium* | k10 | [19 34 23 16] | NO DATA | [24 26 35 19] |
| *Mycobacterium avium* | 104 | [19 34 23 16] | NO DATA | [24 26 35 19] |
| *Mycobacterium tuberculosis* | CSU#93 | [19 31 25 17] | NO DATA | [25 25 34 20] |
| *Mycobacterium tuberculosis* | CDC 1551 | [19 31 24 18] | NO DATA | [25 25 34 20] |
| *Mycobacterium tuberculosis* | H37Rv (lab strain) | [19 31 24 18] | NO DATA | [25 25 34 20] |
| *Mycoplasma pneumoniae* | M129 | NO DATA | NO DATA | NO DATA |
| *Staphylococcus aureus* | MRSA252 | NO DATA | NO DATA | NO DATA |
| *Staphylococcus aureus* | MSSA476 | NO DATA | NO DATA | NO DATA |
| *Staphylococcus aureus* | COL | NO DATA | NO DATA | NO DATA |
| *Staphylococcus aureus* | Mu50 | NO DATA | NO DATA | NO DATA |
| *Staphylococcus aureus* | MW2 | NO DATA | NO DATA | NO DATA |
| *Staphylococcus aureus* | N315 | NO DATA | NO DATA | NO DATA |
| *Staphylococcus aureus* | NCTC 8325 | NO DATA | NO DATA | NO DATA |
| *Streptococcus agalactiae* | NEM316 | NO DATA | NO DATA | NO DATA |
| *Streptococcus equi* | NC_002955 | NO DATA | NO DATA | NO DATA |
| Streptococcus *pyogenes* | MGAS8232 | NO DATA | NO DATA | NO DATA |
| *Streptococcus pyogenes* | MGAS315 | NO DATA | NO DATA | NO DATA |
| *Streptococcus pyogenes* | SSI-1 | NO DATA | NO DATA | NO DATA |
| *Streptococcus pyogenes* | MGAS10394 | NO DATA | NO DATA | NO DATA |
| *Streptococcus pyogenes* | Manfredo (M5) | NO DATA | NO DATA | NO DATA |
| *Streptococcus pyogenes* | SF370 (M1) | NO DATA | NO DATA | NO DATA |
| *Streptococcus pneumoniae* | 670 | NO DATA | NO DATA | NO DATA |
| *Streptococcus pneumoniae* | R6 | [20 30 19 23] | NO DATA | NO DATA |
| *Streptococcus pneumoniae* | TIGR4 | [20 30 19 23] | NO DATA | NO DATA |
| *Streptococcus gordonii* | NCTC7868 | NO DATA | NO DATA | NO DATA |
| *Streptococcus mitis* | NCTC 12261 | NO DATA | NO DATA | NO DATA |
| *Streptococcus mutans* | UA159 | NO DATA | NO DATA | NO DATA |

Four sets of throat samples from military recruits at different military facilities taken at different time points were analyzed using the primers of the present invention. The first set was collected at a military training center from Nov. 1 to Dec. 20, 2002 during one of the most severe outbreaks of pneumonia associated with group A *Streptococcus* in the United States since 1968. During this outbreak, fifty-one throat swabs were taken from both healthy and hospitalized recruits and plated on blood agar for selection of putative group A *Streptococcus* colonies. A second set of 15 original patient specimens was taken during the height of this group A *Streptococcus*-associated respiratory disease outbreak. The third set were historical samples, including twenty-seven isolates of group A *Streptococcus*, from disease outbreaks at this and other military training facilities during previous years. The fourth set of samples was collected from five geographically separated military facilities in the continental U.S. in the winter immediately following the severe November/December 2002 outbreak.

Figure 4:
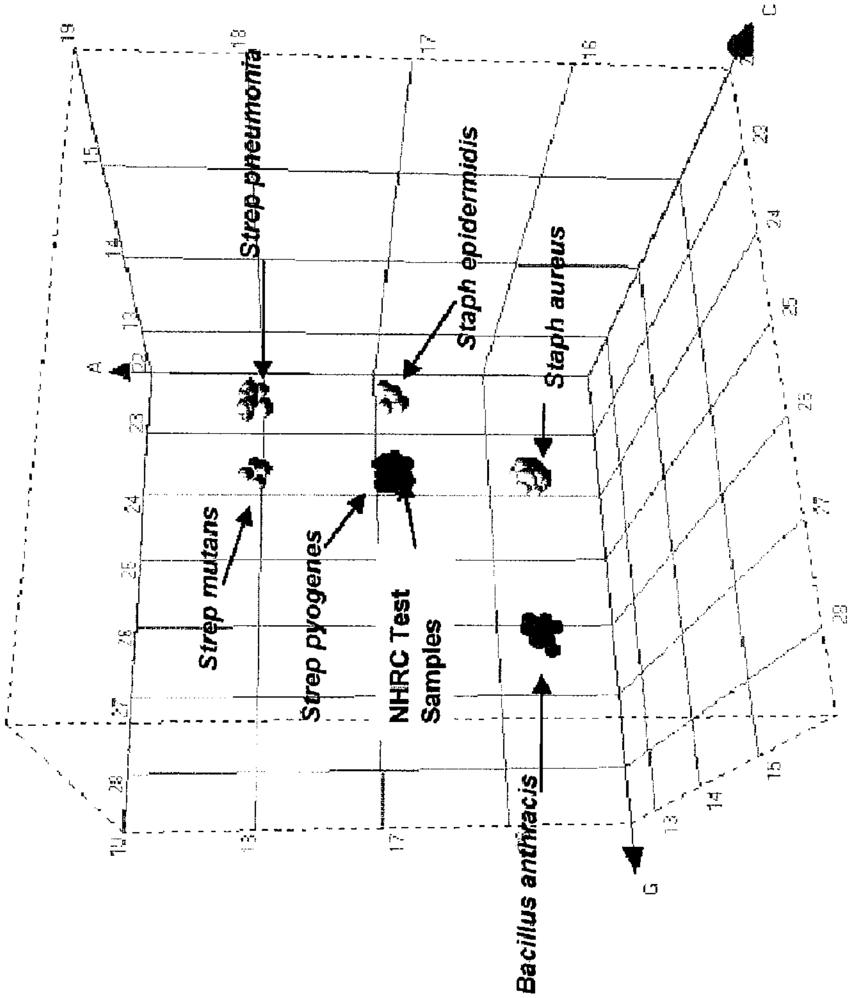
FIG. 4: a representative 3D diagram of base composition (axes A, G and C) of bioagent identifying amplicons obtained with primer pair number 14 (a precursor of primer pair number 348 which targets 16S rRNA). The diagram indicates that the experimentally determined base compositions of the clinical samples (labeled NHRC samples) closely match the base compositions expected for *Streptococcus pyogenes* and are distinct from the expected base compositions of other organisms.

Pure colonies isolated from group A *Streptococcus*-selective media from all four collection periods were analyzed with the surveillance primer set. All samples showed base compositions that precisely matched the four completely sequenced strains of *Streptococcus pyogenes*. Shown in FIG. 4 is a 3D diagram of base composition (axes A, G and C) of bioagent identifying amplicons obtained with primer pair number 14 (a precursor of primer pair number 348 which targets 16S rRNA). The diagram indicates that the experimentally determined base compositions of the clinical samples closely match the base compositions expected for *Streptococcus pyogenes* and are distinct from the expected base compositions of other organisms.

Figure 5:
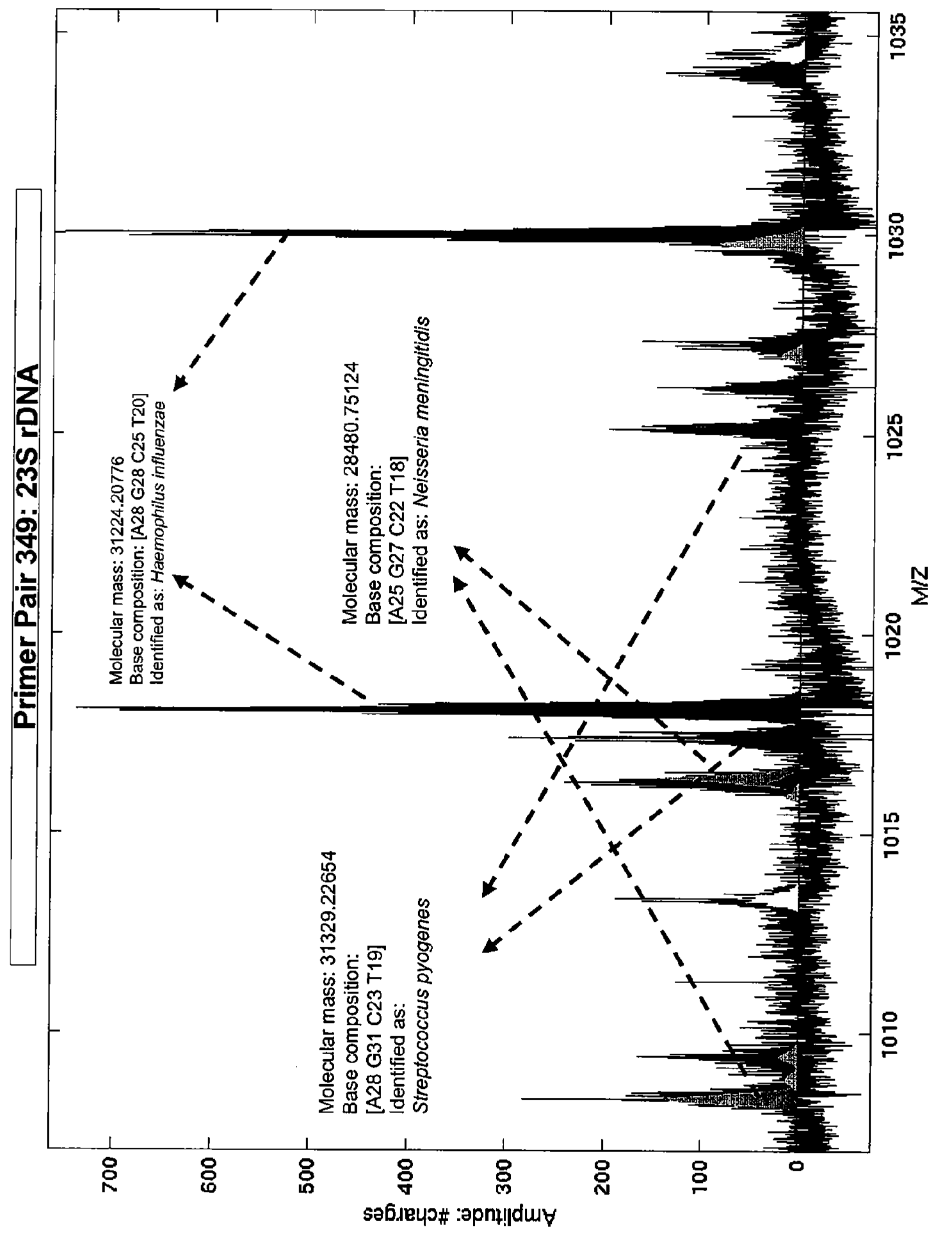
FIG. 5: a representative mass spectrum of amplification products indicating the presence of bioagent identifying amplicons of *Streptococcus pyogenes, Neisseria meningitidis*, and *Haemophilus influenzae* obtained from amplification of nucleic acid from a clinical sample with primer pair number 349 which targets 23S rRNA. Experimentally determined molecular masses and base compositions for the sense strand of each amplification product are shown.

In addition to the identification of *Streptococcus pyogenes*, other potentially pathogenic organisms were identified concurrently. Mass spectral analysis of a sample whose nucleic acid was amplified by primer pair number 349 (SEQ ID NOs: 401:1156) exhibited signals of bioagent identifying amplicons with molecular masses that were found to correspond to analogous base compositions of bioagent identifying amplicons of *Streptococcus pyogenes* (A27 G32 C24 T18), *Neisseria meningitidis* (A25 G27 C22 T18), and *Haemophilus influenzae* (A28 G28 C25 T20) (see FIG. 5 and Table 7B). These organisms were present in a ratio of 4:5:20 as determined by comparison of peak heights with peak height of an internal PCR calibration standard as described in commonly owned U.S. Patent Application Ser. No. 60/545,425 which is incorporated herein by reference in its entirety.

Figure 6:
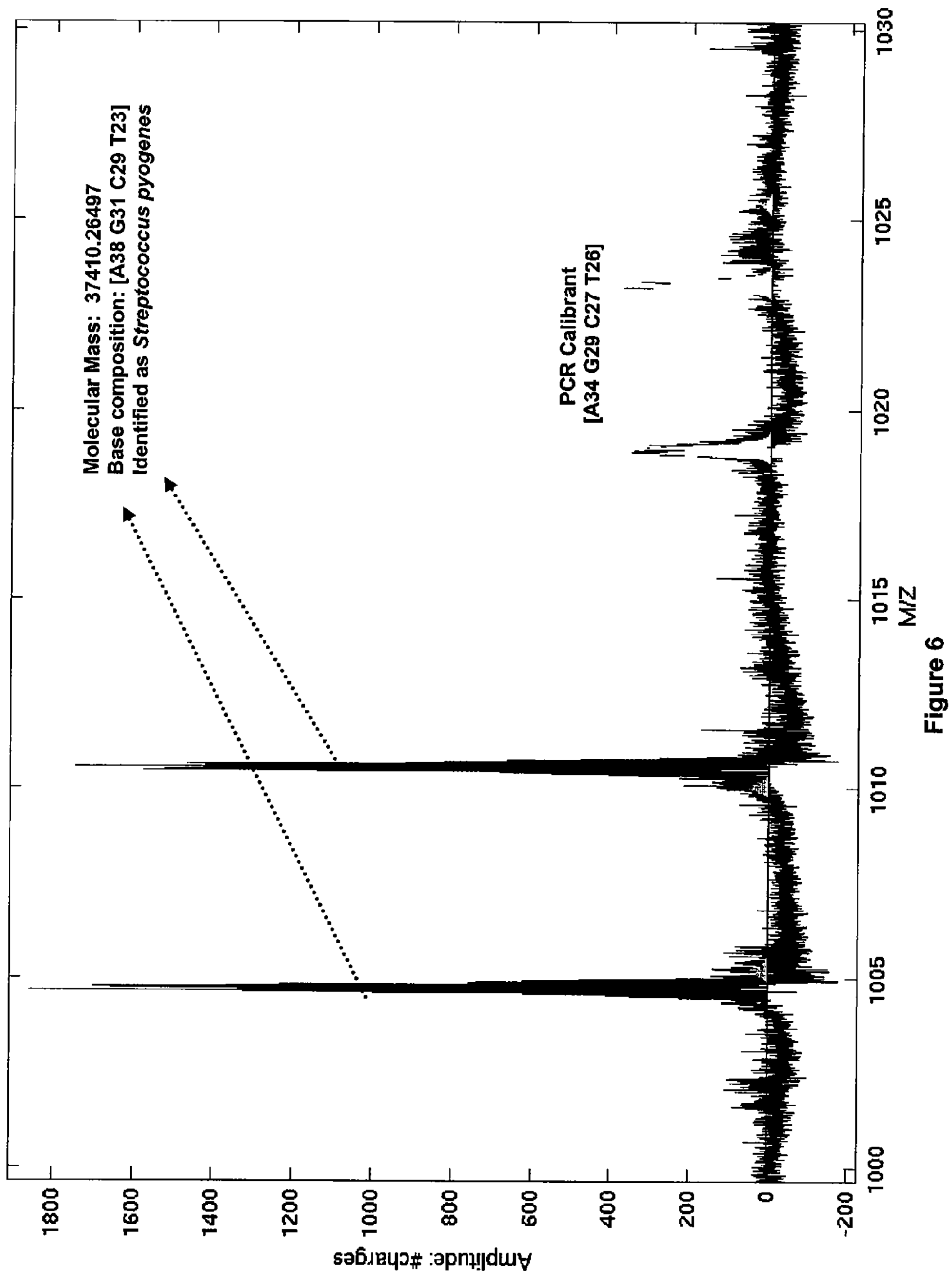
FIG. 6: a representative mass spectrum of amplification products representing a bioagent identifying amplicon of *Streptococcus pyogenes*, and a calibration amplicon obtained from amplification of nucleic acid from a clinical sample with primer pair number 356 which targets rplB. The experimentally determined molecular mass and base composition for the sense strand of the *Streptococcus pyogenes* amplification product is shown.

Since certain division-wide primers that target housekeeping genes are designed to provide coverage of specific divisions of bacteria to increase the confidence level for identification of bacterial species, they are not expected to yield bioagent identifying amplicons for organisms outside of the specific divisions. For example, primer pair number 356 (SEQ ID NOs: 449:1380) primarily amplifies the nucleic acid of members of the classes Bacilli and Clostridia and is not expected to amplify proteobacteria such as *Neisseria meningitidis* and *Haemophilus influenzae*. As expected, analysis of the mass spectrum of amplification products obtained with primer pair number 356 does not indicate the presence of *Neisseria meningitidis* and *Haemophilus influenzae* but does indicate the presence of *Streptococcus pyogenes* (FIGS. 3 and 6, Table 7B). Thus, these primers or types of primers can confirm the absence of particular bioagents from a sample.

The 15 throat swabs from military recruits were found to contain a relatively small set of microbes in high abundance. The most common were *Haemophilus influenza, Neisseria meningitides*, and *Streptococcus pyogenes*. *Staphylococcus epidermidis, Moraxella cattarhalis, Corynebacterium pseudodiphtheriticum*, and *Staphylococcus aureus* were present in fewer samples. An equal number of samples from healthy volunteers from three different geographic locations, were identically analyzed. Results indicated that the healthy volunteers have bacterial flora dominated by multiple, commensal non-beta-hemolytic Streptococcal species, including the viridans group streptococci (*S. parasangunis, S. vestibularis, S. mitis, S. oralis* and *S. pneumoniae*; data not shown), and none of the organisms found in the military recruits were found in the healthy controls at concentrations detectable by mass spectrometry. Thus, the military recruits in the midst of a respiratory disease outbreak had a dramatically different microbial population than that experienced by the general population in the absence of epidemic disease.

Example 7

Triangulation Genotyping Analysis for Determination of emm-Type of *Streptococcus pyogenes* in Epidemic Surveillance As a continuation of the epidemic surveillance investigation of Example 6, determination of sub-species characteristics (genotyping) of *Streptococcus pyogenes*, was carried out based on a strategy that generates strain-specific signatures according to the rationale of Multi-Locus Sequence Typing (MLST). In classic MLST analysis, internal fragments of several housekeeping genes are amplified and sequenced (Enright et al. Infection and Immunity, 2001, 69, 2416-2427). In classic MLST analysis, internal fragments of several housekeeping genes are amplified and sequenced. In the present investigation, bioagent identifying amplicons from housekeeping genes were produced using drill-down primers and analyzed by mass spectrometry. Since mass spectral analysis results in molecular mass, from which base composition can be determined, the challenge was to determine whether resolution of emm classification of strains of *Streptococcus pyogenes* could be determined.

For the purpose of development of a triangulation genotyping assay, an alignment was constructed of concatenated alleles of seven MLST housekeeping genes (glucose kinase (gki), glutamine transporter protein (gtr), glutamate racemase (murI), DNA mismatch repair protein (mutS), xanthine phosphoribosyl transferase (xpt), and acetyl-CoA acetyl transferase (yqiL)) from each of the 212 previously emm-typed strains of *Streptococcus pyogenes*. From this alignment, the number and location of primer pairs that would maximize strain identification via base composition was determined. As a result, 6 primer pairs were chosen as standard drill-down primers for determination of emm-type of *Streptococcus pyogenes*. These six primer pairs are displayed in Table 8. This drill-down set comprises primers with T modifications (note TMOD designation in primer names) which constitutes a functional improvement with regard to prevention of non-templated adenylation (vide supra) relative to originally selected primers which are displayed below in the same row.

TABLE 8

Triangulation Genotyping Analysis Primer Pairs for Group A *Streptococcus* Drill-Down

| Pair No. | Forward Primer Name | Forward Primer (SEQ ID NO:) | Reverse Primer Name | Reverse Primer (SEQ ID NO:) | Target Gene |
|---|---|---|---|---|---|
| 442 | SP101_SPET11_358_387_TMOD_F | 588 | SP101_SPET11_448_473_TMOD_R | 998 | gki |
| 80 | SP101_SPET11_358_387_F | 126 | SP101_SPET11_448_473_TMOD_R | 766 | gki |
| 443 | SP101_SPET11_600_629_TMOD_F | 348 | SP101_SPET11_686_714_TMOD_R | 1018 | gtr |
| 81 | SP101_SPET11_600_629_F | 62 | SP101_SPET11_686_714_R | 772 | gtr |
| 426 | SP101_SPET11_1314_1336_TMOD_F | 363 | SP101_SPET11_1403_1431_TMOD_R | 849 | murI |
| 86 | SP101_SPET11_1314_1336_F | 68 | SP101_SPET11_1403_1431_R | 711 | murI |
| 430 | SP101_SPET11_1807_1835_TMOD_F | 235 | SP101_SPET11_1901_1927_TMOD_R | 1439 | mutS |
| 90 | SP101_SPET11_1807_1835_F | 33 | SP101_SPET11_1901_1927_R | 1412 | mutS |

TABLE 8-continued

Triangulation Genotyping Analysis Primer Pairs for Group A *Streptococcus* Drill-Down

| Pair No. | Forward Primer Name | Forward Primer (SEQ ID NO:) | Reverse Primer Name | Reverse Primer (SEQ ID NO:) | Target Gene |
|---|---|---|---|---|---|
| 438 | SP101_SPET11_3075_3103_TMOD_F | 473 | SP101_SPET11_3168_3196_TMOD_R | 875 | xpt |
| 96 | SP101_SPET11_3075_3103_F | 108 | SP101_SPET11_3168_3196_R | 715 | xpt |
| 441 | SP101_SPET11_3511_3535_TMOD_F | 531 | SP101_SPET11_3605_3629_TMOD_R | 1294 | yqiL |
| 98 | SP101_SPET11_3511_3535_F | 116 | SP101_SPET11_3605_3629_R | 832 | yqiL |

The primers of Table 8 were used to produce bioagent identifying amplicons from nucleic acid present in the clinical samples. The bioagent identifying amplicons which were subsequently analyzed by mass spectrometry and base compositions corresponding to the molecular masses were calculated.

Of the 51 samples taken during the peak of the November/December 2002 epidemic (Table 9A-C rows 1-3), all except three samples were found to represent emm3, a Group A *Streptococcus* genotype previously associated with high respiratory virulence. The three outliers were from samples obtained from healthy individuals and probably represent non-epidemic strains. Archived samples (Tables 9A-C rows 5-13) from historical collections showed a greater heterogeneity of base compositions and emm types as would be expected from different epidemics occurring at different places and dates. The results of the mass spectrometry analysis and emm gene sequencing were found to be concordant for the epidemic and historical samples.

TABLE 9A

Base Composition Analysis of Bioagent Identifying Amplicons of Group A *Streptococcus* samples from Six Military Installations Obtained with Primer Pair Nos. 426 and 430

| # of Instances | emm-type by Mass Spectrometry | emm-Gene Sequencing | Location (sample) | Year | murI (Primer Pair No. 426) | mutS (Primer Pair No. 430) |
|---|---|---|---|---|---|---|
| 48 | 3 | 3 | MCRD San | 2002 | A39 G25 C20 T34 | A38 G27 C23 T33 |
| 2 | 6 | 6 | Diego | | A40 G24 C20 T34 | A38 G27 C23 T33 |
| 1 | 28 | 28 | (Cultured) | | A39 G25 C20 T34 | A38 G27 C23 T33 |
| 15 | 3 | ND | | | A39 G25 C20 T34 | A38 G27 C23 T33 |
| 6 | 3 | 3 | NHRC San | 2003 | A39 G25 C20 T34 | A38 G27 C23 T33 |
| 3 | 5,58 | 5 | Diego- | | A40 G24 C20 T34 | A38 G27 C23 T33 |
| 6 | 6 | 6 | Archive | | A40 G24 C20 T34 | A38 G27 C23 T33 |
| 1 | 11 | 11 | (Cultured) | | A39 G25 C20 T34 | A38 G27 C23 T33 |
| 3 | 12 | 12 | | | A40 G24 C20 T34 | A38 G26 C24 T33 |
| 1 | 22 | 22 | | | A39 G25 C20 T34 | A38 G27 C23 T33 |
| 3 | 25,75 | 75 | | | A39 G25 C20 T34 | A38 G27 C23 T33 |
| 4 | 44/61,82,9 | 44/61 | | | A40 G24 C20 T34 | A38 G26 C24 T33 |
| 2 | 53,91 | 91 | | | A39 G25 C20 T34 | A38 G27 C23 T33 |
| 1 | 2 | 2 | Ft. | 2003 | A39 G25 C20 T34 | A38 G27 C24 T32 |
| 2 | 3 | 3 | Leonard | | A39 G25 C20 T34 | A38 G27 C23 T33 |
| 1 | 4 | 4 | Wood | | A39 G25 C20 T34 | A38 G27 C23 T33 |
| 1 | 6 | 6 | (Cultured) | | A40 G24 C20 T34 | A38 G27 C23 T33 |
| 11 | 25 or 75 | 75 | | | A39 G25 C20 T34 | A38 G27 C23 T33 |
| 1 | 25,75, 33, | 75 | | | A39 G25 C20 T34 | A38 G27 C23 T33 |
| | 34,4,52,84 | | | | A40 G24 C20 T34 | A38 G26 C24 T33 |
| 1 | 44/61 or 82 | 44/61 | | | A40 G24 C20 T34 | A38 G27 C23 T33 |
| | or 9 | | | | A40 G24 C20 T34 | A38 G27 C23 T33 |
| 2 | 5 or 58 | 5 | | | A39 G25 C20 T34 | A38 G27 C23 T33 |
| 3 | 1 | 1 | Ft. Sill | 2003 | A39 G25 C20 T34 | A38 G27 C23 T33 |
| 2 | 3 | 3 | (Cultured) | | A39 G25 C20 T34 | A38 G27 C23 T33 |
| 1 | 4 | 4 | | | A39 G25 C20 T34 | A38 G27 C23 T33 |
| 1 | 28 | 28 | | | A39 G25 C20 T34 | A38 G27 C23 T33 |
| 1 | 3 | 3 | Ft. | 2003 | A40 G24 C20 T34 | A38 G27 C23 T33 |
| 1 | 4 | 4 | Benning | | A39 G25 C20 T34 | A38 G27 C23 T33 |
| 3 | 6 | 6 | (Cultured) | | A40 G24 C20 T34 | A38 G27 C23 T33 |
| 1 | 11 | 11 | | | A40 G24 C20 T34 | A38 G26 C24 T33 |
| 1 | 13 | 94** | | | A40 G24 C20 T34 | A38 G27 C23 T33 |
| 1 | 44/61 or 82 | 82 | | | A39 G25 C20 T34 | A38 G27 C23 T33 |
| | or 9 | | | | A40 G24 C20 T34 | A38 G27 C23 T33 |
| 1 | 5 or 58 | 58 | | | A39 G25 C20 T34 | A38 G27 C24 T32 |
| 1 | 78 or 89 | 89 | | | A40 G24 C20 T34 | A38 G27 C23 T33 |
| 2 | 5 or 58 | ND | Lackland | 2003 | A39 G25 C20 T34 | A38 G27 C23 T33 |
| 1 | 2 | | AFB | | A39 G25 C20 T34 | A38 G27 C23 T33 |
| 1 | 81 or 90 | | (Throat | | A40 G24 C20 T34 | A38 G27 C23 T33 |
| 1 | 78 | | Swabs) | | A38 G26 C20 T34 | A38 G27 C23 T33 |
| 3*** | No detection | | | | No detection | No detection |
| 7 | 3 | ND | MCRD San | 2002 | A39 G25 C20 T34 | A38 G27 C23 T33 |
| 1 | 3 | ND | Diego | | No detection | A38 G27 C23 T33 |
| 1 | 3 | ND | (Throat | | No detection | No detection |
| 1 | 3 | ND | Swabs) | | No detection | No detection |

TABLE 9A-continued

| Base Composition Analysis of Bioagent Identifying Amplicons of Group A *Streptococcus* samples from Six Military Installations Obtained with Primer Pair Nos. 426 and 430 | | | | | | |
|---|---|---|---|---|---|---|
| # of Instances | emm-type by Mass Spectrometry | emm-Gene Sequencing | Location (sample) | Year | murI (Primer Pair No. 426) | mutS (Primer Pair No. 430) |
| 2 | 3 | ND | | | No detection | A38 G27 C23 T33 |
| 3 | No detection | ND | | | No detection | No detection |

TABLE 9B

| Base Composition Analysis of Bioagent Identifying Amplicons of Group A *Streptococcus* samples from Six Military Installations Obtained with Primer Pair Nos. 438 and 441 | | | | | | |
|---|---|---|---|---|---|---|
| #of Instances | emm-type by Mass Spectrometry | emm-Gene Sequencing | Location (sample) | Year | xpt (Primer Pair No. 438) | yqiL (Primer Pair No. 441) |
| 48 | 3 | 3 | MCRD San Diego (Cultured) | 2002 | A30 G36 C20 T36 | A40 G29 C19 T31 |
| 2 | 6 | 6 | | | A30 G36 C20 T36 | A40 G29 C19 T31 |
| 1 | 28 | 28 | | | A30 G36 C20 T36 | A41 G28 C18 T32 |
| 15 | 3 | ND | | | A30 G36 C20 T36 | A40 G29 C19 T31 |
| 6 | 3 | 3 | NHRC San Diego-Archive (Cultured) | 2003 | A30 G36 C20 T36 | A40 G29 C19 T31 |
| 3 | 5,58 | 5 | | | A30 G36 C20 T36 | A40 G29 C19 T31 |
| 6 | 6 | 6 | | | A30 G36 C20 T36 | A40 G29 C19 T31 |
| 1 | 11 | 11 | | | A30 G36 C20 T36 | A40 G29 C19 T31 |
| 3 | 12 | 12 | | | A30 G36 C19 T37 | A40 G29 C19 T31 |
| 1 | 22 | 22 | | | A30 G36 C20 T36 | A40 G29 C19 T31 |
| 3 | 25,75 | 75 | | | A30 G36 C20 T36 | A40 G29 C19 T31 |
| 4 | 44/61,82,9 | 44/61 | | | A30 G36 C20 T36 | A41 G28 C19 T31 |
| 2 | 53,91 | 91 | | | A30 G36 C19 T37 | A40 G29 C19 T31 |
| 1 | 2 | 2 | Ft. Leonard Wood (Cultured) | 2003 | A30 G36 C20 T36 | A40 G29 C19 T31 |
| 2 | 3 | 3 | | | A30 G36 C20 T36 | A40 G29 C19 T31 |
| 1 | 4 | 4 | | | A30 G36 C19 T37 | A41 G28 C19 T31 |
| 1 | 6 | 6 | | | A30 G36 C20 T36 | A40 G29 C19 T31 |
| 11 | 25 or 75 | 75 | | | A30 G36 C20 T36 | A40 G29 C19 T31 |
| 1 | 25,75, 33, 34,4,52,84 | 75 | | | A30 G36 C19 T37 | A40 G29 C19 T31 |
| 1 | 44/61 or 82 or 9 | 44/61 | | | A30 G36 C20 T36 | A41 G28 C19 T31 |
| 2 | 5 or 58 | 5 | | | A30 G36 C20 T36 | A40 G29 C19 T31 |
| 3 | 1 | 1 | Ft. Sill (Cultured) | 2003 | A30 G36 C19 T37 | A40 G29 C19 T31 |
| 2 | 3 | 3 | | | A30 G36 C20 T36 | A40 G29 C19 T31 |
| 1 | 4 | 4 | | | A30 G36 C19 T37 | A41 G28 C19 T31 |
| 1 | 28 | 28 | | | A30 G36 C20 T36 | A41 G28 C18 T32 |
| 1 | 3 | 3 | Ft. Benning (Cultured) | 2003 | A30 G36 C20 T36 | A40 G29 C19 T31 |
| 1 | 4 | 4 | | | A30 G36 C19 T37 | A41 G28 C19 T31 |
| 3 | 6 | 6 | | | A30 G36 C20 T36 | A40 G29 C19 T31 |
| 1 | 11 | 11 | | | A30 G36 C20 T36 | A40 G29 C19 T31 |
| 1 | 13 | 94** | | | A30 G36 C20 T36 | A41 G28 C19 T31 |
| 1 | 44/61 or 82 or 9 | 82 | | | A30 G36 C20 T36 | A41 G28 C19 T31 |
| 1 | 5 or 58 | 58 | | | A30 G36 C20 T36 | A40 G29 C19 T31 |
| 1 | 78 or 89 | 89 | | | A30 G36 C20 T36 | A41 G28 C19 T31 |
| 2 | 5 or 58 | ND | Lackland AFB (Throat Swabs) | 2003 | A30 G36 C20 T36 | A40 G29 C19 T31 |
| 1 | 2 | | | | A30 G36 C20 T36 | A40 G29 C19 T31 |
| 1 | 81 or 90 | | | | A30 G36 C20 T36 | A40 G29 C19 T31 |
| 1 | 78 | | | | A30 G36 C20 T36 | A41 G28 C19 T31 |
| 3*** | No detection | | | | No detection | No detection |
| 7 | 3 | ND | MCRD San Diego (Throat Swabs) | 2002 | A30 G36 C20 T36 | A40 G29 C19 T31 |
| 1 | 3 | ND | | | A30 G36 C20 T36 | A40 G29 C19 T31 |
| 1 | 3 | ND | | | A30 G36 C20 T36 | No detection |
| 1 | 3 | ND | | | No detection | A40 G29 C19 T31 |
| 2 | 3 | ND | | | A30 G36 C20 T36 | A40 G29 C19 T31 |
| 3 | No detection | ND | | | No detection | No detection |

TABLE 9C

Base Composition Analysis of Bioagent Identifying Amplicons of Group A *Streptococcus* samples from Six Military Installations Obtained with Primer Pair Nos. 438 and 441

| # of Instances | emm-type by Mass Spectrometry | emm-Gene Sequencing | Location (sample) | Year | gki (Primer Pair No. 442) | gtr ((Primer Pair No. 443) |
|---|---|---|---|---|---|---|
| 48 | 3 | 3 | MCRD San | 2002 | A32 G35 C17 T32 | A39 G28 C16 T32 |
| 2 | 6 | 6 | Diego | | A31 G35 C17 T33 | A39 G28 C15 T33 |
| 1 | 28 | 28 | (Cultured) | | A30 G36 C17 T33 | A39 G28 C16 T32 |
| 15 | 3 | ND | | | A32 G35 C17 T32 | A39 G28 C16 T32 |
| 6 | 3 | 3 | NHRC San | 2003 | A32 G35 C17 T32 | A39 G28 C16 T32 |
| 3 | 5,58 | 5 | Diego- | | A30 G36 C20 T30 | A39 G28 C15 T33 |
| 6 | 6 | 6 | Archive | | A31 G35 C17 T33 | A39 G28 C15 T33 |
| 1 | 11 | 11 | (Cultured) | | A30 G36 C20 T30 | A39 G28 C16 T32 |
| 3 | 12 | 12 | | | A31 G35 C17 T33 | A39 G28 C15 T33 |
| 1 | 22 | 22 | | | A31 G35 C17 T33 | A38 G29 C15 T33 |
| 3 | 25,75 | 75 | | | A30 G36 C17 T33 | A39 G28 C15 T33 |
| 4 | 44/61,82,9 | 44/61 | | | A30 G36 C18 T32 | A39 G28 C15 T33 |
| 2 | 53,91 | 91 | | | A32 G35 C17 T32 | A39 G28 C16 T32 |
| 1 | 2 | 2 | Ft. | 2003 | A30 G36 C17 T33 | A39 G28 C15 T33 |
| 2 | 3 | 3 | Leonard | | A32 G35 C17 T32 | A39 G28 C16 T32 |
| 1 | 4 | 4 | Wood | | A31 G35 C17 T33 | A39 G28 C15 T33 |
| 1 | 6 | 6 | (Cultured) | | A31 G35 C17 T33 | A39 G28 C15 T33 |
| 11 | 25 or 75 | 75 | | | A30 G36 C17 T33 | A39 G28 C15 T33 |
| 1 | 25,75, 33, | 75 | | | A30 G36 C17 T33 | A39 G28 C15 T33 |
| | 34,4,52,84 | | | | A30 G36 C18 T32 | A39 G28 C15 T33 |
| 1 | 44/61 or 82 | 44/61 | | | A30 G36 C20 T30 | A39 G28 C15 T33 |
| | or 9 | | | | A30 G36 C18 T32 | A39 G28 C15 T33 |
| 2 | 5 or 58 | 5 | | | A32 G35 C17 T32 | A39 G28 C16 T32 |
| 3 | 1 | 1 | Ft. Sill | 2003 | A31 G35 C17 T33 | A39 G28 C15 T33 |
| 2 | 3 | 3 | (Cultured) | | A30 G36 C17 T33 | A39 G28 C16 T32 |
| 1 | 4 | 4 | | | A32 G35 C17 T32 | A39 G28 C16 T32 |
| 1 | 28 | 28 | | | A31 G35 C17 T33 | A39 G28 C15 T33 |
| 1 | 3 | 3 | Ft. | 2003 | A31 G35 C17 T33 | A39 G28 C15 T33 |
| 1 | 4 | 4 | Benning | | A30 G36 C20 T30 | A39 G28 C16 T32 |
| 3 | 6 | 6 | (Cultured) | | A30 G36 C19 T31 | A39 G28 C15 T33 |
| 1 | 11 | 11 | | | A30 G36 C18 T32 | A39 G28 C15 T33 |
| 1 | 13 | 94** | | | A30 G36 C20 T30 | A39 G28 C15 T33 |
| 1 | 44/61,or 82 | 82 | | | A30 G36 C18 T32 | A39 G28 C15 T33 |
| | or 9 | | | | A30 G36 C20 T30 | A39 G28 C15 T33 |
| 1 | 5 or 58 | 58 | | | A30 G36 C17 T33 | A39 G28 C15 T33 |
| 1 | 78 or 89 | 89 | | | A30 G36 C17 T33 | A39 G28 C15 T33 |
| 2 | 5 or 58 | ND | Lackland | 2003 | A30 G36 C18 T32 | A39 G28 C15 T33 |
| 1 | 2 | | AFB | | A30 G36 C18 T32 | A39 G28 C15 T33 |
| 1 | 81 or 90 | | (Throat | | A30 G36 C18 T32 | A39 G28 C15 T33 |
| 1 | 78 | | Swabs) | | A30 G36 C18 T32 | A39 G28 C15 T33 |
| 3*** | No detection | | | | No detection | No detection |
| 7 | 3 | ND | MCRD San | 2002 | A32 G35 C17 T32 | A39 G28 C16 T32 |
| 1 | 3 | ND | Diego | | No detection | No detection |
| 1 | 3 | ND | (Throat | | A32 G35 C17 T32 | A39 G28 C16 T32 |
| 1 | 3 | ND | Swabs) | | A32 G35 C17 T32 | No detection |
| 2 | 3 | ND | | | A32 G35 C17 T32 | No detection |
| 3 | No detection | ND | | | No detection | No detection |

Example 8

Design of Calibrant Polynucleotides based on Bioagent Identifying Amplicons for Identification of Species of Bacteria (Bacterial Bioagent Identifying Amplicons)

This example describes the design of 19 calibrant polynucleotides based on bacterial bioagent identifying amplicons corresponding to the primers of the broad surveillance set (Table 5) and the *Bacillus anthracis* drill-down set (Table 6).

Calibration sequences were designed to simulate bacterial bioagent identifying amplicons produced by the T modified primer pairs shown in Tables 5 and 6 (primer names have the designation "TMOD"). The calibration sequences were chosen as a representative member of the section of bacterial genome from specific bacterial species which would be amplified by a given primer pair. The model bacterial species upon which the calibration sequences are based are also shown in Table 10. For example, the calibration sequence chosen to correspond to an amplicon produced by primer pair no. 361 is SEQ ID NO: 1445. In Table 10, the forward (_F) or reverse (_R) primer name indicates the coordinates of an extraction representing a gene of a standard reference bacterial genome to which the primer hybridizes e.g.: the forward primer name 16S_EC__713__732_TMOD_F indicates that the forward primer hybridizes to residues 713-732 of the gene encoding 16S ribosomal RNA in an *E. coli* reference sequence (in this case, the reference sequence is an extraction consisting of residues 4033120-4034661 of the genomic sequence of *E. coli* K12 (GenBank gi number 16127994). Additional gene coordinate reference information is shown in Table 11. The designation "TMOD" in the primer names indicates that the 5' end of the primer has been modified with a non-matched template T residue which prevents the PCR polymerase from adding non-templated adenosine residues to the 5' end of the amplification product, an occurrence which may result in miscalculation of base composition from molecular mass data (vide supra).

The 19 calibration sequences described in Tables 10 and 11 were combined into a single calibration polynucleotide sequence (SEQ ID NO: 1464—which is herein designated a "combination calibration polynucleotide") which was then cloned into a pCR®-Blunt vector (Invitrogen, Carlsbad, Calif.). This combination calibration polynucleotide can be used in conjunction with the primers of Tables 5 or 6 as an internal standard to produce calibration amplicons for use in determination of the quantity of any bacterial bioagent. Thus, for example, when the combination calibration polynucleotide vector is present in an amplification reaction mixture, a calibration amplicon based on primer pair 346 (16S rRNA) will be produced in an amplification reaction with primer pair 346 and a calibration amplicon based on primer pair 363 (rpoC) will be produced with primer pair 363. Coordinates of each of the 19 calibration sequences within the calibration polynucleotide (SEQ ID NO: 1464) are indicated in Table 11.

TABLE 10

Bacterial Primer Pairs for Production of Bacterial Bioagent Identifying Amplicons and Corresponding Representative Calibration Sequences

| Primer Pair No. | Forward Primer Name | Forward Primer (SEQ ID NO:) | Reverse Primer Name | Reverse Primer (SEQ ID NO:) | Calibration Sequence Model Species | Calibration Sequence (SEQ ID NO:) |
|---|---|---|---|---|---|---|
| 361 | 16S_EC_1090_1111_2_TMOD_ F | 697 | 16S_EC_1175_1196_TMOD_R | 1398 | *Bacillus anthracis* | 1445 |
| 346 | 16S_EC_713_732_TMOD_F | 202 | 16S_EC_789_809_TMOD_R | 1110 | *Bacillus anthracis* | 1446 |
| 347 | 16S_EC_785_806_TMOD_F | 560 | 16S_EC_880_897_TMOD_R | 1278 | *Bacillus anthracis* | 1447 |
| 348 | 16S_EC_960_981_TMOD_F | 706 | 16S_EC_1054_1073_TMOD_R | 895 | *Bacillus anthracis* | 1448 |
| 349 | 23S_EC_1826_1843_TMOD_F | 401 | 23SEC_1906_1924_TMOD_R | 1156 | *Bacillus anthracis* | 1449 |
| 360 | 23S_EC_2646_2667_TMOD_F | 409 | 23S_EC_2745_2765_TMOD_R | 1434 | *Bacillus anthracis* | 1450 |
| 350 | CAPC_BA_274_303_TMOD_F | 476 | CAPC_BA_349_376 _TMOD_R | 1314 | *Bacillus anthracis* | 1451 |
| 351 | CYA_BA_1353_1379_TMOD_F | 355 | CYA_BA_1448_1467_TMOD_R | 1423 | *Bacillus anthracis* | 1452 |
| 352 | INFB_EC_1365_1393_TMOD_F | 687 | INFB_EC_1439_1467_TMOD_R | 1411 | *Bacillus anthracis* | 1453 |
| 353 | LEF BA_ 756 781 _TMOD_F | 220 | LEF_BA_843_872_TMOD_R | 1394 | *Bacillus anthracis* | 1454 |
| 356 | RPLB_EC_650_679_TMOD_F | 449 | RPLB_EC_739_762_TMOD_R | 1380 | *Clostridium botulinum* | 1455 |
| 449 | RPLB_EC_690_710_F | 309 | RPLB_EC_737_758_R | 1336 | *Clostridium botulinum* | 1456 |
| 359 | RPOB_EC_ 1845_1866_TMOD_F | 659 | RPOB_EC_1909_1929_TMOD_R | 1250 | *Yersinia Pestis* | 1457 |
| 362 | RPOB_EC_3799_3821_TMOD_F | 581 | RPOB_EC_3862_3888_TMOD_R | 1325 | *Burkholderia mallei* | 1458 |
| 363 | RPOC_EC_2146_2174_TMOD_F | 284 | RPOC_EC_2227_2245_TMOD_R | 898 | *Burkholderia mallei* | 1459 |
| 354 | RPOC_EC_ 2218_2241_TMOD_F | 405 | RPOC_EC_2313_2337_TMOD_R | 1072 | *Bacillus anthracis* | 1460 |
| 355 | SSPE_ BA_ 115_137_TMOD_F | 255 | SSPE_ BA_ 197_222 _TMOD_ R | 1402 | *Bacillus anthracis* | 1461 |
| 367 | TUFB_EC_957_979_TMOD_F | 308 | TUFB_EC_1034_1058_TMOD_R | 1276 | *Burkholderia mallei* | 1462 |
| 358 | VALS_EC_ 1105_1124_TMOD_F | 385 | VALS_EC_1195_1218_TMOD_R | 1093 | *Yersinia Pestis* | 1463 |

TABLE 11

Primer Pair Gene Coordinate References and Calibration Polynucleotide Sequence Coordinates within the Combination Calibration Polynucleotide

| Bacterial Gene and Species | Gene Extraction Coordinates of Genomic or Plasmid Sequence | Reference GenBank GI No. of Genomic (G) or Plasmid (P) Sequence | Primer Pair No. | Coordinates of Calibration Sequence in Combination Calibration Polynucleotide (SEQ ID NO: 1464) |
|---|---|---|---|---|
| 16S *E. coli* | 4033120..4034661 | 16127994 (G) | 346 | 16..109 |
| 16S *E. coli* | 4033120..4034661 | 16127994 (G) | 347 | 83..190 |
| 16S *E. coli* | 4033120..4034661 | 16127994 (G) | 348 | 246..353 |
| 16S *E. coli* | 4033120..4034661 | 16127994 (G) | 361 | 368..469 |
| 23S *E. coli* | 4166220..4169123 | 16127994 (G) | 349 | 743..837 |
| 23S *E. coli* | 4166220..4169123 | 16127994 (G) | 360 | 865..981 |
| rpoB *E. coli* | 4178823..4182851 | 16127994 (G) | 359 | 1591..1672 |

TABLE 11-continued

Primer Pair Gene Coordinate References and Calibration Polynucleotide Sequence Coordinates within the Combination Calibration Polynucleotide

| Bacterial Gene and Species | Gene Extraction Coordinates of Genomic or Plasmid Sequence | Reference GenBank GI No. of Genomic (G) or Plasmid (P) Sequence | Primer Pair No. | Coordinates of Calibration Sequence in Combination Calibration Polynucleotide (SEQ ID NO: 1464) |
|---|---|---|---|---|
| | (complement strand) | | | |
| rpoB *E. coli* | 4178823..4182851 (complement strand) | 16127994 (G) | 362 | 2081..2167 |
| rpoC *E. coli* | 4182928..4187151 | 16127994 (G) | 354 | 1810..1926 |
| rpoC *E. coli* | 4182928..4187151 | 16127994 (G) | 363 | 2183..2279 |
| infB *E. coli* | 3313655..3310983 (complement strand) | 16127994 (G) | 352 | 1692..1791 |
| tufB *E. coli* | 4173523..4174707 | 16127994 (G) | 367 | 2400..2498 |
| rp1B *E. coli* | 3449001..3448180 | 16127994 (G) | 356 | 1945..2060 |
| rp1B *E. coli* | 3449001..3448180 | 16127994 (G) | 449 | 1986..2055 |
| valS *E. coli* | 4481405..4478550 | 16127994 (G) | 358 | 1462..1572 |
| capC *B. anthracis* | 56074..55628 (complement strand) | 6470151 (P) | 350 | 2517..2616 |
| cya *B. anthracis* | 156626..154288 (complement strand) | 4894216 (P) | 351 | 1338..1449 |
| lef *B. anthracis* | 127442..129921 | 4894216 (P) | 353 | 1121..1234 |
| sspE *B. anthracis* | 226496..226783 | 30253828 (G) | 355 | 1007-1104 |

Example 9

Figure 7:
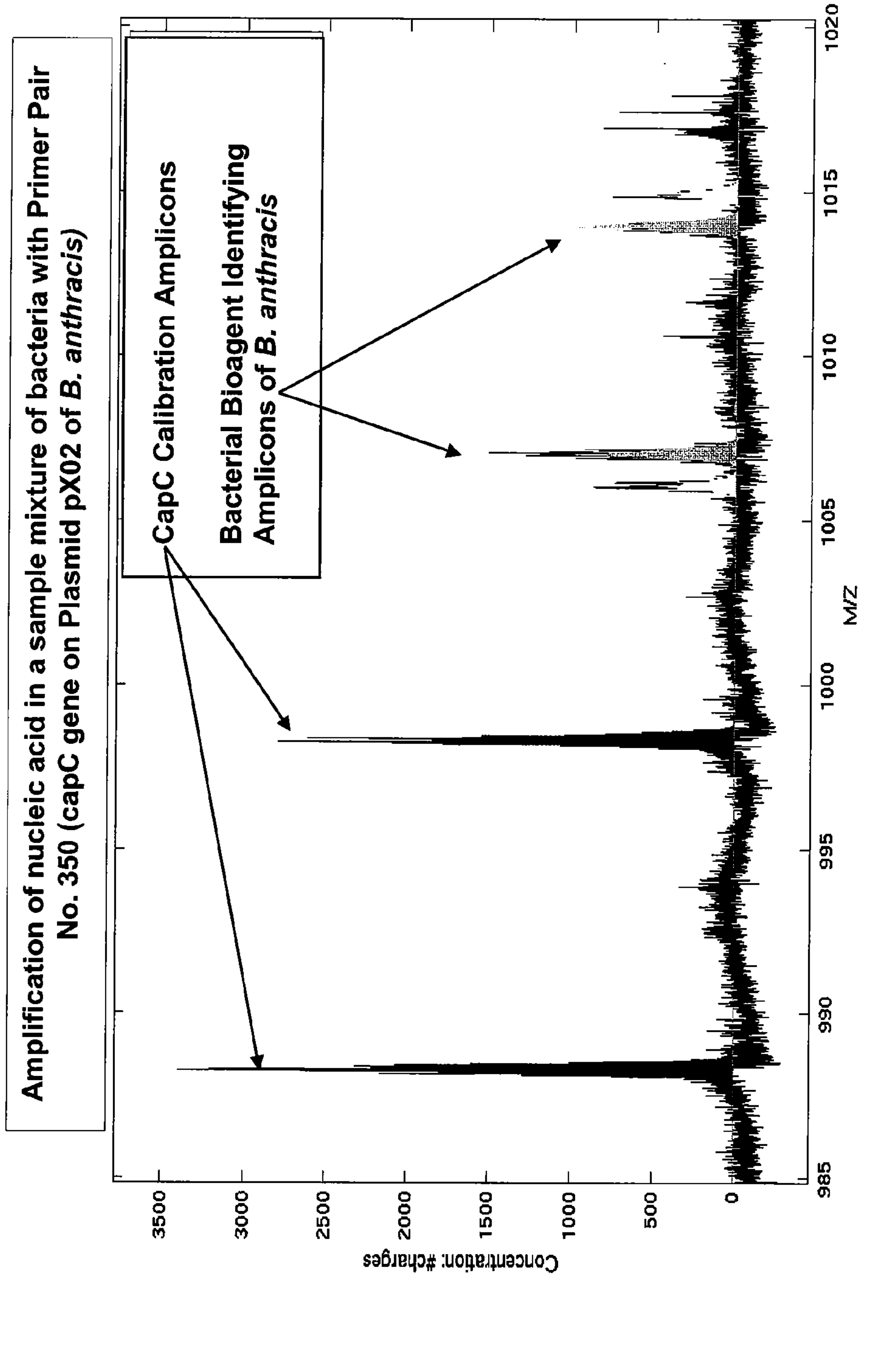
FIG. 7: a representative mass spectrum of an amplified nucleic acid mixture which contained the Ames strain of *Bacillus anthracis*, a known quantity of combination calibration polynucleotide (SEQ ID NO: 1464), and primer pair number 350 which targets the capC gene on the virulence plasmid pX02 of *Bacillus anthracis*. Calibration amplicons produced in the amplification reaction are visible in the mass spectrum as indicated and abundance data (peak height) are used to calculate the quantity of the Ames strain of *Bacillus anthracis.*

Use of a Calibration Polynucleotide for Determining the Quantity of *Bacillus Anthracis* in a Sample Containing a Mixture of Microbes The process described in this example is shown in FIG. 2. The capC gene is a gene involved in capsule synthesis which resides on the pX02 plasmid of *Bacillus anthracis*. Primer pair number 350 (see Tables 10 and 11) was designed to identify *Bacillus anthracis* via production of a bacterial bioagent identifying amplicon. Known quantities of the combination calibration polynucleotide vector described in Example 8 were added to amplification mixtures containing bacterial bioagent nucleic acid from a mixture of microbes which included the Ames strain of *Bacillus anthracis*. Upon amplification of the bacterial bioagent nucleic acid and the combination calibration polynucleotide vector with primer pair no. 350, bacterial bioagent identifying amplicons and calibration amplicons were obtained and characterized by mass spectrometry. A mass spectrum measured for the amplification reaction is shown in FIG. 7. The molecular masses of the bioagent identifying amplicons provided the means for identification of the bioagent from which they were obtained (Ames strain of *Bacillus anthracis*) and the molecular masses of the calibration amplicons provided the means for their identification as well. The relationship between the abundance (peak height) of the calibration amplicon signals and the bacterial bioagent identifying amplicon signals provides the means of calculation of the copies of the pX02 plasmid of the Ames strain of *Bacillus anthracis*. Methods of calculating quantities of molecules based on internal calibration procedures are well known to those of ordinary skill in the art.

Averaging the results of 10 repetitions of the experiment described above, enabled a calculation that indicated that the quantity of Ames strain of *Bacillus anthracis* present in the sample corresponds to approximately 10 copies of pX02 plasmid.

Example 10

Triangulation Genotyping Analysis of *Campylobacter* Species

A series of triangulation genotyping analysis primers were designed as described in Example 1 with the objective of identification of different strains of *Campylobacter jejuni*. The primers are listed in Table 12 with the designation "CJST_CJ." Housekeeping genes to which the primers hybridize and produce bioagent identifying amplicons include: tkt (transketolase), glyA (serine hydroxymethyltransferase), gltA (citrate synthase), aspA (aspartate ammonia lyase), glnA (glutamine synthase), pgm (phosphoglycerate mutase), and uncA (ATP synthetase alpha chain).

TABLE 12

*Campylobacter* Genotyping Primer Pairs

| Primer Pair No. | Forward Primer Name | Forward Primer (SEQ ID NO:) | Reverse Primer Name | Reverse Primer (SEQ ID NO:) | Target Gene |
|---|---|---|---|---|---|
| 1053 | CJST_CJ_1080_1110_F | 681 | CJST_CJ_1166_1198_R | 1022 | gltA |
| 1047 | CJST_CJ_584_616_F | 315 | CJST_CJ_663_692_R | 1379 | glnA |
| 1048 | CJST_CJ_360_394_F | 346 | CJST_CJ_442_476_R | 955 | aspA |
| 1049 | CJST_CJ_2636_2668_F | 504 | CJST_CJ_2753_2777_R | 1409 | tkt |
| 1054 | CJST_CJ_2060_2090_F | 323 | CJST_CJ_2148_2174_R | 1068 | pgm |
| 1064 | CJST_CJ_1680_1713_F | 479 | CJST_CJ_1795_1822_R | 938 | glyA |

The primers were used to amplify nucleic acid from 50 food product samples provided by the USDA, 25 of which contained *Campylobacter jejuni* and 25 of which contained *Campylobacter coli*. Primers used in this study were developed primarily for the discrimination of *Campylobacter jejuni* clonal complexes and for distinguishing *Campylobacter jejuni* from *Campylobacter coli*. Finer discrimination between *Campylobacter coli* types is also possible by using specific primers targeted to loci where closely-related *Campylobacter coli* isolates demonstrate polymorphisms between strains. The conclusions of the comparison of base composition analysis with sequence analysis are shown in Tables 13A-C.

TABLE 13A

Results of Base Composition Analysis of 50 *Campylobacter* Samples with Drill-down MLST Primer Pair Nos: 1048 and 1047

| Group | Species | Isolate origin | MLST type or Clonal Complex by Base Composition analysis | MLST Type or Clonal Complex by Sequence analysis | Strain | Base Composition of Bioagent Identifying Amplicon Obtained with Primer Pair No: 1048 (aspA) | Base Composition of Bioagent Identifying Amplicon Obtained with Primer Pair No: 1047 (glnA) |
|---|---|---|---|---|---|---|---|
| J-1 | *C. jejuni* | Goose | ST 690/692/707/991 | ST 991 | RM3673 | A30 G25 C16 T46 | A47 G21 C16 T25 |
| J-2 | *C. jejuni* | Human | Complex 206/48/353 | ST 356, complex 353 | RM4192 | A30 G25 C16 T46 | A48 G21 C17 T23 |
| J-3 | *C. jejuni* | Human | Complex 354/179 | ST 436 | RM4194 | A30 G25 C15 T47 | A48 G21 C18 T22 |
| J-4 | *C. jejuni* | Human | Complex 257 | ST 257, complex 257 | RM4197 | A30 G25 C16 T46 | A48 G21 C18 T22 |
| J-5 | *C. jejuni* | Human | Complex 52 | ST 52, complex 52 | RM4277 | A30 G25 C16 T46 | A48 G21 C17 T23 |
| J-6 | *C. jejuni* | Human | Complex 443 | ST 51, complex 443 | RM4275 | A30 G25 C15 T47 | A48 G21 C17 T23 |
| | | | | | RM4279 | A30 G25 C15 T47 | A48 G21 C17 T23 |
| J-7 | *C. jejuni* | Human | Complex 42 | ST 604, complex 42 | RM1864 | A30 G25 C15 T47 | A48 G21 C18 T22 |
| J-8 | *C. jejuni* | Human | Complex 42/49/362 | ST 362, complex 362 | RM3193 | A30 G25 C15 T47 | A48 G21 C18 T22 |
| J-9 | *C. jejuni* | Human | Complex 45/283 | ST 147, Complex 45 | RM3203 | A30 G25 C15 T47 | A47 G21 C18 T23 |
| | *C. jejuni* | Human | Consistent with 74 closely related sequence types (none belong to a clonal complex) | ST 828 | RM4183 | A31 G27 C20 T39 | A48 G21 C16 T24 |
| C-1 | *C. coli* | | | ST 832 | RM1169 | A31 G27 C20 T39 | A48 G21 C16 T24 |
| | | | | ST 1056 | RM1857 | A31 G27 C20 T39 | A48 G21 C16 T24 |
| | | Poultry | | ST 889 | RM1166 | A31 G27 C20 T39 | A48 G21 C16 T24 |
| | | | | ST 829 | RM1182 | A31 G27 C20 T39 | A48 G21 C16 T24 |
| | | | | ST 1050 | RM1518 | A31 G27 C20 T39 | A48 G21 C16 T24 |
| | | | | ST 1051 | RM1521 | A31 G27 C20 T39 | A48 G21 C16 T24 |
| | | | | ST 1053 | RM1523 | A31 G27 C20 T39 | A48 G21 C16 T24 |
| | | | | ST 1055 | RM1527 | A31 G27 C20 T39 | A48 G21 C16 T24 |
| | | | | ST 1017 | RM1529 | A31 G27 C20 T39 | A48 G21 C16 T24 |
| | | | | ST 860 | RM1840 | A31 G27 C20 T39 | A48 G21 C16 T24 |
| | | | | ST 1063 | RM2219 | A31 G27 C20 T39 | A48 G21 C16 T24 |
| | | | | ST 1066 | RM2241 | A31 G27 C20 T39 | A48 G21 C16 T24 |
| | | | | ST 1067 | RM2243 | A31 G27 C20 T39 | A48 G21 C16 T24 |
| | | | | ST 1068 | RM2439 | A31 G27 C20 T39 | A48 G21 C16 T24 |
| | | Swine | | ST 1016 | RM3230 | A31 G27 C20 T39 | A48 G21 C16 T24 |
| | | | | ST 1069 | RM3231 | A31 G27 C20 T39 | A48 G21 C16 T24 |
| | | | | ST 1061 | RM1904 | A31 G27 C20 T39 | A48 G21 C16 T24 |
| | | Unknown | | ST 825 | RM1534 | A31 G27 C20 T39 | A48 G21 C16 T24 |
| | | | | ST 901 | RM1505 | A31 G27 C20 T39 | A48 G21 C16 T24 |
| C-2 | *C. coli* | Human | ST 895 | ST 895 | RM1532 | A31 G27 C19 T40 | A48 G21 C16 T24 |
| C-3 | *C. coli* | Poultry | Consistent with 63 closely related sequence types (none belong to a clonal complex) | ST 1064 | RM2223 | A31 G27 C20 T39 | A48 G21 C16 T24 |
| | | | | ST 1082 | RM1178 | A31 G27 C20 T39 | A48 G21 C16 T24 |
| | | | | ST 1054 | RM1525 | A31 G27 C20 T39 | A48 G21 C16 T24 |
| | | | | ST 1049 | RM1517 | A31 G27 C20 T39 | A48 G21 C16 T24 |
| | | Marmoset | | ST 891 | RM1531 | A31 G27 C20 T39 | A48 G21 C16 T24 |

TABLE 13B

Results of Base Composition Analysis of 50 *Campylobacter* Samples with Drill-down MLST Primer Pair Nos: 1053 and 1064

| Group | Species | Isolate origin | MLST type or Clonal Complex by Base Composition analysis | MLST Type or Clonal Complex by Sequence analysis | Strain | Base Composition of Bioagent Identifying Amplicon Obtained with Primer Pair No: 1053 (gltA) | Base Composition of Bioagent Identifying Amplicon Obtained with Primer Pair No: 1064 (glyA) |
|---|---|---|---|---|---|---|---|
| J-1 | *C. jejuni* | Goose | ST 690/692/707/991 | ST 991 | RM3673 | A24 G25 C23 T47 | A40 G29 C29 T45 |

TABLE 13B-continued

Results of Base Composition Analysis of 50 *Campylobacter* Samples with Drill-down MLST Primer Pair Nos: 1053 and 1064

| Group | Species | Isolate origin | MLST type or Clonal Complex by Base Composition analysis | MLST Type or Clonal Complex by Sequence analysis | Strain | Base Composition of Bioagent Identifying Amplicon Obtained with Primer Pair No: 1053 (gltA) | Base Composition of Bioagent Identifying Amplicon Obtained with Primer Pair No: 1064 (glyA) |
|---|---|---|---|---|---|---|---|
| J-2 | *C. jejuni* | Human | Complex 206/48/353 | ST 356, complex 353 | RM4192 | A24 G25 C23 T47 | A40 G29 C29 T45 |
| J-3 | *C. jejuni* | Human | Complex 354/179 | ST 436 | RM4194 | A24 G25 C23 T47 | A40 G29 C29 T45 |
| J-4 | *C. jejuni* | Human | Complex 257 | ST 257, complex 257 | RM4197 | A24 G25 C23 T47 | A40 G29 C29 T45 |
| J-5 | *C. jejuni* | Human | Complex 52 | ST 52, complex 52 | RM4277 | A24 G25 C23 T47 | A39 G30 C26 T48 |
| J-6 | *C. jejuni* | Human | Complex 443 | ST 51, complex 443 | RM4275 | A24 G25 C23 T47 | A39 G30 C28 T46 |
| | | | | | RM4279 | A24 G25 C23 T47 | A39 G30 C28 T46 |
| J-7 | *C. jejuni* | Human | Complex 42 | ST 604, complex 42 | RM1864 | A24 G25 C23 T47 | A39 G30 C26 T48 |
| J-8 | *C. jejuni* | Human | Complex 42/49/362 | ST 362, complex 362 | RM3193 | A24 G25 C23 T47 | A38 G31 C28 T46 |
| J-9 | *C. jejuni* | Human | Complex 45/283 | ST 147, Complex 45 | RM3203 | A24 G25 C23 T47 | A38 G31 C28 T46 |
| | *C. jejuni* | Human | Consistent with 74 | ST 828 | RM4183 | A23 G24 C26 T46 | A39 G30 C27 T47 |
| C-1 | *C. coli* | | closely related | ST 832 | RM1169 | A23 G24 C26 T46 | A39 G30 C27 T47 |
| | | | | ST 1056 | RM1857 | A23 G24 C26 T46 | A39 G30 C27 T47 |
| | | Poultry | sequence types (none belong to a clonal complex) | ST 889 | RM1166 | A23 G24 C26 T46 | A39 G30 C27 T47 |
| | | | | ST 829 | RM1182 | A23 G24 C26 T46 | A39 G30 C27 T47 |
| | | | | ST 1050 | RM1518 | A23 G24 C26 T46 | A39 G30 C27 T47 |
| | | | | ST 1051 | RM1521 | A23 G24 C26 T46 | A39 G30 C27 T47 |
| | | | | ST 1053 | RM1523 | A23 G24 C26 T46 | A39 G30 C27 T47 |
| | | | | ST 1055 | RM1527 | A23 G24 C26 T46 | A39 G30 C27 T47 |
| | | | | ST 1017 | RM1529 | A23 G24 C26 T46 | A39 G30 C27 T47 |
| | | | | ST 860 | RM1840 | A23 G24 C26 T46 | A39 G30 C27 T47 |
| | | | | ST 1063 | RM2219 | A23 G24 C26 T46 | A39 G30 C27 T47 |
| | | | | ST 1066 | RM2241 | A23 G24 C26 T46 | A39 G30 C27 T47 |
| | | | | ST 1067 | RM2243 | A23 G24 C26 T46 | A39 G30 C27 T47 |
| | | | | ST 1068 | RM2439 | A23 G24 C26 T46 | A39 G30 C27 T47 |
| | | Swine | | ST 1016 | RM3230 | A23 G24 C26 T46 | A39 G30 C27 T47 |
| | | | | ST 1069 | RM3231 | A23 G24 C26 T46 | NO DATA |
| | | | | ST 1061 | RM1904 | A23 G24 C26 T46 | A39 G30 C27 T47 |
| | | Unknown | | ST 825 | RM1534 | A23 G24 C26 T46 | A39 G30 C27 T47 |
| | | | | ST 901 | RM1505 | A23 G24 C26 T46 | A39 G30 C27 T47 |
| C-2 | *C. coli* | Human | ST 895 | ST 895 | RM1532 | A23 G24 C26 T46 | A39 G30 C27 T47 |
| C-3 | *C. coli* | Poultry | Consistent with 63 closely related | ST 1064 | RM2223 | A23 G24 C26 T46 | A39 G30 C27 T47 |
| | | | | ST 1082 | RM1178 | A23 G24 C26 T46 | A39 G30 C27 T47 |
| | | | | ST 1054 | RM1525 | A23 G24 C25 T47 | A39 G30 C27 T47 |
| | | | | ST 1049 | RM1517 | A23 G24 C26 T46 | A39 G30 C27 T47 |
| | | Marmoset | sequence types (none belong to a clonal complex) | ST 891 | RM1531 | A23 G24 C26 T46 | A39 G30 C27 T47 |

TABLE 13C

Results of Base Composition Analysis of 50 *Campylobacter* Samples with Drill-down MLST Primer Pair Nos: 1054 and 1049

| Group | Species | Isolate origin | MLST type or Clonal Complex by Base Composition analysis | MLST Type or Clonal Complex by Sequence analysis | Strain | Base Composition of Bioagent Identifying Amplicon Obtained with Primer Pair No: 1054 (pgm) | Base Composition of Bioagent Identifying Amplicon Obtained with Primer Pair No: 1049 (tkt) |
|---|---|---|---|---|---|---|---|
| J-1 | *C. jejuni* | Goose | ST 690/692/707/991 | ST 991 | RM3673 | A26 G33 C18 T38 | A41 G28 C35 T38 |
| J-2 | *C. jejuni* | Human | Complex 206/48/353 | ST 356, complex 353 | RM4192 | A26 G33 C19 T37 | A41 G28 C36 T37 |
| J-3 | *C. jejuni* | Human | Complex 354/179 | ST 436 | RM4194 | A27 G32 C19 T37 | A42 G28 C36 T36 |
| J-4 | *C. jejuni* | Human | Complex 257 | ST 257, complex 257 | RM4197 | A27 G32 C19 T37 | A41 G29 C35 T37 |
| J-5 | *C. jejuni* | Human | Complex 52 | ST 52, complex 52 | RM4277 | A26 G33 C18 T38 | A41 G28 C36 T37 |
| J-6 | *C. jejuni* | Human | Complex 443 | ST 51, complex 443 | RM4275 | A27 G31 C19 T38 | A41 G28 C36 T37 |
| | | | | | RM4279 | A27 G31 C19 T38 | A41 G28 C36 T37 |

TABLE 13C-continued

Results of Base Composition Analysis of 50 *Campylobacter* Samples with Drill-down MLST Primer Pair Nos: 1054 and 1049

| Group | Species | Isolate origin | MLST type or Clonal Complex by Base Composition analysis | MLST Type or Clonal Complex by Sequence analysis | Strain | Base Composition of Bioagent Identifying Amplicon Obtained with Primer Pair No: 1054 (pgm) | Base Composition of Bioagent Identifying Amplicon Obtained with Primer Pair No: 1049 (tkt) |
|---|---|---|---|---|---|---|---|
| J-7 | *C. jejuni* | Human | Complex 42 | ST 604, complex 42 | RM1864 | A27 G32 C19 T37 | A42 G28 C35 T37 |
| J-8 | *C. jejuni* | Human | Complex 42/49/362 | ST 362, complex 362 | RM3193 | A26 G33 C19 T37 | A42 G28 C35 T37 |
| J-9 | *C. jejuni* | Human | Complex 45/283 | ST 147, Complex 45 | RM3203 | A28 G31 C19 T37 | A43 G28 C36 T35 |
| | *C. jejuni* | Human | Consistent with 74 | ST 828 | RM4183 | A27 G30 C19 T39 | A46 G28 C32 T36 |
| C-1 | *C. coli* | | closely | ST 832 | RM1169 | A27 G30 C19 T39 | A46 G28 C32 T36 |
| | | | related | ST 1056 | RM1857 | A27 G30 C19 T39 | A46 G28 C32 T36 |
| | | Poultry | sequence | ST 889 | RM1166 | A27 G30 C19 T39 | A46 G28 C32 T36 |
| | | | types (none | ST 829 | RM1182 | A27 G30 C19 T39 | A46 G28 C32 T36 |
| | | | belong to a | ST 1050 | RM1518 | A27 G30 C19 T39 | A46 G28 C32 T36 |
| | | | clonal | ST 1051 | RM1521 | A27 G30 C19 T39 | A46 G28 C32 T36 |
| | | | complex) | ST 1053 | RM1523 | A27 G30 C19 T39 | A46 G28 C32 T36 |
| | | | | ST 1055 | RM1527 | A27 G30 C19 T39 | A46 G28 C32 T36 |
| | | | | ST 1017 | RM1529 | A27 G30 C19 T39 | A46 G28 C32 T36 |
| | | | | ST 860 | RM1840 | A27 G30 C19 T39 | A46 G28 C32 T36 |
| | | | | ST 1063 | RM2219 | A27 G30 C19 T39 | A46 G28 C32 T36 |
| | | | | ST 1066 | RM2241 | A27 G30 C19 T39 | A46 G28 C32 T36 |
| | | | | ST 1067 | RM2243 | A27 G30 C19 T39 | A46 G28 C32 T36 |
| | | | | ST 1068 | RM2439 | A27 G30 C19 T39 | A46 G28 C32 T36 |
| | | Swine | | ST 1016 | RM3230 | A27 G30 C19 T39 | A46 G28 C32 T36 |
| | | | | ST 1069 | RM3231 | A27 G30 C19 T39 | A46 G28 C32 T36 |
| | | | | ST 1061 | RM1904 | A27 G30 C19 T39 | A46 G28 C32 T36 |
| | | Unknown | | ST 825 | RM1534 | A27 G30 C19 T39 | A46 G28 C32 T36 |
| | | | | ST 901 | RM1505 | A27 G30 C19 T39 | A46 G28 C32 T36 |
| C-2 | *C. coli* | Human | ST 895 | ST 895 | RM1532 | A27 G30 C19 T39 | A45 G29 C32 T36 |
| C-3 | *C. coli* | Poultry | Consistent | ST 1064 | RM2223 | A27 G30 C19 T39 | A45 G29 C32 T36 |
| | | | with 63 | ST 1082 | RM1178 | A27 G30 C19 T39 | A45 G29 C32 T36 |
| | | | closely | ST 1054 | RM1525 | A27 G30 C19 T39 | A45 G29 C32 T36 |
| | | | related | ST 1049 | RM1517 | A27 G30 C19 T39 | A45 G29 C32 T36 |
| | | Marmoset | sequence types (none belong to a clonal complex) | ST 891 | RM1531 | A27 G30 C19 T39 | A45 G29 C32 T36 |

The base composition analysis method was successful in identification of 12 different strain groups. *Campylobacter jejuni* and *Campylobacter coli* are generally differentiated by all loci. Ten clearly differentiated *Campylobacter jejuni* isolates and 2 major *Campylobacter coli* groups were identified even though the primers were designed for strain typing of *Campylobacter jejuni*. One isolate (RM4183) which was designated as *Campylobacter jejuni* was found to group with *Campylobacter coli* and also appears to actually be *Campylobacter* colt by full MLST sequencing.

Example 11

Identification of *Acinetobacter baumannii* Using Broad Range Survey and Division-Wide Primers in Epidemiological Surveillance To test the capability of the broad range survey and division-wide primer sets of Table 5 in identification of *Acinetobacter* species, 183 clinical samples were obtained from individuals participating in, or in contact with individuals participating in Operation Iraqi Freedom (including US service personnel, US civilian patients at the Walter Reed Army Institute of Research (WRAIR), medical staff, Iraqi civilians and enemy prisoners. In addition, 34 environmental samples were obtained from hospitals in Iraq, Kuwait, Germany, the United States and the USNS Comfort, a hospital ship.

Upon amplification of nucleic acid obtained from the clinical samples, primer pairs 346-349, 360, 361, 354, 362 and 363 (Table 5) all produced bacterial bioagent amplicons which identified *Acinetobacter baumannii* in 215 of 217 samples. The organism *Klebsiella pneumoniae* was identified in the remaining two samples. In addition, 14 different strain types (containing single nucleotide polymorphisms relative to a reference strain of *Acinetobacter baumannii*) were identified and assigned arbitrary numbers from 1 to 14. Strain type 1 was found in 134 of the sample isolates and strains 3 and 7 were found in 46 and 9 of the isolates respectively.

The epidemiology of strain type 7 of *Acinetobacter baumannii* was investigated. Strain 7 was found in 4 patients and 5 environmental samples (from field hospitals in Iraq and Kuwait). The index patient infected with strain 7 was a pre-war patient who had a traumatic amputation in March of 2003 and was treated at a Kuwaiti hospital. The patient was subsequently transferred to a hospital in Germany and then to WRAIR. Two other patients from Kuwait infected with strain 7 were found to be non-infectious and were not further monitored. The fourth patient was diagnosed with a strain 7 infection in September of 2003 at WRAIR. Since the fourth patient was not related involved in Operation Iraqi Freedom, it was inferred that the fourth patient was the subject of a nosocomial infection acquired at WRAIR as a result of the spread of strain 7 from the index patient.

The epidemiology of strain type 3 of *Acinetobacter baumannii* was also investigated. Strain type 3 was found in 46 samples, all of which were from patients (US service members, Iraqi civilians and enemy prisoners) who were treated on the USNS Comfort hospital ship and subsequently returned to Iraq or Kuwait. The occurrence of strain type 3 in a single locale may provide evidence that at least some of the infections at that locale were a result of nosocomial infections.

This example thus illustrates an embodiment of the present invention wherein the methods of analysis of bacterial bioagent identifying amplicons provide the means for epidemiological surveillance.

Example 12

Selection and Use of Triangulation Genotyping Analysis Primer Pairs for *Acinetobacter* baumanii To combine the power of high-throughput mass spectrometric analysis of bioagent identifying amplicons with the sub-species characteristic resolving power provided by triangulation genotyping analysis, an additional 21 primer pairs were selected based on analysis of housekeeping genes of the genus *Acinetobacter*. Genes to which the drill-down triangulation genotyping analysis primers hybridize for production of bacterial bioagent identifying amplicons include anthranilate synthase component I (trpE), adenylate kinase (adk), adenine glycosylase (mutY), fumarate hydratase (fumC), and pyrophosphate phospho-hydratase (ppa). These 21 primer pairs are indicated with reference to sequence listings in Table 14. Primer pair numbers 1151-1154 hybridize to and amplify segments of trpE. Primer pair numbers 1155-1157 hybridize to and amplify segments of adk. Primer pair numbers 1158-1164 hybridize to and amplify segments of mutY. Primer pair numbers 1165-1170 hybridize to and amplify segments of fumC. Primer pair number 1171 hybridizes to and amplifies a segment of ppa. Primer pair numbers: 2846-2848 hybridize to and amplify segments of the parC gene of DNA topoisomerase which include a codon known to confer quinolone drug resistance upon sub-types of *Acinetobacter baumannii*. Primer pair numbers 2852-2854 hybridize to and amplify segments of the gyrA gene of DNA gyrase which include a codon known to confer quinolone drug resistance upon sub-types of *Acinetobacter baumannii*. Primer pair numbers 2922 and 2972 are speciating primers which are useful for identifying different species members of the genus *Acinetobacter*. The primer names given in Table 14A (with the exception of primer pair numbers 2846-2848, 2852-2854) indicate the coordinates to which the primers hybridize to a reference sequence which comprises a concatenation of the genes TrpE, efp (elongation factor p), adk, mutT, fumC, and ppa. For example, the forward primer of primer pair 1151 is named AB_MLST-11-OIF007_62_91_F because it hybridizes to the *Acinetobacter* primer reference sequence of strain type 11 in sample 007 of Operation Iraqi Freedom (OIF) at positions 62 to 91. DNA was sequenced from strain type 11 and from this sequence data and an artificial concatenated sequence of partial gene extractions was assembled for use in design of the triangulation genotyping analysis primers. The stretches of arbitrary residues "N"s in the concatenated sequence were added for the convenience of separation of the partial gene extractions (40N for AB_MLST (SEQ ID NO: 1444)).

The hybridization coordinates of primer pair numbers 2846-2848 are with respect to GenBank Accession number X95819. The hybridization coordinates of primer pair numbers 2852-2854 are with respect to GenBank Accession number AY642140. Sequence residue "I" appearing in the forward and reverse primers of primer pair number 2972 represents inosine.

TABLE 14A

Triangulation Genotyping Analysis Primer Pairs for Identification of Sub-species characteristics (Strain Type) of Members of the Bacterial Genus *Acinetobacter*

| Primer Pair No. | Forward Primer Name | Forward Primer (SEQ ID NO:) | Reverse Primer Name | Reverse Primer (SEQ ID NO:) |
|---|---|---|---|---|
| 1151 | AB_MLST-11-OIF007_62_91_F | 454 | AB_MLST-11-OIF007_169_203_R | 1418 |
| 1152 | AB_MLST-11-OIF007_185_214_F | 243 | AB_MLST-11-OIF007_291_324_R | 969 |
| 1153 | AB_MLST-11-OIF007_260_289_F | 541 | AB_MLST-11-OIF007_364_393_R | 1400 |
| 1154 | AB_MLST-11-OIF007_206_239_F | 436 | AB_MLST-11-OIF007_318_344_R | 1036 |
| 1155 | AB_MLST-11-OIF007_522_552_F | 378 | AB_MLST-11-OIF007_587_610_R | 1392 |
| 1156 | AB_MLST-11-OIF007_547_571_F | 250 | AB_MLST-11-OIF007_656_686_R | 902 |
| 1157 | AB_MLST-11-OIF007_601_627_F | 256 | AB_MLST-11-OIF007_710_736_R | 881 |
| 1158 | AB_MLST-11-OIF007_1202_1225_F | 384 | AB_MLST-11-OIF007_1266_1296_R | 878 |
| 1159 | AB_MLST-11-OIF007_1202_1225_F | 384 | AB_MLST-11-OIF007_1299_1316_R | 1199 |
| 1160 | AB_MLST-11-OIF007_1234_1264_F | 694 | AB_MLST-11-OIF007_1335_1362_R | 1215 |
| 1161 | AB_MLST-11-OIF007_1327_1356_F | 225 | AB_MLST-11-OIF007_1422_1448_R | 1212 |
| 1162 | AB_MLST-11-OIF007_1345_1369_F | 383 | AB_MLST-11-OIF007_1470_1494_R | 1083 |
| 1163 | AB_MLST-11-OIF007_1351_1375_F | 662 | AB_MLST-11-OIF007_1470_1494_R | 1083 |
| 1164 | AB_MLST-11-OIF007_1387_1412_F | 422 | AB_MLST-11-OIF007_1470_1494_R | 1083 |
| 1165 | AB_MLST-11-OIF007_1542_1569_F | 194 | AB_MLST-11-OIF007_1656_1680_R | 1173 |
| 1166 | AB_MLST-11-OIF007_1566_1593_F | 684 | AB_MLST-11-OIF007_1656_1680_R | 1173 |
| 1167 | AB_MLST-11-OIF007_1611_1638_F | 375 | AB_MLST-11-OIF007_1731_1757_R | 890 |
| 1168 | AB_MLST-11-OIF007_1726_1752_F | 182 | AB_MLST-11-OIF007_1790_1821_R | 1195 |
| 1169 | AB_MLST-11-OIF007_1792_1826_F | 656 | AB_MLST-11-OIF007_1876_1909_R | 1151 |
| 1170 | AB_MLST-11-OIF007_1792_1826_F | 656 | AB_MLST-11-OIF007_1895_1927_R | 1224 |
| 1171 | AB_MLST-11-OIF007_1970_2002_F | 618 | AB_MLST-11-OIF007_2097_2118_R | 1157 |
| 2846 | PARC_X95819_33_58_F | 302 | PARC_X95819_121_153_R | 852 |
| 2847 | PARC_X95819_33_58_F | 199 | PARC_X95819_157_178_R | 889 |
| 2848 | PARC_X95819_33_58_F | 596 | PARC_X95819_97_128_R | 1169 |
| 2852 | GYRA_AY642140_-1_24_F | 150 | GYRA_AY642140_71_100_R | 1242 |
| 2853 | GYRA_AY642140_26_54_F | 166 | GYRA_AY642140_121_146_R | 1069 |
| 2854 | GYRA_AY642140_26_54_F | 166 | GYRA_AY642140_58_89_R | 1168 |
| 2922 | AB_MLST-11-OIF007_991_1018_F | 583 | AB_MLST-11-OIF007_1110_1137_R | 923 |
| 2972 | AB_MLST-11-OIF007_1007_1034_F | 592 | AB_MLST-11-OIF007_1126_1153_R | 924 |

TABLE 14B

Triangulation Genotyping Analysis Primer Pairs for Identification of Sub-species characteristics (Strain Type) of Members of the Bacterial Genus *Acinetobacter*

| Primer Pair No. | Forward Primer (SEQ ID NO:) | SEQUENCE | Reverse Primer (SEQ ID NO:) | SEQUENCE |
|---|---|---|---|---|
| 1151 | 454 | TGAGATTGCTGAACATTTAATGCTGATTGA | 1418 | TTGTACATTTGAAACAATATGCATGACATGTGAAT |
| 1152 | 243 | TATTGTTTCAAATGTACAAGGTGAAGTGCG | 969 | TCACAGGTTCTACTTCATCAATAATTTCCATTGC |
| 1153 | 541 | TGGAACGTTATCAGGTGCCCCAAAAATTCG | 1400 | TTGCAATCGACATATCCATTTCACCATGCC |
| 1154 | 436 | TGAAGTGCGTGATGATATCGATGCACTTGATGTA | 1036 | TCCGCCAAAAACTCCCCTTTTCACAGG |
| 1155 | 378 | TCGGTTTAGTAAAAGAACGTATTGCTCAACC | 1392 | TTCTGCTTGAGGAATAGTGCGTGG |
| 1156 | 250 | TCAACCTGACTGCGTGAATGGTTGT | 902 | TACGTTCTACGATTTCTTCATCAGGTACATC |
| 1157 | 256 | TCAAGCAGAAGCTTTGGAAGAAGAAGG | 881 | TACAACGTGATAAACACGACCAGAAGC |
| 1158 | 384 | TCGTGCCCGCAATTTGCATAAAGC | 878 | TAATGCCGGGTAGTGCAATCCATTCTTCTAG |
| 1159 | 384 | TCGTGCCCGCAATTTGCATAAAGC | 1199 | TGCACCTGCGGTCGAGCG |
| 1160 | 694 | TTGTAGCACAGCAAGGCAAATTTCCTGAAAC | 1215 | TGCCATCCATAATCACGCCATACTGACG |
| 1161 | 225 | TAGGTTTACGTCAGTATGGCGTGATTATGG | 1212 | TGCCAGTTTCCACATTTCACGTTCGTG |
| 1162 | 383 | TCGTGATTATGGATGGCAACGTGAA | 1083 | TCGCTTGAGTGTAGTCATGATTGCG |
| 1163 | 662 | TTATGGATGGCAACGTGAAACGCGT | 1083 | TCGCTTGAGTGTAGTCATGATTGCG |
| 1164 | 422 | TCTTTGCCATTGAAGATGACTTAAGC | 1083 | TCGCTTGAGTGTAGTCATGATTGCG |
| 1165 | 194 | TACTAGCGGTAAGCTTAAACAAGATTGC | 1173 | TGAGTCGGGTTCACTTTACCTGGCA |
| 1166 | 684 | TTGCCAATGATATTCGTTGGTTAGCAAG | 1173 | TGAGTCGGGTTCACTTTACCTGGCA |
| 1167 | 375 | TCGGCGAAATCCGTATTCCTGAAAATGC | 890 | TACCGGAAGCACCAGCGACATTAATAG |
| 1168 | 182 | TACCACTATTAATGTCGCTGGTGCTTC | 1195 | TGCAACTGAATAGATTGCAGTAAGTTATAAGC |
| 1169 | 656 | TTATAACTTACTGCAATCTATTCAGTTGCTTGGTG | 1151 | TGAATTATGCAAGAAGTGATCAATTTTCTCACGA |
| 1170 | 656 | TTATAACTTACTGCAATCTATTCAGTTGCTTGGTG | 1224 | TGCCGTAACTAACATAAGAGAATTATGCAAGAA |
| 1171 | 618 | TGGTTATGTACCAAATACTTTGTCTGAAGATGG | 1157 | TGACGGCATCGATACCACCGTC |
| 2846 | 302 | TCCAAAAAAATCAGCGCGTACAGTGG | 852 | TAAAGGATAGCGGTAACTAAATGGCTGAGCCAT |
| 2847 | 199 | TACTTGGTAAATACCACCCACATGGTGA | 889 | TACCCCAGTTCCCCTGACCTTC |
| 2848 | 596 | TGGTAAATACCACCCACATGGTGAC | 1169 | TGAGCCATGAGTACCATGGCTTCATAACATGC |
| 2852 | 150 | TAAATCTGCCCGTGTCGTTGGTGAC | 1242 | TGCTAAAGTCTTGAGCCATACGAACAATGG |
| 2853 | 166 | TAATCGGTAAATATCACCCGCATGGTGAC | 1069 | TCGATCGAACCGAAGTTACCCTGACC |
| 2854 | 166 | TAATCGGTAAATATCACCCGCATGGTGAC | 1168 | TGAGCCATACGAACAATGGTTTCATAAACAGC |
| 2922 | 583 | TGGGCGATGCTGCGAAATGGTTAAAAGA | 923 | TAGTATCACCACGTACACCCGGATCAGT |
| 2972 | 592 | TGGGIGATGCTGCIAAATGGTTAAAAGA | 924 | TAGTATCACCACGTACICCIGGATCAGT |

Analysis of bioagent identifying amplicons obtained using the primers of Table 14B for over 200 samples from Operation Iraqi Freedom resulted in the identification of 50 distinct strain type clusters. The largest cluster, designated strain type 11 (ST11) includes 42 sample isolates, all of which were obtained from US service personnel and Iraqi civilians treated at the 28$^{th}$ Combat Support Hospital in Baghdad. Several of these individuals were also treated on the hospital ship USNS Comfort. These observations are indicative of significant epidemiological correlation/linkage.

All of the sample isolates were tested against a broad panel of antibiotics to characterize their antibiotic resistance profiles. As an example of a representative result from antibiotic susceptibility testing, ST11 was found to consist of four different clusters of isolates, each with a varying degree of sensitivity/resistance to the various antibiotics tested which included penicillins, extended spectrum penicillins, cephalosporins, carbepenem, protein synthesis inhibitors, nucleic acid synthesis inhibitors, anti-metabolites, and anti-cell membrane antibiotics. Thus, the genotyping power of bacterial bioagent identifying amplicons, particularly drill-down bacterial bioagent identifying amplicons, has the potential to increase the understanding of the transmission of infections in combat casualties, to identify the source of infection in the environment, to track hospital transmission of nosocomial infections, and to rapidly characterize drug-resistance profiles which enable development of effective infection control measures on a time-scale previously not achievable.

Example 13

Triangulation Genotyping Analysis and Codon Analysis of *Acinetobacter baumannii* Samples from Two Health Care Facilities In this investigation, 88 clinical samples were obtained from Walter Reed Hospital and 95 clinical samples were obtained from Northwestern Medical Center. All samples from both healthcare facilities were suspected of containing sub-types of *Acinetobacter baumannii*, at least some of which were expected to be resistant to quinolone drugs. Each of the 183 samples was analyzed by the method of the present invention. DNA was extracted from each of the samples and amplified with eight triangulation genotyping analysis primer pairs represented by primer pair numbers: 1151, 1156, 1158, 1160, 11, 65, 1167, 1170, and 1171. The DNA was also amplified with speciating primer pair number 2922 and codon analysis primer pair numbers 2846-2848 which interrogate a codon present in the parC gene, and primer pair numbers 2852-2854 which bracket a codon present in the gyrA gene. The parC and gyrA codon mutations are both responsible for causing drug resistance in *Acinetobacter baumannii*. During evolution of drug resistant strains, the gyrA mutation usually occurs before the parC mutation. Amplification products were measured by ESI-TOF mass spectrometry as indicated in Example 4. The base compositions of the amplification products were calculated from the average molecular masses of the amplification products and are shown in Tables 15-18.

The entries in each of the tables are grouped according to strain type number, which is an arbitrary number assigned to *Acinetobacter baumannii* strains in the order of observance beginning from the triangulation genotyping analysis OIF genotyping study described in Example 12. For example, strain type 11 which appears in samples from the Walter Reed Hospital is the same strain as the strain type 11 mentioned in Example 12. Ibis# refers to the order in which each sample was analyzed. Isolate refers to the original sample isolate numbering system used at the location from which the samples were obtained (either Walter Reed Hospital or Northwestern Medical Center). ST=strain type. ND=not detected. Base compositions highlighted with bold type indicate that the base composition is a unique base composition for the amplification product obtained with the pair of primers indicated.

TABLE 15A

Base Compositions of Amplification Products of 88 *A. baumannii* Samples Obtained from Walter Reed Hospital and Amplified with Codon Analysis Primer Pairs Targeting the gyrA Gene

| Species | Ibis# | Isolate | ST | PP No: 2852 gyrA | PP No: 2853 gyrA | PP No: 2854 gyrA |
|---|---|---|---|---|---|---|
| *A. baumannii* | 20 | 1082 | 1 | A25G23C22T31 | A29G28C22T42 | A17G13C14T20 |
| *A. baumannii* | 13 | 854 | 10 | A25G23C21T32 | A29G28C21T43 | A17G13C13T21 |
| *A. baumannii* | 22 | 1162 | 10 | A25G23C21T32 | A29G28C21T43 | A17G13C13T21 |
| *A. baumannii* | 27 | 1230 | 10 | A25G23C21T32 | A29G28C21T43 | A17G13C13T21 |
| *A. baumannii* | 31 | 1367 | 10 | A25G23C21T32 | A29G28C21T43 | A17G13C13T21 |
| *A. baumannii* | 37 | 1459 | 10 | A25G23C21T32 | A29G28C21T43 | A17G13C13T21 |
| *A. baumannii* | 55 | 1700 | 10 | A25G23C21T32 | A29G28C21T43 | A17G13C13T21 |
| *A. baumannii* | 64 | 1777 | 10 | A25G23C21T32 | A29G28C21T43 | A17G13C13T21 |
| *A. baumannii* | 73 | 1861 | 10 | A25G23C21T32 | A29G28C21T43 | A17G13C13T21 |
| *A. baumannii* | 74 | 1877 | 10 | ND | A29G28C21T43 | A17G13C13T21 |
| *A. baumannii* | 86 | 1972 | 10 | A25G23C21T32 | A29G28C21T43 | A17G13C13T21 |
| *A. baumannii* | 3 | 684 | 11 | A25G23C21T32 | A29G28C21T43 | A17G13C13T21 |
| *A. baumannii* | 6 | 720 | 11 | A25G23C21T32 | A29G28C21T43 | A17G13C13T21 |
| *A. baumannii* | 7 | 726 | 11 | A25G23C21T32 | A29G28C21T43 | A17G13C13T21 |
| *A. baumannii* | 19 | 1079 | 11 | A25G23C21T32 | A29G28C21T43 | A17G13C13T21 |
| *A. baumannii* | 21 | 1123 | 11 | A25G23C21T32 | A29G28C21T43 | A17G13C13T21 |
| *A. baumannii* | 23 | 1188 | 11 | A25G23C21T32 | A29G28C21T43 | A17G13C13T21 |
| *A. baumannii* | 33 | 1417 | 11 | A25G23C21T32 | A29G28C21T43 | A17G13C13T21 |
| *A. baumannii* | 34 | 1431 | 11 | A25G23C21T32 | A29G28C21T43 | A17G13C13T21 |
| *A. baumannii* | 38 | 1496 | 11 | A25G23C21T32 | A29G28C21T43 | A17G13C13T21 |
| *A. baumannii* | 40 | 1523 | 11 | A25G23C21T32 | A29G28C21T43 | A17G13C13T21 |
| *A. baumannii* | 42 | 1640 | 11 | A25G23C21T32 | A29G28C21T43 | A17G13C13T21 |
| *A. baumannii* | 50 | 1666 | 11 | A25G23C21T32 | A29G28C21T43 | A17G13C13T21 |
| *A. baumannii* | 51 | 1668 | 11 | A25G23C21T32 | A29G28C21T43 | A17G13C13T21 |
| *A. baumannii* | 52 | 1695 | 11 | A25G23C21T32 | A29G28C21T43 | A17G13C13T21 |
| *A. baumannii* | 65 | 1781 | 11 | A25G23C21T32 | A29G28C21T43 | A17G13C13T21 |
| *A. baumannii* | 44 | 1649 | 12 | A25G23C21T32 | A29G28C21T43 | A17G13C13T21 |
| *A. baumannii* | 49A | 1658.1 | 12 | A25G23C22T31 | A29G28C21T43 | A17G13C13T21 |
| *A. baumannii* | 49B | 1658.2 | 12 | A25G23C21T32 | A29G28C21T43 | A17G13C13T21 |
| *A. baumannii* | 56 | 1707 | 12 | A25G23C21T32 | A29G28C21T43 | A17G13C13T21 |
| *A. baumannii* | 80 | 1893 | 12 | A25G23C21T32 | A29G28C21T43 | A17G13C13T21 |
| *A. baumannii* | 5 | 693 | 14 | A25G23C21T32 | A29G28C21T43 | A17G13C13T21 |
| *A. baumannii* | 8 | 749 | 14 | A25G23C21T32 | A29G28C21T43 | A17G13C13T21 |
| *A. baumannii* | 10 | 839 | 14 | A25G23C21T32 | A29G28C21T43 | A17G13C13T21 |
| *A. baumannii* | 14 | 865 | 14 | A25G23C21T32 | A29G28C21T43 | A17G13C13T21 |
| *A. baumannii* | 16 | 888 | 14 | A25G23C21T32 | A29G28C21T43 | A17G13C13T21 |
| *A. baumannii* | 29 | 1326 | 14 | A25G23C21T32 | A29G28C21T43 | A17G13C13T21 |
| *A. baumannii* | 35 | 1440 | 14 | A25G23C21T32 | A29G28C21T43 | A17G13C13T21 |
| *A. baumannii* | 41 | 1524 | 14 | A25G23C21T32 | A29G28C21T43 | A17G13C13T21 |
| *A. baumannii* | 46 | 1652 | 14 | A25G23C21T32 | A29G28C21T43 | A17G13C13T21 |
| *A. baumannii* | 47 | 1653 | 14 | A25G23C21T32 | A29G28C21T43 | A17G13C13T21 |
| *A. baumannii* | 48 | 1657 | 14 | A25G23C21T32 | A29G28C21T43 | A17G13C13T21 |
| *A. baumannii* | 57 | 1709 | 14 | A25G23C21T32 | A29G28C21T43 | A17G13C13T21 |
| *A. baumannii* | 61 | 1727 | 14 | A25G23C21T32 | A29G28C21T43 | A17G13C13T21 |
| *A. baumannii* | 63 | 1762 | 14 | A25G23C21T32 | A29G28C21T43 | A17G13C13T21 |
| *A. baumannii* | 67 | 1806 | 14 | A25G23C21T32 | A29G28C21T43 | A17G13C13T21 |
| *A. baumannii* | 75 | 1881 | 14 | A25G23C21T32 | A29G28C21T43 | A17G13C13T21 |
| *A. baumannii* | 77 | 1886 | 14 | A25G23C21T32 | A29G28C21T43 | A17G13C13T21 |
| *A. baumannii* | 1 | 649 | 46 | A25G23C21T32 | A29G28C21T43 | A17G13C13T21 |
| *A. baumannii* | 2 | 653 | 46 | A25G23C21T32 | A29G28C21T43 | A17G13C13T21 |
| *A. baumannii* | 39 | 1497 | 16 | A25G23C21T32 | A29G28C21T43 | A17G13C13T21 |
| *A. baumannii* | 24 | 1198 | 15 | A25G23C21T32 | A29G28C21T43 | A17G13C13T21 |
| *A. baumannii* | 28 | 1243 | 15 | A25G23C21T32 | A29G28C21T43 | A17G13C13T21 |
| *A. baumannii* | 43 | 1648 | 15 | A25G23C21T32 | A29G28C21T43 | A17G13C13T21 |
| *A. baumannii* | 62 | 1746 | 15 | A25G23C21T32 | A29G28C21T43 | A17G13C13T21 |
| *A. baumannii* | 4 | 689 | 15 | A25G23C21T32 | A29G28C21T43 | A17G13C13T21 |
| *A. baumannii* | 68 | 1822 | 3 | A25G23C21T32 | A29G28C21T43 | A17G13C13T21 |
| *A. baumannii* | 69 | 1823A | 3 | A25G23C21T32 | A29G28C21T43 | A17G13C13T21 |
| *A. baumannii* | 70 | 1823B | 3 | A25G23C21T32 | A29G28C21T43 | A17G13C13T21 |
| *A. baumannii* | 71 | 1826 | 3 | A25G23C21T32 | A29G28C21T43 | A17G13C13T21 |
| *A. baumannii* | 72 | 1860 | 3 | A25G23C21T32 | A29G28C21T43 | A17G13C13T21 |
| *A. baumannii* | 81 | 1924 | 3 | A25G23C21T32 | A29G28C21T43 | A17G13C13T21 |

TABLE 15A-continued

Base Compositions of Amplification Products of 88 *A. baumannii* Samples Obtained from Walter Reed Hospital and Amplified with Codon Analysis Primer Pairs Targeting the gyrA Gene

| Species | Ibis# | Isolate | ST | PP No: 2852 gyrA | PP No: 2853 gyrA | PP No: 2854 gyrA |
|---|---|---|---|---|---|---|
| *A. baumannii* | 82 | 1929 | 3 | A25G23C21T32 | A29G28C21T43 | A17G13C13T21 |
| *A. baumannii* | 85 | 1966 | 3 | A25G23C21T32 | A29G28C21T43 | A17G13C13T21 |
| *A. baumannii* | 11 | 841 | 3 | A25G23C22T31 | A29G28C22T42 | A17G13C14T20 |
| *A. baumannii* | 32 | 1415 | 24 | A25G23C21T32 | A29G28C21T43 | A17G13C13T21 |
| *A. baumannii* | 45 | 1651 | 24 | A25G23C21T32 | A29G28C21T43 | A17G13C13T21 |
| *A. baumannii* | 54 | 1697 | 24 | A25G23C21T32 | A29G28C21T43 | A17G13C13T21 |
| *A. baumannii* | 58 | 1712 | 24 | A25G23C21T32 | A29G28C21T43 | A17G13C13T21 |
| *A. baumannii* | 60 | 1725 | 24 | A25G23C21T32 | A29G28C21T43 | A17G13C13T21 |
| *A. baumannii* | 66 | 1802 | 24 | A25G23C21T32 | A29G28C21T43 | A17G13C13T21 |
| *A. baumannii* | 76 | 1883 | 24 | A25G23C21T32 | A29G28C21T43 | A17G13C13T21 |
| *A. baumannii* | 78 | 1891 | 24 | A25G23C21T32 | A29G28C21T43 | A17G13C13T21 |
| *A. baumannii* | 79 | 1892 | 24 | A25G23C21T32 | A29G28C21T43 | A17G13C13T21 |
| *A. baumannii* | 83 | 1947 | 24 | A25G23C21T32 | A29G28C21T43 | A17G13C13T21 |
| *A. baumannii* | 84 | 1964 | 24 | A25G23C21T32 | A29G28C21T43 | A17G13C13T21 |
| *A. baumannii* | 53 | 1696 | 24 | A25G23C22T31 | A29G28C22T42 | A17G13C14T20 |
| *A. baumannii* | 36 | 1458 | 49 | A25G23C21T32 | A29G28C21T43 | A17G13C13T21 |
| *A. baumannii* | 59 | 1716 | 9 | A25G23C22T31 | A29G28C22T42 | A17G13C14T20 |
| *A. baumannii* | 9 | 805 | 30 | A25G23C22T31 | A29G28C22T42 | A17G13C14T20 |
| *A. baumannii* | 18 | 967 | 39 | A25G23C22T31 | A29G28C22T42 | A17G13C14T20 |
| *A. baumannii* | 30 | 1322 | 48 | A25G23C22T31 | A29G28C22T42 | A17G13C14T20 |
| *A. baumannii* | 26 | 1218 | 50 | A25G23C22T31 | A29G28C22T42 | A17G13C14T20 |
| *A.* sp. 13TU | 15 | 875 | A1 | A25G23C22T31 | A29G28C22T42 | A17G13C14T20 |
| *A.* sp. 13TU | 17 | 895 | A1 | A25G23C22T31 | A29G28C22T42 | A17G13C14T20 |
| *A.* sp. 3 | 12 | 853 | B7 | A25G22C22T32 | A30G29C22T40 | A17G13C14T20 |
| *A. johnsonii* | 25 | 1202 | NEW1 | A25G22C22T32 | A30G29C22T40 | A17G13C14T20 |
| *A.* sp. 2082 | 87 | 2082 | NEW2 | A25G22C22T32 | **A31G28C22T40** | A17G13C14T20 |

TABLE 15B

Base Compositions Determined from *A. baumannii* DNA Samples Obtained from Walter Reed Hospital and Amplified with Codon Analysis Primer Pairs Targeting the parC Gene

| Species | Ibis# | Isolate | ST | PP No: 2846 parC | PP No: 2847 parC | PP No: 2848 parC |
|---|---|---|---|---|---|---|
| *A. baumannii* | 20 | 1082 | 1 | A33G26C29T33 | A29G28C26T31 | A16G14C15T15 |
| *A. baumannii* | 13 | 854 | 10 | A33G26C28T34 | A29G28C25T32 | A16G14C14T16 |
| *A. baumannii* | 22 | 1162 | 10 | A33G26C28T34 | A29G28C25T32 | A16G14C14T16 |
| *A. baumannii* | 27 | 1230 | 10 | A33G26C28T34 | A29G28C25T32 | A16G14C14T16 |
| *A. baumannii* | 31 | 1367 | 10 | A33G26C28T34 | A29G28C25T32 | A16G14C14T16 |
| *A. baumannii* | 37 | 1459 | 10 | A33G26C28T34 | A29G28C25T32 | A16G14C14T16 |
| *A. baumannii* | 55 | 1700 | 10 | A33G26C28T34 | A29G28C25T32 | A16G14C14T16 |
| *A. baumannii* | 64 | 1777 | 10 | A33G26C28T34 | A29G28C25T32 | A16G14C14T16 |
| *A. baumannii* | 73 | 1861 | 10 | A33G26C28T34 | A29G28C25T32 | A16G14C14T16 |
| *A. baumannii* | 74 | 1877 | 10 | A33G26C28T34 | A29G28C25T32 | A16G14C14T16 |
| *A. baumannii* | 86 | 1972 | 10 | A33G26C28T34 | A29G28C25T32 | A16G14C14T16 |
| *A. baumannii* | 3 | 684 | 11 | A33G26C28T34 | A29G28C25T32 | A16G14C14T16 |
| *A. baumannii* | 6 | 720 | 11 | A33G26C28T34 | A29G28C25T32 | A16G14C14T16 |
| *A. baumannii* | 7 | 726 | 11 | A33G26C28T34 | A29G28C25T32 | A16G14C14T16 |
| *A. baumannii* | 19 | 1079 | 11 | A33G26C28T34 | A29G28C25T32 | A16G14C14T16 |
| *A. baumannii* | 21 | 1123 | 11 | A33G26C28T34 | A29G28C25T32 | A16G14C14T16 |
| *A. baumannii* | 23 | 1188 | 11 | A33G26C28T34 | A29G28C25T32 | A16G14C14T16 |
| *A. baumannii* | 33 | 1417 | 11 | A33G26C28T34 | A29G28C25T32 | A16G14C14T16 |
| *A. baumannii* | 34 | 1431 | 11 | A33G26C28T34 | A29G28C25T32 | A16G14C14T16 |
| *A. baumannii* | 38 | 1496 | 11 | A33G26C28T34 | A29G28C25T32 | A16G14C14T16 |
| *A. baumannii* | 40 | 1523 | 11 | A33G26C28T34 | A29G28C25T32 | A16G14C14T16 |
| *A. baumannii* | 42 | 1640 | 11 | A33G26C28T34 | A29G28C25T32 | A16G14C14T16 |
| *A. baumannii* | 50 | 1666 | 11 | A33G26C28T34 | A29G28C25T32 | A16G14C14T16 |
| *A. baumannii* | 51 | 1668 | 11 | A33G26C28T34 | A29G28C25T32 | A16G14C14T16 |
| *A. baumannii* | 52 | 1695 | 11 | A33G26C28T34 | A29G28C25T32 | A16G14C14T16 |
| *A. baumannii* | 65 | 1781 | 11 | A33G26C28T34 | A29G28C25T32 | A16G14C14T16 |
| *A. baumannii* | 44 | 1649 | 12 | A33G26C28T34 | A29G28C25T32 | A16G14C14T16 |
| *A. baumannii* | 49A | 1658.1 | 12 | A33G26C28T34 | A29G28C25T32 | A16G14C14T16 |
| *A. baumannii* | 49B | 1658.2 | 12 | A33G26C28T34 | A29G28C25T32 | A16G14C14T16 |
| *A. baumannii* | 56 | 1707 | 12 | A33G26C28T34 | A29G28C25T32 | A16G14C14T16 |
| *A. baumannii* | 80 | 1893 | 12 | A33G26C28T34 | A29G28C25T32 | A16G14C14T16 |
| *A. baumannii* | 5 | 693 | 14 | A33G26C28T34 | A29G28C25T32 | A16G14C14T16 |
| *A. baumannii* | 8 | 749 | 14 | A33G26C28T34 | A29G28C25T32 | A16G14C14T16 |
| *A. baumannii* | 10 | 839 | 14 | A33G26C28T34 | A29G28C25T32 | A16G14C14T16 |
| *A. baumannii* | 14 | 865 | 14 | A33G26C28T34 | A29G28C25T32 | A16G14C14T16 |
| *A. baumannii* | 16 | 888 | 14 | A33G26C28T34 | A29G28C25T32 | A16G14C14T16 |

TABLE 15B-continued

Base Compositions Determined from *A. baumannii* DNA Samples Obtained from Walter Reed Hospital and Amplified with Codon Analysis Primer Pairs Targeting the parC Gene

| Species | Ibis# | Isolate | ST | PP No: 2846 parC | PP No: 2847 parC | PP No: 2848 parC |
|---|---|---|---|---|---|---|
| *A. baumannii* | 29 | 1326 | 14 | A33G26C28T34 | A29G28C25T32 | A16G14C14T16 |
| *A. baumannii* | 35 | 1440 | 14 | A33G26C28T34 | A29G28C25T32 | A16G14C14T16 |
| *A. baumannii* | 41 | 1524 | 14 | A33G26C28T34 | A29G28C25T32 | A16G14C14T16 |
| *A. baumannii* | 46 | 1652 | 14 | A33G26C28T34 | A29G28C25T32 | A16G14C14T16 |
| *A. baumannii* | 47 | 1653 | 14 | A33G26C28T34 | A29G28C25T32 | A16G14C14T16 |
| *A. baumannii* | 48 | 1657 | 14 | A33G26C28T34 | A29G28C25T32 | A16G14C14T16 |
| *A. baumannii* | 57 | 1709 | 14 | A33G26C28T34 | A29G28C25T32 | A16G14C14T16 |
| *A. baumannii* | 61 | 1727 | 14 | A33G26C28T34 | A29G28C25T32 | A16G14C14T16 |
| *A. baumannii* | 63 | 1762 | 14 | A33G26C28T34 | A29G28C25T32 | A16G14C14T16 |
| *A. baumannii* | 67 | 1806 | 14 | A33G26C28T34 | A29G28C25T32 | A16G14C14T16 |
| *A. baumannii* | 75 | 1881 | 14 | A33G26C28T34 | A29G28C25T32 | A16G14C14T16 |
| *A. baumannii* | 77 | 1886 | 14 | A33G26C28T34 | A29G28C25T32 | A16G14C14T16 |
| *A. baumannii* | 1 | 649 | 46 | A33G26C28T34 | A29G28C25T32 | A16G14C14T16 |
| *A. baumannii* | 2 | 653 | 46 | A33G26C28T34 | A29G28C25T32 | A16G14C14T16 |
| *A. baumannii* | 39 | 1497 | 16 | A33G26C28T34 | A29G28C25T32 | A16G14C14T16 |
| *A. baumannii* | 24 | 1198 | 15 | A33G26C28T34 | A29G29C23T33 | A16G14C14T16 |
| *A. baumannii* | 28 | 1243 | 15 | A33G26C28T34 | A29G29C23T33 | A16G14C14T16 |
| *A. baumannii* | 43 | 1648 | 15 | A33G26C28T34 | A29G29C23T33 | A16G14C14T16 |
| *A. baumannii* | 62 | 1746 | 15 | A33G26C28T34 | A29G29C23T33 | A16G14C14T16 |
| *A. baumannii* | 4 | 689 | 15 | A34G25C29T33 | A30G27C26T31 | A16G14C15T15 |
| *A. baumannii* | 68 | 1822 | 3 | A33G26C28T34 | A29G28C25T32 | A16G14C14T16 |
| *A. baumannii* | 69 | 1823A | 3 | A33G26C28T34 | A29G28C25T32 | A16G14C14T16 |
| *A. baumannii* | 70 | 1823B | 3 | A33G26C28T34 | A29G28C25T32 | A16G14C14T16 |
| *A. baumannii* | 71 | 1826 | 3 | A33G26C28T34 | A29G28C25T32 | A16G14C14T16 |
| *A. baumannii* | 72 | 1860 | 3 | A33G26C28T34 | A29G28C25T32 | A16G14C14T16 |
| *A. baumannii* | 81 | 1924 | 3 | A33G26C28T34 | A29G28C25T32 | A16G14C14T16 |
| *A. baumannii* | 82 | 1929 | 3 | A33G26C28T34 | A29G28C25T32 | A16G14C14T16 |
| *A. baumannii* | 85 | 1966 | 3 | A33G26C28T34 | A29G28C25T32 | A16G14C14T16 |
| *A. baumannii* | 11 | 841 | 3 | A33G26C29T33 | A29G28C26T31 | A16G14C15T15 |
| *A. baumannii* | 32 | 1415 | 24 | A33G26C29T33 | A29G28C26T31 | A16G14C15T15 |
| *A. baumannii* | 45 | 1651 | 24 | A33G26C29T33 | A29G28C26T31 | A16G14C15T15 |
| *A. baumannii* | 54 | 1697 | 24 | A33G26C29T33 | A29G28C26T31 | A16G14C15T15 |
| *A. baumannii* | 58 | 1712 | 24 | A33G26C29T33 | A29G28C26T31 | A16G14C15T15 |
| *A. baumannii* | 60 | 1725 | 24 | A33G26C29T33 | A29G28C26T31 | A16G14C15T15 |
| *A. baumannii* | 66 | 1802 | 24 | A33G26C29T33 | A29G28C26T31 | A16G14C15T15 |
| *A. baumannii* | 76 | 1883 | 24 | A33G26C29T33 | A29G28C26T31 | A16G14C15T15 |
| *A. baumannii* | 78 | 1891 | 24 | A34G25C29T33 | A30G27C26T31 | A16G14C15T15 |
| *A. baumannii* | 79 | 1892 | 24 | A33G26C29T33 | A29G28C26T31 | A16G14C15T15 |
| *A. baumannii* | 83 | 1947 | 24 | A34G25C29T33 | A30G27C26T31 | A16G14C15T15 |
| *A. baumannii* | 84 | 1964 | 24 | A33G26C29T33 | A29G28C26T31 | A16G14C15T15 |
| *A. baumannii* | 53 | 1696 | 24 | A33G26C29T33 | A29G28C26T31 | A16G14C15T15 |
| *A. baumannii* | 36 | 1458 | 49 | A34G26C29T32 | A30G28C24T32 | A16G14C15T15 |
| *A. baumannii* | 59 | 1716 | 9 | A33G26C29T33 | A29G28C26T31 | A16G14C15T15 |
| *A. baumannii* | 9 | 805 | 30 | A33G26C29T33 | A29G28C26T31 | A16G14C15T15 |
| *A. baumannii* | 18 | 967 | 39 | A33G26C29T33 | A29G28C26T31 | A16G14C15T15 |
| *A. baumannii* | 30 | 1322 | 48 | A33G26C29T33 | A29G28C26T31 | A16G14C15T15 |
| *A. baumannii* | 26 | 1218 | 50 | A33G26C29T33 | A29G28C26T31 | A16G14C15T15 |
| *A.* sp. 13TU | 15 | 875 | A1 | A32G26C28T35 | A28G28C24T34 | A16G14C15T15 |
| *A.* sp. 13TU | 17 | 895 | A1 | A32G26C28T35 | A28G28C24T34 | A16G14C15T15 |
| *A.* sp. 3 | 12 | 853 | B7 | A29G26C27T39 | A26G32C21T35 | A16G14C15T15 |
| *A. johnsonii* | 25 | 1202 | NEW1 | A32G28C26T35 | A29G29C22T34 | A16G14C15T15 |
| *A.* sp. 2082 | 87 | 2082 | NEW2 | **A33G27C26T35** | **A31G28C20T35** | A16G14C15T15 |

TABLE 16A

Base Compositions Determined from *A. baumannii* DNA Samples Obtained from Northwestern Medical Center and Amplified with Codon Analysis Primer Pairs Targeting the gyrA Gene

| Species | Ibis# | Isolate | ST | PP No: 2852 gyrA | PP No: 2853 gyrA | PP No: 2854 gyrA |
|---|---|---|---|---|---|---|
| *A. baumannii* | 54 | 536 | 3 | A25G23C21T32 | A29G28C21T43 | A17G13C13T21 |
| *A. baumannii* | 87 | 665 | 3 | A25G23C21T32 | A29G28C21T43 | A17G13C13T21 |
| *A. baumannii* | 8 | 80 | 10 | A25G23C21T32 | A29G28C21T43 | A17G13C13T21 |
| *A. baumannii* | 9 | 91 | 10 | A25G23C21T32 | A29G28C21T43 | A17G13C13T21 |
| *A. baumannii* | 10 | 92 | 10 | A25G23C21T32 | A29G28C21T43 | A17G13C13T21 |
| *A. baumannii* | 11 | 131 | 10 | A25G23C21T32 | A29G28C21T43 | A17G13C13T21 |
| *A. baumannii* | 12 | 137 | 10 | A25G23C21T32 | A29G28C21T43 | A17G13C13T21 |
| *A. baumannii* | 21 | 218 | 10 | A25G23C21T32 | A29G28C21T43 | A17G13C13T21 |
| *A. baumannii* | 26 | 242 | 10 | A25G23C21T32 | A29G28C21T43 | A17G13C13T21 |
| *A. baumannii* | 94 | 678 | 10 | A25G23C21T32 | A29G28C21T43 | A17G13C13T21 |

TABLE 16A-continued

Base Compositions Determined from *A. baumannii* DNA Samples Obtained from Northwestern Medical Center and Amplified with Codon Analysis Primer Pairs Targeting the gyrA Gene

| Species | Ibis# | Isolate | ST | PP No: 2852 gyrA | PP No: 2853 gyrA | PP No: 2854 gyrA |
|---|---|---|---|---|---|---|
| *A. baumannii* | 1 | 9 | 10 | A25G23C21T32 | A29G28C21T43 | A17G13C13T21 |
| *A. baumannii* | 2 | 13 | 10 | A25G23C21T32 | A29G28C21T43 | A17G13C13T21 |
| *A. baumannii* | 3 | 19 | 10 | A25G23C21T32 | A29G28C21T43 | A17G13C13T21 |
| *A. baumannii* | 4 | 24 | 10 | A25G23C21T32 | A29G28C21T43 | A17G13C13T21 |
| *A. baumannii* | 5 | 36 | 10 | A25G23C21T32 | A29G28C21T43 | A17G13C13T21 |
| *A. baumannii* | 6 | 39 | 10 | A25G23C21T32 | A29G28C21T43 | A17G13C13T21 |
| *A. baumannii* | 13 | 139 | 10 | A25G23C21T32 | A29G28C21T43 | A17G13C13T21 |
| *A. baumannii* | 15 | 165 | 10 | A25G23C21T32 | A29G28C21T43 | A17G13C13T21 |
| *A. baumannii* | 16 | 170 | 10 | A25G23C21T32 | A29G28C21T43 | A17G13C13T21 |
| *A. baumannii* | 17 | 186 | 10 | A25G23C21T32 | A29G28C21T43 | A17G13C13T21 |
| *A. baumannii* | 20 | 202 | 10 | A25G23C21T32 | A29G28C21T43 | A17G13C13T21 |
| *A. baumannii* | 22 | 221 | 10 | A25G23C21T32 | A29G28C21T43 | A17G13C13T21 |
| *A. baumannii* | 24 | 234 | 10 | A25G23C21T32 | A29G28C21T43 | A17G13C13T21 |
| *A. baumannii* | 25 | 239 | 10 | A25G23C21T32 | A29G28C21T43 | A17G13C13T21 |
| *A. baumannii* | 33 | 370 | 10 | A25G23C21T32 | A29G28C21T43 | A17G13C13T21 |
| *A. baumannii* | 34 | 389 | 10 | A25G23C21T32 | A29G28C21T43 | A17G13C13T21 |
| *A. baumannii* | 19 | 201 | 14 | A25G23C21T32 | A29G28C21T43 | A17G13C13T21 |
| *A. baumannii* | 27 | 257 | 51 | A25G23C21T32 | A29G28C21T43 | A17G13C13T21 |
| *A. baumannii* | 29 | 301 | 51 | A25G23C21T32 | A29G28C21T43 | A17G13C13T21 |
| *A. baumannii* | 31 | 354 | 51 | A25G23C21T32 | A29G28C21T43 | A17G13C13T21 |
| *A. baumannii* | 36 | 422 | 51 | A25G23C21T32 | A29G28C21T43 | A17G13C13T21 |
| *A. baumannii* | 37 | 424 | 51 | A25G23C21T32 | A29G28C21T43 | A17G13C13T21 |
| *A. baumannii* | 38 | 434 | 51 | A25G23C21T32 | A29G28C21T43 | A17G13C13T21 |
| *A. baumannii* | 39 | 473 | 51 | A25G23C21T32 | A29G28C21T43 | A17G13C13T21 |
| *A. baumannii* | 40 | 482 | 51 | A25G23C21T32 | A29G28C21T43 | A17G13C13T21 |
| *A. baumannii* | 44 | 512 | 51 | A25G23C21T32 | A29G28C21T43 | A17G13C13T21 |
| *A. baumannii* | 45 | 516 | 51 | A25G23C21T32 | A29G28C21T43 | A17G13C13T21 |
| *A. baumannii* | 47 | 522 | 51 | A25G23C21T32 | A29G28C21T43 | A17G13C13T21 |
| *A. baumannii* | 48 | 526 | 51 | A25G23C21T32 | A29G28C21T43 | A17G13C13T21 |
| *A. baumannii* | 50 | 528 | 51 | A25G23C21T32 | A29G28C21T43 | A17G13C13T21 |
| *A. baumannii* | 52 | 531 | 51 | A25G23C21T32 | A29G28C21T43 | A17G13C13T21 |
| *A. baumannii* | 53 | 533 | 51 | A25G23C21T32 | A29G28C21T43 | A17G13C13T21 |
| *A. baumannii* | 56 | 542 | 51 | A25G23C21T32 | A29G28C21T43 | A17G13C13T21 |
| *A. baumannii* | 59 | 550 | 51 | A25G23C21T32 | A29G28C21T43 | A17G13C13T21 |
| *A. baumannii* | 62 | 556 | 51 | A25G23C21T32 | A29G28C21T43 | A17G13C13T21 |
| *A. baumannii* | 64 | 557 | 51 | A25G23C21T32 | A29G28C21T43 | A17G13C13T21 |
| *A. baumannii* | 70 | 588 | 51 | A25G23C21T32 | A29G28C21T43 | A17G13C13T21 |
| *A. baumannii* | 73 | 603 | 51 | A25G23C21T32 | A29G28C21T43 | A17G13C13T21 |
| *A. baumannii* | 74 | 605 | 51 | A25G23C21T32 | A29G28C21T43 | A17G13C13T21 |
| *A. baumannii* | 75 | 606 | 51 | A25G23C21T32 | A29G28C21T43 | A17G13C13T21 |
| *A. baumannii* | 77 | 611 | 51 | A25G23C21T32 | A29G28C21T43 | A17G13C13T21 |
| *A. baumannii* | 79 | 622 | 51 | A25G23C21T32 | A29G28C21T43 | A17G13C13T21 |
| *A. baumannii* | 83 | 643 | 51 | A25G23C21T32 | A29G28C21T43 | A17G13C13T21 |
| *A. baumannii* | 85 | 653 | 51 | A25G23C21T32 | A29G28C21T43 | A17G13C13T21 |
| *A. baumannii* | 89 | 669 | 51 | A25G23C21T32 | A29G28C21T43 | A17G13C13T21 |
| *A. baumannii* | 93 | 674 | 51 | A25G23C21T32 | A29G28C21T43 | A17G13C13T21 |
| *A. baumannii* | 23 | 228 | 51 | A25G23C21T32 | A29G28C21T43 | A17G13C13T21 |
| *A. baumannii* | 32 | 369 | 52 | A25G23C21T32 | A29G28C21T43 | A17G13C13T21 |
| *A. baumannii* | 35 | 393 | 52 | A25G23C21T32 | A29G28C21T43 | A17G13C13T21 |
| *A. baumannii* | 30 | 339 | 53 | A25G23C21T32 | A29G28C21T43 | A17G13C13T21 |
| *A. baumannii* | 41 | 485 | 53 | A25G23C21T32 | A29G28C21T43 | A17G13C13T21 |
| *A. baumannii* | 42 | 493 | 53 | A25G23C21T32 | A29G28C21T43 | A17G13C13T21 |
| *A. baumannii* | 43 | 502 | 53 | A25G23C21T32 | A29G28C21T43 | A17G13C13T21 |
| *A. baumannii* | 46 | 520 | 53 | A25G23C21T32 | A29G28C21T43 | A17G13C13T21 |
| *A. baumannii* | 49 | 527 | 53 | A25G23C21T32 | A29G28C21T43 | A17G13C13T21 |
| *A. baumannii* | 51 | 529 | 53 | A25G23C21T32 | A29G28C21T43 | A17G13C13T21 |
| *A. baumannii* | 65 | 562 | 53 | A25G23C21T32 | A29G28C21T43 | A17G13C13T21 |
| *A. baumannii* | 68 | 579 | 53 | A25G23C21T32 | A29G28C21T43 | A17G13C13T21 |
| *A. baumannii* | 57 | 546 | 54 | A25G23C21T32 | A29G28C21T43 | A17G13C13T21 |
| *A. baumannii* | 58 | 548 | 54 | A25G23C21T32 | A29G28C21T43 | A17G13C13T21 |
| *A. baumannii* | 60 | 552 | 54 | A25G23C21T32 | A29G28C21T43 | A17G13C13T21 |
| *A. baumannii* | 61 | 555 | 54 | A25G23C21T32 | A29G28C21T43 | A17G13C13T21 |
| *A. baumannii* | 63 | 557 | 54 | A25G23C21T32 | A29G28C21T43 | A17G13C13T21 |
| *A. baumannii* | 66 | 570 | 54 | A25G23C21T32 | A29G28C21T43 | A17G13C13T21 |
| *A. baumannii* | 67 | 578 | 54 | A25G23C21T32 | A29G28C21T43 | A17G13C13T21 |
| *A. baumannii* | 69 | 584 | 54 | A25G23C21T32 | A29G28C21T43 | A17G13C13T21 |
| *A. baumannii* | 71 | 593 | 54 | A25G23C21T32 | A29G28C21T43 | A17G13C13T21 |
| *A. baumannii* | 72 | 602 | 54 | A25G23C21T32 | A29G28C21T43 | A17G13C13T21 |
| *A. baumannii* | 76 | 609 | 54 | A25G23C21T32 | A29G28C21T43 | A17G13C13T21 |
| *A. baumannii* | 78 | 621 | 54 | A25G23C21T32 | A29G28C21T43 | A17G13C13T21 |
| *A. baumannii* | 80 | 625 | 54 | A25G23C21T32 | A29G28C21T43 | A17G13C13T21 |
| *A. baumannii* | 81 | 628 | 54 | A25G23C21T32 | A29G28C21T43 | A17G13C13T21 |
| *A. baumannii* | 82 | 632 | 54 | A25G23C21T32 | A29G28C21T43 | A17G13C13T21 |
| *A. baumannii* | 84 | 649 | 54 | A25G23C21T32 | A29G28C21T43 | A17G13C13T21 |

TABLE 16A-continued

Base Compositions Determined from *A. baumannii* DNA Samples Obtained from Northwestern Medical Center and Amplified with Codon Analysis Primer Pairs Targeting the gyrA Gene

| Species | Ibis# | Isolate | ST | PP No: 2852 gyrA | PP No: 2853 gyrA | PP No: 2854 gyrA |
|---|---|---|---|---|---|---|
| *A. baumannii* | 86 | 655 | 54 | A25G23C21T32 | A29G28C21T43 | A17G13C13T21 |
| *A. baumannii* | 88 | 668 | 54 | A25G23C21T32 | A29G28C21T43 | A17G13C13T21 |
| *A. baumannii* | 90 | 671 | 54 | A25G23C21T32 | A29G28C21T43 | A17G13C13T21 |
| *A. baumannii* | 91 | 672 | 54 | A25G23C21T32 | A29G28C21T43 | A17G13C13T21 |
| *A. baumannii* | 92 | 673 | 54 | A25G23C21T32 | A29G28C21T43 | A17G13C13T21 |
| *A. baumannii* | 18 | 196 | 55 | A25G23C22T31 | A29G28C21T43 | A17G13C13T21 |
| *A. baumannii* | 55 | 537 | 27 | A25G23C21T32 | A29G28C21T43 | A17G13C13T21 |
| *A. baumannii* | 28 | 263 | 27 | A25G23C22T31 | A29G28C22T42 | A17G13C14T20 |
| A. sp. 3 | 14 | 164 | B7 | A25G22C22T32 | A30G29C22T40 | A17G13C14T20 |
| mixture | 7 | 71 | — | ND | ND | A17G13C15T19 |

TABLE 16B

Base Compositions Determined from *A. baumannii* DNA Samples Obtained from Northwestern Medical Center and Amplified with Codon Analysis Primer Pairs Targeting the parC Gene

| Species | Ibis# | Isolate | ST | PP No: 2846 parC | PP No: 2847 parC | PP No: 2848 parC |
|---|---|---|---|---|---|---|
| *A. baumannii* | 54 | 536 | 3 | A33G26C28T34 | A29G28C25T32 | A16G14C14T16 |
| *A. baumannii* | 87 | 665 | 3 | A33G26C28T34 | A29G28C25T32 | A16G14C14T16 |
| *A. baumannii* | 8 | 80 | 10 | A33G26C28T34 | A29G28C25T32 | A16G14C14T16 |
| *A. baumannii* | 9 | 91 | 10 | A33G26C28T34 | A29G28C25T32 | A16G14C14T16 |
| *A. baumannii* | 10 | 92 | 10 | A33G26C28T34 | A29G28C25T32 | ND |
| *A. baumannii* | 11 | 131 | 10 | A33G26C28T34 | A29G28C25T32 | A16G14C14T16 |
| *A. baumannii* | 12 | 137 | 10 | A33G26C28T34 | A29G28C25T32 | A16G14C14T16 |
| *A. baumannii* | 21 | 218 | 10 | A33G26C28T34 | A29G28C25T32 | A16G14C14T16 |
| *A. baumannii* | 26 | 242 | 10 | A33G26C28T34 | A29G28C25T32 | A16G14C14T16 |
| *A. baumannii* | 94 | 678 | 10 | A33G26C28T34 | A29G28C25T32 | A16G14C14T16 |
| *A. baumannii* | 1 | 9 | 10 | A33G26C29T33 | A29G28C26T31 | A16G14C15T15 |
| *A. baumannii* | 2 | 13 | 10 | A33G26C29T33 | A29G28C26T31 | A16G14C15T15 |
| *A. baumannii* | 3 | 19 | 10 | A33G26C29T33 | A29G28C26T31 | A16G14C15T15 |
| *A. baumannii* | 4 | 24 | 10 | A33G26C29T33 | A29G28C26T31 | A16G14C15T15 |
| *A. baumannii* | 5 | 36 | 10 | A33G26C29T33 | A29G28C26T31 | A16G14C15T15 |
| *A. baumannii* | 6 | 39 | 10 | A33G26C29T33 | A29G28C26T31 | A16G14C15T15 |
| *A. baumannii* | 13 | 139 | 10 | A33G26C29T33 | A29G28C26T31 | A16G14C15T15 |
| *A. baumannii* | 15 | 165 | 10 | A33G26C29T33 | A29G28C26T31 | A16G14C15T15 |
| *A. baumannii* | 16 | 170 | 10 | A33G26C29T33 | A29G28C26T31 | A16G14C15T15 |
| *A. baumannii* | 17 | 186 | 10 | A33G26C29T33 | A29G28C26T31 | A16G14C15T15 |
| *A. baumannii* | 20 | 202 | 10 | A33G26C29T33 | A29G28C26T31 | A16G14C15T15 |
| *A. baumannii* | 22 | 221 | 10 | A33G26C29T33 | A29G28C26T31 | A16G14C15T15 |
| *A. baumannii* | 24 | 234 | 10 | A33G26C29T33 | A29G28C26T31 | A16G14C15T15 |
| *A. baumannii* | 25 | 239 | 10 | A33G26C29T33 | A29G28C26T31 | A16G14C15T15 |
| *A. baumannii* | 33 | 370 | 10 | A33G26C29T33 | A29G28C26T31 | A16G14C15T15 |
| *A. baumannii* | 34 | 389 | 10 | A33G26C29T33 | A29G28C26T31 | A16G14C15T15 |
| *A. baumannii* | 19 | 201 | 14 | A33G26C28T34 | A29G28C25T32 | A16G14C14T16 |
| *A. baumannii* | 27 | 257 | 51 | A33G26C28T34 | A29G28C25T32 | A16G14C14T16 |
| *A. baumannii* | 29 | 301 | 51 | A33G26C28T34 | A29G28C25T32 | A16G14C14T16 |
| *A. baumannii* | 31 | 354 | 51 | A33G26C28T34 | A29G28C25T32 | A16G14C14T16 |
| *A. baumannii* | 36 | 422 | 51 | A33G26C28T34 | A29G28C25T32 | A16G14C14T16 |
| *A. baumannii* | 37 | 424 | 51 | A33G26C28T34 | A29G28C25T32 | A16G14C14T16 |
| *A. baumannii* | 38 | 434 | 51 | A33G26C28T34 | A29G28C25T32 | A16G14C14T16 |
| *A. baumannii* | 39 | 473 | 51 | A33G26C28T34 | A29G28C25T32 | A16G14C14T16 |
| *A. baumannii* | 40 | 482 | 51 | A33G26C28T34 | A29G28C25T32 | A16G14C14T16 |
| *A. baumannii* | 44 | 512 | 51 | A33G26C28T34 | A29G28C25T32 | A16G14C14T16 |
| *A. baumannii* | 45 | 516 | 51 | A33G26C28T34 | A29G28C25T32 | A16G14C14T16 |
| *A. baumannii* | 47 | 522 | 51 | A33G26C28T34 | A29G28C25T32 | A16G14C14T16 |
| *A. baumannii* | 48 | 526 | 51 | A33G26C28T34 | A29G28C25T32 | A16G14C14T16 |
| *A. baumannii* | 50 | 528 | 51 | A33G26C28T34 | A29G28C25T32 | A16G14C14T16 |
| *A. baumannii* | 52 | 531 | 51 | A33G26C28T34 | A29G28C25T32 | A16G14C14T16 |
| *A. baumannii* | 53 | 533 | 51 | A33G26C28T34 | A29G28C25T32 | A16G14C14T16 |
| *A. baumannii* | 56 | 542 | 51 | A33G26C28T34 | A29G28C25T32 | A16G14C14T16 |
| *A. baumannii* | 59 | 550 | 51 | A33G26C28T34 | A29G28C25T32 | A16G14C14T16 |
| *A. baumannii* | 62 | 556 | 51 | A33G26C28T34 | A29G28C25T32 | A16G14C14T16 |
| *A. baumannii* | 64 | 557 | 51 | A33G26C28T34 | A29G28C25T32 | A16G14C14T16 |
| *A. baumannii* | 70 | 588 | 51 | A33G26C28T34 | A29G28C25T32 | A16G14C14T16 |
| *A. baumannii* | 73 | 603 | 51 | A33G26C28T34 | A29G28C25T32 | A16G14C14T16 |
| *A. baumannii* | 74 | 605 | 51 | A33G26C28T34 | A29G28C25T32 | A16G14C14T16 |
| *A. baumannii* | 75 | 606 | 51 | A33G26C28T34 | A29G28C25T32 | A16G14C14T16 |
| *A. baumannii* | 77 | 611 | 51 | A33G26C28T34 | A29G28C25T32 | A16G14C14T16 |
| *A. baumannii* | 79 | 622 | 51 | A33G26C28T34 | A29G28C25T32 | A16G14C14T16 |

TABLE 16B-continued

Base Compositions Determined from *A. baumannii* DNA Samples Obtained from Northwestern Medical Center and Amplified with Codon Analysis Primer Pairs Targeting the parC Gene

| Species | Ibis# | Isolate | ST | PP No: 2846 parC | PP No: 2847 parC | PP No: 2848 parC |
|---|---|---|---|---|---|---|
| *A. baumannii* | 83 | 643 | 51 | A33G26C28T34 | A29G28C25T32 | A16G14C14T16 |
| *A. baumannii* | 85 | 653 | 51 | A33G26C28T34 | A29G28C25T32 | A16G14C14T16 |
| *A. baumannii* | 89 | 669 | 51 | A33G26C28T34 | A29G28C25T32 | A16G14C14T16 |
| *A. baumannii* | 93 | 674 | 51 | A33G26C28T34 | A29G28C25T32 | A16G14C14T16 |
| *A. baumannii* | 23 | 228 | 51 | A34G25C29T33 | A30G27C26T31 | A16G14C15T15 |
| *A. baumannii* | 32 | 369 | 52 | A34G25C28T34 | A30G27C25T32 | A16G14C14T16 |
| *A. baumannii* | 35 | 393 | 52 | A34G25C28T34 | A30G27C25T32 | A16G14C14T16 |
| *A. baumannii* | 30 | 339 | 53 | A34G25C29T33 | A30G27C26T31 | A16G14C15T15 |
| *A. baumannii* | 41 | 485 | 53 | A34G25C29T33 | A30G27C26T31 | A16G14C15T15 |
| *A. baumannii* | 42 | 493 | 53 | A34G25C29T33 | A30G27C26T31 | A16G14C15T15 |
| *A. baumannii* | 43 | 502 | 53 | A34G25C29T33 | A30G27C26T31 | A16G14C15T15 |
| *A. baumannii* | 46 | 520 | 53 | A34G25C29T33 | A30G27C26T31 | A16G14C15T15 |
| *A. baumannii* | 49 | 527 | 53 | A34G25C29T33 | A30G27C26T31 | A16G14C15T15 |
| *A. baumannii* | 51 | 529 | 53 | A34G25C29T33 | A30G27C26T31 | A16G14C15T15 |
| *A. baumannii* | 65 | 562 | 53 | A34G25C29T33 | A30G27C26T31 | A16G14C15T15 |
| *A. baumannii* | 68 | 579 | 53 | A34G25C29T33 | A30G27C26T31 | A16G14C15T15 |
| *A. baumannii* | 57 | 546 | 54 | A33G26C28T34 | A29G28C25T32 | A16G14C14T16 |
| *A. baumannii* | 58 | 548 | 54 | A33G26C28T34 | A29G28C25T32 | A16G14C14T16 |
| *A. baumannii* | 60 | 552 | 54 | A33G26C28T34 | A29G28C25T32 | A16G14C14T16 |
| *A. baumannii* | 61 | 555 | 54 | A33G26C28T34 | A29G28C25T32 | A16G14C14T16 |
| *A. baumannii* | 63 | 557 | 54 | A33G26C28T34 | A29G28C25T32 | A16G14C14T16 |
| *A. baumannii* | 66 | 570 | 54 | A33G26C28T34 | A29G28C25T32 | A16G14C14T16 |
| *A. baumannii* | 67 | 578 | 54 | A33G26C28T34 | A29G28C25T32 | A16G14C14T16 |
| *A. baumannii* | 69 | 584 | 54 | A33G26C28T34 | A29G28C25T32 | A16G14C14T16 |
| *A. baumannii* | 71 | 593 | 54 | A33G26C28T34 | A29G28C25T32 | A16G14C14T16 |
| A. *baumannii* | 72 | 602 | 54 | A33G26C28T34 | A29G28C25T32 | A16G14C14T16 |
| *A. baumannii* | 76 | 609 | 54 | A33G26C28T34 | A29G28C25T32 | A16G14C14T16 |
| *A. baumannii* | 78 | 621 | 54 | A33G26C28T34 | A29G28C25T32 | A16G14C14T16 |
| *A. baumannii* | 80 | 625 | 54 | A33G26C28T34 | A29G28C25T32 | A16G14C14T16 |
| *A. baumannii* | 81 | 628 | 54 | A33G26C28T34 | A29G28C25T32 | A16G14C14T16 |
| *A. baumannii* | 82 | 632 | 54 | A33G26C28T34 | A29G28C25T32 | A16G14C14T16 |
| *A. baumannii* | 84 | 649 | 54 | A33G26C28T34 | A29G28C25T32 | A16G14C14T16 |
| *A. baumannii* | 86 | 655 | 54 | A33G26C28T34 | A29G28C25T32 | A16G14C14T16 |
| *A. baumannii* | 88 | 668 | 54 | A33G26C28T34 | A29G28C25T32 | A16G14C14T16 |
| *A. baumannii* | 90 | 671 | 54 | A33G26C28T34 | A29G28C25T32 | A16G14C14T16 |
| *A. baumannii* | 91 | 672 | 54 | A33G26C28T34 | A29G28C25T32 | A16G14C14T16 |
| *A. baumannii* | 92 | 673 | 54 | A33G26C28T34 | A29G28C25T32 | A16G14C14T16 |
| *A. baumannii* | 18 | 196 | 55 | A33G27C28T33 | A29G28C25T31 | A15G14C15T16 |
| *A. baumannii* | 55 | 537 | 27 | A33G26C29T33 | A29G28C26T31 | A16G14C15T15 |
| *A. baumannii* | 28 | 263 | 27 | A33G26C29T33 | A29G28C26T31 | A16G14C15T15 |
| A. sp. 3 | 14 | 164 | B7 | A35G25C29T32 | A30G28C17T39 | A16G14C15T15 |
| mixture | 7 | 71 | — | ND | ND | A17G14C15T14 |

TABLE 17A

Base Compositions Determined from *A. baumannii* DNA Samples Obtained from Walter Reed Hospital and Amplified with Speciating Primer Pair No. 2922 and Triangulation Genotyping Analysis Primer Pair Nos. 1151 and 1156

| Species | Ibis# | Isolate | ST | PP No: 2922 efp | PP No: 1151 trpE | PP No: 1156 Adk |
|---|---|---|---|---|---|---|
| *A. baumannii* | 20 | 1082 | 1 | A45G34C25T43 | A44G35C21T42 | A44G32C26T38 |
| *A. baumannii* | 13 | 854 | 10 | A45G34C25T43 | A44G35C21T42 | A44G32C26T38 |
| *A. baumannii* | 22 | 1162 | 10 | A45G34C25T43 | A44G35C21T42 | A44G32C26T38 |
| *A. baumannii* | 27 | 1230 | 10 | A45G34C25T43 | A44G35C21T42 | A44G32C26T38 |
| *A. baumannii* | 31 | 1367 | 10 | A45G34C25T43 | A44G35C21T42 | A44G32C26T38 |
| *A. baumannii* | 37 | 1459 | 10 | A45G34C25T43 | A44G35C21T42 | A44G32C26T38 |
| *A. baumannii* | 55 | 1700 | 10 | A45G34C25T43 | A44G35C21T42 | A44G32C26T38 |
| *A. baumannii* | 64 | 1777 | 10 | A45G34C25T43 | A44G35C21T42 | A44G32C26T38 |
| *A. baumannii* | 73 | 1861 | 10 | A45G34C25T43 | A44G35C21T42 | A44G32C26T38 |
| *A. baumannii* | 74 | 1877 | 10 | A45G34C25T43 | A44G35C21T42 | A44G32C26T38 |
| *A. baumannii* | 86 | 1972 | 10 | A45G34C25T43 | A44G35C21T42 | A44G32C26T38 |
| *A. baumannii* | 3 | 684 | 11 | A45G34C25T43 | A44G35C21T42 | A44G32C26T38 |
| *A. baumannii* | 6 | 720 | 11 | A45G34C25T43 | A44G35C21T42 | A44G32C26T38 |
| *A. baumannii* | 7 | 726 | 11 | A45G34C25T43 | A44G35C21T42 | A44G32C26T38 |
| *A. baumannii* | 19 | 1079 | 11 | A45G34C25T43 | A44G35C21T42 | A44G32C26T38 |
| *A. baumannii* | 21 | 1123 | 11 | A45G34C25T43 | A44G35C21T42 | A44G32C26T38 |
| *A. baumannii* | 23 | 1188 | 11 | A45G34C25T43 | A44G35C21T42 | A44G32C26T38 |
| *A. baumannii* | 33 | 1417 | 11 | A45G34C25T43 | A44G35C21T42 | A44G32C26T38 |
| *A. baumannii* | 34 | 1431 | 11 | A45G34C25T43 | A44G35C21T42 | A44G32C26T38 |
| *A. baumannii* | 38 | 1496 | 11 | A45G34C25T43 | A44G35C21T42 | A44G32C26T38 |

TABLE 17A-continued

Base Compositions Determined from *A. baumannii* DNA Samples Obtained from Walter Reed Hospital and Amplified with Speciating Primer Pair No. 2922 and Triangulation Genotyping Analysis Primer Pair Nos. 1151 and 1156

| Species | Ibis# | Isolate | ST | PP No: 2922 efp | PP No: 1151 trpE | PP No: 1156 Adk |
|---|---|---|---|---|---|---|
| *A. baumannii* | 40 | 1523 | 11 | A45G34C25T43 | A44G35C21T42 | A44G32C26T38 |
| *A. baumannii* | 42 | 1640 | 11 | A45G34C25T43 | A44G35C21T42 | A44G32C26T38 |
| *A. baumannii* | 50 | 1666 | 11 | A45G34C25T43 | A44G35C21T42 | A44G32C26T38 |
| *A. baumannii* | 51 | 1668 | 11 | A45G34C25T43 | A44G35C21T42 | A44G32C26T38 |
| *A. baumannii* | 52 | 1695 | 11 | A45G34C25T43 | A44G35C21T42 | A44G32C26T38 |
| *A. baumannii* | 65 | 1781 | 11 | A45G34C25T43 | A44G35C21T42 | A44G32C26T38 |
| *A. baumannii* | 44 | 1649 | 12 | A45G34C25T43 | A44G35C21T42 | A44G32C26T38 |
| *A. baumannii* | 49A | 1658.1 | 12 | A45G34C25T43 | A44G35C21T42 | A44G32C26T38 |
| *A. baumannii* | 49B | 1658.2 | 12 | A45G34C25T43 | A44G35C21T42 | A44G32C26T38 |
| *A. baumannii* | 56 | 1707 | 12 | A45G34C25T43 | A44G35C21T42 | A44G32C26T38 |
| *A. baumannii* | 80 | 1893 | 12 | A45G34C25T43 | A44G35C21T42 | A44G32C26T38 |
| *A. baumannii* | 5 | 693 | 14 | A44G35C25T43 | A44G35C22T41 | A44G32C27T37 |
| *A. baumannii* | 8 | 749 | 14 | A44G35C25T43 | A44G35C22T41 | A44G32C27T37 |
| *A. baumannii* | 10 | 839 | 14 | A44G35C25T43 | A44G35C22T41 | A44G32C27T37 |
| *A. baumannii* | 14 | 865 | 14 | A44G35C25T43 | A44G35C22T41 | A44G32C27T37 |
| *A. baumannii* | 16 | 888 | 14 | A44G35C25T43 | A44G35C22T41 | A44G32C27T37 |
| *A. baumannii* | 29 | 1326 | 14 | A44G35C25T43 | A44G35C22T41 | A44G32C27T37 |
| *A. baumannii* | 35 | 1440 | 14 | A44G35C25T43 | ND | A44G32C27T37 |
| *A. baumannii* | 41 | 1524 | 14 | A44G35C25T43 | A44G35C22T41 | A44G32C27T37 |
| *A. baumannii* | 46 | 1652 | 14 | A44G35C25T43 | A44G35C22T41 | A44G32C27T37 |
| *A. baumannii* | 47 | 1653 | 14 | A44G35C25T43 | A44G35C22T41 | A44G32C27T37 |
| *A. baumannii* | 48 | 1657 | 14 | A44G35C25T43 | A44G35C22T41 | A44G32C27T37 |
| *A. baumannii* | 57 | 1709 | 14 | A44G35C25T43 | A44G35C22T41 | A44G32C27T37 |
| *A. baumannii* | 61 | 1727 | 14 | A44G35C25T43 | A44G35C22T41 | A44G32C27T37 |
| *A. baumannii* | 63 | 1762 | 14 | A44G35C25T43 | A44G35C22T41 | A44G32C27T37 |
| *A. baumannii* | 67 | 1806 | 14 | A44G35C25T43 | A44G35C22T41 | A44G32C27T37 |
| *A. baumannii* | 75 | 1881 | 14 | A44G35C25T43 | A44G35C22T41 | A44G32C27T37 |
| *A. baumannii* | 77 | 1886 | 14 | A44G35C25T43 | A44G35C22T41 | A44G32C27T37 |
| *A. baumannii* | 1 | 649 | 46 | A44G35C25T43 | A44G35C22T41 | A44G32C26T38 |
| *A. baumannii* | 2 | 653 | 46 | A44G35C25T43 | A44G35C22T41 | A44G32C26T38 |
| *A. baumannii* | 39 | 1497 | 16 | A44G35C25T43 | A44G35C22T41 | A44G32C27T37 |
| *A. baumannii* | 24 | 1198 | 15 | A44G35C25T43 | A44G35C22T41 | A44G32C26T38 |
| *A. baumannii* | 28 | 1243 | 15 | A44G35C25T43 | A44G35C22T41 | A44G32C26T38 |
| *A. baumannii* | 43 | 1648 | 15 | A44G35C25T43 | A44G35C22T41 | A44G32C26T38 |
| *A. baumannii* | 62 | 1746 | 15 | A44G35C25T43 | A44G35C22T41 | A44G32C26T38 |
| *A. baumannii* | 4 | 689 | 15 | A44G35C25T43 | A44G35C22T41 | A44G32C26T38 |
| *A. baumannii* | 68 | 1822 | 3 | A44G35C24T44 | A44G35C22T41 | A44G32C26T38 |
| *A. baumannii* | 69 | 1823A | 3 | A44G35C24T44 | A44G35C22T41 | A44G32C26T38 |
| *A. baumannii* | 70 | 1823B | 3 | A44G35C24T44 | A44G35C22T41 | A44G32C26T38 |
| *A. baumannii* | 71 | 1826 | 3 | A44G35C24T44 | A44G35C22T41 | A44G32C26T38 |
| *A. baumannii* | 72 | 1860 | 3 | A44G35C24T44 | A44G35C22T41 | A44G32C26T38 |
| *A. baumannii* | 81 | 1924 | 3 | A44G35C24T44 | A44G35C22T41 | A44G32C26T38 |
| *A. baumannii* | 82 | 1929 | 3 | A44G35C24T44 | A44G35C22T41 | A44G32C26T38 |
| *A. baumannii* | 85 | 1966 | 3 | A44G35C24T44 | A44G35C22T41 | A44G32C26T38 |
| *A. baumannii* | 11 | 841 | 3 | A44G35C24T44 | A44G35C22T41 | A44G32C26T38 |
| *A. baumannii* | 32 | 1415 | 24 | A44G35C25T43 | A43G36C20T43 | A44G32C27T37 |
| *A. baumannii* | 45 | 1651 | 24 | A44G35C25T43 | A43G36C20T43 | A44G32C27T37 |
| *A. baumannii* | 54 | 1697 | 24 | A44G35C25T43 | A43G36C20T43 | A44G32C27T37 |
| *A. baumannii* | 58 | 1712 | 24 | A44G35C25T43 | A43G36C20T43 | A44G32C27T37 |
| *A. baumannii* | 60 | 1725 | 24 | A44G35C25T43 | A43G36C20T43 | A44G32C27T37 |
| *A. baumannii* | 66 | 1802 | 24 | A44G35C25T43 | A43G36C20T43 | A44G32C27T37 |
| *A. baumannii* | 76 | 1883 | 24 | ND | A43G36C20T43 | A44G32C27T37 |
| *A. baumannii* | 78 | 1891 | 24 | A44G35C25T43 | A43G36C20T43 | A44G32C27T37 |
| *A. baumannii* | 79 | 1892 | 24 | A44G35C25T43 | A43G36C20T43 | A44G32C27T37 |
| *A. baumannii* | 83 | 1947 | 24 | A44G35C25T43 | A43G36C20T43 | A44G32C27T37 |
| *A. baumannii* | 84 | 1964 | 24 | A44G35C25T43 | A43G36C20T43 | A44G32C27T37 |
| *A. baumannii* | 53 | 1696 | 24 | A44G35C25T43 | A43G36C20T43 | A44G32C27T37 |
| *A. baumannii* | 36 | 1458 | 49 | A44G35C25T43 | A44G35C22T41 | A44G32C27T37 |
| *A. baumannii* | 59 | 1716 | 9 | A44G35C25T43 | A44G35C21T42 | A44G32C26T38 |
| *A. baumannii* | 9 | 805 | 30 | A44G35C25T43 | A44G35C19T44 | A44G32C27T37 |
| *A. baumannii* | 18 | 967 | 39 | A45G34C25T43 | A44G35C22T41 | A44G32C26T38 |
| *A. baumannii* | 30 | 1322 | 48 | A44G35C25T43 | A43G36C20T43 | A44G32C27T37 |
| *A. baumannii* | 26 | 1218 | 50 | A44G35C25T43 | A44G35C21T42 | A44G32C26T38 |
| A. sp. 13TU | 15 | 875 | A1 | A47G33C24T43 | A46G32C20T44 | A44G33C27T36 |
| A. sp. 13TU | 17 | 895 | A1 | A47G33C24T43 | A46G32C20T44 | A44G33C27T36 |
| A. sp.3 | 12 | 853 | B7 | A46G35C24T42 | A42G34C20T46 | A43G33C24T40 |
| *A. johnsonii* | 25 | 1202 | NEW1 | A46G35C23T43 | A42G35C21T44 | A43G33C23T41 |
| A. sp. 2082 | 87 | 2082 | NEW2 | A46G36C22T43 | A42G32C20T48 | A42G34C23T41 |

TABLE 17B

Base Compositions Determined from *A. baumannii* DNA Samples Obtained from Walter Reed Hospital and Amplified with Triangulation Genotyping Analysis Primer Pair Nos. 1158 and 1160 and 1165

| Species | Ibis# | Isolate | ST | PP No: 1158 mutY | PP No: 1160 mutY | PP No: 1165 fumC |
|---|---|---|---|---|---|---|
| *A. baumannii* | 20 | 1082 | 1 | A27G21C25T22 | A32G35C29T33 | A40G33C30T36 |
| *A. baumannii* | 13 | 854 | 10 | A27G21C26T21 | A32G35C28T34 | A40G33C30T36 |
| *A. baumannii* | 22 | 1162 | 10 | A27G21C26T21 | A32G35C28T34 | A40G33C30T36 |
| *A. baumannii* | 27 | 1230 | 10 | A27G21C26T21 | A32G35C28T34 | A40G33C30T36 |
| *A. baumannii* | 31 | 1367 | 10 | A27G21C26T21 | A32G35C28T34 | A40G33C30T36 |
| *A. baumannii* | 37 | 1459 | 10 | A27G21C26T21 | A32G35C28T34 | A40G33C30T36 |
| *A. baumannii* | 55 | 1700 | 10 | A27G21C26T21 | A32G35C28T34 | A40G33C30T36 |
| *A. baumannii* | 64 | 1777 | 10 | A27G21C26T21 | A32G35C28T34 | A40G33C30T36 |
| *A. baumannii* | 73 | 1861 | 10 | A27G21C26T21 | A32G35C28T34 | A40G33C30T36 |
| *A. baumannii* | 74 | 1877 | 10 | A27G21C26T21 | A32G35C28T34 | A40G33C30T36 |
| *A. baumannii* | 86 | 1972 | 10 | A27G21C26T21 | A32G35C28T34 | A40G33C30T36 |
| *A. baumannii* | 3 | 684 | 11 | A27G21C25T22 | A32G34C28T35 | A40G33C30T36 |
| *A. baumannii* | 6 | 720 | 11 | A27G21C25T22 | A32G34C28T35 | A40G33C30T36 |
| *A. baumannii* | 7 | 726 | 11 | A27G21C25T22 | A32G34C28T35 | A40G33C30T36 |
| *A. baumannii* | 19 | 1079 | 11 | A27G21C25T22 | A32G34C28T35 | A40G33C30T36 |
| *A. baumannii* | 21 | 1123 | 11 | A27G21C25T22 | A32G34C28T35 | A40G33C30T36 |
| *A. baumannii* | 23 | 1188 | 11 | A27G21C25T22 | A32G34C28T35 | A40G33C30T36 |
| *A. baumannii* | 33 | 1417 | 11 | A27G21C25T22 | A32G34C28T35 | A40G33C30T36 |
| *A. baumannii* | 34 | 1431 | 11 | A27G21C25T22 | A32G34C28T35 | A40G33C30T36 |
| *A. baumannii* | 38 | 1496 | 11 | A27G21C25T22 | A32G34C28T35 | A40G33C30T36 |
| *A. baumannii* | 40 | 1523 | 11 | A27G21C25T22 | A32G34C28T35 | A40G33C30T36 |
| *A. baumannii* | 42 | 1640 | 11 | A27G21C25T22 | A32G34C28T35 | A40G33C30T36 |
| *A. baumannii* | 50 | 1666 | 11 | A27G21C25T22 | A32G34C28T35 | A40G33C30T36 |
| *A. baumannii* | 51 | 1668 | 11 | A27G21C25T22 | A32G34C28T35 | A40G33C30T36 |
| *A. baumannii* | 52 | 1695 | 11 | A27G21C25T22 | A32G34C28T35 | A40G33C30T36 |
| *A. baumannii* | 65 | 1781 | 11 | A27G21C25T22 | A32G34C28T35 | A40G33C30T36 |
| *A. baumannii* | 44 | 1649 | 12 | A27G21C26T21 | A32G34C29T34 | A40G33C30T36 |
| *A. baumannii* | 49A | 1658.1 | 12 | A27G21C26T21 | A32G34C29T34 | A40G33C30T36 |
| *A. baumannii* | 49B | 1658.2 | 12 | A27G21C26T21 | A32G34C29T34 | A40G33C30T36 |
| *A. baumannii* | 56 | 1707 | 12 | A27G21C26T21 | A32G34C29T34 | A40G33C30T36 |
| *A. baumannii* | 80 | 1893 | 12 | A27G21C26T21 | A32G34C29T34 | A40G33C30T36 |
| *A. baumannii* | 5 | 693 | 14 | A27G21C25T22 | A31G36C28T34 | A40G33C29T37 |
| *A. baumannii* | 8 | 749 | 14 | A27G21C25T22 | A31G36C28T34 | A40G33C29T37 |
| *A. baumannii* | 10 | 839 | 14 | A27G21C25T22 | A31G36C28T34 | A40G33C29T37 |
| *A. baumannii* | 14 | 865 | 14 | A27G21C25T22 | A31G36C28T34 | A40G33C29T37 |
| *A. baumannii* | 16 | 888 | 14 | A27G21C25T22 | A31G36C28T34 | A40G33C29T37 |
| *A. baumannii* | 29 | 1326 | 14 | A27G21C25T22 | A31G36C28T34 | A40G33C29T37 |
| *A. baumannii* | 35 | 1440 | 14 | A27G21C25T22 | A31G36C28T34 | A40G33C29T37 |
| *A. baumannii* | 41 | 1524 | 14 | A27G21C25T22 | A31G36C28T34 | A40G33C29T37 |
| *A. baumannii* | 46 | 1652 | 14 | A27G21C25T22 | A31G36C28T34 | A40G33C29T37 |
| *A. baumannii* | 47 | 1653 | 14 | A27G21C25T22 | A31G36C28T34 | A40G33C29T37 |
| *A. baumannii* | 48 | 1657 | 14 | A27G21C25T22 | A31G36C28T34 | A40G33C29T37 |
| *A. baumannii* | 57 | 1709 | 14 | A27G21C25T22 | A31G36C28T34 | A40G33C29T37 |
| *A. baumannii* | 61 | 1727 | 14 | A27G21C25T22 | A31G36C28T34 | A40G33C29T37 |
| *A. baumannii* | 63 | 1762 | 14 | A27G21C25T22 | A31G36C28T34 | A40G33C29T37 |
| *A. baumannii* | 67 | 1806 | 14 | A27G21C25T22 | A31G36C28T34 | A40G33C29T37 |
| *A. baumannii* | 75 | 1881 | 14 | A27G21C25T22 | A31G36C28T34 | A40G33C29T37 |
| *A. baumannii* | 77 | 1886 | 14 | A27G21C25T22 | A31G36C28T34 | A40G33C29T37 |
| *A. baumannii* | 1 | 649 | 46 | A29G19C26T21 | A31G35C29T34 | A40G33C29T37 |
| *A. baumannii* | 2 | 653 | 46 | A29G19C26T21 | A31G35C29T34 | A40G33C29T37 |
| *A. baumannii* | 39 | 1497 | 16 | A29G19C26T21 | A31G35C29T34 | A40G34C29T36 |
| *A. baumannii* | 24 | 1198 | 15 | A29G19C26T21 | A31G35C29T34 | A40G33C29T37 |
| *A. baumannii* | 28 | 1243 | 15 | A29G19C26T21 | A31G35C29T34 | A40G33C29T37 |
| *A. baumannii* | 43 | 1648 | 15 | A29G19C26T21 | A31G35C29T34 | A40G33C29T37 |
| *A. baumannii* | 62 | 1746 | 15 | A29G19C26T21 | A31G35C29T34 | A40G33C29T37 |
| *A. baumannii* | 4 | 689 | 15 | A29G19C26T21 | A31G35C29T34 | A40G33C29T37 |
| *A. baumannii* | 68 | 1822 | 3 | A27G20C27T21 | A32G35C28T34 | A40G33C30T36 |
| *A. baumannii* | 69 | 1823A | 3 | A27G20C27T21 | A32G35C28T34 | A40G33C30T36 |
| *A. baumannii* | 70 | 1823B | 3 | A27G20C27T21 | A32G35C28T34 | A40G33C30T36 |
| *A. baumannii* | 71 | 1826 | 3 | A27G20C27T21 | A32G35C28T34 | A40G33C30T36 |
| *A. baumannii* | 72 | 1860 | 3 | A27G20C27T21 | A32G35C28T34 | A40G33C30T36 |
| *A. baumannii* | 81 | 1924 | 3 | A27G20C27T21 | A32G35C28T34 | A40G33C30T36 |
| *A. baumannii* | 82 | 1929 | 3 | A27G20C27T21 | A32G35C28T34 | A40G33C30T36 |
| *A. baumannii* | 85 | 1966 | 3 | A27G20C27T21 | A32G35C28T34 | A40G33C30T36 |
| *A. baumannii* | 11 | 841 | 3 | A27G20C27T21 | A32G35C28T34 | A40G33C30T36 |
| *A. baumannii* | 32 | 1415 | 24 | A27G21C26T21 | A32G35C28T34 | A40G33C30T36 |
| *A. baumannii* | 45 | 1651 | 24 | A27G21C26T21 | A32G35C28T34 | A40G33C30T36 |
| *A. baumannii* | 54 | 1697 | 24 | A27G21C26T21 | A32G35C28T34 | A40G33C30T36 |
| *A. baumannii* | 58 | 1712 | 24 | A27G21C26T21 | A32G35C28T34 | A40G33C30T36 |
| *A. baumannii* | 60 | 1725 | 24 | A27G21C26T21 | A32G35C28T34 | A40G33C30T36 |
| *A. baumannii* | 66 | 1802 | 24 | A27G21C26T21 | A32G35C28T34 | A40G33C30T36 |
| *A. baumannii* | 76 | 1883 | 24 | A27G21C26T21 | A32G35C28T34 | A40G33C30T36 |
| *A. baumannii* | 78 | 1891 | 24 | A27G21C26T21 | A32G35C28T34 | A40G33C30T36 |
| *A. baumannii* | 79 | 1892 | 24 | A27G21C26T21 | A32G35C28T34 | A40G33C30T36 |

TABLE 17B-continued

Base Compositions Determined from *A. baumannii* DNA Samples Obtained from Walter Reed Hospital and Amplified with Triangulation Genotyping Analysis Primer Pair Nos. 1158 and 1160 and 1165

| Species | Ibis# | Isolate | ST | PP No: 1158 mutY | PP No: 1160 mutY | PP No: 1165 fumC |
|---|---|---|---|---|---|---|
| *A. baumannii* | 83 | 1947 | 24 | A27G21C26T21 | A32G35C28T34 | A40G33C30T36 |
| *A. baumannii* | 84 | 1964 | 24 | A27G21C26T21 | A32G35C28T34 | A40G33C30T36 |
| *A. baumannii* | 53 | 1696 | 24 | A27G21C26T21 | A32G35C28T34 | A40G33C30T36 |
| *A. baumannii* | 36 | 1458 | 49 | A27G20C27T21 | A32G35C28T34 | A40G33C30T36 |
| *A. baumannii* | 59 | 1716 | 9 | A27G21C25T22 | A32G35C28T34 | A39G33C30T37 |
| *A. baumannii* | 9 | 805 | 30 | A27G21C25T22 | A32G35C28T34 | A39G33C30T37 |
| *A. baumannii* | 18 | 967 | 39 | A27G21C26T21 | A32G35C28T34 | A39G33C30T37 |
| *A. baumannii* | 30 | 1322 | 48 | A28G21C24T22 | A32G35C29T33 | A40G33C30T36 |
| *A. baumannii* | 26 | 1218 | 50 | A27G21C25T22 | A31G36C28T34 | A40G33C29T37 |
| A. sp. 13TU | 15 | 875 | A1 | A27G21C25T22 | A30G36C26T37 | A41G34C28T36 |
| A. sp. 13TU | 17 | 895 | A1 | A27G21C25T22 | A30G36C26T37 | A41G34C28T36 |
| A. sp. 3 | 12 | 853 | B7 | A26G23C23T23 | A30G36C27T36 | A39G37C26T37 |
| *A. johnsonii* | 25 | 1202 | NEW1 | A25G23C24T23 | A30G35C30T34 | A38G37C26T38 |
| A. sp. 2082 | 87 | 2082 | NEW2 | A26G22C24T23 | A31G35C28T35 | A42G34C27T36 |

TABLE 17C

Base Compositions Determined from *A. baumannii* DNA Samples Obtained from Walter Reed Hospital and Amplified with Triangulation Genotyping Analysis Primer Pair Nos. 1167 and 1170 and 1171

| Species | Ibis# | Isolate | ST | PP No: 1167 fumC | PP No: 1170 fumC | PP No: 1171 ppa |
|---|---|---|---|---|---|---|
| *A. baumannii* | 20 | 1082 | 1 | A41G34C34T38 | A38G27C21T50 | A35G37C33T44 |
| *A. baumannii* | 13 | 854 | 10 | A41G34C34T38 | A38G27C21T50 | A35G37C33T44 |
| *A. baumannii* | 22 | 1162 | 10 | A41G34C34T38 | A38G27C21T50 | A35G37C33T44 |
| *A. baumannii* | 27 | 1230 | 10 | A41G34C34T38 | A38G27C21T50 | A35G37C33T44 |
| *A. baumannii* | 31 | 1367 | 10 | A41G34C34T38 | A38G27C21T50 | A35G37C33T44 |
| *A. baumannii* | 37 | 1459 | 10 | A41G34C34T38 | A38G27C21T50 | A35G37C33T44 |
| *A. baumannii* | 55 | 1700 | 10 | A41G34C34T38 | A38G27C21T50 | A35G37C33T44 |
| *A. baumannii* | 64 | 1777 | 10 | A41G34C34T38 | A38G27C21T50 | A35G37C33T44 |
| *A. baumannii* | 73 | 1861 | 10 | A41G34C34T38 | A38G27C21T50 | A35G37C33T44 |
| *A. baumannii* | 74 | 1877 | 10 | A41G34C34T38 | A38G27C21T50 | A35G37C33T44 |
| *A. baumannii* | 86 | 1972 | 10 | A41G34C34T38 | A38G27C21T50 | A35G37C33T44 |
| *A. baumannii* | 3 | 684 | 11 | A41G34C34T38 | A38G27C21T50 | A35G37C33T44 |
| *A. baumannii* | 6 | 720 | 11 | A41G34C34T38 | A38G27C21T50 | A35G37C33T44 |
| *A. baumannii* | 7 | 726 | 11 | A41G34C34T38 | A38G27C21T50 | A35G37C33T44 |
| *A. baumannii* | 19 | 1079 | 11 | A41G34C34T38 | A38G27C21T50 | A35G37C33T44 |
| *A. baumannii* | 21 | 1123 | 11 | A41G34C34T38 | A38G27C21T50 | A35G37C33T44 |
| *A. baumannii* | 23 | 1188 | 11 | A41G34C34T38 | A38G27C21T50 | A35G37C33T44 |
| *A. baumannii* | 33 | 1417 | 11 | A41G34C34T38 | A38G27C21T50 | A35G37C33T44 |
| *A. baumannii* | 34 | 1431 | 11 | A41G34C34T38 | A38G27C21T50 | A35G37C33T44 |
| *A. baumannii* | 38 | 1496 | 11 | A41G34C34T38 | A38G27C21T50 | A35G37C33T44 |
| *A. baumannii* | 40 | 1523 | 11 | A41G34C34T38 | A38G27C21T50 | A35G37C33T44 |
| *A. baumannii* | 42 | 1640 | 11 | A41G34C34T38 | A38G27C21T50 | A35G37C33T44 |
| *A. baumannii* | 50 | 1666 | 11 | A41G34C34T38 | A38G27C21T50 | A35G37C33T44 |
| *A. baumannii* | 51 | 1668 | 11 | A41G34C34T38 | A38G27C21T50 | A35G37C33T44 |
| *A. baumannii* | 52 | 1695 | 11 | A41G34C34T38 | A38G27C21T50 | A35G37C33T44 |
| *A. baumannii* | 65 | 1781 | 11 | A41G34C34T38 | A38G27C21T50 | A35G37C33T44 |
| *A. baumannii* | 44 | 1649 | 12 | A41G34C34T38 | A38G27C21T50 | A35G37C33T44 |
| *A. baumannii* | 49A | 1658.1 | 12 | A41G34C34T38 | A38G27C21T50 | A35G37C33T44 |
| *A. baumannii* | 49B | 1658.2 | 12 | A41G34C34T38 | A38G27C21T50 | A35G37C33T44 |
| *A. baumannii* | 56 | 1707 | 12 | A41G34C34T38 | A38G27C21T50 | A35G37C33T44 |
| *A. baumannii* | 80 | 1893 | 12 | A41G34C34T38 | A38G27C21T50 | A35G37C33T44 |
| *A. baumannii* | 5 | 693 | 14 | A40G35C34T38 | A38G27C21T50 | A35G37C30T47 |
| *A. baumannii* | 8 | 749 | 14 | A40G35C34T38 | A38G27C21T50 | A35G37C30T47 |
| *A. baumannii* | 10 | 839 | 14 | A40G35C34T38 | A38G27C21T50 | A35G37C30T47 |
| *A. baumannii* | 14 | 865 | 14 | A40G35C34T38 | A38G27C21T50 | A35G37C30T47 |
| *A. baumannii* | 16 | 888 | 14 | A40G35C34T38 | A38G27C21T50 | A35G37C30T47 |
| *A. baumannii* | 29 | 1326 | 14 | A40G35C34T38 | A38G27C21T50 | A35G37C30T47 |
| *A. baumannii* | 35 | 1440 | 14 | A40G35C34T38 | A38G27C21T50 | A35G37C30T47 |
| *A. baumannii* | 41 | 1524 | 14 | A40G35C34T38 | A38G27C21T50 | A35G37C30T47 |
| *A. baumannii* | 46 | 1652 | 14 | A40G35C34T38 | A38G27C21T50 | A35G37C30T47 |
| *A. baumannii* | 47 | 1653 | 14 | A40G35C34T38 | A38G27C21T50 | A35G37C30T47 |
| *A. baumannii* | 48 | 1657 | 14 | A40G35C34T38 | A38G27C21T50 | A35G37C30T47 |
| *A. baumannii* | 57 | 1709 | 14 | A40G35C34T38 | A38G27C21T50 | A35G37C30T47 |
| *A. baumannii* | 61 | 1727 | 14 | A40G35C34T38 | A38G27C21T50 | A35G37C30T47 |
| *A. baumannii* | 63 | 1762 | 14 | A40G35C34T38 | A38G27C21T50 | A35G37C30T47 |
| *A. baumannii* | 67 | 1806 | 14 | A40G35C34T38 | A38G27C21T50 | A35G37C30T47 |
| *A. baumannii* | 75 | 1881 | 14 | A40G35C34T38 | A38G27C21T50 | A35G37C30T47 |
| *A. baumannii* | 77 | 1886 | 14 | A40G35C34T38 | A38G27C21T50 | A35G37C30T47 |

TABLE 17C-continued

Base Compositions Determined from *A. baumannii* DNA Samples Obtained from Walter Reed Hospital and Amplified with Triangulation Genotyping Analysis Primer Pair Nos. 1167 and 1170 and 1171

| Species | Ibis# | Isolate | ST | PP No: 1167 fumC | PP No: 1170 fumC | PP No: 1171 ppa |
|---|---|---|---|---|---|---|
| *A. baumannii* | 1 | 649 | 46 | A41G35C32T39 | A37G28C20T51 | A35G37C32T45 |
| *A. baumannii* | 2 | 653 | 46 | A41G35C32T39 | A37G28C20T51 | A35G37C32T45 |
| *A. baumannii* | 39 | 1497 | 16 | A41G35C32T39 | A37G28C20T51 | A35G37C30T47 |
| *A. baumannii* | 24 | 1198 | 15 | A41G35C32T39 | A37G28C20T51 | A35G37C30T47 |
| *A. baumannii* | 28 | 1243 | 15 | A41G35C32T39 | A37G28C20T51 | A35G37C30T47 |
| *A. baumannii* | 43 | 1648 | 15 | A41G35C32T39 | A37G28C20T51 | A35G37C30T47 |
| *A. baumannii* | 62 | 1746 | 15 | A41G35C32T39 | A37G28C20T51 | A35G37C30T47 |
| *A. baumannii* | 4 | 689 | 15 | A41G35C32T39 | A37G28C20T51 | A35G37C30T47 |
| *A. baumannii* | 68 | 1822 | 3 | A41G34C35T37 | A38G27C20T51 | A35G37C31T46 |
| *A. baumannii* | 69 | 1823A | 3 | A41G34C35T37 | A38G27C20T51 | A35G37C31T46 |
| *A. baumannii* | 70 | 1823B | 3 | A41G34C35T37 | A38G27C20T51 | A35G37C31T46 |
| *A. baumannii* | 71 | 1826 | 3 | A41G34C35T37 | A38G27C20T51 | A35G37C31T46 |
| *A. baumannii* | 72 | 1860 | 3 | A41G34C35T37 | A38G27C20T51 | A35G37C31T46 |
| *A. baumannii* | 81 | 1924 | 3 | A41G34C35T37 | A38G27C20T51 | A35G37C31T46 |
| *A. baumannii* | 82 | 1929 | 3 | A41G34C35T37 | A38G27C20T51 | A35G37C31T46 |
| *A. baumannii* | 85 | 1966 | 3 | A41G34C35T37 | A38G27C20T51 | A35G37C31T46 |
| *A. baumannii* | 11 | 841 | 3 | A41G34C35T37 | A38G27C20T51 | A35G37C31T46 |
| *A. baumannii* | 32 | 1415 | 24 | A40G35C34T38 | A39G26C22T49 | A35G37C33T44 |
| *A. baumannii* | 45 | 1651 | 24 | A40G35C34T38 | A39G26C22T49 | A35G37C33T44 |
| *A. baumannii* | 54 | 1697 | 24 | A40G35C34T38 | A39G26C22T49 | A35G37C33T44 |
| *A. baumannii* | 58 | 1712 | 24 | A40G35C34T38 | A39G26C22T49 | A35G37C33T44 |
| *A. baumannii* | 60 | 1725 | 24 | A40G35C34T38 | A39G26C22T49 | A35G37C33T44 |
| *A. baumannii* | 66 | 1802 | 24 | A40G35C34T38 | A39G26C22T49 | A35G37C33T44 |
| *A. baumannii* | 76 | 1883 | 24 | A40G35C34T38 | A39G26C22T49 | A35G37C33T44 |
| *A. baumannii* | 78 | 1891 | 24 | A40G35C34T38 | A39G26C22T49 | A35G37C33T44 |
| *A. baumannii* | 79 | 1892 | 24 | A40G35C34T38 | A39G26C22T49 | A35G37C33T44 |
| *A. baumannii* | 83 | 1947 | 24 | A40G35C34T38 | A39G26C22T49 | A35G37C33T44 |
| *A. baumannii* | 84 | 1964 | 24 | A40G35C34T38 | A39G26C22T49 | A35G37C33T44 |
| *A. baumannii* | 53 | 1696 | 24 | A40G35C34T38 | A39G26C22T49 | A35G37C33T44 |
| *A. baumannii* | 36 | 1458 | 49 | A40G35C34T38 | A39G26C22T49 | A35G37C30T47 |
| *A. baumannii* | 59 | 1716 | 9 | A40G35C32T40 | A38G27C20T51 | A36G35C31T47 |
| *A. baumannii* | 9 | 805 | 30 | A40G35C32T40 | A38G27C21T50 | A35G36C29T49 |
| *A. baumannii* | 18 | 967 | 39 | A40G35C33T39 | A38G27C20T51 | A35G37C30T47 |
| *A. baumannii* | 30 | 1322 | 48 | A40G35C35T37 | A38G27C21T50 | A35G37C30T47 |
| *A. baumannii* | 26 | 1218 | 50 | A40G35C34T38 | A38G27C21T50 | A35G37C33T44 |
| A. sp. 13TU | 15 | 875 | A1 | A41G39C31T36 | A37G26C24T49 | A34G38C31T46 |
| A. sp. 13TU | 17 | 895 | A1 | A41G39C31T36 | A37G26C24T49 | A34G38C31T46 |
| A. sp. 3 | 12 | 853 | B7 | A43G37C30T37 | A36G27C24T49 | A34G37C31T47 |
| *A. johnsonii* | 25 | 1202 | NEW1 | A42G38C31T36 | A40G27C19T50 | A35G37C32T45 |
| A. sp. 2082 | 87 | 2082 | NEW2 | A43G37C32T35 | A37G26C21T52 | A35G38C31T45 |

TABLE 18A

Base Compositions Determined from *A. baumannii* DNA Samples Obtained from Northwestern Medical Center and Amplified with Speciating Primer Pair No. 2922 and Triangulation Genotyping Analysis Primer Pair Nos. 1151 and 1156

| Species | Ibis# | Isolate | ST | PP No: 2922 efp | PP No: 1151 trpE | PP No: 1156 adk |
|---|---|---|---|---|---|---|
| *A. baumannii* | 54 | 536 | 3 | A44G35C24T44 | A44G35C22T41 | A44G32C26T38 |
| *A. baumannii* | 87 | 665 | 3 | A44G35C24T44 | A44G35C22T41 | A44G32C26T38 |
| *A. baumannii* | 8 | 80 | 10 | A45G34C25T43 | A44G35C21T42 | A44G32C26T38 |
| *A. baumannii* | 9 | 91 | 10 | A45G34C25T43 | A44G35C21T42 | A44G32C26T38 |
| *A. baumannii* | 10 | 92 | 10 | A45G34C25T43 | A44G35C21T42 | A44G32C26T38 |
| *A. baumannii* | 11 | 131 | 10 | A45G34C25T43 | A44G35C21T42 | A44G32C26T38 |
| *A. baumannii* | 12 | 137 | 10 | A45G34C25T43 | A44G35C21T42 | A44G32C26T38 |
| *A. baumannii* | 21 | 218 | 10 | A45G34C25T43 | A44G35C21T42 | A44G32C26T38 |
| *A. baumannii* | 26 | 242 | 10 | A45G34C25T43 | A44G35C21T42 | A44G32C26T38 |
| *A. baumannii* | 94 | 678 | 10 | A45G34C25T43 | A44G35C21T42 | A44G32C26T38 |
| *A. baumannii* | 1 | 9 | 10 | A45G34C25T43 | A44G35C21T42 | A44G32C26T38 |
| *A. baumannii* | 2 | 13 | 10 | A45G34C25T43 | A44G35C21T42 | A44G32C26T38 |
| *A. baumannii* | 3 | 19 | 10 | A45G34C25T43 | A44G35C21T42 | A44G32C26T38 |
| *A. baumannii* | 4 | 24 | 10 | A45G34C25T43 | A44G35C21T42 | A44G32C26T38 |
| *A. baumannii* | 5 | 36 | 10 | A45G34C25T43 | A44G35C21T42 | A44G32C26T38 |
| *A. baumannii* | 6 | 39 | 10 | A45G34C25T43 | A44G35C21T42 | A44G32C26T38 |
| *A. baumannii* | 13 | 139 | 10 | A45G34C25T43 | A44G35C21T42 | A44G32C26T38 |
| *A. baumannii* | 15 | 165 | 10 | A45G34C25T43 | A44G35C21T42 | A44G32C26T38 |
| *A. baumannii* | 16 | 170 | 10 | A45G34C25T43 | A44G35C21T42 | A44G32C26T38 |
| *A. baumannii* | 17 | 186 | 10 | A45G34C25T43 | A44G35C21T42 | A44G32C26T38 |
| *A. baumannii* | 20 | 202 | 10 | A45G34C25T43 | A44G35C21T42 | A44G32C26T38 |

TABLE 18A-continued

Base Compositions Determined from *A. baumannii* DNA Samples Obtained from Northwestern Medical Center and Amplified with Speciating Primer Pair No. 2922 and Triangulation Genotyping Analysis Primer Pair Nos. 1151 and 1156

| Species | Ibis# | Isolate | ST | PP No: 2922 efp | PP No: 1151 trpE | PP No: 1156 adk |
|---|---|---|---|---|---|---|
| *A. baumannii* | 22 | 221 | 10 | A45G34C25T43 | A44G35C21T42 | A44G32C26T38 |
| *A. baumannii* | 24 | 234 | 10 | A45G34C25T43 | A44G35C21T42 | A44G32C26T38 |
| *A. baumannii* | 25 | 239 | 10 | A45G34C25T43 | A44G35C21T42 | A44G32C26T38 |
| *A. baumannii* | 33 | 370 | 10 | A45G34C25T43 | A44G35C21T42 | A44G32C26T38 |
| *A. baumannii* | 34 | 389 | 10 | A45G34C25T43 | A44G35C21T42 | A44G32C26T38 |
| *A. baumannii* | 19 | 201 | 14 | A44G35C25T43 | A44G35C22T41 | A44G32C27T37 |
| *A. baumannii* | 27 | 257 | 51 | A44G35C25T43 | A43G36C20T43 | A44G32C26T38 |
| *A. baumannii* | 29 | 301 | 51 | A44G35C25T43 | A43G36C20T43 | A44G32C26T38 |
| *A. baumannii* | 31 | 354 | 51 | A44G35C25T43 | A43G36C20T43 | A44G32C26T38 |
| *A. baumannii* | 36 | 422 | 51 | A44G35C25T43 | A43G36C20T43 | A44G32C26T38 |
| *A. baumannii* | 37 | 424 | 51 | A44G35C25T43 | A43G36C20T43 | A44G32C26T38 |
| *A. baumannii* | 38 | 434 | 51 | A44G35C25T43 | A43G36C20T43 | A44G32C26T38 |
| *A. baumannii* | 39 | 473 | 51 | A44G35C25T43 | A43G36C20T43 | A44G32C26T38 |
| *A. baumannii* | 40 | 482 | 51 | A44G35C25T43 | A43G36C20T43 | A44G32C26T38 |
| *A. baumannii* | 44 | 512 | 51 | A44G35C25T43 | A43G36C20T43 | A44G32C26T38 |
| *A. baumannii* | 45 | 516 | 51 | A44G35C25T43 | A43G36C20T43 | A44G32C26T38 |
| *A. baumannii* | 47 | 522 | 51 | A44G35C25T43 | A43G36C20T43 | A44G32C26T38 |
| *A. baumannii* | 48 | 526 | 51 | A44G35C25T43 | A43G36C20T43 | A44G32C26T38 |
| *A. baumannii* | 50 | 528 | 51 | A44G35C25T43 | A43G36C20T43 | A44G32C26T38 |
| *A. baumannii* | 52 | 531 | 51 | A44G35C25T43 | A43G36C20T43 | A44G32C26T38 |
| *A. baumannii* | 53 | 533 | 51 | A44G35C25T43 | A43G36C20T43 | A44G32C26T38 |
| *A. baumannii* | 56 | 542 | 51 | A44G35C25T43 | A43G36C20T43 | A44G32C26T38 |
| *A. baumannii* | 59 | 550 | 51 | A44G35C25T43 | A43G36C20T43 | A44G32C26T38 |
| *A. baumannii* | 62 | 556 | 51 | A44G35C25T43 | A43G36C20T43 | A44G32C26T38 |
| *A. baumannii* | 64 | 557 | 51 | A44G35C25T43 | A43G36C20T43 | A44G32C26T38 |
| *A. baumannii* | 70 | 588 | 51 | A44G35C25T43 | A43G36C20T43 | A44G32C26T38 |
| *A. baumannii* | 73 | 603 | 51 | A44G35C25T43 | A43G36C20T43 | A44G32C26T38 |
| *A. baumannii* | 74 | 605 | 51 | A44G35C25T43 | A43G36C20T43 | A44G32C26T38 |
| *A. baumannii* | 75 | 606 | 51 | A44G35C25T43 | A43G36C20T43 | A44G32C26T38 |
| *A. baumannii* | 77 | 611 | 51 | A44G35C25T43 | A43G36C20T43 | A44G32C26T38 |
| *A. baumannii* | 79 | 622 | 51 | A44G35C25T43 | A43G36C20T43 | A44G32C26T38 |
| *A. baumannii* | 83 | 643 | 51 | A44G35C25T43 | A43G36C20T43 | A44G32C26T38 |
| *A. baumannii* | 85 | 653 | 51 | A44G35C25T43 | A43G36C20T43 | A44G32C26T38 |
| *A. baumannii* | 89 | 669 | 51 | A44G35C25T43 | A43G36C20T43 | A44G32C26T38 |
| *A. baumannii* | 93 | 674 | 51 | A44G35C25T43 | A43G36C20T43 | A44G32C26T38 |
| *A. baumannii* | 23 | 228 | 51 | A44G35C25T43 | A43G36C20T43 | A44G32C26T38 |
| *A. baumannii* | 32 | 369 | 52 | A44G35C25T43 | A43G36C20T43 | A44G32C26T38 |
| *A. baumannii* | 35 | 393 | 52 | A44G35C25T43 | A43G36C20T43 | A44G32C26T38 |
| *A. baumannii* | 30 | 339 | 53 | A44G35C25T43 | A44G35C19T44 | A44G32C27T37 |
| *A. baumannii* | 41 | 485 | 53 | A44G35C25T43 | A44G35C19T44 | A44G32C27T37 |
| *A. baumannii* | 42 | 493 | 53 | A44G35C25T43 | A44G35C19T44 | A44G32C27T37 |
| *A. baumannii* | 43 | 502 | 53 | A44G35C25T43 | A44G35C19T44 | A44G32C27T37 |
| *A. baumannii* | 46 | 520 | 53 | A44G35C25T43 | A44G35C19T44 | A44G32C27T37 |
| *A. baumannii* | 49 | 527 | 53 | A44G35C25T43 | A44G35C19T44 | A44G32C27T37 |
| *A. baumannii* | 51 | 529 | 53 | A44G35C25T43 | A44G35C19T44 | A44G32C27T37 |
| *A. baumannii* | 65 | 562 | 53 | A44G35C25T43 | A44G35C19T44 | A44G32C27T37 |
| *A. baumannii* | 68 | 579 | 53 | A44G35C25T43 | A44G35C19T44 | A44G32C27T37 |
| *A. baumannii* | 57 | 546 | 54 | A44G35C25T43 | A44G35C20T43 | A44G32C26T38 |
| *A. baumannii* | 58 | 548 | 54 | A44G35C25T43 | A44G35C20T43 | A44G32C26T38 |
| *A. baumannii* | 60 | 552 | 54 | A44G35C25T43 | A44G35C20T43 | A44G32C26T38 |
| *A. baumannii* | 61 | 555 | 54 | A44G35C25T43 | A44G35C20T43 | A44G32C26T38 |
| *A. baumannii* | 63 | 557 | 54 | A44G35C25T43 | A44G35C20T43 | A44G32C26T38 |
| *A. baumannii* | 66 | 570 | 54 | A44G35C25T43 | A44G35C20T43 | A44G32C26T38 |
| *A. baumannii* | 67 | 578 | 54 | A44G35C25T43 | A44G35C20T43 | A44G32C26T38 |
| *A. baumannii* | 69 | 584 | 54 | A44G35C25T43 | A44G35C20T43 | A44G32C26T38 |
| *A. baumannii* | 71 | 593 | 54 | A44G35C25T43 | A44G35C20T43 | A44G32C26T38 |
| *A. baumannii* | 72 | 602 | 54 | A44G35C25T43 | A44G35C20T43 | A44G32C26T38 |
| *A. baumannii* | 76 | 609 | 54 | A44G35C25T43 | A44G35C20T43 | A44G32C26T38 |
| *A. baumannii* | 78 | 621 | 54 | A44G35C25T43 | A44G35C20T43 | A44G32C26T38 |
| *A. baumannii* | 80 | 625 | 54 | A44G35C25T43 | A44G35C20T43 | A44G32C26T38 |
| *A. baumannii* | 81 | 628 | 54 | A44G35C25T43 | A44G35C20T43 | A44G32C26T38 |
| *A. baumannii* | 82 | 632 | 54 | A44G35C25T43 | A44G35C20T43 | A44G32C26T38 |
| *A. baumannii* | 84 | 649 | 54 | A44G35C25T43 | A44G35C20T43 | A44G32C26T38 |
| *A. baumannii* | 86 | 655 | 54 | A44G35C25T43 | A44G35C20T43 | A44G32C26T38 |
| *A. baumannii* | 88 | 668 | 54 | A44G35C25T43 | A44G35C20T43 | A44G32C26T38 |
| *A. baumannii* | 90 | 671 | 54 | A44G35C25T43 | A44G35C20T43 | A44G32C26T38 |
| *A. baumannii* | 91 | 672 | 54 | A44G35C25T43 | A44G35C20T43 | A44G32C26T38 |
| *A. baumannii* | 92 | 673 | 54 | A44G35C25T43 | A44G35C20T43 | A44G32C26T38 |

TABLE 18A-continued

Base Compositions Determined from *A. baumannii* DNA Samples Obtained from Northwestern Medical Center and Amplified with Speciating Primer Pair No. 2922 and Triangulation Genotyping Analysis Primer Pair Nos. 1151 and 1156

| Species | Ibis# | Isolate | ST | PP No: 2922 efp | PP No: 1151 trpE | PP No: 1156 adk |
|---|---|---|---|---|---|---|
| *A. baumannii* | 18 | 196 | 55 | A44G35C25T43 | A44G35C20T43 | A44G32C27T37 |
| *A. baumannii* | 55 | 537 | 27 | A44G35C25T43 | A44G35C19T44 | A44G32C27T37 |
| *A. baumannii* | 28 | 263 | 27 | A44G35C25T43 | A44G35C19T44 | A44G32C27T37 |
| A. sp. 3 | 14 | 164 | B7 | A46G35C24T42 | A42G34C20T46 | A43G33C24T40 |
| mixture | 7 | 71 | ? | mixture | ND | ND |

TABLE 18B

Base Compositions Determined from *A. baumannii* DNA Samples Obtained from Northwestern Medical Center and Amplified with Triangulation Genotyping Analysis Primer Pair Nos. 1158, 1160 and 1165

| Species | Ibis# | Isolate | ST | PP No: 1158 mutY | PP No: 1160 mutY | PP No: 1165 fumC |
|---|---|---|---|---|---|---|
| *A. baumannii* | 54 | 536 | 3 | A27G20C27T21 | A32G35C28T34 | A40G33C30T36 |
| *A. baumannii* | 87 | 665 | 3 | A27G20C27T21 | A32G35C28T34 | A40G33C30T36 |
| *A. baumannii* | 8 | 80 | 10 | A27G21C26T21 | A32G35C28T34 | A40G33C30T36 |
| *A. baumannii* | 9 | 91 | 10 | A27G21C26T21 | A32G35C28T34 | A40G33C30T36 |
| *A. baumannii* | 10 | 92 | 10 | A27G21C26T21 | A32G35C28T34 | A40G33C30T36 |
| *A. baumannii* | 11 | 131 | 10 | A27G21C26T21 | A32G35C28T34 | A40G33C30T36 |
| *A. baumannii* | 12 | 137 | 10 | A27G21C26T21 | A32G35C28T34 | A40G33C30T36 |
| *A. baumannii* | 21 | 218 | 10 | A27G21C26T21 | A32G35C28T34 | A40G33C30T36 |
| *A. baumannii* | 26 | 242 | 10 | A27G21C26T21 | A32G35C28T34 | A40G33C30T36 |
| *A. baumannii* | 94 | 678 | 10 | A27G21C26T21 | A32G35C28T34 | A40G33C30T36 |
| *A. baumannii* | 1 | 9 | 10 | A27G21C26T21 | A32G35C28T34 | A40G33C30T36 |
| *A. baumannii* | 2 | 13 | 10 | A27G21C26T21 | A32G35C28T34 | A40G33C30T36 |
| *A. baumannii* | 3 | 19 | 10 | A27G21C26T21 | A32G35C28T34 | A40G33C30T36 |
| *A. baumannii* | 4 | 24 | 10 | A27G21C26T21 | A32G35C28T34 | A40G33C30T36 |
| *A. baumannii* | 5 | 36 | 10 | A27G21C26T21 | A32G35C28T34 | A40G33C30T36 |
| *A. baumannii* | 6 | 39 | 10 | A27G21C26T21 | A32G35C28T34 | A40G33C30T36 |
| *A. baumannii* | 13 | 139 | 10 | A27G21C26T21 | A32G35C28T34 | A40G33C30T36 |
| *A. baumannii* | 15 | 165 | 10 | A27G21C26T21 | A32G35C28T34 | A40G33C30T36 |
| *A. baumannii* | 16 | 170 | 10 | A27G21C26T21 | A32G35C28T34 | A40G33C30T36 |
| *A. baumannii* | 17 | 186 | 10 | A27G21C26T21 | A32G35C28T34 | A40G33C30T36 |
| *A. baumannii* | 20 | 202 | 10 | A27G21C26T21 | A32G35C28T34 | A40G33C30T36 |
| *A. baumannii* | 22 | 221 | 10 | A27G21C26T21 | A32G35C28T34 | A40G33C30T36 |
| *A. baumannii* | 24 | 234 | 10 | A27G21C26T21 | A32G35C28T34 | A40G33C30T36 |
| *A. baumannii* | 25 | 239 | 10 | A27G21C26T21 | A32G35C28T34 | A40G33C30T36 |
| *A. baumannii* | 33 | 370 | 10 | A27G21C26T21 | A32G35C28T34 | A40G33C30T36 |
| *A. baumannii* | 34 | 389 | 10 | A27G21C26T21 | A32G35C28T34 | A40G33C30T36 |
| *A. baumannii* | 19 | 201 | 14 | A27G21C25T22 | A31G36C28T34 | A40G33C29T37 |
| *A. baumannii* | 27 | 257 | 51 | A27G21C25T22 | A32G35C28T34 | A40G33C29T37 |
| *A. baumannii* | 29 | 301 | 51 | A27G21C25T22 | A32G35C28T34 | A40G33C29T37 |
| *A. baumannii* | 31 | 354 | 51 | A27G21C25T22 | A32G35C28T34 | A40G33C29T37 |
| *A. baumannii* | 36 | 422 | 51 | A27G21C25T22 | A32G35C28T34 | A40G33C29T37 |
| *A. baumannii* | 37 | 424 | 51 | A27G21C25T22 | A32G35C28T34 | A40G33C29T37 |
| *A. baumannii* | 38 | 434 | 51 | A27G21C25T22 | A32G35C28T34 | A40G33C29T37 |
| *A. baumannii* | 39 | 473 | 51 | A27G21C25T22 | A32G35C28T34 | A40G33C29T37 |
| *A. baumannii* | 40 | 482 | 51 | A27G21C25T22 | A32G35C28T34 | A40G33C29T37 |
| *A. baumannii* | 44 | 512 | 51 | A27G21C25T22 | A32G35C28T34 | A40G33C29T37 |
| *A. baumannii* | 45 | 516 | 51 | A27G21C25T22 | A32G35C28T34 | A40G33C29T37 |
| *A. baumannii* | 47 | 522 | 51 | A27G21C25T22 | A32G35C28T34 | A40G33C29T37 |
| *A. baumannii* | 48 | 526 | 51 | A27G21C25T22 | A32G35C28T34 | A40G33C29T37 |
| *A. baumannii* | 50 | 528 | 51 | A27G21C25T22 | A32G35C28T34 | A40G33C29T37 |
| *A. baumannii* | 52 | 531 | 51 | A27G21C25T22 | A32G35C28T34 | A40G33C29T37 |
| *A. baumannii* | 53 | 533 | 51 | A27G21C25T22 | A32G35C28T34 | A40G33C29T37 |
| *A. baumannii* | 56 | 542 | 51 | A27G21C25T22 | A32G35C28T34 | A40G33C29T37 |
| *A. baumannii* | 59 | 550 | 51 | A27G21C25T22 | A32G35C28T34 | A40G33C29T37 |
| *A. baumannii* | 62 | 556 | 51 | A27G21C25T22 | A32G35C28T34 | A40G33C29T37 |
| *A. baumannii* | 64 | 557 | 51 | A27G21C25T22 | A32G35C28T34 | A40G33C29T37 |
| *A. baumannii* | 70 | 588 | 51 | A27G21C25T22 | A32G35C28T34 | A40G33C29T37 |
| *A. baumannii* | 73 | 603 | 51 | A27G21C25T22 | A32G35C28T34 | A40G33C29T37 |
| *A. baumannii* | 74 | 605 | 51 | A27G21C25T22 | A32G35C28T34 | A40G33C29T37 |
| *A. baumannii* | 75 | 606 | 51 | A27G21C25T22 | A32G35C28T34 | A40G33C29T37 |
| *A. baumannii* | 77 | 611 | 51 | A27G21C25T22 | A32G35C28T34 | A40G33C29T37 |
| *A. baumannii* | 79 | 622 | 51 | A27G21C25T22 | A32G35C28T34 | A40G33C29T37 |
| *A. baumannii* | 83 | 643 | 51 | A27G21C25T22 | A32G35C28T34 | A40G33C29T37 |
| *A. baumannii* | 85 | 653 | 51 | A27G21C25T22 | A32G35C28T34 | A40G33C29T37 |
| *A. baumannii* | 89 | 669 | 51 | A27G21C25T22 | A32G35C28T34 | A40G33C29T37 |

TABLE 18B-continued

Base Compositions Determined from *A. baumannii* DNA Samples Obtained from Northwestern Medical Center and Amplified with Triangulation Genotyping Analysis Primer Pair Nos. 1158, 1160 and 1165

| Species | Ibis# | Isolate | ST | PP No: 1158 mutY | PP No: 1160 mutY | PP No: 1165 fumC |
|---|---|---|---|---|---|---|
| *A. baumannii* | 93 | 674 | 51 | A27G21C25T22 | A32G35C28T34 | A40G33C29T37 |
| *A. baumannii* | 23 | 228 | 51 | A27G21C25T22 | A32G35C28T34 | A40G33C29T37 |
| *A. baumannii* | 32 | 369 | 52 | A27G21C25T22 | A32G35C28T34 | A40G33C29T37 |
| *A. baumannii* | 35 | 393 | 52 | A27G21C25T22 | A32G35C28T34 | A40G33C29T37 |
| *A. baumannii* | 30 | 339 | 53 | A28G20C26T21 | A32G34C29T34 | A40G33C30T36 |
| *A. baumannii* | 41 | 485 | 53 | A28G20C26T21 | A32G34C29T34 | A40G33C30T36 |
| *A. baumannii* | 42 | 493 | 53 | A28G20C26T21 | A32G34C29T34 | A40G33C30T36 |
| *A. baumannii* | 43 | 502 | 53 | A28G20C26T21 | A32G34C29T34 | A40G33C30T36 |
| *A. baumannii* | 46 | 520 | 53 | A28G20C26T21 | A32G34C29T34 | A40G33C30T36 |
| *A. baumannii* | 49 | 527 | 53 | A28G20C26T21 | A32G34C29T34 | A40G33C30T36 |
| *A. baumannii* | 51 | 529 | 53 | A28G20C26T21 | A32G34C29T34 | A40G33C30T36 |
| *A. baumannii* | 65 | 562 | 53 | A28G20C26T21 | A32G34C29T34 | A40G33C30T36 |
| *A. baumannii* | 68 | 579 | 53 | A28G20C26T21 | A32G34C29T34 | A40G33C30T36 |
| *A. baumannii* | 57 | 546 | 54 | A27G21C26T21 | A32G34C29T34 | A40G33C30T36 |
| *A. baumannii* | 58 | 548 | 54 | A27G21C26T21 | A32G34C29T34 | A40G33C30T36 |
| *A. baumannii* | 60 | 552 | 54 | A27G21C26T21 | A32G34C29T34 | A40G33C30T36 |
| *A. baumannii* | 61 | 555 | 54 | A27G21C26T21 | A32G34C29T34 | A40G33C30T36 |
| *A. baumannii* | 63 | 557 | 54 | A27G21C26T21 | A32G34C29T34 | A40G33C30T36 |
| *A. baumannii* | 66 | 570 | 54 | A27G21C26T21 | A32G34C29T34 | A40G33C30T36 |
| *A. baumannii* | 67 | 578 | 54 | A27G21C26T21 | A32G34C29T34 | A40G33C30T36 |
| *A. baumannii* | 69 | 584 | 54 | A27G21C26T21 | A32G34C29T34 | A40G33C30T36 |
| *A. baumannii* | 71 | 593 | 54 | A27G21C26T21 | A32G34C29T34 | A40G33C30T36 |
| *A. baumannii* | 72 | 602 | 54 | A27G21C26T21 | A32G34C29T34 | A40G33C30T36 |
| *A. baumannii* | 76 | 609 | 54 | A27G21C26T21 | A32G34C29T34 | A40G33C30T36 |
| *A. baumannii* | 78 | 621 | 54 | A27G21C26T21 | A32G34C29T34 | A40G33C30T36 |
| *A. baumannii* | 80 | 625 | 54 | A27G21C26T21 | A32G34C29T34 | A40G33C30T36 |
| *A. baumannii* | 81 | 628 | 54 | A27G21C26T21 | A32G34C29T34 | A40G33C30T36 |
| *A. baumannii* | 82 | 632 | 54 | A27G21C26T21 | A32G34C29T34 | A40G33C30T36 |
| *A. baumannii* | 84 | 649 | 54 | A27G21C26T21 | A32G34C29T34 | A40G33C30T36 |
| *A. baumannii* | 86 | 655 | 54 | A27G21C26T21 | A32G34C29T34 | A40G33C30T36 |
| *A. baumannii* | 88 | 668 | 54 | A27G21C26T21 | A32G34C29T34 | A40G33C30T36 |
| *A. baumannii* | 90 | 671 | 54 | A27G21C26T21 | A32G34C29T34 | A40G33C30T36 |
| *A. baumannii* | 91 | 672 | 54 | A27G21C26T21 | A32G34C29T34 | A40G33C30T36 |
| *A. baumannii* | 92 | 673 | 54 | A27G21C26T21 | A32G34C29T34 | A40G33C30T36 |
| *A. baumannii* | 18 | 196 | 55 | A27G21C25T22 | A31G36C27T35 | A40G33C29T37 |
| *A. baumannii* | 55 | 537 | 27 | A27G21C25T22 | A32G35C28T34 | A40G33C30T36 |
| *A. baumannii* | 28 | 263 | 27 | A27G21C25T22 | A32G35C28T34 | A40G33C30T36 |
| A. sp. 3 | 14 | 164 | B7 | A26G23C23T23 | A30G36C27T36 | A39G37C26T37 |
| mixture | 7 | 71 | ? | ND | ND | ND |

TABLE 18C

Base Compositions Determined from *A. baumannii* DNA Samples Obtained from Northwestern Medical Center and Amplified with Triangulation Genotyping Analysis Primer Pair Nos. 1167, 1170 and 1171

| Species | Ibis# | Isolate | ST | PP No: 1167 fumC | PP No: 1170 fumC | PP No: 1171 ppa |
|---|---|---|---|---|---|---|
| *A. baumannii* | 54 | 536 | 3 | A41G34C35T37 | A38G27C20T51 | A35G37C31T46 |
| *A. baumannii* | 87 | 665 | 3 | A41G34C35T37 | A38G27C20T51 | A35G37C31T46 |
| *A. baumannii* | 8 | 80 | 10 | A41G34C34T38 | A38G27C21T50 | A35G37C33T44 |
| *A. baumannii* | 9 | 91 | 10 | A41G34C34T38 | A38G27C21T50 | A35G37C33T44 |
| *A. baumannii* | 10 | 92 | 10 | A41G34C34T38 | A38G27C21T50 | A35G37C33T44 |
| *A. baumannii* | 11 | 131 | 10 | A41G34C34T38 | A38G27C21T50 | A35G37C33T44 |
| *A. baumannii* | 12 | 137 | 10 | A41G34C34T38 | A38G27C21T50 | A35G37C33T44 |
| *A. baumannii* | 21 | 218 | 10 | A41G34C34T38 | A38G27C21T50 | A35G37C33T44 |
| *A. baumannii* | 26 | 242 | 10 | A41G34C34T38 | A38G27C21T50 | A35G37C33T44 |
| *A. baumannii* | 94 | 678 | 10 | A41G34C34T38 | A38G27C21T50 | A35G37C33T44 |
| *A. baumannii* | 1 | 9 | 10 | A41G34C34T38 | A38G27C21T50 | A35G37C33T44 |
| *A. baumannii* | 2 | 13 | 10 | A41G34C34T38 | A38G27C21T50 | A35G37C33T44 |
| *A. baumannii* | 3 | 19 | 10 | A41G34C34T38 | A38G27C21T50 | A35G37C33T44 |
| *A. baumannii* | 4 | 24 | 10 | A41G34C34T38 | A38G27C21T50 | A35G37C33T44 |
| *A. baumannii* | 5 | 36 | 10 | A41G34C34T38 | A38G27C21T50 | A35G37C33T44 |
| *A. baumannii* | 6 | 39 | 10 | A41G34C34T38 | A38G27C21T50 | A35G37C33T44 |
| *A. baumannii* | 13 | 139 | 10 | A41G34C34T38 | A38G27C21T50 | A35G37C33T44 |
| *A. baumannii* | 15 | 165 | 10 | A41G34C34T38 | A38G27C21T50 | A35G37C33T44 |
| *A. baumannii* | 16 | 170 | 10 | A41G34C34T38 | A38G27C21T50 | A35G37C33T44 |
| *A. baumannii* | 17 | 186 | 10 | A41G34C34T38 | A38G27C21T50 | A35G37C33T44 |
| *A. baumannii* | 20 | 202 | 10 | A41G34C34T38 | A38G27C21T50 | A35G37C33T44 |
| *A. baumannii* | 22 | 221 | 10 | A41G34C34T38 | A38G27C21T50 | A35G37C33T44 |

TABLE 18C-continued

Base Compositions Determined from *A. baumannii* DNA Samples Obtained from Northwestern Medical Center and Amplified with Triangulation Genotyping Analysis Primer Pair Nos. 1167, 1170 and 1171

| Species | Ibis# | Isolate | ST | PP No: 1167 fumC | PP No: 1170 fumC | PP No: 1171 ppa |
|---|---|---|---|---|---|---|
| *A. baumannii* | 24 | 234 | 10 | A41G34C34T38 | A38G27C21T50 | A35G37C33T44 |
| *A. baumannii* | 25 | 239 | 10 | A41G34C34T38 | A38G27C21T50 | A35G37C33T44 |
| *A. baumannii* | 33 | 370 | 10 | A41G34C34T38 | A38G27C21T50 | A35G37C33T44 |
| *A. baumannii* | 34 | 389 | 10 | A41G34C34T38 | A38G27C21T50 | A35G37C33T44 |
| *A. baumannii* | 19 | 201 | 14 | A40G35C34T38 | A38G27C21T50 | A35G37C30T47 |
| *A. baumannii* | 27 | 257 | 51 | A40G35C34T38 | A38G27C21T50 | A35G37C30T47 |
| *A. baumannii* | 29 | 301 | 51 | A40G35C34T38 | A38G27C21T50 | A35G37C30T47 |
| *A. baumannii* | 31 | 354 | 51 | A40G35C34T38 | A38G27C21T50 | A35G37C30T47 |
| *A. baumannii* | 36 | 422 | 51 | A40G35C34T38 | A38G27C21T50 | A35G37C30T47 |
| *A. baumannii* | 37 | 424 | 51 | A40G35C34T38 | A38G27C21T50 | A35G37C30T47 |
| *A. baumannii* | 38 | 434 | 51 | A40G35C34T38 | A38G27C21T50 | A35G37C30T47 |
| *A. baumannii* | 39 | 473 | 51 | A40G35C34T38 | A38G27C21T50 | A35G37C30T47 |
| *A. baumannii* | 40 | 482 | 51 | A40G35C34T38 | A38G27C21T50 | A35G37C30T47 |
| *A. baumannii* | 44 | 512 | 51 | A40G35C34T38 | A38G27C21T50 | A35G37C30T47 |
| *A. baumannii* | 45 | 516 | 51 | A40G35C34T38 | A38G27C21T50 | A35G37C30T47 |
| *A. baumannii* | 47 | 522 | 51 | A40G35C34T38 | A38G27C21T50 | A35G37C30T47 |
| *A. baumannii* | 48 | 526 | 51 | A40G35C34T38 | A38G27C21T50 | A35G37C30T47 |
| *A. baumannii* | 50 | 528 | 51 | A40G35C34T38 | A38G27C21T50 | A35G37C30T47 |
| *A. baumannii* | 52 | 531 | 51 | A40G35C34T38 | A38G27C21T50 | A35G37C30T47 |
| *A. baumannii* | 53 | 533 | 51 | A40G35C34T38 | A38G27C21T50 | A35G37C30T47 |
| *A. baumannii* | 56 | 542 | 51 | A40G35C34T38 | A38G27C21T50 | A35G37C30T47 |
| *A. baumannii* | 59 | 550 | 51 | A40G35C34T38 | A38G27C21T50 | A35G37C30T47 |
| *A. baumannii* | 62 | 556 | 51 | A40G35C34T38 | A38G27C21T50 | A35G37C30T47 |
| *A. baumannii* | 64 | 557 | 51 | A40G35C34T38 | A38G27C21T50 | A35G37C30T47 |
| *A. baumannii* | 70 | 588 | 51 | A40G35C34T38 | A38G27C21T50 | A35G37C30T47 |
| *A. baumannii* | 73 | 603 | 51 | A40G35C34T38 | A38G27C21T50 | A35G37C30T47 |
| *A. baumannii* | 74 | 605 | 51 | A40G35C34T38 | A38G27C21T50 | A35G37C30T47 |
| *A. baumannii* | 75 | 606 | 51 | A40G35C34T38 | A38G27C21T50 | A35G37C30T47 |
| *A. baumannii* | 77 | 611 | 51 | A40G35C34T38 | A38G27C21T50 | A35G37C30T47 |
| *A. baumannii* | 79 | 622 | 51 | A40G35C34T38 | A38G27C21T50 | A35G37C30T47 |
| *A. baumannii* | 83 | 643 | 51 | A40G35C34T38 | A38G27C21T50 | A35G37C30T47 |
| *A. baumannii* | 85 | 653 | 51 | A40G35C34T38 | A38G27C21T50 | A35G37C30T47 |
| *A. baumannii* | 89 | 669 | 51 | A40G35C34T38 | A38G27C21T50 | A35G37C30T47 |
| *A. baumannii* | 93 | 674 | 51 | A40G35C34T38 | A38G27C21T50 | A35G37C30T47 |
| *A. baumannii* | 23 | 228 | 51 | A40G35C34T38 | A38G27C21T50 | A35G37C30T47 |
| *A. baumannii* | 32 | 369 | 52 | A40G35C34T38 | A38G27C21T50 | A35G37C31T46 |
| *A. baumannii* | 35 | 393 | 52 | A40G35C34T38 | A38G27C21T50 | A35G37C31T46 |
| *A. baumannii* | 30 | 339 | 53 | A40G35C35T37 | A38G27C21T50 | A35G37C31T46 |
| *A. baumannii* | 41 | 485 | 53 | A40G35C35T37 | A38G27C21T50 | A35G37C31T46 |
| *A. baumannii* | 42 | 493 | 53 | A40G35C35T37 | A38G27C21T50 | A35G37C31T46 |
| *A. baumannii* | 43 | 502 | 53 | A40G35C35T37 | A38G27C21T50 | A35G37C31T46 |
| *A. baumannii* | 46 | 520 | 53 | A40G35C35T37 | A38G27C21T50 | A35G37C31T46 |
| *A. baumannii* | 49 | 527 | 53 | A40G35C35T37 | A38G27C21T50 | A35G37C31T46 |
| *A. baumannii* | 51 | 529 | 53 | A40G35C35T37 | A38G27C21T50 | A35G37C31T46 |
| *A. baumannii* | 65 | 562 | 53 | A40G35C35T37 | A38G27C21T50 | A35G37C31T46 |
| *A. baumannii* | 68 | 579 | 53 | A40G35C35T37 | A38G27C21T50 | A35G37C31T46 |
| *A. baumannii* | 57 | 546 | 54 | A40G35C34T38 | A39G26C22T49 | A35G37C31T46 |
| *A. baumannii* | 58 | 548 | 54 | A40G35C34T38 | A39G26C22T49 | A35G37C31T46 |
| *A. baumannii* | 60 | 552 | 54 | A40G35C34T38 | A39G26C22T49 | A35G37C31T46 |
| *A. baumannii* | 61 | 555 | 54 | A40G35C34T38 | A39G26C22T49 | A35G37C31T46 |
| *A. baumannii* | 63 | 557 | 54 | A40G35C34T38 | A39G26C22T49 | A35G37C31T46 |
| *A. baumannii* | 66 | 570 | 54 | A40G35C34T38 | A39G26C22T49 | A35G37C31T46 |
| *A. baumannii* | 67 | 578 | 54 | A40G35C34T38 | A39G26C22T49 | A35G37C31T46 |
| *A. baumannii* | 69 | 584 | 54 | A40G35C34T38 | A39G26C22T49 | A35G37C31T46 |
| *A. baumannii* | 71 | 593 | 54 | A40G35C34T38 | A39G26C22T49 | A35G37C31T46 |
| *A. baumannii* | 72 | 602 | 54 | A40G35C34T38 | A39G26C22T49 | A35G37C31T46 |
| *A. baumannii* | 76 | 609 | 54 | A40G35C34T38 | A39G26C22T49 | A35G37C31T46 |
| *A. baumannii* | 78 | 621 | 54 | A40G35C34T38 | A39G26C22T49 | A35G37C31T46 |
| *A. baumannii* | 80 | 625 | 54 | A40G35C34T38 | A39G26C22T49 | A35G37C31T46 |
| *A. baumannii* | 81 | 628 | 54 | A40G35C34T38 | A39G26C22T49 | A35G37C31T46 |
| *A. baumannii* | 82 | 632 | 54 | A40G35C34T38 | A39G26C22T49 | A35G37C31T46 |
| *A. baumannii* | 84 | 649 | 54 | A40G35C34T38 | A39G26C22T49 | A35G37C31T46 |
| *A. baumannii* | 86 | 655 | 54 | A40G35C34T38 | A39G26C22T49 | A35G37C31T46 |
| *A. baumannii* | 88 | 668 | 54 | A40G35C34T38 | A39G26C22T49 | A35G37C31T46 |
| *A. baumannii* | 90 | 671 | 54 | A40G35C34T38 | A39G26C22T49 | A35G37C31T46 |
| *A. baumannii* | 91 | 672 | 54 | A40G35C34T38 | A39G26C22T49 | A35G37C31T46 |
| *A. baumannii* | 92 | 673 | 54 | A40G35C34T38 | A39G26C22T49 | A35G37C31T46 |
| *A. baumannii* | 18 | 196 | 55 | A42G34C33T38 | A38G27C20T51 | A35G37C31T46 |
| *A. baumannii* | 55 | 537 | 27 | A40G35C33T39 | A38G27C20T51 | A35G37C33T44 |
| *A. baumannii* | 28 | 263 | 27 | A40G35C33T39 | A38G27C20T51 | A35G37C33T44 |
| A. sp. 3 | 14 | 164 | B7 | A43G37C30T37 | A36G27C24T49 | A34G37C31T47 |
| mixture | 7 | 71 | — | ND | ND | ND |

Base composition analysis of the samples obtained from Walter Reed hospital indicated that a majority of the strain types identified were the same strain types already characterized by the Off study of Example 12. This is not surprising since at least some patients from which clinical samples were obtained in OIF were transferred to the Walter Reed Hospital (WRAIR). Examples of these common strain types include: ST10, ST11, ST12, ST14, ST15, ST16 and ST46. A strong correlation was noted between these strain types and the presence of mutations in the gyrA and parC which confer quinolone drug resistance.

In contrast, the results of base composition analysis of samples obtained from Northwestern Medical Center indicate the presence of 4 major strain types: ST10, ST51, ST53 and ST54. All of these strain types have the gyrA quinolone resistance mutation and most also have the parC quinolone resistance mutation, with the exception of ST35. This observation is consistent with the current understanding that the gyrA mutation generally appears before the parC mutation and suggests that the acquisition of these drug resistance mutations is rather recent and that resistant isolates are taking over the wild-type isolates. Another interesting observation was that a single isolate of ST3 (isolate 841) displays a triangulation genotyping analysis pattern similar to other isolates of ST3, but the codon analysis amplification product base compositions indicate that this isolate has not yet undergone the quinolone resistance mutations in gyrA and parC.

The six isolates that represent species other than *Acinetobacter baumannii* in the samples obtained from the Walter Reed Hospital were each found to not carry the drug resistance mutations.

The results described above involved analysis of 183 samples using the methods and compositions of the present invention. Results were provided to collaborators at the Walter Reed hospital and Northwestern Medical center within a week of obtaining samples. This example highlights the rapid throughput characteristics of the analysis platform and the resolving power of triangulation genotyping analysis and codon analysis for identification of and determination of drug resistance in bacteria.

Example 14

Identification of Drug Resistance Genes and Virulence Factors in *Staphylococcus aureus*

An eight primer pair panel was designed for identification of drug resistance genes and virulence factors of *Staphylococcus aureus* and is shown in Table 19. The primer sequences are found in Table 2 and are cross-referenced by the primer pair numbers, primer pair names or SEQ ID NOs listed in Table 19.

TABLE 19

Primer Pairs for Identification of Drug Resistance Genes and Virulence Factors in *Staphylococcus aureus*

| Primer Pair No. | Forward Primer Name | Forward Primer (SEQ ID NO:) | Reverse Primer Name | Reverse Primer (SEQ ID NO:) | Target Gene |
|---|---|---|---|---|---|
| 879 | MECA_Y14051_4507_4530_F | 288 | MECA_Y14051_4555_4581_R | 1269 | mecA |
| 2056 | MECI-R_NC003923-41798-41609_33_60_F | 698 | MECI-RNC003923-41798-41609_86_113_R | 1420 | MecI-R |
| 2081 | ERMANC002952-55890-56621_366_395_F | 217 | ERMA_NC002952-55890-56621_438_465_R | 1167 | ermA |
| 2086 | ERMCNC005908-2004-2738_85_116_F | 399 | ERMCNC005908-2004-2738_173_206_R | 1041 | ermC |
| 2095 | PVLUKNC003923-1529595-1531285_688_713_F | 456 | PVLUKNC003923-1529595-1531285_775_804_R | 1261 | Pv-luk |
| 2249 | TUFBNC002758-615038-616222_696_725_F | 430 | TUFB_NC002758-615038-616222_793_820_R | 1321 | tufB |
| 2256 | NUC_NC002758-894288-894974_316_345_F | 174 | N13CNC002758-894288-894974_396_421_R | 853 | Nuc |
| 2313 | MUPR_X75439_2486_2516_F | 172 | MUPR_X75439_2548_2574_R | 1360 | mupR |

Primer pair numbers 2256 and 2249 are confirmation primers designed with the aim of high level identification of *Staphylococcus aureus*. The nuc gene is a *Staphylococcus aureus*-specific marker gene. The tufB gene is a universal housekeeping gene but the bioagent identifying amplicon defined by primer pair number 2249 provides a unique base composition (A43 G28 C19 T35) which distinguishes *Staphylococcus aureus* from other members of the genus *Staphylococcus*.

High level methicillin resistance in a given strain of *Staphylococcus aureus* is indicated by bioagent identifying amplicons defined by primer pair numbers 879 and 2056. Analyses have indicated that primer pair number 879 is not expected to prime *S. sciuri* homolog or *Enterococcus faecalis/faciem* ampicillin-resistant PBP5 homologs.

Macrolide and erythromycin resistance in a given strain of *Staphylococcus aureus* is indicated by bioagent identifying amplicons defined by primer pair numbers 2081 and 2086.

Resistance to mupriocin in a given strain of *Staphylococcus aureus* is indicated by bioagent identifying amplicons defined by primer pair number 2313.

Virulence in a given strain of *Staphylococcus aureus* is indicated by bioagent identifying amplicons defined by primer pair number 2095. This primer pair can simultaneously and identify the pvl (lukS-PV) gene and the lukD gene which encodes a homologous enterotoxin. A bioagent identifying amplicon of the lukD gene has a six nucleobase length difference relative to the lukS-PV gene.

A total of 32 blinded samples of different strains of *Staphylococcus aureus* were provided by the Center for Disease Control (CDC). Each sample was analyzed by PCR amplification with the eight primer pair panel, followed by purification and measurement of molecular masses of the amplification products by mass spectrometry. Base compositions for the amplification products were calculated. The base compositions provide the information summarized above for each primer pair. The results are shown in Tables 20A and B. One result noted upon un-blinding of the samples is that each of the PVL+ identifications agreed with PVL+ identified in the same samples by standard PCR assays. These results indicate that the panel of eight primer pairs is useful for identification of drug resistance and virulence sub-species characteristics for *Staphylococcus aureus*. It is expected that a kit comprising one or more of the members of this panel will be a useful embodiment of the present invention.

TABLE 20A

Drug Resistance and Virulence Identified in Blinded Samples of Various Strains of *Staphylococcus aureus* with Primer Pair Nos. 2081, 2086, 2095 and 2256

| Sample Index No. | Primer Pair No. 2081 (ermA) | Primer Pair No. 2086 (ermC) | Primer Pair No. 2095 (pv-luk) | Primer Pair No. 2256 (nuc) |
|---|---|---|---|---|
| CDC0010 | − | − | PVL−/lukD+ | + |
| CDC0015 | − | − | PVL+/lukD+ | + |
| CDC0019 | − | + | PVL−/lukD+ | + |
| CDC0026 | + | − | PVL−/lukD+ | + |
| CDC0030 | + | − | PVL−/lukD+ | + |
| CDC004 | − | − | PVL+/lukD+ | + |
| CDC0014 | − | + | PVL+/lukD+ | + |
| CDC008 | − | − | PVL−/lukD+ | + |
| CDC001 | + | − | PVL−/lukD+ | + |
| CDC0022 | + | − | PVL−/lukD+ | + |
| CDC006 | + | − | PVL−/lukD+ | + |
| CDC007 | − | − | PVL−/lukD+ | + |
| CDCVRSA1 | + | − | PVL−/lukD+ | + |
| CDCVRSA2 | + | + | PVL−/lukD+ | + |
| CDC0011 | + | − | PVL−/lukD+ | + |
| CDC0012 | − | − | PVL+/lukD− | + |
| CDC0021 | + | − | PVL−/lukD+ | + |
| CDC0023 | + | − | PVL−/lukD+ | + |
| CDC0025 | + | − | PVL−/lukD+ | + |
| CDC005 | − | − | PVL−/lukD+ | + |
| CDC0018 | + | − | PVL+/lukD− | + |
| CDC002 | − | − | PVL−/lukD+ | + |
| CDC0028 | + | − | PVL−/lukD+ | + |
| CDC003 | − | − | PVL−/lukD+ | + |
| CDC0013 | − | − | PVL+/lukD+ | + |
| CDC0016 | − | − | PVL−/lukD+ | + |
| CDC0027 | + | − | PVL−/lukD+ | + |
| CDC0029 | − | − | PVL+/lukD+ | + |
| CDC0020 | − | + | PVL−/lukD+ | + |
| CDC0024 | − | − | PVL−/lukD+ | + |
| CDC0031 | − | − | PVL−/lukD+ | + |

TABLE 20B

Drug Resistance and Virulence Identified in Blinded Samples of Various Strains of *Staphylococcus aureus* with Primer Pair Nos. 2249, 879, 2056, and 2313

| Sample Index No. | Primer Pair No. 2249 (tufB) | Primer Pair No. 879 (mecA) | Primer Pair No. 2056 (mecI-R) | Primer Pair No. 2313 (mupR) |
|---|---|---|---|---|
| CDC0010 | *Staphylococcus aureus* | + | + | − |
| CDC0015 | *Staphylococcus aureus* | − | − | − |
| CDC0019 | *Staphylococcus aureus* | + | + | − |
| CDC0026 | *Staphylococcus aureus* | + | + | − |

TABLE 20B-continued

Drug Resistance and Virulence Identified in Blinded Samples of Various Strains of *Staphylococcus aureus* with Primer Pair Nos. 2249, 879, 2056, and 2313

| Sample Index No. | Primer Pair No. 2249 (tufB) | Primer Pair No. 879 (mecA) | Primer Pair No. 2056 (mecI-R) | Primer Pair No. 2313 (mupR) |
|---|---|---|---|---|
| CDC0030 | *Staphylococcus aureus* | + | + | − |
| CDC004 | *Staphylococcus aureus* | + | + | − |
| CDC0014 | *Staphylococcus aureus* | + | + | − |
| CDC008 | *Staphylococcus aureus* | + | + | − |
| CDC001 | *Staphylococcus aureus* | + | + | − |
| CDC0022 | *Staphylococcus aureus* | + | + | − |
| CDC006 | *Staphylococcus aureus* | + | + | + |
| CDC007 | *Staphylococcus aureus* | + | + | − |
| CDCVRSA1 | *Staphylococcus aureus* | + | + | − |
| CDCVRSA2 | *Staphylococcus aureus* | + | + | − |
| CDC0011 | *Staphylococcus aureus* | − | − | − |
| CDC0012 | *Staphylococcus aureus* | + | + | − |
| CDC0021 | *Staphylococcus aureus* | + | + | − |
| CDC0023 | *Staphylococcus aureus* | + | + | − |
| CDC0025 | *Staphylococcus aureus* | + | + | − |
| CDC005 | *Staphylococcus aureus* | + | + | − |
| CDC0018 | *Staphylococcus aureus* | + | + | − |
| CDC002 | *Staphylococcus aureus* | + | + | − |
| CDC0028 | *Staphylococcus aureus* | + | + | − |
| CDC003 | *Staphylococcus aureus* | + | + | − |
| CDC0013 | *Staphylococcus aureus* | + | + | − |
| CDC0016 | *Staphylococcus aureus* | + | + | − |
| CDC0027 | *Staphylococcus aureus* | + | + | − |
| CDC0029 | *Staphylococcus aureus* | + | + | − |
| CDC0020 | *Staphylococcus aureus* | − | − | − |
| CDC0024 | *Staphylococcus aureus* | + | + | − |
| CDC0031 | *Staphylococcus scleiferi* | − | − | − |

Example 15

Selection and Use of Triangulation Genotyping Analysis Primer Pairs for *Staphylococcus aureus*

To combine the power of high-throughput mass spectrometric analysis of bioagent identifying amplicons with the sub-species characteristic resolving power provided by triangulation genotyping analysis, a panel of eight triangulation genotyping analysis primer pairs was selected. The primer pairs are designed to produce bioagent identifying amplicons within six different housekeeping genes which are listed in Table 21. The primer sequences are found in Table 2 and are cross-referenced by the primer pair numbers, primer pair names or SEQ ID NOs listed in Table 21.

TABLE 21

| Primer Pair No. | Forward Primer Name | Forward Primer (SEQ ID NO:) | ReversePrimer Name | Reverse Primer (SEQ ID NO:) | Target Gene |
|---|---|---|---|---|---|
| Primer Pairs for Triangulation Genotyping Analysis of *Staphylococcus aureus* | | | | | |
| 2146 | ARCC_NC003923-2725050-2724595_131_161_F | 437 | ARCC_NC003923-2725050-2724595_214_245_R | 1137 | arcC |
| 2149 | AROE_NC003923-1674726-1674277_30_62_F | 530 | AROE_NC003923-1674726-1674277_155_181_R | 891 | aroE |
| 2150 | AROE_NC003923-1674726-1674277_204_232_F | 474 | AROE_NC003923-1674726-1674277_308_335_R | 869 | aroE |
| 2156 | GMK_NC003923-1190906-1191334_301_329_F | 268 | GMK_NC003923-1190906-1191334_403_432_R | 1284 | gmk |
| 2157 | PTA_NC003923-628885-629355_237_263_F | 418 | PTA_NC003923-628885-629355_314_345_R | 1301 | pta |
| 2161 | TPI_NC003923-830671-831072_1_34_F | 318 | TPI_NC003923-830671-831072_97_129_R | 1300 | tpi |
| 2163 | YQI_NC003923-378916-379431_142_167_F | 440 | YQI_NC003923-378916-379431_259_284_R | 1076 | yqi |
| 2166 | YQI_NC003923-378916-379431_275_300_F | 219 | YQI_NC003923-378916-379431_364_396_R | 1013 | yqi |

The same samples analyzed for drug resistance and virulence in Example 14 were subjected to triangulation genotyping analysis. The primer pairs of Table 21 were used to produce amplification products by PCR, which were subsequently purified and measured by mass spectrometry. Base compositions were calculated from the molecular masses and are shown in Tables 22A and 22B.

TABLE 22A

Triangulation Genotyping Analysis of Blinded Samples of Various Strains of *Staphylococcus aureus* with Primer Pair Nos. 2146, 2149, 2150 and 2156

| Sample Index No. | Strain | Primer Pair No. 2146 (arcC) | Primer Pair No. 2149 (aroE) | Primer Pair No. 2150 (aroE) | Primer Pair No. 2156 (gmk) |
|---|---|---|---|---|---|
| CDC0010 | COL | A44 G24 C18 T29 | A59 G24 C18 T51 | A40 G36 C13 T43 | A50 G30 C20 T32 |
| CDC0015 | COL | A44 G24 C18 T29 | A59 G24 C18 T51 | A40 G36 C13 T43 | A50 G30 C20 T32 |
| CDC0019 | COL | A44 G24 C18 T29 | A59 G24 C18 T51 | A40 G36 C13 T43 | A50 G30 C20 T32 |
| CDC0026 | COL | A44 G24 C18 T29 | A59 G24 C18 T51 | A40 G36 C13 T43 | A50 G30 C20 T32 |
| CDC0030 | COL | A44 G24 C18 T29 | A59 G24 C18 T51 | A40 G36 C13 T43 | A50 G30 C20 T32 |
| CDC004 | COL | A44 G24 C18 T29 | A59 G24 C18 T51 | A40 G36 C13 T43 | A50 G30 C20 T32 |
| CDC0014 | COL | A44 G24 C18 T29 | A59 G24 C18 T51 | A40 G36 C13 T43 | A50 G30 C20 T32 |
| CDC008 | ???? | A44 G24 C18 T29 | A59 G24 C18 T51 | A40 G36 C13 T43 | A50 G30 C20 T32 |
| CDC001 | Mu50 | A45 G23 C20 T27 | A58 G24 C18 T52 | A40 G36 C13 T43 | A51 G29 C21 T31 |
| CDC0022 | Mu50 | A45 G23 C20 T27 | A58 G24 C18 T52 | A40 G36 C13 T43 | A51 G29 C21 T31 |
| CDC006 | Mu50 | A45 G23 C20 T27 | A58 G24 C18 T52 | A40 G36 C13 T43 | A51 G29 C21 T31 |
| CDC0011 | MRSA252 | A45 G24 C18 T28 | A58 G24 C19 T51 | A41 G36 C12 T43 | A51 G29 C21 T31 |
| CDC0012 | MRSA252 | A45 G24 C18 T28 | A58 G24 C19 T51 | A41 G36 C12 T43 | A51 G29 C21 T31 |
| CDC0021 | MRSA252 | A45 G24 C18 T28 | A58 G24 C19 T51 | A41 G36 C12 T43 | A51 G29 C21 T31 |
| CDC0023 | ST:110 | A45 G24 C18 T28 | A59 G24 C18 T51 | A40 G36 C13 T43 | A50 G30 C20 T32 |
| CDC0025 | ST:110 | A45 G24 C18 T28 | A59 G24 C18 T51 | A40 G36 C13 T43 | A50 G30 C20 T32 |
| CDC005 | ST:338 | A44 G24 C18 T29 | A59 G23 C19 T51 | A40 G36 C14 T42 | A51 G29 C21 T31 |
| CDC0018 | ST:338 | A44 G24 C18 T29 | A59 G23 C19 T51 | A40 G36 C14 T42 | A51 G29 C21 T31 |
| CDC002 | ST:108 | A46 G23 C20 T26 | A58 G24 C19 T51 | A42 G36 C12 T42 | A51 G29 C20 T32 |
| CDC0028 | ST:108 | A46 G23 C20 T26 | A58 G24 C19 T51 | A42 G36 C12 T42 | A51 G29 C20 T32 |
| CDC003 | ST:107 | A45 G23 C20 T27 | A58 G24 C18 T52 | A40 G36 C13 T43 | A51 G29 C21 T31 |
| CDC0013 | ST:12 | ND | A59 G24 C18 T51 | A40 G36 C13 T43 | A51 G29 C21 T31 |
| CDC0016 | ST:120 | A45 G23 C18 T29 | A58 G24 C19 T51 | A40 G37 C13 T42 | A51 G29 C21 T31 |
| CDC0027 | ST:105 | A45 G23 C20 T27 | A58 G24 C18 T52 | A40 G36 C13 T43 | A51 G29 C21 T31 |
| CDC0029 | MSSA476 | A45 G23 C20 T27 | A58 G24 C19 T51 | A40 G36 C13 T43 | A50 G30 C20 T32 |
| CDC0020 | ST:15 | A44 G23 C21 T27 | A59 G23 C18 T52 | A40 G36 C13 T43 | A50 G30 C20 T32 |
| CD00024 | ST:137 | A45 G23 C20 T27 | A57 G25 C19 T51 | A40 G36 C13 T43 | A51 G29 C22 T30 |
| CDC0031 | *** | No product | No product | No product | No product |

TABLE 22B

Triangulation Genotyping Analysis of Blinded Samples of Various Strains of *Staphylococcus aureus* with Primer Pair Nos. 2146, 2149, 2150 and 2156

| Sample Index No. | Strain | Primer Pair No. 2157 (pta) | Primer Pair No. 2161 (tpi) | Primer Pair No. 2163 (yqi) | Primer Pair No. 2166 (yqi) |
|---|---|---|---|---|---|
| CDC0010 | COL | A32 G25 C23 T29 | A51 G28 C22 T28 | A41 G37 C22 T43 | A37 G30 C18 T37 |
| CDC0015 | COL | A32 G25 C23 T29 | A51 G28 C22 T28 | A41 G37 C22 T43 | A37 G30 C18 T37 |
| CDC0019 | COL | A32 G25 C23 T29 | A51 G28 C22 T28 | A41 G37 C22 T43 | A37 G30 C18 T37 |
| CDC0026 | COL | A32 G25 C23 T29 | A51 G28 C22 T28 | A41 G37 C22 T43 | A37 G30 C18 T37 |
| CDC0030 | COL | A32 G25 C23 T29 | A51 G28 C22 T28 | A41 G37 C22 T43 | A37 G30 C18 T37 |
| CDC004 | COL | A32 G25 C23 T29 | A51 G28 C22 T28 | A41 G37 C22 T43 | A37 G30 C18 T37 |
| CDC0014 | COL | A32 G25 C23 T29 | A51 G28 C22 T28 | A41 G37 C22 T43 | A37 G30 C18 T37 |
| CDC008 | unknown | A32 G25 C23 T29 | A51 G28 C22 T28 | A41 G37 C22 T43 | A37 G30 C18 T37 |
| CDC001 | Mu50 | A33 G25 C22 T29 | A50 G28 C22 T29 | A42 G36 C22 T43 | A36 G31 C19 T36 |
| CDC0022 | Mu50 | A33 G25 C22 T29 | A50 G28 C22 T29 | A42 G36 C22 T43 | A36 G31 C19 T36 |
| CDC006 | Mu50 | A33 G25 C22 T29 | A50 G28 C22 T29 | A42 G36 C22 T43 | A36 G31 C19 T36 |
| CDC0011 | MRSA252 | A32 G25 C23 T29 | A50 G28 C22 T29 | A42 G36 C22 T43 | A37 G30 C18 T37 |
| CDC0012 | MRSA252 | A32 G25 C23 T29 | A50 G28 C22 T29 | A42 G36 C22 T43 | A37 G30 C18 T37 |
| CDC0021 | MRSA252 | A32 G25 C23 T29 | A50 G28 C22 T29 | A42 G36 C22 T43 | A37 G30 C18 T37 |
| CDC0023 | ST:110 | A32 G25 C23 T29 | A51 G28 C22 T28 | A41 G37 C22 T43 | A37 G30 C18 T37 |
| CDC0025 | ST:110 | A32 G25 C23 T29 | A51 G28 C22 T28 | A41 G37 C22 T43 | A37 G30 C18 T37 |
| CDC005 | ST:338 | A32 G25 C24 T28 | A51 G27 C21 T30 | A42 G36 C22 T43 | A37 G30 C18 T37 |
| CDC0018 | ST:338 | A32 G25 C24 T28 | A51 G27 C21 T30 | A42 G36 C22 T43 | A37 G30 C18 T37 |
| CDC002 | ST:108 | A33 G25 C23 T28 | A50 G28 C22 T29 | A42 G36 C22 T43 | A37 G30 C18 T37 |
| CDC0028 | ST:108 | A33 G25 C23 T28 | A50 G28 C22 T29 | A42 G36 C22 T43 | A37 G30 C18 T37 |
| CDC003 | ST:107 | A32 G25 C23 T29 | A51 G28 C22 T28 | A41 G37 C22 T43 | A37 G30 C18 T37 |
| CDC0013 | ST:12 | A32 G25 C23 T29 | A51 G28 C22 T28 | A42 G36 C22 T43 | A37 G30 C18 T37 |
| CDC0016 | ST:120 | A32 G25 C24 T28 | A50 G28 C21 T30 | A42 G36 C22 T43 | A37 G30 C18 T37 |
| CDC0027 | ST:105 | A33 G25 C22 T29 | A50 G28 C22 T29 | A43 G36 C21 T43 | A36 G31 C19 T36 |
| CDC0029 | MSSA476 | A33 G25 C22 T29 | A50 G28 C22 T29 | A42 G36 C22 T43 | A36 G31 C19 T36 |
| CDC0020 | ST:15 | A33 G25 C22 T29 | A50 G28 C21 T30 | A42 G36 C22 T43 | A36 G31 C18 T37 |
| CDC0024 | ST:137 | A33 G25 C22 T29 | A51 G28 C22 T28 | A42 G36 C22 T43 | A37 G30 C18 T37 |
| CDC0031 | *** | A34 G25 C25 T25 | A51 G27 C24 T27 | No product | No product |

Note: *** The sample CDC0031 was identified as *Staphylococcus scleiferi* as indicated in Example 14. Thus, the triangulation genotyping primers designed for *Staphylococcus aureus* would generally not be expected to prime and produce amplification products of this organism. Tables 22A and 22B indicate that amplification products are obtained for this organism only with primer pair numbers 2157 and 2161.

A total of thirteen different genotypes of *Staphylococcus aureus* were identified according to the unique combinations of base compositions across the eight different bioagent identifying amplicons obtained with the eight primer pairs. These results indicate that this eight primer pair panel is useful for analysis of unknown or newly emerging strains of *Staphylococcus aureus*. It is expected that a kit comprising one or more of the members of this panel will be a useful embodiment of the present invention.

Example 16

Selection and Use of Triangulation Genotyping Analysis Primer Pairs for Members of the Bacterial Genus *Vibrio*

To combine the power of high-throughput mass spectrometric analysis of bioagent identifying amplicons with the sub-species characteristic resolving power provided by triangulation genotyping analysis, a panel of eight triangulation genotyping analysis primer pairs was selected. The primer pairs are designed to produce bioagent identifying amplicons within seven different housekeeping genes which are listed in Table 23. The primer sequences are found in Table 2 and are cross-referenced by the primer pair numbers, primer pair names or SEQ ID NOs listed in Table 23.

TABLE 23

Primer Pairs for Triangulation Genotyping Analysis of Members of the Bacterial Genus *Vibrio*

| Primer Pair No. | Forward Primer Name | Forward Primer (SEQ ID NO:) | Reverse Primer Name | Reverse Primer (SEQ ID NO:) | Target Gene |
|---|---|---|---|---|---|
| 1098 | RNASEP_VBC_331_349_F | 325 | RNASEP_VBC_388_414_R | 1163 | RNAse P |
| 2000 | CTXB_NC002505_46_70_F | 278 | CTXB_NC002505_132_162_R | 1039 | ctxB |
| 2001 | FUR_NC002505_87_113_F | 465 | FUR_NC002505_205_228_R | 1037 | fur |
| 2011 | GYRB_NC002505_1161_1190_F | 148 | GYRB_NC002505_1255_1284_R | 1172 | gyrB |
| 2012 | OMPU_NC002505_85_110_F | 190 | OMPU_NC002505_154_180_R | 1254 | ompU |
| 2014 | OMPU_NC002505_431_455_F | 266 | OMPU_NC002505_544_567_R | 1094 | ompU |
| 2323 | CTXA_NC002505-1568114-1567341_122_149_F | 508 | CTXA_NC002505-1568114-1567341_186_214_R | 1297 | ctxA |
| 2927 | GAPA_NC002505_694_721_F | 259 | GAPA_NC_002505_29_58_R | 1060 | gapA |

A group of 50 bacterial isolates containing multiple strains of both environmental and clinical isolates of *Vibrio cholerae,* 9 other *Vibrio* species, and 3 species of Photobacteria were tested using this panel of primer pairs. Base compositions of amplification products obtained with these 8 primer pairs were used to distinguish amongst various species tested, including sub-species differentiation within *Vibrio cholerae* isolates. For instance, the non-O1/non-O139 isolates were clearly resolved from the O1 and the O139 isolates, as were several of the environmental isolates of *Vibrio cholerae* from the clinical isolates.

It is, expected that a kit comprising one or more of the members of this panel will be a useful embodiment of the present invention.

Example 17

Selection and Use of Triangulation Genotyping Analysis Primer Pairs for Members of the Bacterial Genus *Pseudomonas*

To combine the power of high-throughput mass spectrometric analysis of bioagent identifying amplicons with the sub-species characteristic resolving power provided by triangulation genotyping analysis, a panel of twelve triangulation genotyping analysis primer pairs was selected. The primer pairs are designed to produce bioagent identifying amplicons within seven different housekeeping genes which are listed in Table 24. The primer sequences are found in Table 2 and are cross-referenced by the primer pair numbers, primer pair names or SEQ ID NOs listed in Table 24.

TABLE 24

Primer Pairs for Triangulation Genotyping Analysis of Members of the Bacterial Genus *Pseudomonas*

| Primer Pair No. | Forward Primer Name | Forward Primer (SEQ ID NO:) | Reverse Primer Name | Reverse Primer (SEQ ID NO:) | Target Gene |
|---|---|---|---|---|---|
| 2949 | ACS_NC002516-970624-971013_299_316_F | 376 | ACS_NC002516-970624-971013_364_383_R | 1265 | acsA |
| 2950 | ARO_NC002516-26883-27380_4_26_F | 267 | ARO_NC002516-26883-27380_111_128_R | 1341 | aroE |
| 2951 | ARO_NC002516-26883-27380_356_377_F | 705 | ARO_NC002516-26883-27380_459_484_R | 1056 | aroE |
| 2954 | GUA_NC002516-4226546-4226174_155_178_F | 710 | GUA_NC002516-4226546-4226174_265_287_R | 1259 | guaA |
| 2956 | GUA_NC002516-4226546-4226174_242_263_F | 374 | GUA_NC002516-4226546-4226174_355_371_R | 1111 | guaA |
| 2957 | MUT_NC002516-5551158-5550717_5_26_F | 545 | MUT_NC002516-5551158-5550717_99_116_R | 978 | mutL |
| 2959 | NUO_NC002516-2984589-2984954_8_26_F | 249 | NUO_NC002516-2984589-2984954_97_117_R | 1095 | nuoD |
| 2960 | NUO_NC002516-2984589-2984954_218_239_F | 195 | NUO_NC002516-2984589-2984954_301_326_R | 1376 | nuoD |
| 2961 | PPS_NC002516-1915014-1915383_44_63_F | 311 | PPS_NC002516-1915014-1915383_140_165_R | 1014 | pps |
| 2962 | PPS_NC002516-1915014-1915383_240_258_F | 365 | PPS_NC002516-1915014-1915383_341_360_R | 1052 | pps |
| 2963 | TRP_NC002516-671831-672273_24_42_F | 527 | TRP_NC002516-671831-672273_131_150_R | 1071 | trpE |
| 2964 | TRP_NC002516-671831-672273_261_282_F | 490 | TRP_NC002516-671831-672273_362_383_R | 1182 | trpE |

It is expected that a kit comprising one or more of the members of this panel will be a useful embodiment of the present invention.

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

While in accordance with the patent statutes, description of the various embodiments and examples have been provided, the scope of the invention is not to be limited thereto or thereby. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

Each reference (including, but not limited to, journal articles, U.S. and non-U.S. patents, patent application publications, international patent application publications, gene bank gi or accession numbers, internet web sites, and the like) cited in the present application is incorporated herein by reference in its entirety.

What is claimed is:

1. An oligonucleotide primer pair comprising a forward and a reverse primer, wherein said forward primer comprises SEQ ID NO: 590, and wherein said reverse primer comprises SEQ ID NO: 891.

2. The oligonucleotide primer pair of claim 1 wherein said forward primer is SEQ ID NO: 590.

3. The oligonucleotide primer pair of claim 1 wherein said reverse primer is SEQ ID NO: 891.

4. The oligonucleotide primer pair of claim 1 wherein at least one of said forward primer and said reverse primer comprises at least one modified nucleobase.

5. The oligonucleotide primer pair of claim 4 wherein at least one of said at least one modified nucleobase is a mass modified nucleobase.

6. The oligonucleotide primer pair of claim 5 wherein said mass modified nucleobase is 5-Iodo-C.

7. The composition of claim 5 wherein said mass modified nucleobase comprises a molecular mass modifying tag.

8. The oligonucleotide primer pair of claim 4 wherein at least one of said at least one modified nucleobase is a universal nucleobase.

9. The oligonucleotide primer pair of claim 8 wherein said universal nucleobase is inosine.

10. The oligonucleotide primer pair of claim 1 wherein at least one of said forward primer and said reverse primer comprises a non-templated T residue at its 5' end.

11. A kit for identifying, determining one or more characteristics of, or detecting a *Staphylococcus aureus* bioagent comprising the oligonucleotide primer pair of claim 1 and at least one additional primer pair designed to hybridize to a *Staphylococcus aureus* gene encoding arcC, aroE, gmk, pta, tpi, yqi, or a combination thereof.

12. The kit of claim 11 further comprising at least one other additional primer pair designed to hybridize to a *Staphylococcus aureus* gene encoding mecA, mecR1, pvluk, or a combination thereof.

13. The kit of claim 11 wherein said at least one additional primer pair comprises SEQ ID NOs: 437:1232, SEQ ID NOs: 268:1284, SEQ ID NOs: 418:1301, SEQ ID NOs: 318:1300, SEQ ID NOs: 440:1076, SEQ ID NOs: 219:1013, or a combination thereof.

14. The kit of claim 11 wherein said oligonucleotide primer pair of claim 1 and said at least one additional primer pair consists of eight oligonucleotide primer pairs wherein at least one of the primers of said at least one additional primer pair has at least 70% sequence identity with at least one of the primers of the primer pairs represented by: SEQ ID NOs: 437:1232, SEQ ID NOs: 590:891, SEQ ID NOs: 474:869, SEQ ID NOs: 268:1284, SEQ ID NOs: 418:1301, SEQ ID NOs: 318:1300, SEQ ID NOs: 440:1076, and SEQ ID NOs: 219:1013.

15. A method for identifying, determining one or more characteristics of, or detecting a *Staphylococcus aureus* bioagent in a sample comprising:

a) amplifying a nucleic acid from said sample using the oligonucleotide primer pair of claim 1; and b) determining the molecular mass of said at least one amplification product by mass spectrometry.

16. The method of claim 15 further comprising comparing said determined molecular mass to a plurality of molecular masses of bioagent identifying amplicons, each indexed to said oligonucleotide primer pair and a *Staphylococcus aureus* bioagent, wherein a match between said determined molecular mass and one of said plurality of molecular masses identifies, determines one or more characteristic of, or detects said *Staphylococcus aureus* bioagent in said sample.

17. The method of claim 15 further comprising calculating a base composition of said at least one amplification product using said molecular mass.

18. The method of claim 17 further comprising comparing said calculated base composition to a database comprising a plurality of base compositions of bioagent identifying amplicons, each indexed to said oligonucleotide primer pair and a *Staphylococcus aureus* bioagent, wherein a match between said calculated base composition and a base composition in said database identifies, determines one or more characteristics of, or detects said *Staphylococcus aureus* bioagent in said sample.

19. The method of claim 15 further comprising repeating said amplifying and determining steps using at least one additional oligonucleotide primer pair designed to hybridize to a *Staphylococcus aureus* gene encoding arcC, aroE, gmk, pta, tpi, yqi or a combination thereof.

* * * * *